United States Patent
Heilmann et al.

(10) Patent No.: US 9,802,899 B2
(45) Date of Patent: Oct. 31, 2017

(54) HETEROCYCLIC COMPOUNDS AS PESTICIDES

(71) Applicant: BAYER CROPSCIENCE AG, Monheim (DE)

(72) Inventors: Eike Kevin Heilmann, Duesseldorf (DE); Joerg Greul, Leverkusen (DE); Axel Trautwein, Duesseldorf (DE); Hans-Georg Schwarz, Dorsten (DE); Isabelle Adelt, Haan (DE); Roland Andree, Langenfeld (DE); Peter Luemmen, Idstein (DE); Maike Hink, Markgroeningen (DE); Martin Adamczewski, Cologne (DE); Mark Drewes, Langenfeld (DE); Angela Becker, Duesseldorf (DE); Arnd Voerste, Cologne (DE); Ulrich Goergens, Ratingen (DE); Kerstin Ilg, Cologne (DE); Johannes-Rudolf Jansen, Monheim (DE); Daniela Portz, Vettweiss (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/432,501

(22) PCT Filed: Sep. 30, 2013

(86) PCT No.: PCT/EP2013/070371
§ 371 (c)(1),
(2) Date: Mar. 31, 2015

(87) PCT Pub. No.: WO2014/053450
PCT Pub. Date: Apr. 10, 2014

(65) Prior Publication Data
US 2015/0239847 A1    Aug. 27, 2015

(30) Foreign Application Priority Data

Oct. 2, 2012 (EP) .................................... 12186946
Jun. 5, 2013 (EP) .................................... 13170565

(51) Int. Cl.
| | |
|---|---|
| C07D 231/40 | (2006.01) |
| A01N 43/56 | (2006.01) |
| A01N 43/58 | (2006.01) |
| A01N 43/647 | (2006.01) |
| A01N 43/76 | (2006.01) |
| A01N 43/78 | (2006.01) |
| A01N 43/82 | (2006.01) |
| C07D 231/52 | (2006.01) |
| C07D 231/56 | (2006.01) |
| C07D 403/12 | (2006.01) |
| C07D 231/06 | (2006.01) |
| C07D 231/22 | (2006.01) |
| C07D 401/04 | (2006.01) |
| C07D 401/12 | (2006.01) |
| C07D 403/04 | (2006.01) |
| C07D 405/12 | (2006.01) |
| C07D 409/12 | (2006.01) |
| C07D 417/12 | (2006.01) |
| A01N 43/60 | (2006.01) |
| A01N 43/653 | (2006.01) |
| C07D 249/06 | (2006.01) |

(52) U.S. Cl.
CPC .......... *C07D 231/40* (2013.01); *A01N 43/56* (2013.01); *A01N 43/58* (2013.01); *A01N 43/60* (2013.01); *A01N 43/647* (2013.01); *A01N 43/653* (2013.01); *A01N 43/76* (2013.01); *A01N 43/78* (2013.01); *A01N 43/82* (2013.01); *C07D 231/06* (2013.01); *C07D 231/22* (2013.01); *C07D 231/52* (2013.01); *C07D 231/56* (2013.01); *C07D 249/06* (2013.01); *C07D 401/04* (2013.01); *C07D 401/12* (2013.01); *C07D 403/04* (2013.01); *C07D 403/12* (2013.01); *C07D 405/12* (2013.01); *C07D 409/12* (2013.01); *C07D 417/12* (2013.01)

(58) Field of Classification Search
CPC .................................................... C07D 231/40
USPC ........................... 548/371.7, 372.5; 514/407
See application file for complete search history.

(56) References Cited

U.S. PATENT DOCUMENTS

| | | | |
|---|---|---|---|
| 4,435,503 A | 3/1984 | Mihayashi et al. | |
| 4,663,272 A | 5/1987 | Nakamura et al. | |
| 5,518,891 A | 5/1996 | Gibboni et al. | |
| 5,624,941 A | 4/1997 | Barth et al. | |
| 6,124,334 A | 9/2000 | Hutchinson | |
| 8,791,139 B2 | 7/2014 | Fischer et al. | |

(Continued)

FOREIGN PATENT DOCUMENTS

| | | |
|---|---|---|
| DE | 3226163 A1 | 1/1983 |
| DE | 159875 A1 | 4/1983 |

(Continued)

OTHER PUBLICATIONS

Opposition of Costa Rica Patent No. 2015-0182, filed Aug. 12, 2015, and English translation thereof.

(Continued)

*Primary Examiner* — Patricia L Morris
(74) *Attorney, Agent, or Firm* — McBee Moore Woodward & Vanik IP, LLC; Susan McBee; David Woodward

(57) ABSTRACT

The present application relates to the use of heterocyclic compounds for controlling animal pests including arthropods, insects and nematodes, to novel heterocyclic compounds, to processes for their preparation and to intermediates for preparing the heterocyclic compounds.

27 Claims, No Drawings

(56) References Cited

U.S. PATENT DOCUMENTS

| | | |
|---|---|---|
| 8,809,547 B2 | 8/2014 | Bretschneider et al. |
| 2002/0042501 A1 | 4/2002 | Zhang et al. |
| 2004/0006047 A1 | 1/2004 | Schaper et al. |
| 2004/0039037 A1 | 2/2004 | Zhang et al. |
| 2004/0220170 A1 | 11/2004 | Atkinson et al. |
| 2005/0020564 A1 | 1/2005 | Atkinson et al. |
| 2008/0090810 A1 | 4/2008 | Shia et al. |
| 2011/0152332 A1 | 6/2011 | Murata et al. |
| 2013/0261141 A1 | 10/2013 | Bretschneider et al. |
| 2013/0338367 A1 | 12/2013 | Numata et al. |
| 2015/0239847 A1 | 8/2015 | Heilmann et al. |

FOREIGN PATENT DOCUMENTS

| | | |
|---|---|---|
| DE | 4343454 A1 | 6/1995 |
| DE | 102008041216 A1 | 2/2010 |
| EP | 0022578 A1 | 1/1981 |
| EP | 0420803 A2 | 4/1991 |
| EP | 0591103 A1 | 9/1992 |
| EP | 0576357 B1 | 3/1997 |
| EP | 0974337 B1 | 3/2001 |
| JP | S5810738 A | 1/1983 |
| JP | 60218646 A | 11/1985 |
| JP | S60218646 A | 11/1985 |
| JP | S-6142652 A | 3/1986 |
| JP | 52090657 A2 | 4/1987 |
| JP | 7188269 A | 7/1995 |
| JP | 11302177 A | 11/1999 |
| JP | 2003221535 A | 8/2003 |
| JP | 2005504105 A | 2/2005 |
| JP | 200745752 A | 2/2007 |
| JP | 2010202648 A | 9/2010 |
| JP | 2010202648 A2 | 9/2010 |
| JP | 2010202649 A2 | 9/2010 |
| WO | 199803475 A1 | 1/1998 |
| WO | 9828269 A1 | 7/1998 |
| WO | 9857937 A2 | 12/1998 |
| WO | 9932454 A1 | 7/1999 |
| WO | 01062737 A2 | 8/2001 |
| WO | 03074550 A2 | 9/2003 |
| WO | 2004089303 A2 | 10/2004 |
| WO | 2004089306 A2 | 10/2004 |
| WO | 2005092863 A1 | 10/2005 |
| WO | 2006033005 A2 | 3/2006 |
| WO | 2008026965 A1 | 3/2006 |
| WO | 2006056433 A2 | 6/2006 |
| WO | 2006102758 A1 | 10/2006 |
| WO | 2006130403 A1 | 12/2006 |
| WO | 2007002248 A2 | 1/2007 |
| WO | 2007017125 A1 | 2/2007 |
| WO | 2007030567 A2 | 3/2007 |
| WO | 2007037543 A1 | 4/2007 |
| WO | 2007039146 A1 | 4/2007 |
| WO | 2007073297 A1 | 6/2007 |
| WO | 2007093829 A1 | 8/2007 |
| WO | 2008126899 A1 | 10/2008 |
| WO | 2009011850 A2 | 1/2009 |
| WO | 2009077766 A1 | 6/2009 |
| WO | 2009099670 A2 | 8/2009 |
| WO | 2990100438 A2 | 8/2009 |
| WO | 2010005692 A2 | 1/2010 |
| WO | 2010006713 A2 | 1/2010 |
| WO | 2011020883 A9 | 2/2011 |
| WO | 2011051455 A1 | 5/2011 |
| WO | 2011157654 A1 | 12/2011 |
| WO | 2012052412 A1 | 4/2012 |
| WO | 2012061290 A2 | 5/2012 |
| WO | 2012071519 A1 | 5/2012 |
| WO | 2012078593 A2 | 6/2012 |
| WO | 2012108511 A1 | 8/2012 |
| WO | 2013082324 A1 | 6/2013 |
| WO | 2013173218 A1 | 11/2013 |
| WO | 2014053450 A1 | 4/2014 |
| WO | 2014064229 A1 | 5/2014 |
| WO | 2015105129 A1 | 7/2015 |
| WO | 2015144652 A2 | 10/2015 |
| WO | 2015144683 A1 | 10/2015 |
| WO | 2015150252 A1 | 10/2015 |

OTHER PUBLICATIONS

International Search Report from corresponding PCT/EP2013/070371, dated Nov. 18, 2013.

European Search Report from corresponding EP 12 18 6946, dated Mar. 13, 2013.

Research Disclosure, dated May 1980, pp. 165-167.

XP-002692791, 1/1—(c) File Registry, STN GEN Caesar accession No. 1392, Feb. 26, 2013, pp. 1-4.

XP-002692793, 1/1—(c) File Regitry, STN GEN Caesar accession No. 1394, Feb. 26, 2013, pp. 1-6.

XP-002692749, 1/1—(C) File Registry STN GEN Caesar accession No. 1396, Feb. 26, 2013, pp. 1-4.

XP-002692801, 1/1—(C) File Registry STN GEN Caesar accession No. 1393, Feb. 26, 2013, pp. 1-4.

Matysiak et al., "Synthesis and Antimycotic Activity of N-azolyl-2, 4-dihydroxythiobenzamides", Science Direct, Bioorganic & Medicinal Chemistry 11 (2003) pp. 2285-2291, XP-055054430.

XP-55054696, Ambinter—Chemical compounds, Amb10178766, 1 page.

Database Registry [online] Chemical Abstract Service, US; Jul. 29, 2009 (Jul. 29, 2009), Retrieved from STNODatabase accession No. RN 1170047-96-7; N-[1-(2,4-difluorophenyl)-5-methyl-1H-pyrazol-3-yl]-2,4-dimethoxybenzamide. (cited in ISR).

HETEROCYCLIC COMPOUNDS AS PESTICIDES

CROSS REFERENCE TO RELATED APPLICATIONS

This application is a §371 National Stage Application of PCT/EP2013/070371, filed 30 Sep. 2013, which claims priority to EP 12186946.5, filed 2 Oct. 2012 and EP 13170565.9, filed 5 Jun. 2013.

BACKGROUND

Field of the Invention

The present application relates to the use of heterocyclic compounds for controlling animal pests including arthropods, insects and nematodes, to novel heterocyclic compounds, to processes for their preparation and to intermediates for preparing the heterocyclic compounds.

Description of Related Art

The heterocyclic compounds of the formulae (W) and (W2) are known (cf. for the compounds of the formula (W) Registry Numbers 1189645-25-7, 1189474-83-6, 1193202-69-5, 1172407-07-6, 1185158-40-0, 1185036-12-7, 1170986-74-9, 1193179-17-7, 1189458-68-1, 1189956-23-7, 1189915-26-1, 1170047-96-7). A use of these compounds has not been described.

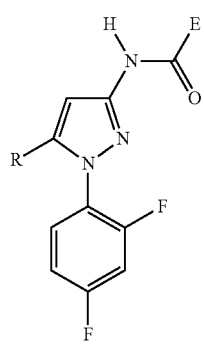

(W)

| No. | R | E |
|---|---|---|
| W-1 | ethyl | 2-(trifluoromethyl)phenyl |
| W-2 | ethyl | 2-bromophenyl |
| W-3 | ethyl | 2-fluorophenyl |
| W-4 | ethyl | 3-methyl-2-thienyl |
| W-5 | ethyl | 2,5-dimethyl-3-furanyl |
| W-6 | H | 2,4-dimethoxyphenyl |
| W-7 | H | 2-(trifluoromethyl)phenyl |
| W-8 | H | 2,4-difluorophenyl |
| W-9 | methyl | 2-bromophenyl |
| W-10 | ethyl | 2,4-difluorophenyl |
| W-11 | H | 2,5-dimethyl-3-furanyl |
| W-12 | methyl | 2,4-dimethoxyphenyl |

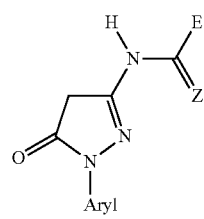

(W2)

| No. | CAS-No. | Reference | Z | E | aryl |
|---|---|---|---|---|---|
| W2-1 | 74202-18-9 | Research Disclosure 1980, 193011, 165.) | O | 2-nitrophenyl | 3,4-dichloro-2,5-dimethoxyphenyl |
| W2-2 | 612092-81-6 | Bioorg. Med. Chem. 2003, 2285. | S | 2,4-dihydroxyphenyl | 2,4,6-trichlorophenyl |
| W2-3 | 111243-44-8 | JP 62-090657 | O | 2-chloro-4-aminophenyl | 2,4,6-trichlorophenyl |
| W2-4 | 101750-33-8 | JP 60-218646 | O | 2-chloro-5-(acryloylamino)phenyl | 2,4,6-trichlorophenyl |
| W2-5 | 87756-39-6 | DE 3226163 | O | 2-chloro-5-aminophenyl | 2,4,6-trichlorophenyl |
| W2-6 | 87756-30-7 | DD 159875 | O | 2-chloro-5-nitrophenyl | 2,4,6-trichlorophenyl |
| W2-7 | 86025-05-0 | DE 3226163 | O | 2-chloro-5-(methacryloylamino)phenyl | 2,4,6-trichlorophenyl |

Derivatives of pyrazole-4-carboxamides are known from JP 2010-202649. The compounds described therein have bactericidal action against plant-damaging bacteria. Intermediates for their preparation are described in JP 2010-202648.

Crop protection compositions, which also include pesticides, have to meet many demands, for example in relation to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection compositions cannot be considered to be complete, and there is a constant need for novel compounds having properties which, compared to the known compounds, are improved at least in respect of individual aspects.

SUMMARY

It was an object of the present invention to provide compounds which widen the spectrum of the pesticides in various aspects.

This object, and further objects which are not stated explicitly but can be discerned or derived from the connections discussed herein, are achieved by the use of novel and known compounds of the formula (I)

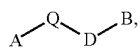
(I)

in which

A represents a radical from the group consisting of

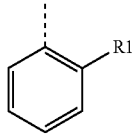
A-1

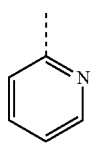
A-2

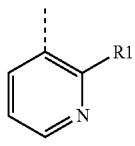
A-3

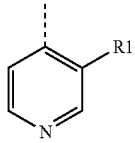
A-4

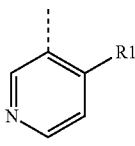
A-5

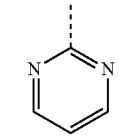
A-6

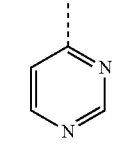
A-7

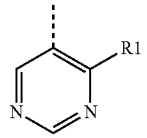
A-8

A-9

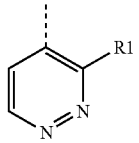
A-10

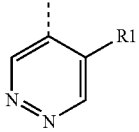
A-11

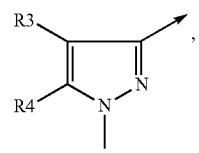
A-12 in which the broken line represents the bond to Q and in which A furthermore carries m substituents R2, Q represents a radical from the group consisting of

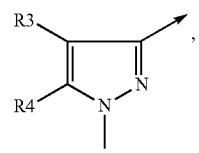
Q-1

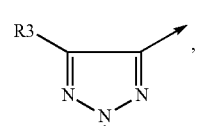
Q-2

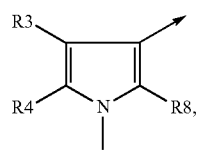
Q-3

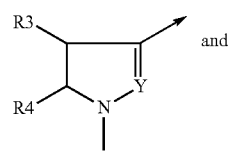
Q-4

-continued
Q-5
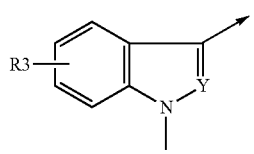
in which the nitrogen is attached to ring A and the arrow in each case represents the bond to D and
D represents the radical of the formula
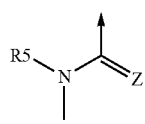
in which the nitrogen is attached to Q and the arrow represents the bond to B,
B represents a radical from the group consisting of
B-1
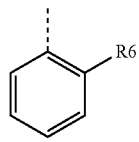
B-2
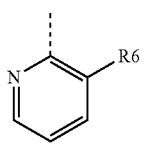
B-3
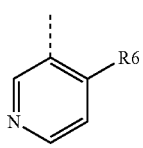
B-4
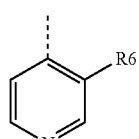
B-5
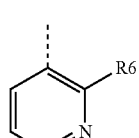
B-6
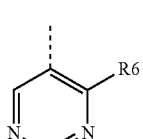
B-7
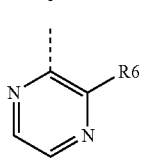
-continued
B-8
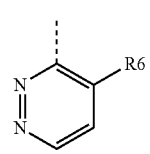
B-9
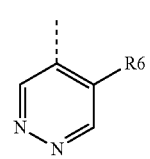
B-10
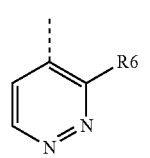
B-11
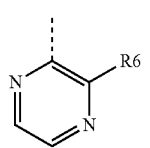
B-12
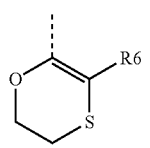
B-13
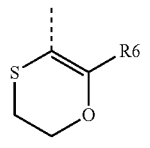
B-14
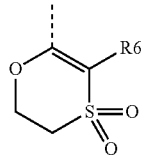
B-15
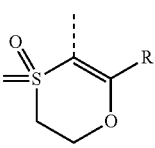
B-16
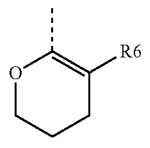
B-17
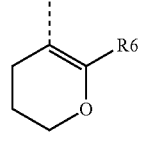

-continued
B-18
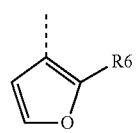
B-19
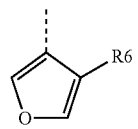
B-20
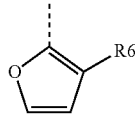
B-21
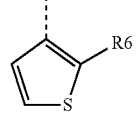
B-22
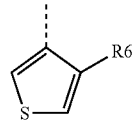
B-23
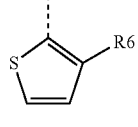
B-24
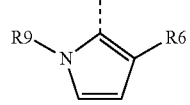
B-25
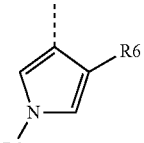
B-26
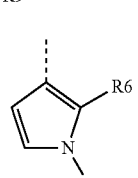
B-27
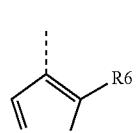
B-28
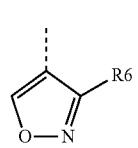
-continued
B-29
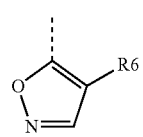
B-30
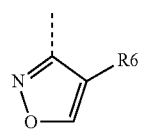
B-31
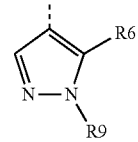
B-32
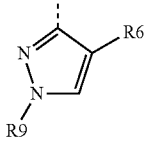
B-33
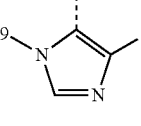
B-34
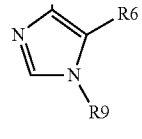
B-35
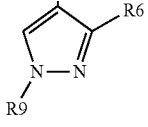
B-36
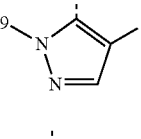
B-37
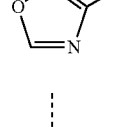

B-39 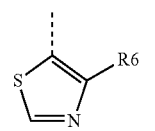

B-40 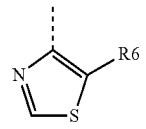

B-41 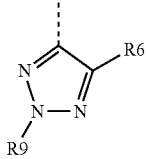

B-42 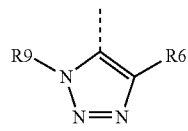

B-43 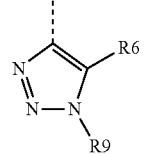

B-44 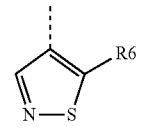

B-45 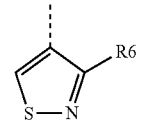

B-46 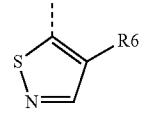

B-47 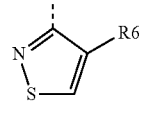

B-48 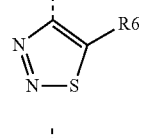

B-49 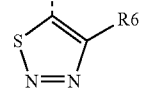

B-50 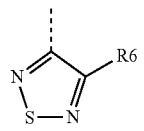

B-51 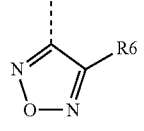

B-52 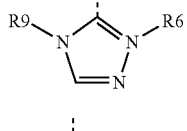

B-53 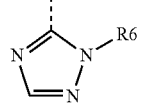

in which the broken line represents the bond to D and in which B furthermore carries n substituents R7, Y represents CR8 or represents nitrogen, Z represents oxygen or sulphur, R1 represents a radical from the group consisting of halogen, cyano, nitro, amino, hydroxy, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, each of which is optionally substituted by one or more identical or different substituents, where the substituents independently of one another are selected from the group consisting of halogen, cyano, nitro, hydroxy, amino, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, aryl, aryloxy, arylthio, heteroaryl, heteroaryloxy and heteroarylthio, R2 represents a radical from the group consisting of halogen, cyano, nitro, amino, hydroxy, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, di-($C_1$-$C_6$- alkyl)-amino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, $C_4$-$C_{12}$-bicycloalkyl, aryl, aryloxy, arylamino, arylthio, heteroaryl, heteroaryloxy, heteroarylamino and heteroarylthio, each of which is optionally substituted by one or more identical or different substituents, where the substituents independently of one another are selected from the group consisting of halogen, cyano, nitro, hydroxy, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, aryl, aryloxy, arylthio, heteroaryl, heteroaryloxy and heteroarylthio, R3 represents a radical from the group consisting of hydrogen, halogen, cyano, nitro, amino, hydroxy, $C_1$-$C_6$-alkyl, $C_1$-$C_6$-alkoxy, $C_1$-$C_6$-haloalkyl and $C_1$-$C_6$-haloalkoxy, R4 represents a radical from the group consisting of hydrogen, halogen, amino, hydroxy, $C_1$-$C_6$-alkyl, $C_1$-$C_6$-alkoxy, $C_1$-$C_6$-haloalkyl and $C_1$-$C_6$-haloalkoxy, R5 represents a radical from the group consisting of hydrogen, $C_1$-$C_6$-alkyl, $C_3$-$C_6$-cycloalkyl, $C_1$-$C_6$-haloalkyl, $C_2$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl or represents C(=O)—B, R6 represents a radical from the group consisting of hydrogen (only in the radicals B-26, B-33, B-36 and B-42), halogen, cyano, nitro, amino, hydroxy, carboxyl, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-haloalkylcarbonylamino, $C_1$-$C_6$-alkylthiocarbonylamino, $C_4$-$C_{12}$-bicycloalkyl, aryl, aryloxy, heteroaryl, heteroaryloxy, each of which is optionally substituted by one or more identical or different substituents, where the substituents independently of one another are selected from the group consisting of halogen, cyano, nitro, hydroxy, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, R7 represents a radical from the group consisting of halogen, nitro, cyano, amino, hydroxy, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, heteroaryl, heteroaryloxy, $C_4$-$C_{12}$-bicycloalkyl, each of which is optionally substituted by one or more identical or different substituents, where the substituents independently of one another are selected from the group consisting of halogen, cyano, nitro, hydroxy, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, R8 represents a radical from the group consisting of hydrogen, halogen, amino, hydroxy, $C_1$-$C_6$-alkyl, $C_1$-$C_6$-alkoxy, $C_1$-$C_6$-haloalkyl and $C_1$-$C_6$-haloalkoxy, R9 represents a radical from the group consisting of hydrogen, $C_1$-$C_6$-alkyl, $C_3$-$C_6$-cycloalkyl, haloalkyl, $C_3$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl, m represents a number from the group consisting of 0, 1, 2 and 3, where for m>1 the radicals R2 may be identical or different and n represents a number from the group consisting of 0, 1, 2 and 3, where for n>1 the radicals R7 may be identical or different, for controlling animal pests.

DETAILED DESCRIPTION OF A PREFERRED EMBODIMENT

It has been found that the known and the novel compounds of the formula (I) have pronounced biological properties and are suitable especially for controlling animal pests, in particular insects, arachnids and nematodes, encountered in agriculture, in forests, in the protection of stored products and materials and in the hygiene sector.

The compounds of the formula (I) may, where appropriate, depending on the nature of the substituents, be in the form of geometric and/or optically active isomers or corresponding isomer mixtures of varying composition. The invention relates both to the use of the pure isomers and to that of the isomer mixtures.

Preferred substituents or ranges for the radicals shown in the compounds of the formula (I) are illustrated below.

A represents a radical from the group consisting of

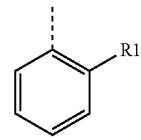

A-1

A-2 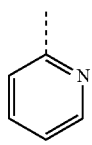

A-3 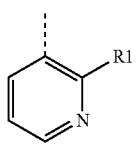

A-4 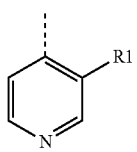

A-5 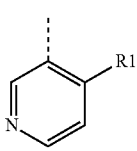

A-6 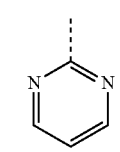

A-7 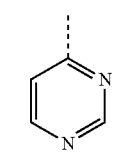

A-8 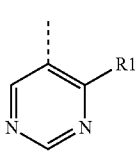

A-9 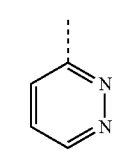

A-10 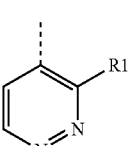

A-11 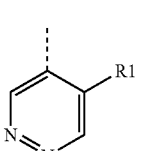

A-12 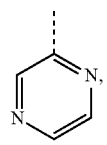

in which the broken line represents the bond to Q and where A furthermore carries m substituents R2, Q represents a radical from the group consisting of Q-1 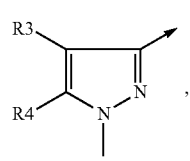

Q-2 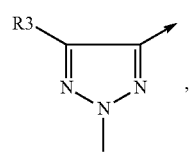

Q-3 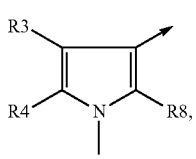

Q-4 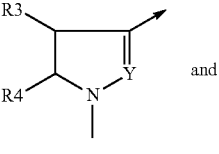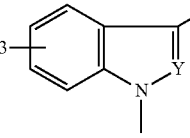 and

Q-5 in which the nitrogen is attached to ring A and the arrow in each case represents the bond to D, D represents the radical of the formula

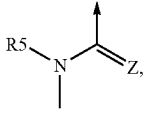

in which the nitrogen is attached to Q and the arrow represents the bond to B.

B represents a radical from the group consisting of
B-1
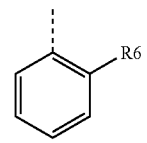
B-2
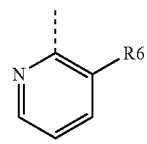
B-3
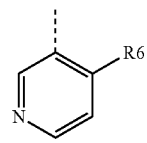
B-4
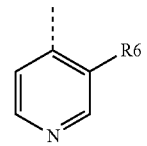
B-5
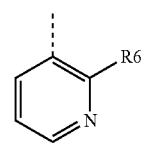
B-6
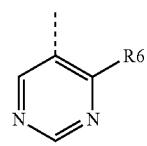
B-7
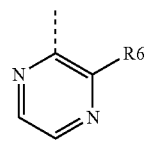
B-8
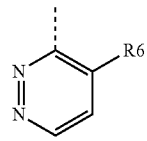
B-9
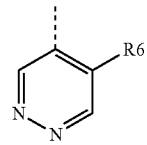
B-10
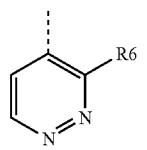
B-11
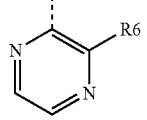
B-12
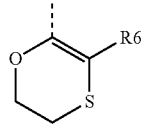
B-13
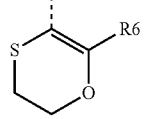
B-14
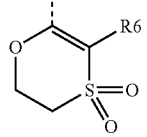
B-15
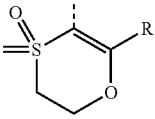
B-16
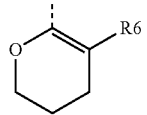
B-17
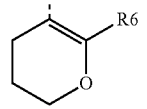
B-18
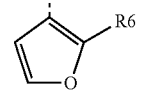
B-19
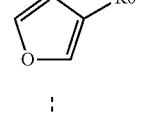
B-20
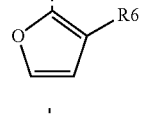
B-21

-continued
B-22 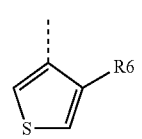
B-23 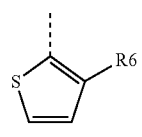
B-24 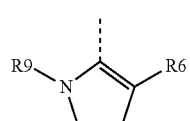
B-25 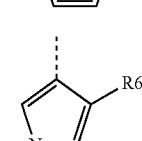
B-26 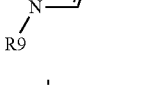
B-27 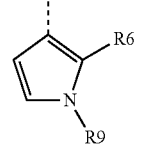
B-28 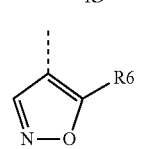
B-29 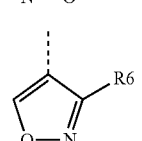
B-30 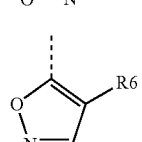
B-31 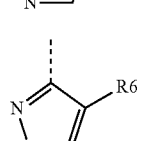
B-32 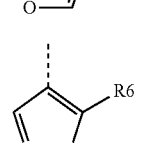
-continued
B-33 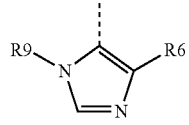
B-34 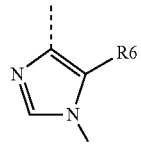
B-35 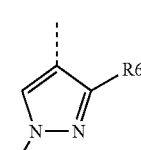
B-36 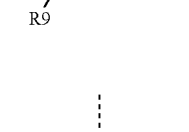
B-37 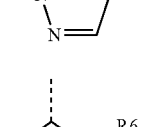
B-38 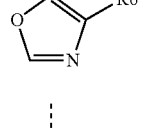
B-39 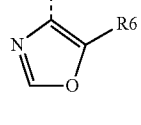
B-40 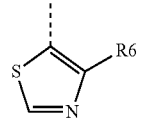
B-41 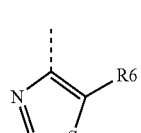
B-42 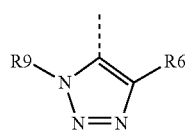

-continued

B-43 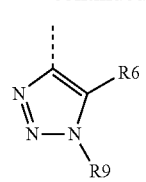

B-44 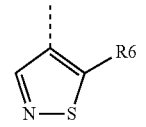

B-45 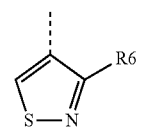

B-46 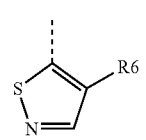

B-47 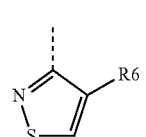

B-48 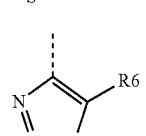

B-49 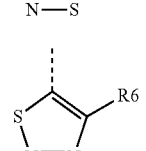

B-50 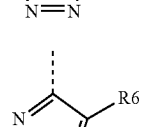

B-51 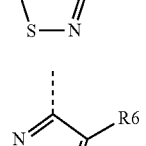

B-52 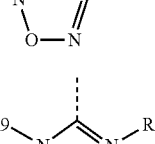

B-53 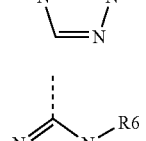

in which the broken line represents the bond to D and in which B furthermore carries n substituents R7.

Y represents CR8 or represents nitrogen.

Z represents oxygen or sulphur.

R1 represents a radical from the group consisting of halogen, cyano, nitro, amino, hydroxy, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, heteroaryl and heteroaryloxy.

R2 represents a radical from the group consisting of halogen, cyano, nitro, amino, hydroxy, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, di-($C_1$-$C_6$-alkyl)-amino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, heteroaryl and heteroaryloxy.

R3 represents a radical from the group consisting of hydrogen, halogen, cyano, nitro, amino, $C_1$-$C_6$-alkyl and $C_1$-$C_6$-haloalkyl.

R4 represents a radical from the group consisting of hydrogen, halogen, amino, hydroxy, $C_1$-$C_6$-alkyl, $C_1$-$C_6$-alkoxy, $C_1$-$C_6$-haloalkyl and $C_1$-$C_6$-haloalkoxy.

R5 represents a radical from the group consisting of hydrogen, $C_1$-$C_6$-alkyl, $C_1$-$C_6$-haloalkyl, cyano-$C_1$-$C_6$-alkyl, $C_2$-$C_6$-alkenyl, $C_3$-$C_6$-alkynyl, $C_3$-$C_6$-cycloalkyl, $C_3$-$C_6$-cycloalkyl-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl, $C_1$-$C_6$-haloalkylsulphonyl and C(=O)—B.

R6 represents a radical from the group consisting of hydrogen (only in the radicals B-26, B-33, B-36 and B-42), halogen, cyano, nitro, amino, hydroxy, carboxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$- alkenylamino, C₃-C₆-alkynylamino, C₃-C₆-cycloalkylamino, C₁-C₆-alkylthio, C₁-C₆-haloalkylthio, C₃-C₆-alkenylthio, C₃-C₆-alkynylthio, C₃-C₆-cycloalkylthio, C₁-C₆-alkylsulphinyl, C₁-C₆-alkylsulphonyl, C₁-C₆-alkylcarbonyl, C₁-C₆-alkoxyimino-C₁-C₆-alkyl, C₁-C₆-alkoxycarbonyl, aminocarbonyl, C₁-C₆-alkylaminocarbonyl, di-(C₁-C₆-alkyl)-aminocarbonyl, aminothiocarbonyl, C₁-C₆-alkylamino sulphonyl, C₁-C₆-alkylsulphonylamino, C₁-C₆-alkylcarbonylamino, C₁-C₄-haloalkylcarbonylamino, C₁-C₆-alkylthiocarbonylamino, aryl, aryloxy, heteroaryl and heteroaryloxy.

R7 represents a radical from the group consisting of halogen, cyano, nitro, amino, hydroxy, C₁-C₆-alkyl, C₁-C₆-haloalkyl, cyano-C₁-C₆-alkyl, C₂-C₆-alkenyl, C₃-C₆-alkynyl, C₃-C₆-cycloalkyl, C₃-C₆-cycloalkyl-C₁-C₆-alkyl, C₁-C₆-alkoxy, C₁-C₆-haloalkoxy, C₃-C₆-alkenyloxy, C₃-C₆-alkynyloxy, C₃-C₆-cycloalkyloxy, C₁-C₆-alkylcarbonyloxy, C₂-C₆-alkenylcarbonyloxy, C₂-C₆-alkynylcarbonyloxy, C₃-C₆-cycloalkylcarbonyloxy, C₁-C₆-alkoxycarbonyloxy, C₁-C₆-alkylsulphonyloxy, C₁-C₆-alkylamino, C₃-C₆-alkenylamino, C₃-C₆-alkynylamino, C₃-C₆-cycloalkylamino, C₁-C₆-alkylthio, C₁-C₆-haloalkylthio, C₃-C₆-alkenylthio, C₃-C₆-alkynylthio, C₃-C₆-cycloalkylthio, C₁-C₆-alkylsulphinyl, C₁-C₆-alkylsulphonyl, C₁-C₆-alkylcarbonyl, C₁-C₆-alkoxyimino-C₁-C₆-alkyl, C₁-C₆-alkoxycarbonyl, aminocarbonyl, C₁-C₆-alkylaminocarbonyl, di-(C₁-C₆-alkyl)-aminocarbonyl, aminothiocarbonyl, C₁-C₆-alkylaminosulphonyl, C₁-C₆-alkylsulphonylamino, C₁-C₆-alkylcarbonylamino, C₁-C₆-alkylthiocarbonylamino, aryl, aryloxy, heteroaryl and heteroaryloxy.

R8 represents a radical from the group consisting of hydrogen, halogen, amino, hydroxy, C₁-C₆-alkyl, C₁-C₆-alkoxy, C₁-C₆-haloalkyl and C₁-C₆-haloalkoxy.

R9 represents a radical from the group consisting of hydrogen, C₁-C₆-alkyl, C₃-C₆-cycloalkyl, C₁-C₆-haloalkyl, C₃-C₆-alkenyl, C₃-C₆-alkynyl, C₃-C₆-cycloalkyl-C₁-C₆-alkyl, cyano-C₁-C₆-alkyl, C₁-C₆-alkylcarbonyl, C₂-C₆-alkenylcarbonyl, C₁-C₆-haloalkylcarbonyl, C₂-C₆-haloalkenylcarbonyl, C₁-C₆-alkoxy-C₁-C₆-alkyl, C₁-C₆-alkoxycarbonyl, C₁-C₆-alkylsulphonyl and C₁-C₆-haloalkylsulphonyl.

m represents a number from the group consisting of 0, 1, 2 and 3, where for m>1 the radicals R2 may be identical or different.

n represents a number from the group consisting of 0, 1, 2 and 3, where for n>1 the radicals R7 may be identical or different.

Particularly preferred substituents or ranges for the radicals shown in the compounds of the formula (I) are illustrated below.

A represents a radical from the group consisting of

A-1

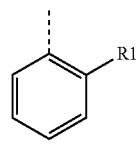

A-2

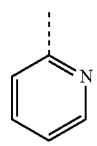

-continued

A-3

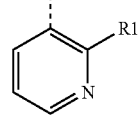

A-4

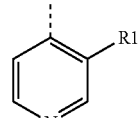

A-5

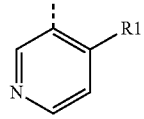

A-6

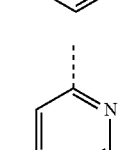

A-7

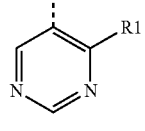

A-8

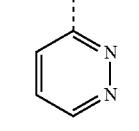

A-9

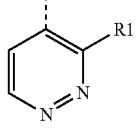

A-10

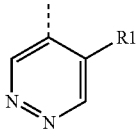

A-11

A-12 in which the broken line represents the bond to Q and where A furthermore carries m substituents R2.

Q represents a radical from the group consisting of

Q-1: pyrazole with R3, R4, N-methyl

Q-2: triazole with R3, N-methyl

Q-3: pyrrole with R3, R4, R8, N-methyl

Q-4: pyrazoline with R3, R4, Y, N-methyl

Q-5: indazole with R3, Y, N-methyl in which the nitrogen is attached to ring A and the arrow in each case represents the bond to D.

D represents the radical of the formula

R5–N(–)–C(=Z)–, in which the nitrogen is attached to Q and the arrow represents the bond to B.

B represents a radical from the group consisting of

B-1: phenyl with R6
B-2: pyridin-3-yl with R6
B-3: pyridin-4-yl with R6
B-4: pyridin-3-yl (alt) with R6
B-5: pyridin-2-yl with R6
B-6: pyrimidin-4-yl with R6
B-7: pyrimidine with R6
B-8: pyridazine with R6
B-9: pyridazine with R6
B-10: pyridazine with R6
B-11: pyrazine with R6
B-12: oxathiine with R6

-continued
B-13 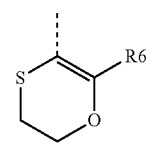
B-14 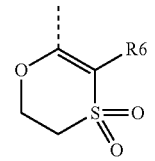
B-15 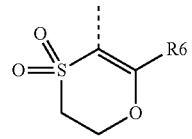
B-16 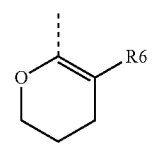
B-17 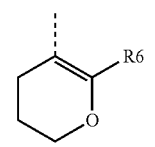
B-18 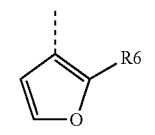
B-19 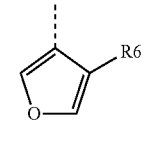
B-20 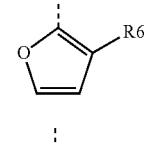
B-21 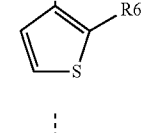
B-22 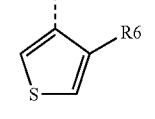
B-23 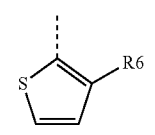
-continued
B-24 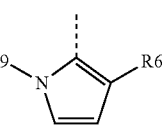
B-25 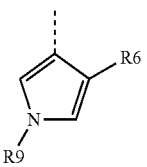
B-26 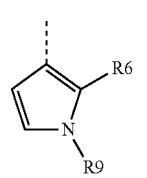
B-27 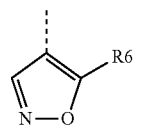
B-28 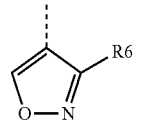
B-29 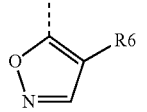
B-30 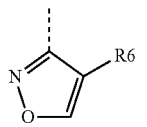
B-31 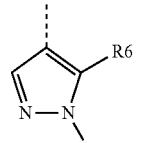
B-32 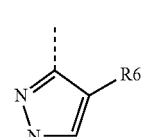
B-33 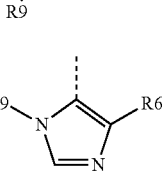

-continued

B-34 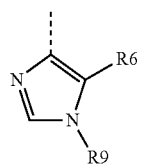

B-35 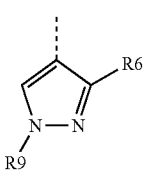

B-36 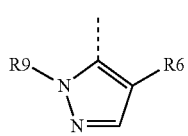

B-37 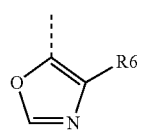

B-38 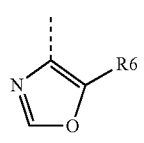

B-39 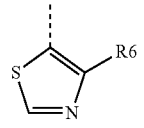

B-40 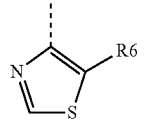

B-41 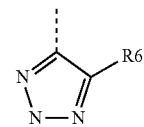

B-42 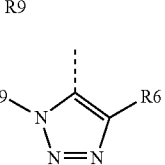

B-43 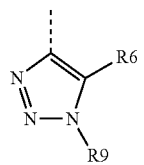

-continued

B-44 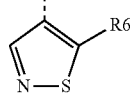

B-45 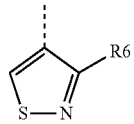

B-46 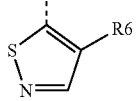

B-47 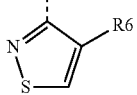

B-48 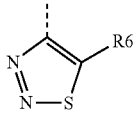

B-49 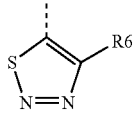

B-50 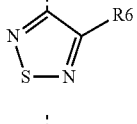

B-51 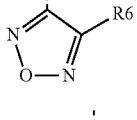

B-52 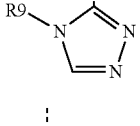

B-53 in which the broken line represents the bond to D and in which B furthermore carries n substituents R7.

Y represents CR8 or represents nitrogen.

Z represents oxygen or sulphur.

R1 represents a radical from the group consisting of halogen, cyano, nitro, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, aryloxy, heteroaryl and heteroaryloxy.

R2 represents a radical from the group consisting of halogen, cyano, nitro, amino, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkylcarbonyl, di-($C_1$-$C_6$-alkyl)-amino, $C_1$-$C_6$-alkoxyimino-$C_1$-$C_6$-alkyl, aryl, aryloxy, heteroaryl and heteroaryloxy.

R3 represents a radical from the group consisting of hydrogen, halogen, cyano, nitro, amino, $C_1$-$C_6$-alkyl and $C_1$-$C_6$-haloalkyl.

R4 represents a radical from the group consisting of hydrogen, halogen, amino, hydroxy, $C_1$-$C_6$-alkyl, $C_1$-$C_6$-alkoxy, $C_1$-$C_6$-haloalkyl and $C_1$-$C_6$-haloalkoxy.

R5 represents a radical from the group consisting of hydrogen, $C_1$-$C_6$-alkyl, $C_1$-$C_6$-haloalkyl, cyano-$C_1$-$C_6$-alkyl, $C_2$-$C_6$-alkenyl, $C_3$-$C_6$-alkynyl, $C_3$-$C_6$-cycloalkyl, $C_3$-$C_6$-cycloalkyl-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl, $C_1$-$C_6$-haloalkylsulphonyl and C(=O)—B.

R6 represents a radical from the group consisting of hydrogen (only in the radicals B-26, B-33, B-36 and B-42), halogen, cyano, nitro, hydroxy, carboxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylsulphinyl, $C_1$-$C_6$-alkylthio, $C_1$-$C_6$-haloalkylthio, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkylcarbonylamino, $C_1$-$C_6$-haloalkylcarbonylamino, aryl, aryloxy, heteroaryl and heteroaryloxy.

R7 represents a radical from the group consisting of halogen, cyano, nitro, hydroxy, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, aryloxy, heteroaryl and heteroaryloxy.

R8 represents a radical from the group consisting of hydrogen, $C_1$-$C_6$-alkyl, $C_1$-$C_6$-alkoxy, $C_1$-$C_6$-haloalkyl and $C_1$-$C_6$-haloalkoxy.

R9 represents a radical from the group consisting of hydrogen, $C_1$-$C_6$-alkyl, $C_3$-$C_6$-cycloalkyl and $C_1$-$C_6$-haloalkyl.

m represents a number from the group consisting of 0, 1, 2 and 3, where for m>1 the radicals R2 may be identical or different.

n represents a number from the group consisting of 0, 1, 2 and 3, where for n>1 the radicals R7 may be identical or different.

Very particularly preferred substituents or ranges of the radicals shown in the compounds of the formula (I) are elucidated below.

A represents a radical from the group consisting of

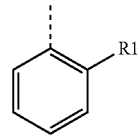
A-1

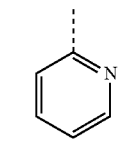
A-2

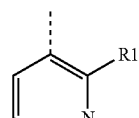
A-3

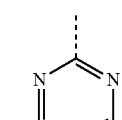
A-6

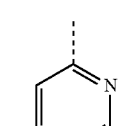
A-7

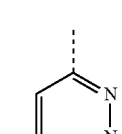
A-9

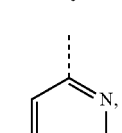
A-12 in which the broken line represents the bond to Q and where A furthermore carries m substituents R2.

Q represents a radical from the group consisting of

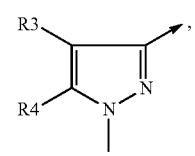
Q-1

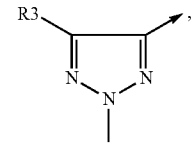
Q-2

Q-3
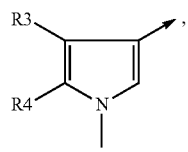
Q-4
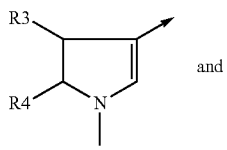
and
Q-5
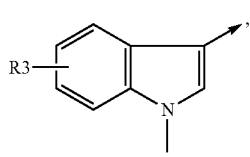
in which the nitrogen is attached to ring A and the arrow in each case represents the bond to D.
D represents the radical of the formula
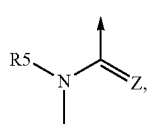
in which the nitrogen is attached to Q and the arrow represents the bond to B.
B represents a radical from the group consisting of
B-1
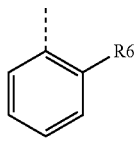
B-2
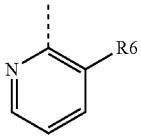
B-3
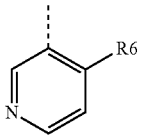
B-4
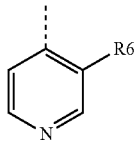
B-5
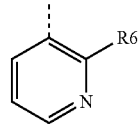
B-6
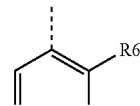
B-10
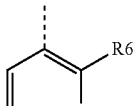
B-11
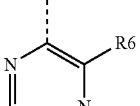
B-13
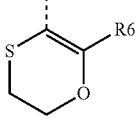
B-18
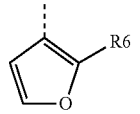
B-21
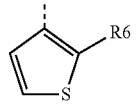
B-23
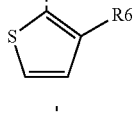
B-25
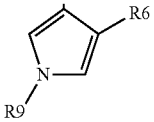
B-27
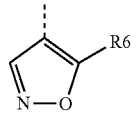
B-31
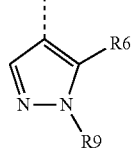

-continued

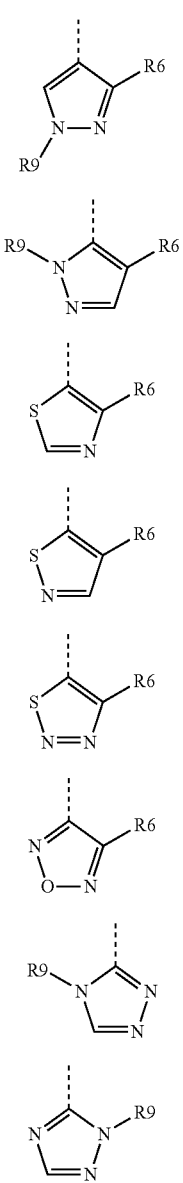

in which the broken line represents the bond to D and in which B furthermore carries n substituents R7.

Z represents oxygen or sulphur.

R1 represents a radical from the group consisting of halogen, cyano, nitro, $C_1$-$C_4$-alkyl, $C_1$-$C_4$-haloalkyl, $C_1$-$C_4$-alkoxy and $C_1$-$C_4$-alkylsulphonyl.

R2 represents a radical from the group consisting of halogen, $C_1$-$C_4$-alkyl and $C_1$-$C_4$-alkoxy.

R3 represents a radical from the group consisting of hydrogen and halogen.

R4 represents a radical from the group consisting of hydrogen and $C_1$-$C_4$-alkyl.

R5 represents a radical from the group consisting of hydrogen, $C_1$-$C_4$-alkyl, $C_3$-$C_4$-alkenyl, $C_3$-$C_4$-alkynyl, $C_3$-$C_6$-cycloalkyl-$C_1$-$C_4$-alkyl, $C_1$-$C_4$-alkylcarbonyl, cyano-$C_1$-$C_4$-alkyl and C(=O)—B.

R6 represents a radical from the group consisting of halogen, nitro, hydroxy, $C_1$-$C_4$-alkyl, $C_1$-$C_4$-alkoxy, $C_1$-$C_4$-alkylthio, $C_1$-$C_4$-alkylsulphonyl, $C_1$-$C_4$-haloalkyl, $C_1$-$C_4$-haloalkoxy, $C_1$-$C_4$-haloalkylthio and heteroaryl.

R7 represents a radical from the group consisting of halogen, $C_1$-$C_4$-alkyl and $C_1$-$C_4$-haloalkyl.

R9 represents a radical from the group consisting of $C_1$-$C_4$-alkyl.

m represents a number from the group consisting of 0, 1, 2 and 3, where for m>1 the radicals R2 may be identical or different.

n represents a number from the group consisting of 0 and 1.

A further group of very particularly preferred substituents or ranges of the radicals shown in the compounds of the formula (I) are illustrated below.

A represents a radical from the group consisting of

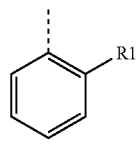   A-1

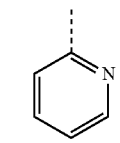   A-2

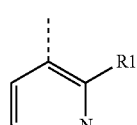   A-3

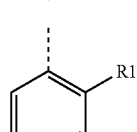   A-4

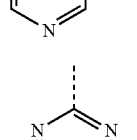   A-6

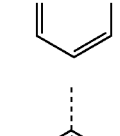   A-7

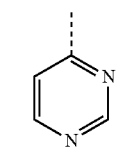   A-9

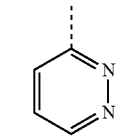   A-12 in which the broken line represents the bond to Q and where A furthermore carries m substituents R2, Q represents a radical from the group consisting of Q-1: pyrazole with R3 at 4-position, R4 at 5-position, N-methyl, arrow at 3-position Q-2: 1,2,3-triazole with R3, N-methyl, arrow Q-3: pyrrole with R3, R4, R8, N-methyl, arrow Q-4: pyrazoline with R3, R4, N-methyl, arrow Q-5: indazole with R3, N-methyl, arrow in which the nitrogen is attached to ring A and the arrow in each case represents the bond to D.

D represents the radical of the formula $$R5-N(CH_3)-C(=Z)-$$

in which the nitrogen is attached to Q and the arrow represents the bond to B.

B represents a radical from the group consisting of

B-1: phenyl with R6
B-2: pyridin-2-yl with R6 at 3-position
B-3: pyridin-3-yl with R6 at 4-position
B-4: pyridin-4-yl with R6 at 3-position
B-5: pyridin-3-yl with R6 at 2-position
B-6: pyrimidin-4-yl with R6
B-7: pyrimidin-5-yl with R6
B-10: pyridazine with R6
B-11: pyrazine with R6
B-13: 1,4-oxathiine with R6
B-15: 1,4-oxathiine-S,S-dioxide with R6
B-17: 3,4-dihydro-2H-pyran with R6

-continued
B-18 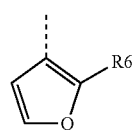
B-19 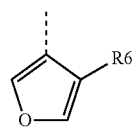
B-20 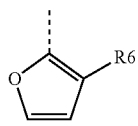
B-21 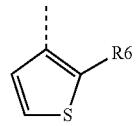
B-23 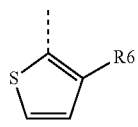
B-24 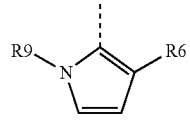
B-25 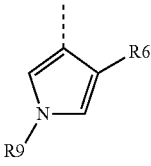
B-27 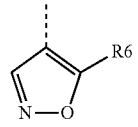
B-28 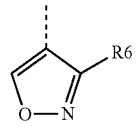
B-29 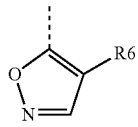
B-30 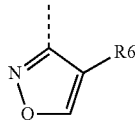
-continued
B-31 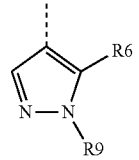
B-32 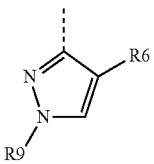
B-33 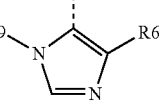
B-34 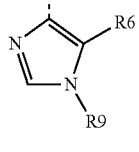
B-35 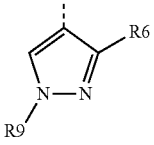
B-36 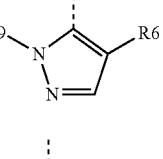
B-39 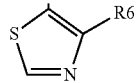
B-46 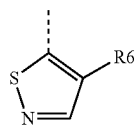
B-48 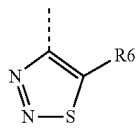
B-49 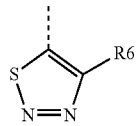

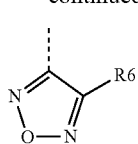

B-51

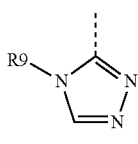

B-52

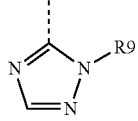

B-53 in which the broken line represents the bond to D and in which B furthermore carries n substituents R7.

Z represents oxygen or sulphur.

R1 represents a radical from the group consisting of halogen, cyano, nitro, $C_1$-$C_4$-alkyl, $C_1$-$C_4$-haloalkyl, $C_1$-$C_4$-alkoxy and $C_1$-$C_4$-alkylsulphonyl.

R2 represents a radical from the group consisting of halogen, cyano, nitro, amino, $C_1$-$C_4$-alkyl, $C_1$-$C_4$-haloalkyl, $C_3$-$C_6$-cycloalkyl, $C_1$-$C_4$-alkoxy, di-($C_1$-$C_6$-alkyl)-amino, acetyl, aryl.

R3 represents a radical from the group consisting of hydrogen, halogen, cyano, nitro, $C_1$-$C_4$-alkyl.

R4 represents a radical from the group consisting of hydrogen, amino, $C_1$-$C_4$-alkyl.

R5 represents a radical from the group consisting of hydrogen, $C_1$-$C_4$-alkyl, $C_3$-$C_4$-alkenyl, $C_3$-$C_4$-alkynyl, $C_3$-$C_6$-cycloalkyl-$C_1$-$C_4$-alkyl, $C_1$-$C_4$-alkylcarbonyl, cyano-$C_1$-$C_4$-alkyl and C(=O)—B.

R6 represents a radical from the group consisting of hydrogen (only in the radicals B-33 and B-36), halogen, cyano, nitro, hydroxy, carboxyl, $C_1$-$C_4$-alkyl, $C_1$-$C_4$-alkoxy, $C_1$-$C_4$-alkylthio, $C_1$-$C_4$-alkylsulphonyl, $C_1$-$C_4$-haloalkyl, $C_3$-$C_6$-cycloalkyl, $C_1$-$C_4$-haloalkoxy, $C_1$-$C_4$-haloalkylthio, acetyl, $C_1$-$C_4$-alkylcarbonylamino, $C_1$-$C_4$-haloalkylcarbonylamino and heteroaryl.

R7 represents a radical from the group consisting of halogen, cyano, nitro, hydroxy, $C_1$-$C_4$ alkyl, $C_1$-$C_4$-haloalkyl and $C_1$-$C_4$-alkoxy.

R9 represents a radical from the group consisting of C1-C4-alkyl and C1-C4-haloalkyl.

m represents a number from the group consisting of 0, 1, 2 and 3, where for m>1 the radicals R2 may be identical or different.

n represents a number from the group consisting of 0, 1, 2 and 3, where for n>1 the radicals R7 may be identical or different.

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (having the same meaning as heteroaryl, also as part of a relatively large unit such as, for example, heteroaryloxy) is selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl and pyrazinyl.

In the particularly preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, het(ero)aryl (also as part of a relatively large unit such as, for example, heteroaryloxy) is selected from the group consisting of furyl, thienyl, pyrrolyl, pyrazolyl, imidazolyl, oxadiazolyl, 1,2,3-triazolyl, 1,2,4-triazolyl, oxazolyl, isoxazolyl and thiazolyl.

In the very particularly preferred definitions, unless stated otherwise, halogen is selected from the group consisting of fluorine, chlorine, bromine and iodine, preferably in turn from the group consisting of fluorine, chlorine and bromine, and het(ero)aryl (also as part of a relatively large unit such as, for example, heteroaryloxy) represents 1,2,4-triazolyl.

Halogen-substituted radicals, for example haloalkyl, are mono- or polyhalogenated, up to the maximum number of possible substituents. In the case of polyhalogenation, the halogen atoms may be identical or different. Halogen denotes fluorine, chlorine, bromine and iodine, in particular fluorine, chlorine and bromine.

Saturated or unsaturated hydrocarbyl radicals, such as alkyl or alkenyl, may in each case be straight-chain or branched as far as possible, including in combination with heteroatoms, as, for example, in alkoxy.

Optionally substituted radicals may be mono- or polysubstituted, where the substituents in the case of polysubstitution may be the same or different.

The radical definitions or elucidations given above in general terms or within areas of preference apply to the end products and correspondingly to the starting materials and intermediates. These radical definitions can be combined with one another as desired, i.e. including combinations between the respective preferred ranges.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the meanings listed above as being very particularly preferred.

The present invention also provides novel compounds of the formula (I) in which A, Q, D and B have the meanings mentioned above, except for the compounds W and W2 described above, in particular W-1 to W-12, W2-1 to W2-3, W2-5 and W2-6. The general or preferred radical definitions or elucidations listed above also apply to the novel compounds of the formula (I). If compounds to be used in accordance with the invention are mentioned in the present application, this includes, unless indicated otherwise, in each case both the compounds of the formula (I) and the novel compounds of the formula (I).

In the groups of compounds below, the individual radicals R and Z have the meanings given above.

In a particular group of compounds of the formula (I) to be used in accordance with the invention, Q represents Q-1

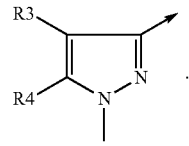

In a further particular group of compounds of the formula (I) to be used in accordance with the invention, Q represents Q-2

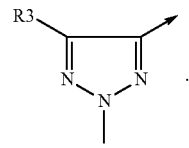

In a further particular group of compounds of the formula (I) to be used in accordance with the invention, Q represents Q-3

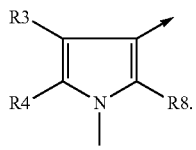

In a further particular group of compounds of the formula (I) to be used in accordance with the invention, Q represents Q-4

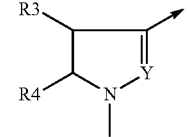

In a further particular group of compounds of the formula (I) to be used in accordance with the invention, Q represents Q-5

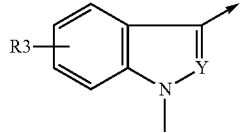

In a further particular group of compounds of the formula (I) to be used in accordance with the invention, A represents

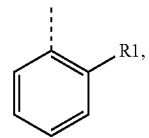

where this radical carries m substituents R2.

In a further particular group of compounds of the formula (I) to be used in accordance with the invention, A represents

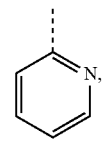

where this radical carries m substituents R2.

In a further particular group of compounds of the formula (I) to be used in accordance with the invention, A represents

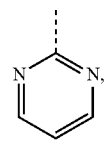

where this radical carries m substituents R2.

In the particular groups of compounds of the formula (I) below, all of which represent preferred embodiments, the radicals A and B may carry further substituents R2 and R7, respectively, as specified above.

A particular group of compounds of the formula (I) are compounds of the formula (A-1)-(Q-1)-D-(B-1)

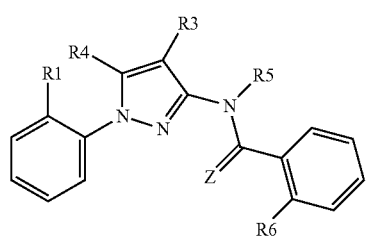

A further particular group of compounds of the formula (I) are compounds of the formula (A-2)-(Q-1)-D-(B-1)

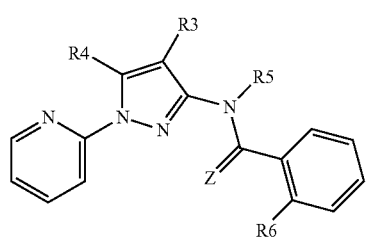

A further particular group of compounds of the formula (I) are compounds of the formula (A-1)-(Q-1)-D-(B-2)

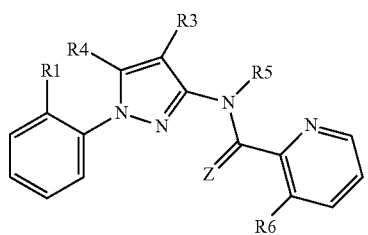

A further particular group of compounds of the formula (I) are compounds of the formula (A-1)-(Q-1)-D-(B-39)

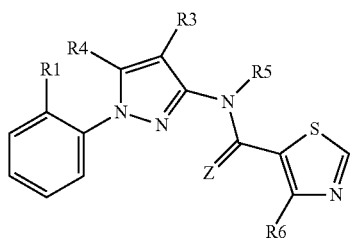

A further particular group of compounds of the formula (I) are compounds of the formula (A-1)-(Q-1)-D-(B-23)

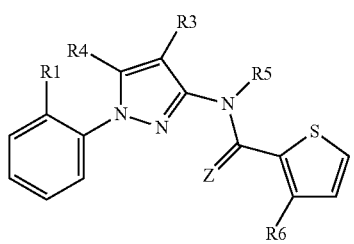

A further particular group of compounds of the formula (I) are compounds of the formula (A-1)-(Q-1)-D-(B-21)

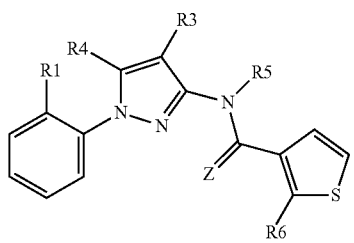

A further particular group of compounds of the formula (I) are compounds of the formula (A-1)-(Q-1)-D-(B-18)

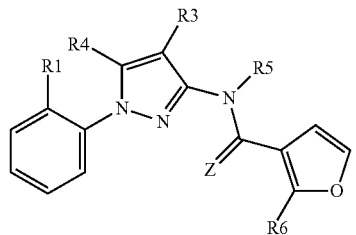

A further particular group of compounds of the formula (I) are compounds of the formula (A-1)-(Q-1)-D-(B-3)

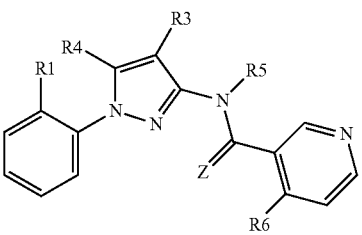

A further particular group of compounds of the formula (I) are compounds of the formula (A-1)-(Q-1)-D-(B-11)

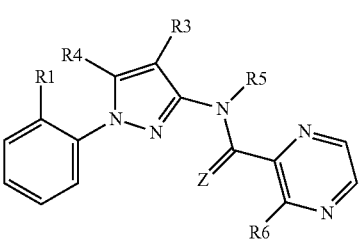

A further particular group of compounds of the formula (I) are compounds of the formula (A-1)-(Q-1)-D-(B-5)

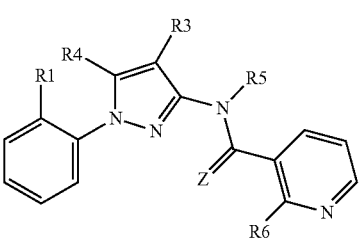

A further particular group of compounds of the formula (I) are compounds of the formula (A-6)-(Q-1)-D-(B-1)

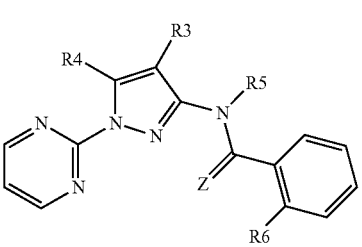

A further particular group of compounds of the formula (I) are compounds of the formula (A-2)-(Q-1)-D-(B-3)

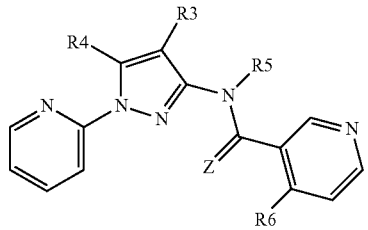

A further particular group of compounds of the formula (I) are compounds of the formula (A-1)-(Q-4)-D-(B-1)

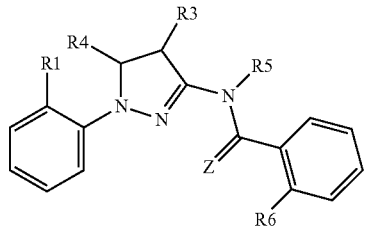

A further particular group of compounds of the formula (I) are compounds of the formula (A-1)-(Q-2)-D-(B-1)

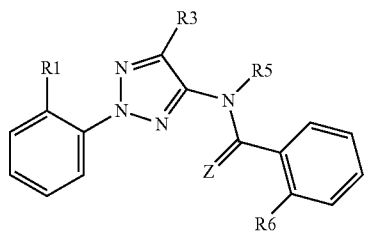

A further particular group of compounds of the formula (I) are compounds of the formula (A-1)-(Q-2)-D-(B-5)

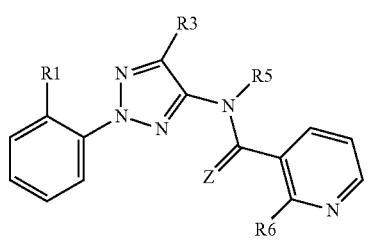

A further particular group of compounds of the formula (I) are compounds of the formula (A-2)-(Q-5)-D-(B-1)

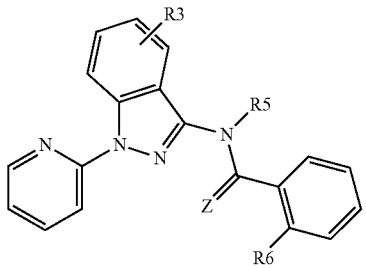

In the same manner as for the particular groups of compounds above, the respective structural formulae may be constructed in a simple manner for the groups of compounds below.

A further particular group of compounds of the formula (I) are compounds of the formula (A-3)-(Q-1)-D-(B-1).
A further particular group of compounds of the formula (I) are compounds of the formula (A-1)-(Q-1)-D-(B-36).
A further particular group of compounds of the formula (I) are compounds of the formula (A-1)-(Q-1)-D-(B-46).
A further particular group of compounds of the formula (I) are compounds of the formula (A-1)-(Q-1)-D-(B-1).
A further particular group of compounds of the formula (I) are compounds of the formula (A-1)-(Q-1)-D-(B-27).
A further particular group of compounds of the formula (I) are compounds of the formula (A-1)-(Q-1)-D-(B-51).
A further particular group of compounds of the formula (I) are compounds of the formula (A-1)-(Q-1)-D-(B-4).
A further particular group of compounds of the formula (I) are compounds of the formula (A-1)-(Q-1)-D-(B-13).
A further particular group of compounds of the formula (I) are compounds of the formula (A-1)-(Q-1)-D-(B-31).
A further particular group of compounds of the formula (I) are compounds of the formula (A-1)-(Q-1)-D-(B-35).
A further particular group of compounds of the formula (I) are compounds of the formula (A-1)-(Q-1)-D-(B-27).
A further particular group of compounds of the formula (I) are compounds of the formula (A-1)-(Q-1)-D-(B-10).
A further particular group of compounds of the formula (I) are compounds of the formula (A-1)-(Q-1)-D-(B-51).
A further particular group of compounds of the formula (I) are compounds of the formula (A-12)-(Q-1)-D-(B-1).
A further particular group of compounds of the formula (I) are compounds of the formula (A-12)-(Q-1)-D-(B-2).
A further particular group of compounds of the formula (I) are compounds of the formula (A-2)-(Q-1)-D-(B-49).
A further particular group of compounds of the formula (I) are compounds of the formula (A-2)-(Q-1)-D-(B-46).
A further particular group of compounds of the formula (I) are compounds of the formula (A-2)-(Q-1)-D-(B-13).
A further particular group of compounds of the formula (I) are compounds of the formula (A-2)-(Q-1)-D-(B-4).
A further particular group of compounds of the formula (I) are compounds of the formula (A-2)-(Q-1)-D-(B-6).
A further particular group of compounds of the formula (I) are compounds of the formula (A-2)-(Q-1)-D-(B-25).
A further particular group of compounds of the formula (I) are compounds of the formula (A-2)-(Q-1)-D-(B-31).
A further particular group of compounds of the formula (I) are compounds of the formula (A-2)-(Q-1)-D-(B-35).
A further particular group of compounds of the formula (I) are compounds of the formula (A-2)-(Q-1)-D-(B-27).
A further particular group of compounds of the formula (I) are compounds of the formula (A-7)-(Q-1)-D-(B-1).

A further particular group of compounds of the formula (I) are compounds of the formula (A-9)-(Q-1)-D-(B-1).

A further particular group of compounds of the formula (I) are compounds of the formula (A-2)-(Q-1)-D-(B-31).

A further particular group of compounds of the formula (I) are compounds of the formula (A-2)-(Q-1)-D-(B-35).

If R4 or R3 in group Q-1 represents hydroxy, Q-1 may also be present in the keto form:

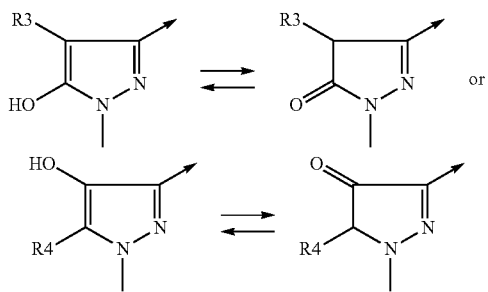

It has additionally been found that the compounds of the formula (I) can be obtained by the processes described below.

Accordingly, the invention also relates to processes for preparing compounds of the formula (I) in which Z represents O,

where A, Q, D and B have the meanings described above, by reacting amines of the formulae (II-1) to (II-5)

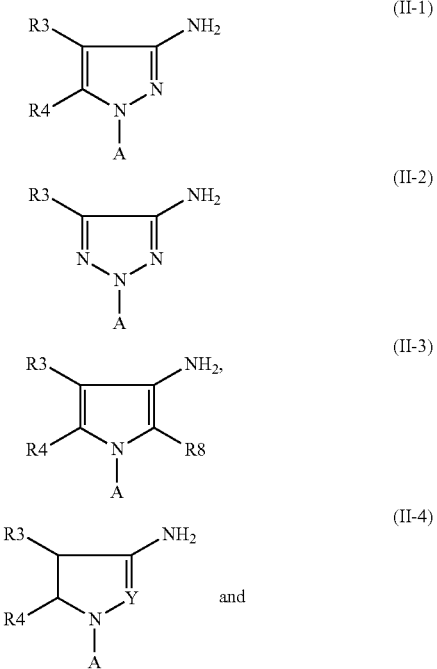

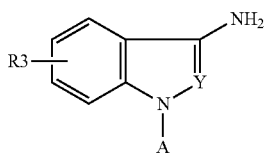

with carboxylic acids or carbonyl halides of the formula (III)

in which

M represents halogen, hydroxy, alkoxy, alkylsulphanyl, acyloxy, sulphonyloxy, N-heterocyclyl (e.g. imidazolyl) or represents hydroxy, B has the meanings given above and Z represents O.

Here, compounds of the formula (III) can be preactivated or be activated in situ. Compounds of the formula (III) can be employed, for example, as acid halides (e.g. M=chlorine). In this case, the reaction is advantageously carried out in the presence of a base such as, for example, triethylamine or sodium hydroxide. However, it is also possible to use carboxylic acids (M=OH) in the presence of coupling reagents such as, for example dicyclohexylcarbodiimide and additives such as 1-hydroxy-1-H-benzotriazole (W. Konig, R. Geiger, *Chem. Ber.* 1970, 103, 788). Use may furthermore be made of coupling reagents such as 1-ethyl-3-(3-dimethylaminopropyl)carbodiimide, 1,1'-carbonyl-1H-imidazole, O-(benzotriazol-1-yl)-N,N,N',N'-tetramethyluronium hexafluorophosphate and similar compounds. Suitable coupling reagents for carrying out the preparation process are, in principle, all compounds which allow an amide bond to be formed (cf., for example, E. Valeur, M. Bradley *Chem. Soc. Rev.* 2009, 38, 606; S.-Y. Han, Y.-A. Kim *Tetrahedron* 2004, 60, 2447). Use may furthermore also be made of symmetric or mixed anhydrides for preparing compounds of the formula (I) (G. W. Anderson, J. E. Zimmerman, F. M. Calahan, *J. Am. Chem. Soc.* 1967, 89, 5012). Here, various chloroformic esters may be employed, for example isobutyl chloroformate and sec-butyl chloroformate. Isovaleryl chloride and pivaloyl chloride, for example, may likewise be used.

b) The compounds of the formula (I) in which Z represents O (oxygen atom) can then optionally be reacted with a sulphurizing agent such as diphosphorus pentasulphide or Lawesson's reagent (cf. C. P. Dell in *Comprehensive Organic Functional Group Transformations*, Vol. 5, eds.: A. L. Katritzky, O. Meth-Cohn, C. W. Rees, Pergamon, Oxford, 1995, S. 565; M. Jesberger, T. P. Davis, L. Barner, *Synthesis* 2003, 13, 1929), to give compounds of the formula (I) in which Z represents S (sulphur atom).

c) Compounds of the formulae (I-1), (I-2) and (I-3)

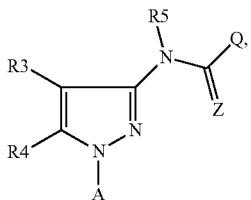

(I-1)

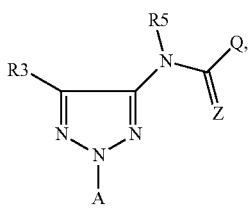

(I-2)

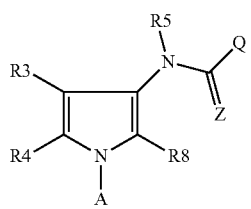

(I-3)

in which R3 represents halogen can be obtained either via the preparation route described above from the corresponding amines of the formulae (II-1), (II-2) and (II-3) in which R3 represents halogen (F, Cl, Br or I), or be synthesized from amides of the formulae (I-1), (I-2) and (I-3) in which R3 represents H (hydrogen) by reaction with a halogenating agent such as N-halosuccinimides (cf, for example, WO2008/092888, Z.-G-Zhao, Z.-X. Wang, *Synth. Comm.* 2007, 37, 137) or 1-chloromethyl-4-fluorodiazoniabicyclo [2.2.2]octane bis(tetrafluoroborate) (P. T. Nyffeler, S. Gonzalez Durón, M. D. Burkart, S. P. Vincent, C-H. Wong, *Angew. Chem. Int. Ed.* 2005, 44, 192).

d) Compounds of the formulae (I-1), (I-2) and (I-3) in which R5 represents hydrogen, can be converted in the presence of a base (for example sodium hydride) and an alkylating (for example methyl iodide) or acylating agent (for example acetic anhydride) into compounds of the formulae (I-1), (I-2) and (I-3) in which R5 represents alkyl or acyl (cf., for example, WO 2005/092863).

e) Compounds of the formula (I-1) can alternatively also be obtained by reacting 1H-pyrazoles of the formula (IV-1)

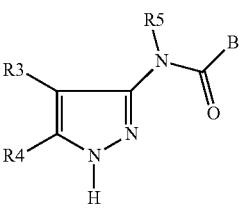

(IV-1)

with aromatics or heteroaromatics of the formula (V)

(V)

which are substituted by a suitable group LG. The reaction can be carried out either in the presence of a base (for example potassium carbonate for, for instance, LG=fluorine (cf. WO 2011/060035) or optionally a catalyst (for example CuI/1,2-cyclohexanediamine, potassium carbonate for, for instance, LG=bromine (cf. WO 2007/039146) or Cu(OAc)$_2$/pyridine for, for instance, LG=B(OH)$_2$ (cf. WO 2005/092863)).

Amines of the formula (II-1)

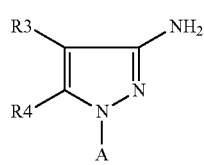

(II-1)

are commercially available or known from the literature, or they can be synthesized by processes known from the literature. Examples which may be mentioned are:
1-(2-methylphenyl)-1H-pyrazole-3-amine (WO 2004/037794),
1-(2-methoxyphenyl)-1H-pyrazole-3-amine (WO 2004/037794),
1-(2-(trifluoromethyl)phenyl)-1H-pyrazole-3-amine (commercially available),
1-(2-cyanophenyl)-1H-pyrazole-3-amine (commercially available),
1-(2-fluorophenyl)-1H-pyrazole-3-amine (WO 2004/037794),
1-(2-chlorophenyl)-1H-pyrazole-3-amine (C. Albert, C. Tironi, *Farmaco Sci.* 1964, 19, 618),
1-(2-chlorophenyl)-5-methyl-1H-pyrazole-3-amine (commercially available)
1-(2-bromophenyl)-1H-pyrazole-3-amine (commercially available),
1-(2,4-difluorophenyl)-1H-pyrazole-3-amine (commercially available),
1-(2,5-dichlorophenyl)-1H-pyrazole-3-amine (commercially available),
1-(pyridin-2-yl)-1H-pyrazole-3-amine (WO 2004/037794),
1-(3-chloropyridin-2-yl)-1H-pyrazole-3-amine (commercially available),
1-(3-fluoropyridin-2-yl)-1H-pyrazole-3-amine (commercially available),
1-(pyrimidin-2-yl)-1H-pyrazole-3-amine (commercially available),
1-(pyridazin-3-yl)-1H-pyrazole-3-amine (commercially available),
1-[2-(methylsulphonyl)phenyl]-1H-pyrazole-3-amine (commercially available),
1-(2,3-difluorophenyl)-1H-pyrazole-3-amine (commercially available),
1-(2,4,5-trifluorophenyl)-1H-pyrazole-3-amine (commercially available),
1-(2,4-dichlorophenyl)-1H-pyrazole-3-amine (commercially available),
1-(2,5-difluorophenyl)-1H-pyrazole-3-amine (commercially available),
1-(2,4-difluorophenyl)-5-ethyl-1H-pyrazole-3-amine (commercially available),
1-(2,4-difluorophenyl)-5-methyl-1H-pyrazole-3-amine (commercially available),
1-(2-nitrophenyl)-1H-pyrazole-3-amine (commercially available), 1-[3-chloro-5-(trifluoromethyl)pyridin-2-yl]-1H-pyrazole-3-amine (commercially available),
1-[3-(trifluoromethyl)pyridin-2-yl]-1H-pyrazole-3-amine (commercially available),
1-(3,5-dichloropyridin-2-yl)-1H-pyrazole-3-amine (commercially available),
1-(3-bromopyridin-2-yl)-1H-pyrazole-3-amine (commercially available),
2-(3-amino-1H-pyrazol-1-yl)nicotinonitrile (commercially available),
3-(3-amino-1H-pyrazol-1-yl)pyrazine-2-carbonitrile (commercially available),
2-(3-amino-1H-pyrazol-1-yl)-6-methylnicotinonitrile (commercially available),
2-(3-amino-1H-pyrazol-1-yl)-4,6-dimethylnicotinonitrile (commercially available),
1-(5-fluoropyridin-2-yl)-1H-pyrazole-3-amine (commercially available).

Novel 1H-pyrazole-3-amines of the formula (II-1) can be obtained as shown in Synthesis Scheme 1.

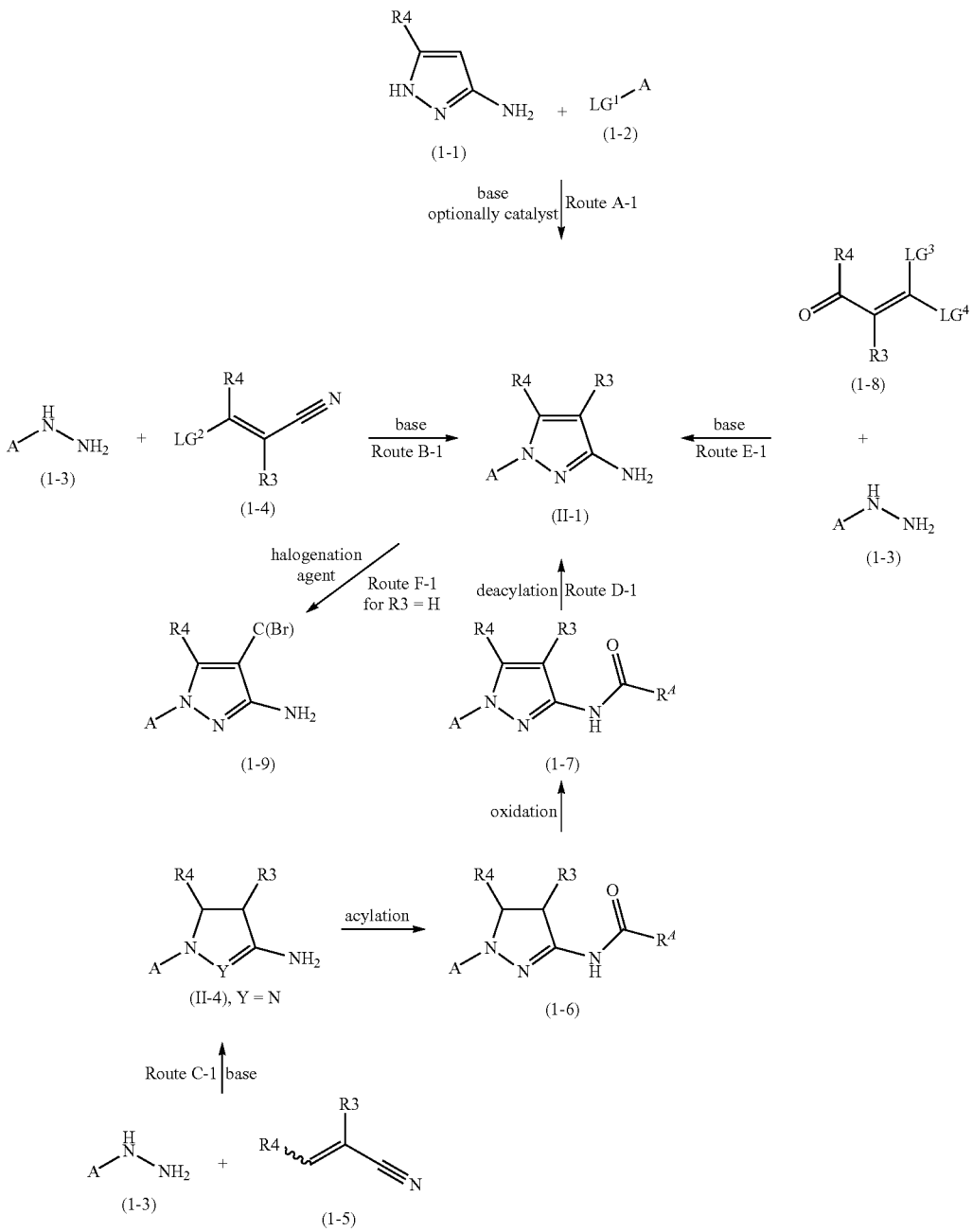

According to route A-1, 1H-pyrazole-3-amines of the formula (1-1) can be reacted with aromatics or heteroaromatics of the formula (1-2) substituted with a suitable group $LG^1$ to react, in the presence of a base (for example potassium tert-butoxide for, for instance, $LG^1$=chlorine (cf. WO 2009/012482) or, for example, caesium carbonate for, for instance, $LG^1$=chlorine (cf. WO 2007/056155)) and optionally a catalyst (for example CuI/N,N-dimethylethane-1,2-diamine, potassium carbonate for, for instance, $LG^1$=iodine (cf. WO2008/153042) or $Pd_2(dba)_3$/xantphos, sodium carbonate for, for instance, $LG^1$=chlorine (cf. Z. Shen, Y. Hong, X. He, W. Mo, B. Hu, N. Sun, X. Hu, *Org. Lett.* 2010, 12, 552)) to give compounds of the formula (II-1).

In an alternative route B-1, an aryl- or hetarylhydrazine of the formula (1-3), which may be present as free hydrazine or as a salt (for example as hydrochloride) can be reacted with an acrylonitrile of the formula (1-4) which is substituted by a leaving group $LG^2$ (for instance $LG^2$=OR where R=alkyl, acyl, sulphonyl, etc.; $LG^2$=SR where R=alkyl, acyl, etc.; $LG^2$=NHR or $NR_2$ where R=alkyl, acyl, sulphonyl; $LG^2$=halogen or cyano) in the presence of a suitable base (for example sodium ethoxide, cf., for instance, WO 2004/037794 or potassium tert-butoxide, cf., for instance, WO 2008/046527) to give the 1H-pyrazole-3-amine of the formula (II-1).

4,5-Dihydro-1H-pyrazole-3-amines of the formula (II-4) in which Y represents N can be prepared via route C-1 from aryl- or hetarylhydrazines (1-3) which can be present as free hydrazines or salts (for example as hydrochlorides) using acrylonitriles of the formula (1-5) in the presence of a suitable base (for example choline) (cf. C. Albert, C. Tironi, *Farmaco Sci.* 1964, 19, 618). Compounds of the formula (II-4) in which Y represents N can likewise be reacted in a sequence of acylation with a suitable acylating agent (for example acetic anhydride for $R^4$=methyl), oxidation with an appropriate oxidizing agent (for example 2,3-dichloro-5,6-dicyano-1,4-benzoquinone) and removal of the acyl group by suitable methods (for example heating in hydrochloric acid, cf. *Greene's protective groups in organic synthesis*, 4th ed., P. G. M. Wuts, T. W. Greene, John Wiley & Sons, Inc., Hoboken, N.J., 2007), to give 1H-pyrazole-3-amines of the formula (II-1).

Access to 1H-pyrazole-3-amines of the formula (II-1) is also provided via route E-1 starting with keto compounds of the formula (1-8) substituted with a leaving group $LG^{3/4}$ (for example $LG^{3/4}$=OR where R=alkyl, acyl, sulphonyl, etc.; $LG^{3/4}$=SR where R=alkyl, acyl, etc.; $LG^{3/4}$=NHR or $NR_2$ where R=hydrogen, alkyl, acyl, sulphonyl; $LG^{3/4}$=halogen). These are initially activated with ammonia via β-enaminoketones ($LG^3$=$NH_2$/$LG^4$=alkoxy) (cf. M. A. P. Martins, W. Cunico, S. Brondani, R. L. Peres, N. Zimmermann, F. A. Rosa, G. F. Fiss, N. Zanatta, H. G. Bonacorso *Synthesis* 2006, 1485) and then, in the presence of suitable bases (for example triethylamine) reacted with free hydrazines or salts thereof (for example hydrochlorides) to give 1H-pyrazole-3-amines of the formula (II-1).

1H-Pyrazole-3-amines of the formula (II-1) can optionally be halogenated via route F-1 if R3 represents H (hydrogen), using suitable halogenating agents (for example N-halosuccinimides) in the 3-position to give compounds of the formula (1-8) in which R3 represents chlorine, bromine or iodine (cf. J. Velcicky, R. Feifel, S. Hawtin, R. Heng, C. Huppertz, G. Koch, M. Kroemer, H. Moebitz, L. Revesz, C. Scheufler, A. Schlapbach *Bioorg. Med. Chem. Letters* 2010, 20, 1293).

Amines of the formula (II-2)

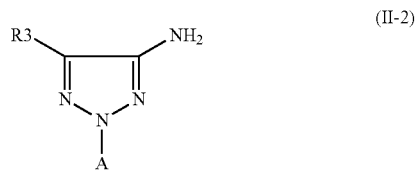

are likewise commercially available. Examples which may be mentioned are:
2-(2-bromophenyl)-2H-1,2,3-triazole-4-amine (commercially available)
2-(2-chlorophenyl)-2H-1,2,3-triazole-4-amine (commercially available)
2-(2-bromophenyl)-5-chloro-2H-1,2,3-triazole-4-amine (commercially available)
2-(3-chloropyridin-2-yl)-2H-1,2,3-triazole-4-amine (commercially available)
2-(3-bromopyridin-2-yl)-2H-1,2,3-triazole-4-amine (commercially available)
5-chloro-2-(3-chloropyridin-2-yl)-2H-1,2,3-triazole-4-amine (commercially available)

Novel amines of the formula (II-2) can be obtained according to Synthesis Scheme 3:

Synthesis Scheme 3

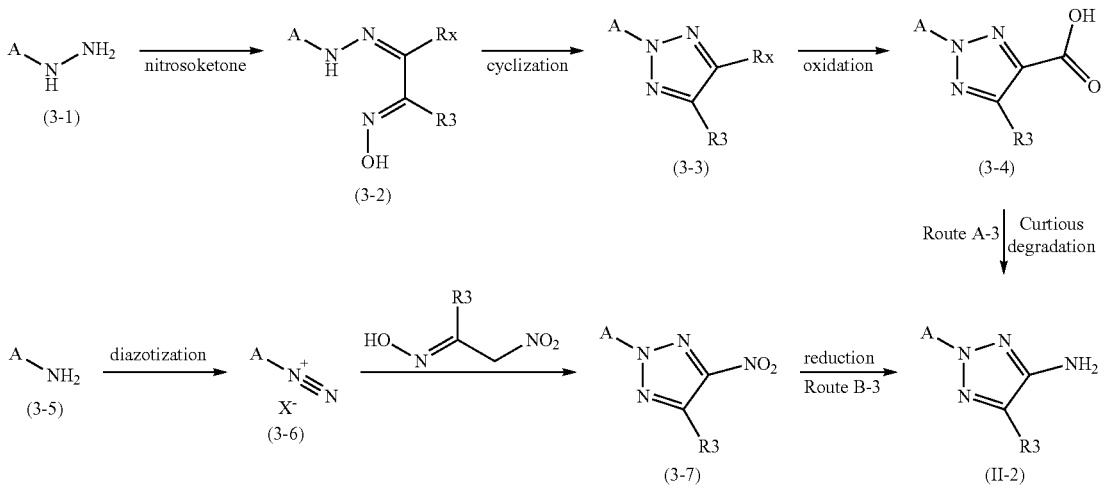

Via route A-3, aromatic hydrazines of the formula (3-1) can be reacted, for example, with a nitrosoketone (for example nitrosoacetone for R3=H, cf. M. Begtrup, J. Holm *J. Chem. Soc., Perkin Trans.* 1, 1981, 503) and then cyclized with the aid of condensing agents (for example acetic anhydride, cf. D. L. Swartz, A. R. Karash, L. A. Berry, D. L. Jaeger *J. Heterocyclic Chem.* 1983, 20, 1561) to give 2H-1,2,3-triazoles of the formula (3-3). Oxidation (for example with sodium chromate(VI) cf. Comprehensive Organic Transformations: A Guide to Functional Group Preparations; Larock, R. C., Ed.; Wiley-VCH: New York, 1999) of (3-3) affords the carboxylic acid (3-4) which can then be converted by Curtius degradation into the 4-amino-2H-1,2,3-triazole (II-2) (cf. P. A. S. Smith *Org. React.* 1946, 337).

Alternatively, route B-3 can also be followed for preparing the 4-amino-2H-1,2,3-triazoles (II-2) (cf. V. M. Nikitin, A. V. Zavodov, L. I. Vereshchagin *Zhurnal Organicheskoi Khimii* 1992, 28, 2334). To this end, an aromatic amine (3-5) is diazotized and the diazonium salt (3-6) is reacted, for example, with metazonic acid (for R3=H). The resulting 4-nitro-2H-1,2,3-triazole (3-7) can then be reduced with, for example, tin(II) chloride to give 4-amino-2H-1,2,3-triazole (II-2).

Amines of the formula (II-3)

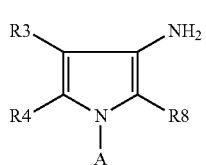

can be obtained via Synthesis Scheme 4.

Synthesis Scheme 4

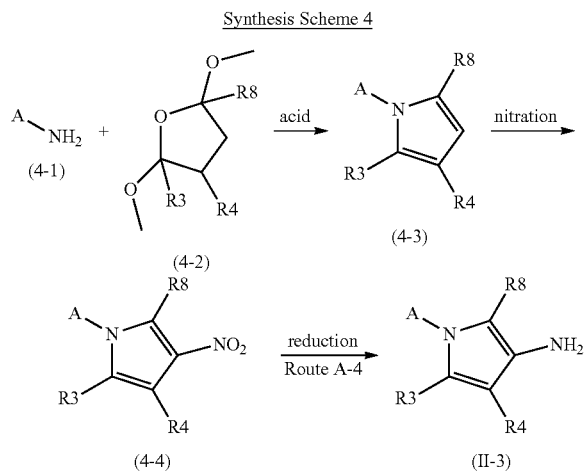

To this end, aromatic amines of the formula (4-1) are reacted, for example, with cyclic acetals of the formula (4-2) under acidic conditions to give the pyrrole (4-3) (for example FeCl₃ cf. N. Azizi, A. Khajeh-Amiria, H. Ghafurib, M. Bolourtchiana, M. R. Saidi *Synlett* 2009, 14, 2245). Nitration of the pyrrole (4-3) to 3-nitro-1H-pyrrole (4-4) (for example with acetyl nitrate, cf. D. Korakas, G. Varvounis *J. Heterocyclic Chem.* 1996, 33, 611) and subsequent reduction (for example with SnCl₂, cf. WO 2009/136995) affords the 3-amino-1H-pyrrole (II-3).

Amines of the formula (II-5)

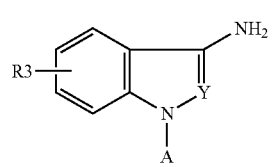

are likewise commercially available. Novel 1H-Indazole-3-amines of the formula (II-5) can be obtained according to Synthesis Scheme 2.

Synthesis Scheme 2

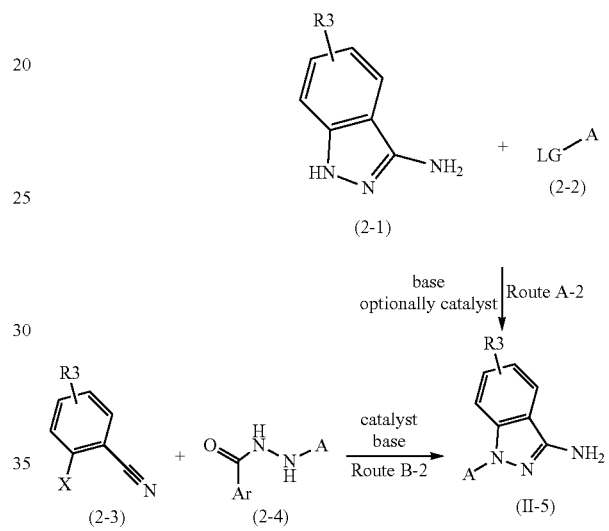

Here, compounds of the formula (2-1) are reacted via route A-2 with aromatics or heteroaromatics of the formula (2-2) substituted by a suitable leaving group LG, to react in the presence of a base (for example sodium hydride for, for instance, LG=chlorine (cf. WO 2008/068171)) and optionally a catalyst (for example CuI/N,N-dimethylethane-1,2-diamine, potassium carbonate for, for instance, LG=bromine (cf. WO 2010/098367) or Pd₂(dba)₃/X-Phos, caesium carbonate for, for instance, LG=chlorine (cf. DE 10 2009/004245)) to give compounds of the formula (II-5). 1H-Indazole-3-amines of the formula (2-1) and aromatics or heteroaromatics of the formula (2-2) are commercially available or can be obtained by known processes.

Via route B-2, it is alternatively possible to convert ortho-halobenzonitriles of the formula (2-3) with hydrazides of the formula (2-4) in the presence of a catalyst and a base (for example copper(I) bromide/4-hydroxy-L-proline; potassium carbonate for X=Br or I and Ar=phenyl, cf. L. Xu, Y. Peng, Q. Pan, Y. Jiang, D. Ma *J. Org. Chem.* 2013, 78, 3400) to give 1H-indazole-3-amines of the formula (II-5).

The processes according to the invention for preparation of the novel compounds of the formula (I) are preferably performed using a diluent. Useful diluents for performance of the processes according to the invention are, as well as water, all inert solvents. Examples include: halohydrocarbons (for example chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (for example methanol, ethanol, isopropanol, butanol), ethers (for example ethyl propyl ether, methyl tert-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, 1,4-dioxane, dichlorodiethyl ether and polyethers of ethylene oxide and/or propylene oxide), amines (for example trimethyl-, triethyl-, tripropyl-, tributylamine, N-methylmorpholine, pyridine and tetramethylenediamine), nitrohydrocarbons (for example nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (for example dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (for example pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, benzene, toluene, xylene, esters (for example methyl, ethyl, butyl and isobutyl acetate, dimethyl, dibutyl and ethylene carbonate); amides (for example hexamethylphosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (for example acetone, acetophenone, methyl ethyl ketone, methyl butyl ketone).

It is of course also possible to perform the process according to the invention in mixtures of the solvents and diluents mentioned.

When performing the process according to the invention, the reaction temperatures can be varied within a relatively wide range. In general, the temperatures employed are between −30° C. and +150° C., preferably between −10° C. and +100° C.

The process according to the invention is generally performed under atmospheric pressure. However, it is also possible to perform the process according to the invention under elevated or reduced pressure—generally at absolute pressures between 0.1 bar and 15 bar.

To perform the process according to the invention, the starting materials are generally used in approximately equimolar amounts. However, it is also possible to use one of the components in a relatively large excess. The reaction is generally carried out in a suitable diluent in the presence of a reaction auxiliary, optionally also under a protective gas atmosphere (for example under nitrogen, argon or helium) and the reaction mixture is generally stirred at the temperature required for several hours. The workup is performed by customary methods (cf. the Preparation Examples).

The basic reaction auxiliaries used to perform the process according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo [4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, 2-picoline, 3-picoline, pyrimidine, acridine, N,N,N',N'-tetramethylenediamine, N,N,N', N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine).

The acidic reaction auxiliaries used to perform the process according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

The active compounds according to the invention or active compounds to be used in accordance with the invention, having good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

pests from the phylum of the Arthropoda, more particularly from the class of the Arachnida, e.g. *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., *Epitrimerus pyri, Eutetranychus* spp., *Eriophyes* spp., *Glycyphagus domesticus, Halotydeus destructor, Hemitarsonemus* spp., *Hyalomma* spp., *Ixodes* spp., *Latrodectus* spp., *Loxosceles* spp., *Metatetranychus* spp., *Neutrombicula autumnalis, Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki*,

*Tarsonemus* spp., *Tetranychus* spp., *Trombicula alfreddugesi*, *Vaejovis* spp., *Vasates lycopersici*.;

from the class of the Chilopoda, e.g. *Geophilus* spp., *Scutigera* spp.;

from the order or the class of the Collembola, e.g. *Onychiurus armatus*.;

from the class of the Diplopoda, e.g. *Blaniulus guttulatus*;

from the class of the Insecta, e.g. from the order of the Blattodea, e.g. *Blattella asahinai*, *Blattella germanica*, *Blatta orientalis*, *Leucophaea maderae*, *Panchlora* spp., *Parcoblatta* spp., *Periplaneta* spp., *Supella longipalpa*;

from the order of the Coleoptera, e.g. *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp., *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sitophilus oryzae*, *Sphenophorus* spp., *Stegobium paniceum*, *Sternechus* spp., *Symphyletes* spp., *Tanymecus* spp., *Tenebrio molitor*, *Tenebrioides mauretanicus*, *Tribolium* spp., *Trogoderma* spp., *Tychius* spp., *Xylotrechus* spp., *Zabrus* spp.;

from the order of the Diptera, e.g. *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia anthropophaga*, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp., *Oscinella frit*, *Paratanytarsus* spp., *Paralauterborniella subcincta*, *Pegomyia* spp., *Phlebotomus* spp., *Phorbia* spp., *Phormia* spp., *Piophila casei*, *Prodiplosis* spp., *Psila rosae*, *Rhagoletis* spp., *Sarcophaga* spp., *Simulium* spp., *Stomoxys* spp., *Tabanus* spp., *Tetanops* spp., *Tipula* spp.;

from the order of the Heteroptera, e.g. *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptocorisa varicornis*, *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order of the Homoptera, e.g. *Acizzia acaciaebaileyanae*, *Acizzia dodonaeae*, *Acizzia uncatoides*, *Acrida turrita*, *Acyrthosipon* spp., *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., *Anuraphis cardui*, *Aonidiella* spp., *Aphanostigma pini*, *Aphis* spp., *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Prosopidopsylla flava*, *Protopulvinaria pyriformis*, *Pseudaulacaspis pentagona*, *Pseudococcus* spp., *Psyllopsis* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoideus titanus*, *Schizaphis graminum*, *Selenaspidus articulatus*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*, *Zygina* spp.;

from the order of the Hymenoptera, e.g. *Acromyrmex* spp., *Athalia* spp., *Atta* spp., *Diprion* spp., *Hoplocampa* spp., *Lasius* spp., *Monomorium pharaonis*, *Sirex* spp., *Solenopsis invicta*, *Tapinoma* spp., *Urocerus* spp., *Vespa* spp., *Xeris* spp.;

from the order of the Isopoda, e.g. *Armadillidium vulgare*, *Oniscus asellus*, *Porcellio scaber*;

from the order of the Isoptera, e.g. *Coptotermes* spp., *Cornitermes cumulans*, *Cryptotermes* spp., *Incisitermes* spp., *Microtermes obesi*, *Odontotermes* spp., *Reticulitermes* spp.;

from the order of the Lepidoptera, e.g. *Achroia grisella, Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamstra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudaletia unipuncta, Pseudoplusia includens, Pyrausta nubilalis, Rachiplusia nu, Schoenobius* spp., *Scirpophaga* spp., *Scirpophaga innotata, Scotia segetum, Sesamia* spp., *Sesamia inferens, Sparganothis* spp., *Spodoptera* spp., *Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., *Tryporyza incertulas, Tuta absoluta, Virachola* spp.;

from the order of the Orthoptera or Saltatoria, e.g. *Acheta domesticus, Dichroplus* spp., *Gryllotalpa* spp., *Hieroglyphus* spp., *Locusta* spp., *Melanoplus* spp., *Schistocerca gregaria;* from the order of the Phthiraptera, e.g. *Damalinia* spp., *Haematopinus* spp., *Linognathus* spp., *Pediculus* spp., *Phylloera vastatrix, Phtirus pubis, Trichodectes* spp.;

from the order of the Psocoptera, e.g. *Lepinotus* spp., *Liposcelis* spp.;

from the order of the Siphonaptera, e.g. *Ceratophyllus* spp., *Ctenocephalides* spp., *Pulex irritans, Tunga penetrans, Xenopsylla cheopsis;* from the order of the Thysanoptera, e.g. *Anaphothrips obscurus, Baliothrips biformis, Drepanothrips reuteri, Enneothrips flavens, Frankliniella* spp., *Heliothrips* spp., *Hercinothrips femoralis, Rhipiphorothrips cruentatus, Scirtothrips* spp., *Taeniothrips cardamomi, Thrips* spp.;

from the order of the Zygentoma (=Thysanura), e.g. *Ctenolepisma* spp., *Lepisma saccharina, Lepismodes inquilinus, Thermobia domestica;* from the class of the Symphyla, e.g. *Scutigerella* spp.;

pests from the phylum of the Mollusca, more particularly from the class of the Bivalvia, e.g. *Dreissena* spp., and also from the class of the Gastropoda, e.g. *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal parasites from the phyla of the Plathelminthes and Nematoda, e.g. *Ancylostoma duodenale, Ancylostoma ceylanicum, Ancylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;* plant pests from the phylum of the Nematoda, i.e. plant-parasitic nematodes, more particularly *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp.

Furthermore, from the sub-kingdom of the Protozoa, the order of the Coccidia, e.g. *Eimeria* spp. can be controlled.

The present invention further relates to formulations and use forms prepared therefrom as crop protection compositions and/or pesticides, for example drench, drip and spray liquors, comprising at least one of the active compounds according to the invention. In some cases, the use forms comprise further crop protection agents and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya bean oil methyl ester, or alkanol alkoxylates, and/or spreaders, for example alkylsiloxanes, and/or salts, for example organic or inorganic ammonium or phosphonium salts, for example ammonium sulphate or diammonium hydrogenphosphate, and/or retention promoters, for example dioctyl sulphosuccinate or hydroxypropyl guar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more active compounds according to the invention, optionally comprise further agrochemically active compounds.

These are preferably formulations or use forms which comprise auxiliaries, for example extenders, solvents, spontaneity promoters, carriers, emulsifiers, dispersants, antifreezes, biocides, thickeners and/or further auxiliaries, for example adjuvants. An adjuvant in this context is a component which enhances the biological effect of the formulation, without the component itself having a biological effect. Examples of adjuvants are agents which promote retention, spreading, attachment to the leaf surface or penetration.

These formulations are produced in a known manner, for example by mixing the active compounds with auxiliaries, for example extenders, solvents and/or solid carriers and/or further auxiliaries, for example surfactants. The formulations are prepared either in suitable installations or else before or during application.

Auxiliaries used may be substances capable of giving the formulation of the active compound, or the application forms prepared from these formulations (such as ready-to-use crop protection compositions, for example, such as spray liquors or seed dressings) particular properties, such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle it is possible to use all suitable carriers. Useful carriers include in particular: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, maize cobs and tobacco stalks.

Liquefied gaseous extenders or solvents can also be used. Particularly suitable extenders or carriers are those which are gaseous at ambient temperature and under atmospheric pressure, for example aerosol propellant gases, such as halogenated hydrocarbons, and also butane, propane, nitrogen and carbon dioxide.

Examples of emulsifiers and/or foam-formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the active compounds and/or one of the inert carriers is insoluble in water and when the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam-formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further auxiliaries may be mineral and vegetable oils.

If appropriate, the formulations and the use forms derived therefrom may also comprise further auxiliaries. Examples of such additives include fragrances, protective colloids, binders, adhesives, thickeners, thixotropic agents, penetrants, retention promoters, stabilizers, sequestrants, complexing agents, humectants, spreaders. In general, the active compounds can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Penetrants contemplated in the present context include all those substances which are commonly used to promote the penetration of agrochemically active compounds into plants. Penetrants are defined in this context by their ability to penetrate from the (generally aqueous) spray liquor and/or from the spray coating into the cuticle of the plant and thereby increase the mobility of active compounds in the cuticle. The method described in the literature (Baur et al., 1997, Pesticide Science 51, 131-152) may be used for the purpose of determining this quality. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations contain preferably between 0.00000001% and 98% by weight of active compound or more preferably between 0.01% and 95% by weight of active compound, more preferably between 0.5% and 90% by weight of active compound, based on the weight of the formulation.

The active compound content of the use forms (crop protection compositions) prepared from the formulations can vary within wide limits. The active compound concentration of the use forms may typically be between 0.00000001% and 95% by weight of active compound, preferably between 0.00001% and 1% by weight, based on the weight of the use form. Application is accomplished in a customary manner appropriate for the use forms.

The active compounds according to the invention or the active compounds to be used in accordance with the invention may be used as such or in formulations thereof, including in a mixture with one or more suitable fungicides, bactericides, acaricides, molluscicides, nematicides, insecticides, microbiologicals, beneficial species, fertilizers, bird repellents, phytotonics, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, such active compound combinations may improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products. By combining the active compounds according to the invention or the active compounds to be used in accordance with the invention with mixing partners, synergistic effects are obtained, i.e. the efficacy of the particular mixture is greater than expected on the basis of the efficacies of the individual components. It is generally possible to use the combinations in premixes, tank mixes or ready mixes, and also in seed applications.

The active compounds identified here by their common names are known and are described, for example, in the pesticide handbook ("The Pesticide Manual" 14th Ed., British Crop Protection Council 2006) or can be found on the Internet (e.g. http://www.alanwood.net/pesticides).

Insecticides/acaricides/nematicides suitable as mixing components are (1) Acetylcholinesterase (AChE) inhibitors, for example
carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
organophosphates, for example acephate, azamethiphos, azinphos-ethyl, azinphos-methyl, cadusafos, chlorethoxyfos, chlorfenvinphos, chlormephos, chlorpyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists, for example
cyclodiene organochlorines, e.g. chlordane and endosulfan; or
phenylpyrazoles (fiprole), e.g. ethiprole and fipronil.

(3) Sodium channel modulators/voltage-dependent sodium channel blockers such as, for example,
pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin; or
DDT; or methoxychlor.

(4) Nicotinergic acetylcholine receptor (nAChR) agonists such as, for example,
neonicotinoids, e.g. acetamiprid, clothianidin, dinotefuran, imidacloprid, nitenpyram, thiacloprid and thiamethoxam; or
nicotine; or
sulfoxaflor.

(5) Nicotinergic acetylcholine receptor (nAChR) allosteric activators such as, for example, spinosyns, e.g. spinetoram and spinosad.

(6) Chloride channel activators such as, for example,
avermectins/milbemycins, for example abamectin, emamectin benzoate, lepimectin and milbemectin.

(7) Juvenile hormone imitators such as, for example,
juvenile hormone analogues, e.g. hydroprene, kinoprene and methoprene; or
fenoxycarb; or pyriproxyfen.

(8) Active compounds with unknown or nonspecific mechanisms of action such as, for example
alkyl halides, e.g. methyl bromide and other alkyl halides; or
chloropicrin; or sulphuryl fluoride; or borax; or tartar emetic.

(9) Selective antifeedants, for example pymetrozine; or flonicamid.

(10) Mite growth inhibitors, for example clofentezine, hexythiazox and diflovidazin; or
etoxazole.

(11) Microbial disruptors of the insect gut membrane, e.g. *Bacillus thuringiensis* subspecies *israelensis*, *Bacillus thuringiensis* subspecies *aizawai*, *Bacillus thuringiensis* subspecies *kurstaki*, *Bacillus thuringiensis* subspecies tenebrionis and B.t. plant proteins: Cry1Ab, Cry1Ac, Cry1Fa, Cry1A.105, Cry2Ab, Vip3A, mCry3A, Cry3Ab, Cry3Bb, Cry34 Ab1/35Ab1; or

*Bacillus sphaericus.*

(12) Oxidative phosphorylation inhibitors, ATP disruptors such as, for example, diafenthiuron; or organotin compounds, e.g. azocyclotin, cyhexatin and fenbutatin oxide; or propargite; or tetradifon.

(13) Oxidative phosphorylation decouplers acting by interrupting the H proton gradient such as, for example, chlorfenapyr, DNOC and sulfluramid.

(14) Nicotinergic acetylcholine receptor antagonists such as, for example, bensultap, cartap hydrochloride, thiocylam, and thiosultap-sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Molting disruptors, dipteran such as, for example, cyromazine.

(18) Ecdysone receptor agonists such as, for example, chromafenozide, halofenozide, methoxyfenozide and tebufenozide.

(19) Octopaminergic agonists such as, for example, amitraz.

(20) Complex-III electron transport inhibitors such as, for example, hydramethylnone; or acequinocyl; or fluacrypyrim.

(21) Complex-I electron transport inhibitors, for example METI acaricides, e.g. fenazaquin, fenpyroximate, pyrimidifen, pyridaben, tebufenpyrad and tolfenpyrad; or rotenone (Derris).

(22) Voltage-dependent sodium channel blockers, for example indoxacarb; or metaflumizone.

(23) Inhibitors of acetyl-CoA carboxylase such as, for example, tetronic and tetramic acid derivatives, e.g. spirodiclofen, spiromesifen and spirotetramat.

(24) Complex-IV electron transport inhibitors such as, for example, phosphines, e.g. aluminium phosphide, calcium phosphide, phosphine and zinc phosphide; or cyanide.

(25) Complex II electron transport inhibitors, such as, for example, cyenopyrafen and cyflumetofen.

(28) Ryanodine receptor effectors such as, for example, diamides, e.g. chlorantraniliprole, cyantraniliprole and flubendiamide.

Further active compounds such as, for example, amidoflumet, azadirachtin, benclothiaz, benzoximate, bifenazate, bromopropylate, chinomethionat, cryolite, dicofol, diflovidazin, fluensulphone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM 1-1582, for example VOTiVO™, BioNem), and the following compounds:

3-bromo-N-{2-bromo-4-chloro-6-[(1-cyclopropylethyl)carbamoyl]phenyl}-1-(3-chloropyridin-2-yl)-1H-pyrazole-5-carboxamide (known from WO 2005/077934), 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), flupyradifurone, 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EPA 0 539 588), 4-{[(6-chloropyrid-3-yl)methyl](methyl)amino}furan-2(5H)-one (known from EP A 0 539 588), {[1-(6-chloropyridin-3-yl)ethyl](methyl)oxido-$\lambda^4$-sulphanylidene}cyanamide (known from WO2007/149134) and its diastereomers {[(1R)-1-(6-chloropyridin-3-yl)ethyl](methyl)oxido-$\lambda^4$-sulphanylidene}cyanamide (A) and {[(1S)-1-(6-chloropyridin-3-yl)ethyl](methyfloxido-$\lambda^4$-sulphanylidene}cyanamide (B) (likewise known from WO 2007/149134) and also diastereomers [(R)-methyl(oxido){(1R)-1-[6-(trifluoromethyl)pyridin-3-yl]ethyl}-$\lambda^4$-sulphanylidene]cyanamide (A1) and [(S)-methyl(oxido){(1S)-1-[6-(trifluoromethyl)pyridin-3-yl]ethyl}-$\lambda^4$-sulphanylidene]cyanamide (A2), identified as diastereomer group A (known from WO 2010/074747, WO 2010/074751), [(R)-methyl(oxido){(1S)-1-[6-(trifluoromethyl)pyridin-3-yl]ethyl}-$\lambda^4$-sulphanylidene]cyanamide (B1) and [(S)-methyl(oxido){(1R)-1-[6-(trifluoromethyl)pyridin-3-yl]ethyl}-$\lambda^4$-sulphanylidene]cyanamide (B2), identified as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-{2-fluoro-4-methyl-5-[(2,2,2-trifluoroethyl)sulphinyl]phenyl}-3-(trifluoromethyl)-1H-1,2,4-triazol-5-amine (known from WO 2006/043635), afidopyropen (known from WO 2008/066153), 2-cyano-3-(difluoromethoxy)-N,N-dimethylbenzenesulphonamide (known from WO 2006/056433), 2-cyano-3-(difluoromethoxy)-N-methylbenzenesulphonamide (known from WO 2006/100288), 2-cyano-3-(difluoromethoxy)-N-ethylbenzenesulphonamide (known from WO 2005/035486), 4-(difluoromethoxy)-N-ethyl-N-methyl-1,2-benzothiazole-3-amine 1,1-dioxide (known from WO 2007/057407), N-[1-(2,3-dimethylphenyl)-2-(3,5-dimethylphenyflethyl]-4,5-dihydro-1,3-thiazol-2-amine (known from WO 2008/104503), {[(2E)-3-(4-chlorophenyl)prop-2-en-1-yl]-5-fluorospiro[indol-3,4'-piperidin]-1(2H)-yl}(2-chloropyridin-4-yl)methanone (known from WO 2003/106457), 3-(2,5-dimethylphenyl)-4-hydroxy-8-methoxy-1,8-diazaspiro[4.5]dec-3-en-2-one (known from WO 2009/049851), 3-(2,5-dimethylphenyl)-8-methoxy-2-oxo-1,8-diazaspiro[4.5]dec-3-en-4-yl ethyl carbonate (known from WO 2009/049851), 4-(but-2-yn-1-yloxy)-6-(3,5-dimethylpiperidin-1-yl)-5-fluoropyrimidine (known from WO 2004/099160), (2,2,3,3,4,4,5,5-octafluoropentyl)(3,3,3-trifluoropropyl)malononitrile (known from WO 2005/063094), (2,2,3,3,4,4,5,5-octafluoropentyl)(3,3,4,4,4-pentafluorobutyl)malononitrile (known from WO 2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO 2007/040280), flometoquin, PF1364 (CAS Reg. No. 1204776-60-2) (known from JP 2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO 2007/075459), 5-[5-(2- chloropyridin-4-yl)-5-(trifluoromethyl)-4,5-dihydro-1,2-oxazol-3-yl]-2-(1H-1,2,4-triazol-1-yl)benzonitrile (known from WO 2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO 2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO 2010/005692), pyflubumide (known from WO 2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO 2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO 2007/101369), 2-{6-[2-(5-fluoropyridin-3-yl)-1,3-thiazol-5-yl]pyridin-2-yl}pyrimidine (known from WO 2010/006713), 2-{6-[2-(pyridin-3-yl)-1,3-thiazol-5-yl]pyridin-2-yl}pyrimidine (known from WO 2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO 2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO 2010/069502), (1E)-N-[(6-chloropyridin-3-yl)methyl]-N'-cyano-N-(2,2-difluoroethyl)ethanimideamide (known from WO 2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN 102057925), methyl 2-[3,5-dibromo-2-({[3-bromo-1-(3-chloropyridin-2-yl)-1H-pyrazol-5-yl]carbonylamino}benzoyl]-2-ethyl-1-methylhydrazinecarboxylate (known from WO 2011/049233), heptafluthrin, pyriminostrobin, flufenoxystrobin and 3-chloro-N²-(2-cyanopropan-2-yl)-N¹-[4-(1,1,1,2,3,3,3-heptafluoropropan-2-yl)-2-methylphenyl]phthalamide (known from WO2012/034472).

Fungicides suitable as mixing components are:

(1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethyl-silyl)propoxy]phenyl}imidoformamide and O-[1-(4-methoxyphenoxy)-3,3-dimethylbutan-2-yl]1H-imidazole-1-carbothioate.

(2) Respiration inhibitors (respiratory chain inhibitors), such as, for example, bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxyl)phenyl]-1H-pyrazole-4-carboxamide, 3-(difluoromethyl)-N-[4-fluoro-2-(1,1,2,3,3,3-hexafluoropropoxyl)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazoline-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]

ethylidene}amino)oxy]methyl}phenyl)-2,4-dihydro-3H-1,2,4-triazol-3-one, methyl(2E)-2-{2-[(cyclopropyl[(4-methoxyphenyl)imino]methyl}sulphanyl)methyl]phenyl-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl) [1,2,4]triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper preparations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations, for example calcium polysulphide, thiram, tolylfluanid, zineb and ziram.

(6) Resistance inductors, for example acibenzolar-S-methyl, isotianil, probenazole and tiadinil.

(7) Amino acid and protein biosynthesis inhibitors, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) ATP production inhibitors, for example fentin acetate, fentin chloride, fentin hydroxide and silthiofam.

(9) Cell wall synthesis inhibitors, for example benthiavalicarb, dimethomorph, flumorph, iprovalicarb, mandipropamid, polyoxins, polyoxorim, validamycin A and valifenalate.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, fthalide, pyroquilon, tricyclazole and 2,2,2-trifluoroethyl {3-methyl-1-[(4-methylbenzoyl)amino]butan-2-yl}carbamate.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, for example chlozolinate, fenpiclonil, fludioxonil, iprodione, procymidone, quinoxyfen and vinclozolin.

(14) Decouplers, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromide, flusulfamide, flutianil, fosetyl-aluminium, fosetyl-calcium, fosetyl-sodium, hexachlorobenzene, irumamycin, methasulfocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrin, tebufloquin, tecloftalam, tolnifanid, triazoxide, trichlamide, zarilamide, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1,2,4]triazolo[1,5-a]pyrimidine-7-amine, ethyl(2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl{6-[({[(1-methyl-1H-tetrazol-5-yl)(phenyl)methyl-idene]amino}oxy)methyl]pyridin-2-yl}carbamate, phenazine-1-carboxylic acid, quinolin-8-ol, quinolin-8-ol sulphate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulphonyl)valinamide, 4-oxo-4-[(2-phenyl-ethyl)amino]butanoic acid and but-3-yn-1-yl {6-[({[(Z)-(1-methyl-1H-tetrazol-5-yl)(phenyl)methylene]amino}oxy)methyl]pyridin-2-yl}carbamate.

All mixing components mentioned in classes (1) to (16) can, if they are capable on the basis of their functional groups, optionally form salts with suitable bases or acids.

The invention can be used to treat all plants and parts of plants. Plants in this context are understood to include all plants and plant populations, such as desired and unwanted wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts should be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested plants and vegetative and generative propagation material, for example seedlings, tubers, rhizomes, cuttings and seeds.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They can be cultivars, varieties, bio- or genotypes.

The treatment of the plants and plant parts with the active compounds, active compound combinations or compositions according to the invention or the active compounds, active compound combinations or compositions to be used in accordance with the invention is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

One preferred direct treatment of the plants is foliar application; in other words, the active compounds, active compound combinations or compositions are applied to the foliage, where the frequency of treatment and the application rate may be adjusted for the infestation pressure of the particular pathogen, pest or weed.

In the case of systemically active compounds, the active compounds, active compound combinations or compositions access the plants via the root system. The plants are then treated by the action of the active compounds, active compound combinations or compositions on the habitat of the plant. This may be done, for example, by drenching, or by mixing into the soil or the nutrient solution, i.e. the locus of the plant (e.g. soil or hydroponic systems) is impregnated with a liquid form of the active compounds, active compound combinations or compositions, or by soil application, i.e. the active compounds, active compound combinations or compositions according to the invention are introduced in solid form (e.g. in the form of granules) into the locus of the plants. In the case of paddy rice crops, this can also be done by metering the invention in a solid application form (for example as granules) into a flooded paddy field.

The control of animal pests by treating the seed of plants has been known for a long time and is the subject of continuous improvements. Nevertheless, the treatment of seed gives rise to a series of problems which cannot always be solved in a satisfactory manner Thus, it is desirable to develop methods for protecting the seed and the germinating plant which dispense with, or at least reduce considerably, the additional application of crop protection compositions during storage, after sowing or after emergence of the plants. It is furthermore desirable to optimize the amount of active compound employed in such a way as to provide optimum protection for the seed and the germinating plant from attack by animal pests, but without damaging the plant itself by the active compound employed. In particular, methods for the treatment of seed should also take into consideration the intrinsic insecticidal or nematicidal properties of pest-resistant or -tolerant transgenic plants in order to achieve optimum protection of the seed and also the germinating plant with a minimum of crop protection products being employed.

The present invention therefore in particular also relates to a method for the protection of seed and germinating plants, from attack by pests, by treating the seed with an active compound according to the invention or an active compound to be used according to the invention. The method according to the invention for protecting seed and germinating plants against attack by pests comprises a method where the seed is treated simultaneously in one operation with an active compound of the formula I and a mixing partner. It also comprises a method where the seed is treated at different times with an active compound of the formula I and a mixing partner.

The invention likewise relates to the use of the active compounds according to the invention for the treatment of seed for protecting the seed and the resulting plant from animal pests.

Furthermore, the invention relates to seed which has been treated with an active compound according to the invention so as to afford protection from animal pests. The invention also relates to seed which has been treated simultaneously with an active compound of the formula I and a mixing partner. The invention furthermore relates to seed which has been treated at different times with an active compound of the formula I and a mixing partner. In the case of seed which has been treated at different points in time with an active compound of the formula I and a mixing partner, the individual active compounds of the composition according to the invention may be present on the seed in different layers. Here, the layers comprising an active compound of the formula (I) and a mixing partner may optionally be separated by an intermediate layer. The invention also relates to seed where an active compound of the formula I and a mixing partner have been applied as component of a coating or as a further layer or further layers in addition to a coating.

Furthermore, the invention relates to seed which, after the treatment with the active compound of the formula (I) or an active compound combination comprising the active compound of the formula (I), has been subjected to a film-coating process to prevent dust abrasion on the seed.

One of the advantages of the present invention is that the particular systemic properties of the compositions according to the invention mean that treatment of the seed with these compositions not only protects the seed itself, but also the resulting plants after emergence, from animal pests. In this manner, the immediate treatment of the crop at the time of sowing or shortly thereafter can be dispensed with.

It has to be considered a further advantage that by treatment of the seed with active compound of the formula (I) or active compound combination comprising the active compound of the formula (I), germination and emergence of the treated seed may be enhanced.

It is likewise to be considered advantageous that the active compounds of the formula (I) and the active compound combinations mentioned can be used in particular also for transgenic seed.

It may also be mentioned that the active compounds of the formula (I) can be employed in combination with compositions of signalling technology, leading, for example, to better colonization by symbionts such as, for example rhizobia, mycorrhizae and/or endophytic bacteria, and/or to optimized nitrogen fixation.

The compositions according to the invention are suitable for protection of seed of any plant variety which is used in agriculture, in the greenhouse, in forests or in horticulture. In particular, this takes the form of seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, bean, cruciferous vegetables, onions and lettuce), fruit plants, lawns and ornamental plants. The treatment of the seed of cereals (such as wheat, barley, rye and oats), maize, soya beans, cotton, canola, oilseed rape and rice is of particular importance.

As already mentioned above, the treatment of transgenic seed with active compounds of the formula (I) or an active compound combination is also of particular importance. This takes the form of seed of plants which, as a rule, comprise at least one heterologous gene which governs the expression of a polypeptide with in particular insecticidal and/or nematicidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. The gene involved is more preferably a heterologous gene which originates from *Bacillus thuringiensis*.

Within the context of the present invention, the active compound of the formula (I) is applied to the seed alone (or as an active compound combination) or in suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This should be ensured particularly in the case of active compounds which can exhibit phytotoxic effects at particular application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds/active compound combinations which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds or active compound combinations with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemically active compounds. Usable with preference are alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Nonionic or anionic dispersants or mixtures of nonionic or anionic dispersants are usable with preference. Suitable nonionic dispersants include especially ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical compounds. Silicone antifoams and magnesium stearate can preferably be used.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Cellulose derivatives, acrylic acid derivatives, xanthan, modified clays and finely divided silica are preferred.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel", vol. 2, Springer Verlag, 1970, pp. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, and beets, or else a wide variety of different vegetable seed. The seed dressing formulations usable in accordance with the invention, or the dilute preparations thereof, can also be used to dress seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

The application rate of the seed dressing formulations usable in accordance with the invention can be varied within a relatively wide range. It is guided by the particular content of the active compound(s) in the formulations and by the seed. The application rates of active compounds/active compound combinations are generally between 0.001 and 50 g per kilogram of seed, preferably between 0.01 and 15 g per kilogram of seed.

The prior art does not disclose whether the active compounds of the formula (I) are effective against biotic stress factors and/or abiotic stress of plants or with respect to plant growth.

It has now been found that the active compounds of the formula (I) according to the invention are suitable for enhancing the defences of the plant (pathogen control in plants).

It is known that plants react to natural stress conditions such as, for example, cold temperatures, heat, drought, injury, attack by pathogens (viruses, bacteria, fungi), insects etc., but also to herbicides, with specific or unspecific defence mechanisms (Pflanzenbiochemie [Plant Biochemistry], pp. 393-462, Spektrum Akademischer Verlag, Heidelberg, Berlin, Oxford, Hans W. Heldt, 1996.; Biochemistry and Molecular Biology of Plants, pp. 1102-1203, American Society of Plant Physiologists, Rockville, Md., eds. Buchanan, Gruissem, Jones, 2000). Here, for example, cell wall components generated by injury or specific pathogen-derived signal substances serve as inductors of plant signal transduction chains which finally lead to the formation of defensive molecules directed against the stress factor. These can be, for example, (a) low-molecular-weight substances such as, for example, phytoalexins, (b) non-enzymatic proteins such as pathogenesis-related proteins (PR proteins), (c) enzymatic proteins such as chitinases, glucanases, or (d) specific inhibitors of essentiel proteins such as protease inhibitors, xylanase inhibitors, which attack the pathogen directly or interfere with its proliferation (Dangl and Jones, Nature 411, 826-833, 2001; Kessler and Baldwin, Annual Review of Plant Biology, 53, 299-328, 2003).

An additional defence mechanism it the so-called hypersensitivity reaction (HR) which is mediated via oxidative stress and causes death of plant tissue in the region of the centre of an infection, thus preventing the spread of plant pathogens which are dependent on living cells (Pennazio, New Microbiol. 18, 229-240, 1995).

During the progression of an infection, messenger substances of the plant transmit signals to tissues not infected, triggering defence reactions in these tissues and preventing secondary infections (Systemic acquired resistance, SAR) (Ryals et al., The Plant Cell 8, 1809-1819, 1996).

A number of signalling substances which are endogenous to plants and are involved in stress tolerance or pathogenic defence are already known. Examples here include salicylic acid, benzoic acid, jasmonic acid or ethylene (Biochemistry and Molecular Biology of Plants, p. 850-929, American Society of Plant Physiologists, Rockville, Md., eds. Buchanan, Gruissem, Jones, 2000). Some of these substances or the stable synthetic derivatives and derived structures thereof are also effective on external application to plants or in seed dressing, and activate defence reactions which cause elevated stress tolerance or pathogen tolerance of the plant (Sembdner, Parthier, 1993, Ann. Rev. Plant Physiol. Plant Mol. Biol. 44, 569-589, 1993). The salicylate-mediated defence is directed in particular against phytopathogenic fungi, bacteria and viruses (Ryals et al., The Plant Cell 8, 1809-1819, 1996).

A known synthetic product which has a function similar to that of salicylic acid and can mediate a protective effect against phytopathogenic fungi, bacteria and viruses is benzothiadiazole (CGA 245704; common name: acibenzolar-S-methyl; trade name: Bion®) (Achuo et al., Plant Pathology 53 (1), 65-72, 2004; Tamblyn et al., Pesticide Science 55 (6), 676-677, 1999; EP-OS [European Published Specification] 0 313 512).

Other compounds which belong to the group of the oxylipins, for example jasmonic acid, and the protective mechanisms they trigger are particularly effective against harmful insects (Walling, J. Plant Growth Regul. 19, 195-216, 2000).

Furthermore, it is known that treatment of plants with insecticides from the group of the neonicotinoids (chloronicotinyls) leads to increased resistance of the plant to abiotic stress. This applies in particular to imidacloprid (Brown et al., Beltwide Cotton Conference Proceedings 2231-2237, 2004). This protection is caused by modifying physiological and biochemical properties of the plant cells, for example by improving membrane stability, increasing carbohydrate concentration, increasing polyol concentration and antioxidant activity (Gonias et al., Beltwide Cotton Conference Proceedings 2225-2229, 2004).

Also known is the effect of chloronicotinyls on biotic stress factors (Crop Protection 19 (5), 349-354, 2000; Journal of Entomological Science 37(1), 101-112, 2002; Annals of Biology (Hisar, India) 19 (2), 179-181, 2003). Insecticides from the group of the neonicotinoids (chloronicotinyls), for example, lead to an increased expression of genes from the group of the pathogenesis-related proteins (PR proteins). PR proteins support plants primarily in the defence of biotic stressors such as, for example, phytopathogenic fungi, bacteria and viruses (DE 10 2005 045 174 A; DE 10 2005 022 994 A and WO 2006/122662 A; Thielert Pflanzenschutz-Nachrichten Bayer, 59 (1), 73-86, 2006; Francis et al., European Journal of Plant Pathology, publ. online 23.1.2009).

Furthermore, it is known that treatment of genetically modified plants with insecticides from the group of the neonicotinoids (chloronicotinyls) results in an improved stress tolerance of the plant (EP 1 731 037 A), for example also with respect to the herbicide glyphosate (WO 2006/015697 A).

It is thus known that plants possess several endogenous reaction mechanisms which can cause effective defence against a wide variety of harmful organisms (biotic stress) and/or abiotic stress.

The rearing of healthy young plants of uniform growth is an essential prerequisite for the cultivation on large areas and economical crop management of agricultural, horticultural and forestry crop plants.

Numerous methods for rearing young plants are established in agriculture, forestry and horticulture. Here, the rearing substrates used are, in addition to steamed soil, also special substrates based, inter alia, on peat mosses, coconut fibres, rock wool such as Grodan®, pumice, expanded clay such as Lecaton® or Lecadan®, clay granules such as Seramis®, foams such as Baystrat®, vermiculite, perlite, synthetic soil such as Hygromull®, or combinations of these substrates, into which seed, either dressed with fungicides and/or insecticides, or undressed seed is sown.

In specific crops such as tobacco, young plants are increasingly reared by the float method or floating method (Leal, R. S., The use of Confidor S in the float, a new tobacco seedlings production system in the South of Brazil. Pflanzenschutz-Nachrichten Bayer (German edition) (2001), 54(3), pages 337 to 352; Rudolph, R. D.; Rogers, W. D.; The efficacy of imidacloprid treatment for reduction in the severity of insect vectored virus diseases of tobacco. Pflanzenschutz-Nachrichten Bayer (German edition) (2001), 54(3), pages 311 to 336). In this method, the seed is sown in special containers, for example Styropor tablets with holes, in special rearing soil based on peat culture substrate, and then cultivated in containers with a suitable nutrient solution until the desired transplantation size is reached (Figure 1). Here, the containers are allowed to float on the nutrient solution, hence the name of the rearing method (Leal, 2001, vide supra). For a number of years, for controlling sucking pests, insecticides from the class of the neonicotinoids (chloronicotinyls) have been used in the floating method. Usually, in the float method the plants are sprayed with neonicotinoid (chloronicotinyls) insecticides shortly before transplantation, or they are watered with neonicotinoid (chloronicotinyls) insecticides immediately before or during transplantation, a procedure referred to as drenching (Leal, 2001, vide supra.; Rudolph and Rogers, 2001, vide supra). Both application methods are technically relatively complicated.

Here, to protect the emerging seed or planting stock against fungal pathogens and pests, fungicides and insecticides are used up to transplantation. Here, the choice of crop protection compositions, the location and the timing of the application and the application rate of the compositions depends especially on the type of fungal diseases and pests encountered, on the specific mode of action and duration of action of the compositions and on their compatibility with plants, and they can therefore be adapted directly to the specific requirements of different crops and regions.

Here, independently of any insect control, the active compounds of the formula (I) lead to good protection of the plants against damage by fungal, bacterial or viral pathogens.

Without wishing to be tied to a theory, it is currently assumed that the defence of the pathogens is effected by induction of PR proteins as a result of a treatment with at least one active compound of the formula (I).

The advantages described are evident, in particular, in the use according to the invention in the treatment of seed, in soil treatment, in specific rearing and cultivation methods (for example floating box, rockwool, hydroponic), but also in stem and foliar treatment. Combinations of an active compound of the formula (I) with, inter alia, insecticides, fungicides and bactericides show synergistic effects in the controlling of plant diseases. In addition, the combined use of the active compounds of the formula (I) with genetically modified cultivars with a view to increased tolerance to abiotic stress leads to a synergistic improvement of growth.

Finally, in accordance with the invention, it has also been found that the active compounds of the formula (I) are suitable not only for increasing pathogen defence in plants, but also for improving plant growth and/or for enhancing the resistance of plants to plant diseases caused by fungi, bacteria, viruses, MLO (*Mycoplasma*-like organisms) and/or RLO (*Rickettsia*-like organisms), in particular to soil-borne fungal diseases, and/or for increasing the resistance of plants to abiotic stress factors.

Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

The present invention therefore provides, firstly, the use of at least one active compound of the formula (I) for enhancing plants' intrinsic defences and/or for improving plant growth and/or for enhancing the resistance of plants to plant diseases caused by fungi, bacteria, viruses, MLO (*Mycoplasma*-like organisms) and/or RLO (*Rickettsia*-like organisms), in particular to soil-borne fungal diseases, and/or for enhancing the resistance of plants to abiotic stress factors.

In the context of the present invention, the term plant growth is to be understood as meaning various advantages of plants not directly associated with the known pesticidal activity, preferably insecticidal activity, of the active compounds of the formula (I). Such advantageous properties are, for example, the improved plant characteristics mentioned below: accelerated germination and emergence of seed and planting stock, improved root growth with regard to surface area and depth, increased stolon or tiller formation, stronger and more productive stolons and tillers, improvement in shoot growth, increased lodging resistance, increased shoot base diameter, increased leaf area, greener leaf colour, higher yields of nutrients and constituents, for example carbohydrates, fats, oils, proteins, vitamins, minerals, essential oils, dyes, fibres, better fibre quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soils and water, enhanced tolerance to UV radiation, enhanced tolerance to ozone stress, improved compatibility with respect to herbicides and other plant treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

As is known, the various advantages for plants, which have been mentioned further above, can be combined in part, and generally applicable terms can be used to describe them. Such terms are, for example, the following names: phytotonic effect, resistance to stress factors, less plant stress, plant health, healthy plants, plant fitness, plant wellness, plant concept, vigour effect, stress shield, protective shield, crop health, crop health properties, crop health products, crop health management, crop health therapy, plant health, plant health properties, plant health products, plant health management, plant health therapy, greening effect or regreening effect, freshness, or other terms with which a person skilled in the art is quite familiar It has furthermore been found that active compounds of the formula (I) lead to an increased expression of genes from the group of the pathogenesis-related proteins (PR proteins). PR proteins support the plants primarily in the defence of biotic stressors such as phytopathogenic fungi, bacteria and viruses. As a result, after application of active compounds of the formula (I) the plants are better protected against infections by phytopathogenic fungi, bacteria and viruses. In the required application of insecticides, fungicides and bactericides in a mixture with active compounds of the formula (I), as well as in sequential application, the action of the latter is supported.

In accordance with the invention, it has additionally been found that the application, to plants or in their environment, of the active compounds of the formula (I) in combination with a fertilizer as defined below has a synergistic growth-enhancing effect.

Fertilizers which can be employed in accordance with the invention together with the active compounds or compositions which have been explained in greater detail hereinabove are generally organic and inorganic nitrogen-containing compounds such as, for example, ureas, urea/formaldehyde condensates, amino acids, ammonium salts and ammonium nitrates, potassium salts (preferably chlorides, sulphates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonia nitrate sulphate (general formula $(NH_4)_2SO_4NH_4NO_3$), ammonium phosphate and ammonium sulphate. These fertilizers are generally known to the person skilled in the art; see also, for example, Ullmann's Encyclopedia of Industrial Chemistry, 5th edition, Vol. A 10, pages 323 to 431, Verlagsgesellschaft, Weinheim, 1987.

The fertilizers may also contain salts of micronutrients (preferably calcium, sulphur, boron, manganese, magnesium, iron, copper, zinc, molybdenum and cobalt) and phytohormones (for example vitamin B1 and indole-3-acetic acid (IAA)) or mixtures thereof. Fertilizers used in accordance with the invention may also contain other salts such as monoammonium phosphate (MAP), diammonium phosphate (DAP), potassium sulphate, potassium chloride or magnesium sulphate. Suitable amounts for the secondary nutrients, or trace elements, are amounts of 0.5 to 5% by weight, based on the overall fertilizer. Other possible ingredients are crop protection agents, insecticides or fungicides, growth regulators or mixtures of these. This will be explained in more detail further below.

The fertilizers can be employed for example in the form of powders, granules, prills or compactates. However, the fertilizers can also be employed in liquid form, dissolved in an aqueous medium. In this case, dilute aqueous ammonia may also be employed as nitrogen fertilizer. Further possible ingredients for fertilizers are described, for example, in Ullmann's Encyclopedia of Industrial Chemistry, 5th edition, 1987, volume A 10, pages 363 to 401, DE-A 41 28 828, DE-A 19 05 834 and DE-A 196 31 764.

The general composition of the fertilizers which, within the scope of the present invention, may take the form of straight and/or compound fertilizers, for example composed of nitrogen, potassium or phosphorus, may vary within a wide range. In general, a content of 1 to 30% by weight of nitrogen (preferably 5 to 20% by weight), 1 to 20% by weight of potassium (preferably 3 to 15% by weight) and a content of 1 to 20% by weight of phosphorus (preferably 3 to 10% by weight) is advantageous. The microelement content is usually in the ppm range, preferably in the range from 1 to 1000 ppm.

In the context of the present invention, the fertilizer and the active compound of the formula (I) may be administered simultaneously, i.e. synchronously. However, it is also possible first to apply the fertilizer and then the active compound of the formula (I), or first to apply the active compound of the formula (I) and then the fertilizer. In the case of nonsynchronous application of the active compound of the formula (I) and the fertilizer, the application within the scope of the present invention is, however, carried out in a functional context, in particular within a period of from in general 24 hours, preferably 18 hours, especially preferably 12 hours, specifically 6 hours, more specifically 4 hours, even more specifically within 2 hours. In very particular embodiments of the present invention, the active compounds of the general formula (I) according to the invention and the fertilizer are applied within a time frame of less than 1 hour, preferably less than 30 minutes, more preferably less than 15 minutes.

In addition, it is possible to prepare dimensionally stable mixtures, for example in the form of rods, granules, tablets etc., starting with at least one active compound to be used in accordance with the invention and at least one fertilizer. For preparing a corresponding dimensionally stable mixture, the appropriate components can be mixed with one another and optionally be extruded, or the at least one active compound of the formula (I) to be used in accordance with the invention can be applied to the fertilizer. If appropriate, use may also be made of formulation auxiliaries in the dimensionally stable mixtures, for example of extenders or adhesives, to achieve dimensional stability of the resulting mixture. By virtue of the corresponding dimensional stability, the corresponding mixtures are particularly suitable for use in the "Home & Garden" field, i.e. for a private user or hobby gardener, who can use the dimensionally stable mixture or the components thereof in a predetermined, clearly defined amount and without particular aids.

Independently thereof, the mixtures comprising at least one of the active compounds to be used in accordance with the invention and the at least one fertilizer may also be present in liquid form such that—for example in the case of a professional user in the field of agriculture—the resulting mixture may be applied as a tank mix.

Through the use of at least one of the active compounds to be used in accordance with the invention and at least one fertilizer, it is possible to achieve increased root growth which, in turn, allows a higher nutrient uptake and thus promotes plant growth.

The active compounds to be used in accordance with the invention, if appropriate in combination with fertilizers, can preferably be employed in the following plants, the enumeration which follows not being limiting.

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term useful plants as used in the present context refers to crop plants which are employed as plants for obtaining foodstuffs, feedstuffs, fuels or for industrial purposes.

The useful plants include, for example, the following types of plants: turf, vines, cereals, for example wheat, barley, rye, oats, triticale, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soya beans; oil crops, for example oilseed rape, mustard, poppies, olives, sunflowers, coconuts, castor oil plants, cacao beans and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, Cinnamomum, camphor, or also plants such as tobacco, nuts, coffee, aubergine, sugar cane, tea, pepper, grapevines, hops, bananas, latex plants and ornamentals, for example flowers, shrubs, deciduous trees and coniferous trees such as conifers. This enumeration does not constitute a limitation.

Particularly suitable target crops are the plants below: cotton, aubergine, turf, pome fruit, stone fruit, soft fruit, maize, wheat, barley, cucumber, tobacco, vines, rice, cereals, pear, beans, soya beans, oilseed rape, tomato, bell pepper, melons, cabbage, potatoes and apples.

Examples of trees include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which may be mentioned are: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus.*

Particularly preferred trees which may be mentioned are: from the tree species *Pinus: P. radiate, P. ponderosa, P. contorta, P. sylvestre, P. strobes*; from the tree species *Eucalyptus: E. grandis, E. globulus, E. camadentis.*

Very particularly preferred trees which may be mentioned are: horse chestnut, Platanaceae, linden tree, maple tree.

The present invention can also be applied to any turfgrasses, including cool-season turfgrasses and warm-season turfgrasses. Examples of cool-season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchard grass (*Dactylis glomerata* L.), weeping alkaligrass (*Puccinellia distans* (L.) Parl.) and crested dog's-tail (*Cynosurus cristatus* L.).

Examples of warm-season turfgrasses are Bermuda grass (*Cynodon* spp. L. C. Rich), zoysia grass (*Zoysia* spp. Willd.), St. Augustine grass (*Stenotaphrum secundatum* Walt Kuntze), centipede grass (*Eremochloa ophiuroides* Munro Hack.), carpet grass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Cool-season turfgrasses are generally preferred for the use in accordance with the invention. Particular preference is given to bluegrass, bentgrass and redtop, fescues and ryegrasses. Bentgrass is especially preferred.

The active compounds of the formula (I) and their compositions are suitable for controlling animal pests in the hygiene sector. In particular, the invention can be applied in the domestic sector, in the hygiene sector and in the protection of stored products, especially for controlling insects, arachnids and mites encountered in enclosed spaces such as dwellings, factory halls, offices, vehicle cabins. For controlling animal pests, the active compounds or compositions are used alone or in combination with other active compounds and/or auxiliaries. They are preferably used in domestic insecticide products. The active compounds according to the invention are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

They are used, for example, in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

In addition, the active compounds of the formula (I) can be used to control a multitude of different pests, including, for example, harmful sucking insects, biting insects and other pests which are plant parasites, stored material pests, pests which destroy industrial material, and hygiene pests including parasites in the animal health sector, and for the control thereof, for example the elimination and eradication thereof. The present invention thus also includes a method for controlling pests.

In the animal health field, i.e. in the field of veterinary medicine, the active compounds according to the present invention are active against animal parasites, in particular ectoparasites or endoparasites. The term endoparasites includes in particular helminths and protozoans, such as coccidia. Ectoparasites are typically and preferably arthropods, in particular insects and acarids.

In the field of veterinary medicine the compounds according to the invention are suitable, with favourable homeotheum toxicity, for controlling parasites which occur in animal breeding and animal husbandry in livestock, breeding, zoo, laboratory, experimental and domestic animals. They are active against all or specific stages of development of the parasites.

Agricultural livestock include, for example, mammals, such as sheep, goats, horses, donkeys, camels, buffaloes, rabbits, reindeers, fallow deers, and in particular cattle and pigs; or poultry such as turkeys, ducks, geese, and in particular chickens; or fish or crustaceans e.g. in aquaculture; or as the case may be insects such as bees.

Domestic animals include, for example, mammals, such as hamsters, guinea pigs, rats, mice, chinchillas, ferrets or in particular dogs, cats; cage birds; reptiles; amphibians or aquarium fish.

According to a preferred embodiment, the compounds according to the invention are administered to mammals.

According to another preferred embodiment, the compounds according to the invention are administered to birds, namely cage birds or in particular poultry.

By using the active compounds according to the invention to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling" as used herein with regard to the animal health field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

Exemplary arthropods include, without any limitation:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp.,

*Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.; from the order of the Heteropterida, for example *Cimex* spp., *Triatoma* spp., *Rhodnius* spp., *Panstrongylus* spp.; as well as nuisance and hygiene pests from the order of the Blattarida.

Further, among the arthropods, the following acari may be mentioned by way of example, without any limitation:

from the subclass of the Acari (Acarina) and the order of the Metastigmata, for example from the family of argasidae like *Argas* spp., *Ornithodorus* spp., *Otobius* spp., from the family of Ixodidae like *Ixodes* spp., *Amblyomma* spp., *Rhipicephalus* (*Boophilus*) spp *Dermacentor* spp., *Haemophysalis* spp., *Hyalomma* spp., *Rhipicephalus* spp. (the original genus of multi-host ticks); from the order of mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Exemplary parasitic protozoa include, without any limitation:

Mastigophora (*Flagellata*), such as, for example, Trypanosomatidae, for example, *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, such as, for example, Trichomonadidae, for example, *Giardia lamblia*, *G. canis*.

Sarcomastigophora (Rhizopoda), such as Entamoebidae, for example, *Entamoeba histolytica*, Hartmanellidae, for example, *Acanthamoeba* sp., *Harmanella* sp.

Apicomplexa (Sporozoa), such as Eimeridae, for example, *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, *E.* spec., *E. stiedai*, *E. suis*, *E. tenella*, *E. truncata*, *E. truttae*, *E. zuernii*, *Globidium* spec., *Isospora belli*, *I. canis*, *I. felis*, *I. ohioensis*, *I. rivolta*, *I.* spec., *I. suis*, *Cystisospora* spec., *Cryptosporidium* spec., in particular *C. parvum*; such as Toxoplasmadidae, for example, *Toxoplasma gondii*, *Hammondia heydornii*, *Neospora caninum*, *Besnoitia besnoitii*; such as Sarcocystidae, for example, *Sarcocystis bovicanis*, *S. bovihominis*, *S. ovicanis*, *S. ovifelis*, *S. neurona*, *S.* spec., *S. suihominis*, such as Leucozoidae, for example, *Leucozytozoon simondi*, such as Plasmodiidae, for example, *Plasmodium berghei*, *P. falciparum*, *P. malariae*, *P. ovale*, *P. vivax*, *P.* spec., such as Piroplasmea, for example, *Babesia argentina*, *B. bovis*, *B. canis*, *B.* spec., *Theileria parva*, *Theileria* spec., such as Adeleina, for example, *Hepatozoon canis*, *H.* spec.

Exemplary pathogenic endoparasites, which are helminths, include platyhelmintha (e.g. monogenea, cestodes and trematodes), nematodes, acanthocephala, and pentastoma. Additional exemplary helminths include, without any limitation:

Monogenea: e.g.: *Gyrodactylus* spp., *Dactylogyrus* spp., *Polystoma* spp.

Cestodes: From the order of the Pseudophyllidea for example: *Diphyllobothrium* spp., *Spirometra* spp., *Schistocephalus* spp., *Ligula* spp., *Bothridium* spp., *Diplogonoporus* spp.

From the order of the Cyclophyllida for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of the Digenea for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.

Nematodes: Trichinellida for example: *Trichuris* spp., *Capillaria* spp., *Trichomosoides* spp., *Trichinella* spp.

From the order of the Tylenchida for example: *Micronema* spp., *Strongyloides* spp.

From the order of the Rhabditina for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.

From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal keeping, the administration of the active compounds according to the invention is carried out by methods generally known in the art, such as enterally, parenterally, dermally or nasally in the form of suitable preparations. Administration can be carried out prophylactically or therapeutically.

Thus, one embodiment of the present invention refers to compounds according to the invention for use as a medicament.

Another aspect refers to compounds according to the invention for use as an antiendoparasitical agent, in particular a helminthicidal agent or antiprotozoic agent. For example, compounds according to the invention for use as an antiendoparasitical agent, in particular a helminthicidal agent or antiprotozoic agent, e.g., in animal husbandry, in animal breeding, in animal housing, in the hygiene sector.

Yet another aspect refers to compounds according to the invention for use as an antiectoparasitical agent, in particular an arthropodicidal agent such as an insecticidal agent or acaricidal agent. For example, compounds according to the invention for use as an antiectoparasitical agent, in particular an arthropodicidal agent such as an insecticidal agent or acaricidal agent, e.g., in animal husbandry, in animal breeding, in animal housing, in the hygiene sector.

The active compounds of the formula (I) and compositions comprising them are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protecting wood is particularly preferred.

In one embodiment according to the invention, the compositions according to the invention comprise at least one further insecticide and/or at least one fungicide.

In a further embodiment, this composition according to the invention is a ready-to-use composition, i.e. it can be applied to the material in question without further modifications. Suitable further insecticides or fungicides are those mentioned above.

Surprisingly, it has also been found that the active compounds and compositions according to the invention can be employed for protecting objects which come into contact with saltwater or brackish water, in particular hulls, screens, nets, buildings, moorings and signalling systems, against fouling. Likewise, the active compounds and compositions according to the invention can be used alone or in combinations with other active compounds as antifouling compositions.

The Preparation and Use Examples which follow illustrate the invention without limiting it.

PREPARATION EXAMPLES

Synthesis Example 1

2-BromoN-[1-(2-methylphenyl)-1H-pyrazol-3-yl]benzamide (Compound I-1-1 in Table 1)

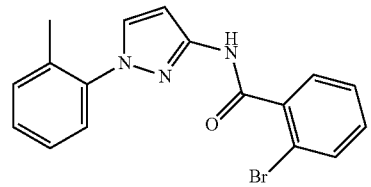 [SMILES: Cc1ccccc1-n1ccc(NC(=O)c2ccccc2Br)n1]

1-(2-Methylphenyl)-1H-pyrazole-3-amine (255 mg) was initially charged in N,N-dimethylformamide (2 ml), 2-(7-aza-1H-benzotriazol-1-yl)-1,1,3,3-tetramethyluronium hexafluorophosphate (482 mg) and diisopropylethylamine (0.59 ml) were added at room temperature and the mixture was stirred for 1 h. A solution of 2-bromobenzoic acid (200 mg) in N,N-dimethylformamide (1 ml) was then added, and the mixture was stirred for a further 2 h. Ice-cold water was then added, and the reaction mixture was extracted with dichloromethane. The combined organic phases were washed successively with sodium bicarbonate solution, water and saturated sodium chloride solution, dried over sodium sulphate and concentrated to dryness under reduced pressure. The residue was purified by column chromatography on silica gel using the mobile phase petroleum ether/ethyl acetate (isocratic with 12% ethyl acetate in petroleum ether). This gave 150 mg of the title compound. HPLC-MS: log P=2.79; mass (m/z): 356.0 (M+H)$^+$; $^1$H-NMR (DMSO-D$_6$) 2.26 (s, 3H), 6.87 (d, 1H), 7.32-7.42 (m, 5H), 7.44-7.48 (m, 1H), 7.52-7.54 (m, 1H), 7.68-7.70 (m, 1H), 7.98 (d, 1H), 11.13 (br. s, 1H).

Synthesis Example 2

2-Chloro-N-[1-(2,6-dimethylphenyl)-1H-pyrazol-3-yl]benzamide (Compound I-1-61 in Table 1)

Step 1: 1-(2,6-Dimethylphenyl)-1H-pyrazole-3-amine (via route B-1)

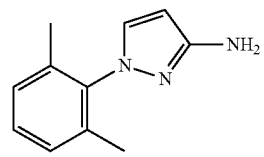

2,6-Dimethylphenylhydrazine hydrochloride (3.50 g) was initially charged in ethanol (30 ml), sodium methoxide solution (3.29 g in 20 ml of ethanol) and 3-ethoxyacrylonitrile (2.95 g) were added and the mixture was heated under reflux for 9 h and then stirred at room temperature overnight. The reaction mixture was then concentrated under reduced pressure, taken up in ethyl acetate, washed with water, dried over sodium sulphate and concentrated to dryness under reduced pressure. The residue was initially purified by column chromatography on silica gel using the mobile phase cyclohexane/ethyl acetate (gradient=2 h from 100% cyclohexane to 100% ethyl acetate) and then chromatographed by preparative HPLC using the mobile phase water/acetonitrile (gradient=40 min from 10% acetonitrile in water to 100% acetonitrile). This gave 39 mg of the title compound. HPLC-MS: log P=0.62; mass (m/z): 188.1 (M+H)$^+$; $^1$H-NMR (CD$_3$CN) 2.00 (s, 6H), 4.03 (br. s, 2H), 5.57 (d, 1H), 7.21-7.23 (m, 2H), 7.30-7.33 (m, 1H), 7.36 (d, 1H).

Step 2: 2-Chloro-N-[1-(2,6-dimethylphenyl)-1H-pyrazol-3-yl]benzamide

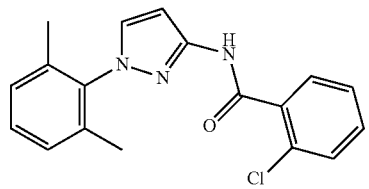 [SMILES: Cc1cccc(C)c1-n1ccc(NC(=O)c2ccccc2Cl)n1]

1-(2,6-Dimethylphenyl)-1H-pyrazole-3-amine (37 mg) was initially charged in dichloromethane (2 ml), triethylamine (0.14 ml) and a solution of 2-chlorobenzoyl chloride (35 mg) in dichloromethane (1 ml) were added at 0° C. and the mixture was stirred at room temperature overnight. The reaction mixture was then diluted with dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 15 mg of the title compound. HPLC-MS: log P=2.63; mass (m/z): 324.1 (M+H)$^+$; $^1$H-NMR (CD$_3$CN) 1.96 (s, 6H), 6.71 (d, 1H), 7.18-7.20 (m, 2H), 7.29-7.44 (m, 6H), 7.65-7.66 (d, 1H), 8.46 (br. s, 1H).

Synthesis Example 3

2-Bromo-N-[1-(2,3-difluorophenyl)-1H-pyrazol-3-yl]benzamide (Compound I-1-63 in Table 1)

Step 1: 1-(2,3-Difluorophenyl)-1H-pyrazole-3-amine (via route B-1)

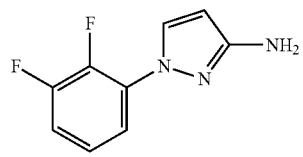 [SMILES: Nc1ccn(-c2cccc(F)c2F)n1]

2,3-Difluorophenylhydrazine hydrochloride (5.00 g) was initially charged in ethanol (30 ml), sodium methoxide solution (4.49 g in 20 ml of ethanol) and 3-ethoxyacrylonitrile (4.03 g) were added and the mixture was heated under reflux overnight. The reaction mixture was then concentrated under reduced pressure, taken up in ethyl acetate, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 1.79 g of the title compound. HPLC-MS: log P=1.56; mass (m/z): 196.0 (M+H)$^+$; $^1$H-NMR (CD$_3$CN) 4.26 (br. s, 2H), 5.89 (d, 1H), 7.05-7.12 (m, 1H), 7.16-7.22 (m, 1H), 7.54-7.59 (m, 1H), 7.82-7.84 (m, 1H). 193 mg of 1-(2-ethoxy-3-fluorophenyl)-1H-pyrazole-3-amine were obtained as a by-product: HPLC-MS: log P=2.04; mass (m/z): 222.1 (M+H)$^+$; $^1$H-NMR (CD$_3$CN) 1.32 (t, 3H), 4.08 (q, 2H), 4.56 (br. s, 2H), 4.65 (d, 1H), 7.00-7.11 (m, 3H), 7.46 (d, 1H).

Step 2: 2-Bromo-N-[1-(2,3-difluorophenyl)-1H-pyrazol-3-yl]benzamide

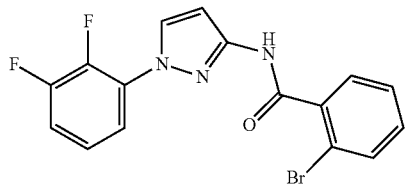 [SMILES: O=C(Nc1ccn(-c2cccc(F)c2F)n1)c1ccccc1Br]

1-(2,3-Difluorophenyl)-1H-pyrazole-3-amine (100 mg) was initially charged in dichloromethane (2 ml), triethylamine (0.36 ml) and a solution of 2-bromobenzoyl chloride (113 mg) in dichloromethane (1 ml) were added at 0° C. and the mixture was stirred at room temperature overnight. The reaction mixture was then diluted with dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 116 mg of the title compound. HPLC-MS: log P=2.97; mass (m/z): 376.0 (M+H)$^+$; $^1$H-NMR (CD$_3$CN) 7.03-7.04 (m, 1H), 7.20-7.29 (m, 2H), 7.36-7.47 (m, 2H), 7.53-7.58 (m, 2H), 7.66-7.68 (m, 1H), 8.03-8.04 (m, 1H), 9.30 (br. s, 1H).

Synthesis Example 4

N-[1-(2,5-Difluorophenyl)-1H-pyrazol-3-yl]-5-fluoro-1-methyl-3-(trifluoromethyl)-1H-pyrazole-4-carboxamide (Compound I-1-72 in Table 1)

Step 1: 1-(2,5-Difluorophenyl)-1H-pyrazole-3-amine (via route B-1)

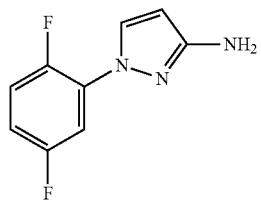 [SMILES: Nc1ccn(-c2cc(F)ccc2F)n1]

2,5-Difluorophenylhydrazine (3.62 g) was initially charged in ethanol (10 ml), sodium methoxide solution (4.07 g in 10 ml of ethanol) and 3-ethoxyacrylonitrile (3.66 g) were added and the mixture was heated under reflux overnight. The reaction mixture was then concentrated under reduced pressure, taken up in ethyl acetate, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 2.88 g of the title compound. HPLC-MS: log P=1.58; mass (m/z): 196.1 (M+H)+; ¹H-NMR (CD₃CN) 4.26 (br. s, 2H), 5.87 (d, 1H), 6.87-6.93 (m, 1H), 7.21-7.28 (m, 1H), 7.53-7.58 (m, 1H), 7.86-7.88 (m, 1H).

Step 2: N-[1-(2,5-Difluorophenyl)-1H-pyrazol-3-yl]-5-fluoro-1-methyl-3-(trifluoromethyl)-1H-pyrazole-4-carboxamide

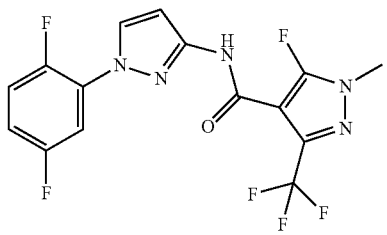 [SMILES: Cn1nc(C(F)(F)F)c(C(=O)Nc2ccn(-c3cc(F)ccc3F)n2)c1F]

5-Fluoro-1-methyl-3-(trifluoromethyl)-1H-pyrazole-4-carboxylic acid (130 mg) was initially charged in dichloromethane (4 ml), 1-ethyl-3-(3-dimethylaminopropyl)carbodiimide (147 mg) and 1-hydroxy-1-H-benzotriazole (104 mg) were added at 0° C. and the mixture was stirred for 30 min. A solution of 1-(2,5-difluorophenyl)-1H-pyrazole-3-amine (100 mg) in dichloromethane (1 ml) was then added, and the mixture was stirred at room temperature overnight. The reaction mixture was then diluted with dichloromethane, washed with water, dried over sodium sulphate and concentrated to dryness under reduced pressure. The residue was initially purified by column chromatography on silica gel using the mobile phase cyclohexane/ethyl acetate (gradient=2 h from 100% cyclohexane to 100% ethyl acetate) and then chromatographed by preparative HPLC using the mobile phase water/acetonitrile (gradient=40 min from 10% acetonitrile in water to 100% acetonitrile). This gave 16 mg of the title compound. HPLC-MS: log P=2.93; mass (m/z): 390.1 (M+H)+; ¹H-NMR (CD₃CN) 3.85 (s, 3H), 6.97 (d, 1H), 7.07-7.14 (m, 1H), 7.34-7.40 (m, 1H), 7.61-7.66 (m, 1H), 8.09-8.10 (m, 1H), 9.08 (br. s, 1H).

Synthesis Example 5

2-Chloro-N-[1-(2-ethoxy-6-fluorophenyl)-1H-pyrazol-3-yl]benzamide (Compound I-1-117 in Table 1)

Step 1: 1-(2-Ethoxy-6-fluorophenyl)-1H-pyrazole-3-amine (via route B-1)

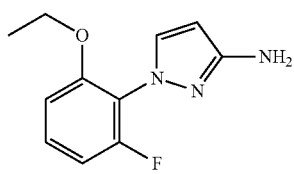 [SMILES: CCOc1cccc(F)c1-n1ccc(N)n1]

2,6-Difluorophenylhydrazine (5.00 g) was initially charged in ethanol (30 ml), sodium methoxide solution (4.49 g in 20 ml of ethanol) and 3-ethoxyacrylonitrile (4.03 g) were added and the mixture was heated under reflux overnight. The reaction mixture was then concentrated under reduced pressure, taken up in ethyl acetate, washed with water, dried over sodium sulphate and concentrated to dryness under reduced pressure. The residue was then once more dissolved in ethanol (50 ml) and heated under reflux for a further night. The reaction mixture was then once more concentrated under reduced pressure, taken up in ethyl acetate, washed with water, dried over sodium sulphate and concentrated to dryness under reduced pressure. The residue was then purified by column chromatography on silica gel using the mobile phase cyclohexane/ethyl acetate (gradient=2 h from 100% cyclohexane to 100% ethyl acetate). This gave 152 mg of the title compound. HPLC-MS: log P=1.47; mass (m/z): 222.1 (M+H)+; ¹H-NMR (CD₃CN) 1.27 (t, 3H), 3.80-4.20 (m, 4H), 5.75 (d, 1H), 6.81-6.86 (m, 1H), 6.90-6.92 (m, 1H), 7.31-7.36 (m, 2H).

Step 2: 2-Chloro-N-[1-(2-ethoxy-6-fluorophenyl)-1H-pyrazol-3-yl]benzamide

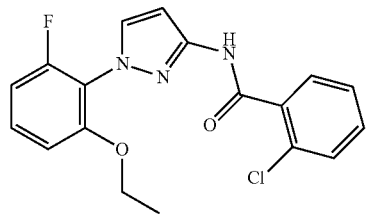 [SMILES: CCOc1cccc(F)c1-n1ccc(NC(=O)c2ccccc2Cl)n1]

1-(2-Ethoxy-6-fluorophenyl)-1H-pyrazole-3-amine (71 mg) was initially charged in dichloromethane (2 ml), triethylamine (0.22 ml) and a solution of 2-chlorobenzoyl chloride (56 mg) in dichloromethane (1 ml) were added at 0° C. and the mixture was stirred at room temperature overnight. The reaction mixture was then diluted with dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 60 mg of the title compound. HPLC-MS: log P=2.84; mass (m/z): 360.1 (M+H)+; ¹H-NMR (CD₃CN) 1.30 (t, 3H), 4.12 (q, 2H), 6.89-7.00 (m, 3H), 7.42-7.53 (m, 4H), 7.61-7.62 (m, 1H), 7.66-7.67 (m, 1H), 9.31 (br. s, 1H).

Synthesis Example 6

2-Bromo-N-[1-(2,6-difluorophenyl)-4,5-dihydro-1H-pyrazol-3-yl]benzamide (Compound I-4-2 in Table 2)

Step 1: 1-(2,6-Difluorophenyl)-4,5-dihydro-1H-pyrazole-3-amine (via route C-1)

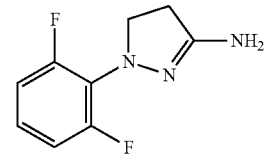 [SMILES: NC1=NN(c2c(F)cccc2F)CC1]

2,6-Difluorophenylhydrazine hydrochloride (2.00 g) was initially charged in ethanol (20 ml), sodium ethoxide (21% strength in ethanol, 3.02 g) was slowly added dropwise at room temperature, the mixture was stirred for 10 min, acrylonitrile (0.80 ml) was added and the mixture was heated under reflux overnight. The reaction mixture was then concentrated under reduced pressure, taken up in dichloromethane, washed with water, dried over sodium sulphate and concentrated to dryness under reduced pressure. What remained were 1.40 g of the crude product which was used without further purification for the next step.

Step 2: 2-Bromo-N-[1-(2,6-difluorophenyl)-4,5-dihydro-1H-pyrazol-3-yl]benzamide

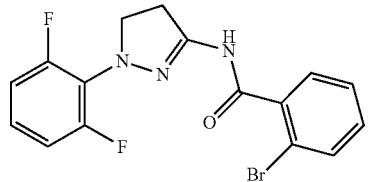 [SMILES: O=C(NC1=NN(c2c(F)cccc2F)CC1)c1ccccc1Br]

1-(2,6-Difluorophenyl)-4,5-dihydro-1H-pyrazole-3-amine (150 mg) was initially charged in dichloromethane (2 ml), triethylamine (0.32 ml) and a solution of 2-bromobenzoyl chloride (167 mg) in dichloromethane (1 ml) were added at 0° C. and the mixture was stirred at 0° C. for 6 h and at room temperature overnight. The reaction mixture was then diluted with dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 15 mg of the title compound. HPLC-MS: log P=2.80; mass (m/z): 380.0 (M+H)$^+$; $^1$H-NMR (CD$_3$CN) 3.45 (t, 2H), 3.79 (t, 2H), 6.93-7.01 (m, 2H), 7.10-7.18 (m, 1H), 7.36-7.40 (m, 1H), 7.43-7.47 (m, 1H), 7.50-7.53 (m, 1H), 7.66-7.68 (m, 1H), 9.04 (br. s, 1H).

Synthesis Example 7

N-[1-(2,6-Difluorophenyl)-1H-pyrazol-3-yl]-3-(trifluoromethyl)pyridine-2-carboxamide (Compound I-1-91 in Table 1)

Step 1: N-[1-(2,6-Difluorophenyl)-4,5-dihydro-1H-pyrazol-3-yl]acetamide

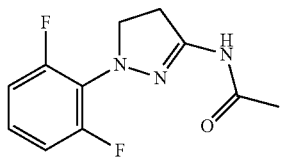 [SMILES: CC(=O)NC1=NN(c2c(F)cccc2F)CC1]

With ice cooling, 1-(2,6-difluorophenyl)-4,5-dihydro-1H-pyrazole-3-amine (1.40 g as a crude mixture from Synthesis Example 6, Step 1) was dissolved in acetic anhydride (6 ml) and stirred at room temperature overnight. The mixture was then diluted with ethyl acetate, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 537 mg of the title compound. HPLC-MS: log P=1.46; mass (m/z): 240.0 (M+H)$^+$; $^1$H-NMR (DMSO-D$_6$) 1.99 (s, 3H), 3.26 (t, 2H), 3.65 (t, 2H), 7.04-7.10 (m, 2H), 7.11-7.18 (m, 1H), 10.59 (br. s, 1H).

Step 2: N-[1-(2,6-Difluorophenyl)-1H-pyrazol-3-yl]acetamide

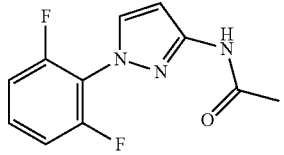 [SMILES: CC(=O)Nc1ccn(-c2c(F)cccc2F)n1]

N-[1-(2,6-Difluorophenyl)-4,5-dihydro-1H-pyrazol-3-yl]acetamide (200 mg) was initially charged in 1,4-dioxane (1 ml), 2,3-dichloro-5,6-dicyano-1,4-benzoquinone (209 mg) was added and the mixture was stirred at room temperature for 30 min. The reaction mixture was filtered and the filtrate was concentrated to dryness under reduced pressure. The residue was purified by column chromatography on silica gel using the mobile phase cyclohexane/ethyl acetate (gradient=2 h from 100% cyclohexane to 100% ethyl acetate). This gave 140 mg of the title compound. HPLC-MS: log P=1.33; mass (m/z): 238.0 (M+H)$^+$; $^1$H-NMR (CD$_3$CN) 2.07 (s, 3H), 6.84 (d, 1H), 7.14-7.20 (m, 2H), 7.47-7.53 (m, 1H), 7.65-7.66 (m, 1H), 8.76 (br. s, 1H).

Step 3: 1-(2,6-Difluorophenyl)-1H-pyrazole-3-amine (via route D-1)

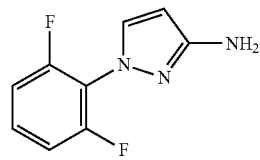 [SMILES: Nc1ccn(-c2c(F)cccc2F)n1]

N-[1-(2,6-Difluorophenyl)-1H-pyrazol-3-yl]acetamide (50 mg) was initially charged in water (1 ml), concentrated hydrochloric acid (0.07 ml) was added and the mixture was heated under reflux for 8 h. The reaction mixture was then made alkaline with concentrated aqueous sodium hydroxide solution and extracted with dichloromethane. The organic phase was concentrated to dryness under reduced pressure. This gave 25 mg of the title compound. HPLC-MS: log P=1.13; mass (m/z): 196.1 (M+H)$^+$; $^1$H-NMR (CD$_3$CN) 4.12 (br. s, 2H), 5.83 (d, 1H), 7.09-7.16 (m, 2H), 7.37-7.44 (m, 1H), 7.46-7.47 (m, 1H).

Step 4: N-[1-(2,6-Difluorophenyl)-1H-pyrazol-3-yl]-3-(trifluoromethyl)pyridine-2-carboxamide

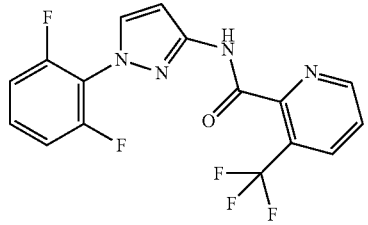 [SMILES: O=C(Nc1ccn(-c2c(F)cccc2F)n1)c1ncccc1C(F)(F)F]

3-(Trifluoromethyl)pyridine-2-carboxylic acid (76 mg) was initially charged in dichloromethane (2 ml), 1-ethyl-3-(3-dimethylaminopropyl)carbodiimide (95 mg) and 1-hydroxy-1H-benzotriazole (67 mg) were added at 0° C. and the mixture was stirred for 1 h. A solution of 1-(2,6-difluorophenyl)-1H-pyrazole-3-amine (66 mg) in dichloromethane (1 ml) was then added, and the mixture was stirred at room temperature overnight. The reaction mixture was then diluted with dichloromethane, washed with water, dried over sodium sulphate and concentrated to dryness under reduced pressure. The residue was initially purified by column chromatography on silica gel using the mobile phase cyclohexane/ethyl acetate (gradient=2 h from 100% cyclohexane to 100% ethyl acetate) and then chromatographed by preparative HPLC using the mobile phase water/acetonitrile (gradient=40 min from 10% acetonitrile in water to 100% acetonitrile). This gave 55 mg of the title compound. HPLC-MS: log P=2.22; mass (m/z): 369.0 (M+H)$^+$; $^1$H-NMR (CD$_3$CN) 6.98-6.99 (m, 1H), 7.17-7.21 (m, 2H), 7.48-7.55 (m, 1H), 7.66-7.73 (m, 1H), 7.76-7.77 (m, 1H), 8.08-8.10 (m, 1H), 8.80-8.82 (m, 1H), 9.30 (br. s, 1H).

Synthesis Example 8

N-[1-(2,6-Dichlorophenyl)-1H-pyrazol-3-yl]-2-iodobenzamide (Compound I-1-123 in Table 1)

Step 1: 1-(2,6-Dichlorophenyl)-1H-pyrazole-3-amine (via route B-1)

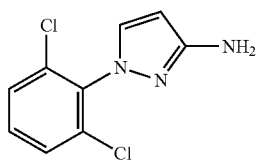 [SMILES: Nc1ccn(-c2c(Cl)cccc2Cl)n1]

2,6-Dichlorophenylhydrazine (10.0 g) was initially charged in ethanol (65 ml), sodium methoxide solution (3.04 g in 35 ml of ethanol) and 3-ethoxyacrylonitrile (6.82 g) were added, and the mixture was stirred at 80° C. for 12 h and at room temperature for 2 d. The reaction mixture was then concentrated under reduced pressure, taken up in ethyl acetate, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 832 mg of the title compound. HPLC-MS: log P=1.47; mass (m/z): 228.1 (M+H)$^+$; $^1$H-NMR (CD$_3$CN) 4.09 (br. s, 2H), 5.81 (d, 1H), 7.35-7.43 (m, 2H), 7.51-7.53 (m, 2H).

Step 2: N-[1-(2,6-Dichlorophenyl)-1H-pyrazol-3-yl]-2-iodobenzamide

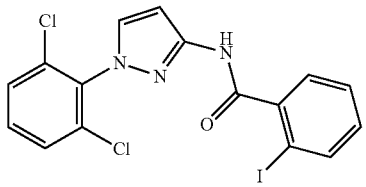 [SMILES: O=C(Nc1ccn(-c2c(Cl)cccc2Cl)n1)c1ccccc1I]

1-(2,6-Dichlorophenyl)-1H-pyrazole-3-amine (150 mg) was initially charged in dichloromethane (2 ml), triethylamine (0.28 ml) and a solution of 2-iodobenzoyl chloride (175 mg) in dichloromethane (1 ml) were added at 0° C. and the mixture was stirred at room temperature overnight. The reaction mixture was then diluted with dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 150 mg of the title compound. HPLC-MS: log P=3.04; mass (m/z): 457.9 (M+H)$^+$; $^1$H-NMR (CD$_3$CN) 6.99-7.00 (m, 1H), 7.18-7.23 (m, 1H), 7.46-7.52 (m, 3H), 7.56-7.58 (m, 2H), 7.66-7.67 (m, 1H), 7.94-7.96 (m, 1H), 9.16 (br. s, 1H).

Synthesis Example 9

N-[1-(3,5-Difluoropyridin-2-yl)-1H-pyrazol-3-yl]-2,6-difluorobenzamide (Compound I-1-146 in Table 1)

Step 1: 1-(3,5-Difluoropyridin-2-yl)-1H-pyrazole-3-amine (via route A-1)

1H-Pyrazole-3-amine (1.80 g) was initially charged in acetonitrile (50 ml), 2,3,5-trifluoropyridine (2.88 g) and potassium carbonate (5.99 g) were added and the mixture was heated under reflux overnight. The reaction mixture was then concentrated under reduced pressure, taken up in dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 610 mg of the title compound. HPLC-MS: log P=0.81; mass (m/z): 197.1 (M+H)$^+$; $^1$H-NMR (CD$_3$CN) 4.27 (br. s, 2H), 5.88 (d, 1H), 7.56-7.62 (m, 1H), 7.99-8.00 (m, 1H), 8.17-8.18 (m, 1H).

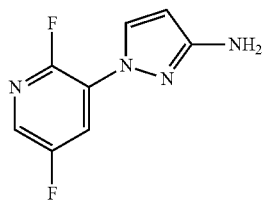 [SMILES: Nc1ccn(-c2cc(F)cnc2F)n1]

410 mg of the isomeric 1-(2,5-difluoropyridin-3-yl)-1H-pyrazole-3-amine were isolated as a further product. HPLC-MS: log P=1.15; mass (m/z): 197.0 (M+H)$^+$; 1H-NMR (CD$_3$CN) 4.39 (br. s, 2H), 5.92 (d, 1H), 7.80-7.82 (m, 1H), 7.94-7.95 (m, 1H), 8.02-8.07 (m, 1H).

Step 2: N-[1-(3,5-Difluoropyridin-2-yl)-1H-pyrazol-3-yl]-2,6-difluorobenzamide

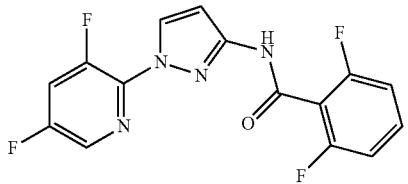 [SMILES: O=C(Nc1ccn(-c2ncc(F)cc2F)n1)c1c(F)cccc1F]

1-(3,5-Difluoropyridin-2-yl)-1H-pyrazole-3-amine (66 mg) was initially charged in dichloromethane (2 ml), triethylamine (0.14 ml) and a solution of 2,6-difluorobenzoyl chloride (59 mg) in dichloromethane (1 ml) were added at 0° C. and the mixture was stirred at room temperature overnight. The reaction mixture was then diluted with dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 107 mg of the title compound. HPLC-MS: log P=2.19; mass (m/z): 337.1 (M+H)$^+$; $^1$H-NMR (CD$_3$CN) 7.02-7.03 (m, 1H), 7.06-7.12 (m, 2H), 7.48-7.56 (m, 1H), 7.65-7.70 (m, 1H), 8.21-8.22 (m, 1H), 8.26-8.27 (m, 1H), 9.51 (br. s, 1H).

Synthesis Example 10

2-Bromo-N-[1-(3,5,6-trifluoropyridin-2-yl)-1H-pyrazol-3-yl]benzamide (Compound I-1-164 in Table 1)

Step 1: 1-(3,5,6-Trifluoropyridin-2-yl)-1H-pyrazole-3-amine (via route A-1)

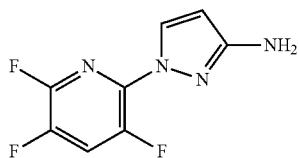 [SMILES: Nc1ccn(-c2nc(F)c(F)cc2F)n1]

1H-Pyrazole-3-amine (2.00 g) was initially charged in acetonitrile (75 ml), 2,3,5,6-tetrafluoropyridine (3.64 g) and potassium carbonate (6.65 g) were added and the mixture was heated under reflux overnight. The reaction mixture was subsequently triturated with tert-butyl methyl ether and filtered. The filtrate was concentrated to dryness under reduced pressure. What remained were 2.51 g of the title compound. HPLC-MS: log P=1.15; mass (m/z): 215.1 (M+H)$^+$; $^1$H-NMR (DMSO-D$_6$) 5.35 (br. s, 2H), 5.86 (d, 1H), 8.00 (d, 1H), 8.40-8.45 (m, 1H).

Step 2: 2-Bromo-N-[1-(3,5,6-trifluoropyridin-2-yl)-1H-pyrazol-3-yl]benzamide

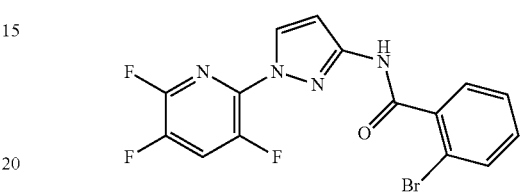

Analogously to Synthesis Example 9 Step 2, 1-(3,5,6-trifluoropyridin-2-yl)-1H-pyrazole-3-amine (150 mg) was reacted with 2-bromobenzoyl chloride (169 mg) and triethylamine (0.29 ml) in dichloromethane. Purification by column chromatography gave 145 mg of the title compound. HPLC-MS: log P=2.68; mass (m/z): 396.9 (M+H)$^+$; 1H-NMR [DMSO-D$_6$] 7.02 (d, 1H), 7.38-7.43 (m, 1H), 7.45-7.49 (m, 1H), 7.53-7.55 (m, 1H), 7.68-7.70 (m, 1H), 8.32 (d, 1H), 8.55-8.61 (m, 1H), 11.41 (s, 1H).

Synthesis Example 11

N-[1-(2-Chloropyridin-3-yl)-1H-pyrazol-3-yl]-2-iodobenzamide (Compound I-1-139 in Table 1)

Step 1: 1-(2-Chloropyridin-3-yl)-1H-pyrazole-3-amine (via route A-1)

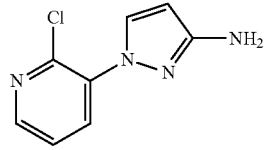 [SMILES: Nc1ccn(-c2cccnc2Cl)n1]

1H-Pyrazole-3-amine (2.00 g) was initially charged in dimethyl sulphoxide (25 ml), 2-chloro-3-fluoropyridine (3.17 g) and potassium carbonate (6.65 g) were added and the mixture was stirred at 120° C. overnight. The reaction mixture was then diluted with dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 2.16 g of the title compound. HPLC-MS: log P=0.62; mass (m/z): 179.1 (M+H)$^+$; $^1$H-NMR (CD$_3$CN) 4.23 (br. s, 2H), 5.87 (d, 1H), 7.41-7.44 (m, 1H), 7.86 (d, 1H), 7.92-7.94 (m, 1H), 8.28-8.30 (m, 1H).

Step 2: N-[1-(2-Chloropyridin-3-yl)-1H-pyrazol-3-yl]-2-iodobenzamide

Analogously to Synthesis Example 9 Step 2, 1-(2-chloropyridin-3-yl)-1H-pyrazole-3-amine (100 mg) was reacted with 2-iodobenzoyl chloride (137 mg) and triethylamine (0.22 ml) in dichloromethane. Purification by column chromatography gave 96 mg of the title compound. HPLC-MS: log P=2.27; mass (m/z): 424.9 (M+H)$^+$; 1H-NMR [CD$_3$CN] 7.02 (d, 1H), 7.19-7.24 (m, 1H), 7.49-7.52 (m, 3H), 7.94-7.96 (m, 2H), 8.00-8.01 (m, 1H), 8.42-8.44 (m, 1H), 9.21 (s, 1H).

Synthesis Example 12

N-[1-(5,6-Difluoropyrimidin-4-yl)-1H-pyrazol-3-yl]-2-(trifluoromethyl)benzamide (Compound I-1-169 in Table 1)

Step 1: 1-(5,6-Difluoropyrimidin-4-yl)-1H-pyrazole-3-amine (via route A-1)

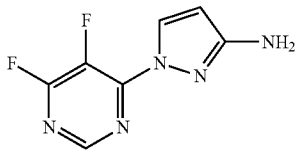

1H-Pyrazole-3-amine (1.25 g) was initially charged in acetonitrile (75 ml), 4,5,6-trifluoropyrimidine (2.02 g) and potassium carbonate (4.16 g) were added and the mixture was heated under reflux overnight. The reaction mixture was then diluted with dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 379 mg of the title compound. HPLC-MS: log P=0.86; mass (m/z): 198.1 (M+H)$^+$; $^1$H-NMR (DMSO-D$_6$) 5.73 (br. s, 2H), 6.01 (d, 1H), 8.34 (d, 1H), 8.46 (s, 1H).

Step 2: N-[1-(5,6-Difluoropyrimidin-4-yl)-1H-pyrazol-3-yl]-2-(trifluoromethyl)benzamide

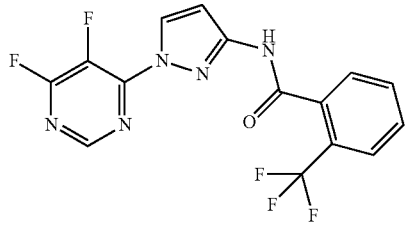 [SMILES: O=C(Nc1ccn(-c2ncnc(F)c2F)n1)c1ccccc1C(F)(F)F]

Analogously to Synthesis Example 9 Step 2, 1-(5,6-difluoropyridin-3-yl)-1H-pyrazole-3-amine (62 mg) was reacted with 2-(trifluoromethyl)benzoyl chloride (66 mg) and triethylamine (0.13 ml) in dichloromethane. Purification by column chromatography gave 6 mg of the title compound. HPLC-MS: log P=2.62; mass (m/z): 370.1 (M+H)$^+$; 1H-NMR [DMSO-D$_6$] 7.12 (d, 1H), 7.69-7.84 (m, 4H), 8.66-8.67 (m, 2H), 11.69 (s, 1H).

Synthesis Example 13

2-Chloro-N-[1-(3-fluoropyrazin-2-yl)-1H-pyrazol-3-yl]benzamide (Compound I-1-174 in Table 1)

Step 1: 1-(3-Fluoropyrazin-2-yl)-1H-pyrazole-3-amine (via route A-1)

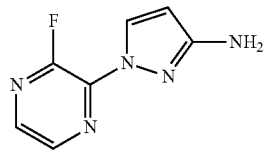 [SMILES: Nc1ccn(-c2nccnc2F)n1]

1H-Pyrazole-3-amine (2.00 g) was initially charged in acetonitrile (75 ml), 2,3-difluoropyrazine (2.79 g) and potassium carbonate (6.65 g) were added and the mixture was heated under reflux overnight. The reaction mixture was then diluted with dichloromethane, washed with water, dried over sodium sulphate and concentrated to dryness under reduced pressure. The residue was triturated with tert-butyl methyl ether and the precipitated solid was separated off, washed and dried. This gave 2.24 g of the title compound. HPLC-MS: log P=0.49; mass (m/z): 180.0 (M+H)$^+$; $^1$H-NMR [DMSO-D$_6$] 5.44 (br. s, 2H), 5.92 (d, 1H), 8.07-8.09 (m, 1H), 8.22 (d, 1H), 8.52-8.54 (s, 1H).

Step 2: 2-Chloro-N-[1-(3-fluoropyrazin-2-yl)-1H-pyrazol-3-yl]benzamide

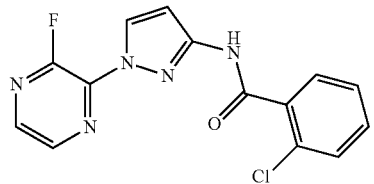 [SMILES: O=C(Nc1ccn(-c2nccnc2F)n1)c1ccccc1Cl]

Analogously to Synthesis Example 9 Step 2, 1-(3-fluoropyrazin-2-yl)-1H-pyrazole-3-amine (150 mg) was reacted with 2-chlorobenzoyl chloride (162 mg) and triethylamine (0.35 ml) in dichloromethane. Purification by column chromatography gave 188 mg of the title compound. HPLC-MS: log P=2.03; mass (m/z): 318.1 (M+H)$^+$; 1H-NMR [DMSO-D$_6$] 7.08 (d, 1H), 7.41-7.59 (m, 4H), 8.30-8.31 (m, 1H), 8.51 (d, 1H), 8.54-8.55 (m, 1H), 11.49 (s, 1H).

Synthesis Example 14

2-Chloro-N-[1-(2-chlorophenyl)-1H-pyrazol-3-yl]benzamide (Compound I-1-20 in Table 1)

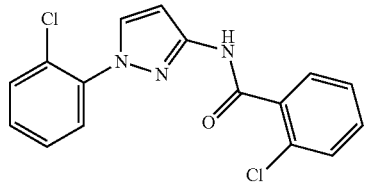 [SMILES: O=C(Nc1ccn(-c2ccccc2Cl)n1)c1ccccc1Cl]

Analogously to Synthesis Example 9 Step 2, 1-(2-chloropyridin-3-yl)-1H-pyrazole-3-amine (300 mg) was reacted with 2-chlorobenzoyl chloride (271 mg) and triethylamine (1.08 ml) in dichloromethane. Purification by column chromatography gave 386 mg of the title compound. HPLC-MS: log P=2.80; mass (m/z): 332.0 (M+H)$^+$; $^1$H-NMR (CD$_3$CN) 6.97 (d, 1H), 7.34-7.55 (m, 6H), 7.58-7.61 (m, 2H), 7.88 (d, 1H), 9.22 (br. s, 1H).

Synthesis Example 15

2-Chloro-N-[1-(2-chlorophenyl)-1H-pyrazol-3-yl]-N-methylbenzamide (Compound I-1-21 in Table 1)

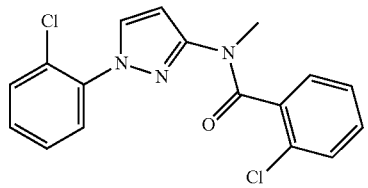 [SMILES: CN(C(=O)c1ccccc1Cl)c1ccn(-c2ccccc2Cl)n1]

2-Chloro-N-[1-(2-chlorophenyl)-1H-pyrazol-3-yl]benzamide (100 mg) was initially charged in tetrahydrofuran (2 ml), sodium hydride (13 mg) was added at 0° C. and the mixture was stirred with cooling for 30 min. Iodomethane (0.02 ml) was then added, and the mixture was stirred at 0° C. for a further 6 h and at room temperature overnight. The mixture was then diluted with ethyl acetate, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 84 mg of the title compound. HPLC-MS: log P=3.14; mass (m/z): 346.0 (M+H)$^+$; $^1$H-NMR (CD$_3$CN) (2 rotamers about 2:1) 3.28; 3.46 (2 s, 3H), 6.02; 7.94 (2 m, 1H), 7.14-7.63 (m, 9H).

Synthesis Example 16

2-Chloro-N-[1-(2-chlorophenyl)-4-fluoro-1H-pyrazol-3-yl]benzamide (Compound I-1-27 in Table 1)

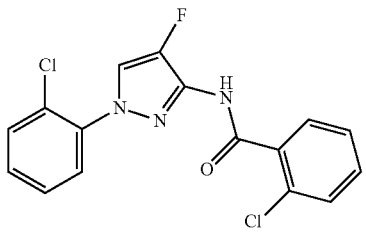 [SMILES: O=C(Nc1nn(-c2ccccc2Cl)cc1F)c1ccccc1Cl]

Under argon, 2-chloro-N-[1-(2-chlorophenyl)-1H-pyrazol-3-yl]benzamide (151 mg) was initially charged in acetonitrile (2 ml), Selectfluor (646 mg) was added and the mixture was stirred at room temperature for 2 d. The reaction mixture was then taken up in dichloromethane and filtered, and the filtrate was concentrated to dryness under reduced pressure. The residue was initially purified by column chromatography on silica gel using the mobile phase cyclohexane/ethyl acetate (gradient=2 h from 100% cyclohexane to 100% ethyl acetate) and then chromatographed by preparative HPLC using the mobile phase water/acetonitrile (gradient=40 min from 10% acetonitrile in water to 100% acetonitrile).

This gave 12 mg of the title compound. HPLC-MS: log P=2.70; mass (m/z): 350.0 (M+H)$^+$; $^1$H-NMR (DMSO-D$_6$) 7.44-7.62 (m, 7H), 7.68-7.71 (m, 1H), 8.39 (d, 1H), 10.73 (s, 1H).

Synthesis Example 17

N-[4-Chloro-1-(2-chlorophenyl)-1H-pyrazol-3-yl]-2-(trifluoromethyl)benzamide (Compound I-1-15 in Table 1)

Step 1: 4-Chloro-1-(2-chlorophenyl)-1H-pyrazole-3-amine (via route F-1)

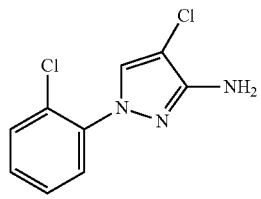

1-(2-Chlorophenyl)-1H-pyrazole-3-amine (266 mg) was initially charged in tetrahydrofuran (9 ml), N-chlorosuccinimide (202 mg) was added and the mixture was stirred at room temperature for 4 h. The reaction mixture was then poured onto ice, stirred vigorously and extracted with ethyl acetate. The organic phase was dried over sodium sulphate and concentrated to dryness under reduced pressure. This gave 413 mg of the crude title compound which was reacted further without further purification. HPLC-MS: log P=2.14; mass (m/z): 228.1 (M+H)$^+$; $^1$H-NMR (CD$_3$CN) 7.34-7.43 (m, 2H), 7.50-7.56 (m, 2H), 7.83 (s, 1H).

Step 2: N-[4-Chloro-1-(2-chlorophenyl)-1H-pyrazol-3-yl]-2-(trifluoromethyl)benzamide

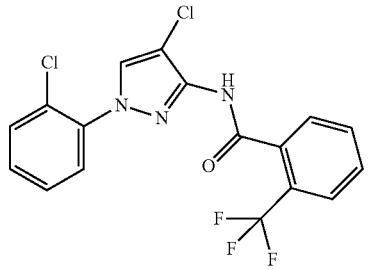

4-Chloro-1-(2-chlorophenyl)-1H-pyrazole-3-amine (66 mg) was initially charged in toluene (2 ml), triethylamine (0.28 ml) and a solution of 2-(trifluoromethyl)benzoyl chloride (140 mg) in toluene (1 ml) were added at 0° C. and the mixture was stirred at 80° C. overnight. Silver(I) cyanide (117 mg) was then added, and the mixture was stirred at room temperature for a further 2 days. The reaction mixture was subsequently diluted with ethyl acetate, washed with water, dried over sodium sulphate and concentrated to dryness under reduced pressure. The residue was initially purified by column chromatography on silica gel using the mobile phase cyclohexane/ethyl acetate (gradient=2 h from 100% cyclohexane to 100% ethyl acetate) and then chromatographed by preparative HPLC using the mobile phase water/acetonitrile (gradient=40 min from 10% acetonitrile in water to 100% acetonitrile). This gave 16 mg of the title compound. HPLC-MS: log P=3.06; mass (m/z): 399.9 (M+H)$^+$; $^1$H-NMR (CD$_3$CN) 7.48-7.89 (m, 8H), 8.05 (s, 1H), 8.68 (br. s, 1H).

Synthesis Example 18

N-[4-Bromo-1-(2-chlorophenyl)-1H-pyrazol-3-yl]-2-(trifluoromethyl)benzamide (Compound I-1-16 in Table 1)

Step 1: 4-Bromo-1-(2-chlorophenyl)-1H-pyrazole-3-amine (via route F-1)

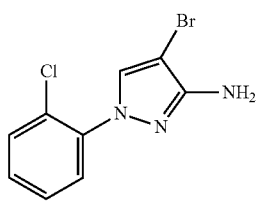 [SMILES: Nc1nn(-c2ccccc2Cl)cc1Br]

1-(2-Chlorophenyl)-1H-pyrazole-3-amine (266 mg) was initially charged in tetrahydrofuran (7 ml), N-bromosuccinimide (269 mg) was added and the mixture was stirred at room temperature for 3 h. The reaction mixture was then poured onto ice, stirred vigorously and extracted with ethyl acetate. The organic phase was dried over sodium sulphate and concentrated to dryness under reduced pressure. This gave 442 mg of the crude title compound which were reacted further without further purification. HPLC-MS: log P=2.23; mass (m/z): 272.0 (M+H)$^+$; $^1$H-NMR (CD$_3$CN) 4.27 (br. s, 2H), 7.35-7.43 (m, 2H), 7.50-7.56 (m, 2H), 7.83 (s, 1H).

Step 2: N-[4-Bromo-1-(2-chlorophenyl)-1H-pyrazol-3-yl]-2-(trifluoromethyl)benzamide

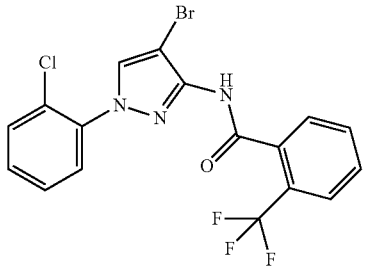 [SMILES: O=C(Nc1nn(-c2ccccc2Cl)cc1Br)c1ccccc1C(F)(F)F]

4-Bromo-1-(2-chlorophenyl)-1H-pyrazole-3-amine (165 mg) was initially charged in toluene (2 ml), triethylamine (0.25 ml) and a solution of 2-(trifluoromethyl)benzoyl chloride (126 mg) in toluene (1 ml) were added at 0° C. and the mixture was stirred at 80° C. overnight. Silver(I) cyanide (97 mg) was then added, and the mixture was stirred at room temperature for a further 2 days. The reaction mixture was subsequently diluted with ethyl acetate, washed with water, dried over sodium sulphate and concentrated to dryness under reduced pressure. The residue was initially purified by column chromatography on silica gel using the mobile phase cyclohexane/ethyl acetate (gradient=2 h from 100% cyclohexane to 100% ethyl acetate) and then chromatographed by preparative HPLC using the mobile phase water/acetonitrile (gradient=40 min from 10% acetonitrile in water to 100% acetonitrile). This gave 18 mg of the title compound. HPLC-MS: log P=3.11; mass (m/z): 444.0 (M+H)$^+$; $^1$H-NMR (CD$_3$CN) 7.48-7.49 (m, 2H), 7.57-7.58 (m, 1H), 7.62-7.63 (m, 1H), 7.69-7.70 (m, 1H), 7.75-7.76 (m, 2H), 7.83-7.84 (m, 1H), 8.06 (s, 1H), 8.59 (br. s, 1H).

Synthesis Example 19

N-[4-Iodo-1-(2-chlorophenyl)-1H-pyrazol-3-yl]-2-(trifluoromethyl)benzamide (Compound I-1-17 in Table 1)

Step 1: 4-Iodo-1-(2-chlorophenyl)-1H-pyrazole-3-amine (via route F-1)

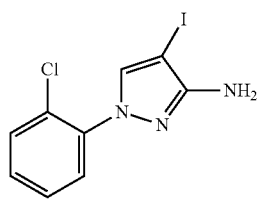 [SMILES: Nc1nn(-c2ccccc2Cl)cc1I]

1-(2-Chlorophenyl)-1H-pyrazole-3-amine (266 mg) was initially charged in tetrahydrofuran (7 ml), N-iodosuccinimide (340 mg) was added and the mixture was stirred at room temperature for 3 h. The reaction mixture was then poured onto ice, stirred vigorously and extracted with ethyl acetate. The organic phase was dried over sodium sulphate and concentrated to dryness under reduced pressure. This gave 557 mg of the crude title compound which were reacted further without further purification. HPLC-MS: log P=2.36;

mass (m/z): 320.0 (M+H)+; 1H-NMR (CD3CN) 7.35-7.42 (m, 2H), 7.49-7.56 (m, 2H), 7.81 (s, 1H).

Step 2: N-[4-Iodo-1-(2-chlorophenyl)-1H-pyrazol-3-yl]-2-(trifluoromethyl)benzamide

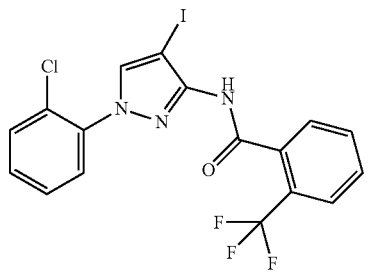 [SMILES: O=C(Nc1nn(-c2ccccc2Cl)cc1I)c1ccccc1C(F)(F)F]

4-Iodo-1-(2-chlorophenyl)-1H-pyrazol-3-amine (180 mg) was initially charged in toluene (3 ml), triethylamine (0.24 ml) and a solution of 3-(trifluoromethyl)benzoyl chloride (117 mg) in toluene (2 ml) were added at 0° C. and the mixture was stirred at 80° C. overnight. Silver(I) cyanide (91 mg) was then added, and the mixture was stirred at room temperature for a further 2 days. The reaction mixture was subsequently diluted with ethyl acetate, washed with water, dried over sodium sulphate and concentrated to dryness under reduced pressure. The residue was initially purified by column chromatography on silica gel using the mobile phase cyclohexane/ethyl acetate (gradient=2 h from 100% cyclohexane to 100% ethyl acetate) and then chromatographed by preparative HPLC using the mobile phase water/acetonitrile (gradient=40 min from 10% acetonitrile in water to 100% acetonitrile). This gave 11 mg of the title compound. HPLC-MS: log P=3.16; mass (m/z): 491.9 (M+H)+; 1H-NMR (CD3CN) 7.48-7.49 (m, 2H), 7.56-7.57 (m, 1H), 7.61-7.64 (m, 1H), 7.68-7.71 (m, 1H), 7.75-7.78 (m, 2H), 7.83-7.85 (m, 1H), 8.05 (s, 1H), 8.60 (br. s, 1H).

The novel 1H-pyrazole-3-amines of the formula (II-1) below were obtained analogously to the given Synthesis Examples: 1-(2,3-Dichlorophenyl)-1H-pyrazole-3-amine: analogously to Synthesis Example 3, Step 1, starting with 2,3-dichlorophenylhydrazine hydrochloride: HPLC-MS: log P=1.97; mass (m/z): 228.0 (M+H)+; 1H-NMR (CD3CN) 4.16 (br. s, 2H), 5.84 (d, 1H), 7.39-7.41 (m, 1H), 7.50-7.52 (m, 1H), 7.59-7.60 (m, 1H), 7.73 (d, 1H).

1-(3-Chloro-2-fluorophenyl)-1H-pyrazole-3-amine: analogously to Synthesis Example 3, Step 1, starting with 3-chloro-2-fluorophenylhydrazine hydrochloride: HPLC-MS: log P=1.90; mass (m/z): 212.0 (M+H)+; 1H-NMR (DMSO-D6) 5.22 (br. s, 2H), 5.82 (d, 1H), 7.25-7.30 (m, 1H), 7.36-7.40 (m, 1H), 7.67-7.71 (m, 1H), 7.90-7.10 (m, 1H). 1-(3-Chloro-2-ethoxyphenyl)-1H-pyrazole-3-amine was obtained as a by-product: HPLC-MS: log P=2.13; mass (m/z): 238.0 (M+H)+; 1H-NMR (DMSO-D6) 1.24 (t, 3H), 3.78 (q, 2H), 5.08 (br. s, 2H), 5.78 (d, 1H), 7.17-7.21 (m, 1H), 7.30-7.33 (m, 1H), 7.56-7.59 (m, 1H), 7.97 (d, 1H).

1-(2-Chloro-6-ethoxyphenyl)-1H-pyrazole-3-amine: analogously to Synthesis Example 5, Step 1, starting with 2-chloro-6-fluorophenylhydrazine hydrochloride: HPLC-MS: log P=2.13; mass (m/z): 238.0 (M+H)+; 1H-NMR (DMSO-D6) 1.34 (t, 3H), 4.11 (q, 2H), 4.99 (br. s, 2H), 7.09-7.12 (m, 1H), 7.24-7.33 (m, 3H).

1-(2-Chloro-4-methylphenyl)-1H-pyrazole-3-amine: analogously to Synthesis Example 3, Step 1, starting with 2-chloro-4-methylphenylhydrazine hydrochloride: HPLC-MS: log P=1.85; mass (m/z): 208.1 (M+H)+; 1H-NMR (CD3CN) 2.35 (s, 3H), 4.08 (br. s, 2H), 5.79 (d, 1H), 7.19-7.20 (m, 1H), 7.36-7.38 (m, 2H), 7.64 (d, 1H).

1-(3,5-Difluoro-6-methylpyridin-2-yl)-1H-pyrazole-3-amine: analogously to Synthesis Example 9, Step 1, starting with 2,3,5-trifluoro-6-methylpyridine: HPLC-MS: log P=1.25; mass (m/z): 211.1 (M+H)+; 1H-NMR (DMSO-D6) 2.40-2.41 (m, 3H), 5.18 (br. s, 2H), 5.80 (d, 1H), 7.97-8.02 (m, 2H). 1-(2,5-Difluoro-6-methylpyridin-3-yl)-1H-pyrazole-3-amine was obtained as a by-product: HPLC-MS: log P=1.50; mass (m/z): 211.1 (M+H)+; 1H-NMR (DMSO-D6) 2.36-2.37 (m, 3H), 5.34 (br. s, 2H), 5.84 (d, 1H), 7.92-7.98 (m, 2H).

1-(5-Chloropyrazin-2-yl)-1H-pyrazole-3-amine: analogously to Synthesis Example 13, Step 1, starting with 2,5-dichloropyrazine: HPLC-MS: (m/z): 196.1 (M+H)+.

1-(6-Fluoropyrazin-2-yl)-1H-pyrazole-3-amine: analogously to Synthesis Example 13, Step 1, starting with 2,6-difluoropyrazine: HPLC-MS: log P=0.90; mass (m/z): 180.1 (M+H)+; 1H-NMR (DMSO-D6) 5.61 (br. s, 2H), 5.94 (d, 1H), 8.18 (d, 1H), 8.36 (d, 1H), 8.78 (d, 1H).

1-(3-Methoxypyrazin-2-yl)-1H-pyrazole-3-amine: analogously to Synthesis Example 13, Step 1, starting with 2-chloro-3-methoxypyrazine.

4-(3-Amino-1H-pyrazol-1-yl)pyrimidine-5-carbonitrile: analogously to Synthesis Example 12, Step 1, starting with 4-chloropyrimidine-5-carbonitrile: HPLC-MS: log P=0.59; mass (m/z): 187.1.

1-(5-Chloro-3-fluoropyridin-2-yl)-1H-pyrazole-3-amine: analogously to Synthesis Example 9, Step 1, starting with 5-chloro-2,3-difluoropyridine: HPLC-MS: log P=1.27; mass (m/z): 213.0 (M+H)+; 1H-NMR (DMSO-D6) 5.30 (s, 2H), 5.86 (d, 1H), 8.12 (d, 1H), 8.17-8.20 (m, 1H), 8.31 (d, 1H).

1-(3-Chloro-5-fluoropyridin-2-yl)-1H-pyrazole-3-amine: analogously to Synthesis Example 9, Step 1, starting with 3-chloro-2,5-difluoropyridine: HPLC-MS: log P=0.98; mass (m/z): 213.0 (M+H)+; 1H-NMR (DMSO-D6) 5.11 (s, 2H), 5.76-5.78 (m, 1H), 7.91-7.92 (m, 1H), 8.23-8.26 (m, 1H), 8.47-8.48 (m, 1H).

Synthesis Example 20

N-[2-(2-Chlorophenyl)-2H-1,2,3-triazol-4-yl]-2-(trifluoromethyl)benzamide (Compound I-2-1 in Table 3)

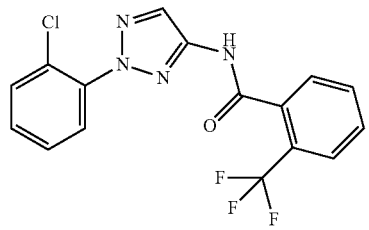 [SMILES: O=C(Nc1cnn(-c2ccccc2Cl)n1)c1ccccc1C(F)(F)F]

Analogously to Synthesis Example 9 Step 2, 2-(2-chlorophenyl)-2H-1,2,3-triazole-4-amine (150 mg) was reacted with 2-(trifluoromethyl)benzoyl chloride (160 mg) and triethylamine (0.32 ml) in dichloromethane. Purification by column chromatography and preparative HPLC gave 171 mg of the title compound. HPLC-MS: log P=3.02; mass (m/z): 367.0 (M+H)+; 1H-NMR (CD3CN) 7.48-7.55 (m, 2H), 7.60-7.66 (m, 2H), 7.68-7.77 (m, 3H), 7.83-7.85 (m, 1H), 8.36 (s, 1H), 9.54 (br. s, 1H).

Synthesis Example 21

N-[2-(2,6-Difluorophenyl)-2H-1,2,3-triazol-4-yl]-2-(trifluoromethyl)benzamide (Compound I-2-35 in Table 5)

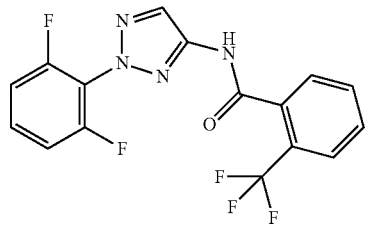 [SMILES: O=C(Nc1cnn(-c2c(F)cccc2F)n1)c1ccccc1C(F)(F)F]

Synthesis scheme for the intermediate 2-(2,6-difluorophenyl)-2H-1,2,3-triazole-4-amine (IX) (via route A-3)

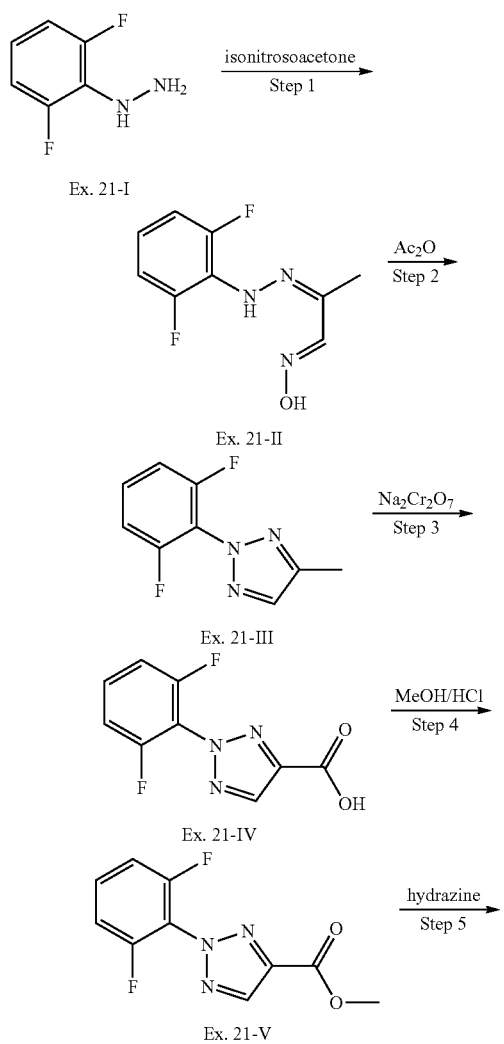

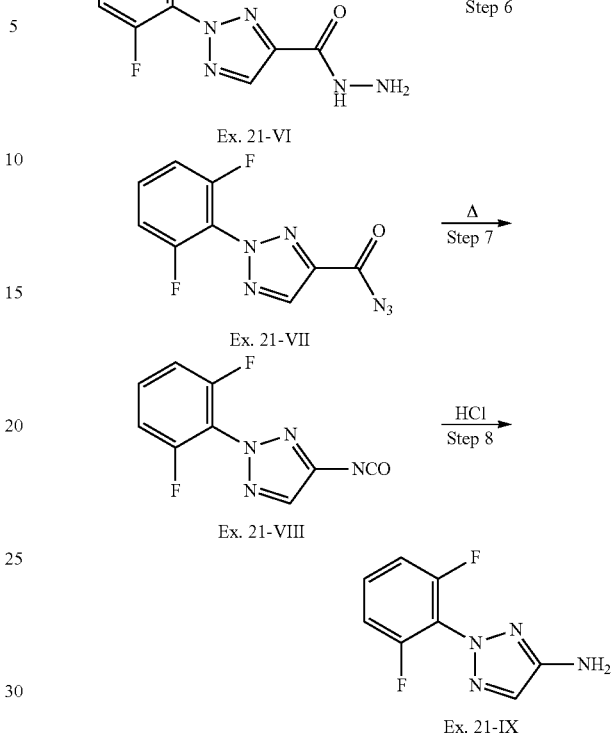

Step 1: 2-[2-(2,6-Difluorophenyl)hydrazinylidene]propanal oxime (Ex. 21-II)

0.1 mol of 2,6-difluorophenylhydrazine (Ex. 21-I) and 0.12 mol of isonitrosoacetone were heated under reflux in ethanol for 3 h. After cooling to room temperature, the precipitated solid was filtered off, washed with ethanol and dried. This gave 75% of theory of the hydrazone oxime (Ex. 21-II).

Step 2: 2-(2,6-Difluorophenyl)-4-methyl-2H-1,2,3-triazole (Ex. 21-III)

A solution of 0.1 mol of the hydrazone oxime (Ex. 21-II) in acetic anhydride was heated slowly to 120° C. and stirred at this temperature for 2 h. Excess acetic anhydride was removed on a rotary evaporator. The methyltriazole formed (Ex. 21-III) (65% of theory) was processed further without further work-up.

Step 3: 2-(2,6-Difluorophenyl)-2H-1,2,3-triazole-4-carboxylic acid (Ex. 21-IV)

A little at a time, 0.2 mol of sodium dichromate was added to a well-stirred solution of 0.1 mol of methyltriazole (Ex. 21-III) in 66% strength sulphuric acid. Each individual portion of dichromate was added only after the yellow-orange colour of the $Cr^{6+}$ in the flask had disappeared. Moreover, the portions were added such that the temperature in the flask remained at about 80-90° C. The mixture was then heated on a steam bath for 1 h. After cooling, the mixture was poured into about the same amount of ice and allowed to stand overnight. The precipitated acid (Ex. 21-IV) was filtered off, washed with water and dried. This gave 50% of theory of the acid (Ex. 21-IV).

Step 4: Methyl 2-(2,6-difluorophenyl)-2H-1,2,3-triazole-4-carboxylate (Ex. 21-V)

Hydrogen chloride was bubbled for 2 h through a boiling solution of the acid (Ex. 21-IV) in methanol. After cooling, white crystals of the ester (Ex. 21-V) were filtered off (85% of theory).

Step 5: 2-(2,6-Difluorophenyl)-2H-1,2,3-triazole-4-carbohydrazide (Ex. 21-VI)

The ester (Ex. 21-V) was boiled with an excess of 1.5 eq. of hydrazine hydrate in ethanol for 4 h. After cooling, the crystals of the hydrazide (Ex. 21-VI) were boiled with water and dried. This gave 90% of theory.

Step 6: 2-(2,6-Difluorophenyl)-2H-1,2,3-triazole-4-carbonyl azide (Ex. 21-VII)

An aqueous solution of sodium nitrite was added to a suspension of the hydrazide (Ex. 21-VI) in 20% strength aqueous hydrochloric acid. After further stirring at 10° C., the crystals of the acyl azide (Ex. 21-VII) were filtered off, washed with water and dried at room temperature under reduced pressure. This gave 75% of theory.

Step 7: 2-(2,6-Difluorophenyl)-2H-1,2,3-triazole-4-carbonyl isocyanate (Ex. 21-VIII)

The dried acyl azide (Ex. 21-VII) was boiled in toluene until the evolution of gas had ended (about 2 h). The toluene was then removed on a rotary evaporator and the viscous residue of the isocyanate (Ex. 21-VIII) was directly reacted further without further purification. This gave about 90% of theory.

Step 8: 2-(2,6-Difluorophenyl)-2H-1,2,3-triazole-4-amine (Ex. 21-IX)

The isocyanate (Ex. 21-VIII) was hydrolysed by 30 min of boiling in hydrochloric acid. Residual volatile substances were removed on a rotary evaporator, and the residue was treated with sodium carbonate solution. The precipitated crystals were filtered off, washed with water and recrystallized from hexane. This gave 70% of theory of the amine (Ex. 21-IX). HPLC-MS: log P=1.16; mass (m/z): 197.0 (M+H)$^+$; $^1$H-NMR (CD$_3$CN) 5.46 (b, 2H), 7.33-7.38 (m, 3H), 7.56-7.64 (m, 1H).

N-[2-(2,6-Difluorophenyl)-2H-1,2,3-triazol-4-yl]-2-(trifluoromethyl)benzamide (Compound I-2-35 in Table 5)

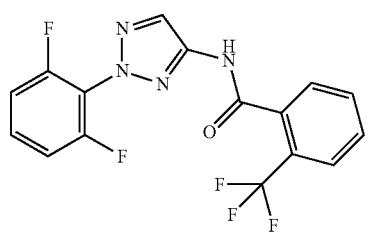 [SMILES: O=C(Nc1cnn(-c2c(F)cccc2F)n1)c1ccccc1C(F)(F)F]

Analogously to Synthesis Example 9 Step 2, 2-(2,6-difluorophenyl)-2H-1,2,3-triazole-4-amine (150 mg) was reacted with 2-(trifluoromethyl)benzoyl chloride (160 mg) and triethylamine (0.21 ml) in 3.9 ml of dichloromethane. Purification by column chromatography and preparative HPLC gave 143 mg of the title compound. HPLC-MS: log P=2.80; mass (m/z): 369.1 (M+H)$^+$; $^1$H-NMR (CD$_3$CN) 7.45-7.49 (m, 2H), 7.70-7.77 (m, 4H), 7.78-7.88 (m, 1H), 8.45 (s, 1H), 11.83 (s, 1H).

Synthesis Example 22

N-[1-(3,5-Difluoropyridin-2-yl)-5-fluoro-1H-indazol-3-yl]-2-(trifluoromethyl)benzamide (Compound I-5-2 in Table 4)

Step 1: 1-(3,5-Difluoropyridin-2-yl)-5-fluoro-1H-indazole-3-amine (via route A-2)

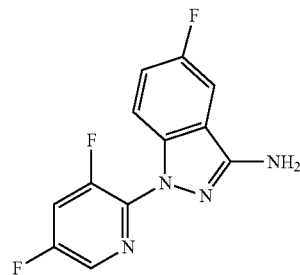 [SMILES: Nc1nn(-c2ncc(F)cc2F)c2ccc(F)cc12]

Under argon, 5-fluoro-1H-indazole-3-amine (100 mg) was initially charged in N,N-dimethylformamide (1 ml), sodium hydride (16 mg) was added and the mixture was stirred at room temperature for 30 min. A solution of 2,3,5-trifluoropyridine (88 mg in 0.5 ml of N,N-dimethylformamide) was added dropwise, and the mixture was stirred at room temperature for 2 days. The reaction mixture was then taken up in ethyl acetate, washed with water, dried over sodium sulphate and concentrated to dryness under reduced pressure. This gave 121 mg of the crude title compound which were reacted further without further purification. HPLC-MS: log P=2.09; mass (m/z): 265.1 (M+H)$^+$; $^1$H-NMR (DMSO-D$_6$) 6.14 (br. s, 2H), 7.31-7.39 (m, 1H), 7.41-7.47 (m, 1H), 7.63-7.71 (m, 1H), 8.07-8.16 (m, 1H), 8.20-8.22 (m, 1H).

Step 2: N-[1-(3,5-Difluoropyridin-2-yl)-5-fluoro-1H-indazol-3-yl]-2-(trifluoromethyl)benzamide

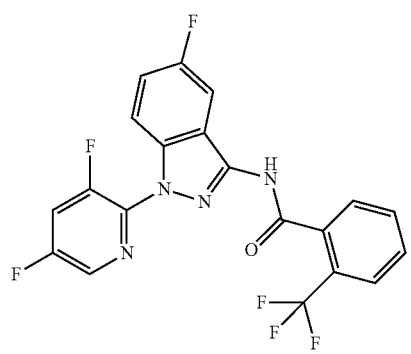 [SMILES: O=C(Nc1nn(-c2ncc(F)cc2F)c2ccc(F)cc12)c1ccccc1C(F)(F)F]

1-(3,5-Difluoropyridin-2-yl)-1H-pyrazole-3-amine (121 mg) was initially charged in acetonitrile (3 ml), potassium carbonate (284 mg) and 2-(trifluoromethyl)benzoyl chloride (287 mg) were added at room temperature and the mixture was stirred overnight. The reaction mixture was then diluted with ethyl acetate, washed with water, dried over sodium sulphate and concentrated to dryness under reduced pressure. The residue was chromatographed by preparative HPLC using the mobile phase water/acetonitrile (gradient=40 min from 10% acetonitrile in water to 100% acetonitrile). This gave 13 mg of the title compound. HPLC-MS: log P=3.37; mass (m/z): 437.1 (M+H)$^+$; $^1$H-NMR (DMSO-D$_6$) 7.47-7.52 (m, 1H), 7.64-7.67 (m, 1H), 7.74-7.77 (m, 1H), 7.81-7.89 (m, 3H), 7.98-8.05 (m, 1H), 8.32-8.45 (m, 1H), 8.57-8.58 (m, 1H), 11.47 (s, 1H).

Synthesis Example 23

N-{1-[3-Fluoro-4-(4-fluorophenyl)pyridin-2-yl]-1H-pyrazol-3-yl}-2-(trifluoromethyl)benzamide (Compound I-1-640 in Table 1)

Step 1: 1-(3-Fluoro-4-iodopyridin-2-yl)-1H-pyrazole-3-amine (via A-1)

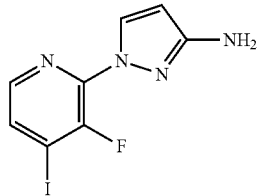 [SMILES: Nc1ccn(-c2nccc(I)c2F)n1]

A mixture of 3-aminopyrazole (0.50 g), 2,3-difluoro-4-iodopyridine (1.45 g), potassium carbonate (3.3 g) and 10 ml anhydrous dimethyl sulphoxide was stirred at 85° C. for 48 hours. For work-up, 100 ml of water were added at room temperature and the mixture was extracted with ethyl acetate. The organic phase was dried with magnesium sulphate and then concentrated completely and chromatographed on silica gel using an ethyl acetate/methanol gradient. This gave 705 mg of the title compound. HPLC-MS: log P=1.38; mass (m/z): 304.9 (M+H)$^+$; $^1$H-NMR (DMSO-D$_6$) 5.91 (m, 1H), 7.62 (m, 1H), 7.85 (m, 1H), 8.08 (m, 1H).

Step 2: N-[1-(3-Fluoro-4-iodopyridin-2-yl)-1H-pyrazol-3-yl]-2-(trifluoromethyl)benzamide (Compound I-1-576 in Table 1)

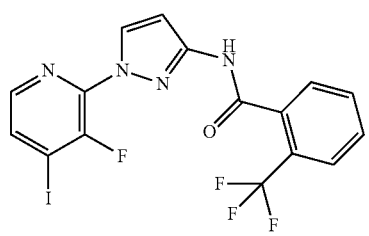 [SMILES: O=C(Nc1ccn(-c2nccc(I)c2F)n1)c1ccccc1C(F)(F)F]

With ice cooling, 2-(trifluoromethyl)benzoyl chloride (412 mg) was added to a solution of 1-(3-fluoro-4-iodopyridin-2-yl)-1H-pyrazole-3-amine (600 mg) and triethylamine (0.83 ml) in dichloromethane (12 ml), and the mixture was stirred at 0° C. for one hour and then warmed to room temperature overnight. The mixture was concentrated completely and the resulting residue was partitioned between ethyl acetate and semisaturated sodium bicarbonate solution. The organic phase was concentrated and chromatographed on silica gel using a methylene chloride/methanol gradient. This gave 650 mg of the title compound. HPLC-MS: log P=2.96; mass (m/z): 476.9 (M+H)$^+$; $^1$H-NMR (CD$_3$CN) 7.05 (m, 1H), 7.6 (br m, 3H), 7.76 (br m, 2H), 7.92 (m, 1H), 8.29 (m, 1H), 9.54 (br s, 1H).

Step 3: N-{1-[3-Fluoro-4-(4-fluorophenyl)pyridin-2-yl]-1H-pyrazol-3-yl}-2-(trifluoromethyl)benzamide

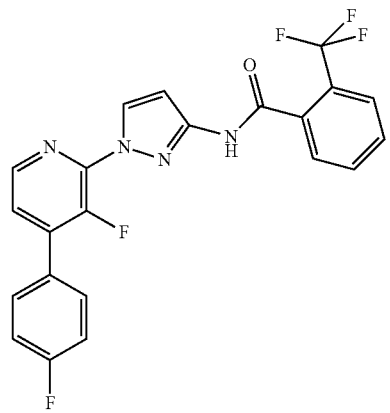 [SMILES: O=C(Nc1ccn(-c2nccc(-c3ccc(F)cc3)c2F)n1)c1ccccc1C(F)(F)F]

A mixture of N-[1-(3-fluoro-4-iodopyridin-2-yl)-1H-pyrazol-3-yl]-2-(trifluoromethyl)benzamide (200 mg), 4-fluoroboronic acid (117 mg), sodium carbonate (170 mg), 1,1'-bis(diphenylphosphino)ferrocenepalladium(II) chloride (15 mg), 1,2-dimethoxyethane (3 ml) and water (1 ml) was heated at 85° C. for 6 hours. The reaction mixture was concentrated, the residue was triturated with ethyl acetate and filtered off and the filtrate was washed with water, dried and concentrated again.

The residue obtained in this manner was chromatographed on silica gel using a cyclohexane/ethyl acetate gradient. This gave 81 mg of the title compound. HPLC-MS: log P=3.40; mass (m/z): 445.1 (M+H)$^+$; $^1$H-NMR (DMSO-D$_6$) 6.99 (m, 1H), 7.42 (m, 2H), 7.61-7.85 (m, 7H), 8.42 (m, 2H), 11.46 (s, 1H).

Synthesis Example 24

2-{[1-(4-Amino-2,6-difluorophenyl)-1H-pyrazol-3-yl]carbamoyl}benzoic acid (Compound I-1-643 in Table 1)

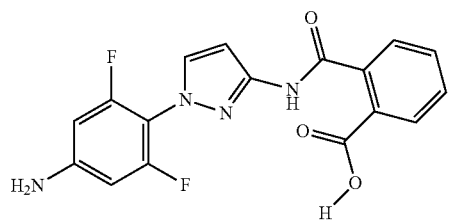 [SMILES: Nc1cc(F)c(-n2ccc(NC(=O)c3ccccc3C(=O)O)n2)c(F)c1]

Step 1: 2-{[1-(2,6-Difluoro-4-nitrophenyl)-1H-pyrazol-3-yl]carbamoyl}benzoic acid

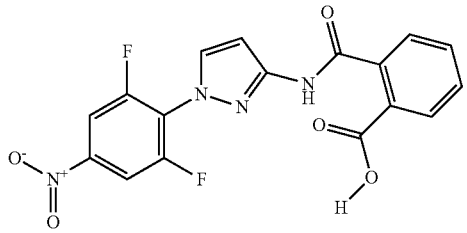 [SMILES: O=C(O)c1ccccc1C(=O)Nc1ccn(-c2c(F)cc([N+](=O)[O-])cc2F)n1]

Under argon and at −20° C., 60% sodium hydride (2.27 g) was added a little at a time to a solution of 2-(1H-pyrazol-3-yl)-1H-isoindole-1,3(2H)-dione (5.90 g) and 3,4,5-trifluoronitrobenzene (5.05 g) in tetrahydrofuran (120 ml). During the addition, the temperature did not exceed −5° C. After 6 hours, the reaction mixture was allowed to warm to room temperature, stirred into 300 ml of water and extracted with ethyl acetate. After drying, the combined organic phases were dried over magnesium sulphate and filtered, and the filtrate was concentrated completely. This gave 8.5 g of the title compound. HPLC-MS: log P=1.85, mass (m/z): 389.0 (M+H)$^+$. The residue obtained in this manner was used for the next step without further purification.

Step 2: 2-{[1-(4-Amino-2,6-difluorophenyl)-1H-pyrazol-3-yl]carbamoyl}benzoic acid

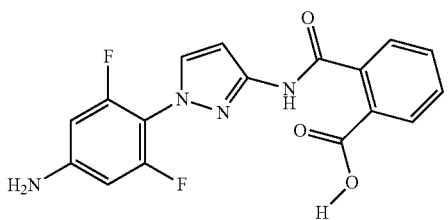 [SMILES: Nc1cc(F)c(-n2ccc(NC(=O)c3ccccc3C(=O)O)n2)c(F)c1]

In an autoclave, a mixture of the above 2-{[1-(2,6-difluoro-4-nitrophenyl)-1H-pyrazol-3-yl]carbamoyl}benzoic acid (6.56 g), methanol (50 ml) and 250 mg Pd/C (10%) was hydrogenated under a hydrogen pressure of 4 bar at room temperature for 4 days. Removal of the catalyst by filtration and concentration of the organic phase by evaporation gave 6.2 g of the title compound having a content of 70% of theory. HPLC-MS: log P=1.38, mass (m/z): 359.1 (M+H)$^+$; $^1$H-NMR (DMSO-D$_6$) 4.10 (m, 2H), 6.07 (s, 2H), 6.33 (m, 2H), 6.85 (m, 1H), 7.41 (m, 2H), 7.67 (m, 1H), 7.74 (m, 1H), 7.77 (br s, 1H)

Synthesis Example 25

N-[1-(3-Cyanopyridin-2-yl)-1H-pyrazol-3-yl]-2-(trifluoromethyl)benzamide (Compound (I-1-575) in Table 1)

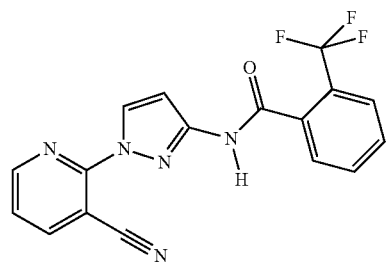 [SMILES: N#Cc1cccnc1-n1ccc(NC(=O)c2ccccc2C(F)(F)F)n1]

Step 1: N-(1H-Pyrazol-3-yl)-2-(trifluoromethyl)benzamide

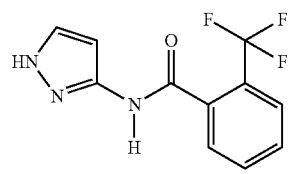 [SMILES: O=C(Nc1cc[nH]n1)c1ccccc1C(F)(F)F]

With exclusion of moisture, a solution of 3-aminopyrazole (43.9 g) and triethylamine (52.4 g) in acetonitrile (400 ml) was stirred at 0° C. for one hour. A solution of 2-(trifluoromethyl)benzoyl chloride (109.1 g) in acetonitrile (50 ml) was then added dropwise such that the internal temperature did not exceed 7° C. The reaction was allowed to warm to room temperature overnight, diluted with 600 ml of water and extracted with ethyl acetate. The combined organic phases were dried over magnesium sulphate, filtered and concentrated. The residue obtained in this manner was dissolved in isopropanol (500 ml) under reflux. After cooling to room temperature, the crystals that had separated out were isolated (48.6 g). This was the title compound with one molar equivalent of isopropanol of crystallization. HPLC-MS: log P=1.33, mass (m/z): 255.9 (M+H)$^+$; $^1$H-NMR (DMSO-D$_6$) 1.03 (m, 6H), 3.77 (m, 1H), 4.33 (m, 1H), 6.60 (m, 1H), 7.60-7.81 (m, 5H), 10.97 (s, 1H), 12.41 (m, 1H),

Step 2: N-[1-(3-Cyanopyridin-2-yl)-1H-pyrazol-3-yl]-2-(trifluoromethyl)benzamide

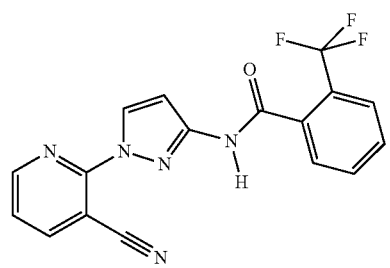 [SMILES: N#Cc1cccnc1-n1ccc(NC(=O)c2ccccc2C(F)(F)F)n1]

A solution of N-(1H-pyrazol-3-yl)-2-(trifluoromethyl)benzamide×isopropanol (222 mg) in 50 ml of dimethylformamide was concentrated to dryness under reduced pressure. The residue was taken up in anhydrous dimethylformamide (3 ml), potassium carbonate was added and the resulting mixture was stirred vigorously for 5 minutes. 2-Chloronicotinonitrile (88 mg) was then added, the mixture was stirred for 6 hours at 50° C., water (50 ml) was then added at room temperature, the mixture was extracted with ethyl acetate and the combined organic phases were dried over magnesium sulphate and evaporated to dryness. Chromatography on silica gel using a cyclohexane/ethyl acetate gradient gave the title compound (149 mg). HPLC-MS: log P=2.55, mass (m/z): 358.0 (M+H)+; $^1$H-NMR (DMSO-D$_6$) 7.06 (m, 1H), 7.53 (m, 1H), 7.69-7.84 (m, 4H), 8.46 (m, 1H), 7.60-7.81 (m, 4H), 8.46 (m, 1H), 8.60 (m, 1H), 8.74 (m, 1H), 11.61 (s, 1H).

The novel 2-(trifluoromethyl)benzamides below were obtained analogously to the given Synthesis Examples:

Synthesis Example 26

N-[1-(2,6-Difluoro-4-nitrophenyl)-1H-pyrazol-3-yl]-2-(trifluoromethyl)benzamide (Compound (I-1-229) in Table 1)

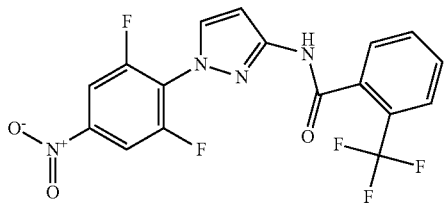 [SMILES: O=C(Nc1ccn(-c2c(F)cc([N+](=O)[O-])cc2F)n1)c1ccccc1C(F)(F)F]

Analogously to Synthesis Example 25, Step 2, starting with 3,4,5-trifluoronitrobenzene: HPLC-MS: log P=2.86; mass (m/z): 413.0 (M+H)+; 1H-NMR (CD$_3$CN) 7.02 (m, 1H), 7.60-7.95 (m, 4H), 8.13 (m, 1H), 8.36 (m, 1H), 11.45 (s, 1H).

Synthesis Example 27

N-{1-[2,6-Difluoro-4-(trifluoromethyl)phenyl]-1H-pyrazol-3-yl}-2-(trifluoromethyl)benzamide (Compound (I-1-230) in Table 1)

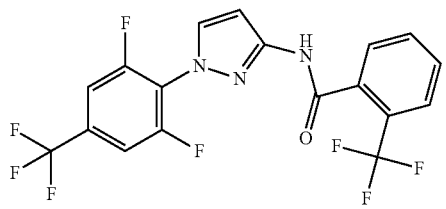 [SMILES: O=C(Nc1ccn(-c2c(F)cc(C(F)(F)F)cc2F)n1)c1ccccc1C(F)(F)F]

Analogously to Synthesis Example 25, Step 2, starting with 1,2,3-trifluoro-5-(trifluoromethyl)benzene: HPLC-MS: log P=3.39; mass (m/z): 436.0 (M+H)+; 1H-NMR (DMSO-D$_6$) 6.98 (m, 1H), 7.68-7.14 (m, 2H), 7.77 (m, 1H), 7.81 (m, 1H), 7.97 (m, 2H), 8.14 (m, 1H), 11.40 (s, 1H).

Synthesis Example 28

N-[1-(4-Cyano-2,6-difluorophenyl)-1H-pyrazol-3-yl]-2-(trifluoromethyl)benzamide (Compound (I-1-228) in Table 1)

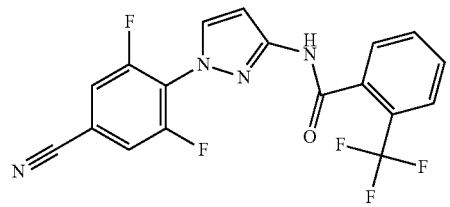 [SMILES: N#Cc1cc(F)c(-n2ccc(NC(=O)c3ccccc3C(F)(F)F)n2)c(F)c1]

Analogously to Synthesis Example 25, Step 2, starting with 3,4,5-trifluorobenzonitrile: HPLC-MS: log P=2.66; mass (m/z): 393.0 (M+H)+; 1H-NMR (DMSO-D$_6$) 6.99 (m, 1H), 7.68-7.71 (m, 2H), 7.75 (m, 1H), 7.82 (m, 1H), 8.09-8.14 (m, 3H), 11.41 (s, 1H).

Synthesis Example 29

N-[1-(2-Cyano-4,6-difluorophenyl)-1H-pyrazol-3-yl]-2-(trifluoromethyl)benzamide (Compound (I-1-393) in Table 1)

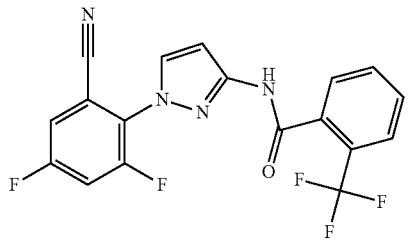 [SMILES: N#Cc1cc(F)cc(F)c1-n1ccc(NC(=O)c2ccccc2C(F)(F)F)n1]

Analogously to Synthesis Example 25, Step 2, starting with 2,3,5-trifluorobenzonitrile: HPLC-MS: log P=2.65; mass (m/z): 393.0 (M+H)+; 1H-NMR (DMSO-D$_6$) 7.00 (m, 1H), 7.68-7.71 (m, 2H), 7.75 (m, 1H), 7.83 (m, 1H), 8.04-8.11 (m, 2H), 8.17 (m, 1H), 11.44 (s, 1H).

Synthesis Example 30

N-[1-(4-Acetyl-2,6-difluorophenyl)-1H-pyrazol-3-yl]-2-(trifluoromethyl)benzamide (Compound (I-1-584) in Table 1)

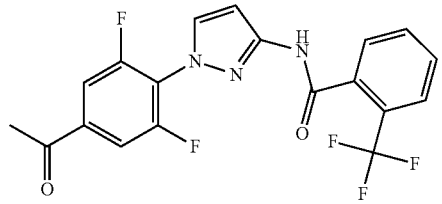 [SMILES: CC(=O)c1cc(F)c(-n2ccc(NC(=O)c3ccccc3C(F)(F)F)n2)c(F)c1]

Analogously to Synthesis Example 25, Step 2, starting with 3,4,5-trifluoroacetophenone: HPLC-MS: log P=2.70;

mass (m/z): 410.0 (M+H)+; 1H-NMR (DMSO-D$_6$) 2.65 (s, 3H), 6.99 (m, 1H), 7.68-7.71 (m, 2H), 7.75 (m, 1H), 7.83 (m, 1H), 7.90-7.93 (m, 2H), 8.11 (m, 1H), 11.44 (s, 1H).

Synthesis Example 31

N-{1-[3-Cyano-6-(trifluoromethyl)pyridin-2-yl]-1H-pyrazol-3-yl}-2-(trifluoromethyl)benzamide (Compound (I-1-569) in Table 1)

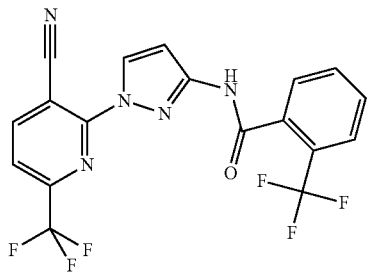 [SMILES: N#Cc1ccc(C(F)(F)F)nc1-n1ccc(NC(=O)c2ccccc2C(F)(F)F)n1]

Analogously to Synthesis Example 25, Step 2, starting with 2-chloro-6-(trifluoromethyl)nicotinonitrile: HPLC-MS: log P=3.41; mass (m/z): 426.1 (M+H)+; 1H-NMR (DMSO-D$_6$) 7.11 (m, 1H), 7.67-7.73 (m, 2H), 7.77 (m, 1H), 7.84 (m, 1H), 7.99 (m, 1H), 8.60 (m, 1H), 8.77 (m, 1H), 11.71 (s, 1H).

Synthesis Example 32

N-{1-[3-Cyano-4-(4-fluorophenyl)pyridin-2-yl]-1H-pyrazol-3-yl}-2-(trifluoromethyl)benzamide (Compound (I-1-641) in Table 1)

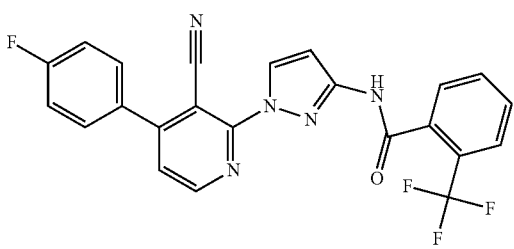 [SMILES: N#Cc1c(-c2ccc(F)cc2)ccnc1-n1ccc(NC(=O)c2ccccc2C(F)(F)F)n1]

Analogously to Synthesis Example 25, Step 2, starting with 2-chloro-4-(4-fluorophenyl)nicotinonitrile: HPLC-MS: log P=3.41; mass (m/z): 426.1 (M+H)+; 1H-NMR (DMSO-D$_6$) 7.11 (m, 1H), 7.67-7.73 (m, 2H), 7.77 (m, 1H), 7.84 (m, 1H), 7.99 (m, 1H), 8.60 (m, 1H), 8.77 (m, 1H), 11.71 (s, 1H).

Synthesis Example 33

N-{1-[3-Cyano-6-methyl-4-(trifluoromethyl)pyridin-2-yl]-1H-pyrazol-3-yl}-2-(trifluoromethyl)benzamide (Compound (I-1-571) in Table 1)

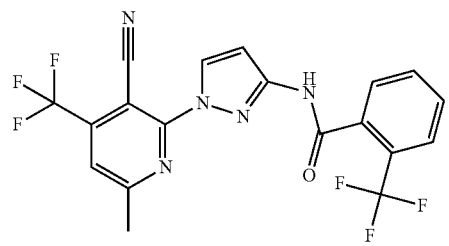 [SMILES: Cc1cc(C(F)(F)F)c(C#N)c(-n2ccc(NC(=O)c3ccccc3C(F)(F)F)n2)n1]

Analogously to Synthesis Example 25, Step 2, starting with 2-chloro-6-methyl-4-(trifluoromethyl)nicotinonitrile: HPLC-MS: log P=3.49; mass (m/z): 440.0 (M+H)+; 1H-NMR (DMSO-D$_6$) 2.70 (s, 3H), 7.09 (m, 1H), 7.69-7.73 (m, 2H), 7.76 (m, 1H), 7.83 (m, 1H), 7.89 (m, 1H), 8.62 (m, 1H), 11.66 (s, 1H).

Synthesis Example 34

N-[1-(6-Chloro-3-cyanopyridin-2-yl)-1H-pyrazol-3-yl]-2-(trifluoromethyl)benzamide (Compound (I-1-607) in Table 1)

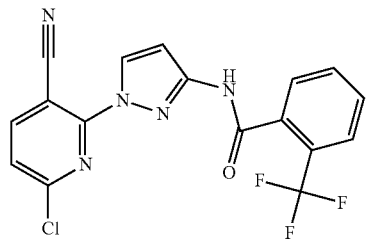 [SMILES: N#Cc1ccc(Cl)nc1-n1ccc(NC(=O)c2ccccc2C(F)(F)F)n1]

Analogously to Synthesis Example 25, Step 2, starting with 2,6-dichloronicotinonitrile: HPLC-MS: log P=3.14; mass (m/z): 392.0/394.1 (M+H)$^+$; 1H-NMR (DMSO-D$_6$) 7.08 (m, 1H), 7.64 (m, 1H), 7.69-7.72 (m, 2H), 7.76 (m, 1H), 7.82 (m, 1H), 8.48 (m, 1H), 8.55 (m, 1H), 11.66 (s, 1H).

Synthesis Example 35

N-[1-(6-Chloro-5-cyanopyridin-2-yl)-1H-pyrazol-3-yl]-2-(trifluoromethyl)benzamide (Compound (I-1-608) in Table 1)

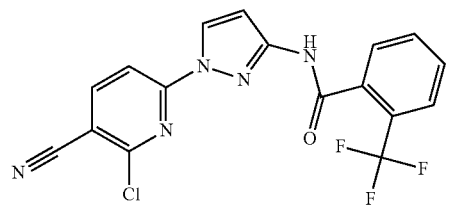 [SMILES: N#Cc1ccc(-n2ccc(NC(=O)c3ccccc3C(F)(F)F)n2)nc1Cl]

Analogously to Synthesis Example 25, Step 2, likewise starting with 2,6-dichloronicotinonitrile, as a mixture with Synthesis Example 34: HPLC-MS: log P=3.17; mass (m/z): 392.0/394.1 (M+H)+; 1H-NMR (DMSO-D$_6$) 7.06 (m, 1H), 7.70-7.86 (m, 5H), 8.54 (m, 1H), 8.60 (m, 1H), 11.62 (s, 1H).

Synthesis Example 36

N-{1-[3-Cyano-6-(diethylamino)pyridin-2-yl]-1H-pyrazol-3-yl}-2-(trifluoromethyl)benzamide (Compound (I-1-568) in Table 1)

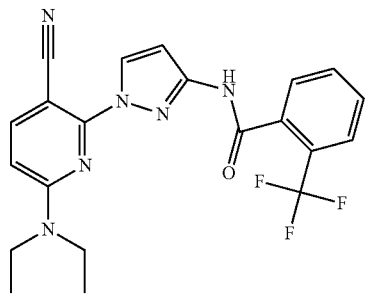 [SMILES: CCN(CC)c1ccc(C#N)c(-n2ccc(NC(=O)c3ccccc3C(F)(F)F)n2)n1]

Analogously to Synthesis Example 25, Step 2, starting with 2-chloro-6-(diethylamino)nicotinonitrile: HPLC-MS: log P=3.76; mass (m/z): 429.1 (M+H)+; 1H-NMR (DMSO-D$_6$) 1.17 (m, 6H), 3.60 (br, 4H), 6.66 (m, 1H), 7.00 (m, 1H), 7.69 (m, 2H), 7.76 (m, 1H), 7.81 (m, 1H), 7.86 (m, 1H), 8.48 (m, 1H), 11.52 (s, 1H).

Synthesis Example 37

N-[1-(2-Chloro-3-cyanopyridin-4-yl)-1H-pyrazol-3-yl]-2-(trifluoromethyl)benzamide (Compound (I-1-585) in Table 1)

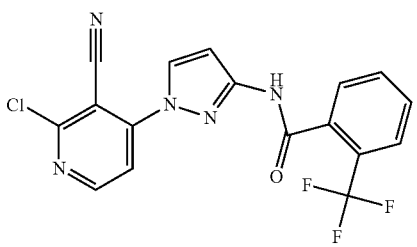 [SMILES: N#Cc1c(-n2ccc(NC(=O)c3ccccc3C(F)(F)F)n2)ccnc1Cl]

Analogously to Synthesis Example 25, Step 2, starting with 2,4-dichloronicotinonitrile: HPLC-MS: log P=2.67; mass (m/z): 391.9/394.0 (M+H)$^+$; 1H-NMR (DMSO-D$_6$) 7.15 (m, 1H), 7.71 (m, 2H), 7.79 (m, 1H), 7.84 (m, 1H), 7.95 (m, 1H), 8.67-8.70 (m, 2H), 11.69 (s, 1H).

Synthesis Example 38

N-[1-(4-Chloro-3-cyanopyridin-2-yl)-1H-pyrazol-3-yl]-2-(trifluoromethyl)benzamide (Compound (I-1-586) in Table 1)

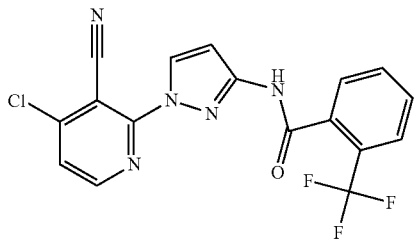 [SMILES: N#Cc1c(Cl)ccnc1-n1ccc(NC(=O)c2ccccc2C(F)(F)F)n1]

Analogously to Synthesis Example 25, Step 2, likewise starting with 2,4-dichloronicotinonitrile, formed as a mixture with Synthesis Example 36 and isolated by chromatography on silica gel using a cyclohexane/ethyl acetate gradient: HPLC-MS: log P=2.67; mass (m/z): 391.9/394.0 (M+H)$^+$; 1H-NMR (DMSO-D$_6$) 7.08 (m, 1H), 7.71 (m, 2H), 7.78 (m, 1H), 7.85 (m, 1H), 8.58 (m, 1H), 8.68 (m, 2H), 11.66 (s, 1H).

Synthesis Example 39

N-[1-(3-Cyano-6-propylpyridin-2-yl)-1H-pyrazol-3-yl]-2-(trifluoromethyl)benzamide (Compound (I-1-573) in Table 1)

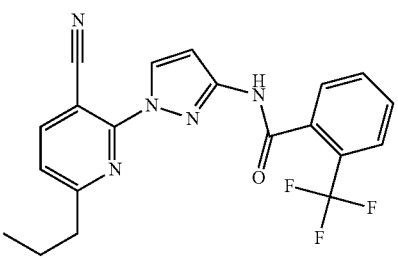 [SMILES: CCCc1ccc(C#N)c(-n2ccc(NC(=O)c3ccccc3C(F)(F)F)n2)n1]

Analogously to Synthesis Example 25, Step 2, starting with 2-chloro-6-propylnicotinonitrile: HPLC-MS: log P=3.80; mass (m/z): 400.1 (M+H)$^+$; 1H-NMR (DMSO-D$_6$) 0.95 (m, 3H), 1.77 (m, 2H), 2.82 (m, 2H), 7.05 (m, 1H), 7.40 (m, 1H), 7.70 (m, 2H), 7.76 (m, 1H), 7.83 (m, 1H), 7.95 (m, 1H), 8.32 (m, 1H), 8.58 (m, 1H), 11.59 (s, 1H).

Synthesis Example 40

N-{1-[3-Cyano-6-cyclopropyl-4-(trifluoromethyl)pyridin-2-yl]-1H-pyrazol-3-yl}-2-(trifluoromethyl)benzamide (Compound (I-1-570) in Table 1)

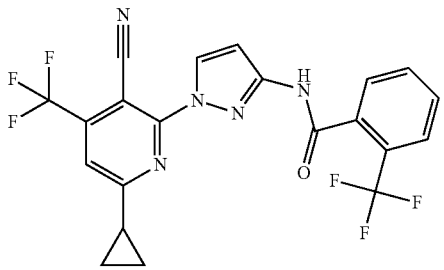 [SMILES: N#Cc1c(C(F)(F)F)cc(C2CC2)nc1-n1ccc(NC(=O)c2ccccc2C(F)(F)F)n1]

Analogously to Synthesis Example 25, Step 2, starting with 2-chloro-6-cyclopropyl-4-(trifluoromethyl)nicotinonitrile: HPLC-MS: log P=3.99; mass (m/z): 466.1 (M+H)$^+$; 1H-NMR (DMSO-D$_6$) 1.24 (m, 4H), 2.47 (m, 1H), 7.07 (m, 1H), 7.77 (m, 2H), 7.83 (m, 1H), 7.96 (s, 1H), 8.59 (m, 1H), 8.58 (m, 1H), 11.64 (s, 1H).

Synthesis Example 41

N-[1-(4-Amino-2,6-difluorophenyl)-1H-pyrazol-3-yl]-2-(trifluoromethyl)benzamide (Compound (I-1-227) in Table 1)

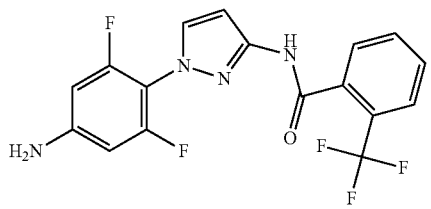 [SMILES: Nc1cc(F)c(-n2ccc(NC(=O)c3ccccc3C(F)(F)F)n2)c(F)c1]

Analogously to Synthesis Example 24, Step 2, starting with N-[1-(2,6-difluoro-4-nitrophenyl)-1H-pyrazol-3-yl]-2-(trifluoromethyl)benzamide (Synthesis Example 26, 1.00 g), 830 mg of the title compound were obtained: HPLC-MS: log P=2.32; mass (m/z): 383.1 (M+H)$^+$; 1H-NMR (DMSO-D$_6$) 6.09 (m, 2H), 6.33 (m, 2H), 6.80 (m, 1H), 7.68 (m, 2H), 7.55 (m, 1H), 7.81 (m, 2H), 11.18 (s, 1H).

Synthesis Example 42

N-[1-(4-Acetamido-2,6-difluorophenyl)-1H-pyrazol-3-yl]-2-(trifluoromethyl)benzamide (Compound (I-1-583) in Table 1)

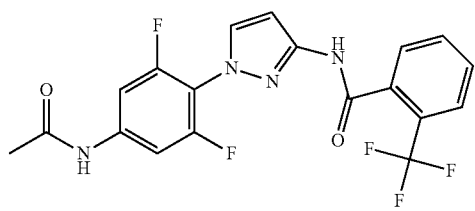 [SMILES: CC(=O)Nc1cc(F)c(-n2ccc(NC(=O)c3ccccc3C(F)(F)F)n2)c(F)c1]

A mixture of N-[1-(4-amino-2,6-difluorophenyl)-1H-pyrazol-3-yl]-2-(trifluoromethyl)benzamide (100 mg) and acetic anhydride (1 g) was stirred at room temperature for one hour and diluted with water (30 ml), and the title compound (98 mg) was isolated by filtration: HPLC-MS: log P=2.28; mass (m/z): 425.1 (M+H)$^+$; 1H-NMR (DMSO-D$_6$) 2.11 (s, 3H), 6.89 (m, 1H), 7.52 (m, 2H), 7.69 (m, 2H), 7.76 (m, 1H), 7.82 (m, 1H), 7.99 (m, 1H), 10.51 (s, 1H), 11.96 (s, 1H).

Synthesis Example 43

N-[1-(3-Cyanopyrazin-2-yl)-1H-pyrazol-3-yl]-2-(trifluoromethyl)benzamide (Compound (I-1-574) in Table 1)

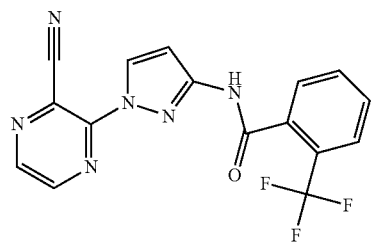 [SMILES: N#Cc1nccnc1-n1ccc(NC(=O)c2ccccc2C(F)(F)F)n1]

Analogously to Synthesis Example 25, Step 2, starting with 3-chloropyrazine-2-carbonitrile: HPLC-MS: log P=2.47; mass (m/z): 359.0 (M+H)$^+$; 1H-NMR (DMSO-D$_6$) 7.12 (m, 1H), 7.72 (m, 2H), 7.78 (m, 1H), 7.83 (m, 1H), 8.63 (m, 1H), 8.75 (m, 1H), 8.85 (m, 1H), 11.71 (s, 1H).

Synthesis Example 44

N-[1-(6-Chloro-5-cyano-3-fluoropyridin-2-yl)-1H-pyrazol-3-yl]-2-(trifluoromethyl)benzamide (Compound (I-1-606) in Table 1)

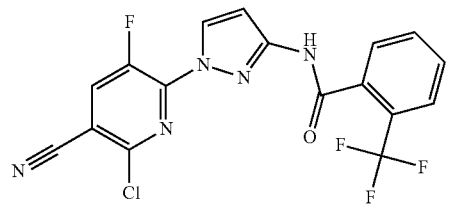 [SMILES: N#Cc1cc(F)c(-n2ccc(NC(=O)c3ccccc3C(F)(F)F)n2)nc1Cl]

Analogously to Synthesis Example 25, Step 2, starting with 2,6-dichloro-5-fluoronicotinonitrile: HPLC-MS: log P=2.94; mass (m/z): 410.0/411.9 (M+H)$^+$; 1H-NMR (DMSO-D$_6$) 7.11 (m, 1H), 7.70 (m, 2H), 7.77 (m, 1H), 7.83 (m, 1H), 8.52 (m, 1H), 8.80 (m, 1H), 8.85 (m, 1H), 11.89 (s, 1H).

Synthesis Example 45

N-[2-(3,5-Difluoropyridin-2-yl)-2H-1,2,3-triazol-4-yl]-2-(trifluoromethyl)benzamide (Compound (I-2-63) in Table 3)

Synthesis scheme for the intermediate 2-(3,5-difluoropyridin-2-yl)-2H-1,2,3-triazole-4-amine (Ex.45-V) (via route A-3)

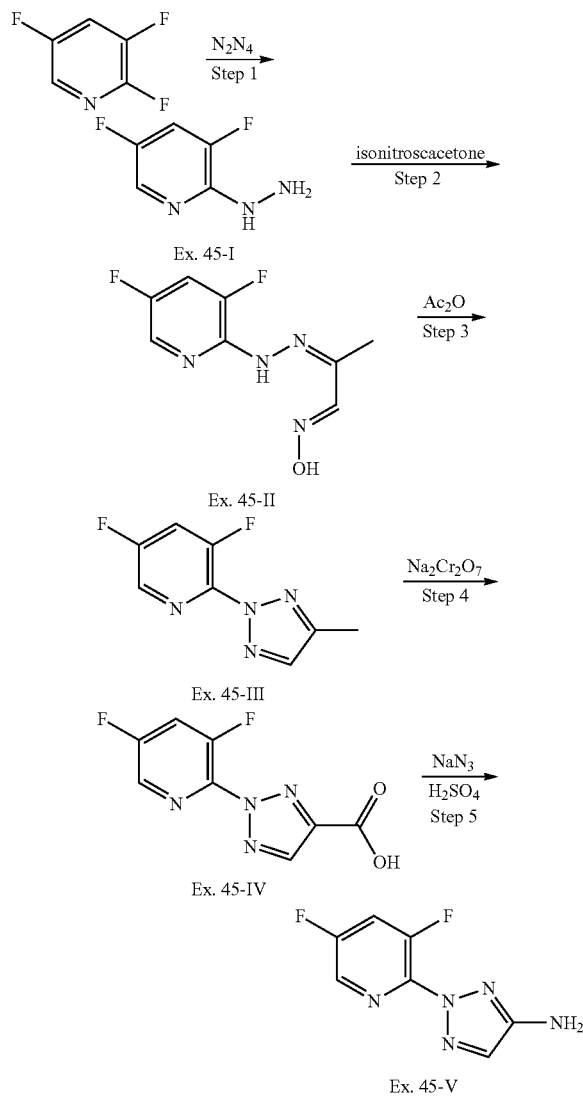

Step 1: 3,5-Difluoro-2-hydrazinopyridine (Ex. 45-I)

25 g of 2,3,5-trifluoropyridine together with excess hydrazine hydrate were heated under reflux for 1 h. The reaction mixture was then subjected to steam distillation, and about 1 l of distillate were collected. The distillate was extracted 5 times with in each case 250 ml of dichloromethane, the organic phases were dried over sodium sulphate and the solvent was then removed on a rotary evaporator. This gave crude hydrazino-3,5-difluoropyridine (48% of theory) which was reacted in the next step without further work-up.

Step 2: 2-[2-(3,5-Difluoropyridin-2-yl)hydrazinylidene]propanal oxime (Ex. 45-II)

The hydrazino-3,5-difluoropyridine from the first step (Ex. 45-I) was heated under reflux with a 20% excess of isonitrosoacetone in ethanol for 3 h. After cooling, a precipitate was obtained which was filtered off and washed with ethanol. This gave crude propanal oxime (65% of theory) which was reacted in the next step without further work-up.

Step 3: 3,5-Difluoro-2-(4-methyl-2H-1,2,3-triazol-2-yl) (Ex. 45-III)

A solution of 0.1 mol of the hydrazone oxime (Ex. 45-II) in acetic anhydride was slowly heated to 130° C. and stirred at this temperature for 2 h. Excess acetic anhydride was removed on a rotary evaporator, and the methyltriazole formed (Ex. 45-III) (70% of theory) was processed further without further work-up.

Step 4: 2-(3,5-Difluoropyridin-2-yl)-2H-1,2,3-triazole-4-carboxylic acid (Ex. 45-IV)

Sodium dichromate (0.2 mol) was added in small portions to a well-stirred solution of methyltriazole (Ex. 45-III, 0.1 mol) in 66% strength sulphuric acid. Each individual portion of dichromate was added only after the yellow-orange colour of the $Cr^{6+}$ in the flask had disappeared. Moreover, the portions were added such that the temperature in the flask remained at about 80-90° C. The mixture was then heated on a steam bath for 1 h. After cooling, the mixture was poured into about the same amount of ice and allowed to stand overnight. The precipitated acid was filtered off, washed with water and dried. This gave 50% of theory of the acid (Ex. 45-IV).

Step 5: 2-(3,5-Difluoropyridin-2-yl)-2H-1,2,3-triazole-4-amine (Ex.45-V)

Sodium azide was added in small portions to a stirred mixture of the acid from precursor (Ex. 45-IV) in 50 ml of chloroform and 50 ml of conc. sulphuric acid over a period of 2 h. The reaction was stirred at 55° C. for a further 2 h. After cooling, the mixture was poured into about the same amount of ice and allowed to stand overnight, the solids were then filtered off and the mother liquor was made alkaline using ammonia solution. The precipitated amide was filtered off, washed with water and dried. This gave 70% of theory. HPLC-MS: log P=0.65; mass (m/z): 198.0 $(M+H)^+$; $^1$H-NMR (DMSO-$D_6$) 5.61 (s, 2H), 7.38 (s, 1H), 8.21-8.25 (m, 1H), 8.45 (s, 1H).

N-[2-(3,5-Difluoropyridin-2-yl)-2H-1,2,3-triazol-4-yl]-2-(trifluoromethyl)benzamide (Compound (I-2-63) in Table 3)

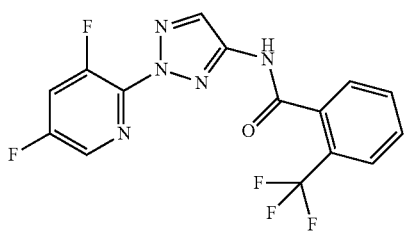 [SMILES: O=C(Nc1cnn(-c2ncc(F)cc2F)n1)c1ccccc1C(F)(F)F]

Analogously to Synthesis Example 9 Step 2, 2-(3,5-difluoropyridin-2-yl)-2H-1,2,3-triazole-4-amine (Ex. 45-V; 174 mg) was reacted with 2-(trifluoromethyl)benzoyl chloride (150 mg) and triethylamine (0.23 ml) in 4 ml of dichloromethane. Purification by column chromatography and preparative HPLC gave 207 mg of the title compound. HPLC-MS: log P=2.38; mass (m/z): 370.0 (M+H)+; $^1$H-NMR (DMSO-D$_6$) 7.72-7.83 (m, 3H), 8.35-8.40 (m, 1H), 8.45-8.47 (m, 1H), 8.57-8-58 (s, 1H), 11.96-11-97 (d, 1H).

Analogously to Ex. 45-V, the novel intermediates below were obtained (via route A-3):

2-(3-Fluoropyridin-2-yl)-2H-1,2,3-triazole-4-amine

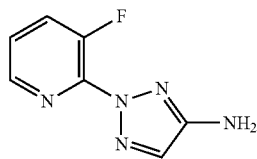 [SMILES: Nc1cnn(-c2ncccc2F)n1]

HPLC-MS: log P=0.40; mass (m/z): 180.0 (M+H)+; $^1$H-NMR (DMSO-D$_6$) 5.61 (s, 2H), 7.39 (s, 1H), 7.48-7.52 (m, 1H), 7.95-8.00 (m, 1H), 8.35-8.36 (m, 1H).

2-[5-(Trifluoromethyl)pyridin-2-yl]-2H-1,2,3-triazole-4-amine

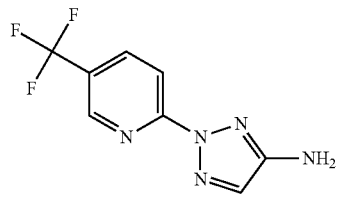 [SMILES: Nc1cnn(-c2ccc(C(F)(F)F)cn2)n1]

HPLC-MS: log P=1.53; mass (m/z): 230.0 (M+H)+; $^1$H-NMR (DMSO-D$_6$) 5.86 (s, 2H), 7.48 (s, 1H), 7.91-7.94 (m, 1H), 8.29-8.31 (m, 1H), 8.8 (s, 1H).

2-(3,5-Dichloropyridin-2-yl)-2H-1,2,3-triazole-4-amine

HPLC-MS: log P=1.38; mass (m/z): 229.9 (M+H)+; $^1$H-NMR (DMSO-D$_6$) 5.60 (s, 2H), 7.38 (s, 1H), 8.48-8.49 (d, 1H), 8.58-8.59 (d, 1H).

2-[3-Chloro-5-(trifluoromethyl)pyridin-2-yl]-2H-1,2,3-triazole-4-amine

HPLC-MS: log P=1.74; mass (m/z): 263.9 (M+H)+; $^1$H-NMR (DMSO-D$_6$) 5.76 (s, 2H), 7.48 (s, 1H), 8.68-8.69 (d, 1H), 8.89-8.90 (d, 1H).

Synthesis Example 46

N-[1-(2,6-Difluorophenyl)-1H-pyrrol-3-yl]-2-(trifluoromethyl)benzamide (Compound (I-3-1) in Table 5)

Synthesis scheme for the intermediate: 1-(2,6-Difluorophenyl)-1H-pyrrole-3-amine (Ex.46-III) (via route A-4)

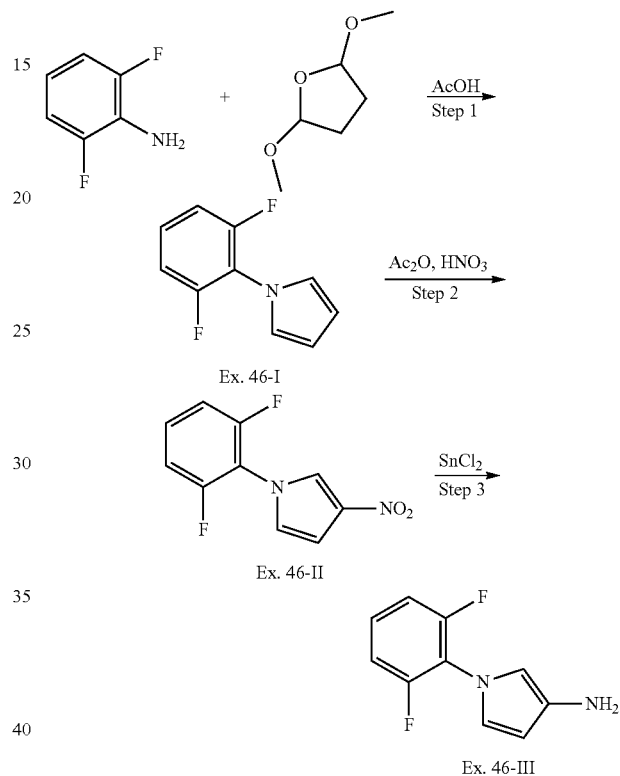

Step 1: 1-(2,6-Difluorophenyl)-1H-pyrrole (Ex. 46-I)

With stirring, 0.39 mol of 2,5-dimethoxytetrahydrofuran was slowly added dropwise to 0.39 mol of 2,6-difluoroaniline in 100 ml of glacial acetic acid, and the mixture was stirred at 100° C. for another 1 h. After cooling to room temperature, the glacial acetic acid was removed on a rotary evaporator and the residue was concentrated repeatedly with toluene. Purification of the residue by column chromatography using cyclohexane/ethyl acetate (10:1 to 1:1) gave 5.6 g, 78% of theory, of the desired pyrrole having a purity of 96% (LCMS). HPLC-MS: log P=2.98; $^1$H-NMR (CD$_3$CN) 6.28-6.29 (m, 2H), 6.95-7.00 (m, 2H), 7.30-7.35 (m, 2H), 7.45-7.52 (m, 1H).

Step 2: 1-(2,6-Difluorophenyl)-3-nitro-M-pyrrole (Ex. 46-II)

At −10° C., 162 ml of acetic anhydride were carefully added dropwise to 2 ml of conc. nitric acid. At −40° C., this mixture was then added dropwise to a solution of 5.4 g (0.31 mol) of 1-(2,6-difluorophenyl)-1H-pyrrole in 80 ml of acetic anhydride The mixture was then stirred at this temperature for a further 2 h. The reaction mixture was poured onto ice and extracted three times with chloroform. After drying of the organic phase over sodium sulphate, the solvent was removed on a rotary evaporator. Purification of the residue by column chromatography using cyclohexane/ethyl acetate (10:1 to 1:1) gave, in addition to the 2-nitro isomer, 3.2 g (48% of theory) of the desired 3-nitropyrrole having a purity of 99% (LCMS). HPLC-MS: log P=2.58; mass (m/z): 225.1 (M+H)+; $^1$H-NMR (CD$_3$CN) 6.60-6.62 (m, 1H), 7.37-7.42 (m, 2H), 7.55-7.58 (m, 2H), 7.62-7.70 (m, 1H).

Step 3: 1-(2,6-Difluorophenyl)-1H-pyrrole-3-amine (Ex. 46-III)

At 80° C., 575 mg (2.57 mmol) of the 3-nitropyrrole and 2.43 g (12.8 mmol) of tin chloride in 17 ml of ethyl acetate were stirred overnight. After cooling, the mixture was filtered off and the solvent was removed on a rotary evaporator. The residue obtained in this manner was used directly and without further work-up for the next reaction.

N-[1-(2,6-Difluorophenyl)-1H-pyrrol-3-yl]-2-(trifluoromethyl)benzamide (Compound (I-3-1) in Table 5)

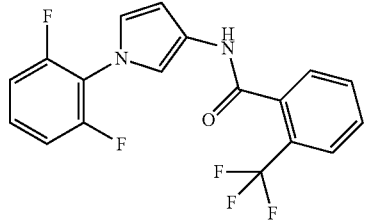 [SMILES: O=C(Nc1ccn(-c2c(F)cccc2F)c1)c1ccccc1C(F)(F)F]

Analogously to Synthesis Example 9 Step 2, the crude 1-(2,6-difluorophenyl)-1H-pyrrole-3-amine (85 mg) was reacted with 2-(trifluoromethyl)benzoyl chloride (92 mg) and triethylamine (0.12 ml) in 1.3 ml of dichloromethane. Purification by column chromatography and preparative HPLC gave 26 mg of the title compound. HPLC-MS: log P=2.96; mass (m/z): 367.0 (M+H)+; $^1$H-NMR (DMSO-D$_6$) 6.31-6.32 (m, 1H), 6.92-6.94 (m, 1H), 7.31-7.39 (m, 3H), 7.48-7.52 (m, 1H), 7.66-7.84 (m, 4H).

Synthesis Example 47

N-[1-(2-Chlorophenyl)-1H-indazol-3-yl]-2-(trifluoromethyl)benzamide (Compound (I-5-8) in Table 4)

Step 1: 1-(2-Chlorophenyl)-1H-indazole-3-amine (via route B-2)

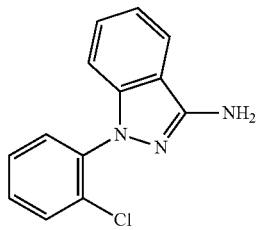 [SMILES: Nc1nn(-c2ccccc2Cl)c2ccccc12]

Under argon, 2-iodobenzonitrile (500 mg), N'-(2-chlorophenyl)benzohydrazide (646 mg), potassium carbonate (1207 mg), copper(I) bromide (31 mg) and trans-4-hydroxy-L-proline (57 mg) were stirred in dimethyl sulphoxide (7.5 ml) at 90° C. for 48 h. After cooling, the reaction mixture was taken up in ethyl acetate, washed with saturated ammonium chloride solution and saturated sodium chloride solution, adsorbed on silica gel and purified by column chromatography on silica gel using the mobile phase cyclohexane/ethyl acetate. 226 mg of the title compound were obtained. HPLC-MS: log P=2.32; mass (m/z): 244.0 (M+H)+; $^1$H-NMR (DMSO-D$_6$) 5.83 (br. s, 2H), 7.01-7.09 (m, 2H), 7.31-7.35 (m, 1H), 7.42-7.49 (m, 3H), 7.67-7.69 (m, 1H), 7.82-7.84 (m, 1H).

Step 2: N-[1-(2-Chlorophenyl)-1H-indazol-3-yl]-2-(trifluoromethyl)benzamide (Compound I-5-8 in Table 4)

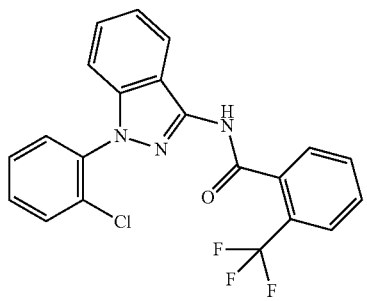 [SMILES: O=C(Nc1nn(-c2ccccc2Cl)c2ccccc12)c1ccccc1C(F)(F)F]

Analogously to Synthesis Example 9 Step 2, 1-(2-chlorophenyl)-1H-indazole-3-amine (174 mg) was reacted with 2-(trifluoromethyl)benzoyl chloride (47 mg) and triethylamine (0.6 ml) in 4 ml of dichloromethane. Purification by column chromatography and preparative HPLC gave 20 mg of the title compound. HPLC-MS: log P=3.54; mass (m/z): 416.0 (M+H)+; $^1$H-NMR (DMSO-D$_6$) 7.19-7.28 (m, 2H), 7.45-7.49 (m, 1H), 7.57-7.63 (m, 3H), 7.65-7.95 (m, 6H), 11.31 (s, 1H).

Analogously to Ex. 47 Step 1, 4-(3-amino-4-fluoro-1H-indazol-1-yl)-2,5-difluorobenzonitrile can be obtained from 2-fluoro-6-iodobenzonitrile and N'-(4-cyano-2,5-difluorophenyl)benzohydrazide.

Synthesis Example 48

N-[1-(3,5-Difluoro-1-oxidopyridin-2-yl)-1H-pyrazol-3-yl]-2-(trifluoromethyl)benzamide (Compound I-1-438 in Table 1)

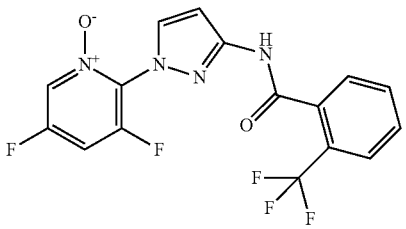 [SMILES: O=C(Nc1ccn(-c2c(F)cc(F)c[n+]2[O-])n1)c1ccccc1C(F)(F)F]

N-[1-(3,5-Difluoropyridin-2-yl)-1H-pyrazol-3-yl]-2-(trifluoromethyl)benzamide (I-1-75 in Table 1; 150 mg) was stirred with hydrogen peroxide-urea (153 mg) in 3 ml of dichloromethane for 30 min. On an ice bath at 0-5° C., trifluoroacetic anhydride (342 mg) was then added dropwise, and the mixture was stirred overnight. Sodium sulphite solution was then added, and the mixture was washed with water, dried over sodium sulphate and then concentrated on a rotary evaporator. Purification by column chromatography and preparative HPLC gave 35 mg of the title compound.

HPLC-MS: log P=1.69; mass (m/z): 385.1 (M+H)$^+$; $^1$H-NMR (DMSO-D$_6$) 6.95-6.96 (d, 1H), 7.68-7.78 (m, 4H), 7.82-7.96 (m, 1H), 8.05-8.06 (m, 1H), 8.83-8.85 (m, 1H), 11.33 (s, 1H).

The compounds for the formulae (I-1), (I-4), (I-2), (I-5) and (I-3) described in Tables 1 to 5 are likewise preferred compounds which were obtained according to or analogously to the Synthesis Examples described above.

TABLE 1

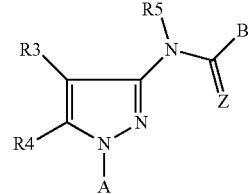

(I-1)

| Compound No. | A | B | R3 | R4 | R5 | Z |
|---|---|---|---|---|---|---|
| I-1-1 Synthesis Example 1 | 2-methylphenyl | 2-bromophenyl | H | H | H | O |
| I-1-2 | 2-methoxyphenyl | 2-bromophenyl | H | H | H | O |
| I-1-3 | 2-methoxyphenyl | 2,5-dimethyl-3-furanyl | H | H | H | O |
| I-1-4 | 2-(trifluoromethyl)phenyl | 2-chlorophenyl | H | H | H | O |
| I-1-5 | 2-(trifluoromethyl)phenyl | 2-iodophenyl | H | H | H | O |
| I-1-6 | 2-(trifluoromethyl)phenyl | 2-(trifluoromethyl)phenyl | H | H | H | O |
| I-1-7 | 2-(trifluoromethyl)phenyl | 1-(difluoromethyl)-1H-pyrazol-5-yl | H | H | H | O |
| I-1-8 | 2-cyanophenyl | 2-chlorophenyl | H | H | H | O |
| I-1-9 | 2-cyanophenyl | 2-(trifluoromethyl)phenyl | H | H | H | O |
| I-1-10 | 2-fluorophenyl | 2-bromophenyl | H | H | H | O |
| I-1-11 | 2-chlorophenyl | 2-methylphenyl | H | H | H | O |
| I-1-12 | 2-chlorophenyl | 2-ethylphenyl | H | H | H | O |
| I-1-13 | 2-chlorophenyl | 2-difluoromethylphenyl | H | H | H | O |
| I-1-14 | 2-chlorophenyl | 2-(trifluoromethyl)phenyl | H | H | H | O |
| I-1-15 Synthesis Example 17 | 2-chlorophenyl | 2-(trifluoromethyl)phenyl | Cl | H | H | O |
| I-1-16 Synthesis Example 18 | 2-chlorophenyl | 2-(trifluoromethyl)phenyl | Br | H | H | O |
| I-1-17 Synthesis Example 19 | 2-chlorophenyl | 2-(trifluoromethyl)phenyl | I | H | H | O |
| I-1-18 | 2-chlorophenyl | 2-trifluoromethoxyphenyl | H | H | H | O |
| I-1-19 | 2-chlorophenyl | 2-fluorophenyl | H | H | H | O |
| I-1-20 Synthesis Example 14 | 2-chlorophenyl | 2-chlorophenyl | H | H | H | O |
| I-1-21 Synthesis Example 15 | 2-chlorophenyl | 2-chlorophenyl | H | H | methyl | O |
| I-1-22 | 2-chlorophenyl | 2-chlorophenyl | H | H | ethyl | O |
| I-1-23 | 2-chlorophenyl | 2-chlorophenyl | H | H | 1-propyn-2-yl | O |
| I-1-24 | 2-chlorophenyl | 2-chlorophenyl | H | H | cyclopropyl methyl | O |
| I-1-25 | 2-chlorophenyl | 2-chlorophenyl | H | H | cyanomethyl | O |
| I-1-26 | 2-chlorophenyl | 2-chlorophenyl | H | H | allyl | O |
| I-1-27 Synthesis Example 16 | 2-chlorophenyl | 2-chlorophenyl | F | H | H | O |
| I-1-28 | 2-chlorophenyl | 2-chlorophenyl | Cl | H | H | O |
| I-1-29 | 2-chlorophenyl | 2-chlorophenyl | Br | H | H | O |
| I-1-30 | 2-chlorophenyl | 2-chlorophenyl | I | H | H | O |
| I-1-31 | 2-chlorophenyl | 2-chlorophenyl | H | methyl | H | O |
| I-1-32 | 2-chlorophenyl | 2-bromophenyl | H | H | H | O |
| I-1-33 | 2-chlorophenyl | 2-iodophenyl | H | H | H | O |
| I-1-34 | 2-chlorophenyl | 2-iodophenyl | Cl | H | H | O |

TABLE 1-continued (I-1)

| Compound No. | A | B | R3 | R4 | R5 | Z |
|---|---|---|---|---|---|---|
| I-1-35 | 2-chlorophenyl | 2-iodophenyl | H | methyl | H | O |
| I-1-36 | 2-chlorophenyl | 2,6-difluorophenyl | H | H | H | O |
| I-1-37 | 2-chlorophenyl | 2-chloro-6-fluorophenyl | H | H | H | O |
| I-1-38 | 2-chlorophenyl | 3-methylpyridin-2-yl | H | H | H | O |
| I-1-39 | 2-chlorophenyl | 3-trifluoromethylpyridin-2-yl | H | H | H | O |
| I-1-40 | 2-chlorophenyl | 3-chloropyridin-2-yl | H | H | H | O |
| I-1-41 | 2-chlorophenyl | 2-methylpyridin-3-yl | H | H | H | O |
| I-1-42 | 2-chlorophenyl | 2-(trifluoromethyl)pyridin-3-yl | H | H | H | O |
| I-1-43 | 2-chlorophenyl | 2-chloropyridin-3-yl | H | H | H | O |
| I-1-44 | 2-chlorophenyl | 3-trifluoromethyl-2-pyrazinyl | H | H | H | O |
| I-1-45 | 2-chlorophenyl | 2,5-dimethyl-3-furanyl | H | H | H | O |
| I-1-46 | 2-chlorophenyl | 3-methyl-2-thienyl | H | H | H | O |
| I-1-47 | 2-chlorophenyl | 2-iodo-3-thienyl | H | H | H | O |
| I-1-48 | 2-chlorophenyl | 5-chloro-1,3-dimethyl-1H-pyrazol-4-yl | H | H | H | O |
| I-1-49 | 2-chlorophenyl | 3-difluoromethyl-5-fluor-1-methyl-1H-pyrazol-4-yl | H | H | H | O |
| I-1-50 | 2-bromophenyl | 2-(trifluoromethyl)phenyl | H | H | H | O |
| I-1-51 | 2-bromophenyl | 2-chlorophenyl | H | H | H | O |
| I-1-52 | 2-bromophenyl | 2-bromophenyl | H | H | H | O |
| I-1-53 | 2-bromophenyl | 2-iodophenyl | H | H | H | O |
| I-1-54 | 2-bromophenyl | 3-(trifluoromethyl)pyridine-2-yl | H | H | H | O |
| I-1-55 | 2-bromophenyl | 3-chloropyridin-2-yl | H | H | H | O |
| I-1-56 | 2-bromophenyl | 2-(trifluoromethyl)pyridin-3-yl | H | H | H | O |
| I-1-57 | 2-bromophenyl | 2-chloropyridin-3-yl | H | H | H | O |
| I-1-58 | 2-bromophenyl | 3-difluoromethyl-5-fluor-1-methyl-1H-pyrazol-4-yl | H | H | H | O |
| I-1-59 | 2-bromophenyl | 5-fluor-1-methyl-3-trifluoromethyl-1H-pyrazol-4-yl | H | H | H | O |
| I-1-60 | 2-bromophenyl | 3-methyl-2-thienyl | H | H | H | O |
| I-1-61 Synthesis Example 2 | 2,6-dimethylphenyl | 2-chlorophenyl | H | H | H | O |
| I-1-62 | 2,3-difluorophenyl | 2-(trifluoromethyl)phenyl | H | H | H | O |
| I-1-63 Synthesis Example 3 | 2,3-difluorophenyl | 2-bromophenyl | H | H | H | O |
| I-1-64 | 2,3-difluorophenyl | 2-(trifluoromethyl)phenyl | H | H | H | O |
| I-1-65 | 2,3-difluorophenyl | 2-(trifluoromethyl)phenyl | H | H | H | O |
| I-1-66 | 2,3-difluorophenyl | 2-chlorophenyl | H | H | H | O |
| I-1-67 | 2,3-difluorophenyl | 2-iodophenyl | H | H | H | O |
| I-1-68 | 2,3-difluorophenyl | 3-(trifluoromethyl)pyridin-2-yl | H | H | H | O |
| I-1-69 | 2,5-difluorophenyl | 2-methylpyridin-3-yl | H | H | H | O |
| I-1-70 | 2,5-difluorophenyl | 2-(trifluoromethyl)pyridin-3-yl | H | H | H | O |
| I-1-71 | 2,5-difluorophenyl | 3-methyl-2-thienyl | H | H | H | O |
| I-1-72 Synthesis Example 4 | 2,5-difluorophenyl | 5-fluor-1-methyl-3-trifluoromethyl-1H-pyrazol-4-yl | H | H | H | O |
| I-1-73 | 2,6-difluorophenyl | 2-methylphenyl | H | H | H | O |
| I-1-74 | 2,6-difluorophenyl | 2-difluoromethylphenyl | H | H | H | O |
| I-1-75 | 2,6-difluorophenyl | 2-(trifluoromethyl)phenyl | H | H | H | O |
| I-1-76 | 2,6-difluorophenyl | 2-(trifluoromethyl)phenyl | H | H | H | O |
| I-1-77 | 2,6-difluorophenyl | 2-(trifluoromethyl)phenyl | H | H | H | O |
| I-1-78 | 2,6-difluorophenyl | 2-ethylphenyl | H | H | H | O |
| I-1-79 | 2,6-difluorophenyl | 2-trifluoromethoxyphenyl | H | H | H | O |
| I-1-80 | 2,6-difluorophenyl | 2-(methylsulphonyl)phenyl | H | H | H | O |
| I-1-81 | 2,6-difluorophenyl | 2-chlorophenyl | H | H | H | O |
| I-1-82 | 2,6-difluorophenyl | 2-bromophenyl | H | H | H | O |
| I-1-83 | 2,6-difluorophenyl | 2-iodophenyl | H | H | H | O |
| I-1-84 | 2,6-difluorophenyl | 2,6-difluorophenyl | H | H | H | O |
| I-1-85 | 2,6-difluorophenyl | 2-chloro-6-fluorophenyl | H | H | H | O |
| I-1-86 | 2,6-difluorophenyl | 2-nitrophenyl | H | H | H | O |
| I-1-87 | 2,6-difluorophenyl | 2-hydroxyphenyl | H | H | H | O |
| I-1-88 | 2,6-difluorophenyl | 2-[(trifluoromethyl)sulphenyl]phenyl | H | H | H | O |
| I-1-89 | 2,6-difluorophenyl | 2-(1H-1,2,4-triazol-1-yl)phenyl | H | H | H | O |
| I-1-90 | 2,6-difluorophenyl | 3-methylpyridin-2-yl | H | H | H | O |

TABLE 1-continued

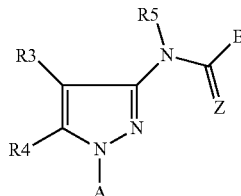
(I-1)

| Compound No. | A | B | R3 | R4 | R5 | Z |
|---|---|---|---|---|---|---|
| I-1-91 Synthesis Example 7 | 2,6-difluorophenyl | 3-(trifluoromethyl)pyridin-2-yl | H | H | H | O |
| I-1-92 | 2,6-difluorophenyl | 3-chloropyridin-2-yl | H | H | H | O |
| I-1-93 | 2,6-difluorophenyl | 2-(trifluoromethyl)pyridin-3-yl | H | H | H | O |
| I-1-94 | 2,6-difluorophenyl | 4-(trifluoromethyl)pyridin-3-yl | H | H | H | O |
| I-1-95 | 2,6-difluorophenyl | 2-chloropyridin-3-yl | H | H | H | O |
| I-1-96 | 2,6-difluorophenyl | 2-bromopyridin-3-yl | H | H | H | O |
| I-1-97 | 2,6-difluorophenyl | 3-(trifluoromethyl)pyridine-4-yl | H | H | H | O |
| I-1-98 | 2,6-difluorophenyl | 3-ethylpyridazin-4-yl | H | H | H | O |
| I-1-99 | 2,6-difluorophenyl | 3-(trifluoromethyl)pyrazin-2-yl | H | H | H | O |
| I-1-100 | 2,6-difluorophenyl | 3-chloropyrazin-2-yl | H | H | H | O |
| I-1-101 | 2,6-difluorophenyl | 2-methyl-5,6-dihydro-1,4-oxathiin-3-yl | H | H | H | O |
| I-1-102 | 2,6-difluorophenyl | 2-(trifluoromethyl)-5,6-dihydro-1,4-oxathiin-3-yl | H | H | H | O |
| I-1-103 | 2,6-difluorophenyl | 3-methyl-2-thienyl | H | H | H | O |
| I-1-104 | 2,6-difluorophenyl | 3-iodo-2-thienyl | H | H | H | O |
| I-1-105 | 2,6-difluorophenyl | 2-iodo-3-thienyl | H | H | H | O |
| I-1-106 | 2,6-difluorophenyl | 5-(difluoromethyl)-3-methyl-1,2-oxazol-4-yl | H | H | H | O |
| I-1-107 | 2,6-difluorophenyl | 1,3-dimethyl-1H-pyrazol-4-yl | H | H | H | O |
| I-1-108 | 2,6-difluorophenyl | 3-iodo-1-methyl-1H-pyrazol-4-yl | H | H | H | O |
| I-1-109 | 2,6-difluorophenyl | 1,3,5-trimethyl-1H-pyrazol-4-yl | H | H | H | O |
| I-1-110 | 2,6-difluorophenyl | 1,3-dimethyl-5-fluor-1H-pyrazol-4-yl | H | H | H | O |
| I-1-111 | 2,6-difluorophenyl | 1-(difluoromethyl)-1H-pyrazol-5-yl | H | H | H | O |
| I-1-112 | 2,6-difluorophenyl | 5-fluoro-1-methyl-3-(trifluoromethyl)-1H-pyrazol-4-yl | H | H | H | O |
| I-1-113 | 2,6-difluorophenyl | 2,4-dimethyl-1,3-thiazol-5-yl | H | H | H | O |
| I-1-114 | 2,6-difluorophenyl | 2-methyl-4-trifluoromethyl-1,3-thiazol-5-yl | H | H | H | O |
| I-1-115 | 2,6-difluorophenyl | 3,4-dichloro-1,2-thiazol-5-yl | H | H | H | O |
| I-1-116 | 2,6-difluorophenyl | 4-methyl-1,2,5-oxadiazol-3-yl | H | H | H | O |
| I-1-117 Synthesis Example 5 | 2-ethoxy-6-fluorophenyl | 2-chlorophenyl | H | H | H | O |
| I-1-118 | 2,5-dichlorophenyl | 2-chlorophenyl | H | H | H | O |
| I-1-119 | 2,5-dichlorophenyl | 2-bromophenyl | H | H | H | O |
| I-1-120 | 2,6-dichlorophenyl | 2-(trifluoromethyl)phenyl | H | H | H | O |
| I-1-121 | 2,6-dichlorophenyl | 2-chlorophenyl | H | H | H | O |
| I-1-122 | 2,6-dichlorophenyl | 2-bromophenyl | H | H | H | O |
| I-1-123 Synthesis Example 8 | 2,6-dichlorophenyl | 2-iodophenyl | H | H | H | O |
| I-1-124 | 2,6-dichlorophenyl | 2-(trifluoromethyl)pyridin-3-yl | H | H | H | O |
| I-1-125 | 2-nitrophenyl | 2-chlorophenyl | H | H | H | O |
| I-1-126 | 2-(methylsulphonyl)phenyl | 2-chlorophenyl | H | H | H | O |
| I-1-127 | 2-pyridyl | 2-bromophenyl | H | H | H | O |
| I-1-128 | 3-fluoropyridin-2-yl | 2-(trifluoromethyl)phenyl | H | H | H | O |
| I-1-129 | 3-fluoropyridin-2-yl | 2-chlorophenyl | H | H | H | O |
| I-1-130 | 3-fluoropyridin-2-yl | 2-bromophenyl | H | H | H | O |
| I-1-131 | 3-fluoropyridin-2-yl | 2-iodophenyl | H | H | H | O |
| I-1-132 | 3-fluoropyridin-2-yl | 2,6-difluorophenyl | H | H | H | O |
| I-1-133 | 3-fluoropyridin-2-yl | 2-(trifluoromethyl)pyridin-3-yl | H | H | H | O |
| I-1-134 | 3-fluoropyridin-2-yl | 2-(trifluoromethyl)pyridin-3-yl | H | H | 2-(trifluoromethyl)-pyridin-3-ylcarbonyl | O |
| I-1-135 | 3-chloropyridin-2-yl | 2-(trifluoromethyl)phenyl | H | H | H | O |
| I-1-136 | 3-chloropyridin-2-yl | 2-chlorophenyl | H | H | H | O |
| I-1-137 | 3-chloropyridin-2-yl | 2-bromophenyl | H | H | H | O |
| I-1-138 | 3-chloropyridin-2-yl | 2-iodophenyl | H | H | H | O |
| I-1-139 Synthesis Example 11 | 2-chloropyridin-3-yl | 2-iodophenyl | H | H | H | O |

TABLE 1-continued (I-1)

| Compound No. | A | B | R3 | R4 | R5 | Z |
|---|---|---|---|---|---|---|
| I-1-140 | 3,5-difluoropyridin-2-yl | 2-(trifluoromethyl)phenyl | H | H | H | O |
| I-1-141 | 3,5-difluoropyridin-2-yl | 2-(trifluoromethyl)phenyl | H | H | H | O |
| I-1-142 | 3,5-difluoropyridin-2-yl | 2-(trifluoromethyl)phenyl | H | H | Acetyl | O |
| I-1-143 | 3,5-difluoropyridin-2-yl | 2-chlorophenyl | H | H | H | O |
| I-1-144 | 3,5-difluoropyridin-2-yl | 2-bromophenyl | H | H | H | O |
| I-1-145 | 3,5-difluoropyridin-2-yl | 2-iodophenyl | H | H | H | O |
| I-1-146 Synthesis Example 9 | 3,5-difluoropyridin-2-yl | 2,6-difluorophenyl | H | H | H | O |
| I-1-147 | 3,5-difluoropyridin-2-yl | 2-nitrophenyl | H | H | H | O |
| I-1-148 | 3,5-difluoropyridin-2-yl | 2-hydroxyphenyl | H | H | H | O |
| I-1-149 | 3,5-difluoropyridin-2-yl | 2-[(trifluoromethyl)sulphanyl]phenyl | H | H | H | O |
| I-1-150 | 3,5-difluoropyridin-2-yl | 2-(1H-1,2,4-triazol-1-yl)phenyl | H | H | H | O |
| I-1-151 | 3,5-difluoropyridin-2-yl | 2-(trifluoromethyl)pyridin-3-yl | H | H | H | O |
| I-1-152 | 3,5-difluoropyridin-2-yl | 2-chloropyridin-3-yl | H | H | H | O |
| I-1-153 | 3,5-difluoropyridin-2-yl | 3-(trifluoromethyl)pyridin-4-yl | H | H | H | O |
| I-1-154 | 3,5-difluoropyridin-2-yl | 4-(trifluoromethyl)pyrimidin-5-yl | H | H | H | O |
| I-1-155 | 3,5-difluoropyridin-2-yl | 2-(trifluoromethyl)-5,6-dihydro-1,4-oxathiin-3-yl | H | H | H | O |
| I-1-156 | 3,5-difluoropyridin-2-yl | 1-methyl-4-(trifluoromethyl)-1H-pyrrol-3-yl | H | H | H | O |
| I-1-157 | 3,5-difluoropyridin-2-yl | 5-(difluoromethyl)-3-methyl-1,2-oxazol-4-yl | H | H | H | O |
| I-1-158 | 3,5-difluoropyridin-2-yl | 5-fluoro-1-methyl-3-(trifluoromethyl)-1H-pyrazol-4-yl | H | H | H | O |
| I-1-159 | 3,5-difluoropyridin-2-yl | 3,4-dichloro-1,2-thiazol-5-yl | H | H | H | O |
| I-1-160 | 3,5-difluoropyridin-2-yl | 4-methyl-1,2,3-thiadiazol-5-yl | H | H | H | O |
| I-1-161 | 2,5-difluoropyridin-2-yl | 2-iodophenyl | H | H | H | O |
| I-1-162 | 3,5,6-trifluoropyridin-2-yl | 2-(trifluoromethyl)phenyl | H | H | H | O |
| I-1-163 | 3,5,6-trifluoropyridin-2-yl | 2-chlorophenyl | H | H | H | O |
| I-1-164 Synthesis Example 10 | 3,5,6-trifluoropyridin-2-yl | 2-bromophenyl | H | H | H | O |
| I-1-165 | 3,5,6-trifluoropyridin-2-yl | 2-iodophenyl | H | H | H | O |
| I-1-166 | 3,5,6-trifluoropyridin-2-yl | 2,6-difluorophenyl | H | H | H | O |
| I-1-167 | 3,5,6-trifluoropyridin-2-yl | 3-(trifluoromethyl)pyridin-2-yl | H | H | H | O |
| I-1-168 | 2-pyrimidinyl | 2-bromophenyl | H | H | H | O |
| I-1-169 Synthesis Example 12 | 5,6-difluoropyrimidin-4-yl | 2-(trifluoromethyl)phenyl | H | H | H | O |
| I-1-170 | 5,6-difluoropyrimidin-4-yl | 2-bromophenyl | H | H | H | O |
| I-1-171 | 5,6-difluoropyrimidin-4-yl | 2,6-difluorophenyl | H | H | H | O |
| I-1-172 | 3-pyridazinyl | 2-chlorophenyl | H | H | H | O |
| I-1-173 | 3-fluoropyrazin-2-yl | 2-(trifluoromethyl)phenyl | H | H | H | O |
| I-1-174 Synthesis Example 13 | 3-fluoropyrazin-2-yl | 2-chlorophenyl | | | | |
| I-1-175 | 3-fluoropyrazin-2-yl | 2-bromophenyl | H | H | H | O |
| I-1-176 | 3-fluoropyrazin-2-yl | 2-iodophenyl | H | H | H | O |
| I-1-177 | 3-fluoropyrazin-2-yl | 2,6-difluorophenyl | H | H | H | O |
| I-1-178 | 3-fluoropyrazin-2-yl | 3-(trifluoromethyl)pyridin-2-yl | H | H | H | O |
| I-1-179 | 2-(methylsulphonyl)phenyl | 2-(trifluoromethyl)phenyl | H | H | H | O |
| I-1-180 | 2-(methylsulphonyl)phenyl | 2-(trifluoromethyl)pyridin-3-yl | H | H | H | O |
| I-1-181 | 2-(methylsulphonyl)phenyl | 2,6-difluorophenyl | H | H | H | O |
| I-1-182 | 2-(methylsulphonyl)phenyl | 2-bromophenyl | H | H | H | O |
| I-1-183 | 3-chloro-5-fluorpyridin-2-yl | 2-(trifluoromethyl)phenyl | H | H | H | O |
| I-1-184 | 2-(methylsulphonyl)phenyl | 2-iodophenyl | H | H | H | O |
| I-1-185 | 2-(trifluoromethyl)phenyl | 1,3,5-trimethyl-1H-pyrazol-4-yl | H | H | H | O |
| I-1-186 | 2-(trifluoromethyl)phenyl | 2-bromophenyl | H | H | H | O |
| I-1-187 | 2,3-dichlorophenyl | 2-bromophenyl | H | H | H | O |
| I-1-188 | 2,3-dichlorophenyl | 2-chlorophenyl | H | H | H | O |
| I-1-189 | 2,3-difluorophenyl | 2-chlorophenyl | H | H | H | O |
| I-1-190 | 2,3-difluorophenyl | 2-iodophenyl | H | H | H | O |
| I-1-191 | 2,4,5-trifluorophenyl | 2-(trifluoromethyl)phenyl | H | H | H | O |
| I-1-192 | 2,4,5-trifluorophenyl | 2-(trifluoromethyl)pyridin-3-yl | H | H | H | O |
| I-1-193 | 2,4,5-trifluorophenyl | 2-(trifluoromethyl)phenyl | H | H | H | O |

TABLE 1-continued (I-1)

| Compound No. | A | B | R3 | R4 | R5 | Z |
|---|---|---|---|---|---|---|
| I-1-194 | 2,4,5-trifluorophenyl | 2-bromophenyl | H | H | H | O |
| I-1-195 | 2,4,5-trifluorophenyl | 2-chlorophenyl | H | H | H | O |
| I-1-196 | 2,4,5-trifluorophenyl | 2-iodophenyl | H | H | H | O |
| I-1-197 | 2,4-dichlorophenyl | 2-(trifluoromethyl)phenyl | H | H | H | O |
| I-1-198 | 2,4-dichlorophenyl | 2-(trifluoromethyl)phenyl | H | H | H | O |
| I-1-199 | 2,4-dichlorophenyl | 2-bromophenyl | H | H | H | O |
| I-1-200 | 2,4-dichlorophenyl | 2-chlorophenyl | H | H | H | O |
| I-1-201 | 2,4-difluorophenyl | 2-(trifluoromethyl)phenyl | H | ethyl | H | O |
| I-1-202 | 2,4-difluorophenyl | 2-(trifluoromethyl)phenyl | H | methyl | H | O |
| I-1-203 | 2,4-difluorophenyl | 2-(trifluoromethyl)pyridin-3-yl | H | methyl | H | O |
| I-1-204 | 2,4-difluorophenyl | 2-(trifluoromethyl)pyridin-3-yl | H | ethyl | H | O |
| I-1-205 | 2,4-difluorophenyl | 2,4-difluorophenyl | H | H | H | O |
| I-1-206 | 2,4-difluorophenyl | 2,6-difluorophenyl | H | methyl | H | O |
| I-1-207 | 2,4-difluorophenyl | 2,6-difluorophenyl | H | ethyl | H | O |
| I-1-208 | 2,4-difluorophenyl | 2-bromophenyl | H | methyl | H | O |
| I-1-209 | 2,4-difluorophenyl | 2-bromophenyl | H | H | H | O |
| I-1-210 | 2,4-difluorophenyl | 2-bromopyridin-3-yl | H | methyl | H | O |
| I-1-211 | 2,4-difluorophenyl | 2-chlorophenyl | H | H | H | O |
| I-1-212 | 2,4-difluorophenyl | 2-chlorophenyl | H | methyl | H | O |
| I-1-213 | 2,4-difluorophenyl | 2-chlorophenyl | H | ethyl | H | O |
| I-1-214 | 2,4-difluorophenyl | 2-iodophenyl | H | methyl | H | O |
| I-1-215 | 2,4-difluorophenyl | 2-iodophenyl | H | ethyl | H | O |
| I-1-216 | 2,4-difluorophenyl | 3-methyl-2-thienyl | H | ethyl | H | O |
| I-1-217 | 2,5-difluoro-4-methyl-pyridin-3-yl | 2-(trifluoromethyl)phenyl | H | H | H | O |
| I-1-218 | 2,5-difluorophenyl | 2-chloropyridin-3-yl | H | H | H | O |
| I-1-219 | 2,5-difluorophenyl | 2-iodo-3-thienyl | H | H | H | O |
| I-1-220 | 2,5-difluorophenyl | 3-chloropyridin-2-yl | H | H | H | O |
| I-1-221 | 2,5-difluorophenyl | 3-iodo-2-thienyl | H | H | H | O |
| I-1-222 | 2,5-difluorophenyl | 3-iodofuran-2-yl | H | H | H | O |
| I-1-223 | 2,5-difluorophenyl | 5-fluoro-1-methyl-3-(difluoromethyl)-1H-pyrazol-4-yl | | | | |
| I-1-224 | 2,5-difluoropyridin-3-yl | 2-(trifluoromethyl)phenyl | H | H | H | O |
| I-1-225 | 2,5-difluoropyridin-3-yl | 2-chlorophenyl | H | H | H | O |
| I-1-226 | 2,6-dichlorophenyl | 2-(trifluoromethoxy)pyridin-3-yl | H | H | H | O |
| I-1-227 Synthesis Example 41 | 2,6-difluoro-4-aminophenyl | 2-(trifluoromethyl)phenyl | H | H | H | O |
| I-1-228 Synthesis Example 28 | 2,6-difluoro-4-cyanphenyl | 2-(trifluoromethyl)phenyl | H | H | H | O |
| I-1-229 Synthesis Example 26 | 2,6-difluoro-4-nitrophenyl | 2-(trifluoromethyl)phenyl | H | H | H | O |
| I-1-230 Synthesis Example 27 | 2,6-difluoro-4-trifluor-methyl)phenyl | 2-(trifluoromethyl)phenyl | H | H | H | O |
| I-1-231 | 2,6-difluorophenyl | 1-(difluoromethyl)-4-fluor-3-methyl-1H-pyrazol-5-yl | H | H | H | O |
| I-1-232 | 2,6-difluorophenyl | 1,3-dimethyl-1H-pyrazol-5-yl | H | H | H | O |
| I-1-233 | 2,6-difluorophenyl | 1,3-dimethyl-4-nitro-1H-pyrazol-5-yl | H | H | H | O |
| I-1-234 | 2,6-difluorophenyl | 1,5-dimethyl-4-nitro-1H-pyrazol-3-yl | H | H | H | O |
| I-1-235 | 2,6-difluorophenyl | 1-ethyl-4-iodo-1H-pyrazol-5-yl | H | H | H | O |
| I-1-236 | 2,6-difluorophenyl | 1-methyl-1H-1,2,4-triazol-5-yl | H | H | H | O |
| I-1-237 | 2,6-difluorophenyl | 1-methyl-3-(pentafluorethyl)-4-(trifluormethyl)-1H-pyrazol-5-yl | H | H | H | O |
| I-1-238 | 2,6-difluorophenyl | 1-methyl-3,5-bis(trifluormethyl)-1H-pyrazol-4-yl | H | H | H | O |
| I-1-239 | 2,6-difluorophenyl | 1-methyl-3-nitro-1H-pyrrol-2-yl | H | H | H | O |
| I-1-240 | 2,6-difluorophenyl | 1-methyl-4-(trifluormethyl)-1H-pyrrol-3-yl | H | H | H | O |
| I-1-241 | 2,6-difluorophenyl | 1-methyl-4-nitro-1H-pyrazol-3-yl | H | H | H | O |
| I-1-242 | 2,6-difluorophenyl | 1-methyl-5-nitro-1H-imidazol-4-yl | H | H | H | O |
| I-1-243 | 2,6-difluorophenyl | 1-oxido-2-(trifluormethyl)pyridin-3-yl | H | H | H | O |
| I-1-244 | 2,6-difluorophenyl | 1-sec-butyl-4-chloro-1H-pyrazol-5-yl | H | H | H | O |
| I-1-245 | 2,6-difluorophenyl | 1-sec-butyl-4-iodo-1H-pyrazol-5-yl | H | H | H | O |

TABLE 1-continued (I-1)

| Compound No. | A | B | R3 | R4 | R5 | Z |
|---|---|---|---|---|---|---|
| I-1-246 | 2,6-difluorophenyl | 2-(2,2,2-trifluoroethyl)pyridin-3-yl | H | H | H | O |
| I-1-247 | 2,6-difluorophenyl | 2-(difluoromethoxy)phenyl | H | H | H | O |
| I-1-248 | 2,6-difluorophenyl | 2-(difluoromethyl)pyridin-3-yl | H | H | H | O |
| I-1-249 | 2,6-difluorophenyl | 2-(methylsulphanyl)pyridin-3-yl | H | H | H | O |
| I-1-250 | 2,6-difluorophenyl | 2-(trifluoromethoxy)pyridin-3-yl | H | H | H | O |
| I-1-251 | 2,6-difluorophenyl | 2-(trifluoromethyl)phenyl | Cl | H | H | O |
| I-1-252 | 2,6-difluorophenyl | 2-(trifluoromethyl)phenyl | Br | H | H | O |
| I-1-253 | 2,6-difluorophenyl | 2-(trifluoromethyl)phenyl | H | H | methyl | O |
| I-1-254 | 2,6-difluorophenyl | 2-(trifluoromethyl)phenyl | H | H | ethyl | O |
| I-1-255 | 2,6-difluorophenyl | 2-(trifluoromethyl)phenyl | H | H | allyl | O |
| I-1-256 | 2,6-difluorophenyl | 2-(trifluoromethyl)phenyl | H | H | 1-propyl-2-yl | O |
| I-1-257 | 2,6-difluorophenyl | 2-(trifluoromethyl)phenyl | I | H | H | O |
| I-1-258 | 2,6-difluorophenyl | 2-(trifluoromethyl)phenyl | H | H | cyclopropylmethyl | O |
| I-1-259 | 2,6-difluorophenyl | 2-(trifluoromethyl)phenyl | H | H | cyanomethyl | O |
| I-1-260 | 2,6-difluorophenyl | 2-(trifluoromethyl)phenyl | H | H | 2-propyl | O |
| I-1-261 | 2,6-difluorophenyl | 2-(trifluoromethyl)phenyl | H | H | 1-propyl | O |
| I-1-262 | 2,6-difluorophenyl | 2-(trifluoromethyl)phenyl | H | H | ethoxymethyl | O |
| I-1-263 | 2,6-difluorophenyl | 2-(trifluoromethyl)phenyl | H | H | but-2-yl-1-yl | O |
| I-1-264 | 2,6-difluorophenyl | 2-(trifluoromethyl)phenyl | H | H | 2,2-difluoroethyl | O |
| I-1-265 | 2,6-difluorophenyl | 2-(trifluoromethyl)phenyl | H | H | 2,2,2-trifluoroethyl | O |
| I-1-266 | 2,6-difluorophenyl | 2,3-dichlorophenyl | H | H | H | O |
| I-1-267 | 2,6-difluorophenyl | 2,6-dichlorophenyl | H | H | H | O |
| I-1-268 | 2,6-difluorophenyl | 2,6-dimethylphenyl | H | H | H | O |
| I-1-269 | 2,6-difluorophenyl | 2-acetamidophenyl | H | H | H | O |
| I-1-270 | 2,6-difluorophenyl | 2-acetylphenyl | H | H | H | O |
| I-1-271 | 2,6-difluorophenyl | 2-chloro-6-methoxyphenyl | H | H | H | O |
| I-1-272 | 2,6-difluorophenyl | 2-cyanophenyl | H | H | H | O |
| I-1-273 | 2,6-difluorophenyl | 2-cyclopropylphenyl | H | H | H | O |
| I-1-274 | 2,6-difluorophenyl | 2-ethyl-6-fluorophenyl | H | H | H | O |
| I-1-275 | 2,6-difluorophenyl | 2-ethylpyridin-3-yl | H | H | H | O |
| I-1-276 | 2,6-difluorophenyl | 2-fluoro-6-(trifluormethyl)phenyl | H | H | H | O |
| I-1-277 | 2,6-difluorophenyl | 2-fluoro-6-iodophenyl | H | H | H | O |
| I-1-278 | 2,6-difluorophenyl | 2-fluorophenyl | H | H | H | O |
| I-1-279 | 2,6-difluorophenyl | 2-fluoropyridin-3-yl | H | H | H | O |
| I-1-280 | 2,6-difluorophenyl | 2-methoxyphenyl | H | H | H | O |
| I-1-281 | 2,6-difluorophenyl | 2-methyl-3-furanyl | H | H | H | O |
| I-1-282 | 2,6-difluorophenyl | 3-(difluoromethyl)-2-thienyl | H | H | H | O |
| I-1-283 | 2,6-difluorophenyl | 3-(difluoromethyl)-5-fluor-1-methyl-pyrazol-4-yl | H | H | H | O |
| I-1-284 | 2,6-difluorophenyl | 3-(trifluoromethyl)-2-thienyl | H | H | H | O |
| I-1-285 | 2,6-difluorophenyl | 3-ethylpyrazin-2-yl | H | H | H | O |
| I-1-286 | 3-chloro-5-fluoropyridin-2-yl | 2,6-difluorophenyl | H | H | H | O |
| I-1-287 | 2,6-difluorophenyl | 3-fluoro-2-(trifluoromethyl)phenyl | H | H | H | O |
| I-1-288 | 2,6-difluorophenyl | 3-iodo-2-furanyl | H | H | H | O |
| I-1-289 | 2,6-difluorophenyl | 3-isobutyl-1-methyl-4-nitro-1H-pyrazol-5-yl | H | H | H | O |
| I-1-290 | 2,6-difluorophenyl | 3-isopropyl-1-methyl-4-nitro-1H-pyrazol-5-yl | H | H | H | O |
| I-1-291 | 2,6-difluorophenyl | 3-methyl-5-(trifluormethyl)-1,2-oxazol-4-yl | H | H | H | O |
| I-1-292 | 2,6-difluorophenyl | 3-tert-butyl-1-methyl-4-nitro-1H-pyrazol-5-yl | H | H | H | O |
| I-1-293 | 2,6-difluorophenyl | 3-tert-butyl-4-chloro-1-methyl-1H-pyrazol-5-yl | H | H | H | O |
| I-1-294 | 2,6-difluorophenyl | 4-(difluoromethyl)-1,3-dimethyl-1H-pyrazol-5-yl | H | H | H | O |

TABLE 1-continued (I-1)

$$\text{Structure with R3, R4, R5, N, B, Z, A substituents on pyrazole}$$

| Compound No. | A | B | R3 | R4 | R5 | Z |
|---|---|---|---|---|---|---|
| I-1-295 | 2,6-difluorophenyl | 4-(trifluoromethyl)pyrimidin-5-yl | H | H | H | O |
| I-1-296 | 2,6-difluorophenyl | 4,5,6-trifluoro-2-(trifluormethyl)phenyl | H | H | H | O |
| I-1-297 | 2,6-difluorophenyl | 4,5-dimethyl-1,2-oxazol-3-yl | H | H | H | O |
| I-1-298 | 2,6-difluorophenyl | 4-bromo-1,3-dimethyl-1H-pyrazol-5-yl | H | H | H | O |
| I-1-299 | 2,6-difluorophenyl | 4-bromo-1-ethyl-1H-pyrazol-5-yl | H | H | H | O |
| I-1-300 | 2,6-difluorophenyl | 4-bromo-1-ethyl-3-methyl-1H-pyrazol-5-yl | H | H | H | O |
| I-1-301 | 2,6-difluorophenyl | 4-bromo-1-methyl-1H-pyrazol-3-yl | H | H | H | O |
| I-1-302 | 2,6-difluorophenyl | 4-bromo-1-methyl-1H-pyrazol-5-yl | H | H | H | O |
| I-1-303 | 2,6-difluorophenyl | 4-bromo-1-methyl-3-(trifluoromethyl)-1H-pyrazol-5-yl | H | H | H | O |
| I-1-304 | 2,6-difluorophenyl | 4-bromo-2,5-dimethyl-3-furanyl | H | H | H | O |
| I-1-305 | 2,6-difluorophenyl | 4-bromothiophen-3-yl | H | H | H | O |
| I-1-306 | 2,6-difluorophenyl | 4-chloro-1-(difluormethyl)-3-methyl-1H-pyrazol-5-yl | H | H | H | O |
| I-1-307 | 2,6-difluorophenyl | 4-chloro-1,3-dimethyl-1H-pyrazol-5-yl | H | H | H | O |
| I-1-308 | 2,6-difluorophenyl | 4-chloro-1-ethyl-1H-pyrazol-5-yl | H | H | H | O |
| I-1-309 | 2,6-difluorophenyl | 4-chloro-1-ethyl-3-methyl-1H-pyrazol-5-yl | H | H | H | O |
| I-1-310 | 2,6-difluorophenyl | 4-chloro-1-isopropyl-3-nitro-1H-pyrazol-5-yl | H | H | H | O |
| I-1-311 | 2,6-difluorophenyl | 4-chloro-1-methyl-1H-pyrazol-5-yl | H | H | H | O |
| I-1-312 | 2,6-difluorophenyl | 4-chloro-1-methyl-3-nitro-1H-pyrazol-5-yl | H | H | H | O |
| I-1-313 | 2,6-difluorophenyl | 4-chloro-1-methyl-3-propyl-1H-pyrazol-5-yl | H | H | H | O |
| I-1-314 | 2,6-difluorophenyl | 4-chloro-1-methyl-5-propyl-1H-pyrazol-3-yl | H | H | H | O |
| I-1-315 | 2,6-difluorophenyl | 4-chloro-1-propyl-1H-pyrazol-3-yl | H | H | H | O |
| I-1-316 | 2,6-difluorophenyl | 4-chloro-3-ethyl-1-methyl-1H-pyrazol-5-yl | H | H | H | O |
| I-1-317 | 2,6-difluorophenyl | 4-cyano-1-methyl-3-(pentafluorethyl)-1H-pyrazol-5-yl | H | H | H | O |
| I-1-318 | 2,6-difluorophenyl | 4-cyano-1-methyl-3-(trifluoromethyl)-1H-pyrazol-5-yl | H | H | H | O |
| I-1-319 | 2,6-difluorophenyl | 4-cyclopropyl-1,2,3-thiadiazol-5-yl | H | H | H | O |
| I-1-320 | 2,6-difluorophenyl | 4-fluoro-1,3-dimethyl-1H-pyrazol-5-yl | H | H | H | O |
| I-1-321 | 2,6-difluorophenyl | 4-fluoro-1-methyl-1H-pyrazol-5-yl | H | H | H | O |
| I-1-322 | 2,6-difluorophenyl | 4-fluoro-2-(trifluoromethyl)phenyl | H | H | H | O |
| I-1-323 | 2,6-difluorophenyl | 4-iodo-1-isobutyl-1H-pyrazol-5-yl | H | H | H | O |
| I-1-324 | 2,6-difluorophenyl | 4-iodo-1-methyl-1H-pyrazol-5-yl | H | H | H | O |
| I-1-325 | 2,6-difluorophenyl | 4-iodo-1-propyl-1H-pyrazol-5-yl | H | H | H | O |
| I-1-326 | 2,6-difluorophenyl | 4-methyl-1,2,3-thiadiazol-5-yl | H | H | H | O |
| I-1-327 | 2,6-difluorophenyl | 4-methyl-1,2-oxazol-5-yl | H | H | H | O |
| I-1-328 | 2,6-difluorophenyl | 4-methyl-4H-1,2,4-triazol-3-yl | H | H | H | O |
| I-1-329 | 2,6-difluorophenyl | 5-chloro-2-(trifluoromethyl)phenyl | H | H | H | O |
| I-1-330 | 2,6-difluorophenyl | 5-chloropyrimidin-4-yl | H | H | H | O |
| I-1-331 | 2,6-difluorophenyl | 5-fluoro-2-(trifluoromethyl)phenyl | H | H | H | O |
| I-1-332 | 2,6-difluorophenyl | 5-methyl-1,2,3-thiadiazol-4-yl | H | H | H | O |
| I-1-333 | 2,6-difluorophenyl | 6-methyl-3,4-dihydro-2H-pyran-5-yl | H | H | H | O |
| I-1-334 | 2-bromophenyl | 2,6-difluorophenyl | H | H | H | O |
| I-1-335 | 2-bromophenyl | 2-fluoro-6-(trifluormethyl)phenyl | H | H | H | O |
| I-1-336 | 2-bromophenyl | 3-methylpyridin-2-yl | H | H | H | O |
| I-1-337 | 2-chloro-3-cyanpyridin-4-yl Synthesis Example 37 | 2-(trifluoromethyl)phenyl | H | H | H | O |
| I-1-338 | 2-chloro-4-methylphenyl | 2-bromophenyl | H | H | H | O |
| I-1-339 | 2-chloro-4-methylphenyl | 2-chlorophenyl | H | H | H | O |
| I-1-340 | 2-chloro-6-ethoxyphenyl | 2-(trifluoromethyl)phenyl | H | H | H | O |
| I-1-341 | 2-chlorophenyl | 2-(methylsulphonyl)phenyl | H | H | H | O |
| I-1-342 | 2-chlorophenyl | 2-(methylsulphonyl)phenyl | H | methyl | H | O |
| I-1-343 | 2-chlorophenyl | 2-(trifluoromethoxy)phenyl | H | methyl | H | O |
| I-1-344 | 2-chlorophenyl | 2-(trifluoromethoxy)pyridin-3-yl | H | H | H | O |
| I-1-345 | 2-chlorophenyl | 2-(trifluoromethyl)phenyl | methyl | H | H | O |
| I-1-346 | 2-chlorophenyl | 2-(trifluoromethyl)phenyl | cyano | H | H | O |
| I-1-347 | 2-chlorophenyl | 2-(trifluoromethyl)phenyl | H | methyl | H | O |
| I-1-348 | 2-chlorophenyl | 2-(trifluoromethyl)pyridin-3-yl | methyl | H | H | O |

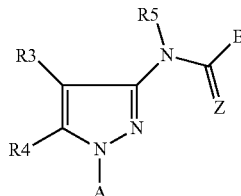

(I-1)

| Compound No. | A | B | R3 | R4 | R5 | Z |
|---|---|---|---|---|---|---|
| I-1-349 | 2-chlorophenyl | 2-(trifluoromethyl)pyridin-3-yl | H | methyl | H | O |
| I-1-350 | 2-chlorophenyl | 2,3-dichlorophenyl | H | H | H | O |
| I-1-351 | 2-chlorophenyl | 2,6-dichlorophenyl | H | H | H | O |
| I-1-352 | 2-chlorophenyl | 2,6-difluorophenyl | methyl | H | H | O |
| I-1-353 | 2-chlorophenyl | 2,6-dimethylphenyl | H | H | H | O |
| I-1-354 | 2-chlorophenyl | 2-bromophenyl | methyl | H | H | O |
| I-1-355 | 2-chlorophenyl | 2-bromophenyl | H | amino | H | O |
| I-1-356 | 2-chlorophenyl | 2-bromophenyl | H | methyl | H | O |
| I-1-357 | 2-chlorophenyl | 2-bromopyridin-3-yl | methyl | H | H | O |
| I-1-358 | 2-chlorophenyl | 2-bromopyridin-3-yl | H | H | H | O |
| I-1-359 | 2-chlorophenyl | 2-bromopyridin-3-yl | H | methyl | H | O |
| I-1-360 | 2-chlorophenyl | 2-chlorophenyl | methyl | H | H | O |
| I-1-361 | 2-chlorophenyl | 2-chlorophenyl | H | amino | H | O |
| I-1-362 | 2-chlorophenyl | 2-chlorophenyl | cyano | H | H | O |
| I-1-363 | 2-chlorophenyl | 2-chloropyrazin-3-yl | H | H | H | O |
| I-1-364 | 2-chlorophenyl | 2-fluoropyridin-3-yl | H | H | H | O |
| I-1-365 | 2-chlorophenyl | 2-iodophenyl | methyl | H | H | O |
| I-1-366 | 2-chlorophenyl | 2-iodophenyl | Br | H | H | O |
| I-1-367 | 2-chlorophenyl | 2-iodophenyl | I | H | H | O |
| I-1-368 | 2-chlorophenyl | 2-iodophenyl | cyano | H | H | O |
| I-1-369 | 2-chlorophenyl | 2-iodopyridin-3-yl | H | H | H | O |
| I-1-370 | 2-chlorophenyl | 2-methyl-3-furanyl | H | H | H | O |
| I-1-371 | 2-chlorophenyl | 2-methyl-4-(trifluormethyl)-1,3-thiazol-5-yl | H | H | H | O |
| I-1-372 | 2-chlorophenyl | 2-methyl-5,6-dihydro-1,4-oxathiin-3-yl | H | H | H | O |
| I-1-373 | 2-chlorophenyl | 2-tert-butylphenyl | H | H | H | O |
| I-1-374 | 2-chlorophenyl | 3-(difluoromethyl)-2-thienyl | H | H | H | O |
| I-1-375 | 2-chlorophenyl | 3-(trifluoromethyl)-2-thienyl | H | H | H | O |
| I-1-376 | 2-chlorophenyl | 3-(trifluoromethyl)pyridin-2-yl | H | methyl | H | O |
| I-1-377 | 2-chlorophenyl | 3-chloro-2-thienyl | H | H | H | O |
| I-1-378 | 2-chlorophenyl | 3-iodo-2-furanyl | H | H | H | O |
| I-1-379 | 2-chlorophenyl | 3-iodo-2-thienyl | H | H | H | O |
| I-1-380 | 2-chlorophenyl | 4-(trifluoromethyl)pyridin-3-yl | H | methyl | H | O |
| I-1-381 | 2-chlorophenyl | 4-chloropyridin-3-yl | H | H | H | O |
| I-1-382 | 2-chlorophenyl | 5-fluoro-1,3-dimethyl-1H-pyrazol-4-yl | H | H | H | O |
| I-1-383 | 2-chlorophenyl | 5-fluoro-1-methyl-3-(trifluormethyl)-1H-pyrazol-4-yl | H | H | H | O |
| I-1-384 | 2-chlorphenyl | 6-fluoro-2-(trifluoromethyl)phenyl | H | H | H | O |
| I-1-385 | 2-chloropyrazin-5-yl | 2-(trifluoromethyl)phenyl | H | H | H | O |
| I-1-386 | 2-chloropyrazin-5-yl | 2-(trifluoromethyl)pyridin-3-yl | H | H | H | O |
| I-1-387 | 2-chloropyrazin-5-yl | 2,6-difluorophenyl | H | H | H | O |
| I-1-388 | 2-chloropyrazin-5-yl | 2-bromophenyl | H | H | H | O |
| I-1-389 | 2-chloropyrazin-5-yl | 2-chlorophenyl | H | H | H | O |
| I-1-390 | 2-chloropyrazin-5-yl | 2-iodophenyl | H | H | H | O |
| I-1-391 | 2-chloropyridin-3-yl | 2-(trifluoromethyl)phenyl | H | H | H | O |
| I-1-392 | 2-chloropyridin-3-yl | 2-chlorophenyl | H | H | H | O |
| I-1-393 Synthesis Example 29 | 2-cyano-4,6-difluorophenyl | 2-(trifluoromethyl)phenyl | H | H | H | O |
| I-1-394 | 2-cyanophenyl | 2-iodophenyl | H | H | H | O |
| I-1-395 | 2-ethoxy-3-chlorophenyl | 2-(trifluoromethyl)pyridin-3-yl | H | H | H | O |
| I-1-396 | 2-ethoxy-3-fluorophenyl | 2-bromophenyl | H | H | H | O |
| I-1-397 | 2-ethoxy-3-fluorophenyl | 2-chlorophenyl | H | H | H | O |
| I-1-398 | 2-chloro-6-ethoxyphenyl | 2-bromophenyl | H | H | H | O |
| I-1-399 | 2-ethoxy-6-fluorophenyl | 2-bromophenyl | H | H | H | O |
| I-1-400 | 2-fluorophenyl | 2,5-dimethylfuran-3-yl | H | H | H | O |
| I-1-401 | 2-fluoropyrazin-6-yl | 2-(trifluoromethyl)phenyl | H | H | H | O |
| I-1-402 | 2-fluoropyrazin-6-yl | 2-(trifluoromethyl)pyridin-3-yl | H | H | H | O |
| I-1-403 | 2-fluoropyrazin-6-yl | 2,6-difluorophenyl | H | H | H | O |
| I-1-404 | 2-fluoropyrazin-6-yl | 2-bromopyridin-3-yl | H | H | H | O |
| I-1-405 | 2-fluoropyrazin-6-yl | 2-iodophenyl | H | H | H | O |
| I-1-406 | 2-methoxyphenyl | 2-(trifluoromethyl)phenyl | H | H | H | O |
| I-1-407 | 2-methoxyphenyl | 2-(trifluoromethyl)pyridin-3-yl | H | H | H | O |
| I-1-408 | 2-methoxyphenyl | 2,6-difluorophenyl | H | H | H | O |
| I-1-409 | 2-methoxyphenyl | 2-bromopyridin-3-yl | H | H | H | O |

TABLE 1-continued (I-1)

| Compound No. | A | B | R3 | R4 | R5 | Z |
|---|---|---|---|---|---|---|
| I-1-410 | 2-methoxyphenyl | 2-chlorophenyl | H | H | H | O |
| I-1-411 | 2-methoxyphenyl | 2-iodophenyl | H | H | H | O |
| I-1-412 | 2-methoxypyrazin-3-yl | 2,5-dimethylfuran-3-yl | H | H | H | O |
| I-1-413 | 2-methoxypyrazin-3-yl | 2-bromophenyl | H | H | H | O |
| I-1-414 | 2-methylphenyl | 2,5-dimethylfuran-3-yl | H | H | H | O |
| I-1-415 | 2-nitrophenyl | 2-(trifluoromethyl)phenyl | H | H | H | O |
| I-1-416 | 2-nitrophenyl | 2-(trifluoromethyl)pyridin-3-yl | H | H | H | O |
| I-1-417 | 2-nitrophenyl | 2,6-difluorophenyl | H | H | H | O |
| I-1-418 | 2-nitrophenyl | 2-bromophenyl | H | H | H | O |
| I-1-419 | 2-nitrophenyl | 2-iodophenyl | H | H | H | O |
| I-1-420 | 2-pyridyl | 2-chlorophenyl | H | H | H | O |
| I-1-421 | 3-chloro-5-(trifluoromethyl)pyridin-2-yl | 2-iodophenyl | H | H | H | O |
| I-1-422 | 3-(trifluoromethyl)pyridin-2-yl | 2-(trifluoromethyl)phenyl | H | H | H | O |
| I-1-423 | 3-(trifluoromethyl)pyridin-2-yl | 2,6-difluorophenyl | H | H | H | O |
| I-1-424 | 3-(trifluoromethyl)pyridin-2-yl | 2-bromophenyl | H | H | H | O |
| I-1-425 | 3-(trifluoromethyl)pyridin-2-yl | 2-chlorophenyl | H | H | H | O |
| I-1-426 | 3-(trifluoromethyl)pyridin-2-yl | 2-(trifluoromethyl)pyridin-3-yl | H | H | H | O |
| I-1-427 | 3-(trifluoromethyl)pyridin-2-yl | 2-iodophenyl | H | H | H | O |
| I-1-428 | 3,5-dichloropyridin-2-yl | 2-(trifluoromethyl)phenyl | H | H | H | O |
| I-1-429 | 3,5-dichloropyridin-2-yl | 2,6-difluorophenyl | H | H | H | O |
| I-1-430 | 3,5-dichloropyridin-2-yl | 2-bromophenyl | H | H | H | O |
| I-1-431 | 3,5-dichloropyridin-2-yl | 2-bromopyridin-3-yl | H | H | H | O |
| I-1-432 | 3,5-dichloropyridin-2-yl | 2-chlorophenyl | H | H | H | O |
| I-1-433 | 3,5-dichloropyridin-2-yl | 2-iodophenyl | H | H | H | O |
| I-1-434 | 3,5-dichloropyridin-2-yl | 3-fluoro-2-(trifluoromethyl)phenyl | H | H | H | O |
| I-1-435 | 3,5-dichloropyridin-2-yl | 3-iodo-1-methyl-1H-pyrazol-4-yl | H | H | H | O |
| I-1-436 | 3,5-dichloropyridin-2-yl | 4-fluoro-2-(trifluoromethyl)phenyl | H | H | H | O |
| I-1-437 | 3,5-dichloropyridin-2-yl | 5-chloro-2-(trifluoromethyl)phenyl | H | H | H | O |
| I-1-438 | 3,5-difluoro-1-oxidopyridin-2-yl Synthesis Example 48 | 2-(trifluoromethyl)phenyl | H | H | H | O |
| I-1-439 | 3,5-difluoro-6-methyl-pyridin-2-yl | 2-(trifluoromethyl)phenyl | H | H | H | O |
| I-1-440 | 3,5-difluoro-6-methyl-pyridin-2-yl | 2-(trifluoromethyl)pyridin-3-yl | H | H | H | O |
| I-1-441 | 3,5-difluoro-6-methyl-pyridin-2-yl | 2,6-difluorophenyl | H | H | H | O |
| I-1-442 | 3,5-difluoro-6-methyl-pyridin-2-yl | 2-bromophenyl | H | H | H | O |
| I-1-443 | 3,5-difluoropyridin-2-yl | 1-(difluoromethyl)-1H-pyrazol-5-yl | H | H | H | O |
| I-1-444 | 3,5-difluoropyridin-2-yl | 1-(difluoromethyl)-4-fluor-3-methyl-1H-pyrazol-5-yl | H | H | H | O |
| I-1-445 | 3,5-difluoropyridin-2-yl | 1,3,5-trimethyl-1H-pyrazol-4-yl | H | H | H | O |
| I-1-446 | 3,5-difluoropyridin-2-yl | 1,3-dimethyl-1H-pyrazol-4-yl | H | H | H | O |
| I-1-447 | 3,5-difluoropyridin-2-yl | 1,3-dimethyl-4-nitro-1H-pyrazol-5-yl | H | H | H | O |
| I-1-448 | 3,5-difluoropyridin-2-yl | 1,5-dimethyl-4-nitro-1H-pyrazol-3-yl | H | H | H | O |
| I-1-449 | 3,5-difluoropyridin-2-yl | 1-methyl-1H-1,2,4-triazol-5-yl | H | H | H | O |
| I-1-450 | 3,5-difluoropyridin-2-yl | 1-methyl-3-(pentafluorethyl)-4-(trifluormethyl)-1H-pyrazol-5-yl | H | H | H | O |
| I-1-451 | 3,5-difluoropyridin-2-yl | 1-methyl-3,5-bis(trifluormethyl)-1H-pyrazol-4-yl | H | H | H | O |
| I-1-452 | 3,5-difluoropyridin-2-yl | 1-methyl-3-nitro-1H-pyrrol-2-yl | H | H | H | O |
| I-1-453 | 3,5-difluoropyridin-2-yl | 1-methyl-4-nitro-1H-pyrazol-3-yl | H | H | H | O |
| I-1-454 | 3,5-difluoropyridin-2-yl | 1-methyl-5-nitro-1H-imidazol-4-yl | H | H | H | O |
| I-1-455 | 3,5-difluoropyridin-2-yl | 1-sec-butyl-4-chloro-1H-pyrazol-5-yl | H | H | H | O |
| I-1-456 | 3,5-difluoropyridin-2-yl | 1-sec-butyl-4-iodo-1H-pyrazol-5-yl | H | H | H | O |
| I-1-457 | 3,5-difluoropyridin-2-yl | 2-(2,2,2-trifluoroethyl)pyridin-3-yl | H | H | H | O |
| I-1-458 | 3,5-difluoropyridin-2-yl | 2-(difluoromethoxy)phenyl | H | H | H | O |
| I-1-459 | 3,5-difluoropyridin-2-yl | 2-(difluoromethoxy)phenyl | H | H | H | O |

TABLE 1-continued (I-1)

| Compound No. | A | B | R3 | R4 | R5 | Z |
|---|---|---|---|---|---|---|
| I-1-460 | 3,5-difluoropyridin-2-yl | 2-(difluoromethyl)pyridin-3-yl | H | H | H | O |
| I-1-461 | 3,5-difluoropyridin-2-yl | 2-(methylsulphanyl)pyridin-3-yl | H | H | H | O |
| I-1-462 | 3,5-difluoropyridin-2-yl | 2-(methylsulphonyl)phenyl | H | H | H | O |
| I-1-463 | 3,5-difluoropyridin-2-yl | 2-(trifluoromethoxy)phenyl | H | H | H | O |
| I-1-464 | 3,5-difluoropyridin-2-yl | 2-(trifluoromethoxy)pyridin-3-yl | H | H | H | O |
| I-1-465 | 3,5-difluoropyridin-2-yl | 2-(trifluoromethyl)phenyl | F | H | H | O |
| I-1-466 | 3,5-difluoropyridin-2-yl | 2-(trifluoromethyl)phenyl | H | H | H | O |
| I-1-467 | 3,5-difluoropyridin-2-yl | 2-(trifluoromethyl)phenyl | H | H | methyl | O |
| I-1-468 | 3,5-difluoropyridin-2-yl | 2-(trifluoromethyl)phenyl | H | H | ethyl | O |
| I-1-469 | 3,5-difluoropyridin-2-yl | 2-(trifluoromethyl)phenyl | H | H | allyl | O |
| I-1-470 | 3,5-difluoropyridin-2-yl | 2-(trifluoromethyl)phenyl | H | H | 1-propyn-2-yl | O |
| I-1-471 | 3,5-difluoropyridin-2-yl | 2-(trifluoromethyl)phenyl | H | H | cyclopropylmethyl | O |
| I-1-472 | 3,5-difluoropyridin-2-yl | 2-(trifluoromethyl)phenyl | H | H | cyanomethyl | O |
| I-1-473 | 3,5-difluoropyridin-2-yl | 2-(trifluoromethyl)phenyl | Cl | H | H | O |
| I-1-474 | 3,5-difluoropyridin-2-yl | 2-(trifluoromethyl)phenyl | Br | H | H | O |
| I-1-475 | 3,5-difluoropyridin-2-yl | 2-(trifluoromethyl)phenyl | nitro | H | H | O |
| I-1-476 | 3,5-difluoropyridin-2-yl | 2,3-dichlorophenyl | H | H | H | O |
| I-1-477 | 3,5-difluoropyridin-2-yl | 2,3-dichlorophenyl | H | H | 2,3-dichlorophenylcarbonyl | O |
| I-1-478 | 3,5-difluoropyridin-2-yl | 2,4-dimethyl-1,3-thiazol-5-yl | H | H | H | O |
| I-1-479 | 3,5-difluoropyridin-2-yl | 2,6-dichlorophenyl | H | H | H | O |
| I-1-480 | 3,5-difluoropyridin-2-yl | 2,6-dimethylphenyl | H | H | H | O |
| I-1-481 | 3,5-difluoropyridin-2-yl | 2-acetylphenyl | H | H | H | O |
| I-1-482 | 3,5-difluoropyridin-2-yl | 2-bromopyridin-3-yl | H | H | H | O |
| I-1-483 | 3,5-difluoropyridin-2-yl | 2-chloro-5-methoxyphenyl | H | H | H | O |
| I-1-484 | 3,5-difluoropyridin-2-yl | 2-chloro-6-fluorophenyl | H | H | H | O |
| I-1-485 | 3,5-difluoropyridin-2-yl | 2-chloropyrazin-3-yl | H | H | H | O |
| I-1-486 | 3,5-difluoropyridin-2-yl | 2-cyclopropylphenyl | H | H | H | O |
| I-1-487 | 3,5-difluoropyridin-2-yl | 2-ethyl-6-fluorophenyl | H | H | H | O |
| I-1-488 | 3,5-difluoropyridin-2-yl | 2-ethylphenyl | H | H | H | O |
| I-1-489 | 3,5-difluoropyridin-2-yl | 2-ethylpyrazin-3-yl | H | H | H | O |
| I-1-490 | 3,5-difluoropyridin-2-yl | 2-ethylpyridin-3-yl | H | H | H | O |
| I-1-491 | 3,5-difluoropyridin-2-yl | 2-fluoro-6-(trifluormethyl)phenyl | H | H | H | O |
| I-1-492 | 3,5-difluoropyridin-2-yl | 2-fluoro-6-iodophenyl | H | H | H | O |
| I-1-493 | 3,5-difluoropyridin-2-yl | 2-fluorophenyl | H | H | H | O |
| I-1-494 | 3,5-difluoropyridin-2-yl | 2-iodo-3-thienyl | H | H | H | O |
| I-1-495 | 3,5-difluoropyridin-2-yl | 2-iodopyridin-3-yl | H | H | H | O |
| I-1-496 | 3,5-difluoropyridin-2-yl | 2-methoxyphenyl | H | H | H | O |
| I-1-497 | 3,5-difluoropyridin-2-yl | 2-methyl-4-(trifluormethyl)-1,3-thiazol-5-yl | H | H | H | O |
| I-1-498 | 3,5-difluoropyridin-2-yl | 2-methyl-5,6-dihydro-1,4-oxathiin-3-yl | H | H | H | O |
| I-1-499 | 3,5-difluoropyridin-2-yl | 2-methylphenyl | H | H | H | O |
| I-1-500 | 3,5-difluoropyridin-2-yl | 3-(difluoromethyl)-5-fluor-1-methyl-pyrazol-4-yl | H | H | H | O |
| I-1-501 | 3,5-difluoropyridin-2-yl | 3-(trifluoromethyl)pyrazin-2-yl | H | H | H | O |
| I-1-502 | 3,5-difluoropyridin-2-yl | 3-(trifluoromethyl)pyridin-2-yl | H | H | H | O |
| I-1-503 | 3,5-difluoropyridin-2-yl | 3-chloro-2-thienyl | H | H | H | O |
| I-1-504 | 3,5-difluoropyridin-2-yl | 3-chloropyridin-2-yl | H | H | H | O |
| I-1-505 | 3,5-difluoropyridin-2-yl | 3-ethylpyridazin-4-yl | H | H | H | O |
| I-1-506 | 3,5-difluoropyridin-2-yl | 3-fluoro-6-(trifluormethyl)phenyl | H | H | H | O |
| I-1-507 | 3,5-difluoropyridin-2-yl | 3-iodo-2-thienyl | H | H | H | O |
| I-1-508 | 3,5-difluoropyridin-2-yl | 3-isobutyl-1-methyl-4-nitro-1H-pyrazol-5-yl | H | H | H | O |
| I-1-509 | 3,5-difluoropyridin-2-yl | 3-isopropyl-1-methyl-4-nitro-1H-pyrazol-5-yl | H | H | H | O |
| I-1-510 | 3,5-difluoropyridin-2-yl | 3-methyl-2-thienyl | H | H | H | O |
| I-1-511 | 3,5-difluoropyridin-2-yl | 3-methyl-5-(trifluormethyl)-1,2-oxazol-4-yl | H | H | H | O |

TABLE 1-continued (I-1)

| Compound No. | A | B | R3 | R4 | R5 | Z |
|---|---|---|---|---|---|---|
| I-1-512 | 3,5-difluoropyridin-2-yl | 3-tert-butyl-1-methyl-4-nitro-1H-pyrazol-5-yl | H | H | H | O |
| I-1-513 | 3,5-difluoropyridin-2-yl | 3-tert-butyl-4-chloro-1-methyl-1H-pyrazol-5-yl | H | H | H | O |
| I-1-514 | 3,5-difluoropyridin-2-yl | 4-(difluoromethyl)-1,3-dimethyl-1H-pyrazol-5-yl | H | H | H | O |
| I-1-515 | 3,5-difluoropyridin-2-yl | 4-(trifluoromethyl)pyridin-3-yl | H | H | H | O |
| I-1-516 | 3,5-difluoropyridin-2-yl | 4,5,6-trifluoro-2-(trifluormethyl)phenyl | H | H | H | O |
| I-1-517 | 3,5-difluoropyridin-2-yl | 4-bromo-1,3-dimethyl-1H-pyrazol-5-yl | H | H | H | O |
| I-1-518 | 3,5-difluoropyridin-2-yl | 4-bromo-1-ethyl-1H-pyrazol-5-yl | H | H | H | O |
| I-1-519 | 3,5-difluoropyridin-2-yl | 4-bromo-1-ethyl-3-methyl-1H-pyrazol-5-yl | H | H | H | O |
| I-1-520 | 3,5-difluoropyridin-2-yl | 4-bromo-1-methyl-1H-pyrazol-3-yl | H | H | H | O |
| I-1-521 | 3,5-difluoropyridin-2-yl | 4-bromo-1-methyl-1H-pyrazol-5-yl | H | H | H | O |
| I-1-522 | 3,5-difluoropyridin-2-yl | 4-bromo-1-methyl-3-(trifluormethyl)-1H-pyrazol-5-yl | H | H | H | O |
| I-1-523 | 3,5-difluoropyridin-2-yl | 4-bromo-2,5-dimethyl-3-furanyl | H | H | H | O |
| I-1-524 | 3,5-difluoropyridin-2-yl | 4-bromothiophen-3-yl | H | H | H | O |
| I-1-525 | 3,5-difluoropyridin-2-yl | 4-chloro-1-(difluormethyl-3-methyl-1H-pyrazol-5-yl | H | H | H | O |
| I-1-526 | 3,5-difluoropyridin-2-yl | 4-chloro-1-ethyl-1H-pyrazol-5-yl | H | H | H | O |
| I-1-527 | 3,5-difluoropyridin-2-yl | 4-chloro-1-ethyl-3-methyl-1H-pyrazol-5-yl | H | H | H | O |
| I-1-528 | 3,5-difluoropyridin-2-yl | 4-chloro-1-isopropyl-3-nitro-1H-pyrazol-5-yl | H | H | H | O |
| I-1-529 | 3,5-difluoropyridin-2-yl | 4-chloro-1-methyl-1H-pyrazol-5-yl | H | H | H | O |
| I-1-530 | 3,5-difluoropyridin-2-yl | 4-chloro-1-methyl-3-nitro-1H-pyrazol-5-yl | H | H | H | O |
| I-1-531 | 3,5-difluoropyridin-2-yl | 4-chloro-1-methyl-3-propyl-1H-pyrazol-5-yl | H | H | H | O |
| I-1-532 | 3,5-difluoropyridin-2-yl | 4-chloro-1-methyl-5-propyl-1H-pyrazol-3-yl | H | H | H | O |
| I-1-533 | 3,5-difluoropyridin-2-yl | 4-chloro-1-propyl-1H-pyrazol-3-yl | H | H | H | O |
| I-1-534 | 3,5-difluoropyridin-2-yl | 4-chloro-3-ethyl-1-methyl-1H-pyrazol-5-yl | H | H | H | O |
| I-1-535 | 3,5-difluoropyridin-2-yl | 4-cyano-1-methyl-3-(pentafluorethyl)-1H-pyrazol-5-yl | H | H | H | O |
| I-1-536 | 3,5-difluoropyridin-2-yl | 4-cyano-1-methyl-3-(trifluormethyl)-1H-pyrazol-5-yl | H | H | H | O |
| I-1-537 | 3,5-difluoropyridin-2-yl | 4-cyclopropyl-1,2,3-thiadiazol-5-yl | H | H | H | O |
| I-1-538 | 3,5-difluoropyridin-2-yl | 4-fluoro-1-methyl-1H-pyrazol-5-yl | H | H | H | O |
| I-1-539 | 3,5-difluoropyridin-2-yl | 4-iodo-1-isobutyl-1H-pyrazol-5-yl | H | H | H | O |
| I-1-540 | 3,5-difluoropyridin-2-yl | 4-iodo-1-methyl-1H-pyrazol-5-yl | H | H | H | O |
| I-1-541 | 3,5-difluoropyridin-2-yl | 4-iodo-1-propyl-1H-pyrazol-5-yl | H | H | H | O |
| I-1-542 | 3,5-difluoropyridin-2-yl | 4-methyl-1,2,5-oxadiazol-3-yl | H | H | H | O |
| I-1-543 | 3,5-difluoropyridin-2-yl | 4-methyl-1,2-oxazol-5-yl | H | H | H | O |
| I-1-544 | 3,5-difluoropyridin-2-yl | 4-methyl-4H-1,2,4-triazol-3-yl | H | H | H | O |
| I-1-545 | 3,5-difluoropyridin-2-yl | 5-chloropyrimidin-4-yl | H | H | H | O |
| I-1-546 | 3,5-difluoropyridin-2-yl | 5-methyl-1,2,3-thiadiazol-4-yl | H | H | H | O |
| I-1-547 | 3,5-difluoropyridin-2-yl | 5-methyl-1,2-oxazol-4-yl | H | H | H | O |
| I-1-548 | 3,5-difluoropyridin-2-yl | 6-methyl-3,4-dihydro-2H-pyran-5-yl | H | H | H | O |
| I-1-549 | 3-bromopyridin-2-yl | 2-(trifluoromethyl)phenyl | H | H | H | O |
| I-1-550 | 3-bromopyridin-2-yl | 2-(trifluoromethyl)pyridin-3-yl | H | H | H | O |
| I-1-551 | 3-bromopyridin-2-yl | 2,6-difluorophenyl | H | H | H | O |
| I-1-552 | 3-bromopyridin-2-yl | 2-bromophenyl | H | H | H | O |
| I-1-553 | 3-bromopyridin-2-yl | 2-chlorophenyl | H | H | H | O |
| I-1-554 | 3-bromopyridin-2-yl | 2-iodophenyl | H | H | H | O |
| I-1-555 | 3-chloro-2-fluorophenyl | 2-(trifluoromethyl)phenyl | H | H | H | O |
| I-1-556 | 3-chloro-2-fluorophenyl | 2,6-difluorophenyl | H | H | H | O |
| I-1-557 | 3-chloro-2-fluorophenyl | 2-bromophenyl | H | H | H | O |
| I-1-558 | 3-chloro-2-fluorophenyl | 2-bromopyridin-3-yl | H | H | H | O |
| I-1-559 | 3-chloro-2-fluorophenyl | 2-chlorophenyl | H | H | H | O |
| I-1-560 | 3-chloro-5-(trifluormethyl)pyridin-2-yl | 2-(trifluoromethyl)phenyl | H | H | H | O |

TABLE 1-continued

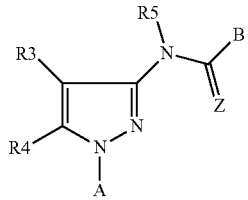

(I-1)

| Compound No. | A | B | R3 | R4 | R5 | Z |
|---|---|---|---|---|---|---|
| I-1-561 | 3-chloro-5-(trifluoromethyl)pyridin-2-yl | 2-chlorophenyl | H | H | H | O |
| I-1-562 | 3-chloropyridin-2-yl | 2-(trifluoromethyl)pyridin-3-yl | H | H | H | O |
| I-1-563 | 3-chloropyridin-2-yl | 2,5-dimethylfuran-3-yl | H | H | H | O |
| I-1-564 | 3-chloropyridin-2-yl | 2,6-difluorophenyl | H | H | H | O |
| I-1-565 | 3-chloropyridin-2-yl | 2-bromopyridin-3-yl | H | H | H | O |
| I-1-566 | 3-chloropyridin-2-yl | 2-iodo-3-thienyl | H | H | H | O |
| I-1-567 | 3-cyano-4,6-dimethyl-pyridin-2-yl | 2-(trifluoromethyl)phenyl | H | H | H | O |
| I-1-568 Synthesis Example 36 | 3-cyano-6-(diethylamino)pyridin-2-yl | 2-(trifluoromethyl)phenyl | H | H | H | O |
| I-1-569 Synthesis Example 31 | 3-cyano-6-(trifluoromethyl)pyridin-2-yl | 2-(trifluoromethyl)phenyl | H | H | H | O |
| I-1-570 Synthesis Example 40 | 3-cyano-6-cyclopropyl-4-(trifluormethyl)pyridin-2-yl | 2-(trifluoromethyl)phenyl | H | H | H | O |
| I-1-571 Synthesis Example 33 | 3-cyano-6-methyl-4-(trifluormethyl)pyridin-2-yl | 2-(trifluoromethyl)phenyl | H | H | H | O |
| I-1-572 | 3-cyano-6-methylpyridin-2-yl | 2-(trifluoromethyl)phenyl | H | H | H | O |
| I-1-573 Synthesis Example 39 | 3-cyano-6-propylpyridin-2-yl | 2-(trifluoromethyl)phenyl | H | H | H | O |
| I-1-574 Synthesis Example 43 | 3-cyanopyrazin-2-yl | 2-(trifluoromethyl)phenyl | H | H | H | O |
| I-1-575 Synthesis Example 25 | 3-cyanopyridin-2-yl | 2-(trifluoromethyl)phenyl | H | H | H | O |
| I-1-576 | 3-fluoro-4-iodopyridin-2-yl | 2-(trifluoromethyl)phenyl | H | H | H | O |
| I-1-577 | 3-fluoropyridin-2-yl | 2-(trifluoromethoxy)pyridin-3-yl | H | H | H | O |
| I-1-578 | 3-fluoropyridin-2-yl | 2-bromopyridin-3-yl | H | H | H | O |
| I-1-579 | 3-fluoropyridin-2-yl | 2-chloropyridin-3-yl | H | H | H | O |
| I-1-580 | 3-fluoropyridin-2-yl | 2-fluoro-6-(trifluormethyl)phenyl | H | H | H | O |
| I-1-581 | 3-fluoropyridin-2-yl | 2-iodo-3-thienyl | H | H | H | O |
| I-1-582 | 3-fluoropyridin-2-yl | 3-iodo-2-furanyl | H | H | H | O |
| I-1-583 Synthesis Example 42 | 4-acetamido-2,6-difluorophenyl | 2-(trifluoromethyl)phenyl | H | H | H | O |
| I-1-584 Synthesis Example 30 | 4-acetyl-2,6-difluorophenyl | 2-(trifluoromethyl)phenyl | H | H | H | O |
| I-1-585 Synthesis Example 37 | 2-chloro-3-cyanpyridin-4-yl | 2-(trifluoromethyl)phenyl | H | H | H | O |
| I-1-586 Synthesis Example 38 | 4-chloro-3-cyanpyridin-2-yl | 2-(trifluoromethyl)phenyl | H | H | H | O |
| I-1-587 | 5-chloro-3-fluorpyridin-2-yl | 2-(trifluoromethyl)phenyl | H | H | H | O |
| I-1-588 | 5-chloro-3-fluorpyridin-2-yl | 2,6-difluorophenyl | H | H | H | O |
| I-1-589 | 5-chloro-3-fluorpyridin-2-yl | 2-bromophenyl | H | H | H | O |
| I-1-590 | 5-chloro-3-fluorpyridin-2-yl | 2-chlorophenyl | H | H | H | O |
| I-1-591 | 5-chloro-3-fluorpyridin-2-yl | 2-fluoro-6-(trifluormethyl)phenyl | H | H | H | O |
| I-1-592 | 5-chloro-3-fluorpyridin-2-yl | 2-iodo-3-thienyl | H | H | H | O |
| I-1-593 | 5-chloro-3-fluorpyridin-2-yl | 2-iodophenyl | H | H | H | O |
| I-1-594 | 5-cyanopyrimidin-4-yl | 2-(trifluoromethyl)phenyl | H | H | H | O |
| I-1-595 | 5-cyanopyrimidin-4-yl | 2,6-difluorophenyl | H | H | H | O |
| I-1-596 | 5-fluoropyridin-2-yl | 2-(trifluoromethyl)phenyl | H | H | H | O |
| I-1-597 | 5-fluoropyridin-2-yl | 2-(trifluoromethylpyridin-3-yl | H | H | H | O |
| I-1-598 | 5-fluoropyridin-2-yl | 2,6-difluorophenyl | H | H | H | O |
| I-1-599 | 5-fluoropyridin-2-yl | 2-iodophenyl | H | H | H | O |
| I-1-600 | 5-fluoropyrimidin-2-yl | 2-(trifluoromethyl)phenyl | H | H | H | O |
| I-1-601 | 5-fluoropyrimidin-2-yl | 2-(trifluoromethyl)pyridin-3-yl | H | H | H | O |

TABLE 1-continued

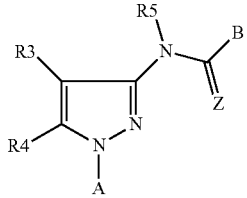

(I-1)

| Compound No. | A | B | R3 | R4 | R5 | Z |
|---|---|---|---|---|---|---|
| I-1-602 | 5-fluoropyrimidin-2-yl | 2,6-difluorophenyl | H | H | H | O |
| I-1-603 | 5-fluoropyrimidin-2-yl | 2-bromophenyl | H | H | H | O |
| I-1-604 | 5-fluoropyrimidin-2-yl | 2-chlorophenyl | H | H | H | O |
| I-1-605 | 5-fluoropyrimidin-2-yl | 2-iodophenyl | H | H | H | O |
| I-1-606 Synthesis Example 44 | 6-chloro-5-cyan-3-fluor-pyridin-2-yl | 2-(trifluoromethyl)phenyl | H | H | H | O |
| I-1-607 Synthesis Example 34 | 6-chloro-3-cyanpyridin-2-yl | 2-(trifluoromethyl)phenyl | H | H | H | O |
| I-1-608 Synthesis Example 35 | 6-chloro-5-cyanpyridin-2-yl | 2-(trifluoromethyl)phenyl | H | H | H | O |
| I-1-609 | pyrimidin-2-yl | 2,5-dimethylfuran-3-yl | H | H | H | O |
| I-1-610 | 2,6-difluorophenyl | 2-(2,2,2-trifluoroethyl)phenyl | H | H | H | O |
| I-1-611 | 2,6-difluorophenyl | 2-(difluoromethyl)-5,6-dihydro-1,4-oxathiin-3-yl | H | H | H | O |
| I-1-612 | 2,6-difluorophenyl | 2-[(trifluoroacetyl)amino]phenyl | H | H | H | O |
| I-1-613 | 2,6-difluorophenyl | 2-bromo-6-fluorophenyl | H | H | H | O |
| I-1-614 | 2,6-difluorophenyl | 2-chloro-6-(trifluormethyl)phenyl | H | H | H | O |
| I-1-615 | 2,6-difluorophenyl | 3-methyl-5,6-dihydro-1,4-dioxin-2-yl | H | H | H | O |
| I-1-616 | 2,6-difluorophenyl | 2-methyl-5,6-dihydro-4,4-dioxo-1,4-oxathiin-3-yl | H | H | H | O |
| I-1-617 | 2-cyano-3-fluorophenyl | 2-(trifluoromethyl)phenyl | H | H | H | O |
| I-1-618 | 2-cyano-3-fluorophenyl | 2-(trifluoromethyl)pyridin-3-yl | H | H | H | O |
| I-1-619 | 2-cyano-3-fluorophenyl | 2,6-difluorophenyl | H | H | H | O |
| I-1-620 | 2-cyano-3-fluorophenyl | 2-bromophenyl | H | H | H | O |
| I-1-621 | 2-cyano-3-fluorophenyl | 2-chlorophenyl | H | H | H | O |
| I-1-622 | 2-cyano-3-fluorophenyl | 2-chloropyridin-3-yl | H | H | H | O |
| I-1-623 | 2-cyano-3-fluorophenyl | 2-fluoro-6-(trifluormethyl)phenyl | H | H | H | O |
| I-1-624 | 2-cyano-3-fluorophenyl | 2-iodo-3-thienyl | H | H | H | O |
| I-1-625 | 2-cyano-3-fluorophenyl | 2-iodophenyl | H | H | H | O |
| I-1-626 | 2-cyano-4-fluorophenyl | 2-(trifluoromethyl)phenyl | H | H | H | O |
| I-1-627 | 2-cyano-4-fluorophenyl | 2-(trifluoromethyl)pyridin-3-yl | H | H | H | O |
| I-1-628 | 2-cyano-4-fluorophenyl | 2,6-difluorophenyl | H | H | H | O |
| I-1-629 | 2-cyano-4-fluorophenyl | 2-bromophenyl | H | H | H | O |
| I-1-630 | 2-cyano-4-fluorophenyl | 2-chlorophenyl | H | H | H | O |
| I-1-631 | 2-cyano-4-fluorophenyl | 2-chloropyridin-3-yl | H | H | H | O |
| I-1-632 | 2-cyano-4-fluorophenyl | 2-fluoro-6-(trifluormethyl)phenyl | H | H | H | O |
| I-1-633 | 2-cyano-4-fluorophenyl | 2-iodo-3-thienyl | H | H | H | O |
| I-1-634 | 2-cyano-4-fluorophenyl | 2-iodophenyl | H | H | H | O |
| I-1-635 | 3,5-difluoropyridin-2-yl | 2-(2,2,2-trifluoroethyl)phenyl | H | H | H | O |
| I-1-636 | 3,5-difluoropyridin-2-yl | 2-(difluoromethyl)-5,6-dihydro-1,4-oxathiin-3-yl | H | H | H | O |
| I-1-637 | 3,5-difluoropyridin-2-yl | 2-bromo-6-fluorophenyl | H | H | H | O |
| I-1-638 | 3,5-difluoropyridin-2-yl | 2-chloro-6-(trifluormethyl)phenyl | H | H | H | O |
| I-1-639 | 3,5-difluoropyridin-2-yl | 3-methyl-5,6-dihydro-1,4-dioxin-2-yl | H | H | H | O |
| I-1-640 Synthesis Example 23 | 3,5-difluoropyridin-2-yl | 2-methyl-5,6-dihydro-4,4-dioxo-1,4-oxathiin-3-yl | H | H | H | O |
| I-1-641 Synthesis Example 32 | 3-cyano-4-(4-fluoro-phenyl)pyridin-2-yl | 2-(trifluoromethyl)phenyl | H | H | H | O |
| I-1-642 | 3-fluoro-4-(4-fluoro phenyl)pyridin-2-yl | 2-(trifluoromethyl)phenyl | H | H | H | O |
| I-1-643 Synthesis Example 24 | 4-amino-2,6-difluorophenyl | 2-carboxyphenyl | H | H | H | O |
| I-1-644 | 2,6-difluorophenyl | 1-methyl-1H-imidazol-5-yl | H | H | H | O |
| I-1-645 | 2,6-difluorophenyl | 1-methyl-1H-pyrrol-2-yl | H | H | H | O |
| I-1-646 | 3,5-difluoropyridin-2-yl | 1-methyl-1H-imidazol-5-yl | H | H | H | O |
| I-1-647 | 3,5-difluoropyridin-2-yl | 1-methyl-1H-pyrrol-2-yl | H | H | H | O |

TABLE 2

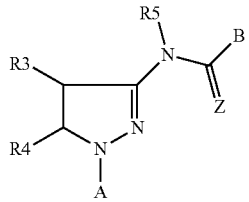

(I-4)

| Compound No. | A | B | R3 | R4 | R5 | Z |
|---|---|---|---|---|---|---|
| I-4-1 | 2,6-difluorophenyl | 2-chlorophenyl | H | H | H | O |
| I-4-2 Synthesis Example 6 | 2,6-difluorophenyl | 2-bromophenyl | H | H | H | O |
| I-4-3 | 2,6-difluorophenyl | 2,6-difluorophenyl | H | H | H | O |
| I-4-4 | 2,6-difluorophenyl | 2-iodophenyl | H | H | H | O |
| I-4-5 | 2,6-difluorophenyl | 2-methylphenyl | H | H | H | O |
| I-4-6 | 2,6-difluorophenyl | 2-methylphenyl | H | H | 2-methylpyridin-3-ylcarbonyl | O |
| I-4-7 | 2,6-difluorophenyl | 2-(trifluoromethyl)phenyl | H | H | H | O |
| I-4-8 | 2-chlorophenyl | 2-bromophenyl | H | H | H | O |

TABLE 3

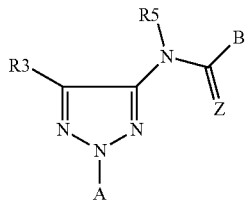

(I-2)

| Compound No. | A | B | R3 | R5 | Z |
|---|---|---|---|---|---|
| I-2-1 Synthesis Example 20 | 2-chlorophenyl | 2-(trifluoromethyl)phenyl | H | H | O |
| I-2-2 | 2-chlorophenyl | 2-chlorophenyl | H | H | O |
| I-2-3 | 2-chlorophenyl | 2-iodophenyl | H | H | O |
| I-2-4 | 2-chlorophenyl | 2-(trifluoromethyl)pyridin-3-yl | H | H | O |
| I-2-5 | 2-chlorophenyl | 2-chloropyridin-3-yl | H | H | O |
| I-2-6 | 2-bromophenyl | 2-(trifluoromethyl)phenyl | H | H | O |
| I-2-7 | 2-bromophenyl | 2-chlorophenyl | H | H | O |
| I-2-8 | 2-bromophenyl | 2-(trifluoromethyl)pyridin-3-yl | H | H | O |
| I-2-9 | 2-bromophenyl | 2-chloropyridin-3-yl | H | H | O |
| I-2-10 | 3-chloropyridin-2-yl | 2-(trifluoromethyl)phenyl | H | H | O |
| I-2-11 | 3-chloropyridin-2-yl | 2-(trifluoromethyl)phenyl | Cl | H | O |
| I-2-12 | 3-chloropyridin-2-yl | 2-chlorophenyl | H | H | O |
| I-2-13 | 3-chloropyridin-2-yl | 2-bromophenyl | H | H | O |
| I-2-14 | 3-chloropyridin-2-yl | 2-iodophenyl | H | H | O |
| I-2-15 | 3-chloropyridin-2-yl | 2,6-difluorophenyl | H | H | O |
| I-2-16 | 3-chloropyridin-2-yl | 5-fluoro-1-methyl-3-(trifluormethyl)-1H-pyrazol-4-yl | H | H | O |
| I-2-17 | 3-bromopyridin-2-yl | 2-(trifluoromethyl)phenyl | H | H | O |
| I-2-18 | 3-bromopyridin-2-yl | 2-iodophenyl | H | H | O |
| I-2-19 | 2-chlorophenyl | 2-(trifluoromethyl)phenyl | Cl | H | O |
| I-2-20 | 2-chlorophenyl | 2-(trifluoromethyl)phenyl | Cl | 2-(trifluoromethyl)phenylcarbonyl | O |
| I-2-21 | 2-chlorophenyl | 2-(trifluoromethyl)phenyl | methyl | H | O |
| I-2-22 | 2-chlorophenyl | 2-(trifluoromethyl)phenyl | methyl | 2-(trifluoromethyl)phenylcarbonyl | O |
| I-2-23 | 2-bromophenyl | 2-chloropyridin-3-yl | Cl | 2-chloropyridin-3-ylcarbonyl | O |
| I-2-24 | 2-chlorophenyl | 2-iodophenyl | methyl | H | O |
| I-2-25 | 2-chlorophenyl | 2-iodophenyl | methyl | 2-iodophenylcarbonyl | O |
| I-2-26 | 2-bromophenyl | 2-(trifluoromethyl)phenyl | Cl | H | O |
| I-2-27 | 2-bromophenyl | 2-(trifluoromethyl)phenyl | Cl | 2-(trifluoromethyl)phenylcarbonyl | O |
| I-2-28 | 2-bromophenyl | 2-(trifluoromethyl)pyridin-3-yl | Cl | H | O |
| I-2-29 | 2-bromophenyl | 2-chlorophenyl | Cl | H | O |

TABLE 3-continued

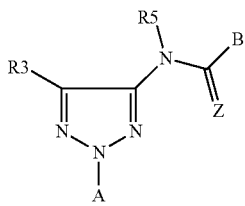

(I-2)

| Compound No. | A | B | R3 | R5 | Z |
|---|---|---|---|---|---|
| I-2-30 | 2-bromophenyl | 2-chlorophenyl | Cl | 2-chlorophenyl carbonyl | O |
| I-2-31 | 2-bromophenyl | 2-chloropyridin-3-yl | Cl | H | O |
| I-2-32 | 2-bromophenyl | 2-iodophenyl | Cl | H | O |
| I-2-33 | 2-bromophenyl | 2-iodophenyl | H | H | O |
| I-2-34 | 2-bromophenyl | 2-iodophenyl | Cl | 2-iodophenyl-carbonyl | O |
| I-2-35 Synthesis Example 21 | 2,6-difluorophenyl | 2-(trifluoromethyl)phenyl | H | H | O |
| I-2-36 | 2,6-difluorophenyl | 2-bromophenyl | H | H | O |
| I-2-37 | 2,6-difluorophenyl | 2-bromopyridin-3-yl | H | H | O |
| I-2-38 | 2,6-difluorophenyl | 2-chlorophenyl | H | H | O |
| I-2-39 | 2,6-difluorophenyl | 2-fluoro-6-(trifluormethyl)phenyl | H | H | O |
| I-2-40 | 2,6-difluorophenyl | 2-iodo-3-thienyl | H | H | O |
| I-2-41 | 2,6-difluorophenyl | 2-iodophenyl | H | H | O |
| I-2-42 | 5-(trifluoromethyl)pyridin-2-yl | 2-(trifluoromethyl)phenyl | H | H | O |
| I-2-43 | 5-(trifluoromethyl)pyridin-2-yl | 2-iodophenyl | H | H | O |
| I-2-44 | 3-fluoropyridin-2-yl | 2-(trifluoromethyl)phenyl | H | H | O |
| I-2-45 | 3-fluoropyridin-2-yl | 2-(trifluoromethyl)pyridin-3-yl | H | H | O |
| I-2-46 | 3-fluoropyridin-2-yl | 2-bromophenyl | H | H | O |
| I-2-47 | 3-fluoropyridin-2-yl | 2-bromopyridin-3-yl | H | H | O |
| I-2-48 | 3-fluoropyridin-2-yl | 2-chlorophenyl | H | H | O |
| I-2-49 | 3-fluoropyridin-2-yl | 2-fluoro-6-(trifluormethyl)phenyl | H | H | O |
| I-2-50 | 3-fluoropyridin-2-yl | 2-iodo-3-thienyl | H | H | O |
| I-2-51 | 3-fluoropyridin-2-yl | 2-iodophenyl | H | H | O |
| I-2-52 | 3-chloropyridin-2-yl | 2-(trifluoromethyl)phenyl | H | 2-(trifluoromethyl)phenylcarbonyl | O |
| I-2-53 | 3-chloropyridin-2-yl | 2-(trifluoromethyl)phenyl | methyl | H | O |
| I-2-54 | 3-chloropyridin-2-yl | 2-(trifluoromethyl)phenyl | methyl | 2-(trifluoromethyl)phenylcarbonyl | O |
| I-2-55 | 3-chloropyridin-2-yl | 2-(trifluoromethyl)pyridin-3-yl | H | H | O |
| I-2-56 | 3-chloropyridin-2-yl | 2-chloropyridin-3-yl | H | H | O |
| I-2-57 | 3-chloropyridin-2-yl | 2-fluoro-6-(trifluormethyl)phenyl | H | H | O |
| I-2-58 | 3-chloropyridin-2-yl | 2-iodo-3-thienyl | H | H | O |
| I-2-59 | 3-chloropyridin-2-yl | 2-iodophenyl | methyl | H | O |
| I-2-60 | 3-chloropyridin-2-yl | 2-iodophenyl | Cl | H | O |
| I-2-61 | 3-chloropyridin-2-yl | 2-iodophenyl | methyl | 2-iodophenyl-carbonyl | O |
| I-2-62 | 2,5-difluoropyridin-3-yl | 2-(trifluoromethyl)phenyl | H | H | O |
| I-2-63 Synthesis Example 45 | 3,5-dichloropyridin-2-yl | 2-(trifluoromethyl)phenyl | H | H | O |
| I-2-64 | 3,5-dichloropyridin-2-yl | 2-(trifluoromethyl)pyridin-3-yl | H | H | O |
| I-2-65 | 3,5-dichloropyridin-2-yl | 2-iodophenyl | H | H | O |
| I-2-66 | 3,5-difluoropyridin-2-yl | 2-(trifluoromethyl)phenyl | H | H | O |
| I-2-67 | 3,5-difluoropyridin-2-yl | 2-(trifluoromethyl)pyridin-3-yl | H | H | O |
| I-2-68 | 3,5-difluoropyridin-2-yl | 2-bromophenyl | H | H | O |
| I-2-69 | 3,5-difluoropyridin-2-yl | 2-bromopyridin-3-yl | H | H | O |
| I-2-70 | 3,5-difluoropyridin-2-yl | 2-chlorophenyl | H | H | O |
| I-2-71 | 3,5-difluoropyridin-2-yl | 2-fluoro-6-(trifluormethyl)phenyl | H | H | O |
| I-2-72 | 3,5-difluoropyridin-2-yl | 2-iodo-3-thienyl | H | H | O |
| I-2-73 | 3,5-difluoropyridin-2-yl | 2-iodophenyl | H | H | O |
| I-2-74 | 3-chloro-5-(trifluormethyl)pyridin-2-yl | 2-(trifluoromethyl)phenyl | H | H | O |
| I-2-75 | 3-chloro-5-(trifluormethyl)pyridin-2-yl | 2-iodophenyl | H | H | O |

TABLE 3-continued

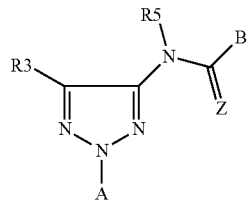

(I-2)

| Compound No. | A | B | R3 | R5 | Z |
|---|---|---|---|---|---|
| I-2-76 | 2,6-difluorophenyl | 2-(trifluoromethyl)pyridin-3-yl | H | H | O |
| I-2-77 | 2,6-difluorophenyl | 2,6-difluorophenyl | H | H | O |
| I-2-78 | 2,6-difluorophenyl | 3-(difluoromethyl)-1-methyl-1H-pyrazol-4-yl | H | H | O |
| I-2-79 | 2,6-difluorophenyl | 3-(trifluoromethyl)pyrazin-2-yl | H | H | O |
| I-2-80 | 2,6-difluorophenyl | 3-(trifluoromethyl)pyridin-2-yl | H | H | O |
| I-2-81 | 2,6-difluorophenyl | 3-(trifluoromethyl)pyridin-4-yl | H | H | O |
| I-2-82 | 2,6-difluorophenyl | 3-(trifluoromethyl)thiophen-2-yl | H | H | O |
| I-2-83 | 2,6-difluorophenyl | 4-(trifluoromethyl)pyridin-3-yl | H | H | O |
| I-2-84 | 3,5-difluoropyridin-2-yl | 3-(trifluoromethyl)pyridin-2-yl | H | H | O |
| I-2-85 | 3,5-difluoropyridin-2-yl | 3-(trifluoromethyl)thiophen-2-yl | H | H | O |

TABLE 4

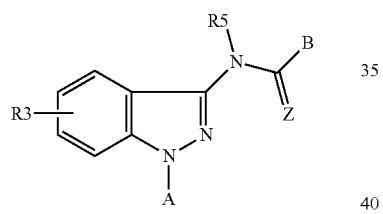

(I-5)

| Compound No. | A | B | R3 | R5 | Z |
|---|---|---|---|---|---|
| I-5-1 | 3,5-difluoropyridin-2-yl | 2-(trifluoromethyl)phenyl | H | H | O |
| I-5-2 Synthesis Example 22 | 3,5-difluoropyridin-2-yl | 2-(trifluoromethyl)phenyl | 5-F | H | O |
| I-5-3 | 3,5-difluoropyridin-2-yl | 2-bromophenyl | H | H | O |
| I-5-4 | 3-fluoropyridin-2-yl | 2-bromophenyl | H | H | O |
| I-5-5 | 3-chloro-5-(trifluormethyl)pyridin-2-yl | 2-bromophenyl | H | H | O |
| I-5-6 | 2,5-difluoropyridin-3-yl | 2-bromophenyl | H | H | O |
| I-5-7 | 2,5-difluoropyridin-3-yl | 2-(trifluoromethyl)phenyl | 5-F | H | O |
| I-5-8 Synthesis Example 47 | 2-chlorophenyl | 2-(trifluoromethyl)phenyl | H | H | O |
| I-5-9 | 2-chlorophenyl | 2-(trifluoromethyl)pyridin-3-yl | H | H | O |
| I-5-10 | 2,5-difluoro-4-cyanphenyl | 2-(trifluoromethyl)phenyl | 4-F | H | O |
| I-5-11 | 2,5-difluoro-4-cyanphenyl | 2,6-difluorophenyl | 4-F | H | O |

TABLE 5

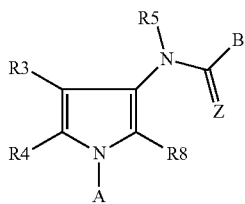

(I-3)

| Compound No. | A | B | R3 | R4 | R5 | R8 | Z |
|---|---|---|---|---|---|---|---|
| I-3-1 Synthesis Example 46 | 2,6-difluorophenyl | 2-(trifluoromethyl)phenyl | H | H | H | H | O |
| I-3-2 | 2,6-difluorophenyl | 2,6-difluorophenyl | H | H | H | H | O |
| I-3-3 | 2,6-difluorophenyl | 2-iodophenyl | H | H | H | H | O |
| I-3-4 | 2,6-difluorophenyl | 2-chloro-4-methoxyphenyl | H | H | H | H | O |
| I-3-5 | 2,6-difluorophenyl | 2-(trifluoromethyl)pyridin-3-yl | H | H | H | H | O |
| I-3-6 | 2,6-difluorophenyl | 3-iodo-2-furanyl | H | H | H | H | O |
| I-3-7 | 2,6-difluorophenyl | 2-iodo-3-thienyl | H | H | H | H | O |

HPLC-MS[1]) and $^1$H-NMR data[2])
Compound No.
HPLC-MS[1]) and $^1$H-NMR data[2])
I-1-1
see Synthesis Example 1
I-1-2
HPLC-MS: log P=2.69; mass (m/z): 372.0 (M+H)$^+$; $^1$H-NMR [DMSO-D$_6$] 3.33 (s, 3H), 6.86 (d, 1H), 7.05-7.09 (m, 1H), 7.24-7.26 (m, 1H), 7.32-7.42 (m, 2H), 7.46-7.49 (m, 1H), 7.51-7.54 (m, 1H), 7.58-7.60 (m, 1H), 7.68-7.70 (m, 1H), 8.12 (d, 1H), 11.17 (s, 1H).
I-1-3
HPLC-MS: log P=2.87; mass (m/z): 312.1 (M+H)$^+$; $^1$H-NMR [DMSO-D$_6$] 2.24 (s, 3H), 2.52 (s, 3H), 3.88 (s, 3H), 6.79-6.80 (m, 1H), 6.83-6.84 (m, 1H), 7.05-7.10 (m, 1H), 7.23-7.25 (m, 1H), 7.31-7.35 (m, 1H), 7.62-7.65 (m, 1H), 8.10 (d, 1H), 10.48 (s, 1H).
I-1-4
HPLC-MS: log P=2.92; mass (m/z): 366.0 (M+H)$^+$; $^1$H-NMR [CD$_3$CN] 6.97 (d, 1H), 7.40-7.60 (m, 5H), 7.64-7.68 (m, 1H), 7.74-7.78 (m, 2H), 7.86-7.88 (m, 1H), 9.18 (br. s, 1H).
I-1-5
HPLC-MS: log P=3.05; mass (m/z): 458.0 (M+H)$^+$; $^1$H-NMR [CD$_3$CN] 6.96-6.97 (m, 1H), 7.17-7.24 (m, 1H), 7.45-7.50 (m, 2H), 7.54-7.56 (m, 1H), 7.64-7.68 (m, 1H), 7.74-7.78 (m, 2H), 7.86-7.88 (m, 1H), 7.93-7.95 (m, 1H), 9.17 (br. s, 1H).
I-1-6
HPLC-MS: log P=2.75; mass (m/z): 372.1 (M+H)$^+$; $^1$H-NMR [DMSO-D$_6$] 6.90 (d, 1H), 7.41 (s, 1H), 7.64-7.67 (m, 1H), 7.73-7.77 (m, 1H), 7.85-7.89 (m, 1H), 7.92-7.96 (m, 2H), 8.00 (d, 1H), 8.32 (t, 1H), 11.53 (s, 1H).
I-1-7
HPLC-MS: log P=3.05; mass (m/z): 400.1 (M+H)$^+$; $^1$H-NMR [CD$_3$CN] 6.94-6.95 (m, 1H), 7.54-7.55 (m, 1H), 7.64-7.82 (m, 7H), 7.86-7.88 (m, 1H), 9.23 (br. s, 1H).
I-1-8
HPLC-MS: log P=2.38; mass (m/z): 323.1 (M+H)$^+$; $^1$H-NMR [CD$_3$CN] 7.07 (d, 1H), 7.40-7.52 (m, 4H), 7.59-7.62 (m, 1H), 7.69-7.71 (m, 1H), 7.75-7.79 (m, 1H), 7.85-7.87 (m, 1H), 8.12 (d, 1H), 9.39 (br. s, 1H).
I-1-9
HPLC-MS: log P=2.55; mass (m/z): 357.1 (M+H)$^+$; $^1$H-NMR [CD$_3$CN] 7.05 (d, 1H), 7.48-7.52 (m, 1H), 7.65-7.86 (m, 7H), 8.11 (d, 1H), 9.39 (br. s, 1H).
I-1-10
HPLC-MS: log P=2.78; mass (m/z): 360.01 (M+H)$^+$; $^1$H-NMR [DMSO-D$_6$] 6.95 (d, 1H), 7.34-7.50 (m, 5H), 7.53-7.55 (m, 1H), 7.69-7.71 (m, 1H), 7.73-7.77 (m, 1H), 8.16-8.17 (m, 1H), 11.27 (s, 1H).
I-1-11
HPLC-MS: log P=2.86; mass (m/z): 312.0 (M+H)$^+$; $^1$H-NMR [CD$_3$CN] 2.45 (s, 3H), 6.98-6.99 (m, 1H), 7.25-7.31 (m, 3H), 7.36-7.45 (m, 3H), 7.47-7.54 (m, 2H), 7.58-7.60 (m, 1H), 7.88 (d, 1H), 9.07 (br. s, 1H).
I-1-12
HPLC-MS: log P=3.30; mass (m/z): 326.1 (M+H)$^+$; $^1$H-NMR [CD$_3$CN] 1.25 (t, 3H), 2.84 (q, 2H), 7.01 (d, 1H), 7.28-7.32 (m, 1H), 7.37-7.38 (m, 1H), 7.43-7.52 (m, 4H), 7.55-7.58 (m, 1H), 7.61-7.64 (m, 1H), 7.91 (d, 1H), 9.13 (br. s, 1H).
I-1-13
HPLC-MS: log P=3.03; mass (m/z): 348.1 (M+H)$^+$; $^1$H-NMR [CD$_3$CN] 6.97 (d, 1H), 7.30 (t, 1H), 7.41-7.48 (m, 2H), 7.52-7.56 (m, 1H), 7.59-7.69 (m, 3H), 7.76-7.81 (m, 2H), 7.81-7.89 (m, 1H), 9.32 (br. s, 1H).
I-1-14
HPLC-MS: log P=2.96; mass (m/z): 366.0 (M+H)$^+$; $^1$H-NMR [CD$_3$CN] 6.95 (d, 1H), 7.41-7.47 (m, 2H), 7.51-7.54 (m, 1H), 7.57-7.60 (m, 1H), 7.65-7.74 (m, 3H), 7.80-7.82 (m, 1H), 7.88 (d, 1H), 9.26 (br. s, 1H).
I-1-15
see Synthesis Example 17
I-1-16
see Synthesis Example 18
I-1-17
see Synthesis Example 19
I-1-18
HPLC-MS: log P=3.28; mass (m/z): 382.0 (M+H)$^+$; $^1$H-NMR [CD$_3$CN] 6.96 (d, 1H), 7.40-7.56 (m, 4H), 7.59-7.65 (m, 3H), 7.77-7.80 (m, 1H), 7.89 (d, 1H), 9.23 (br. s, 1H).
I-1-19
HPLC-MS: log P=2.89; mass (m/z): 316.0 (M+H)$^+$; $^1$H-NMR [CD$_3$CN] 6.99 (d, 1H), 7.24-7.29 (m, 1H), 7.32-7.36 (m, 1H), 7.41-7.48 (m, 2H), 7.53-7.62 (m, 3H), 7.89-7.93 (m, 2H), 9.17 (br. s, 1H).
I-1-20
see Synthesis Example 14
I-1-21
see Synthesis Example 15
I-1-22
HPLC-MS: log P=3.41; mass (m/z): 360.0 (M+H)$^+$; $^1$H-NMR [CD$_3$CN] 1.28 (t, 3H), 3.95 (q, 2H), 6.10 (d, 1H), 7.21-7.33 (m, 4H), 7.37-7.54 (m, 4H), 7.61-7.64 (m, 1H).
I-1-23
HPLC-MS: log P=3.25; mass (m/z): 370.0 (M+H)$^+$; $^1$H-NMR [CD$_3$CN] 2.54 (s, 1H), 4.72 (s, 2H), 6.15 (s, 1H), 7.22-7.34 (m, 4H), 7.39-7.41 (m, 3H), 7.53-7.54 (m, 1H), 7.66 (s, 1H).
I-1-24
HPLC-MS: log P=3.85; mass (m/z): 386.1 (M+H)$^+$; $^1$H-NMR [CD$_3$CN] 0.29-0.30 (m, 2H), 0.48-0.50 (m, 2H), 1.13-1.21 (m, 1H), 3.81 (d, 2H), 6.13 (d, 1H), 7.15-7.34 (m, 5H), 7.39-7.41 (m, 2H), 7.52-7.55 (m, 1H), 7.62 (d, 1H).

I-1-25

HPLC-MS: log P=3.04; mass (m/z): 371.0 (M+H)$^+$; $^1$H-NMR [CD$_3$CN] 4.87 (s, 2H), 5.99 (s, 1H), 7.24-7.45 (m, 7H), 7.55-7.56 (m, 1H), 7.66 (s, 1H).

I-1-26

HPLC-MS: log P=3.56; mass (m/z): 372.1 (M+H)$^+$; $^1$H-NMR [DMSO-D$_6$] 4.51 (d, 2H), 5.18 (d, 1H), 5.33 (d, 1H), 5.89-5.99 (m, 1H), 6.12 (d, 1H), 7.19-7.50 (m, 7H), 7.59-7.61 (m, 1H), 7.89 (d, 1H).

I-1-27 see Synthesis Example 16

I-1-28

HPLC-MS: log P=2.88; mass (m/z): 366.0 (M+H)$^+$; $^1$H-NMR [CD$_3$CN] 7.42-7.63 (m, 8H), 8.05 (s, 1H), 8.62 (br. s, 1H).

I-1-29

HPLC-MS: log P=2.99; mass (m/z): 409.9 (M+H)$^+$; $^1$H-NMR [CD$_3$CN] 7.44-7.63 (m, 8H), 8.06 (s, 1H), 8.58 (br. s, 1H).

I-1-30

HPLC-MS: log P=3.01; mass (m/z): 457.9 (M+H)$^+$; $^1$H-NMR [CD$_3$CN] 7.42-7.66 (m, 8H), 8.05 (s, 1H), 8.55 (br. s, 1H).

I-1-31

HPLC-MS: log P=2.45; mass (m/z): 346.1 (M+H)$^+$; $^1$H-NMR [CD$_3$CN] 2.28 (s, 3H), 6.48 (s, 1H), 7.32-7.36 (m, 1H), 7.39-7.50 (m, 5H), 7.56-7.59 (m, 1H), 8.50 (br. s, 1H).

I-1-32

HPLC-MS: log P=2.83; mass (m/z): 376.0 (M+H)$^+$; $^1$H-NMR [CD$_3$CN] 6.97 (d, 1H), 7.37-7.47 (m, 4H), 7.53-7.56 (m, 2H), 7.59-7.60 (m, 1H), 7.68-7.69 (m, 1H), 7.89 (d, 1H), 9.20 (br. s, 1H).

I-1-33

HPLC-MS: log P=2.95; mass (m/z): 423.9 (M+H)$^+$; $^1$H-NMR [CD$_3$CN] 6.97 (d, 1H), 7.18-7.24 (m, 1H), 7.39-7.55 (m, 5H), 7.58-7.61 (m, 1H), 7.89 (d, 1H), 7.93-7.95 (m, 1H), 9.17 (br. s, 1H).

I-1-34

HPLC-MS: log P=3.10; mass (m/z): 457.9 (M+H)$^+$; $^1$H-NMR [CD$_3$CN] 7.21-7.25 (m, 1H), 7.48-7.62 (m, 6H), 7.97-7.98 (m, 1H), 8.05 (s, 1H), 8.56 (br. s, 1H).

I-1-35

HPLC-MS: log P=2.53; mass (m/z): 438.0 (M+H)$^+$; $^1$H-NMR [CD$_3$CN] 2.28 (s, 3H), 6.49 (s, 1H), 7.12-7.17 (m, 1H), 7.24-7.29 (m, 1H), 7.38-7.49 (m, 4H), 7.56-7.58 (m, 1H), 7.84-7.86 (m, 1H), 8.46 (br. s, 1H).

I-1-36

HPLC-MS: log P=2.65; mass (m/z): 334.0 (M+H)$^+$; $^1$H-NMR [CD$_3$CN] 6.95 (d, 1H), 7.03-7.13 (m, 2H), 7.41-7.49 (m, 2H), 7.50-7.56 (m, 2H), 7.59-7.62 (m, 1H), 7.88 (d, 1H), 9.46 (br. s, 1H).

I-1-37

HPLC-MS: log P=2.84; mass (m/z): 350.0 (M+H)$^+$; $^1$H-NMR [CD$_3$CN] 6.97 (d, 1H), 7.20-7.23 (m, 1H), 7.35-7.37 (m, 1H), 7.42-7.50 (m, 3H), 7.52-7.55 (m, 1H), 7.59-7.61 (m, 1H), 7.89 (d, 1H), 9.37 (br. s, 1H).

I-1-38

HPLC-MS: log P=3.24; mass (m/z): 313.1 (M+H)$^+$; $^1$H-NMR [CD$_3$CN] 2.78 (s, 3H), 7.06 (d, 1H), 7.43-7.52 (m, 3H), 7.61-7.65 (m, 2H), 7.78-7.80 (m, 1H), 7.94 (d, 1H), 8.52-8.54 (m, 1H), 10.51 (br. s, 1H).

I-1-39

HPLC-MS: log P=2.99; mass (m/z): 367.0 (M+H)$^+$; $^1$H-NMR [CD$_3$CN] 7.02 (d, 1H), 7.44-7.52 (m, 2H), 7.57-7.65 (m, 2H), 7.75-7.78 (m, 1H), 7.93-7.94 (m, 1H), 8.31-8.34 (m, 1H), 8.88-8.89 (m, 1H), 10.04 (br. s, 1H).

I-1-40

HPLC-MS: log P=2.79; mass (m/z): 333.1 (M+H)$^+$; $^1$H-NMR [CD$_3$CN] 7.03 (d, 1H), 7.42-7.48 (m, 2H), 7.54-7.61 (m, 3H), 7.92 (d, 1H), 7.97-7.99 (m, 1H), 8.58-8.59 (m, 1H), 10.09 (br. s, 1H).

I-1-41

HPLC-MS: log P=1.44; mass (m/z): 313.1 (M+H)$^+$; $^1$H-NMR [CD$_3$CN] 2.62 (s, 3H), 6.98 (d, 1H), 7.24-7.27 (m, 1H), 7.40-7.47 (m, 2H), 7.52-7.54 (m, 1H), 7.58-7.60 (m, 1H), 7.83-7.89 (m, 2H), 8.53-8.55 (m, 1H), 9.25 (br. s, 1H).

I-1-42

HPLC-MS: log P=2.48; mass (m/z): 367.1 (M+H)$^+$; $^1$H-NMR [CD$_3$CN] 6.95 (d, 1H), 7.42-7.47 (m, 2H), 7.53-7.54 (m, 1H), 7.59-7.61 (m, 1H), 7.71-7.73 (m, 1H), 7.89 (d, 1H), 8.08-8.10 (m, 1H), 8.81-8.82 (m, 1H), 9.35 (br. s, 1H).

I-1-43

HPLC-MS: log P=2.19; mass (m/z): 333.0 (M+H)$^+$; $^1$H-NMR [CD$_3$CN] 6.97 (d, 1H), 7.38-7.48 (m, 3H), 7.51-7.55 (m, 1H), 7.59-7.62 (m, 1H), 7.89 (d, 1H), 7.97-7.99 (m, 1H), 8.48-8.50 (m, 1H), 9.35 (br. s, 1H).

I-1-44

HPLC-MS: log P=2.74; mass (m/z): 368.0 (M+H)$^+$; $^1$H-NMR [CD$_3$CN] 6.99 (d, 1H), 7.41-7.49 (m, 2H), 7.55-7.62 (m, 2H), 7.92 (d, 1H), 8.90 (s, 2H), 9.84 (br. s, 1H).

I-1-45

HPLC-MS: log P=3.05; mass (m/z): 316.1 (M+H)$^+$; $^1$H-NMR [DMSO-D$_6$] 2.23 (s, 3H), 2.52 (s, 3H), 6.78 (s, 1H), 6.88 (d, 1H), 7.45-7.53 (m, 2H), 7.60-7.62 (m, 1H), 7.67-7.69 (m, 1H), 8.05 (d, 1H), 10.51 (br. s, 1H).

I-1-46

HPLC-MS: log P=2.96; mass (m/z): 318.0 (M+H)$^+$; $^1$H-NMR [CD$_3$CN] 2.53 (s, 3H), 6.92 (d, 1H), 6.99 (d, 1H), 7.40-7.49 (m, 3H), 7.54-7.60 (m, 2H), 7.87-7.88 (m, 1H), 8.76 (br. s, 1H).

I-1-47

HPLC-MS: log P=3.05; mass (m/z): 430.0 (M+H)$^+$; $^1$H-NMR [CD$_3$CN] 6.96 (d, 1H), 7.25 (d, 1H), 7.40-7.48 (m, 2H), 7.53-7.56 (m, 1H), 7.58-7.61 (m, 1H), 7.63-7.64 (m, 1H), 7.88 (d, 1H), 9.08 (br. s, 1H).

I-1-48

HPLC-MS: log P=2.46; mass (m/z): 350.0 (M+H)$^+$; $^1$H-NMR [CD$_3$CN] 2.38 (s, 3H), 3.77 (s, 3H), 6.93 (d, 1H), 7.39-7.47 (m, 2H), 7.53-7.55 (m, 1H), 7.58-7.60 (m, 1H), 7.86 (d, 1H), 8.75 (br. s, 1H).

I-1-49

HPLC-MS: log P=2.59; mass (m/z): 370.0 (M+H)$^+$; $^1$H-NMR [CD$_3$CN] 3.79 (s, 3H), 6.89 (d, 1H), 7.10 (t, 1H), 7.40-7.48 (m, 2H), 7.53-7.56 (m, 1H), 7.58-7.61 (m, 1H), 7.87 (d, 1H), 8.62 (br. s, 1H).

I-1-50

HPLC-MS: log P=3.07; mass (m/z): 410.1 (M+H)$^+$; $^1$H-NMR [CD$_3$CN] 6.94 (d, 1H), 7.36-7.40 (m, 1H), 7.48-7.52 (m, 2H), 7.65-7.83 (m, 6H), 9.22 (br. s, 1H).

I-1-51

HPLC-MS: log P=2.83; mass (m/z): 376.0 (M+H)$^+$; $^1$H-NMR [CD$_3$CN] 6.97 (d, 1H), 7.36-7.39 (m, 1H), 7.41-7.43 (m, 1H), 7.46-7.52 (m, 4H), 7.59-7.61 (m, 1H), 7.76-7.78 (m, 1H), 7.83 (d, 1H), 9.19 (br. s, 1H).

I-1-52

HPLC-MS: log P=2.86; mass (m/z): 419.9 (M+H)$^+$; $^1$H-NMR [CD$_3$CN] 6.96 (d, 1H), 7.36-7.40 (m, 2H), 7.45-7.47 (m, 1H), 7.49-7.51 (m, 2H), 7.55-7.56 (m, 1H), 7.68-7.69 (m, 1H), 7.76-7.78 (m, 1H), 7.83 (d, 1H), 9.17 (br. s, 1H).

I-1-53

HPLC-MS: log P=3.07; mass (m/z): 467.9 (M+H)$^+$; $^1$H-NMR [CD$_3$CN] 6.96 (d, 1H), 7.19-7.23 (m, 1H), 7.35-

7.40 (m, 1H), 7.46-7.51 (m, 4H), 7.76-7.78 (m, 1H), 7.84 (d, 1H), 7.93-7.95 (m, 1H), 9.19 (br. s, 1H).

I-1-54

HPLC-MS: log P=2.99; mass (m/z): 411.0 (M+H)$^+$; $^1$H-NMR [CD$_3$CN] 6.99 (d, 1H), 7.35-7.40 (m, 1H), 7.48-7.54 (m, 3H), 7.72-7.79 (m, 2H), 7.86 (d, 1H), 8.28-8.31 (m, 1H), 8.85-8.86 (m, 1H), 10.01 (br. s, 1H).

I-1-55

HPLC-MS: log P=2.76; mass (m/z): 377.0 (M+H)$^+$; $^1$H-NMR [CD$_3$CN] 7.01 (d, 1H), 7.35-7.40 (m, 1H), 7.48-7.56 (m, 3H), 7.77-7.79 (m, 1H), 7.86 (d, 1H), 7.96-7.99 (m, 1H), 8.58-8.59 (m, 1H), 10.08 (br. s, 1H).

I-1-56

HPLC-MS: log P=2.54; mass (m/z): 411.0 (M+H)$^+$; $^1$H-NMR [CD$_3$CN] 6.94 (d, 1H), 7.36-7.40 (m, 1H), 7.48-7.53 (m, 2H), 7.70-7.73 (m, 1H), 7.76-7.79 (m, 1H), 7.84 (d, 1H), 8.08-8.10 (m, 1H), 8.80-8.82 (m, 1H), 9.30 (br. s, 1H).

I-1-57

HPLC-MS: log P=2.37; mass (m/z): 377.0 (M+H)$^+$; $^1$H-NMR [CD$_3$CN] 6.96 (d, 1H), 7.35-7.41 (m, 1H), 7.44-7.47 (m, 1H), 7.49-7.51 (m, 2H), 7.76-7.78 (m, 1H), 7.84 (d, 1H), 7.97-8.00 (m, 1H), 8.48-8.50 (m, 1H), 9.34 (br. s, 1H).

I-1-58

HPLC-MS: log P=2.63; mass (m/z): 414.0 (M+H)$^+$; $^1$H-NMR [CD$_3$CN] 3.79 (s, 3H), 6.88 (d, 1H), 7.11 (t, 1H), 7.35-7.41 (m, 1H), 7.49-7.51 (m, 2H), 7.76-7.79 (m, 1H), 7.82 (d, 1H), 8.69 (br. s, 1H).

I-1-59

HPLC-MS: log P=3.00; mass (m/z): 431.9 (M+H)$^+$; $^1$H-NMR [CD$_3$CN] 3.81 (s, 3H), 6.88 (d, 1H), 7.36-7.41 (m, 1H), 7.49-7.51 (m, 2H), 7.76-7.78 (m, 1H), 7.82 (d, 1H), 9.00 (br. s, 1H).

I-1-60

HPLC-MS: log P=3.16; mass (m/z): 362.0 (M+H)$^+$; $^1$H-NMR [CD$_3$CN] 2.53 (s, 3H), 6.91 (d, 1H), 6.98-6.99 (m, 1H), 7.34-7.38 (m, 1H), 7.48-7.50 (m, 3H), 7.75-7.77 (m, 1H), 7.82 (d, 1H), 8.77 (br. s, 1H).

I-1-61 see Synthesis Example 2

I-1-62

HPLC-MS: log P=3.07; mass (m/z): 368.1 (M+H)$^+$; $^1$H-NMR [CD$_3$CN] 7.02 (d, 1H), 7.20-7.30 (m, 2H), 7.54-7.58 (m, 1H), 7.66-7.76 (m, 3H), 7.80-7.82 (m, 1H), 8.03-8.04 (m, 1H), 9.34 (br. s, 1H).

I-1-63 see Synthesis Example 3

I-1-64

HPLC-MS: log P=3.02; mass (m/z): 368.0 (M+H)$^+$; $^1$H-NMR [DMSO-D$_6$] 6.92 (d, 1H), 7.24-7.29 (m, 1H), 7.54-7.60 (m, 1H), 7.67-7.71 (m, 2H), 7.74-7.84 (m, 3H), 8.13-8.14 (m, 1H), 11.35 (br. s, 1H).

I-1-65

HPLC-MS: log P=3.13; mass (m/z): 368.1 (M+H)$^+$; $^1$H-NMR [CD$_3$CN] 7.01 (d, 1H), 7.03-7.09 (m, 1H), 7.30-7.36 (m, 1H), 7.52-7.57 (m, 1H), 7.66-7.74 (m, 3H), 7.80-7.82 (m, 1H), 8.07-8.08 (m, 1H), 9.39 (br. s, 1H).

I-1-66

HPLC-MS: log P=3.02; mass (m/z): 334.0 (M+H)$^+$; $^1$H-NMR [CD$_3$CN] 7.03-7.09 (m, 2H), 7.31-7.36 (m, 1H), 7.39-7.60 (m, 5H), 8.07-8.08 (m, 1H), 9.37 (br. s, 1H).

I-1-67

HPLC-MS: log P=3.10; mass (m/z): 426.0 (M+H)$^+$; $^1$H-NMR [CD$_3$CN] 7.03-7.09 (m, 2H), 7.18-7.24 (m, 1H), 7.30-7.36 (m, 1H), 7.45-7.50 (m, 1H), 7.53-7.58 (m, 1H), 7.93-7.95 (m, 1H), 8.07-8.09 (m, 1H), 9.30 (br. s, 1H).

I-1-68

HPLC-MS: log P=3.29; mass (m/z): 369.0 (M+H)$^+$; $^1$H-NMR [CD$_3$CN] 7.05-7.10 (m, 2H), 7.31-7.37 (m, 1H), 7.60-7.65 (m, 1H), 7.78-7.79 (m, 1H), 8.11 (s, 1H), 8.30-8.32 (m, 1H), 8.92 (br. s, 1H), 10.14 (s, 1H).

I-1-69

HPLC-MS: log P=1.53; mass (m/z): 315.1 (M+H)$^+$; $^1$H-NMR [CD$_3$CN] 7.04-7.09 (m, 2H), 7.24-7.28 (m, 1H), 7.30-7.37 (m, 1H), 7.54-7.58 (m, 1H), 7.83-7.85 (m, 1H), 8.07-8.08 (m, 1H), 8.54-8.56 (m, 1H), 9.33 (br. s, 1H).

I-1-70

HPLC-MS: log P=2.60; mass (m/z): 369.1 (M+H)$^+$; $^1$H-NMR [CD$_3$CN] 7.01 (d, 1H), 7.05-7.11 (m, 1H), 7.31-7.37 (m, 1H), 7.53-7.58 (m, 1H), 7.70-7.74 (m, 1H), 8.08-8.09 (m, 2H), 8.81-8.82 (m, 1H), 9.47 (br. s, 1H).

I-1-71

HPLC-MS: log P=3.24; mass (m/z): 320.0 (M+H)$^+$; $^1$H-NMR [CD$_3$CN] 2.54 (s, 3H), 6.97-7.00 (m, 2H), 7.03-7.09 (m, 1H), 7.30-7.36 (m, 1H), 7.49-7.51 (m, 1H), 7.57-7.62 (m, 1H), 8.05-8.07 (m, 1H), 8.83 (br. s, 1H).

I-1-72 see Synthesis Example 4

I-1-73

HPLC-MS: log P=2.60; mass (m/z): 314.1 (M+H)$^+$; $^1$H-NMR [CD$_3$CN] 2.40 (s, 3H), 6.95-6.96 (m, 1H), 7.24-7.38 (m, 5H), 7.43-7.47 (m, 1H), 7.54-7.61 (m, 1H), 7.98-7.99 (m, 1H), 10.94 (br. s, 1H).

I-1-74

HPLC-MS: log P=2.73; mass (m/z): 350.0 (M+H)$^+$; $^1$H-NMR [CD$_3$CN] 7.01 (d, 1H), 7.15-7.48 (m, 3H), 7.49-7.55 (m, 1H), 7.61-7.69 (m, 2H), 7.77-7.81 (m, 3H), 9.37 (br. s, 1H).

I-1-75

HPLC-MS: log P=2.68; mass (m/z): 368.1 (M+H)$^+$; $^1$H-NMR [CD$_3$CN] 6.99 (d, 1H), 7.16-7.22 (m, 2H), 7.47-7.54 (m, 1H), 7.65-7.76 (m, 4H), 7.80-7.82 (m, 1H), 9.30 (br. s, 1H).

I-1-76

HPLC-MS: log P=2.61; mass (m/z): 386.1 (M+H)$^+$; $^1$H-NMR [CD$_3$CN] 7.13-7.23 (m, 2H), 7.50-7.57 (m, 1H), 7.67-7.77 (m, 3H), 7.82-7.84 (m, 2H), 8.76 (br. s, 1H).

I-1-77

HPLC-MS: log P=3.33; mass (m/z): 384.0 (M+H)$^+$; $^1$H-NMR [CD$_3$CN] 7.18-7.24 (m, 2H), 7.50-7.60 (m, 4H), 7.65-7.69 (m, 1H), 7.73-7.75 (m, 1H), 7.83-7.84 (m, 1H), 10.67 (br. s, 1H).

I-1-78

HPLC-MS: log P=2.92; mass (m/z): 328.1 (M+H)$^+$; $^1$H-NMR [CD$_3$CN] 1.22 (t, 3H), 2.81 (q, 2H), 7.01 (d, 1H), 7.16-7.21 (m, 2H), 7.25-7.29 (m, 1H), 7.33-7.35 (m, 1H), 7.40-7.44 (m, 1H), 7.47-7.54 (m, 2H), 7.74-7.75 (m, 1H), 9.07 (br. s, 1H).

I-1-79

HPLC-MS: log P=2.96; mass (m/z): 384.0 (M+H)$^+$; $^1$H-NMR [CD$_3$CN] 7.00 (d, 1H), 7.15-7.21 (m, 2H), 7.43-7.55 (m, 3H), 7.60-7.65 (m, 1H), 7.76-7.80 (m, 2H), 9.21 (br. s, 1H).

I-1-80

HPLC-MS: log P=1.95; mass (m/z): 378.0 (M+H)$^+$; $^1$H-NMR [CD$_3$CN] 3.31 (s, 3H), 6.98 (d, 1H), 7.17-7.22 (m, 2H), 7.49-7.53 (m, 1H), 7.70-7.81 (m, 4H), 8.06-8.08 (m, 1H), 9.35 (br. s, 1H).

I-1-81

HPLC-MS: log P=2.55; mass (m/z): 334.0 (M+H)$^+$; $^1$H-NMR [CD$_3$CN] 7.01 (d, 1H), 7.17-7.21 (m, 2H), 7.41-7.43 (m, 1H), 7.46-7.44 (m, 3H), 7.60-7.61 (m, 1H), 7.76 (d, 1H), 9.20 (br. s, 1H).

I-1-82
HPLC-MS: log P=2.59; mass (m/z): 378.0 (M+H)$^+$; $^1$H-NMR [CD$_3$CN] 7.01 (d, 1H), 7.17-7.21 (m, 2H), 7.38-7.40 (m, 1H), 7.45-7.48 (m, 1H), 7.49-7.54 (m, 1H), 7.55-7.57 (m, 1H), 7.68-7.69 (m, 1H), 7.76 (d, 1H), 9.18 (br. s, 1H).

I-1-83
HPLC-MS: log P=2.67; mass (m/z): 426.1 (M+H)$^+$; $^1$H-NMR [CD$_3$CN] 7.01 (d, 1H), 7.16-7.23 (m, 3H), 7.46-7.54 (m, 3H), 7.76 (d, 1H), 7.93-7.95 (m, 1H), 9.15 (br. s, 1H).

I-1-84
HPLC-MS: log P=2.42; mass (m/z): 336.1 (M+H)$^+$; $^1$H-NMR [CD$_3$CN] 6.99 (d, 1H), 7.08-7.13 (m, 2H), 7.17-7.22 (m, 2H), 7.48-7.57 (m, 1H), 7.77 (d, 1H), 9.40 (br. s, 1H).

I-1-85
HPLC-MS: log P=2.60; mass (m/z): 352.0 (M+H)$^+$; $^1$H-NMR [CD$_3$CN] 7.02 (d, 1H), 7.20-7.24 (m, 3H), 7.37-7.39 (m, 1H), 7.49-7.54 (m, 2H), 7.80 (d, 1H), 9.62 (br. s, 1H).

I-1-86
HPLC-MS: log P=2.20; mass (m/z): 345.0 (M+H)$^+$; $^1$H-NMR [DMSO-D$_6$] 6.92 (d, 1H), 7.32-7.41 (m, 2H), 7.56-7.64 (m, 1H), 7.71-7.77 (m, 2H), 7.82-7.87 (m, 1H), 8.07 (d, 1H), 8.11-8.13 (m, 1H), 11.46 (s, 1H).

I-1-87
HPLC-MS: log P=2.66; mass (m/z): 316.0 (M+H)$^+$; $^1$H-NMR [DMSO-D$_6$] 6.95-7.02 (m, 3H), 7.36-7.47 (m, 3H), 7.58-7.65 (m, 1H), 8.05-8.08 (m, 1H), 11.02 (s, 1H), 11.89 (s, 1H).

I-1-88
HPLC-MS: log P=3.15; mass (m/z): 400.0 (M+H)$^+$; $^1$H-NMR [DMSO-D$_6$] 6.95 (d, 1H), 7.36-7.40 (m, 2H), 7.57-7.68 (m, 3H), 7.74-7.81 (m, 2H), 8.07-8.08 (m, 1H), 11.34 (s, 1H).

I-1-89
HPLC-MS: log P=1.66; mass (m/z): 367.1 (M+H)$^+$; $^1$H-NMR [DMSO-D$_6$] 6.78 (d, 1H), 7.32-7.37 (m, 2H), 7.55-7.60 (m, 2H), 7.64-7.71 (m, 3H), 7.98 (d, 1H), 8.13 (s, 1H), 8.88 (s, 1H), 11.13 (s, 1H).

I-1-90
HPLC-MS: log P=2.86; mass (m/z): 315.1 (M+H)$^+$; $^1$H-NMR [CD$_3$CN] 2.74 (s, 3H), 7.06 (d, 1H), 7.17-7.23 (m, 2H), 7.45-7.54 (m, 2H), 7.75-7.77 (m, 2H), 8.48-8.50 (m, 1H), 10.47 (br. s, 1H).

I-1-91
see Synthesis Example 7

I-1-92
HPLC-MS: log P=2.40; mass (m/z): 335.1 (M+H)$^+$; $^1$H-NMR [CD$_3$CN] 7.01 (d, 1H), 7.20-7.26 (m, 2H), 7.50-7.59 (m, 2H), 7.81 (d, 1H), 7.99-8.02 (m, 1H), 8.60-8.62 (m, 1H), 10.15 (br. s, 1H).

I-1-93
HPLC-MS: log P=2.68; mass (m/z): 369.1 (M+H)$^+$; 1H-NMR [CD$_3$CN] 7.03 (d, 1H), 7.17-7.23 (m, 2H), 7.48-7.55 (m, 1H), 7.72-7.75 (m, 1H), 7.78 (d, 1H), 8.28-8.30 (m, 1H), 8.85-8.86 (m, 1H), 10.04 (br. s, 1H).

I-1-94
HPLC-MS: log P=2.16; mass (m/z): 369.0 (M+H)$^+$; $^1$H-NMR [CD$_3$CN] 7.00 (d, 1H), 7.17-7.22 (m, 2H), 7.48-7.55 (m, 1H), 7.74-7.78 (m, 2H), 8.91-8.94 (m, 2H), 9.44 (br. s, 1H).

I-1-95
HPLC-MS: log P=1.96; mass (m/z): 335.1 (M+H)$^+$; $^1$H-NMR [CD$_3$CN] 7.01 (d, 1H), 7.17-7.21 (m, 2H), 7.44-7.55 (m, 2H), 7.77 (d, 1H), 7.97-8.00 (m, 1H), 8.48-8.50 (m, 1H), 9.36 (br. s, 1H).

I-1-96
HPLC-MS: log P=1.97; mass (m/z): 378.9 (M+H)$^+$; $^1$H-NMR [CD$_3$CN] 7.00 (d, 1H), 7.16-7.22 (m, 2H), 7.46-7.54 (m, 2H), 7.77 (d, 1H), 7.89-7.91 (m, 1H), 8.45-8.46 (m, 1H), 9.32 (br. s, 1H).

I-1-97
HPLC-MS: log P=2.16; mass (m/z): 368.1 (M+H)$^+$; $^1$H-NMR [DMSO-D$_6$] 6.92 (d, 1H), 7.36-7.41 (m, 2H), 7.57-7.64 (m, 1H), 7.77-7.79 (m, 1H), 8.10 (d, 1H), 8.98-9.00 (m, 1H), 9.07 (s, 1H), 11.56 (s, 1H).

I-1-98
HPLC-MS: log P=1.73; mass (m/z): 330.1 (M+H)$^+$; $^1$H-NMR [DMSO-D$_6$] 1.30 (t, 3H), 3.05 (q, 2H), 6.96 (d, 1H), 7.36-7.40 (m, 2H), 7.57-7.65 (m, 1H), 7.75 (d, 1H), 8.10 (d, 1H), 9.24-9.26 (m, 1H), 11.54 (s, 1H).

I-1-99
HPLC-MS: log P=2.45; mass (m/z): 370.0 (M+H)$^+$; $^1$H-NMR [CD$_3$CN] 7.02 (d, 1H), 7.16-7.23 (m, 2H), 7.48-7.56 (m, 1H), 7.80 (d, 1H), 8.89-8.90 (m, 2H), 9.86 (br. s, 1H).

I-1-100
HPLC-MS: log P=2.15; mass (m/z): 336.0 (M+H)$^+$; $^1$H-NMR [CD$_3$CN] 7.05 (d, 1H), 7.17-7.24 (m, 2H), 7.50-7.56 (m, 1H), 7.79 (d, 1H), 8.61-8.63 (m, 2H), 9.92 (br. s, 1H).

I-1-101
HPLC-MS: log P=2.41; mass (m/z): 338.1 (M+H)$^+$; $^1$H-NMR [DMSO-D$_6$] 2.01 (s, 3H) 3.02-3.04 (m, 2H), 4.26-4.28 (m, 2H), 6.79 (d, 1H), 7.34-7.39 (m, 2H), 7.55-7.61 (m, 1H), 7.99 (d, 1H), 10.40 (s, 1H).

I-1-102
HPLC-MS: log P=2.56; mass (m/z): 391.0 (M+H)$^+$; $^1$H-NMR [DMSO-D$_6$] 3.23-3.25 (m, 2H), 4.36-4.39 (m, 2H), 6.78 (d, 1H), 7.34-7.40 (m, 2H), 7.56-7.63 (m, 1H), 8.03 (d, 1H), 11.38 (s, 1H).

I-1-103
HPLC-MS: log P=2.64; mass (m/z): 320.1 (M+H)$^+$; $^1$H-NMR [CD$_3$CN] 2.53 (s, 3H), 6.95 (d, 1H), 6.98-7.00 (m, 1H), 7.17-7.22 (m, 2H), 7.47-7.54 (m, 2H), 7.73 (d, 1H), 8.72 (br. s, 1H).

I-1-104
HPLC-MS: log P=2.96; mass (m/z): 431.8 (M+H)$^+$; $^1$H-NMR [CD$_3$CN] 6.96 (d, 1H), 7.18-7.23 (m, 2H), 7.26-7.27 (m, 1H), 7.48-7.55 (m, 1H), 7.61-7.63 (m, 1H), 7.76 (d, 1H), 9.23 (br. s, 1H).

I-1-105
HPLC-MS: log P=2.76; mass (m/z): 431.9 (M+H)$^+$; $^1$H-NMR [CD$_3$CN] 6.99 (d, 1H), 7.16-7.22 (m, 2H), 7.25-7.27 (m, 1H), 7.47-7.55 (m, 1H), 7.63-7.64 (m, 1H), 7.75 (d, 1H), 9.12 (br. s, 1H).

I-1-106
HPLC-MS: log P=2.53; mass (m/z): 355.0 (M+H)$^+$; $^1$H-NMR [DMSO-D$_6$] 2.43 (s, 3H), 6.92 (d, 1H), 7.29-7.55 (m, 3H), 7.58-7.65 (m, 1H), 8.10 (d, 1H), 11.39 (s, 1H).

I-1-107
HPLC-MS: log P=1.71; mass (m/z): 318.1 (M+H)$^+$; $^1$H-NMR [CD$_3$CN] 2.41 (s, 3H), 3.80 (s, 3H), 6.96 (d, 1H), 7.16-7.22 (m, 2H), 7.48-7.53 (m, 1H), 7.70 (d, 1H), 7.96 (s, 1H), 8.69 (br. s, 1H).

I-1-108
HPLC-MS: log P=2.03; mass (m/z): 430.0 (M+H)$^+$; $^1$H-NMR [DMSO-D$_6$] 3.89 (s, 3H), 6.91 (d, 1H), 7.35-7.39 (m, 2H), 7.56-7.63 (m, 1H), 8.03 (d, 1H), 8.38 (s, 1H), 10.72 (br. s, 1H).

I-1-109
HPLC-MS: log P=1.77; mass (m/z): 332.1 (M+H)$^+$; $^1$H-NMR [DMSO-D$_6$] 2.25 (s, 3H), 2.36 (s, 3H), 3.67 (s, 3H), 6.88 (d, 1H), 7.35-7.39 (m, 2H), 7.55-7.63 (m, 1H), 8.00 (d, 1H), 10.22 (br. s, 1H).

I-1-110
HPLC-MS: log P=1.98; mass (m/z): 336.0 (M+H)$^+$; $^1$H-NMR [CD$_3$CN] 2.36 (s, 3H), 3.65 (s, 3H), 6.93 (d, 1H), 7.15-7.21 (m, 2H), 7.46-7.53 (m, 1H), 7.71-7.72 (m, 1H), 8.41 (br. s, 1H).

I-1-111
HPLC-MS: log P=2.40; mass (m/z): 340.1 (M+H)$^+$; $^1$H-NMR [DMSO-D$_6$] 6.93 (d, 1H), 7.37-7.41 (m, 3H), 7.58-7.65 (m, 1H), 7.93 (d, 1H), 8.11 (d, 1H), 8.32 (t, 1H), 11.57 (s, 1H).

I-1-112
HPLC-MS: log P=2.53; mass (m/z): 390.0 (M+H)$^+$; $^1$H-NMR [DMSO-D$_6$] 3.85 (s, 3H), 6.87 (d, 1H), 7.36-7.40 (m, 2H), 7.57-7.64 (m, 1H), 8.06 (d, 1H), 11.09 (s, 1H).

I-1-113
HPLC-MS: log P=2.09; mass (m/z): 335.1 (M+H)$^+$; $^1$H-NMR [CD$_3$CN] 2.60 (s, 3H), 2.64 (s, 3H), 6.93 (d, 1H), 7.15-7.21 (m, 2H), 7.46-7.54 (m, 1H), 7.73-7.74 (m, 1H), 8.91 (br. s, 1H).

I-1-114
HPLC-MS: log P=2.58; mass (m/z): 389.1 (M+H)$^+$; $^1$H-NMR [CD$_3$CN] 2.73 (s, 3H), 6.92-6.93 (m, 1H), 7.17-7.22 (m, 2H), 7.48-7.55 (m, 1H), 7.75-7.76 (m, 1H), 9.42 (br. s, 1H).

I-1-115
HPLC-MS: log P=3.33; mass (m/z): 374.0 (M+H)$^+$; $^1$H-NMR [DMSO-D$_6$] 6.92 (d, 1H), 7.37-7.42 (m, 2H), 7.58-7.65 (m, 1H), 8.12 (d, 1H), 11.65 (s, 1H).

I-1-116
HPLC-MS: log P=2.53; mass (m/z): 306.1 (M+H)$^+$; $^1$H-NMR [DMSO-D$_6$] 2.55 (s, 3H) 6.92 (d, 1H), 7.36-7.42 (m, 2H), 7.58-7.66 (m, 1H), 8.12 (d, 1H), 11.79 (s, 1H).

I-1-117
see Synthesis Example 5

I-1-118
HPLC-MS: log P=3.36; mass (m/z): 366.0 (M+H)$^+$; $^1$H-NMR [CD$_3$CN] 7.00 (d, 1H), 7.41-7.44 (m, 2H), 7.46-7.52 (m, 2H), 7.56-7.60 (m, 3H), 7.95 (d, 1H), 9.27 (br. s, 1H).

I-1-119
HPLC-MS: log P=3.40; mass (m/z): 409.9 (M+H)$^+$; $^1$H-NMR [CD$_3$CN] 7.00 (d, 1H), 7.38-7.48 (m, 3H), 7.55-7.58 (m, 2H), 7.60-7.61 (m, 1H), 7.68-7.70 (m, 1H), 7.95 (d, 1H), 9.22 (br. s, 1H).

I-1-120
HPLC-MS: log P=3.05; mass (m/z): 399.9 (M+H)$^+$; $^1$H-NMR [CD$_3$CN] 6.97 (d, 1H), 7.46-7.50 (m, 1H), 7.56-7.58 (m, 1H), 7.65-7.74 (m, 1H), 7.80-7.82 (m, 1H), 9.30 (br. s, 1H).

I-1-121
HPLC-MS: log P=2.84; mass (m/z): 366.0 (M+H)$^+$; $^1$H-NMR [CD$_3$CN] 7.00 (d, 1H), 7.40-7.52 (m, 4H), 7.56-7.61 (m, 3H), 7.66 (d, 1H), 9.25 (br. s, 1H).

I-1-122
HPLC-MS: log P=2.88; mass (m/z): 410.0 (M+H)$^+$; $^1$H-NMR [CD$_3$CN] 6.99 (d, 1H), 7.38-7.41 (m, 1H), 7.44-7.50 (m, 2H), 7.55-7.58 (m, 3H), 7.66-7.69 (m, 2H), 9.18 (br. s, 1H).

I-1-123
see Synthesis Example 8

I-1-124
HPLC-MS: log P=2.57; mass (m/z): 401.0 (M+H)$^+$; $^1$H-NMR [CD$_3$CN] 6.97 (d, 1H), 7.47-7.51 (m, 1H), 7.57-7.59 (m, 2H), 7.67 (d, 1H), 7.70-7.73 (m, 1H), 8.08-8.10 (m, 1H), 8.80-8.82 (m, 1H), 9.36 (br. s, 1H).

I-1-125
HPLC-MS: log P=2.46; mass (m/z): 343.0 (M+H)$^+$; $^1$H-NMR [DMSO-D$_6$] 6.96 (d, 1H), 7.39-7.55 (m, 4H), 7.61-7.65 (m, 1H), 7.79-7.86 (m, 2H), 8.00-8.03 (m, 1H), 8.24-8.26 (m, 1H), 11.26 (s, 1H).

I-1-126
HPLC-MS: log P=1.96; mass (m/z): 376.1 (M+H)$^+$; $^1$H-NMR [DMSO-D$_6$] 2.54 (s, 3H), 6.88 (d, 1H), 7.43-7.65 (m, 5H), 7.72-7.77 (m, 1H), 7.86-7.90 (m, 1H), 8.05 (d, 1H), 8.10-8.12 (m, 1H), 11.20 (s, 1H).

I-1-127
HPLC-MS: log P=2.36; mass (m/z): 343.0 (M+H)$^+$; $^1$H-NMR [CD$_3$CN] 7.00 (d, 1H), 7.24-7.26 (m, 1H), 7.38-7.41 (m, 1H), 7.46-7.48 (m, 1H), 7.56-7.57 (m, 1H), 7.69-7.70 (m, 1H), 7.77-7.79 (m, 1H), 7.88-7.90 (m, 1H), 8.41-8.42 (m, 1H), 8.52 (d, 1H), 9.24 (br. s, 1H).

I-1-128
HPLC-MS: log P=2.24; mass (m/z): 351.0 (M+H)$^+$; $^1$H-NMR [CD$_3$CN] 7.03 (d, 1H), 7.33-7.37 (m, 1H), 7.60-7.77 (m, 5H), 8.27-8.30 (m, 2H), 9.53 (br. s, 1H).

I-1-129
HPLC-MS: log P=2.05; mass (m/z): 317.0 (M+H)$^+$; $^1$H-NMR [CD$_3$CN] 7.06 (d, 1H), 7.34-7.38 (m, 2H), 7.40-7.47 (m, 2H), 7.55-7.57 (m, 1H), 7.69-7.74 (m, 1H), 8.28-8.31 (m, 2H), 9.54 (br. s, 1H).

I-1-130
HPLC-MS: log P=2.12; mass (m/z): 361.0 (M+H)$^+$; $^1$H-NMR [CD$_3$CN] 7.05 (d, 1H), 7.32-7.42 (m, 3H), 7.50-7.53 (m, 1H), 7.62-7.64 (m, 1H), 7.69-7.74 (m, 1H), 8.28-8.31 (m, 2H), 9.45 (br. s, 1H).

I-1-131
HPLC-MS: log P=2.22; mass (m/z): 409.0 (M+H)$^+$; $^1$H-NMR [CD$_3$CN] 7.05 (d, 1H), 7.15-7.20 (m, 1H), 7.34-7.38 (m, 1H), 7.42-7.49 (m, 2H), 7.70-7.75 (m, 1H), 7.90-7.92 (m, 1H), 8.29-8.31 (m, 2H), 9.40 (br. s, 1H).

I-1-132
HPLC-MS: log P=1.99; mass (m/z): 319.0 (M+H)$^+$; $^1$H-NMR [CD$_3$CN] 7.03-7.07 (m, 3H), 7.35-7.39 (m, 1H), 7.45-7.52 (m, 1H), 7.70-7.75 (m, 1H), 8.28-8.31 (m, 2H), 9.62 (br. s, 1H).

I-1-133
HPLC-MS: log P=1.83; mass (m/z): 352.0 (M+H)$^+$; $^1$H-NMR [CD$_3$CN] 6.99 (d, 1H), 7.36-7.40 (m, 1H), 7.69-7.75 (m, 2H), 8.07-8.09 (m, 1H), 8.30-8.31 (m, 2H), 8.79-8.80 (m, 1H), 9.52 (br. s, 1H).

I-1-134
HPLC-MS: log P=2.93; mass (m/z): 525.1 (M+H)$^+$; $^1$H-NMR [CD$_3$CN] 6.61 (d, 1H), 7.40-7.45 (m, 1H), 7.62-7.65 (m, 2H), 7.70-7.75 (m, 1H), 8.07-8.09 (m, 2H), 8.21 (d, 1H), 8.26-8.28 (m, 1H), 8.73-8.81 (m, 2H).

I-1-135
HPLC-MS: log P=2.41; mass (m/z): 367.0 (M+H)$^+$; $^1$H-NMR [CD$_3$CN] 6.99 (d, 1H), 7.37-7.43 (m, 1H), 7.63-7.72 (m, 3H), 7.78-7.80 (m, 1H), 7.98-8.01 (m, 1H), 8.10 (d, 1H), 8.43-8.45 (m, 1H), 9.44 (br. s, 1H).

I-1-136
HPLC-MS: log P=2.21; mass (m/z): 333.0 (M+H)$^+$; $^1$H-NMR [CD$_3$CN] 7.01 (d, 1H), 7.38-7.51 (m, 4H), 7.58-7.60 (m, 1H), 7.99-8.02 (m, 1H), 8.10 (d, 1H), 8.44-8.45 (m, 1H), 9.31 (br. s, 1H).

I-1-137
HPLC-MS: log P=2.23; mass (m/z): 376.9 (M+H)$^+$; $^1$H-NMR [DMSO-D$_6$] 6.95 (d, 1H), 7.38-7.42 (m, 1H), 7.45-7.49 (m, 1H), 7.52-7.55 (m, 2H), 7.68-7.70 (m, 1H), 8.19-8.22 (m, 1H), 8.26 (d, 1H), 8.52-8.53 (m, 1H), 11.28 (br. s, 1H).

I-1-138

HPLC-MS: log P=2.36; mass (m/z): 424.9 (M+H)$^+$; $^1$H-NMR [CD$_3$CN] 7.01 (d, 1H), 7.18-7.22 (m, 1H), 7.38-7.41 (m, 1H), 7.45-7.51 (m, 2H), 7.92-7.94 (m, 1H), 8.00-8.02 (m, 1H), 8.11 (d, 1H), 8.44-8.46 (m, 1H), 9.29 (br. s, 1H).

I-1-139 see Synthesis Example 11

I-1-140

HPLC-MS: log P=2.48; mass (m/z): 369.1 (M+H)$^+$; $^1$H-NMR [CD$_3$CN] 7.03 (d, 1H), 7.62-7.70 (m, 4H), 7.77-7.79 (m, 1H), 8.20 (d, 1H), 8.25 (d, 1H), 9.47 (br. s, 1H).

I-1-141

HPLC-MS: log P=2.72; mass (m/z): 495.0 (M+H)$^+$; $^1$H-NMR [CD$_3$CN] 7.70-7.91 (m, 5H), 8.30 (s, 1H), 8.37 (s, 1H), 8.65 (br. s, 1H).

I-1-142

HPLC-MS: log P=2.97; mass (m/z): 411.1 (M+H)$^+$; $^1$H-NMR [DMSO-D$_6$] 2.31 (s, 3H), 6.67 (d, 1H), 7.59-7.70 (m, 3H), 7.76-7.78 (m, 1H), 8.25-8.30 (m, 1H), 8.38 (d, 1H), 8.49 (d, 1H).

I-1-143

HPLC-MS: log P=2.32; mass (m/z): 335.0 (M+H)$^+$; $^1$H-NMR [CD$_3$CN] 7.06 (d, 1H), 7.34-7.38 (m, 1H), 7.40-7.47 (m, 2H), 7.54-7.56 (m, 1H), 7.62-7.67 (m, 1H), 8.21 (d, 1H), 8.25 (d, 1H), 9.55 (br. s, 1H).

I-1-144

HPLC-MS: log P=2.36; mass (m/z): 378.9 (M+H)$^+$; $^1$H-NMR [CD$_3$CN] 7.05 (d, 1H), 7.34-7.38 (m, 1H), 7.41-7.45 (m, 1H), 7.52-7.54 (m, 1H), 7.64-7.69 (m, 2H), 8.21 (d, 1H), 8.26 (d, 1H), 9.42 (br. s, 1H).

I-1-145

HPLC-MS: log P=2.45; mass (m/z): 426.9 (M+H)$^+$; $^1$H-NMR [CD$_3$CN] 7.05 (d, 1H), 7.15-7.19 (m, 1H), 7.42-7.48 (m, 2H), 7.64-7.69 (m, 1H), 7.89-7.91 (m, 1H), 8.22 (d, 1H), 8.26 (d, 1H), 9.42 (br. s, 1H).

I-1-146 see Synthesis Example 9

I-1-147

HPLC-MS: log P=2.00; mass (m/z): 346.0 (M+H)$^+$; $^1$H-NMR [DMSO-D$_6$] 6.98 (d, 1H), 7.72-7.77 (m, 2H), 7.83-7.87 (m, 1H), 8.12-8.14 (m, 1H), 8.23-8.28 (m, 1H), 8.36-8.37 (m, 1H), 8.48 (d, 1H), 11.58 (s, 1H).

I-1-148

HPLC-MS: log P=2.48; mass (m/z): 317.1 (M+H)$^+$; $^1$H-NMR [DMSO-D$_6$] 6.96-7.03 (m, 3H), 7.44-7.48 (m, 1H), 8.06-8.09 (m, 1H), 8.25-8.30 (m, 1H), 8.35-8.36 (m, 1H), 8.49 (d, 1H), 11.08 (s, 1H), 11.89 (s, 1H).

I-1-149

HPLC-MS: log P=2.98; mass (m/z): 401.0 (M+H)$^+$; $^1$H-NMR [DMSO-D$_6$] 6.95 (d, 1H), 7.62-7.68 (m, 2H), 7.75-7.81 (m, 2H), 8.23-8.29 (m, 1H), 8.36 (d, 1H), 8.48-8.49 (m, 1H), 11.46 (s, 1H).

I-1-150

HPLC-MS: log P=1.47; mass (m/z): 368.1 (M+H)$^+$; $^1$H-NMR [DMSO-D$_6$] 6.84 (d, 1H), 7.58-7.60 (m, 1H), 7.65-7.70 (m, 3H), 8.11 (s, 1H), 8.19-8.27 (m, 2H), 8.44 (d, 1H), 8.88 (s, 1H), 11.22 (s, 1H).

I-1-151

HPLC-MS: log P=2.02; mass (m/z): 370.1 (M+H)$^+$; $^1$H-NMR [CD$_3$CN] 6.99-7.02 (m, 1H), 7.65-7.73 (m, 2H), 8.08-8.10 (m, 1H), 8.22-8.28 (m, 2H), 8.80-8.82 (m, 1H), 9.44 (br. s, 1H).

I-1-152

HPLC-MS: log P=1.72; mass (m/z): 336.0 (M+H)$^+$; $^1$H-NMR [CD$_3$CN] 7.04 (d, 1H), 7.43-7.46 (m, 1H), 7.65-7.70 (m, 1H), 7.97-7.99 (m, 1H), 8.22 (d, 1H), 8.27 (d, 1H), 8.48-8.49 (m, 1H), 9.40 (br. s, 1H).

I-1-153

HPLC-MS: log P=1.96; mass (m/z): 369.1 (M+H)$^+$; $^1$H-NMR [DMSO-D$_6$] 6.97 (d, 1H), 7.77 (d, 1H), 8.24-8.29 (m, 1H), 8.37-8.38 (m, 1H), 8.49 (d, 1H), 8.99 (d, 1H), 9.07 (s, 1H), 11.70 (s, 1H).

I-1-154

HPLC-MS: log P=2.00; mass (m/z): 370.1 (M+H)$^+$; $^1$H-NMR [DMSO-D$_6$] 6.99 (d, 1H), 8.24-8.30 (m, 1H), 8.40-8.41 (m, 1H), 8.49 (d, 1H), 9.39 (s, 1H), 9.56 (s, 1H), 11.80 (s, 1H).

I-1-155

HPLC-MS: log P=2.35; mass (m/z): 392.0 (M+H)$^+$; $^1$H-NMR [DMSO-D$_6$] 3.23-3.26 (m, 2H), 4.37-4.39 (m, 2H), 6.83 (d, 1H), 8.23-8.29 (m, 1H), 8.32 (d, 1H), 8.47 (d, 1H), 11.51 (s, 1H).

I-1-156

HPLC-MS: log P=2.31; mass (m/z): 371.1 (M+H)$^+$; $^1$H-NMR [DMSO-D$_6$] 3.70 (s, 3H), 6.95 (d, 1H), 7.40 (d, 1H), 7.85 (d, 1H), 8.22-8.29 (m, 2H), 8.47 (d, 1H), 10.71 (s, 1H).

I-1-157

HPLC-MS: log P=2.33; mass (m/z): 356.0 (M+H)$^+$; $^1$H-NMR [DMSO-D$_6$] 2.42 (s, 3H), 6.96 (d, 1H), 7.42 (t, 1H), 8.24-8.30 (m, 1H), 8.37 (d, 1H), 8.48-8.49 (m, 1H), 11.51 (s, 1H).

I-1-158

HPLC-MS: log P=2.36; mass (m/z): 391.0 (M+H)$^+$; $^1$H-NMR [DMSO-D$_6$] 3.86 (s, 3H), 6.92 (d, 1H), 8.24-8.29 (m, 1H), 8.35 (d, 1H), 8.47-8.48 (m, 1H), 11.21 (s, 1H).

I-1-159

HPLC-MS: log P=3.06; mass (m/z): 375.0 (M+H)$^+$; $^1$H-NMR [DMSO-D$_6$] 6.96 (d, 1H), 8.25-8.30 (m, 1H), 8.39 (d, 1H), 8.49 (d, 1H), 11.78 (s, 1H).

I-1-160

HPLC-MS: log P=1.91; mass (m/z): 323.1 (M+H)$^+$; $^1$H-NMR [DMSO-D$_6$] 2.83 (s, 3H), 6.99 (d, 1H), 8.25-8.30 (m, 1H), 8.37-8.38 (m, 1H), 8.49 (d, 1H), 11.82 (s, 1H).

I-1-161

HPLC-MS: log P=2.75; mass (m/z): 426.9 (M+H)$^+$; $^1$H-NMR [CD$_3$CN] 7.08 (d, 1H), 7.20-7.25 (m, 1H), 7.41-7.50 (m, 2H), 7.93-7.98 (m, 2H), 8.06-8.11 (m, 1H), 8.16-8.17 (m, 1H), 9.31 (s, 1H).

I-1-162

HPLC-MS: log P=2.78; mass (m/z): 387.0 (M+H)$^+$; $^1$H-NMR [DMSO-D$_6$] 7.00 (d, 1H), 7.68-7.72 (m, 2H), 7.75-7.77 (m, 1H), 7.82-7.84 (m, 1H), 8.33 (d, 1H), 8.55-8.61 (m, 1H), 11.51 (s, 1H).

I-1-163

HPLC-MS: log P=2.64; mass (m/z): 353.1 (M+H)$^+$; $^1$H-NMR [DMSO-D$_6$] 7.02 (d, 1H), 7.41-7.58 (m, 4H), 8.33 (d, 1H), 8.55-8.61 (m, 1H), 11.43 (s, 1H).

I-1-164 see Synthesis Example 10

I-1-165

HPLC-MS: log P=3.04; mass (m/z): 445.0 (M+H)$^+$; $^1$H-NMR [DMSO-D$_6$] 7.02 (d, 1H), 7.18-7.24 (m, 1H), 7.46-7.50 (m, 2H), 7.90-7.92 (m, 1H), 8.32 (d, 1H), 8.55-8.61 (m, 1H), 11.35 (s, 1H).

I-1-166

HPLC-MS: log P=2.51; mass (m/z): 355.0 (M+H)$^+$; $^1$H-NMR [DMSO-D$_6$] 7.01 (d, 1H), 7.18-7.25 (m, 2H), 7.54-7.62 (m, 1H), 8.35 (d, 1H), 8.56-8.62 (m, 1H), 11.74 (s, 1H).

I-1-167

HPLC-MS: log P=3.88; mass (m/z): 388.0 (M+H)$^+$; $^1$H-NMR [DMSO-D$_6$] 7.00 (d, 1H), 7.80-7.84 (m, 1H), 8.00-8.01 (m, 1H), 8.19-8.22 (m, 1H), 8.34-8.35 (m, 1H), 8.39-8.45 (m, 1H), 8.56-8.62 (m, 1H), 8.84 (d, 1H), 11.68 (s, 1H).

I-1-168

HPLC-MS: log P=1.72; mass (m/z): 344.0 (M+H)$^+$; $^1$H-NMR [DMSO-D$_6$] 7.02 (d, 1H), 7.42-7.58 (m, 4H), 7.70-7.75 (m, 1H), 8.64 (d, 1H), 8.84 (d, 2H), 11.44 (br. s, 1H).

I-1-169 see Synthesis Example 12

I-1-170

HPLC-MS: log P=2.46; mass (m/z): 379.9 (M+H)$^+$; $^1$H-NMR [DMSO-D$_6$] 7.14 (d, 1H), 7.33-7.50 (m, 2H), 7.54-7.57 (m, 1H), 7.69-7.71 (m, 1H), 8.64-8.67 (m, 2H), 11.59 (s, 1H).

I-1-171

HPLC-MS: log P=2.29; mass (m/z): 338.0 (M+H)$^+$; $^1$H-NMR [DMSO-D$_6$] 7.12 (d, 1H), 7.20-7.26 (m, 2H), 7.55-7.63 (m, 1H), 8.66-8.69 (m, 2H), 11.91 (s, 1H).

I-1-173

HPLC-MS: log P=2.24; mass (m/z): 352.0 (M+H)$^+$; $^1$H-NMR [DMSO-D$_6$] 7.06 (d, 1H), 7.69-7.72 (m, 2H), 7.75-7.77 (m, 1H), 7.82-7.84 (m, 1H), 8.30-8.33 (m, 1H), 8.51 (d, 1H), 8.53-8.56 (m, 1H), 11.57 (s, 1H).

I-1-174 see Synthesis Example 10d

I-1-175

HPLC-MS: log P=2.09; mass (m/z): 362.0 (M+H)$^+$; $^1$H-NMR [DMSO-D$_6$] 7.08 (d, 1H), 7.39-7.43 (m, 1H), 7.46-7.49 (m, 1H), 7.54-7.56 (m, 1H), 7.69-7.71 (m, 1H), 8.30-8.31 (m, 1H), 8.51 (d, 1H), 8.54-8.55 (m, 1H), 11.47 (s, 1H).

I-1-176

HPLC-MS: log P=2.18; mass (m/z): 409.9 (M+H)$^+$; $^1$H-NMR [DMSO-D$_6$] 7.08 (d, 1H), 7.20-7.25 (m, 1H), 7.47-7.51 (m, 2H), 7.91-7.93 (m, 1H), 8.30-8.31 (m, 1H), 8.51 (d, 1H), 8.54-8.55 (m, 1H), 11.41 (s, 1H).

I-1-177

HPLC-MS: log P=1.94; mass (m/z): 320.1 (M+H)$^+$; $^1$H-NMR [DMSO-D$_6$] 7.06 (d, 1H), 7.20-7.25 (m, 2H), 7.54-7.62 (m, 1H), 8.31-8.32 (m, 1H), 8.53-8.56 (m, 2H), 11.80 (s, 1H).

I-1-178

HPLC-MS: log P=1.77; mass (m/z): 353.0 (M+H)$^+$; $^1$H-NMR [DMSO-D$_6$] 7.06 (d, 1H), 7.81-7.84 (m, 1H), 8.20-8.22 (m, 1H), 8.31-8.32 (m, 1H), 8.53-8.56 (m, 1H), 8.84-8.85 (m, 1H), 11.74 (s, 1H).

I-1-179:

HPLC-MS: log P=2.13; mass (m/z): 410.1 (M+H)$^+$; $^1$H-NMR (400.0 MHz, DMSO-D$_6$): δ=11.261 (2.7); 8.123 (1.6); 8.119 (1.7); 8.103 (1.9); 8.099 (1.9); 8.057 (3.3); 8.051 (3.2); 7.901 (0.7); 7.897 (0.8); 7.881 (1.7); 7.878 (1.6); 7.862 (2.3); 7.859 (2.4); 7.841 (1.7); 7.808 (0.5); 7.790 (1.5); 7.771 (1.3); 7.766 (1.5); 7.763 (1.3); 7.746 (1.8); 7.743 (1.8); 7.732 (1.2); 7.727 (1.2); 7.724 (1.0); 7.713 (1.5); 7.705 (1.9); 7.694 (0.6); 7.686 (1.2); 7.656 (2.0); 7.653 (1.9); 7.636 (1.8); 7.633 (1.6); 6.861 (3.5); 6.855 (3.5); 3.456 (16.0); 3.324 (82.6); 2.675 (0.4); 2.670 (0.5); 2.666 (0.4); 2.540 (55.9); 2.523 (1.6); 2.510 (30.5); 2.506 (59.9); 2.501 (77.4); 2.496 (54.9); 2.492 (25.8); 2.332 (0.4); 2.328 (0.5); 2.323 (0.4); 2.074 (0.5); 0.008 (0.6); 0.000 (15.6); −0.009 (0.5)

I-1-180:

HPLC-MS: log P=2.00; mass (m/z): 411.1 (M+H)$^+$; $^1$H-NMR (400.0 MHz, DMSO-D$_6$): δ=11.337 (2.8); 8.938 (1.5); 8.928 (1.5); 8.390 (1.5); 8.372 (1.6); 8.129 (1.6); 8.125 (1.7); 8.109 (1.9); 8.105 (1.9); 8.074 (3.3); 8.067 (3.2); 7.908 (0.7); 7.904 (0.8); 7.889 (1.7); 7.885 (1.7); 7.870 (1.2); 7.866 (1.1); 7.821 (1.0); 7.808 (1.1); 7.801 (1.0); 7.789 (1.0); 7.776 (1.2); 7.773 (1.3); 7.757 (1.7); 7.754 (1.8); 7.738 (0.9); 7.735 (0.8); 7.669 (2.0); 7.667 (2.0); 7.650 (1.8); 7.647 (1.7); 6.871 (3.5); 6.865 (3.5); 3.461 (16.0); 3.332 (224.0); 2.995 (0.4); 2.711 (0.6); 2.675 (0.5); 2.671 (0.6); 2.666 (0.5); 2.541 (149.2); 2.524 (1.9); 2.519 (2.9); 2.511 (34.6); 2.506 (68.5); 2.502 (89.3); 2.497 (64.4); 2.493 (31.2); 2.367 (0.6); 2.333 (0.4); 2.329 (0.6); 2.324 (0.4); 2.074 (1.0); 0.008 (0.4); 0.000 (9.8)

I-1-181:

HPLC-MS: log P=1.86; mass (m/z): 378.1 (M+H)$^+$; $^1$H-NMR (400.0 MHz, DMSO-D$_6$): δ=11.465 (2.7); 8.125 (1.6); 8.122 (1.7); 8.106 (1.9); 8.102 (1.9); 8.075 (3.2); 8.069 (3.2); 7.907 (0.7); 7.903 (0.8); 7.887 (1.7); 7.884 (1.7); 7.868 (1.2); 7.864 (1.2); 7.776 (1.2); 7.773 (1.3); 7.756 (1.7); 7.754 (1.8); 7.737 (0.9); 7.734 (0.8); 7.658 (2.0); 7.656 (2.0); 7.639 (1.8); 7.636 (1.7); 7.631 (0.5); 7.614 (0.7); 7.609 (0.7); 7.593 (1.3); 7.576 (0.7); 7.572 (0.8); 7.555 (0.8); 7.555 (0.4); 7.274 (0.5); 7.268 (2.3); 7.248 (3.3); 7.227 (2.0); 7.220 (0.4); 6.870 (3.5); 6.864 (3.5); 3.456 (16.0); 3.367 (0.7); 3.334 (243.8); 3.303 (0.7); 3.289 (0.3); 2.995 (0.5); 2.711 (0.6); 2.675 (0.4); 2.671 (0.5); 2.666 (0.4); 2.541 (168.5); 2.524 (2.6); 2.511 (32.7); 2.506 (63.5); 2.502 (82.5); 2.497 (60.3); 2.493 (30.1); 2.368 (0.6); 2.333 (0.4); 2.328 (0.5); 2.324 (0.4); 2.074 (0.7); 0.000 (1.9)

I-1-182:

HPLC-MS: log P=2.00; mass (m/z): 422.1 (M+H)$^+$; $^1$H-NMR (400.0 MHz, DMSO-D$_6$): δ=11.188 (2.9); 8.121 (1.7); 8.118 (1.8); 8.101 (1.9); 8.098 (1.9); 8.056 (3.3); 8.050 (3.3); 7.900 (0.8); 7.896 (0.8); 7.881 (1.7); 7.877 (1.7); 7.862 (1.2); 7.858 (1.1); 7.764 (1.2); 7.761 (1.3); 7.744 (1.8); 7.741 (1.9); 7.725 (2.6); 7.707 (2.1); 7.705 (2.0); 7.651 (2.0); 7.648 (2.0); 7.631 (1.8); 7.629 (1.6); 7.566 (1.1); 7.561 (1.3); 7.547 (2.1); 7.543 (2.1); 7.512 (1.0); 7.509 (1.1); 7.493 (2.0); 7.490 (1.9); 7.475 (1.0); 7.472 (0.9); 7.442 (1.3); 7.437 (1.3); 7.423 (1.5); 7.418 (1.5); 7.404 (0.7); 7.399 (0.7); 6.882 (3.5); 6.876 (3.5); 3.475 (16.0); 3.327 (122.0); 2.675 (0.3); 2.670 (0.5); 2.666 (0.32541 (54.6); 2.541 (54.6); 2.524 (1.5); 2.519 (2.3); 2.510 (28.0); 2.506 (55.8); 2.501 (72.8); 2.497 (52.0); 2.492 (24.5); 2.332 (0.3); 2.328 (0.5); 2.323 (0.3); 2.074 (0.5); 0.000 (6.9)

I-1-183:

HPLC-MS: log P=2.64; mass (m/z): 384.9 (M+H)$^+$; $^1$H-NMR [DMSO-D$_6$] 6.93 (d, 1H), 7.67-7.84 (m, 4H). 8.20 (d, 1H), 8.40-8.42 (m, 1H), 8.61-8.62 (m, 1H), 11.37 (s, 1H).

I-1-184:

HPLC-MS: log P=2.10; mass (m/z): 468.0 (M+H)$^+$; $^1$H-NMR (400.0 MHz, DMSO-D$_6$): δ=11.129 (3.2); 8.122 (1.8); 8.118 (1.8); 8.102 (2.0); 8.099 (2.0); 8.055 (3.3); 8.048 (3.3); 7.945 (2.2); 7.925 (2.5); 7.900 (0.8); 7.896 (0.8); 7.881 (1.8); 7.877 (1.7); 7.861 (1.3); 7.858 (1.1); 7.763 (1.3); 7.760 (1.3); 7.743 (2.0); 7.741 (2.0); 7.724 (0.9); 7.721 (0.9); 7.656 (2.2); 7.637 (1.9); 7.522 (0.5); 7.503 (1.8); 7.485 (4.3); 7.471 (0.7); 7.251 (1.0); 7.244 (1.0); 7.234 (1.1); 7.231 (1.2); 7.224 (1.0); 7.215 (0.9); 7.208 (0.8); 6.880 (3.4); 6.874 (3.4); 3.482 (16.0); 3.335 (303.3); 2.675 (0.5); 2.671 (0.6); 2.666 (0.5); 2.541 (52.4); 2.524 (2.5); 2.511 (38.8); 2.506 (74.3); 2.502 (95.3); 2.497 (68.5); 2.493 (33.2); 2.333 (0.5); 2.329 (0.6); 2.324 (0.4); 2.074 (0.8); 0.000 (2.6)

I-1-185:

HPLC-MS: log P=2.16; mass (m/z): 364.1 (M+H)$^+$; $^1$H-NMR (400.0 MHz, DMSO-D$_6$): δ=10.164 (2.5); 8.315 (0.6); 7.941 (1.2); 7.938 (1.2); 7.921 (1.4); 7.918 (1.4); 7.901 (2.0); 7.895 (1.9); 7.860 (0.5); 7.841 (1.3); 7.822

(0.9); 7.730 (0.9); 7.711 (1.3); 7.691 (0.5); 7.644 (1.6); 7.624 (1.3); 6.857 (3.0); 6.850 (3.0); 5.756 (0.5); 3.667 (14.4); 3.321 (243.6); 2.689 (0.7); 2.680 (0.7); 2.675 (1.5); 2.670 (2.1); 2.666 (1.4); 2.661 (0.7); 2.524 (6.3); 2.519 (10.2); 2.510 (112.4); 2.506 (224.0); 2.501 (294.8); 2.497 (21.2); 2.492 (98.1); 2.360 (15.9); 2.337 (0.8); 2.333 (1.5); 2.328 (2.0); 2.324 (1.4); 2.319 (0.7); 2.258 (16.0); 1.259 (0.5); 1.235 (0.4); 0.146 (0.7); 0.008 (6.5); 0.000 (180.4); −0.009 (5.4); −0.150 (0.7)

I-1-186:
HPLC-MS: log P=2.96; mass (m/z): 411.9 (M+H)$^+$; $^1$H-NMR (400.0 MHz, DMSO-D$_6$): δ=11.178 (12.3); 7.967 (10.7); 7.961 (10.7); 7.945 (6.5); 7.927 (7.4); 7.925 (7.5); 7.868 (2.8); 7.866 (2.8); 7.848 (6.7); 7.829 (4.5); 7.740 (4.7); 7.721 (7.0); 7.699 (9.7); 7.696 (8.7); 7.679 (9.4); 7.676 (9.2); 7.655 (8.3); 7.635 (6.8); 7.547 (5.6); 7.542 (6.3); 7.528 (9.4); 7.524 (9.6); 7.482 (4.4); 7.479 (4.7); 7.463 (9.2); 7.460 (8.8); 7.445 (5.1); 7.442 (4.7); 7.430 (0.3); 7.427 (0.3); 7.416 (6.1); 7.411 (6.1); 7.396 (7.1); 7.392 (7.0); 7.377 (3.4); 7.373 (3.1); 6.917 (16.0); 6.910 (15.8); 5.756 (9.8); 4.038 (0.7); 4.020 (0.7); 3.325 (108.8); 2.675 (0.6); 2.670 (0.8); 2.666 (0.6); 2.524 (2.6); 2.510 (44.5); 2.506 (89.2); 2.501 (117.8); 2.497 (85.2); 2.492 (40.8); 2.333 (0.6); 2.328 (0.8); 2.323 (0.6); 1.989 (3.2); 1.397 (2.1); 1.336 (1.4); 1.299 (0.4); 1.259 (0.6); 1.250 (1.8); 1.235 (0.6); 1.192 (0.9); 1.175 (1.8); 1.159 (0.7); 1.157 (1.0); 0.991 (0.6); 0.008 (2.1); 0.000 (59.3); −0.009 (1.9)

I-1-187:
HPLC-MS: log P=3.41; mass (m/z): 411.9 (M+H)$^+$; $^1$H-NMR (601.6 MHz, CD$_3$CN): δ=9.253 (3.0); 9.237 (0.9); 7.894 (11.2); 7.889 (11.3); 7.685 (6.3); 7.684 (6.5); 7.672 (7.6); 7.669 (13.4); 7.665 (12.6); 7.624 (0.4); 7.623 (0.4); 7.612 (0.5); 7.610 (0.5); 7.553 (5.4); 7.550 (5.7); 7.541 (7.1); 7.538 (7.4); 7.532 (0.4); 7.520 (9.4); 7.506 (16.0); 7.470 (10.6); 7.468 (5.7); 7.466 (13.4); 7.456 (13.7); 7.454 (9.0); 7.452 (6.7); 7.443 (4.4); 7.441 (4.2); 7.415 (0.5); 7.413 (0.5); 7.400 (5.0); 7.397 (4.9); 7.387 (5.8); 7.384 (5.7); 7.374 (3.3); 7.371 (3.2); 7.302 (0.4); 7.277 (0.4); 6.987 (12.3); 6.983 (12.1); 2.185 (0.7); 2.183 (0.9); 2.174 (405.2); 2.056 (0.4); 2.052 (0.6); 2.048 (0.4); 1.973 (1.1); 1.966 (3.4); 1.958 (2.7); 1.954 (3.3); 1.950 (35.9); 1.946 (67.5); 1.942 (102.0); 1.938 (69.7); 1.934 (34.2); 1.929 (1.0); 1.925 (0.4); 1.831 (0.4); 1.827 (0.6); 1.823 (0.4); 1.436 (14.3); 1.268 (0.4); 1.216 (1.3); 1.204 (2.5); 1.192 (1.2); 1.029 (1.1); 1.017 (2.2); 1.005 (1.1); 0.005 (0.8); 0.000 (27.7); −0.006 (0.7)

I-1-188:
HPLC-MS: log P=3.38; mass (m/z): 366.0 (M+H)$^+$; $^1$H-NMR (601.6 MHz, CD$_3$CN): δ=9.307 (3.0); 9.242 (0.4); 7.891 (11.4); 7.886 (11.5); 7.663 (11.7); 7.660 (12.1); 7.590 (5.4); 7.588 (5.6); 7.578 (6.5); 7.575 (6.6); 7.514 (9.2); 7.509 (3.8); 7.507 (4.4); 7.500 (16.0); 7.496 (8.8); 7.494 (8.8); 7.482 (4.6); 7.479 (4.6); 7.470 (6.7); 7.465 (12.1); 7.462 (9.7); 7.456 (3.8); 7.454 (3.8); 7.451 (5.9); 7.447 (5.7); 7.443 (0.5); 7.441 (0.4); 7.421 (5.2); 7.419 (5.1); 7.409 (7.1); 7.407 (6.9); 7.402 (0.6); 7.396 (3.1); 7.394 (3.0); 7.390 (0.4); 7.386 (0.4); 6.990 (12.1); 6.986 (12.0); 5.449 (8.5); 2.189 (0.5); 2.177 (268.1); 2.052 (0.4); 1.973 (1.0); 1.966 (2.3); 1.958 (1.8); 1.954 (2.3); 1.950 (24.2); 1.946 (44.6); 1.942 (67.1); 1.938 (46.0); 1.934 (22.7); 1.929 (0.6); 1.827 (0.4); 1.435 (1.7); 1.266 (0.4); 1.215 (0.4); 1.210 (0.7); 1.203 (0.6); 1.198 (1.4); 1.191 (0.3); 1.186 (0.7); 1.024 (0.7); 1.012 (1.4); 1.000 (0.7); 0.005 (0.5); 0.000 (17.6); −0.006 (0.5)

I-1-189:
HPLC-MS: log P=3.01; mass (m/z): 334.0 (M+H)$^+$; $^1$H-NMR (400.0 MHz, CD$_3$CN): δ=9.336 (3.6); 8.042 (7.0); 8.036 (12.5); 8.030 (7.0); 7.598 (6.8); 7.596 (6.9); 7.580 (10.1); 7.576 (11.3); 7.567 (3.0); 7.559 (6.2); 7.543 (2.7); 7.539 (4.2); 7.534 (2.6); 7.516 (2.9); 7.512 (4.1); 7.496 (12.1); 7.492 (16.0); 7.487 (8.4); 7.473 (10.4); 7.469 (9.4); 7.453 (4.5); 7.449 (4.1); 7.429 (8.0); 7.424 (7.2); 7.410 (8.8); 7.406 (8.5); 7.392 (4.1); 7.388 (3.8); 7.294 (1.5); 7.280 (2.0); 7.273 (4.9); 7.270 (5.0); 7.262 (5.7); 7.259 (6.1); 7.254 (13.3); 7.246 (4.5); 7.238 (8.6); 7.232 (4.9); 7.225 (2.3); 7.221 (4.3); 7.216 (4.5); 7.200 (1.6); 7.195 (1.3); 7.042 (12.4); 7.035 (12.2); 5.447 (1.9); 2.155 (42.5); 1.964 (1.9); 1.958 (2.5); 1.952 (17.5); 1.946 (32.4); 1.940 (45.1); 1.934 (31.1); 1.927 (16.0); 1.376 (0.5); 1.372 (1.2); 1.339 (0.5); 1.284 (0.7); 1.276 (1.4); 1.263 (0.6); 0.008 (1.6); 0.000 (42.7); −0.009 (1.3)

I-1-190:
HPLC-MS: log P=3.09; mass (m/z): 425.9 (M+H)$^+$; $^1$H-NMR (400.0 MHz, DMSO-D$_6$): δ=11.255 (8.9); 8.316 (1.2); 8.233 (4.7); 8.226 (8.6); 8.220 (4.6); 8.202 (0.4); 8.196 (0.3); 7.927 (6.7); 7.907 (7.5); 7.612 (2.3); 7.595 (3.8); 7.591 (4.0); 7.574 (2.6); 7.503 (1.2); 7.483 (6.9); 7.476 (9.7); 7.469 (16.0); 7.458 (4.5); 7.441 (2.3); 7.437 (2.8); 7.433 (2.8); 7.415 (1.7); 7.411 (1.6); 7.392 (1.8); 7.388 (1.9); 7.372 (3.3); 7.367 (2.8); 7.357 (2.5); 7.353 (2.9); 7.336 (3.2); 7.332 (1.0); 7.250 (0.5); 7.237 (3.0); 7.230 (3.1); 7.222 (3.1); 7.217 (3.7); 7.215 (3.6); 7.210 (2.9); 7.203 (2.7); 7.195 (2.3); 6.989 (9.2); 6.983 (8.9); 4.027 (0.3); 4.008 (0.3); 3.322 (248.2); 2.943 (0.5); 2.675 (2.7); 2.671 (3.6); 2.666 (2.7); 2.607 (0.4); 2.541 (3.1); 2.506 (397.8); 2.502 (510.3); 2.497 (379.1); 2.333 (2.6); 2.328 (3.5); 2.324 (2.6); 1.989 (0.7); 1.398 (12.3); 1.257 (0.4); 1.239 (0.8); 1.222 (0.4); 1.175 (0.4); 0.000 (37.9); −0.008 (1.8)

I-1-191:
HPLC-MS: log P=4.04; mass (m/z): 386.1 (M+H)$^+$; $^1$H-NMR (400.0 MHz, DMSO-D$_6$): δ=11.402 (13.3); 8.316 (0.4); 8.187 (7.5); 8.181 (14.2); 8.174 (7.3); 7.937 (2.9); 7.918 (3.2); 7.909 (5.4); 7.891 (6.2); 7.882 (3.9); 7.875 (5.0); 7.866 (4.6); 7.856 (3.8); 7.844 (8.7); 7.823 (9.8); 7.790 (2.7); 7.771 (7.5); 7.753 (6.4); 7.719 (5.7); 7.700 (7.2); 7.684 (11.0); 7.666 (6.2); 6.951 (16.0); 6.944 (15.9); 3.384 (0.5); 3.333 (420.8); 3.299 (0.5); 2.677 (0.9); 2.672 (1.2); 2.668 (0.8); 2.542 (49.0); 2.525 (5.4); 2.512 (74.4); 2.507 (143.2); 2.503 (184.3); 2.498 (132.1); 2.494 (64.5); 2.334 (0.9); 2.329 (1.1); 2.325 (0.8); 1.234 (0.5); 0.000 (0.4)

I-1-192:
HPLC-MS: log P=3.42; mass (m/z): 387.1 (M+H)$^+$; $^1$H-NMR (400.0 MHz, DMSO-D$_6$): δ=11.569 (10.2); 8.852 (5.8); 8.842 (5.8); 8.315 (0.4); 8.200 (16.0); 8.194 (6.4); 8.182 (6.2); 7.941 (2.1); 7.923 (2.4); 7.913 (4.0); 7.896 (4.4); 7.882 (3.9); 7.872 (3.0); 7.838 (2.9); 7.861 (2.7); 7.853 (3.7); 7.845 (5.3); 7.833 (6.9); 7.825 (4.7); 7.813 (4.4); 6.956 (12.5); 6.950 (12.4); 3.386 (0.3); 3.332 (293.6); 2.676 (0.7); 2.672 (1.0); 2.667 (0.7); 2.542 (30.9); 2.525 (3.6); 2.512 (68.7); 2.507 (129.8); 2.503 (163.2); 2.498 (115.5); 2.494 (55.1); 2.338 (0.4); 2.334 (0.8); 2.330 (1.0); 2.325 (0.7); 1.235 (0.5); 0.000 (0.5)

I-1-193:
HPLC-MS: log P=3.73; mass (m/z): 354.0 (M+H)$^+$; $^1$H-NMR (400.0 MHz, DMSO-D$_6$): δ=56 (3.8); 7.539 (1.7); 7.250 (2.2); 7.244 (11.1); 7.223 (16.0); 7.203 (9.3); 7.196 (2.0); 6.956 (15.3); 6.949 (15.1); 3.367 (0.5); 3.330 (314.3); 3.297 (0.3); 2.712 (0.7); 2.676 (0.8); 2.672 (1.0); 2.668 (0.7); 2.542 (179.6); 2.525 (3.3); 2.511 (63.1); 2.507 (122.4); 2.503 (157.5); 2.498 (113.9); 2.494 (55.3); 2.465 (0.3); 2.368 (0.7); 2.334 (0.8); 2.329 (1.0); 2.325 (0.8); 1.234 (0.6); 0.000 (0.6)

I-1-194:
HPLC-MS: log P=3.99; mass (m/z): 396.0 (M+H)+;
$^1$H-NMR (400.0 MHz, DMSO-D$_6$): δ=686 (10.2); 7.541 (5.2); 7.537 (6.2); 7.523 (10.5); 7.518 (10.7); 7.493 (5.3); 7.491 (5.6); 7.475 (10.1); 7.472 (9.7); 961 (15.7); 3.385 (0.3); 3.368 (0.8); 3.332 (495.1); 3.300 (0.9); 3.284 (0.4); 2.996 (0.4); 2.711 (1.4); 2.676 (0.9); 2.671 (1.2); 2.667 (0.9); 2.561 (1.9); 2.542 (342.9); 2.524 (5.0); 2.511 (77.3); 2.507 (151.1); 2.502 (196.3); 2.498 (140.9); 2.493 (68.1); 2.368 (1.5); 2.333 (0.9); 2.329 (1.2); 2.324 (0.9); 1.234 (0.7); 0.000 (0.5)

I-1-195:
HPLC-MS: log P=3.94; mass (m/z): 352.1 (M+H)+;
$^1$H-NMR (400.0 MHz, DMSO-D$_6$): δ=7.881 (3.8); 7.873 (5.0); 7.864 (5.6); 7.853 (3.5); 7.845 (4.6); 7.825 (2.7); 7.573 (6.8); 7.569 (7.4); 7.555 (15.1); 7.551 (10.7); 7.537 (12.1); 7.535 (12.5); 7.517 (5.4); 7.513 (5.6); 7.499 (9.3); 7.494 (7.7); 7.479 (5.0); 7.474 (4.1); 7.453 (7.5); 7.450 (7.2); 7.435 (9.2); 7.432 (8.9); 7.417 (3.4); 7.413 (3.1); 6.970 (16.0); 6.964 (15.7); 3.384 (0.5); 3.331 (472.9); 3.313 (1.8); 3.301 (0.6); 2.996 (0.4); 2.712 (1.6); 2.676 (1.0); 2.671 (1.4); 2.667 (1.0); 2.662 (0.5); 2.594 (0.4); 2.584 (0.5); 2.562 (2.3); 2.542 (380.9); 2.511 (86.0); 2.507 (165.9); 2.502 (213.6); 2.498 (151.8); 2.493 (71.8); 2.368 (1.6); 2.334 (1.0); 2.329 (1.4); 2.325 (1.0); 1.234 (0.7); 0.000 (0.5)

I-1-196:
HPLC-MS: log P=4.10; mass (m/z): 444.0 (M+H)+;
$^1$H-NMR (400.0 MHz, DMSO-D$_6$): δ=85 (6.8); 7.483 (6.6); 7.468 (16.0); 7.462 (11.0); 7.449 (2.9); 7.443 (1.4); 7.238 (4.1); 7.232 (3.9); 7.221 (4.4); 7.21 (84.1); 2.507 (166.0); 2.502 (216.0); 2.498 (153.6); 2.493 (72.5); 2.334 (1.0); 2.329 (1.3); 2.324 (0.9); 1.235 (0.6); 0.000 (0.5)

I-1-197:
HPLC-MS: log P=3.51; mass (m/z): 400.0 (M+H)+;
$^1$H-NMR (400.0 MHz, DMSO-D$_6$): δ=7; 2.324 (0.5); 1.398 (0.8); 0.008 (0.7); 0.000 (22.7); −0.009 (0.6)

I-1-198:
HPLC-MS: log P=3.25; mass (m/z): 368.0 (M+H)+;
$^1$H-NMR (400.0 MHz, DMSO-D$_6$): δ=11.549 (8.6); 8.315 (0.8); 8.130 (10.9); 8.124 (10.7); 7.895 (9.5); 7.889 (9.7); 7.649 (4.9); 7.627 (16.0); 7.612 (10.9); 7.606 (10.8); 7.590 (5.3); 7.585 (5.5); 7.573 (1.8); 7.568 (4.5); 7.564 (1.6); 7.552 (2.3); 7.547 (2.7); 7.531 (1.2); 7.244 (1.4); 7.238 (8.0); 7.218 (10.9); 7.197 (6.6); 7.190 (1.3); 6.917 (12.1); 6.911 (11.9); 3.322 (326.0); 3.300 (0.5); 2.680 (0.7); 2.675 (1.4); 2.671 (2.0); 2.666 (1.4); 2.662 (0.6); 2.541 (1.0); 2.524 (4.8); 2.519 (8.1); 2.511 (114.4); 2.506 (232.5); 2.502 (305.0); 2.497 (213.2); 2.493 (97.5); 2.338 (0.7); 2.333 (1.4); 2.328 (1.9); 2.324 (1.4); 2.319 (0.6); 1.989 (0.4); 1.398 (12.4); 1.120 (0.4); 1.104 (0.4); 0.008 (2.0); 0.000 (60.1); −0.009 (1.8)

I-1-199:
HPLC-MS: log P=3.44; mass (m/z): 411.9 (M+H)+;
$^1$H-NMR (400.0 MHz, CD$_3$CN): δ=9.307 (2.9); 7.892 (9.9); 7.885 (10.0); 7.682 (5.7); 7.680 (5.7); 7.661 (16.0); 7.656 (11.9); 7.613 (0.4); 7.594 (0.4); 7.590 (0.4); 7.550 (4.2); 7.550 (4.2); 7.546 (4.7); 7.531 (6.4); 7.527 (6.8); 7.518 (6.3); 7.496 (13.7); 7.467 (12.5); 7.462 (10.0); 7.448 (8.0); 7.446 (10.9); 7.440 (4.9); 7.430 (4.1); 7.427 (3.9); 7.400 (4.7); 7.396 (4.7); 7.381 (5.7); 7.376 (5.5); 7.362 (2.6); 7.357 (2.4); 6.985 (10.2); 6.979 (10.1); 5.447 (2.3); 2.205 (116.2); 2.133 (0.4); 2.108 (0.4); 1.977 (0.5); 1.972 (1.8); 1.965 (44.2); 1.959 (2.3); 1.953 (17.7); 1.947 (33.4); 1.941 (47.5); 1.935 (33.4); 1.928 (17.4); 1.435 (0.8); 1.268 (0.8); 1.221 (0.3); 1.203 (0.6); 1.135 (0.4)

I-1-200:
HPLC-MS: log P=3.40; mass (m/z): 366.0 (M+H)+;
$^1$H-NMR (400.0 MHz, CD$_3$CN): δ=9.281 (3.7); 7.892 (11.4); 7.886 (11.9); 7.666 (11.8); 7.661 (13.0); 7.616 (0.4); 7.600 (5.5); 7.597 (6.0); 7.582 (6.7); 7.578 (7.3); 7.527 (7.3); 7.519 (3.4); 7.515 (4.4); 7.505 (16.0); 7.499 (11.0); 7.495 (11.6); 7.491 (7.4); 7.487 (6.2); 7.472 (15.9); 7.466 (13.3); 7.450 (7.4); 7.445 (5.9); 7.432 (5.7); 7.427 (5.6); 7.413 (7.0); 7.409 (7.0); 7.395 (2.9); 7.391 (2.9); 7.377 (0.4); 6.988 (11.5); 6.982 (11.8); 5.447 (3.2); 3.282 (1.3); 3.268 (1.4); 2.193 (194.5); 2.133 (1.1); 2.123 (0.3); 2.120 (0.4); 2.114 (0.6); 2.108 (0.7); 2.102 (0.5); 2.095 (0.3); 1.976 (1.7); 1.965 (126.9); 1.953 (32.6); 1.947 (59.7); 1.940 (84.0); 1.934 (60.0); 1.928 (32.1); 1.894 (0.4); 1.792 (0.8); 1.775 (0.4); 1.769 (0.6); 1.763 (0.4); 1.436 (5.1); 1.292 (0.5); 1.269 (1.3); 1.200 (0.4); 1.101 (0.5); 1.014 (0.3); 0.911 (0.4); 0.000 (1.1)

I-1-201:
HPLC-MS: log P=4.15; mass (m/z): 396.1 (M+H)+;
$^1$H-NMR (400.0 MHz, DMSO-D$_6$): δ=11.145 (5.8); 7.835 (3.0); 7.816 (3.7); 7.780 (1.1); 7.762 (3.1); 7.744 (2.5); 7.708 (2.4); 7.691 (3.7); 7.676 (1.9); 7.669 (3.9); 7.659 (4.1); 7.655 (3.9); 7.647 (2.2); 7.641 (2.9); 7.632 (1.6); 7.610 (1.5); 7.603 (1.5); 7.588 (1.8); 7.584 (2.0); 7.581 (2.0); 7.577 (1.8); 7.561 (1.4); 7.555 (1.4); 7.307 (1.2); 7.304 (1.1); 7.286 (2.0); 7.268 (1.2); 7.265 (1.1); 7.261 (1.0); 6.726 (8.9); 3.399 (0.4); 3.389 (0.4); 3.361 (2.2); 3.339 (401.4); 3.298 (0.3); 2.717 (0.7); 2.678 (1.0); 2.673 (0.8); 2.571 (0.7); 2.58 (56); 2.513 (121.0); 2.508 (156.2); 2.504 (114.3); 2.482 (6.2); 2.463 (6.0); 2.444 (2.0); 2.374 (0.7); 2.340 (0.8); 2.335 (1.0); 2.331 (0.8); 2.090 (0.6); 1.955 (0.7); 1.243 (0.5); 1.165 (7.7); 1.146 (16.0); 1.127 (7.4); 1.115 (0.4)

I-1-202:
HPLC-MS: log P=3.78; mass (m/z): 382.1 (M+H)+;
$^1$H-NMR (400.0 MHz, DMSO-D$_6$): δ=11.124 (4.3); 7.827 (2.4); 7.807 (3.1); 7.772 (1.0); 7.753 (2.5); 7.735 (2.1); 7.700 (1.9); 7.680 (3.1); 7.663 (2.0); 7.657 (2.9); 7.650 (3.4); 7.642 (2.4); 7.633 (2.8); 7.620 (1.1); 7.603 (1.0); 7.596 (1.1); 7.576 (1.6); 7.554 (1.1); 7.547 (1.0); 7.301 (0.9); 7.297 (0.9); 7.280 (1.6); 7.261 (0.8); 7.258 (0.8); 7.254 (0.8); 6.710 (6.2); 3.332 (91.6); 2.541 (26.7); 2.506 (38.9); 2.502 (48.6); 2.498 (35.5); 2.329 (0.3); 2.165 (16.0)

I-1-203:
HPLC-MS: log P=3.19; mass (m/z): 383.1 (M+H)+;
$^1$H-NMR (400.0 MHz, DMSO-D$_6$): δ=11.293 (4.8); 8.835 (2.4); 8.825 (2.5); 8.166 (2.3); 8.149 (2.5); 7.828 (2.1); 7.816 (2.1); 7.809 (2.0); 7.797 (1.9); 7.686 (1.0); 7.671 (1.1); 7.664 (2.1); 7.649 (2.1); 7.642 (1.2); 7.627 (1.1); 7.607 (1.1); 7.600 (1.1); 7.584 (1.3); 7.580 (1.6); 7.574 (1.3); 7.558 (1.1); 7.551 (1.1); 7.307 (0.8); 7.304 (0.9); 7.300 (0.8); 7.283 (1.6); 7.278 (1.5); 7.265 (0.8); 7.262 (0.8); 7.258 (0.7); 6.716 (6.5); 3.333 (82.7); 2.712 (0.5); 2.672 (0.3); 2.542 (109.4); 2.525 (1.5); 2.507 (37.6); 2.503 (47.7); 2.498 (34.5); 2.369 (0.5); 2.330 (0.4); 2.173 (16.0)

I-1-204:
HPLC-MS: log P=3.58; mass (m/z): 397.1 (M+H)+;
$^1$H-NMR (400.0 MHz, DMSO-D$_6$): δ=11.306 (5.6); 8.836 (3.0); 8.825 (2.9); 8.169 (2.8); 8.150 (3.0); 7.831 (2.6); 7.819 (2.6); 7.812 (2.4); 7.800 (2.3); 7.693 (1.2); 7.677 (1.4); 7.670 (2.5); 7.655 (2.5); 7.648 (1.5); 7.633 (1.3); 7.608 (1.3); 7.601 (1.4); 7.585 (1.6); 7.581 (1.9); 7.579 (1.9); 7.575 (1.7); 7.559 (1.3); 7.552 (1.3); 7.307 (1.0); 7.304 (1.1); 7.300 (1.0); 7.283 (1.9); 7.278 (1.8); 7.264 (0.9); 7.261 (1.0); 7.257 (0.9); 6.725 (8.7); 3.328 (102.1); 2.712 (0.7); 2.676 (0.4); 2.672 (0.6); 2.667 (0.5); 2.582 (0.3); 2.542 (153.4); 2.511 (34.2); 2.507 (65.4); 2.502 (85.3); 2.498 (62.1); 2.483 (7.4); 2.464 (6.0); 2.445 (2.0);

I-1-205:

HPLC-MS: mass (m/z): 336.1 (M+H)$^+$; $^1$H-NMR (601.6 MHz, DMSO-D$_6$): δ=11.203 (2.4); 8.144 (8.6); 8.140 (15.6); 8.136 (8.6); 7.803 (3.2); 7.793 (3.9); 7.788 (6.8); 7.779 (8.6); 7.773 (4.9); 7.766 (8.2); 7.755 (7.1); 7.741 (3.4); 7.605 (4.3); 7.601 (4.4); 7.590 (4.8); 7.586 (8.5); 7.581 (4.8); 7.571 (4.4); 7.566 (4.3); 7.420 (3.5); 7.416 (3.7); 7.402 (6.3); 7.387 (3.7); 7.383 (3.5); 7.290 (3.6); 7.288 (3.5); 7.277 (6.5); 7.275 (6.4); 7.273 (6.4); 7.262 (3.5); 7.259 (3.3); 7.224 (4.4); 7.221 (4.3); 7.210 (7.9); 7.207 (7.7); 7.196 (4.0); 7.193 (3.8); 6.933 (16.0); 6.929 (16.0); 6.687 (0.3); 5.359 (0.3); 5.325 (0.7); 3.366 (3290.1); 2.998 (0.5); 2.619 (3.5); 2.616 (4.8); 2.613 (3.5); 2.544 (8.8); 2.525 (8.2); 2.522 (10.6); 2.519 (11.4); 2.510 (255.3); 2.507 (544.6); 2.504 (751.0); 2.501 (558.6); 2.499 (264.8); 2.392 (3.4); 2.389 (4.7); 2.386 (3.4); 2.294 (0.5); 2.020 (0.8); 2.008 (1.4); 1.995 (1.1); 1.985 (0.7); 1.976 (0.7); 1.940 (0.4); 1.506 (1.1); 1.453 (0.5); 1.280 (0.9); 1.235 (5.5); 0.865 (1.0); 0.853 (2.5); 0.842 (1.2); 0.005 (2.7); 0.000 (80.1); −0.006 (2.7)

I-1-206:

HPLC-MS: log P=3.42; mass (m/z): 350.1 (M+H)$^+$; $^1$H-NMR (400.0 MHz, DMSO-D$_6$): δ=11.338 (4.4); 7.685 (1.0); 7.670 (1.1); 7.663 (2.2); 7.648 (2.2); 7.641 (1.2); 7.626 (1.1); 7.608 (1.1); 7.601 (1.2); 7.594 (0.7); 7.585 (1.4); 7.578 (2.6); 7.574 (2.2); 7.557 (2.7); 7.552 (2.0); 7.540 (1.1); 7.535 (1.3); 7.519 (0.6); 7.308 (0.8); 7.305 (0.9); 7.301 (0.8); 7.298 (0.8); 7.285 (1.5); 7.279 (1.4); 7.266 (0.8); 7.262 (0.8); 7.259 (0.7); 7.256 (0.7); 7.233 (0.7); 7.226 (3.9); 7.226 (3.9); 7.206 (5.4); 7.186 (3.2); 7.179 (0.7); 6.715 (6.3); 3.329 (65.2); 2.712 (0.5); 2.542 (115.3); 2.530 (0.7); 2.525 (1.2); 2.520 (1.6); 2.511 (17.7); 2.507 (34.9); 2.502 (45.2); 2.498 (32.2); 2.493 (15.3); 2.368 (0.5); 2.329 (0.4); 2.168 (16.0)

I-1-207:

HPLC-MS: log P=3.84; mass (m/z): 364.1 (M+H)$^+$; $^1$H-NMR (400.0 MHz, DMSO-D$_6$): δ=11.351 (5.0); 7.689 (1.1); 7.674 (1.3); 7.667 (2.4); 7.652 (2.4); 7.645 (1.4); 7.630 (1.3); 7.608 (1.3); 7.601 (1.4); 7.596 (0.9); 7.585 (1.7); 7.579 (3.0); 7.575 (2.7); 7.558 (3.5); 7.553 (2.0); 7.541 (1.3); 7.537 (1.5); 7.520 (0.7); 7.307 (1.0); 7.304 (1.0); 7.300 (1.0); 7.284 (1.7); 7.278 (1.7); 7.265 (0.9); 7.262 (0.9); 7.258 (0.9); 7.235 (0.8); 7.228 (4.3); 7.208 (6.1); 7.188 (3.6); 7.180 (0.7); 6.725 (8.4); 3.327 (84.3); 3.308 (0.4); 2.711 (0.6); 2.676 (0.4); 2.671 (0.5); 2.667 (0.3); 2.565 (0.6); 2.542 (146.2); 2.511 (28.7); 2.507 (55.8); 2.502 (72.0); 2.498 (51.9); 2.493 (25.2); 2.477 (5.6); 2.458 (5.5); 2.439 (1.9); 2.368 (0.6); 2.333 (0.4); 2329 (0.5); 2.324 (0.4); 1.154 (7.7); 1.135 (16.0); 1.116 (7.4)

I-1-208:

HPLC-MS: log P=3.63; mass (m/z): 392.0 (M+H)$^+$; $^1$H-NMR (400.0 MHz, DMSO-D$_6$): δ=11.020 (4.4); 7.691 (2.9); 7.672 (4.2); 7.657 (1.4); 7.650 (2.2); 7.635 (2.3); 7.628 (1.3); 7.613 (1.2); 7.603 (1.1); 7.597 (1.1); 7.581 (1.3); 7.574 (1.6); 7.570 (1.3); 7.554 (1.1); 7.547 (1.1); 7.510 (1.3); 7.505 (1.6); 7.491 (3.7); 7.486 (3.8); 7.477 (2.0); 7.475 (2.0); 7.459 (3.1); 7.456 (2.9); 7.440 (1.4); 7.438 (1.3); 7.410 (2.1); 7.405 (2.0); 7.391 (2.3); 7.386 (2.1); 7.373 (1.2); 7.367 (1.0); 7.305 (0.8); 7.302 (0.9); 7.295 (0.9); 7.281 (1.6); 7.275 (1.5); 7.262 (0.8); 7.259 (0.8); 7.255 (0.8); 6.723 (6.2); 3.328 (209.9); 3.298 (0.5); 3.292 (0.4); 2.711 (0.6); 2.676 (0.6); 2.671 (0.8); 2.666 (0.6); 2.559 (0.8); 2.541 (146.5); 2.524 (2.9); 2.511 (51.7); 2.506 (99.1); 2.502 (126.3); 2.497 (90.0); 2.493 (43.1); 2.367 (0.6); 2.333 (0.6); 2.329 (0.8); 2.324 (0.6); 2.164 (16.0); 2.059 (0.4); 1.236 (0.4); 0.000 (0.4)

I-1-209:

HPLC-MS: log P=2.95; mass (m/z): 378.0 (M+H)$^+$; $^1$H-NMR (400.0 MHz, CD$_3$CN): δ=9.270 (0.3); 9.223 (3.6); 7.952 (7.8); 7.946 (14.9); 7.940 (7.9); 7.765 (3.7); 7.750 (4.1); 7.743 (7.9); 7.728 (7.9); 7.720 (4.3); 7.705 (4.2); 7.694 (9.4); 7.692 (9.1); 7.675 (10.8); 7.672 (10.5); 7.596 (0.3); 7.589 (0.3); 7.564 (6.7); 7.560 (7.2); 7.545 (10.0); 7.541 (10.5); 7.482 (5.6); 7.479 (5.9); 7.463 (11.8); 7.460 (11.4); 7.444 (6.6); 7.441 (5.9); 7.411 (8.0); 7.407 (8.0); 7.391 (9.0); 7.387 (8.7); 7.373 (4.4); 7.368 (4.0); 7.206 (4.2); 7.199 (4.8); 7.183 (4.5); 7.176 (8.8); 7.169 (5.1); 7.154 (4.1); 7.147 (4.8); 7.123 (3.3); 7.119 (3.4); 7.116 (2.8); 7.113 (2.7); 7.103 (3.9); 7.100 (5.5); 7.096 (5.5); 7.093 (4.7); 7.080 (3.1); 7.077 (3.1); 7.074 (2.7); 7.070 (2.6); 6.992 (16.0); 6.985 (15.7); 2.207 (0.5); 2.199 (0.7); 2.191 (1.4); 2.174 (186.7); 2.170 (344.6); 2.168 (275.4); 2.167 (301.3); 2.133 (0.5); 2.120 (0.5); 2.114 (0.8); 2.108 (1.3); 2.101 (0.8); 2.095 (0.5); 1.964 (34.9); 1.958 (4.1); 1.952 (68.7); 1.946 (134.9); 1.940 (198.0); 1.934 (134.1); 1.928 (67.4); 1.921 (1.6); 1.915 (0.6); 1.781 (0.5); 1.775 (0.8); 1.769 (1.1); 1.762 (0.7); 1.756 (0.3); 1.270 (0.8); 0.000 (1.7)

I-1-210:

HPLC-MS: log P=2.89; mass (m/z): 395.0 (M+H)$^+$; $^1$H-NMR (400.0 MHz, DMSO-D$_6$): δ=11.199 (4.5); 8.471 (3.0); 8.466 (3.2); 8.459 (3.2); 8.454 (3.1); 7.959 (2.9); 7.954 (3.0); 7.940 (3.4); 7.935 (3.1); 7.680 (1.0); 7.664 (1.1); 7.657 (2.2); 7.642 (2.1); 7.635 (1.2); 7.620 (1.1); 7.607 (1.1); 7.600 (1.1); 7.584 (1.3); 7.580 (1.5); 7.578 (1.5); 7.574 (1.3); 7.556 (3.9); 7.551 (1.4); 7.544 (3.2); 7.538 (3.0); 7.526 (2.9); 7.308 (0.8); 7.305 (0.9); 7.301 (0.8); 7.298 (0.8); 7.298 (0.8); 7.284 (1.5); 7.279 (1.4); 7.265 (0.8); 7.262 (0.8); 7.258 (0.7); 6.728 (6.3); 3.328 (191.1); 2.995 (0.4); 2.711 (0.4); 2.711 (0.7); 2.676 (0.6); 2.671 (0.8); 2.667 (0.6); 2.572 (0.4); 2.565 (0.5); 2.541 (178.2); 2.524 (2.8); 2.511 (47.3); 2.507 (94.0); 2.502 (122.0); 2.497 (86.5); 2.493 (40.9); 2.367 (0.7); 2.333 (0.6); 2.329 (0.8); 2.324 (0.5); 2.171 (16.0); 1.235 (0.4); 0.000 (0.5)

I-1-211:

HPLC-MS: log P=2.91; mass (m/z): 334.0 (M+H)$^+$; $^1$H-NMR (400.0 MHz, CD$_3$CN): δ=9.251 (3.9); 7.952 (8.2); 7.945 (15.2); 7.939 (8.1); 7.766 (3.8); 7.751 (4.1); 7.743 (7.8); 7.728 (7.9); 7.720 (4.3); 7.706 (4.1); 7.607 (7.5); 7.603 (7.2); 7.588 (9.5); 7.584 (9.5); 7.524 (3.7); 7.520 (5.2); 7.504 (13.1); 7.501 (14.7); 7.496 (9.3); 7.492 (8.5); 7.479 (12.6); 7.474 (10.8); 7.459 (5.8); 7.454 (4.8); 7.438 (9.5); 7.433 (8.5); 7.419 (10.2); 7.415 (10.0); 7.401 (4.6); 7.397 (4.0); 7.388 (0.4); 7.205 (4.6); 7.198 (5.3); 7.183 (4.8); 7.176 (9.6); 7.169 (5.6); 7.154 (4.4); 7.147 (5.4); 7.122 (3.6); 7.119 (3.7); 7.116 (3.0); 7.112 (2.9); 7.102 (4.3); 7.099 (5.9); 7.096 (6.1); 7.092 (5.1); 7.089 (3.4); 7.080 (3.4); 7.076 (3.5); 7.073 (3.0); 7.069 (2.8); 6.995 (16.0); 6.988 (15.6); 5.447 (1.9); 4.068 (0.5); 4.050 (0.5); 2.213 (0.5); 2.203 (0.7); 2.175 (222.4); 2.170 (346.5); 2.169 (324.8); 2.147 (0.6); 2.133 (0.4); 2.120 (0.5); 2.114 (0.8); 2.108 (1.1); 2.101 (0.8); 2.095 (0.3); 1.976 (0.5); 1.972 (2.7); 1.965 (30.8); 1.958 (4.1); 1.953 (65.1); 1.946 (125.9); 1.940 (181.9); 1.934 (122.2); 1.928 (61.6); 1.921 (1.1); 1.915 (0.5); 1.781 (0.3); 1.775 (0.7); 1.769 (1.0); 1.763 (0.6); 1.756 (0.4); 1.436 (1.4); 1.268 (0.9); 1.221 (0.7); 1.204 (1.3); 1.186 (0.6); 0.000 (1.8)

I-1-212:

HPLC-MS: log P=3.58; mass (m/z): 348.1 (M+H)$^+$; $^1$H-NMR (400.0 MHz, DMSO-D$_6$): δ=11.037 (4.4); 7.671 (1.0); 7.656 (1.2); 7.649 (2.2); 7.634 (2.2); 7.627 (1.3);

7.612 (1.2); 7.603 (1.2); 7.596 (1.2); 7.580 (1.4); 7.576 (1.6); 7.574 (1.6); 7.570 (1.4); 7.554 (1.3); 7.547 (1.5); 7.541 (3.8); 7.537 (3.7); 7.522 (6.2); 7.518 (7.4); 7.498 (1.6); 7.493 (1.8); 7.479 (3.1); 7.474 (1.9); 7.460 (1.2); 7.455 (1.4); 7.437 (2.4); 7.434 (2.4); 7.419 (2.9); 7.416 (2.5); 7.400 (0.8); 7.397 (1.0); 7.305 (0.8); 7.302 (0.9); 7.298 (0.9); 7.295 (0.8); 7.281 (1.5); 7.276 (1.5); 7.262 (0.8); 7.259 (0.8); 7.255 (0.7); 7.252 (0.7); 6.725 (6.3); 3.331 (129.3); 2.711 (0.5); 2.671 (0.4); 2.569 (0.4); 2.541 (127.3); 2.524 (1.4); 2.511 (22.4); 2.506 (45.1); 2.502 (59.2); 2.497 (42.4); 2.493 (20.2); 2.367 (0.5); 2.329 (0.4); 2.324 (0.3); 2.164 (16.0)

I-1-213:

HPLC-MS: log P=3.99; mass (m/z): 362.1 (M+H)$^+$; $^1$H-NMR (400.0 MHz, DMSO-D$_6$): δ=11.051 (5.5); 7.676 (1.3); 7.661 (1.4); 7.654 (2.6); 7.639 (2.5); 7.632 (1.5); 7.617 (1.3); 7.603 (1.4); 7.596 (1.4); 7.580 (1.7); 7.577 (1.9); 7.574 (1.9); 7.570 (1.6); 7.554 (1.6); 7.547 (1.9); 7.542 (4.5); 7.523 (7.6); 7.520 (7.9); 7.499 (2.0); 7.495 (2.1); 7.481 (3.7); 7.476 (2.6); 7.462 (1.7); 7.457 (1.6); 7.450 (0.4); 7.440 (2.8); 7.436 (2.7); 7.421 (3.4); 7.418 (2.9); 7.402 (1.1); 7.400 (1.1); 7.305 (1.0); 7.301 (1.1); 7.297 (1.1); 7.281 (1.9); 7.275 (1.8); 7.262 (1.0); 7.259 (1.0); 7.255 (0.9); 6.739 (8.6); 3.331 (170.4); 3.310 (0.6); 2.712 (0.6); 2.675 (0.4); 2.671 (0.5); 2.667 (0.4); 2.541 (144.9); 2.511 (31.7); 2.507 (61.0); 2.502 (78.4); 2.498 (56.3); 2.493 (28.6); 2.474 (5.9); 2.455 (5.8); 2.437 (1.9); 2.368 (0.6); 2.334 (0.4); 2.32934 (0.5); 2.3294 (0.4); 1.156 (7.8); 1.138 (16.0); 1.119 (7.3); 0.998 (0.5)

I-1-214:

HPLC-MS: log P=3.73; mass (m/z): 440.1 (M+H)$^+$; $^1$H-NMR (400.0 MHz, DMSO-D$_6$): δ=10.966 (4.7); 7.912 (3.2); 7.894 (3.4); 7.675 (1.0); 7.660 (1.1); 7.653 (2.1); 7.638 (2.1); 7.631 (1.4); 7.616 (1.1); 7.601 (1.1); 7.595 (1.1); 7.578 (1.4); 7.574 (1.6); 7.552 (1.1); 7.545 (1.1); 7.488 (1.0); 7.486 (1.0); 7.469 (2.9); 7.451 (2.8); 7.449 (2.7); 7.438 (3.5); 7.433 (4.0); 7.419 (1.7); 7.414 (1.5); 7.304 (0.9); 7.301 (0.9); 7.297 (0.9); 7.280 (1.7); 7.261 (0.8); 7.258 (0.8); 7.258 (0.9); 7.254 (0.9); 7.219 (1.6); 7.215 (1.6); 7.200 (2.2); 7.196 (2.2); 7.182 (1.5); 7.177 (1.4); 6.727 (6.4); 3.332 (58.6); 2.711 (0.4); 2.541 (83.7); 2.524 (0.8); 2.511 (13.1); 2.506 (25.4); 2.502 (32.7); 2.497 (23.4); 2.493 (11.2); 2.368 (0.4); 2.167 (16.0); 2.120 (0.4); 2.067 (0.7)

I-1-215:

HPLC-MS: log P=4.15; mass (m/z): 454.0 (M+H)$^+$; $^1$H-NMR (400.0 MHz, DMSO-D$_6$): δ=10.985 (6.3); 7.921 (4.2); 7.901 (4.5); 7.688 (1.2); 7.673 (1.5); 7.666 (2.6); 7.651 (2.6); 7.644 (1.7); 7.629 (1.5); 7.610 (1.5); 7.603 (1.6); 7.583 (2.4); 7.581 (2.4); 7.561 (1.4); 7.554 (1.5); 7.496 (1.4); 7.477 (4.0); 7.459 (3.7); 7.444 (4.4); 7.440 (5.0); 7.425 (2.2); 7.421 (1.8); 7.307 (1.3); 7.304 (1.4); 7.287 (2.4); 7.265 (1.3); 7.261 (1.2); 7.227 (2.0); 7.223 (2.1); 7.208 (3.1); 7.205 (3.1); 7.190 (1.7); 7.185 (1.6); 6.743 (9.2); 3.338 (262.3); 2.717 (0.7); 2.677 (0.8); 2.547 (136.3); 2.512 (96.7); 2.508 (122.2); 2.504 (95.1); 2.482 (7.1); 2.463 (6.5); 2.445 (2.3); 2.374 (0.7); 2.335 (0.8); 2.091 (0.6); 2.026 (0.7); 1.241 (0.4); 1.168 (7.9); 1.149 (16.0); 1.131 (7.6); 1.114 (0.5)

I-1-217:

HPLC-MS: log P=3.06; mass (m/z): 383.0 (M+H)$^+$; $^1$H-NMR (400.0 MHz, DMSO-D$_6$): δ=11.451 (6.6); 8.316 (0.4); 8.254 (3.6); 8.248 (6.4); 8.242 (3.4); 8.156 (2.6); 8.134 (3.5); 8.115 (2.6); 7.984 (0.6); 7.965 (0.6); 7.961 (0.6); 7.942 (0.6); 7.932 (0.7); 7.925 (1.3); 7.918 (0.7); 7.843 (3.6); 7.824 (4.6); 7.790 (1.3); 7.772 (3.6); 7.754 (3.2); 7.721 (2.8); 7.701 (3.5); 7.685 (5.4); 7.667 (3.0); 6.979 (7.7); 6.973 (7.6); 5.842 (1.5); 5.836 (1.4); 5.757 (9.3); 5.337 (1.8); 3.322 (161.8); 2.679 (0.6); 2.675 (1.3); 2.671 (1.7); 2.666 (1.2); 2.524 (5.3); 2.510 (99.1); 2.506 (193.9); 2.502 (251.8); 2.497 (182.5); 2.493 (88.3); 2.456 (0.6); 2.432 (15.9); 2.425 (16.0); 2.367 (3.4); 2.360 (3.4); 2.337 (0.7); 2.333 (1.3); 2.328 (1.7); 2.324 (1.2); 1.989 (1.0); 1.336 (1.0); 1.298 (0.6); 1.259 (0.9); 1.249 (1.2); 1.235 (0.6); 1.175 (0.5); 0.008 (2.0); 0.000 (54.6); −0.008 (1.9)

I-1-218:

HPLC-MS: log P=2.28; mass (m/z): 335.1 (M+H)$^+$; $^1$H-NMR (400.0 MHz, CD$_3$CN): δ=9.462 (3.5); 8.505 (8.8); 8.500 (9.4); 8.493 (9.4); 8.488 (9.3); 8.093 (8.5); 8.087 (15.6); 8.081 (8.6); 7.995 (9.6); 7.990 (9.7); 7.976 (10.4); 7.971 (10.2); 7.593 (3.7); 7.585 (4.0); 7.577 (4.2); 7.569 (7.4); 7.561 (4.2); 7.553 (3.9); 7.545 (3.8); 7.475 (11.1); 7.463 (11.2); 7.456 (10.7); 7.444 (10.1); 7.371 (3.8); 7.359 (4.0); 7.348 (4.8); 7.342 (4.4); 7.336 (5.0); 7.330 (4.2); 7.319 (4.6); 7.307 (4.5); 7.105 (2.6); 7.097 (4.8); 7.088 (3.4); 7.086 (3.6); 7.082 (3.2); 7.077 (5.5); 7.074 (4.9); 7.069 (3.4); 7.065 (3.1); 7.063 (3.0); 7.055 (4.0); 7.046 (2.3); 7.028 (16.0); 7.022 (15.8); 5.449 (0.4); 4.068 (0.4); 4.050 (0.4); 2.464 (0.3); 2.175 (115.2); 2.115 (0.4); 2.109 (0.5); 2.103 (0.3); 1.972 (2.1); 1.966 (2.4); 1.960 (3.5); 1.954 (31.8); 1.948 (59.8); 1.942 (84.2); 1.935 (57.9); 1.929 (29.6); 1.776 (0.9); 1.770 (0.5); 1.764 (0.3); 1.436 (0.7); 1.372 (5.4); 1.340 (0.7); 1.284 (1.0); 1.276 (6.2); 1.221 (0.5); 1.204 (0.9); 1.186 (0.5); 0.146 (0.6); 0.008 (5.5); 0.000 (139.7); −0.009 (5.6); −0.150 (0.6)

I-1-219:

HPLC-MS: log P=3.25; mass (m/z): 431.9 (M+H)$^+$; $^1$H-NMR (400.0 MHz, DMSO-D$_6$): δ=11.040 (6.0); 8.227 (3.4); 8.227 (3.4); 8.221 (6.5); 8.214 (3.5); 7.814 (7.3); 7.800 (7.8); 7.655 (1.5); 7.647 (1.6); 7.639 (1.7); 7.631 (2.8); 7.623 (1.7); 7.616 (1.6); 7.608 (1.5); 7.581 (1.5); 7.569 (1.6); 7.558 (1.9); 7.553 (1.8); 7.546 (1.9); 7.541 (1.7); 7.530 (1.7); 7.517 (1.7); 7.411 (5.9); 7.397 (5.6); 7.281 (1.0); 7.273 (1.8); 7.262 (1.5); 7.258 (1.3); 7.253 (2.2); 7.250 (1.9); 7.245 (1.4); 7.241 (1.2); 7.231 (1.5); 7.222 (0.8); 6.990 (3.6); 6.984 (3.6); 5.757 (16.0); 3.338 (10.3); 2.512 (11.5); 2.507 (14.9); 2.503 (11.0); 1.992 (0.4); 1.396 (1.3)

I-1-220:

HPLC-MS: log P=3.00; mass (m/z): 335.0 (M+H)$^+$; $^1$H-NMR (400.0 MHz, CD$_3$CN): δ=10.173 (3.4); 8.614 (7.7); 8.611 (8.1); 8.603 (8.1); 8.600 (8.1); 8.113 (6.9); 8.106 (12.9); 8.100 (7.0); 8.000 (7.2); 7.997 (7.5); 7.979 (8.1); 7.976 (8.1); 7.664 (3.2); 7.656 (3.4); 7.648 (3.5); 7.640 (6.4); 7.632 (3.6); 7.624 (3.4); 7.616 (3.3); 7.578 (8.1); 7.567 (8.1); 7.558 (7.6); 7.546 (7.3); 7.425 (0.5); 7.419 (0.5); 7.376 (3.0); 7.364 (3.2); 7.353 (3.9); 7.347 (3.5); 7.341 (4.0); 7.335 (3.4); 7.324 (3.7); 7.312 (3.6); 7.240 (0.4); 7.235 (0.4); 7.172 (0.4); 7.165 (0.4); 7.102 (2.2); 7.093 (4.2); 7.082 (16.0); 7.076 (15.6); 7.066 (3.1); 7.061 (2.7); 7.051 (3.2); 7.043 (1.7); 5.448 (1.0); 2.468 (0.4); 2.463 (0.5); 2.459 (0.4); 2.149 (379.2); 2.121 (2.2); 2.114 (2.0); 2.108 (2.2); 2.102 (1.5); 2.096 (0.9); 1.965 (12.1); 1.958 (17.5); 1.953 (121.2); 1.947 (224.8); 1.941 (311.8); 1.934 (217.2); 1.928 (114.5); 1.781 (0.7); 1.775 (1.3); 1.769 (1.8); 1.763 (1.3); 1.757 (0.7); 1.372 (11.0); 1.340 (1.2); 1.285 (1.9); 1.276 (11.2); 1.269 (3.1); 1.216 (1.7); 0.881 (0.5); 0.858 (0.4); 0.146 (2.0); 0.008 (19.1); 0.000 (421.4); −0.008 (20.7); −0.150 (2.0)

I-1-221:

HPLC-MS: log P=3.57; mass (m/z): 403.1 (M+H)$^+$; $^1$H-NMR (400.0 MHz, DMSO-D$_6$): δ=11.061 (8.8); 8.237 (5.0); 8.230 (9.8); 8.224 (5.1); 7.809 (13.3); 7.796 (13.7); 7.656 (2.3); 7.648 (2.5); 7.640 (2.6); 7.632 (4.5); 7.624

(2.5); 7.617 (2.5); 7.609 (2.3); 7.587 (2.1); 7.575 (2.3); 7.564 (2.7); 7.559 (2.5); 7.552 (2.7); 7.546 (2.5); 7.536 (2.5); 7.523 (2.4); 7.293 (2.0); 7.286 (16.0); 7.273 (15.3); 7.265 (3.6); 7.262 (3.0); 7.257 (2.0); 7.253 (1.8); 7.251 (1.7); 7.242 (2.2); 7.234 (1.1); 6.937 (9.7); 6.930 (9.7); 5.757 (1.4); 3.326 (12.4); 2.673 (0.4); 2.512 (24.2); 2.508 (46.1); 2.503 (59.5); 2.499 (43.300099 (43.3); 2.495 (21.5); 2.330 (0.4); 1.232 (0.8); 1.181 (0.4); 0.000 (3.7)

I-1-222:
HPLC-MS: log P=3.14; mass (m/z): 415.9 (M+H)$^+$; $^1$H-NMR (400.0 MHz, DMSO-D$_6$): δ=10.963 (7.2); 8.316 (0.6); 8.224 (4.4); 8.218 (9.1); 8.211 (4.6); 7.945 (11.9); 7.940 (12.1); 7.666 (1.9); 7.657 (2.1); 7.650 (2.2); 7.642 (4.0); 7.634 (2.2); 7.626 (2.2); 7.618 (2.0); 7.584 (1.8); 7.572 (2.0); 7.561 (2.2); 7.555 (2.1); 7.549 (2.3); 7.543 (2.1); 7.532 (2.2); 7.520 (2.1); 7.284 (1.3); 7.276 (2.4); 7.267 (1.6); 7.265 (1.8); 7.261 (1.5); 7.256 (2.8); 7.253 (2.4); 7.248 (1.6); 7.245 (1.4); 7.242 (1.4); 7.234 (1.9); 7.225 (0.9); 6.931 (10.2); 6.922 (16.0); 6.918 (13.2); 3.324 (151.7); 2.676 (1.0); 2.671 (1.4); 2.667 (1.0); 2.662 (0.5); 2.525 (3.6); 2.520 (5.6); 2.511 (79.5); 2.507 (163.0); 2.502 (215.9); 2.498 (156.7); 2.493 (76.2); 2.338 (0.5); 2.333 (1.0); 2.329 (1.4); 2.324 (1.0); 1.398 (0.4); 1.135 (0.5); 1.117 (1.3); 1.099 (0.7); 0.008 (1.1); 0.000 (35.4); −0.009 (1.3)

I-1-223:
HPLC-MS: log P=2.71; mass (m/z): 372.1 (M+H)$^+$; $^1$H-NMR (400.0 MHz, CD$_3$CN): δ=8.672 (1.2); 8.068 (2.8); 8.062 (5.3); 8.055 (2.8); 7.625 (1.4); 7.617 (1.4); 7.610 (1.4); 7.602 (2.7); 7.594 (1.4); 7.586 (1.4); 7.578 (1.4); 7.426 (0.4); 7.420 (0.4); 7.368 (1.3); 7.355 (1.4); 7.345 (1.6); 7.339 (1.4); 7.332 (1.6); 7.327 (1.4); 7.316 (1.5); 7.304 (1.5); 7.235 (3.4); 7.101 (6.6); 7.090 (1.7); 7.082 (1.1); 7.079 (1.1); 7.076 (1.0); 7.071 (1.8); 7.067 (1.5); 7.062 (1.1); 7.059 (0.9); 7.056 (0.9); 7.048 (1.3); 7.040 (0.7); 6.967 (3.3); 6.942 (5.4); 6.936 (5.3); 5.448 (2.3); 3.804 (15.2); 3.802 (16.0); 3.788 (0.3); 3.408 (0.3); 2.172 (5.9); 2.121 (0.4); 2.115 (0.4); 2.109 (0.4); 2.102 (0.3); 1.965 (1.3); 1.959 (1.7); 1.953 (13.0); 1.947 (24.0); 1.941 (33.2); 1.935 (22.7); 1.929 (11.6); 1.372 (5.7); 1.340 (0.8); 1.285 (1.3); 1.276 (6.5); 1.268 (1.2); 0.008 (1.7); 0.000 (42.7); −0.009 (1.6)

I-1-224:
HPLC-MS: log P=2.72; mass (m/z): 369.0 (M+H)$^+$; $^1$H-NMR (400.0 MHz, CD$_3$CN): δ=9.424 (5.5); 8.163 (13.6); 8.103 (3.3); 8.097 (3.6); 8.084 (6.0); 8.078 (6.2); 8.064 (3.5); 8.058 (3.5); 7.980 (12.1); 7.829 (7.3); 7.809 (11.2); 7.757 (2.7); 7.740 (7.6); 7.721 (9.4); 7.700 (9.1); 7.687 (16.0); 7.671 (7.7); 7.060 (13.7); 7.054 (12.7); 5.449 (13.4); 2.164 (73.5); 2.114 (0.5); 2.109 (0.5); 1.972 (2.2); 1.953 (26.4); 1.947 (44.4); 1.941 (55.6); 1.935 (39.2); 1.930 (21.0); 1.769 (0.4); 1.372 (4.5); 1.311 (0.7); 1.294 (0.8); 1.276 (4.6); 1.221 (0.4); 1.204 (0.7); 1.186 (0.4); 0.000 (13.7)

I-1-225:
HPLC-MS: log P=2.59; mass (m/z): 335.0 (M+H)$^+$; $^1$H-NMR (400.0 MHz, CD$_3$CN): δ=9.382 (3.2); 8.168 (5.8); 8.162 (10.4); 8.155 (6.2); 8.105 (2.4); 8.098 (2.8); 8.085 (4.1); 8.079 (4.5); 8.066 (2.5); 8.059 (2.7); 7.982 (6.3); 7.975 (10.4); 7.969 (6.1); 7.602 (6.0); 7.583 (7.8); 7.526 (2.2); 7.522 (3.4); 7.506 (10.3); 7.502 (16.0); 7.498 (8.6); 7.484 (8.4); 7.480 (8.1); 7.465 (3.5); 7.460 (3.3); 7.442 (6.4); 7.437 (6.0); 7.423 (7.2); 7.419 (7.2); 7.406 (3.1); 7.401 (3.1); 7.082 (9.8); 7.076 (10.0); 5.447 (1.5); 2.165 (37.0); 2.110 (0.4); 2.088 (0.6); 1.966 (1.8); 1.960 (2.2); 1.955 (16.0); 1.948 (30.2); 1.942 (42.2); 1.936 (29.7); 1.930 (15.7); 0.008 (0.5); 0.000 (13.2); −0.008 (0.7)

I-1-226:
HPLC-MS: log P=3.21; mass (m/z): 417.0 (M+H)$^+$; $^1$H-NMR (400.0 MHz, CD$_3$CN): δ=9.373 (2.7); 8.428 (4.0); 8.424 (4.3); 8.416 (4.4); 8.412 (4.2); 8.286 (4.2); 8.282 (4.1); 8.267 (4.5); 8.263 (4.2); 7.675 (7.4); 7.669 (7.5); 7.589 (7.8); 7.587 (7.6); 7.568 (16.0); 7.512 (6.2); 7.494 (4.9); 7.489 (4.2); 7.479 (4.5); 7.470 (4.1); 7.467 (4.7); 7.460 (4.3); 7.448 (3.8); 7.426 (0.4); 7.000 (7.5); 6.994 (7.4); 5.449 (0.9); 4.067 (0.6); 4.049 (0.6); 2.163 (40.7); 1.972 (2.9); 1.965 (1.7); 1.954 (13.5); 1.947 (24.6); 1.941 (33.7); 1.935 (24.2); 1.929 (13.2); 1.436 (5.6); 1.372 (3.8); 1.308 (0.3); 1.291 (0.4); 1.276 (4.0); 1.221 (0.8); 1.203 (1.5); 1.186 (0.8); 0.00 (8.2)

I-1-227 see Synthesis Example 41
I-1-228 see Synthesis Example 28
I-1-229 see Synthesis Example 26
I-1-230 see Synthesis Example 27

I-1-231:
HPLC-MS: log P=2.89; mass (m/z): 372.1 (M+H)$^+$; $^1$H-NMR (601.6 MHz, DMSO-D$_6$): δ=11.473 (2.7); 8.113 (3.0); 8.109 (2.8); 7.977 (1.0); 7.880 (2.6); 7.784 (1.2); 7.648 (0.4); 7.638 (0.9); 7.634 (0.8); 7.624 (1.6); 7.613 (0.9); 7.609 (1.0); 7.599 (0.4); 7.408 (2.7); 7.394 (4.9); 7.380 (2.4); 6.909 (2.4); 6.906 (2.4); 3.401 (999.7); 3.400 (1251.1); 3.395 (262.8); 3.394 (254.6); 3.002 (1.3); 2.625 (0.6); 2.552 (43.7); 2.534 (0.9); 2.531 (1.1); 2.528 (1.1); 2.516 (66.1); 2.513 (92.4); 2.510 (68.4); 2.507 (33.5); 2.397 (0.6); 2.284 (16.0); 1.265 (0.3); 1.242 (1.8); 0.861 (0.4)

I-1-232:
HPLC-MS: log P=2.10; mass (m/z): 318.1 (M+H)$^+$; $^1$H-NMR (400.0 MHz, CD$_3$CN): δ=9.141 (0.7); 7.743 (1.7); 7.740 (1.6); 7.737 (1.8); 7.546 (0.3); 7.531 (0.6); 7.525 (0.6); 7.515 (0.4); 7.509 (1.3); 7.503 (0.5); 7.494 (0.6); 7.488 (0.8); 7.472 (0.4); 7.218 (0.5); 7.213 (2.1); 7.200 (0.4); 7.192 (3.5); 7.183 (0.6); 7.171 (1.8); 7.162 (0.4); 6.968 (2.5); 6.962 (2.5); 6.663 (4.3); 4.051 (16.0); 2.214 (14.4); 2.181 (19.9); 1.973 (0.6); 1.966 (0.4); 1.959 (0.5); 1.954 (4.7); 1.947 (9.0); 1.941 (12.7); 1.935 (9.0); 1.929 (4.9); 1.436 (1.0); 1.372 (1.1); 1.276 (1.2); 0.008 (0.7); 0.000 (16.5); −0.008 (1.0)

I-1-233:
HPLC-MS: log P=2.23; mass (m/z): 363.1 (M+H)$^+$; $^1$H-NMR (601.6 MHz, DMSO-D$_6$): δ=11.869 (2.2); 8.142 (1.6); 8.138 (1.5); 7.634 (0.5); 7.630 (0.5); 7.624 (0.4); 7.620 (0.9); 7.616 (0.4); 7.610 (0.5); 7.606 (0.6); 7.411 (1.6); 7.397 (2.8); 7.384 (1.3); 6.982 (2.9); 6.977 (2.9); 3.858 (16.0); 3.350 (162.4); 2.552 (14.7); 2.531 (0.4); 2.519 (10.8); 2.516 (24.2); 2.513 (34.6); 2.510 (25.1); 2.507 (11.7); 2.458 (14.3)

I-1-234:
HPLC-MS: log P=2.03; mass (m/z): 363.1 (M+H)$^+$; $^1$H-NMR (400.0 MHz, DMSO-D$_6$): δ=11.356 (2.8); 8.316 (0.6); 8.071 (2.1); 8.065 (2.1); 7.619 (0.7); 7.614 (0.6); 7.598 (1.3); 7.582 (0.6); 7.576 (0.9); 7.561 (0.4); 7.398 (2.2); 7.376 (3.8); 7.356 (1.8); 6.915 (3.3); 6.909 (3.3); 5.756 (1.8); 3.867 (16.0); 3.324 (234.7); 2.675 (1.3); 2.671 (1.8); 2.666 (1.3); 2.607 (14.8); 2.541 (0.9); 2.524 (4.6); 2.510 (106.6); 2.506 (210.0); 2.502 (272.4); 2.497 (195.8); 2.440 (0.4); 2.333 (1.3); 2.328 (1.8); 2.324 (1.3); 0.146 (1.0); 0.008 (8.2); 0.000 (205.9); −0.008 (7.5); −0.150 (1.0)

I-1-235:
HPLC-MS: log P=2.76; mass (m/z): 444.0 (M+H)$^+$; $^1$H-NMR (601.6 MHz, DMSO-D$_6$): δ=11.302 (4.6); 8.106 (3.7); 7.648 (0.6); 7.638 (1.3); 7.634 (1.3); 7.623 (10.9); 7.613 (1.5); 7.610 (1.5); 7.599 (0.6); 7.409 (3.8); 7.395 (6.8); 7.381 (3.3); 6.947 (4.2); 6.943 (4.2); 4.287 (1.8); 4.275 (5.5); 4.263 (5.5); 4.251 (1.9); 3.371 (0.7); 3.347 (1213.1); 2.625 (1.0); 2.552 (5.7); 2.534 (1.4); 2.531 (1.8);

2.528 (1.9); 2.519 (53.5); 2.516 (114.3); 2.513 (158.9); 2.510 (116.8); 2.507 (56.9); 2.397 (1.0); 1.356 (7.5); 1.344 (16.0); 1.332 (7.6); 1.246 (0.7); 0.011 (0.7)

I-1-236:

HPLC-MS: log P=1.93; mass (m/z): 305.0 (M+H)$^+$; $^1$H-NMR (400.0 MHz, DMSO-D$_6$): δ=11.049 (1.4); 8.316 (0.5); 8.139 (5.0); 8.100 (1.8); 8.094 (1.8); 7.639 (0.6); 7.633 (0.5); 7.624 (0.4); 7.618 (1.2); 7.612 (0.4); 7.602 (0.5); 7.597 (0.8); 7.581 (0.3); 7.407 (2.0); 7.386 (3.3); 7.366 (1.5); 6.895 (2.7); 6.888 (2.7); 4.174 (16.0); 3.324 (380.4); 2.675 (1.7); 2.670 (2.4); 2.666 (1.7); 2.661 (0.8); 2.541 (1.8); 2.524 (7.0); 2.510 (134.1); 2.506 (270.62501 (357.5); 2.501 (357.5); 2.49 (259.9); 2.492 (125.8); 2.337 (0.8); 2.333 (1.7); 2.328 (2.3); 2.324 (1.7); 2.074 (4.9); 1.258 (0.4); 0.146 (0.4); 0.008 (2.9); 0.000 (86.4); −0.008 (2.7); −0.150 (0.4)

I-1-237:

HPLC-MS: log P=3.84; mass (m/z): 490.1 (M+H)$^+$; $^1$H-NMR (601.6 MHz, DMSO-D$_6$): δ=12.018 (3.8); 8.157 (2.7); 8.154 (2.6); 7.652 (0.4); 7.641 (0.8); 7.638 (0.8); 7.627 (1.4); 7.616 (0.8); 7.613 (0.8); 7.602 (0.4); 7.416 (2.4); 7.401 (4.3); 7.388 (2.0); 6.953 (4.1); 6.949 (3.9); 4.017 (16.0); 3.884 (0.5); 3.349 (1067.7); 2.625 (0.8); 2.553 (18.2); 2.534 (1.4); 2.531 (1.8); 2.516 (99.1); 2.513 (128.0); 2.510 (91.0); 2.397 (0.8); 1.246 (0.5); 0.011 (0.8)

I-1-238:

HPLC-MS: log P=2.99; mass (m/z): 440.0 (M+H)$^+$; $^1$H-NMR (400.0 MHz, DMSO-D$_6$): δ=11.589 (5.2); 8.083 (3.7); 8.080 (3.3); 8.077 (3.7); 7.638 (0.6); 7.622 (1.3); 7.616 (1.0); 7.606 (0.9); 7.601 (2.6); 7.595 (1.0); 7.584 (1.1); 7.579 (1.7); 7.564 (0.8); 7.408 (0.7); 7.399 (4.4); 7.378 (7.3); 7.357 (3.4); 6.876 (7.0); 6.870 (6.9); 5.757 (0.4); 4.126 (16.0); 4.092 (0.9); 4.021 (0.4); 3.325 (34.8); 2.982 (2.1); 2.829 (2.1); 2.672 (0.3); 2.525 (1.2); 2.520 (1.8); 2.512 (19.3); 2.507 (38.5); 2.503 (50.6); 2.498 (36.4); 2.493 (17.3); 1.989 (0.7); 1.259 (0.4); 1.236 (2.4); 1.175 (0.4); 0.000 (0.3)

I-1-239:

HPLC-MS: log P=2.50; mass (m/z): 348.1 (M+H)$^+$; $^1$H-NMR (400.0 MHz, DMSO-D$_6$): δ=11.094 (3.0); 8.230 (2.8); 8.225 (2.9); 8.055 (2.2); 8.050 (2.2); 7.826 (3.4); 7.821 (3.3); 7.626 (0.7); 7.621 (0.6); 7.610 (0.5); 7.604 (1.4); 7.589 (0.7); 7.583 (0.9); 7.567 (0.4); 7.404 (2.2); 7.382 (3.9); 7.362 (1.7); 6.896 (3.4); 6.890 (3.4); 5.757 (6.0); 3.975 (16.0); 3.328 (95.8); 2.675 (0.7); 2.671 (0.7); 2.541 (0.4); 2.506 (80.6); 2.502 (104.7); 2.498 (77.1); 2.333 (0.5); 2.329 (0.7); 2.324 (0.5); 0.008 (0.9); 0.000 (22.6); −0.008 (1.0)

I-1-240:

HPLC-MS: log P=2.52; mass (m/z): 371.1 (M+H)$^+$; $^1$H-NMR (400.0 MHz, DMSO-D$_6$): δ=10.607 (3.5); 7.997 (2.5); 7.994 (2.3); 7.991 (2.4); 7.798 (2.7); 7.793 (2.7); 7.624 (0.4); 7.608 (0.9); 7.602 (0.7); 7.592 (0.6); 7.587 (1.7); 7.581 (0.6); 7.570 (0.8); 7.565 (1.1); 7.550 (0.5); 7.393 (3.3); 7.389 (5.1); 7.368 (4.7); 7.347 (2.2); 7.341 (0.6); 6.895 (4.3); 6.889 (4.3); 4.101 (0.6); 4.088 (0.6); 3.688 (16.0); 3.327 (7.0); 3.178 (3.0); 3.165 (2.9); 2.525 (0.4); 2.512 (6.2); 2.507 (12.1); 2.503 (15.9); 2.498 (11.6); 2.494 (5.6); 1.250 (0.4)

I-1-241:

HPLC-MS: log P=1.90; mass (m/z): 349.1 (M+H)$^+$; $^1$H-NMR (400.0 MHz, DMSO-D$_6$): δ=11.412 (2.9); 8.894 (5.3); 8.083 (2.2); 8.078 (2.1); 7.636 (0.3); 7.620 (0.7); 7.615 (0.6); 7.599 (1.4); 7.593 (0.5); 7.583 (0.7); 7.578 (0.9); 7.562 (0.6); 7.400 (2.3); 7.379 (3.9); 7.358 (1.8); 6.927 (3.5); 6.921 (3.3); 5.757 (1.1); 3.945 (16.0); 3.326 (107.5); 2.675 (0.5); 2.671 (0.7); 2.667 (0.5); 2.541 (0.4); 2.506 (83.8); 2.502 (103.4); 2.498 (72.2); 2.333 (0.5); 2.329 (0.7); 2.324 (0.5); 0.146 (0.3); 0.000 (74.5); −0.008 (2.8); −0.149 (0.4)

I-1-242:

HPLC-MS: log P=1.81; mass (m/z): 349.1 (M+H)$^+$; $^1$H-NMR (400.0 MHz, DMSO-D$_6$): δ=11.214 (3.1); 8.316 (0.6); 8.082 (5.3); 8.073 (2.4); 8.067 (2.4); 7.634 (0.4); 7.618 (0.8); 7.612 (0.7); 7.602 (0.5); 7.596 (1.5); 7.591 (0.6); 7.580 (0.7); 7.575 (1.0); 7.559 (0.4); 7.397 (2.6); 7.376 (4.3); 7.355 (2.0); 6.925 (3.9); 6.919 (3.9); 5.756 (0.4); 3.926 (16.0); 3.323 (161.8); 2.675 (1.0); 2.671 (1.4); 2.666 (1.0); 2.541 (0.7); 2.524 (3.2); 2.519 (5.2); 2.511 (79.2); 2.506 (163.8); 2.502 (217.8); 2.497 (156.8); 2.493 (75.7); 2.333 (1.0); 2.328 (1.4); 2.324 (1.0); 0.146 (0.7); 0.008 (5.3); 0.000 (156.3); −0.009 (5.9); −0.150 (0.7)

I-1-243:

HPLC-MS: log P=1.80; mass (m/z): 385.0 (M+H)$^+$; $^1$H-NMR (400.0 MHz, DMSO-D$_6$): δ=11.619 (12.2); 11.093 (0.4); 11.082 (1.0); 8.623 (8.5); 8.607 (8.6); 8.490 (1.2); 8.316 (0.9); 8.097 (9.2); 8.092 (9.2); 7.890 (0.3); 7.825 (6.9); 7.85 (6.9); 7.05 (10.1); 7.744 (0.6); 7.730 (5.4); 7.713 (6.6); 7.694 (3.7); 7.665 (0.4); 7.638 (1.3); 7.622 (2.8); 7.617 (2.6); 7.601 (5.6); 7.595 (2.5); 7.585 (2.8); 7.579 (3.7); 7.564 (1.6); 7.443 (0.7); 7.422 (1.3); 7.402 (9.8); 7.381 (16.0); 7.360 (7.2); 7.261 (0.4); 7.240 (0.5); 6.905 (13.8); 6.899 (13.6); 6.075 (0.4); 6.069 (0.4); 3.322 (135.5); 2.675 (2.2); 2.671 (2.9); 2.666 (2.2); 2.506 (347.5); 2.502 (443.3); 2.497 (328.0); 2.333 (2.2); 2.328 (2.8); 2.324 (2.1); 0.146 (0.5); 0.008 (5.1); 0.000 (108.9); −0.008 (5.0); −0.150 (0.5)

I-1-244:

HPLC-MS: log P=3.58; mass (m/z): 380.1 (M+H)$^+$; $^1$H-NMR (601.6 MHz, DMSO-D$_6$): δ=11.415 (5.6); 8.107 (4.4); 8.104 (4.5); 7.700 (9.1); 7.649 (0.6); 7.638 (1.4); 7.634 (1.3); 7.624 (2.5); 7.614 (1.4); 7.610 (1.6); 7.600 (0.7); 7.410 (4.1); 7.396 (7.3); 7.382 (3.5); 6.948 (5.3); 6.944 (5.4); 4.550 (0.9); 4.539 (1.5); 4.525 (1.5); 4.515 (1.0); 3.345 (469.7); 2.625 (0.6); 2.552 (11.6); 2.534 (0.9); 2.531 (1.2); 2.528 (1.2); 2.519 (32.6); 2.516 (72.2); 2.513 (101.6); 2.510 (75.7); 2.507 (37.7); 2.397 (0.6); 1.879 (0.9); 1.866 (1.3); 1.856 (1.5); 1.841 (1.7); 1.829 (1.3); 1.817 (0.4); 1.765 (0.3); 1.753 (1.2); 1.744 (1.5); 1.741 (1.5); 1.731 (1.9); 1.718 (1.3); 1.709 (0.9); 1.429 (13.0); 1.418 (13.1); 1.246 (0.5); 0.737 (7.5); 0.724 (16.0); 0.712 (7.4); 0.010 (0.7)

I-1-245:

HPLC-MS: log P=3.47; mass (m/z): 472.1 (M+H)$^+$; $^1$H-NMR (601.6 MHz, DMSO-D$_6$): δ=11.343 (6.8); 8.102 (4.9); 8.099 (4.9); 7.641 (11.4); 7.624 (2.7); 7.613 (1.5); 7.610 (1.7); 7.599 (0.7); 7.410 (4.4); 7.395 (7.9); 7.382 (3.8); 6.947 (6.4); 6.943 (6.5); 4.471 (1.0); 4.461 (1.7); 4.447 (1.7); 4.437 (1.1); 3.346 (1159.5); 2.625 (1.1); 2.552 (81.9); 2.534 (1.7); 2.531 (2.2); 2.528 (2.1); 2.519 (58.6); 2.516 (125.8); 2.513 (173.8); 2.510 (126.2); 2.507 (59.8); 2.397 (1.1); 1.871 (0.9); 1.858 (1.3); 1.848 (1.6); 1.834 (1.7); 1.821 (1.3); 1.809 (0.4); 1.753 (0.3); 1.741 (1.2); 1.731 (1.6); 1.719 (2.0); 1.706 (1.3); 1.697 (0.9); 1.414 (14.6); 1.403 (14.7); 1.269 (0.4); 1.246 (0.8); 0.731 (7.6); 0.719 (16.0); 0.706 (7.4); 0.011 (1.3)

I-1-246:

HPLC-MS: log P=2.35; mass (m/z): 382.1 (M+H)$^+$; $^1$H-NMR (400.0 MHz, DMSO-D$_6$): δ=11.441 (10.5); 8.704 (7.3); 8.700 (7.9); 8.692 (7.8); 8.688 (7.6); 8.092 (6.9); 8.087 (9.0); 8.083 (9.0); 8.077 (8.9); 8.073 (9.2); 8.068 (7.2); 7.643 (1.4); 7.627 (3.1); 7.621 (2.4); 7.611 (2.1); 7.606 (6.0); 7.600 (2.3); 7.589 (2.6); 7.584 (3.9); 7.569 (1.8); 7.540 (6.7); 7.528 (6.7); 7.520 (6.5); 7.508 (6.3); 7.413

(1.6); 7.404 (9.8); 7.383 (16.0); 7.362 (7.4); 6.962 (13.3); 6.955 (13.2); 4.143 (3.2); 4.115 (10.1); 4.087 (10.5); 4.058 (3.6); 3.328 (195.5); 2.676 (0.6); 2.671 (0.9); 2.667 (0.6); 2.541 (34.1); 2.525 (2.9); 2.520 (4.6); 2.511 (49.4); 2.507 (99.5); 2.502 (131.9); 2.498 (95.5); 2.493 (45.7); 2.333 (0.6); 2.329 (0.9); 2.324 (0.6); 0.008 (0.9); 0.000 (27.4); −0.009 (0.8)

I-1-247:
HPLC-MS: log P=2.74; mass (m/z): 366.1 (M+H)$^+$; $^1$H-NMR (400.0 MHz, DMSO-D$_6$): δ=11.038 (10.5); 8.056 (8.2); 8.050 (8.2); 7.636 (6.9); 7.632 (6.8); 7.617 (8.1); 7.613 (9.5); 7.604 (2.3); 7.598 (5.9); 7.592 (2.4); 7.581 (5.5); 7.577 (6.7); 7.561 (7.4); 7.541 (4.6); 7.537 (4.0); 7.395 (9.8); 7.388 (6.9); 7.383 (2.5); 7.374 (16.0); 7.364 (6.2); 7.362 (6.1); 7.354 (7.9); 7.345 (9.6); 7.343 (9.3); 7.326 (3.8); 7.324 (3.8); 7.278 (7.4); 7.258 (6.5); 7.204 (12.5); 7.019 (6.2); 6.941 (13.1); 6.935 (13.0); 5.756 (3.7); 4.038 (0.4); 4.020 (0.4); 3.324 (103.6); 2.679 (0.4); 2.675 (0.8); 2.670 (1.1); 2.666 (0.8); 2.524 (3.3); 2.519 (5.3); 2.510 (62.0); 2.506 (123.2); 2.501 (161.2); 2.497 (115.7); 2.492 (54.7); 2.337 (0.4); 2.333 (0.8); 2.328 (1.1); 2.324 (0.8); 1.989 (1.5); 1.299 (0.8); 1.259 (1.2); 1.235 (1.8); 1.192 (0.5); 1.175 (0.9); 1.157 (0.5); 0.008 (1.5); 0.000 (40.7); −0.009 (1.2)

I-1-248:
HPLC-MS: log P=1.99; mass (m/z): 351.1 (M+H)$^+$; $^1$H-NMR (400.0 MHz, DMSO-D$_6$): δ=20.009 (0.4); 11.503 (11.6); 8.805 (6.8); 8.796 (6.9); 8.793 (6.7); 8.315 (2.2); 8.190 (6.2); 8.171 (6.6); 8.089 (9.0); 8.083 (9.0); 7.700 (4.7); 7.688 (4.9); 7.680 (4.7); 7.668 (4.4); 7.643 (1.3); 7.627 (2.7); 7.622 (2.6); 7.606 (5.5); 7.590 (2.8); 7.585 (3.6); 7.569 (1.6); 7.404 (9.3); 7.382 (16.0); 7.362 (7.3); 7.340 (4.9); 7.205 (10.7); 7.070 (5.3); 6.961 (12.9); 6.955 (12.8); 3.321 (780.9); 2.675 (5.7); 2.670 (7.7); 2.666 (5.7); 2.540 (4.4); 2.506 (888.4); 2.501 (1153.4); 2.497 (832.1); 2.332 (5.5); 2.328 (7.3); 2.324 (5.4); 0.146 (0.4); 0.008 (3.6); 0.000 (92.4); −0.009 (3.1); −0.150 (0.4)

I-1-249:
HPLC-MS: log P=2.38; mass (m/z): 347.0 (M+H)$^+$; $^1$H-NMR (400.0 MHz, DMSO-D$_6$): δ=11.252 (2.1); 8.579 (1.6); 8.575 (1.8); 8.567 (1.7); 8.563 (1.7); 8.071 (2.0); 8.066 (2.1); 7.966 (1.4); 7.962 (1.4); 7.947 (1.5); 7.943 (1.5); 7.624 (0.6); 7.619 (0.6); 7.608 (0.5); 7.603 (1.3); 7.598 (0.5); 7.587 (0.6); 7.581 (0.8); 7.566 (0.4); 7.401 (2.2); 7.380 (3.7); 7.359 (1.7); 7.233 (1.6); 7.220 (1.6); 7.214 (1.6); 7.201 (1.5); 6.947 (1.7); 6.941 (1.7); 5.758 (1.8); 3.332 (13.9); 2.507 (9.7); 2.503 (12.6); 2.498 (9.4); 2.466 (16.0); 0.000 (0.4)

I-1-250:
HPLC-MS: log P=2.77; mass (m/z): 385.0 (M+H)$^+$; $^1$H-NMR (400.0 MHz, CD$_3$CN): δ=9.340 (3.1); 8.430 (6.0); 8.426 (6.1); 8.418 (6.3); 8.414 (5.9); 8.288 (6.3); 8.283 (5.9); 8.269 (6.6); 8.264 (6.0); 7.769 (8.7); 7.553 (1.4); 7.538 (3.0); 7.532 (3.0); 7.522 (2.2); 7.516 (6.2); 7.510 (2.2); 7.501 (3.2); 7.495 (3.7); 7.480 (7.9); 7.467 (6.4); 7.461 (6.2); 7.448 (5.8); 7.426 (0.3); 7.241 (0.3); 7.235 (0.4); 7.216 (8.9); 7.195 (16.0); 7.174 (7.9); 7.010 (10.8); 7.003 (10.2); 5.447 (1.3); 2.140 (48.9); 2.119 (0.3); 2.113 (0.5); 2.107 (0.6); 2.101 (0.4); 1.963 (1.2); 1.952 (27.6); 1.946 (51.2); 1.939 (71.3); 1.933 (48.7); 1.927 (24.7); 1.768 (0.4); 1.372 (4.7); 1.341 (0.8); 1.285 (1.2); 1.277 (5.0); 0.146 (0.6); 0.008 (5.6); 0.000 (118.5); −0.008 (4.4); −0.149 (0.6)

I-1-251:
HPLC-MS: log P=2.73; mass (m/z): 402.0 (M+H)$^+$; $^1$H-NMR (400.0 MHz, CD$_3$CN): δ=8.661 (4.1); 7.944 (10.5); 7.841 (5.5); 7.822 (7.1); 7.740 (16.0); 7.704 (4.8); 7.691 (4.9); 7.591 (1.4); 7.571 (3.4); 7.555 (5.6); 7.538 (3.7); 7.534 (3.8); 7.518 (1.8); 7.426 (0.6); 7.420 (0.6); 7.239 (7.3); 7.217 (12.7); 7.196 (6.5); 7.171 (0.8); 7.165 (0.7); 7.150 (0.5); 7.144 (0.4); 5.446 (0.6); 4.085 (0.5); 4.067 (1.5); 4.049 (1.6); 4.032 (0.5); 2.145 (72.1); 2.119 (0.7); 2.113 (0.7); 2.106 (0.8); 2.100 (0.6); 2.094 (0.3); 1.971 (7.4); 1.963 (4.1); 1.951 (40.1); 1.945 (73.6); 1.939 (100.3); 1.933 (68.8); 1.927 (35.3); 1.774 (0.4); 1.767 (0.6); 1.761 (0.4); 1.436 (3.7); 1.372 (8.6); 1.340 (1.7); 1.307 (0.4); 1.285 (2.6); 1.276 (9.8); 1.271 (3.8); 1.221 (1.9); 1.203 (3.6); 1.185 (1.8); 0.881 (0.5); 0.146 (0.8); 0.008 (9.1); 0.000 (174.0); −0.009 (6.7); −0.150 (0.8)

I-1-252:
HPLC-MS: log P=2.77; mass (m/z): 447.9 (M+H)$^+$; $^1$H-NMR (400.0 MHz, CD$_3$CN): δ=8.586 (5.1); 7.956 (11.2); 7.841 (5.9); 7.822 (7.7); 7.748 (16.0); 7.711 (4.4); 7.701 (5.4); 7.693 (4.9); 7.683 (4.2); 7.593 (1.6); 7.577 (3.5); 7.572 (3.7); 7.556 (6.3); 7.540 (4.0); 7.535 (4.1); 7.519 (1.9); 7.447 (0.4); 7.426 (0.8); 7.420 (0.7); 7.240 (8.2); 7.219 (13.8); 7.197 (7.0); 7.171 (1.0); 7.165 (0.8); 7.150 (0.6); 7.144 (0.5); 3.908 (0.7); 3.850 (0.8); 2.133 (57.0); 2.119 (0.7); 2.112 (0.9); 2.106 (1.1); 2.100 (0.8); 2.094 (0.4); 1.963 (7.2); 1.957 (9.7); 1.951 (68.3); 1.945 (125.7); 1.939 (172.2); 1.933 (116.7); 1.927 (59.3); 1.914 (1.0); 1.780 (0.4); 1.773 (0.7); 1.767 (0.6); 1.761 (0.7); 1.755 (0.4); 1.372 (13.0); 1.340 (2.6); 1.285 (3.6); 1.276 (14.9); 1.270 (3.8); 1.216 (0.5); 1.162 (0.5); 1.146 (0.4); 0.881 (0.6); 0.866 (0.6); 0.848 (0.4); 0.146 (1.2); 0.008 (10.1); 0.000 (270.2); −0.009 (8.6); −0.150 (1.2)

I-1-253:
HPLC-MS: log P=3.08; mass (m/z): 382.1 (M+H)$^+$; $^1$H-NMR (400.0 MHz, DMSO-D$_6$): δ=8.130 (3.2); 7.907 (2.1); 7.887 (2.7); 7.868 (4.4); 7.845 (1.0); 7.826 (2.2); 7.807 (1.7); 7.745 (1.6); 7.719 (3.6); 7.702 (4.0); 7.684 (2.7); 7.655 (0.5); 7.634 (1.0); 7.618 (1.7); 7.597 (1.4); 7.576 (2.2); 7.558 (5.8); 7.550 (6.7); 7.540 (5.3); 7.519 (1.1); 7.407 (2.5); 7.385 (4.7); 7.365 (4.6); 7.313 (3.7); 7.291 (6.2); 7.27 (2.9); 7.097 (3.5); 7.092 (3.4); 5.984 (4.9); 5.978 (4.8); 5.758 (1.0); 4.038 (0.5); 4.020 (0.6); 3.409 (24.8); 3.323 (260.0); 3.145 (6.0); 2.680 (0.9); 2.675 (1.9); 2.671 (2.6); 2.662 (0.9); 2.524 (7.2); 2.519 (11.4); 2.511 (145.7); 2.506 (294.0); 2.502 (387.7); 2.497 (279.3); 2.493 (133.4); 2.338 (0.9); 2.333 (1.9); 2.328 (2.6); 2.324 (1.9); 2.320 (0.9); 1.989 (2.3); 1.398 (1.1); 1.351 (0.4); 1.298 (0.3); 1.259 (0.5); 1.235 (0.9); 1.192 (0.7); 1.175 (1.3); 1.157 (0.7); 0.146 (0.7); 0.008 (5.3); 0.000 (156.8); −0.009 (4.8); −0.150 (0.7)

I-1-254:
HPLC-MS: log P=3.31; mass (m/z): 396.1 (M+H)$^+$; $^1$H-NMR (400.0 MHz, DMSO-D$_6$): δ=8.317 (0.6); 8.121 (1.2); 7.907 (0.8); 7.880 (5.4); 7.875 (5.1); 7.846 (0.4); 7.830 (0.8); 7.811 (0.6); 7.751 (0.7); 7.731 (1.7); 7.711 (1.1); 7.689 (2.6); 7.676 (2.8); 7.666 (2.9); 7.634 (0.4); 7.615 (0.7); 7.597 (1.1); 7.581 (1.7); 7.576 (1.7); 7.560 (3.1); 7.544 (2.3); 7.531 (5.4); 7.521 (7.1); 7.511 (5.1); 7.495 (0.6); 7.409 (0.9); 7.388 (1.5); 7.366 (0.8); 7.334 (3.2); 7.324 (4.2); 7.316 (6.6); 7.295 (8.0); 7.274 (3.8); 7.007 (1.2); 7.002 (1.2); 6.061 (6.5); 6.055 (6.3); 3.895 (2.4); 3.883 (2.4); 3.793 (0.4); 3.778 (0.4); 3.757 (0.4); 3.740 (0.3); 3.472 (0.4); 3.454 (0.3); 3.322 (129.0); 2.680 (0.8); 2.675 (1.7); 2.671 (2.3); 2.666 (1.7); 2.662 (0.8); 2.524 (10.5); 2.511 (139.7); 2.506 (267.9); 2.502 (343.4); 2.497 (243.9); 2.493 (114.9); 2.337 (0.9); 2.333 (1.8); 2.328 (2.3); 2.324 (1.7); 2.319 (0.8); 2.074 (0.7); 1.754 (0.5); 1.212 (7.7); 1.194 (16.0); 1.177 (7.4); 1.096 (1.5); 1.080 (2.6); 1.063 (1.3); 0.146 (0.9); 0.008 (9.2); 0.000 (222.2); −0.009 (7.7); −0.150 (0.9)

I-1-255:
HPLC-MS: log P=3.44; mass (m/z): 408.2 (M+H)+;
1H-NMR (400.0 MHz, DMSO-D6): δ=8.316 (0.5); 8.121 (2.1); 7.864 (11.6); 7.799 (1.6); 7.782 (1.3); 7.703 (6.1); 7.691 (6.7); 7.647 (2.1); 7.629 (2.3); 7.606 (1.8); 7.586 (2.8); 7.542 (15.4); 7.532 (16.0); 7.400 (1.9); 7.378 (3.2); 7.352 (7.7); 7.344 (7.3); 7.304 (8.3); 7.283 (13.3); 7.261 (6.5); 7.008 (2.1); 6.080 (12.1); 5.954 (1.3); 5.941 (2.2); 5.928 (2.4); 5.915 (3.2); 5.900 (3.2); 5.885 (2.5); 5.872 (2.5); 5.859 (1.3); 5.848 (0.4); 5.785 (0.7); 5.772 (0.7); 5.756 (0.6); 5.305 (6.5); 5.262 (5.7); 5.188 (6.7); 5.162 (6.3); 5.064 (1.4); 5.039 (1.2); 4.892 (1.2); 4.849 (1.1); 4.507 (10.9); 4.434 (0.7); 4.419 (0.8); 4.382 (0.9); 4.069 (0.8); 4.033 (0.6); 3.323 (65.6); 2.671 (1.9); 2.629 (0.5); 2.506 (264.1); 2.502 (261.6); 2.359 (0.5); 2.331 (1.9); 1.236 (1.0); 0.002 (3.1); 0.000 (4.3)

I-1-256:
HPLC-MS: log P=3.14; mass (m/z): 406.1 (M+H)+;
1H-NMR (400.0 MHz, DMSO-D6): δ=8.315 (3.3); 8.151 (1.3); 8.121 (0.3); 7.903 (12.0); 7.847 (1.0); 7.760 (1.1); 7.714 (5.9); 7.701 (6.9); 7.692 (6.4); 7.599 (2.2); 7.577 (4.5); 7.559 (16.0); 7.545 (15.4); 7.536 (12.8); 7.392 (1.7); 7.371 (1.4); 7.340 (6.7); 7.327 (7.9); 7.316 (12.7); 7.294 (15.6); 7.273 (7.2); 7.018 (1.2); 6.132 (12.3); 6.126 (12.2); 4.749 (0.3); 4.680 (15.5); 4.532 (0.5) 0.150 (0.7)

I-1-257:
HPLC-MS: log P=2.86; mass (m/z): 493.9 (M+H)+;
1H-NMR (400.0 MHz, CD3CN): δ=22 (0.5); 2.403 (1.2); 2.383 (0.8); 2.212 (0.7); 2.192 (1.0); 2.160 (74.4); 2.113 (0.4); 2.107 (0.4); 1.971 (7.3); 1.964 (2.9); 1.958 (3.9); 1.952 (23.6); 1.946 (43.1); 1.940 (58.7); 1.933 (40.1); 1.927 (20.5); 1.768 (0.4); 1.436 (3.3); 1.383 (0.6); 1.372 (14.8); 1.340 (2.8); 1.309 (0.4); 1.285 (3.9); 1.276 (16.0); 1.221 (2.0); 1.217 (0.8); 1.203 (3.8); 1.185 (1.9); 0.882 (0.4); 0.146 (0.4); 0.008 (3.3); 0.000 (80.1); −0.009 (2.8); −0.150 (0.4)

I-1-258:
HPLC-MS: log P=3.68; mass (m/z): 422.1 (M+H)+;
1H-NMR (400.0 MHz, DMSO-D6): δ=10.8); 7.525 (11.4); 7.514 (9.8); 7.410 (0.8); 7.390 (1.3); 7.367 (0.9); 7.319 (12.5); 7.299 (16.0); 7.277 (6.7); 6.958 (1.1); 6.047 (11.5); 6.041 (11.4); 3.769 (4.8); 3.561 (0.5); 3.545 (0.5); 3.466 (0.5); 3.451 (0.5); 3.323 (194.1); 2.676 (1.7); 2.671 (2.3); 2.666 (1.7); 2.662 (0.8); 2.541 (1.4); 2.524 (6.6); 2.511 (135.1); 2.507 (274.6); 2.502 (362.1); 2.497 (258.9); 2.493 (123.1); 2.333 (1.6); 2.329 (2.2); 2.324 (1.6); 1.118 (1.2); 1.107 (2.3); 1.100 (2.3); 1.089 (3.5); 1.077 (2.5); 1.070 (2.5); 1.058 (1.4); 1.039 (0.5); 0.999 (0.4); 0.985 (0.5); 0.456 (9.7); 0.436 (9.1); 0.390 (0.3); 0.311 (1.2); 0.295 (1.1); 0.257 (3.4); 0.245 (11.0); 0.233 (10.3); 0.222 (2.7); 0.000 (1.5); −0.029 (1.4)

I-1-259:
HPLC-MS: log P=2.90; mass (m/z): 407.1 (M+H)+;
1H-NMR (400.0 MHz, DMSO-D6): δ=1 (2.0); 2.510 (135.9); 2.506 (260.7); 2.502 (335.1); 2.497 (240.7); 2.463 (1.0); 2.333 (1.6); 2.329 (2.2); 2.074 (4.3); 1.755 (0.7); 0.146 (0.8); 0.025 (0.6); 0.008 (8.1); 0.000 (183.5); −0.007 (6.5); −0.008 (7.1); −0.149 (0.9)

I-1-260:
HPLC-MS: log P=3.50; mass (m/z): 410.1 (M+H)+;
1H-NMR (601.6 MHz, DMSO-D6): δ=19.970 (0.9); 8.314 (1.7); 7.884 (4.8); 7.880 (4.9); 7.623 (2.8); 7.611 (3.2); 7.588 (1.4); 7.577 (2.4); 7.562 (1.5); 7.486 (1.0); 7.474 (3.0); 7.464 (5.3); 7.453 (5.7); 7.318 (6.6); 7.305 (9.3); 7.291 (3.3); 6.204 (5.6); 6.200 (5.8); 4.922 (0.8); 4.911 (2.1); 4.900 (2.9); 4.889 (2.1); 3.324 (377.8); 3.320 (448.0); 3.319 (443.5); 2.616 (3.5); 2.613 (5.1); 2.610 (3.9); 2.541 (1.4); 2.522 (6.9); 2.519 (9.1); 2.516 (8.6); 2.507 (239.3); 2.504 (543.6); 2.501 (773.8); 2.498 (589.8); 2.496 (299.2); 2.389 (3.6); 2.386 (5.1); 2.383 (3.9); 1.163 (15.8); 1.152 (16.0); 0.005 (3.2); 0.000 (118.1)

I-1-261:
HPLC-MS: log P=3.64; mass (m/z): 410.1 (M+H)+;
1H-NMR (601.6 MHz, DMSO-D6): δ=8.115 (0.6); 7.901 (0.4); 7.887 (0.5); 7.874 (4.5); 7.870 (4.5); 7.827 (0.4); 7.733 (0.4); 7.708 (0.5); 7.684 (2.3); 7.676 (2.5); 7.669 (2.6); 7.581 (0.6); 7.571 (1.3); 7.567 (1.3); 7.7556 (2.4); 7.546 (1.4); 7.542 (1.5); 7.531 (1.0); 7.521 (4.5); 7.513 (5.6); 7.506 (4.8); 7.496 (0.6); 7.400 (0.4); 7.385 (0.7); 7.372 (0.4); 7.312 (2.7); 7.305 (5.7); 7.298 (3.1); 7.291 (7.1); 7.277 (3.5); 6.969 (0.6); 6.086 (6.2); 6.082 (6.2); 3.863 (1.6); 3.322 (54.5); 2.614 (0.4); 2.611 (0.3); 2.523 (0.7); 2.520 (0.8); 2.517 (0.7); 2.508 (21.2); 2.505 (47.3); 2.502 (67.5); 2.499 (48.6); 2.496 (22.9); 2.386 (0.4); 2.383 (0.3); 1.645 (0.5); 1.633 (2.6); 1.621 (5.4); 1.608 (5.6); 1.596 (3.0); 1.584 (0.8); 0.936 (7.7); 0.923 (16.0); 0.911 (7.3); 0.643 (0.7); 0.631 (1.3); 0.619 (0.7); 0.005 (0.5); 0.000 (19.7); −0.006 (0.7)

I-1-262:
HPLC-MS: log P=3.40; mass (m/z): 426.1 (M+H)+;
1H-NMR (400.0 MHz, DMSO-D6): δ=8.316 (0.4); 8.143 (1.0); 8.143 (1.0); 7.900 (7.4); 7.807 (0.9); 7.687 (5.1); 7.587 (1.7); 7.568 (3.0); 7.550 (4.5); 7.527 (9.5); 7.518 (9.3); 7.391 (1.5); 7.326 (5.3); 7.306 (6.4); 7.284 (8.9); 7.263 (4.3); 6.896 (0.9); 6.270 (7.3); 5.278 (13.6); 5.114 (0.4); 4.887 (0.4); 3.699 (3.1); 3.682 (8.0); 3.665 (8.1); 3.648 (3.3); 3.322 (104.8); 2.675 (1.3); 2.671 (1.6); 2.666 (1.2); 2.540 (0.9); 2.506 (201.4); 2.502 (251.0); 2.497 (182.3); 2.333 (1.2); 2.328 (1.6); 2.324 (1.2); 1.158 (8.6); 1.141 (16.0); 1.124 (8.9); 0.954 (2.2); 0.146 (0.5); 0.007 (8.4); −0.001 (103.4); −0.150 (0.5)

I-1-263:
HPLC-MS: log P=3.40; mass (m/z): 420.1 (M+H)+;
1H-NMR (400.0 MHz, DMSO-D6): δ=8.133 (1.0); 7.887 (6.4); 7.834 (0.8); 7.687 (3.8); 7.681 (3.8); 7.539 (8.9); 7.391 (1.3); 7.314 (7.2); 7.292 (6.8); 7.272 (3.1); 7.015 (0.9); 6.135 (6.0); 4.628 (8.9); 4.482 (0.3); 4.474 (0.3); 4.443 (0.5); 4.271 (0.5); 3.322 (31.8); 3.314 (26.7); 2.667 (1.1); 2.502 (153.1); 2.498 (159.5); 2.329 (1.1); 2.325 (1.1); 1.782 (16.0); 1.688 (2.9); 0.000 (6.1); −0.003 (3.6); −0.008 (4.3)

I-1-264:
HPLC-MS: log P=3.38; mass (m/z): 432.1 (M+H)+;
1H-NMR (400.0 MHz, DMSO-D6): δ=8.316 (0.5); 8.189 (0.4); 7.893 (10.1); 7.849 (0.4); 7.837 (0.4); 7.765 (0.5); 7.728 (4.7); 7.718 (5.5); 7.714 (5.7); 7.706 (5.9); 7.601 (1.8); 7.580 (5.3); 7.571 (14.2); 7.564 (16.0); 7.558 (13.3); 7.549 (14.3); 7.528 (1.8); 7.370 (5.8); 7.362 (5.9); 7.358 (5.7); 7.349 (4.9); 7.319 (8.8); 7.298 (15.1); 7.277 (7.0); 7.021 (0.4); 6.449 (1.4); 6.439 (2.7); 6.429 (1.4); 6.310 (2.8); 6.300 (5.6); 6.290 (2.9); 6.171 (1.3); 6.161 (2.8); 6.151 (1.5); 6.092 (11.9); 6.086 (11.7); 4.355 (3.3); 4.346 (3.6); 4.319 (6.7); 4.310 (6.7); 4.282 (3.7); 4.273 (3.4); 3.322 (79.8); 2.676 (0.9); 2.671 (1.3); 2.666 (0.9); 2.662 (0.4); 2.541 (0.7); 2.524 (3.3); 2.511 (72.5); 2.506 (146.7); 2.502 (194.1); 2.497 (140.3); 2.493 (67.6); 2.338 (0.4); 2.333 (0.9); 2.329 (1.3); 2.324 (0.9); 0.008 (0.5); 0.000 (15.4); −0.009 (0.6)

I-1-265:
HPLC-MS: log P=3.59; mass (m/z): 450.0 (M+H)+;
1H-NMR (400.0 MHz, DMSO-D6): δ=8.316 (0.5); 7.920 (10.3); 7.916 (10.2); 7.732 (4.8); 7.723 (5.4); 7.710 (6.1); 7.605 (1.7); 7.589 (3.9); 7.583 (4.6); 7.565 (14.1); 7.553 (13.5); 7.546 (13.0); 7.530 (3.1); 7.347 (6.1); 7.334 (5.9);

7.324 (6.6); 7.315 (9.9); 7.294 (16.0); 7.273 (7.5); 6.213 (11.6); 6.207 (11.4); 4.774 (4.2); 4.756 (4.2); 3.322 (90.8); 2.675 (1.0); 2.671 (1.4); 2.666 (1.1); 2.541 (0.7); 2.524 (3.7); 2.510 (83.4); 2.506 (165.6); 2.502 (217.9); 2.497 (158.5); 2.493 (77.0); 2.333 (1.1); 2.328 (1.5); 2.324 (1.1); 0.008 (0.6); 0.000 (16.1); −0.009 (0.6)

I-1-266:
HPLC-MS: log P=2.93; mass (m/z): 368.0 (M+H)$^+$; $^1$H-NMR (400.0 MHz, DMSO-D$_6$): δ=11.332 (11.3); 8.212 (0.5); 8.206 (0.6); 8.077 (8.5); 8.071 (8.6); 7.757 (7.2); 7.753 (7.8); 7.737 (8.5); 7.733 (8.7); 7.640 (1.5); 7.624 (3.1); 7.618 (2.5); 7.608 (2.1); 7.603 (5.8); 7.597 (2.3); 7.586 (2.7); 7.581 (3.7); 7.563 (6.8); 7.559 (6.9); 7.544 (10.2); 7.540 (9.2); 7.478 (9.6); 7.459 (13.1); 7.439 (6.0); 7.417 (0.8); 7.399 (9.9); 7.378 (16.0); 7.357 (7.4); 6.946 (14.3); 6.940 (14.4); 6.928 (1.2); 6.729 (0.9); 5.757 (6.7); 3.323 (58.3); 2.675 (0.7); 2.671 (0.9); 2.666 (0.7); 2.541 (31.2); 2.524 (2.8); 2.511 (53.6); 2.506 (107.0); 2.502 (140.6); 2.497 (102.8); 2.493 (50.5); 2.348 (3.6); 2.337 (0.5); 2.333 (0.8); 2.328 (1.0); 2.324 (0.7); 0.008 (1.4); 0.000 (39.7); −0.009 (1.4)

I-1-267:
HPLC-MS: log P=2.72; mass (m/z): 368.1 (M+H)$^+$; $^1$H-NMR (400.0 MHz, DMSO-D$_6$): δ=11.468 (5.9); 8.080 (4.4); 8.077 (3.8); 8.074 (4.4); 7.640 (0.8); 7.624 (1.7); 7.618 (1.2); 7.608 (1.1); 7.602 (3.3); 7.597 (1.2); 7.586 (1.3); 7.581 (2.2); 7.564 (7.7); 7.560 (8.8); 7.543 (15.4); 7.541 (16.0); 7.497 (8.3); 7.480 (5.2); 7.474 (4.2); 7.457 (3.1); 7.410 (0.8); 7.406 (1.4); 7.401 (5.5); 7.388 (1.0); 7.380 (8.8); 7.359 (4.1); 7.354 (1.1); 6.949 (8.8); 6.943 (8.7); 3.406 (0.3); 3.390 (0.6); 3.343 (380.7); 3.321 (1.7); 3.301 (0.5); 3.291 (0.4); 2.676 (0.4); 2.672 (0.6); 2.667 (0.4); 2.542 (50.0); 2.532 (0.5); 2.525 (1.8); 2.520 (3.0); 2.512 (34.4); 2.507 (69.0); 2.503 (90.9); 2.498 (65.3); 2.493 (30.6); 2.334 (0.4); 2.329 (0.6); 2.325 (0.4); 0.000 (0.9)

I-1-268:
HPLC-MS: log P=2.68; mass (m/z): 328.1 (M+H)$^+$; $^1$H-NMR (400.0 MHz, CD$_3$CN): δ=9.056 (0.47752 (1.1); 7.752 (1.1); 7.749 (1.0); 7.746 (1.1); 7.523 (0.4); 7.518 (0.4); 7.502 (0.9); 7.486 (0.4); 7.480 (0.5); 7.238 (0.6); 7.219 (1.1); 7.210 (0.4); 7.205 (1.5); 7.200 (1.2); 7.192 (0.3); 7.184 (2.3); 7.163 (1.2); 7.101 (2.3); 7.082 (1.7); 7.042 (1.8); 7.035 (1.8); 2.316 (16.0); 2.150 (7.5); 1.963 (0.5); 1.957 (0.7); 1.951 (3.7); 1.945 (6.6); 1.939 (9.0); 1.933 (6.2); 1.927 (3.2); 1.372 (0.8); 1.276 (0.8); 0.008 (0.5); 0.000 (11.0); −0.009 (0.5)

I-1-269:
HPLC-MS: log P=2.20; mass (m/z): 357.0 (M+H)$^+$; $^1$H-NMR (400.0 MHz, DMSO-D$_6$): δ=11.210 (1.8); 10.533 (1.1); 8.177 (1.1); 8.156 (1.2); 8.072 (2.3); 8.066 (2.3); 7.823 (1.5); 7.805 (1.6); 7.646 (0.4); 7.631 (0.7); 7.625 (0.7); 7.615 (0.6); 7.609 (1.4); 7.593 (0.7); 7.588 (0.9); 7.573 (0.5); 7.524 (0.9); 7.521 (0.9); 7.503 (1.7); 7.485 (1.0); 7.482 (0.9); 7.405 (2.5); 7.384 (4.1); 7.363 (1.9); 7.188 (1.1); 7.170 (1.9); 7.152 (0.9); 6.940 (2.2); 6.934 (2.2); 3.325 (42.1); 2.675 (0.4); 2.671 (0.5); 2.541 (0.5); 2.506 (53.8); 2.502 (68.6); 2.497 (49.8); 2.328 (0.4); 2.260 (0.5); 2.087 (16.0); 2.027 (0.3); 1.909 (2.2); 1.235 (1.0); 0.008 (2.9); 0.000 (61.0); −0.008 (2.6)

I-1-270:
HPLC-MS: log P=2.38; mass (m/z): 342.1 (M+H)$^+$; $^1$H-NMR (400.0 MHz, DMSO-D$_6$): δ=8.316 (0.7); 7.804 (2.8); 7.785 (3.3); 7.770 (1.1); 7.768 (1.1); 7.752 (2.5); 7.750 (2.4); 7.733 (1.9); 7.731 (1.7); 7.646 (3.5); 7.628 (3.5); 7.610 (5.1); 7.603 (2.8); 7.594 (1.3); 7.515 (4.3); 7.482 (0.5); 7.466 (1.0); 7.460 (0.8); 7.450 (1.0); 7.445 (2.0); 7.439 (0.8); 7.428 (0.9); 7.423 (1.3); 7.408 (0.6); 7.263 (0.9); 7.257 (3.4); 7.236 (5.7); 7.215 (2.5); 7.209 (0.6); 5.757 (1.5); 5.757 (0.5); 5.130 (4.5); 5.124 (4.4); 3.322 (330.5); 2.680 (1.2); 2.675 (2.4); 2.671 (3.2); 2.666 (2.3); 2.661 (1.2); 2.612 (0.4); 2.524 (10.6); 2.519 (16.2); 2.510 (174.5); 2.506 (347.1); 2.501 (454.2); 2.497 (323.8); 2.492 (151.3); 2.337 (0.9); 2.333 (2.1); 2.328 (2.9); 2.324 (2.1); 2.319 (0.9); 1.903 (16.0); 1.298 (1.4); 1.259 (2.1); 1.235 (1.1); 0.146 (0.9); 0.008 (8.0); 0.000 (229.0); −0.009 (7.1); −0.150 (0.9)

I-1-271:
HPLC-MS: log P=2.47; mass (m/z): 363.1 (M+H)$^+$; $^1$H-NMR (400.0 MHz, DMSO-D$_6$): δ=11.146 (2.3); 8.038 (1.7); 8.032 (1.8); 7.617 (0.6); 7.611 (0.5); 7.602 (0.4); 7.596 (1.2); 7.580 (0.5); 7.575 (0.8); 7.559 (0.4); 7.423 (1.4); 7.402 (2.8); 7.394 (2.1); 7.382 (2.3); 7.373 (3.4); 7.352 (1.6); 7.102 (2.4); 7.096 (2.8); 7.080 (2.0); 7.076 (2.5); 6.936 (3.2); 6.930 (3.3); 3.811 (16.0); 3.328 (486.3); 2.995 (0.4); 2.680 (0.7); 2.675 (1.2); 2.671 (1.6); 2.666 (1.2); 2.541 (53.6); 2.524 (5.1); 2.519 (8.0); 2.511 (91.0); 2.506 (182.0); 2.502 (239.8); 2.497 (172.9); 2.493 (82.2); 2.338 (0.5); 2.333 (1.1); 2.328 (1.5); 2.324 (1.1); 0.008 (0.6); 0.000 (16.7); −0.009 (0.4)

I-1-272:
HPLC-MS: log P=2.48; mass (m/z): 325.1 (M+H)$^+$; $^1$H-NMR (400.0 MHz, CD$_3$CN): δ=10.113 (5.2); 9.387 (0.4); 8.021 (7.9); 8.003 (9.3); 7.945 (10.2); 7.932 (4.2); 7.914 (7.5); 7.896 (9.4); 7.883 (2.7); 7.875 (1.5); 7.869 (1.5); 7.861 (1.4); 7.830 (3.3); 7.812 (7.7); 7.794 (5.3); 7.779 (8.6); 7.776 (8.5); 7.761 (10.4); 7.758 (9.4); 7.742 (3.6); 7.740 (3.2); 7.591 (1.8); 7.576 (4.0); 7.570 (3.7); 7.560 (2.8); 7.554 (8.1); 7.548 (2.9); 7.539 (4.0); 7.533 (4.7); 7.517 (2.3); 7.266 (8.9); 7.245 (16.0); 7.231 (3.6); 7.224 (7.8); 7.210 (1.6); 7.045 (8.0); 7.039 (7.8); 6.675 (1.8); 6.669 (1.8); 2.727 (0.4); 2.463 (0.4); 2.184 (0.7); 2.153 (83.5); 2.120 (0.5); 2.114 (0.7); 2.108 (0.8); 2.101 (0.6); 1.964 (5.2); 1.958 (6.4); 1.953 (47.9); 1.946 (89.3); 1.940 (124.6); 1.934 (86.0); 1.928 (44.1); 1.775 (0.5); 1.769 (0.7); 1.763 (0.5); 1.267 (0.4); 0.008 (1.5); 0.000 (42.2); −0.009 (1.4)

I-1-273:
HPLC-MS: log P=2.89; mass (m/z): 340.2 (M+H)$^+$; $^1$H-NMR (400.0 MHz, DMSO-D$_6$): δ=11.037 (8.6); 8.039 (7.7); 7.635 (1.1); 7.619 (2.5); 7.614 (2.2); 7.597 (4.8); 7.581 (2.5); 7.576 (3.1); 7.560 (1.4); 7.401 (7.3); 7.393 (8.7); 7.382 (8.5); 7.372 (16.0); 7.351 (11.4); 7.335 (4.2); 7.234 (4.5); 7.216 (7.0); 7.197 (3.0); 6.981 (7.4); 6.969 (10.7); 6.963 (14.8); 5.756 (3.7); 3.323 (59.0); 2.675 (0.8); 2.670 (1.0); 2.666 (0.8); 2.540 (0.8); 2.506 (126.6); 2.501 (157.1); 2.497 (113.6); 2.332 (0.8); 2.328 (1.0); 2.324 (0.8); 2.257 (0.9); 2.244 (2.0); 2.236 (2.3); 2.223 (3.8); 2.210 (2.3); 2.202 (2.0); 2.189 (1.0); 1.989 (0.7); 1.175 (0.4); 0.954 (2.5); 0.943 (7.7); 0.938 (7.9); 0.928 (4.7); 0.922 (7.6); 0.917 (7.6); 0.907 (2.9); 0.705 (3.1); 0.691 (9.4); 0.682 (8.8); 0.678 (8.6); 0.666 (2.5); 0.146 (0.4); 0.008 (4.3); 0.000 (84.1); −0.008 (3.2); −0.150 (0.4)

I-1-274:
HPLC-MS: log P=2.85; mass (m/z): 346.1 (M+H)$^+$; $^1$H-NMR (400.0 MHz, DMSO-D$_6$): δ=11.297 (4.4); 8.315 (0.3); 8.062 (3.4); 8.056 (3.5); 7.637 (0.6); 7.621 (1.2); 7.616 (1.0); 7.605 (0.8); 7.600 (2.3); 7. 594 (0.9); 7.583 (1.0); 7.578 (1.5); 7.563 (0.7); 7.437 (1.1); 7.421 (1.4); 7.417 (2.2); 7.402 (3.3); 7.397 (5.5); 7.381 (2.5); 7.376 (6.6); 7.355 (3.1); 7.171 (3.6); 7.153 (3.1); 7.144 (2.0); 7.121 (3.0); 7.100 (1.6); 6.953 (5.9); 6.947 (5.9); 3.327 (306.3); 2.678 (2.1); 2.671 (1.8); 2.666 (1.7); 2.660 (5.5); 2.641 (5.4); 2.622 (1.8); 2.541 (42.5); 2.524 (4.3); 2.519 (7.1); 2.511 (82.9); 2.506 (164.3); 2.502 (213.7); 2.497

(155.5); 2.493 (76.3); 2.337 (0.5); 2.333 (1.0); 2.328 (1.4); 2.324 (1.0); 2.074 (7.1); 1.259 (0.4); 1.235 (0.6); 1.203 (7.2); 1.184 (16.0); 1.165 (7.0); 1.149 (0.7); 0.008 (1.1); 0.000 (32.5); −0.009 (1.3)

I-1-275:
HPLC-MS: log P=1.47; mass (m/z): 329.1 (M+H)$^+$;
$^1$H-NMR (400.0 MHz, DMSO-D$_6$): δ=11.235 (3.8); 8.593 (2.5); 8.588 (2.7); 8.580 (2.7); 8.576 (2.7); 8.315 (0.7); 8.068 (3.1); 8.062 (3.1); 7.872 (1.8); 7.868 (1.9); 7.853 (2.0); 7.849 (2.0); 7.639 (0.5); 7.623 (1.2); 7.617 (0.9); 7.607 (0.8); 7.602 (2.4); 7.596 (0.9); 7.585 (1.1); 7.580 (1.6); 7.564 (0.7); 7.398 (3.8); 7.377 (6.3); 7.357 (3.0); 7.335 (2.0); 7.323 (2.1); 7.316 (2.1); 7.304 (1.9); 6.965 (4.9); 6.958 (4.9); 3.334 (505.9); 2.915 (1.7); 2.897 (5.3); 2.878 (5.4); 2.859 (1.8); 2.680 (1.2); 2.675 (2.5); 2.671 (3.5); 2.666 (2.5); 2.662 (1.2); 2.541 (60.7); 2.524 (10.3); 2.519 (15.9); 2.511 (199.0); 2.506 (400.9); 2.502 (526.4); 2.497 (373.9); 2.492 (174.8); 2.419 (0.4); 2.338 (1.2); 2.333 (2.5); 2.328 (3.5); 2.324 (2.4); 2.319 (1.1); 2.074 (13.8); 1.298 (0.6); 1.259 (1.0); 1.248 (7.5); 1.229 (16.0); 1.210 (7.1); 1.147 (0.3); 0.008 (2.8); 0.000 (83.4); −0.009 (2.2)

I-1-276:
HPLC-MS: log P=2.72; mass (m/z): 386.1 (M+H)$^+$;
$^1$H-NMR (400.0 MHz, DMSO-D$_6$): δ=11.563 (9.8); 8.090 (8.0); 8.084 (8.0); 7.774 (0.8); 7.754 (2.5); 7.746 (1.4); 7.735 (5.8); 7.721 (9.3); 7.701 (16.0); 7.685 (4.5); 7.680 (3.4); 7.639 (1.3); 7.623 (2.6); 7.617 (2.3); 7.607 (1.8); 7.601 (5.3); 7.596 (2.2); 7.585 (2.4); 7.580 (3.4); 7.564 (1.5); 7.401 (8.6); 7.379 (14.4); 7.359 (6.5); 6.927 (13.6); 6.921 (13.5); 3.517 (0.6); 3.351 (103.3); 2.714 (0.5); 2.544 (105.9); 2.527 (0.8); 2.522 (0.8); 2.513 (10.6); 2.509 (21.8); 2.504 (29.2); 2.500 (21.8); 2.496 (10.8); 2.370 (0.5); 0.000 (2.0)

I-1-277:
HPLC-MS: log P=2.74; mass (m/z): 431.8 (M+H)$^+$;
$^1$H-NMR (400.0 MHz, DMSO-D$_6$): δ=11.408 (2.5); 8.080 (1.8); 8.074 (1.8); 7.740 (1.9); 7.722 (1.9); 7.720 (2.0); 7.623 (0.6); 7.617 (0.5); 7.608 (0.4); 7.602 (1.2); 7.596 (0.5); 7.586 (0.5); 7.581 (0.8); 7.565 (0.4); 7.410 (0.3); 7.401 (2.1); 7.379 (4.1); 7.359 (3.3); 7.337 (1.1); 7.335 (1.1); 7.284 (1.0); 7.268 (1.1); 7.264 (1.2); 7.249 (1.2); 7.243 (0.6); 7.228 (0.6); 6.943 (3.3); 6.937 (3.2); 4.116 (1.0); 4.13 (3.1); 4.103 (3.1); 4.089 (3.1); 4.076 (1.1); 3.328 (12.9); 3.176 (16.0); 3.163 (15.4); 2.524 (0.3); 2.510 (5.9); 2.506 (11.7); 2.501 (15.3); 2.497 (10.9); 2.492 (5.1); 0.008 (0.3); 0.000 (9.3)

I-1-278:
HPLC-MS: log P=2.60; mass (m/z): 318.1 (M+H)$^+$;
$^1$H-NMR (400.0 MHz, DMSO-D$_6$): δ=11.109 (8.0); 8.066 (7.6); 8.060 (7.5); 7.695 (2.5); 7.691 (2.9); 7.676 (4.8); 7.672 (5.4); 7.657 (3.0); 7.653 (3.0); 7.640 (1.5); 7.625 (3.1); 7.618 (2.4); 7.609 (2.0); 7.603 (6.2); 7.597 (3.6); 7.592 (2.3); 7.586 (3.0); 7.582 (5.1); 7.579 (4.3); 7.576 (3.2); 7.572 (2.7); 7.565 (3.9); 7.560 (3.0); 7.558 (3.8); 7.553 (2.2); 7.544 (2.1); 7.539 (1.8); 7.409 (1.5); 7.405 (2.6); 7.400 (9.8); 7.387 (2.0); 7.379 (16.0); 7.358 (7.6); 7.352 (2.5); 7.346 (4.6); 7.326 (9.0); 7.321 (5.3); 7.319 (4.5); 7.310 (9.0); 7.308 (8.3); 7.300 (3.7); 7.298 (3.6); 7.291 (4.5); 7.289 (3.7); 6.945 (10.0); 6.939 (9.8); 3.424 (0.4); 3.412 (0.5); 3.399 (0.6); 3.344 (657.4); 2.712 (0.4); 2.681 (0.3); 2.676 (0.7); 2.672 (1.0); 2.667 (0.8); 2.663 (0.4); 2.542 (109.0); 2.525 (2.9); 2.520 (4.5); 2.512 (57.6); 2.507 (116.9); 2.503 (155.0); 2.498 (111.8); 2.494 (53.0); 2.368 (0.4); 2.339 (0.4); 2.334 (0.8); 2.330 (1.0); 2.325 (0.8); 2.320 (0.4); 0.000 (4.6)

I-1-279:
HPLC-MS: log P=2.00; mass (m/z): 319.1 (M+H)$^+$;
$^1$H-NMR (400.0 MHz, DMSO-D$_6$): δ=11.330 (9.6); 8.391 (5.3); 8.381 (5.1); 8.379 (5.2); 8.317 (0.4); 8.269 (3.1); 8.265 (3.0); 8.251 (3.8); 8.246 (5.8); 8.241 (3.3); 8.227 (3.3); 8.222 (2.9); 8.088 (8.6); 8.083 (8.4); 7.643 (1.5); 7.627 (3.1); 7.621 (2.7); 7.612 (2.3); 7.606 (6.1); 7.600 (2.6); 7.590 (2.9); 7.585 (3.9); 7.569 (1.9); 7.519 (0.4); 7.507 (3.7); 7.502 (3.8); 7.494 (3.9); 7.489 (5.6); 7.484 (3.8); 7.476 (3.5); 7.471 (3.3); 7.404 (9.6); 7.383 (16.0); 7.362 (7.4); 6.946 (12.0); 6.940 (11.6); 3.324 (126.4); 3.063 (2.4); 2.998 (0.5); 2.897 (0.5); 2.680 (0.7); 2.675 (1.3); 2.671 (1.7); 2.666 (1.3); 2.662 (0.6); 2.541 (32.6); 2.524 (6.8); 2.511 (100.3); 2.506 (194.4); 2.502 (252.1); 2.497 (182.2); 2.493 (87.8); 2.338 (0.6); 2.333 (1.2); 2.329 (1.7); 2.324 (1.2); 2.320 (0.6); 0.008 (2.4)

I-1-280
HPLC-MS: log P=2.75; mass (m/z): 330.1 (M+H)$^+$;
$^1$H-NMR (400.0 MHz, DMSO-D$_6$): δ=10.544 (2.3); 8.047 (1.9); 8.042 (1.9); 7.782 (1.5); 7.777 (1.6); 7.762 (1.6); 7.758 (1.6); 7.642 (0.4); 7.627 (0.7); 7.620 (0.6); 7.611 (0.5); 7.605 (1.5); 7.599 (0.5); 7.589 (0.6); 7.584 (0.9); 7.568 (0.4); 7.553 (0.8); 7.548 (0.8); 7.534 (1.1); 7.532 (1.3); 7.528 (1.3); 7.528 (1.14 (1.0); 7.509 (1.0); 7.405 (0.4); 7.400 (0.6); 7.395 (2.4); 7.383 (0.5); 7.374 (3.9); 7.354 (1.8); 7.348 (0.5); 7.210 (2.1); 7.189 (1.8); 7.106 (1.2); 7.104 (1.2); 7.087 (2.0); 7.086 (2.0); 7.069 (1.0); 7.067 (1.0); 6.960 (3.1); 6.953 (3.1); 5.756 (0.6); 3.931 (16.0); 3.324 (20.7); 2.524 (0.7); 2.519 (1.1); 2.511 (12.2); 2.506 (24.6); 2.502 (32.6); 2.497 (23.4); 2.493 (11.1); 0.008 (0.6); 0.000 (18.2); −0.009 (0.6)

I-1-281:
HPLC-MS: log P=2.43; mass (m/z): 304.1 (M+H)$^+$;
$^1$H-NMR (400.0 MHz, CD$_3$CN): δ=8.776 (0.7); 7.719 (1.8); 7.716 (1.8); 7.713 (1.7); 7.523 (0.6); 7.517 (0.6); 7.507 (0.4); 7.502 (1.3); 7.496 (0.5); 7.486 (0.7); 7.480 (0.8); 7.465 (0.4); 7.390 (2.6); 7.385 (2.5); 7.218 (0.4); 7.208 (2.1); 7.196 (0.5); 7.187 (3.6); 7.178 (0.4); 7.166 (1.8); 6.977 (2.6); 6.971 (2.5); 6.820 (2.7); 6.815 (2.5); 5.446 (1.0); 2.666 (0.5); 2.587 (16.0); 2.522 (1.4); 2.138 (3.5); 1.963 (0.7); 1.952 (5.6); 1.945 (10.3); 1.939 (13.9); 1.933 (9.4); 1.927 (4.8); 1.372 (0.7); 1.276 (0.9); 1.269 (0.5); 0.000 (5.1)

I-1-282:
HPLC-MS: log P=2.80; mass (m/z): 356.0 (M+H)$^+$;
$^1$H-NMR (400.0 MHz, DMSO-D$_6$): δ=11.324 (9.3); 11.220 (0.4); 8.212 (0.5); 8.205 (0.5); 8.094 (0.4); 8.082 (7.5); 8.076 (7.4); 7.917 (10.0); 7.905 (10.6); 7.649 (1.3); 7.633 (2.7); 7.628 (2.2); 7.617 (1.9); 7.612 (5.3); 7.606 (2.1); 7.595 (2.3); 7.590 (3.4); 7.575 (1.6); 7.565 (4.2); 7.426 (9.5); 7.416 (2.4); 7.409 (16.0); 7.396 (12.8); 7.386 (14.6); 7.365 (6.8); 7.288 (4.4); 6.934 (0.9); 6.927 (0.9); 6.895 (12.3); 6.889 (12.5); 6.729 (0.8); 5.757 (2.8); 3.324 (116.7); 3.051 (0.4); 2.680 (0.5); 2.675 (1.0); 2.671 (1.3); 2.666 (1.0); 2.662 (0.5); 2.541 (7.1); 2.524 (4.0); 2.519 (6.4); 2.511 (76.7); 2.506 (152.6); 2.502 (199.6); 2.497 (143.6); 2.493 (68.4); 2.347 (2.9); 2.338 (0.6); 2.333 (1.0); 2.328 (1.4); 2.324 (1.0); 2.320 (0.5); 0.008 (1.8); 0.000 (53.6); −0.009 (1.7)

I-1-283:
HPLC-MS: log P=2.27; mass (m/z): 372.0 (M+H)$^+$;
$^1$H-NMR (400.0 MHz, DMSO-D$_6$): δ=10.784 (4.2); 8.317 (0.5); 8.057 (3.6); 8.051 (3.6); 7.639 (0.6); 7.623 (1.2); 7.618 (1.1); 7.607 (1.0); 7.602 (2.4); 7.586 (1.3); 7.580 (1.6); 7.565 (0.8); 7.399 (4.1); 7.378 (6.8); 7.357 (3.3); 7.266 (2.1); 7.131 (4.8); 6.997 (3.2); 6.861 (4.2); 6.855 (4.1); 4.170 (0.4); 3.810 (16.0); 3.537 (0.6); 3.321 (520.2); 3.035 (0.4); 2.861 (0.3); 2.795 (0.4); 2.718 (0.4); 2.675

(6.3); 2.670 (8.4); 2.666 (6.1); 2.541 (12.5); 2.523 (32.0); 2.510 (491.8); 2.506 (943.2); 2.501 (1214.7); 2.497 (877.5); 2.492 (424.1); 2.412 (0.5); 2.332 (5.9); 2.328 (8.0); 2.323 (5.8); 1.235 (0.3); 1.147 (0.8); 0.933 (0.5); 0.146 (1.3); 0.008 (12.2); 0.000 (297.3); −0.009 (10.4); −0.150 (1.3)

I-1-284:
HPLC-MS: log P=2.82; mass (m/z): 374.0 (M+H)$^+$; $^1$H-NMR (400.0 MHz, DMSO-D$_6$): δ=11.493 (7.8); 8.316 (1.2); 8.082 (8.3); 8.076 (8.1); 7.923 (7.9); 7.910 (8.3); 7.646 (1.4); 7.631 (2.9); 7.625 (2.3); 7.615 (1.9); 7.609 (5.7); 7.603 (2.1); 7.593 (2.5); 7.588 (3.7); 7.572 (1.6); 7.448 (15.3); 7.435 (14.5); 7.404 (9.7); 7.383 (16.0); 7.362 (7.3); 6.888 (6.9); 6.882 (6.8); 3.321 (329.2); 2.679 (2.0); 2.675 (4.3); 2.670 (5.8); 2.666 (4.3); 2.661 (2.0); 2.596 (0.3); 2.524 (18.6); 2.510 (332.4); 2.506 (666.1); 2.501 (876.1); 2.497 (627.6); 2.492 (297.5); 2.417 (0.5); 2.337 (2.0); 2.333 (4.1); 2.328 (5.8); 2.324 (4.1); 2.319 (1.9); 1.398 (0.9); 1.336 (0.6); 1.298 (0.4); 1.258 (0.5); 1.250 (0.7); 0.146 (2.3); 0.008 (19.4); 0.000 (544.0); −0.009 (17.4); −0.021 (0.7); −0.150 (2.3)

I-1-285:
HPLC-MS: log P=2.65; mass (m/z): 330.1 (M+H)$^+$; $^1$H-NMR (400.0 MHz, DMSO-D$_6$): δ=11.119 (3.4); 8.758 (5.0); 8.752 (5.2); 8.583 (4.6); 8.577 (4.2); 8.316 (0.4); 8.098 (2.8); 8.092 (2.8); 7.645 (0.5); 7.629 (1.0); 7.623 (0.8); 7.613 (0.7); 7.608 (2.0); 7.602 (0.7); 7.591 (0.8); 7.586 (1.3); 7.571 (0.6); 7.414 (0.5); 7.404 (3.4); 7.383 (5.5); 7.362 (2.6); 7.357 (0.7); 6.975 (5.2); 6.969 (5.1); 3.324 (200.9); 3.310 (1.5); 3.106 (1.7); 3.087 (5.3); 3.068 (5.4); 3.050 (1.8); 2.680 (0.4); 2.675 (0.9); 2.671 (1.3); 2.666 (0.9); 2.662 (0.4); 2.541 (8.9); 2.524 (3.3); 2.519 (5.5); 2.511 (71.7); 2.506 (145.0); 2.502 (190.3); 2.497 (134.9); 2.493 (63.2); 2.338 (0.4); 2.333 (0.9); 2.328 (1.2); 2.324 (0.9); 2.319 (0.4); 2.074 (6.1); 1.287 (7.3); 1.268 (16.0); 1.259 (0.7); 1.249 (7.3); 1.235 (0.6); 0.008 (1.5); 0.000 (45.7); −0.009 (1.3)

I-1-286:
HPLC-MS: log P=2.33; mass (m/z): 352.9 (M+H)$^+$; $^1$H-NMR [CD$_3$CN] 6.98 (d, 1H), 7.05-7.11 (m, 2H), 7.50-7.55 (m, 1H), 7.91-7.92 (m, 1H), 8.03 (d, 1H), 8.39 (d, 1H), 9.43 (br. s, 1H).

I-1-287:
HPLC-MS: log P=2.76; mass (m/z): 386.1 (M+H)$^+$; $^1$H-NMR (400.0 MHz, DMSO-D$_6$): δ=11.415 (10.6); 8.074 (8.2); 8.068 (8.1); 7.851 (1.9); 7.838 (2.2); 7.831 (3.9); 7.818 (3.9); 7.811 (2.7); 7.798 (2.4); 7.634 (3.8); 7.623 (3.2); 7.616 (4.3); 7.607 (5.5); 7.601 (7.1); 7.596 (2.4); 7.585 (5.3); 7.580 (4.6); 7.564 (1.7); 7.497 (7.0); 7.478 (6.3); 7.408 (1.5); 7.399 (9.6); 7.378 (16.0); 7.357 (7.5); 6.905 (15.3); 6.899 (15.2); 4.583 (0.4); 3.512 (3.8); 3.492 (0.6); 3.478 (0.7); 3.466 (0.5); 3.463 (0.4); 3.456 (0.4); 3.424 (1.1); 3.411 (1.2); 3.397 (1.3); 3.339 (1044.4); 3.277 (0.5); 2.995 (0.4); 2.712 (0.5); 2.681 (0.6); 2.676 (1.3); 2.672 (1.8); 2.667 (1.3); 2.663 (0.6); 2.542 (136.0); 2.525 (5.1); 2.520 (7.9); 2.512 (98.7); 2.507 (197.8); 2.502 (262.0); 2.498 (190.3); 2.493 (90.8); 2.368 (0.5); 2.338 (0.6); 2.334 (1.2); 2.329 (1.7); 2.325 (1.2); 2.320 (0.6); 2.074 (0.6); 1.235 (0.8); 0.008 (0.8); 0.000 (25.2); −0.009 (0.7)

I-1-288:
HPLC-MS: log P=2.64; mass (m/z): 415.9 (M+H)$^+$; $^1$H-NMR (400.0 MHz, DMSO-D$_6$): δ=10.883 (10.6); 8.053 (7.9); 8.047 (7.8); 7.922 (15.8); 7.917 (16.0); 7.641 (1.2); 7.625 (2.6); 7.619 (2.2); 7.610 (1.8); 7.604 (5.1); 7.598 (2.1); 7.588 (2.4); 7.583 (3.3); 7.567 (1.5); 7.408 (1.5); 7.399 (8.8); 7.378 (14.3); 7.357 (6.6); 6.909 (16.0); 6.904 (15.9); 6.887 (12.9); 6.881 (12.6); 5.757 (15.4); 3.329 (22.4); 2.512 (19.9); 2.508 (38.2); 2.503 (49.3); 2.499 (35.5); 2.495 (17.0); 2.087 (2.7); 1.990 (1.1); 1.397 (0.7); 1.175 (0.5); 0.008 (1.6); 0.000 (31.5); −0.008 (1.1)

I-1-289:
HPLC-MS: log P=3.19; mass (m/z): 405.1 (M+H)$^+$; $^1$H-NMR (601.6 MHz, DMSO-D$_6$): δ=11.886 (2.7); 8.140 (1.6); 8.136 (1.7); 7.631 (0.5); 7.627 (0.5); 7.617 (1.0); 7.606 (0.5); 7.603 (0.6); 7.410 (1.7); 7.396 (2.9); 7.382 (1.4); 6.980 (2.9); 6.976 (3.0); 3.870 (16.0); 3.358 (196.3); 2.760 (3.9); 2.748 (4.1); 2.553 (49.9); 2.534 (0.4); 2.531 (0.5); 2.528 (0.4); 2.519 (11.2); 2.516 (25.8); 2.513 (37.1); 2.510 (27.8); 2.507 (13.9); 2.046 (0.4); 2.035 (0.7); 2.024 (0.9); 2.013 (0.8); 2.001 (0.4); 0.951 (13.6); 0.940 (13.5)

I-1-290:
HPLC-MS: log P=2.93; mass (m/z): 391.1 (M+H)$^+$; $^1$H-NMR (601.6 MHz, DMSO-D$_6$): δ=11.859 (2.7); 8.138 (1.8); 8.134 (1.8); 7.633 (0.5); 7.629 (0.5); 7.619 (1.0); 7.608 (0.5); 7.605 (0.7); 7.410 (1.8); 7.396 (3.1); 7.382 (1.5); 6.978 (3.0); 6.974 (3.0); 3.869 (16.0); 3.519 (0.4); 3.508 (1.0); 3.496 (1.4); 3.485 (1.0); 3.473 (0.4); 3.349 (170.5); 2.552 (53.4); 2.534 (0.5); 2.531 (0.5); 2.519 (8.2); 2.516 (17.4); 2.513 (24.1); 2.510 (18.0); 2.507 (8.9); 1.285 (14.7); 1.273 (14.7)

I-1-291:
HPLC-MS: log P=2.80; mass (m/z): 373.1 (M+H)$^+$; $^1$H-NMR (400.0 MHz, DMSO-D$_6$): δ=11.653 (2.1); 8.316 (0.3); 8.112 (1.9); 8.106 (1.9); 7.631 (0.6); 7.625 (0.6); 7.615 (0.5); 7.609 (1.3); 7.604 (0.5); 7.593 (0.6); 7.588 (0.8); 7.572 (0.4); 7.406 (2.1); 7.385 (3.5); 7.364 (1.6); 6.912 (3.1); 6.905 (3.1); 3.326 (270.7); 2.680 (0.6); 2.675 (1.2); 2.671 (1.7); 2.666 (1.2); 2.662 (0.6); 2.541 (2.4); 2.524 (5.2); 2.519 (8.2); 2.511 (94.7); 2.506 (189.4); 2.502 (249.0); 2.497 (180.2); 2.493 (87.3); 2.422 (16.0); 2.337 (0.5); 2.333 (1.2); 2.328 (1.6); 2.324 (1.2); 2.319 (0.5); 2.074 (3.4); 1.235 (0.4); 0.008 (1.4); 0.000 (40.9); −0.009 (1.4)

I-1-292:
HPLC-MS: log P=3.33; mass (m/z): 405.1 (M+H)$^+$; $^1$H-NMR (601.6 MHz, DMSO-D$_6$): δ=11.866 (1.1); 8.130 (0.8); 8.126 (0.8); 7.616 (0.4); 7.408 (0.7); 7.393 (1.3); 7.380 (0.6); 6.962 (1.3); 6.958 (1.3); 3.841 (6.8); 3.3754 (253.8); 3.3745 (256.5); 2.552 (20.7); 2.534 (0.4); 2.531 (0.5); 2.528 (0.5); 2.519 (8.5); 2.516 (17.7); 2.513 (24.3); 2.510 (18.0); 2.507 (8.8); 1.401 (16.0)

I-1-293:
HPLC-MS: log P=4.15; mass (m/z): 394.1 (M+H)$^+$; $^1$H-NMR (601.6 MHz, DMSO-D$_6$): δ=11.298 (0.9); 8.087 (0.8); 8.084 (0.8); 7.611 (0.5); 7.396 (0.8); 7.382 (1.4); 7.368 (0.7); 6.923 (0.8); 6.920 (0.8); 3.843 (5.2); 3.340 (158.7); 2.542 (10.3); 2.523 (0.3); 2.520 (0.4); 2.517 (0.4); 2.508 (13.3); 2.505 (29.0); 2.502 (40.4); 2.499 (29.7); 2.497 (14.6); 1.352 (16.0)

I-1-294:
HPLC-MS: log P=2.34; mass (m/z): 368.1 (M+H)$^+$; $^1$H-NMR (601.6 MHz, DMSO-D$_6$): δ=11.537 (3.0); 8.107 (3.1); 8.104 (3.1); 7.646 (0.5); 7.636 (1.2); 7.632 (1.1); 7.621 (2.1); 7.611 (1.1); 7.607 (1.4); 7.597 (0.6); 7.408 (3.5); 7.393 (6.2); 7.380 (3.0); 7.109 (1.1); 7.018 (2.4); 6.941 (2.6); 6.938 (2.6); 6.927 (1.3); 3.858 (15.0); 3.349 (973.1); 2.628 (0.7); 2.625 (1.0); 2.622 (0.8); 2.552 (19.9); 2.534 (1.5); 2.531 (1.9); 2.528 (1.8); 2.519 (53.0); 2.516 (118.1); 2.513 (166.3); 2.510 (120.3); 2.507 (57.5); 2.400 (0.8); 2.397 (1.1); 2.394 (0.8); 2.303 (0.5); 2.270 (16.0); 1.246 (0.6); 0.010 (0.4)

I-1-295:
HPLC-MS: log P=2.25; mass (m/z): 370.0 (M+H)$^+$; $^1$H-NMR (400.0 MHz, CD$_3$CN): δ=9.479 (1.6); 9.444 (13.2); 9.182 (16.0); 7.788 (7.7); 7.785 (7.4); 7.783 (7.4);

7.559 (1.3); 7.550 (0.4); 7.543 (2.8); 7.537 (2.5); 7.528 (1.9); 7.522 (5.6); 7.516 (2.0); 7.506 (2.7); 7.500 (3.2); 7.485 (1.6); 7.427 (0.5); 7.420 (0.5); 7.241 (0.4); 7.236 (0.6); 7.227 (2.2); 7.218 (8.3); 7.205 (2.9); 7.197 (13.9); 7.188 (1.8); 7.176 (7.1); 7.167 (1.4); 6.993 (10.7); 6.986 (10.7); 6.972 (1.2); 6.966 (1.1); 5.447 (12.0); 4.085 (0.4); 4.067 (1.3); 4.050 (1.3); 4.032 (0.4); 2.147 (20.3); 2.143 (17.2); 2.107 (0.4); 1.971 (5.9); 1.964 (2.2); 1.958 (2.7); 1.952 (20.5); 1.946 (38.1); 1.940 (53.1); 1.933 (36.7); 1.927 (19.0); 1.436 (1.9); 1.383 (0.3); 1.372 (8.7); 1.340 (1.5); 1.300 (0.4); 1.285 (2.2); 1.277 (9.3); 1.221 (1.6); 1.217 (0.4); 1.203 (3.0); 1.185 (1.5); 0.008 (0.7); 0.000 (17.7); −0.009 (0.6)

I-1-296:
HPLC-MS: log P=3.14; mass (m/z): 422.0 (M+H)$^+$; $^1$H-NMR (400.0 MHz, DMSO-D$_6$): δ=11.952 (0.3); 11.701 (11.4); 8.316 (0.6); 8.112 (8.3); 8.106 (8.4); 8.090 (2.3); 8.086 (2.5); 8.069 (2.8); 8.065 (2.8); 8.060 (2.6); 8.047 (2.3); 7.642 (1.3); 7.626 (2.8); 7.620 (2.3); 7.610 (1.9); 7.604 (5.6); 7.599 (2.1); 7.588 (2.5); 7.583 (3.6); 7.567 (1.6); 7.404 (9.5); 7.383 (16.0); 7.362 (7.3); 7.280 (0.3); 6.910 (14.6); 6.904 (14.6); 5.756 (0.5); 3.323 (119.2); 3.021 (0.5); 2.829 (0.5); 2.676 (1.0); 2.671 (1.4); 2.667 (1.0); 2.541 (0.8); 2.524 (3.7); 2.511 (80.1); 2.507 (161.9); 2.502 (212.2); 2.498 (150.7); 2.493 (71.2); 2.333 (1.0); 2.329 (1.4); 2.324 (1.0); 2.179 (0.5); 1.259 (0.5); 1.236 (7.0); 0.854 (0.7); 0.146 (0.3); 0.008 (2.6); 0.000 (74.7); −0.008 (2.4)

I-1-297:
HPLC-MS: log P=2.76; mass (m/z): 319.1 (M+H)$^+$; $^1$H-NMR (400.0 MHz, DMSO-D$_6$): δ=11.180 (3.1); 8.075 (2.9); 8.069 (2.8); 7.648 (0.4); 7.632 (0.9); 7.626 (0.8); 7.616 (0.7); 7.611 (1.9); 7.605 (0.7); 7.595 (0.9); 7.589 (1.2); 7.574 (0.5); 7.402 (3.1); 7.381 (5.2); 7.360 (2.4); 6.894 (3.7); 6.887 (3.6); 3.325 (92.7); 2.675 (0.5); 2.671 (0.7); 2.666 (0.5); 2.541 (0.5); 2.524 (1.8); 2.510 (42.2); 2.506 (82.7); 2.502 (106.4); 2.497 (75.8); 2.493 (35.9); 2.399 (15.2); 2.333 (0.5); 2.329 (0.7); 2.324 (0.5); 2.071 (16.0); 1.989 (0.3); 0.000 (42.0); −0.008 (1.4)

I-1-298:
HPLC-MS: log P=2.76; mass (m/z): 398.0 (M+H)$^+$; $^1$H-NMR (601.6 MHz, DMSO-D$_6$): δ=11.235 (2.3); 8.102 (2.1); 8.099 (2.1); 7.647 (0.3); 7.637 (0.7); 7.633 (0.7); 7.623 (1.4); 7.612 (0.7); 7.608 (0.9); 7.598 (0.4); 7.407 (2.3); 7.393 (4.1); 7.379 (2.0); 6.940 (1.9); 6.936 (1.9); 3.881 (14.2); 3.354 (657.5); 2.628 (0.3); 2.625 (0.5); 2.622 (0.3); 2.552 (9.2); 2.534 (0.7); 2.531 (0.8); 2.528 (0.8); 2.519 (23.5); 2.516 (52.2); 2.513 (73.6); 2.510 (53.9); 2.507 (25.7); 2.397 (0.5); 2.394 (0.4); 2.168 (16.0); 0.010 (0.5)

I-1-299:
HPLC-MS: log P=2.84; mass (m/z): 398.0 (M+H)$^+$; $^1$H-NMR (601.6 MHz, DMSO-D$_6$): δ=11.354 (4.1); 8.108 (3.4); 8.105 (3.4); 7.672 (7.7); 7.648 (0.5); 7.638 (1.2); 7.634 (1.1); 7.623 (2.1); 7.613 (1.2); 7.609 (1.4); 7.599 (0.6); 7.408 (3.5); 7.394 (6.2); 7.381 (3.0); 6.947 (3.8); 6.943 (3.8); 4.294 (1.6); 4.282 (5.1); 4.270 (5.2); 4.258 (1.8); 3.355 (364.0); 3.353 (606.6); 3.005 (0.9); 2.625 (0.5); 2.552 (54.1); 2.534 (0.8); 2.531 (1.0); 2.528 (1.0); 2.519 (27.5); 2.516 (59.1); 2.513 (81.5); 2.510 (59.6); 2.507 (29.0); 2.397 (0.5); 1.367 (7.4); 1.355 (16.0); 1.343 (7.5); 1.246 (0.4); 0.010 (0.5)

I-1-300:
HPLC-MS: log P=3.15; mass (m/z): 412.0 (M+H)$^+$; $^1$H-NMR (601.6 MHz, DMSO-D$_6$): δ=11.267 (2.3); 8.100 (2.0); 8.097 (2.0); 7.648 (0.3); 7.638 (0.7); 7.634 (0.7); 7.623 (1.4); 7.613 (0.7); 7.609 (0.9); 7.599 (0.4); 7.407 (2.2); 7.393 (3.9); 7.379 (1.9); 6.939 (2.1); 6.935 (2.1); 4.226 (1.0); 4.214 (2.9); 4.202 (3.0); 4.190 (1.0); 3.351 (498.7); 2.625 (0.4); 2.552 (3.9); 2.534 (0.6); 2.531 (0.8); 2.519 (21.5); 2.516 (47.9); 2.513 (67.3); 2.510 (48.7); 2.507 (23.6); 2.397 (0.4); 2.181 (16.0); 1.346 (4.7); 1.334 (10.3); 1.322 (4.7); 0.010 (0.5)

I-1-301:
HPLC-MS: log P=2.37; mass (m/z): 384.0 (M+H)$^+$; $^1$H-NMR (400.0 MHz, DMSO-D$_6$): δ=10.334 (2.2); 8.316 (0.7); 8.109 (5.4); 8.042 (1.7); 8.036 (1.7); 7.620 (0.6); 7.615 (0.5); 7.605 (0.4); 7.599 (1.2); 7.593 (0.5); 7.582 (0.5); 7.577 (0.8); 7.562 (0.3); 7.396 (2.0); 7.375 (3.3); 7.354 (1.6); 6.880 (2.3); 6.873 (2.3); 3.925 (16.0); 3.324 (216.8); 2.675 (1.1); 2.671 (1.5); 2.666 (1.1); 2.541 (1.0); 2.524 (3.9); 2.511 (88.5); 2.506 (180.0); 2.502 (236.5); 2.497 (168.4); 2.493 (79.2); 2.333 (1.1); 2.328 (1.5); 2.324 (1.1); 0.146 (0.8); 0.008 (6.3); 0.000 (174.5); −0.009 (5.7); −0.150 (0.7)

I-1-302:
HPLC-MS: log P=2.50; mass (m/z): 382.0 (M+H)$^+$; $^1$H-NMR (601.6 MHz, DMSO-D$_6$): δ=11.319 (2.5); 8.110 (2.2); 8.106 (2.3); 7.657 (5.0); 7.648 (0.5); 7.638 (0.8); 7.634 (0.7); 7.623 (1.5); 7.613 (0.8); 7.609 (1.0); 7.599 (0.4); 7.409 (2.5); 7.395 (4.3); 7.381 (2.1); 6.949 (2.2); 6.945 (2.3); 3.949 (16.0); 3.351 (381.4); 3.005 (0.7); 2.625 (0.3); 2.552 (35.7); 2.534 (0.6); 2.531 (0.7); 2.528 (0.6); 2.519 (16.5); 2.516 (36.9); 2.513 (52.2); 2.510 (38.7); 2.507 (18.8); 2.397 (0.3)

I-1-303:
HPLC-MS: log P=3.37; mass (m/z): 452.0 (M+H)$^+$; $^1$H-NMR (601.6 MHz, DMSO-D$_6$): δ=11.645 (3.6); 8.129 (2.6); 8.125 (2.6); 7.643 (0.4); 7.632 (0.8); 7.629 (0.8); 7.618 (1.5); 7.608 (0.8); 7.604 (0.9); 7.594 (0.4); 7.403 (2.5); 7.389 (4.3); 7.375 (2.1); 6.950 (4.0); 6.946 (4.0); 4.024 (16.0); 3.340 (237.0); 2.995 (1.4); 2.614 (0.4); 2.542 (95.9); 2.524 (0.6); 2.520 (0.8); 2.517 (0.7); 2.509 (21.2); 2.506 (47.7); 2.503 (67.6); 2.499 (48.5); 2.496 (23.1); 2.387 (0.4); 2.384 (0.3); 0.000 (0.7)

I-1-304:
HPLC-MS: log P=3.38; mass (m/z): 398.0 (M+H)$^+$; $^1$H-NMR (400.0 MHz, DMSO-D$_6$): δ=10.720 (3.2); 8.043 (2.7); 8.037 (2.7); 7.635 (0.4); 7.619 (0.8); 7.614 (0.8); 7.603 (0.6); 7.598 (1.7); 7.592 (0.7); 7.582 (0.8); 7.577 (1.1); 7.561 (0.5); 7.393 (3.0); 7.372 (4.9); 7.351 (2.2); 6.893 (2.2); 6.887 (2.2); 5.757 (0.8); 3.327 (95.9); 2.676 (0.3); 2.671 (0.4); 2.667 (0.3); 2.506 (52.2); 2.502 (68.5); 2.497 (50.3); 2.395 (15.8); 2.333 (0.4); 2.329 (0.5); 2.324 (0.4); 2.248 (16.0); 2.232 (0.8); 0.008 (0.8); 0.000 (17.4); −0.008 (0.7)

I-1-305:
HPLC-MS: log P=2.61; mass (m/z): 385.9 (M+H)$^+$; $^1$H-NMR (400.0 MHz, DMSO-D$_6$): δ=11.108 (9.1); 8.316 (0.6); 8.212 (11.4); 8.203 (11.7); 8.053 (8.5); 8.047 (8.5); 7.773 (14.7); 7.765 (14.0); 7.638 (1.3); 7.623 (2.9); 7.617 (2.4); 7.607 (2.0); 7.601 (5.7); 7.596 (2.2); 7.585 (2.6); 7.580 (3.7); 7.564 (1.6); 7.399 (9.7); 7.377 (16.0); 7.357 (7.2); 6.922 (7.2); 6.917 (7.2); 5.757 (1.0); 4.056 (0.4); 4.038 (1.2); 4.020 (1.2); 4.002 (0.4); 3.327 (323.2); 2.689 (1.0); 2.675 (1.1); 2.671 (1.5); 2.666 (1.1); 2.541 (1.1); 2.524 (5.0); 2.511 (86.5); 2.506 (173.0); 2.502 (227.5); 2.497 (164.2); 2.493 (79.4); 2.333 (1.0); 2.329 (1.4); 2.324 (1.1); 1.989 (5.2); 1.398 (1.0); 1.351 (0.4); 1.259 (0.4); 1.233 (0.6); 1.193 (1.4); 1.175 (2.7); 1.157 (1.4); 0.008 (2.7); 0.000 (66.0); −0.008 (2.5)

I-1-306:
HPLC-MS: log P=3.11; mass (m/z): 388.0 (M+H)$^+$; $^1$H-NMR (601.6 MHz, DMSO-D$_6$): δ=11.612 (3.2); 8.121 (2.6); 8.117 (2.8); 7.943 (1.0); 7.847 (2.4); 7.752 (1.2); 7.651

(0.4); 7.641 (0.8); 7.637 (0.8); 7.626 (1.5); 7.616 (0.8); 7.612 (1.0); 7.602 (0.4); 7.409 (2.5); 7.395 (4.5); 7.381 (2.1); 6.931 (3.4); 6.927 (3.5); 3.409 (2.1); 3.406 (2.9); 3.385 (2693.6); 3.359 (2.2); 2.625 (0.8); 2.552 (8.8); 2.534 (1.2); 2.531 (1.5); 2.528 (1.5); 2.519 (43.2); 2.516 (94.9); 2.513 (133.7); 2.510 (99.7); 2.507 (49.2); 2.2397 (0.8); 2.275 (16.0); 1.243 (1.0); 0.008 (0.5)

I-1-307:
HPLC-MS: log P=2.78; mass (m/z): 352.1 (M+H)$^+$; $^1$H-NMR (400.0 MHz, CD$_3$CN): δ=9.141 (0.8); 7.772 (1.9); 7.769 (1.8); 7.766 (1.9); 7.552 (0.3); 7.536 (0.7); 7.530 (0.7); 7.520 (0.4); 7.515 (1.5); 7.509 (0.5); 7.499 (0.7); 7.493 (0.9); 7.478 (0.4); 7.222 (0.4); 7.218 (0.6); 7.213 (2.3); 7.200 (0.5); 7.192 (3.8); 7.183 (0.5); 7.171 (1.9); 7.162 (0.4); 6.987 (1.8); 6.981 (1.8); 4.014 (16.0); 2.210 (17.3); 2.177 (0.7); 2.156 (4.7); 1.959 (0.4); 1.953 (3.6); 1.947 (6.7); 1.941 (9.5); 1.935 (6.6); 1.929 (3.5); 1.371 (1.0); 1.276 (1.1); 0.008 (0.5); 0.000 (12.8); −0.009 (0.6)

I-1-308:
HPLC-MS: log P=2.61; mass (m/z): 352.1 (M+H)$^+$; $^1$H-NMR (601.6 MHz, DMSO-D$_6$): δ=10.355 (3.9); 8.180 (10.0); 8.055 (2.7); 8.051 (2.7); 7.633 (0.4); 7.623 (0.9); 7.619 (0.8); 7.612 (0.6); 7.608 (1.7); 7.605 (0.6); 7.598 (0.8); 7.594 (1.1); 7.584 (0.4); 7.400 (2.9); 7.386 (4.9); 7.372 (2.5); 6.899 (2.9); 6.895 (2.9); 4.217 (2.0); 4.205 (6.1); 4.193 (6.2); 4.181 (2.0); 3.386 (0.3); 3.384 (0.3); 3.379 (0.4); 3.373 (0.9); 3.359 (357.8); 3.343 (0.4); 3.339 (0.7); 3.337 (0.7); 2.552 (28.7); 2.534 (0.4); 2.531 (0.5); 2.528 (0.5); 2.519 (12.4); 2.516 (27.6); 2.513 (38.8); 2.510 (27.9); 2.507 (12.9); 1.446 (7.3); 1.434 (16.0); 1.422 (7.4)

I-1-309:
HPLC-MS: log P=3.15; mass (m/z): 366.1 (M+H)$^+$; $^1$H-NMR (601.6 MHz, DMSO-D$_6$): δ=11.237 (2.3); 8.102 (2.2); 8.098 (2.2); 7.649 (0.3); 7.638 (0.7); 7.634 (0.7); 7.624 (1.4); 7.613 (0.7); 7.610 (0.8); 7.599 (0.4); 7.408 (2.3); 7.394 (4.0); 7.380 (1.9); 6.938 (1.9); 6.934 (1.9); 4.239 (1.0); 4.227 (3.1); 4.215 (3.1); 4.203 (1.0); 3.346 (381.3); 3.006 (1.7); 2.625 (0.4); 2.552 (81.0); 2.534 (0.7); 2.531 (0.8); 2.528 (0.8); 2.519 (22.8); 2.516 (50.5); 2.513 (71.5); 2.510 (52.9); 2.507 (25.4); 2.397 (0.4); 2.184 (16.0); 1.347 (4.8); 1.335 (10.4); 1.323 (4.8); 1.246 (0.3); 0.011 (0.5)

I-1-310:
HPLC-MS: log P=3.28; mass (m/z): 411.1 (M+H)$^+$; $^1$H-NMR (601.6 MHz, DMSO-D$_6$): δ=11.875 (3.1); 8.147 (2.1); 8.143 (2.1); 7.637 (0.7); 7.633 (0.6); 7.622 (1.2); 7.612 (0.7); 7.608 (0.8); 7.598 (0.3); 7.408 (2.1); 7.394 (3.6); 7.380 (1.8); 6.961 (3.6); 6.957 (3.6); 4.900 (0.4); 4.889 (1.2); 4.878 (1.6); 4.867 (1.2); 4.856 (0.4); 3.364 (0.4); 3.337 (831.4); 2.995 (1.4); 2.617 (0.6); 2.614 (0.8); 2.611 (0.6); 2.542 (64.8); 2.523 (1.4); 2.520 (1.7); 2.517 (1.7); 2.508 (42.8); 2.505 (93.3); 2.502 (129.3); 2.499 (92.8); 2.496 (43.5); 2.390 (0.6); 2.386 (0.8); 2.383 (0.6); 1.477 (15.9); 1.467 (16.0); 1.235 (0.5); 0.000 (1.3)

I-1-311:
HPLC-MS: log P=2.46; mass (m/z): 338.0 (M+H)$^+$; $^1$H-NMR (601.6 MHz, DMSO-D$_6$): δ=11.297 (2.2); 8.110 (2.2); 8.106 (2.2); 7.665 (4.3); 7.648 (0.4); 7.638 (0.8); 7.634 (0.7); 7.623 (1.4); 7.613 (0.8); 7.609 (0.9); 7.599 (0.4); 7.409 (2.4); 7.395 (4.1); 7.381 (2.0); 6.946 (1.9); 6.942 (1.9); 3.949 (16.0); 3.353 (587.8); 3.005 (0.6); 2.625 (0.5); 2.622 (0.3); 2.552 (32.7); 2.534 (0.7); 2.531 (0.8); 2.528 (0.8); 2.519 (26.8); 2.516 (56.6); 2.513 (77.3); 2.510 (56.3); 2.507 (27.1); 2.400 (0.4); 2.397 (0.5); 2.394 (0.4)

I-1-312:
HPLC-MS: log P=2.70; mass (m/z): 383.0 (M+H)$^+$; $^1$H-NMR (400.0 MHz, DMSO-D$_6$): δ=11.784 (0.3); 11.027 (2.6); 8.315 (0.4); 8.080 (1.9); 8.074 (1.9); 7.631 (0.7); 7.625 (0.6); 7.615 (0.5); 7.609 (1.3); 7.604 (0.6); 7.593 (0.6); 7.588 (0.8); 7.572 (0.4); 7.414 (0.7); 7.405 (2.2); 7.384 (3.6); 7.363 (1.7); 6.955 (0.4); 6.949 (0.4); 6.900 (2.1); 6.894 (2.0); 5.756 (0.8); 4.230 (16.0); 4.078 (1.9); 3.321 (134.4); 2.675 (0.9); 2.671 (1.1); 2.666 (0.8); 2.541 (0.7); 2.523 (3.8); 2.510 (67.6); 2.506 (130.2); 2.502 (168.1); 2.497 (120.8); 2.493 (58.3); 2.333 (0.8); 2.328 (1.1); 2.324 (0.8); 1.234 (0.4); 0.008 (3.2); 0.000 (70.6); −0.009 (2.4); −0.150 (0.3)

I-1-313:
HPLC-MS: log P=3.68; mass (m/z): 380.1 (M+H)$^+$; $^1$H-NMR (601.6 MHz, DMSO-D$_6$): δ=11.222 (2.5); 8.101 (2.4); 8.098 (2.3); 7.647 (0.4); 7.636 (0.9); 7.632 (0.8); 7.622 (1.5); 7.612 (0.8); 7.608 (1.0); 7.598 (0.4); 7.407 (2.5); 7.393 (4.5); 7.379 (2.2); 6.936 (2.0); 6.933 (2.0); 3.893 (16.0); 3.351 (861.8); 2.628 (0.5); 2.625 (0.7); 2.553 (21.2); 2.544 (2.8); 2.532 (5.9); 2.519 (43.2); 2.516 (84.1); 2.513 (113.6); 2.510 (82.3); 2.507 (39.8); 2.397 (0.7); 1.667 (0.3); 1.654 (1.6); 1.642 (3.0); 1.630 (3.1); 1.617 (1.7); 1.605 (0.4); 1.246 (0.6); 0.951 (4.5); 0.939 (9.0); 0.927 (4.3); 0.011 (0.8)

I-1-314:
HPLC-MS: log P=3.32; mass (m/z): 380.1 (M+H)$^+$; $^1$H-NMR (400.0 MHz, DMSO-D$_6$): δ=10.247 (2.4); 8.040 (1.9); 8.034 (1.8); 7.619 (0.6); 7.614 (0.5); 7.604 (0.4); 7.598 (1.2); 7.592 (0.5); 7.582 (0.6); 7.577 (0.8); 7.561 (0.3); 7.396 (2.0); 7.375 (3.4); 7.354 (1.5); 6.880 (2.4); 6.874 (2.4); 5.758 (0.9); 3.883 (16.0); 3.327 (27.1); 2.710 (1.7); 2.692 (2.9); 2.673 (2.0); 2.511 (13.2); 2.507 (26.1); 2.502 (33.9); 2.498 (24.2); 2.493 (11.5); 1.614 (1.1); 1.595 (2.0); 1.576 (2.0); 1.558 (1.1); 0.945 (3.6); 0.927 (7.5); 0.908 (3.2); 0.008 (0.3); 0.000 (8.5)

I-1-315:
HPLC-MS: log P=3.05; mass (m/z): 366.0 (M+H)$^+$; $^1$H-NMR (400.0 MHz, DMSO-D$_6$): δ=10.341 (4.9); 8.170 (11.5); 8.049 (3.7); 8.043 (3.8); 7.636 (0.6); 7.621 (1.2); 7.615 (1.1); 7.605 (0.8); 7.599 (2.4); 7.594 (1.0); 7.583 (1.1); 7.578 (1.6); 7.562 (0.7); 7.398 (4.1); 7.377 (6.9); 7.356 (3.1); 6.890 (4.4); 6.884 (4.4); 4.132 (4.0); 4.115 (7.9); 4.097 (4.1); 3.327 (30.2); 2.511 (18.8); 2.507 (37.7); 2.503 (49.7); 2.498 (36.5); 1.895 (0.5); 1.876 (2.5); 1.858 (4.9); 1.840 (5.0); 1.822 (2.6); 1.804 (0.6); 0.865 (7.8); 0.847 (16.0); 0.828 (7.2); 0.008 (0.5); 0.000 (12.0); −0.008 (0.5)

I-1-316:
HPLC-MS: log P=3.24; mass (m/z): 366.1 (M+H)$^+$; $^1$H-NMR (601.6 MHz, DMSO-D$_6$): δ=11.213 (2.2); 8.100 (2.1); 8.096 (2.1); 7.647 (0.4); 7.636 (0.8); 7.632 (0.7); 7.626 (0.6); 7.622 (1.5); 7.612 (0.7); 7.608 (0.9); 7.597 (0.4); 7.406 (2.4); 7.392 (4.1); 7.378 (2.1); 6.936 (1.7); 6.932 (1.7); 3.892 (16.0); 3.361 (437.6); 3.358 (597.8); 2.628 (0.4); 2.625 (0.5); 2.622 (0.4); 2.594 (1.3); 2.581 (4.2); 2.569 (4.3); 2.556 (1.5); 2.552 (4.2); 2.534 (0.8); 2.531 (1.0); 2.528 (1.0); 2.519 (25.8); 2.516 (56.6); 2.513 (78.4); 2.510 (56.2); 2.507 (26.2); 2.400 (0.4); 2.397 (0.5); 2.394 (0.4); 2.394 (0.4); 1.245 (0.4); 1.210 (5.4); 1.198 (11.6); 1.185 (5.4); 0.010 (0.6)

I-1-317:
HPLC-MS: log P=3.37; mass (m/z): 447.1 (M+H)$^+$; $^1$H-NMR (601.6 MHz, DMSO-D$_6$): δ=12.168 (3.0); 8.170 (2.7); 8.166 (2.7); 7.655 (0.4); 7.644 (0.8); 7.630 (1.5); 7.616 (0.9); 7.606 (0.4); 7.419 (2.4); 7.405 (4.2); 7.391 (2.0); 6.972 (3.5); 6.968 (3.5); 4.145 (16.0); 3.428 (1.0); 3.418 (0.6); 3.386 (3294.8); 3.385 (2796.6); 3.358 (5.6); 3.339 (2.1); 3.296 (0.7); 2.628 (0.9); 2.625 (1.2); 2.622 (0.9); 2.552 (101.5); 2.534 (2.1); 2.531 (2.6); 2.528 (2.5); 2.519 (62.7); 2.516 (136.0); 2.513 (190.4); 2.510 (138.3);

2.507 (65.1); 2.436 (0.4); 2.397 (1.2); 2.394 (0.9); 2.310 (0.4); 1.266 (0.4); 1.243 (1.2); 0.008 (1.1)

I-1-318:
HPLC-MS: log P=2.98; mass (m/z): 397.1 (M+H)$^+$;
$^1$H-NMR (601.6 MHz, DMSO-D$_6$): δ=12.125 (3.0); 8.303 (1.3); 8.150 (2.7); 8.147 (2.7); 7.649 (0.4); 7.638 (0.8); 7.634 (0.8); 7.624 (1.5); 7.613 (0.9); 7.610 (1.0); 7.599 (0.4); 7.406 (2.4); 7.392 (4.3); 7.378 (2.1); 6.971 (3.4); 6.967 (3.4); 4.130 (16.0); 3.395 (2352.3); 2.625 (0.6); 2.622 (0.4); 2.552 (7.5); 2.534 (0.9); 2.531 (1.2); 2.528 (1.1); 2.519 (32.1); 2.516 (70.3); 2.513 (97.0); 2.510 (69.9); 2.507 (32.5); 2.400 (0.5); 2.397 (0.6); 1.241 (1.5); 0.861 (0.4); 0.005 (0.5)

I-1-319:
HPLC-MS: log P=2.68; mass (m/z): 348.0 (M+H)$^+$;
$^1$H-NMR (400.0 MHz, DMSO-D$_6$): δ=11.731 (5.2); 8.316 (0.4); 8.111 (8.7); 8.108 (7.0); 8.105 (8.6); 7.650 (1.4); 7.634 (3.1); 7.628 (2.3); 7.618 (2.0); 7.613 (6.0); 7.607 (2.1); 7.596 (2.5); 7.591 (3.8); 7.575 (1.7); 7.417 (1.5); 7.413 (2.7); 7.408 (9.9); 7.395 (1.9); 7.387 (16.0); 7.366 (7.5); 7.361 (2.1); 6.945 (5.6); 6.940 (5.5); 5.757 (7.3); 3.322 (215.2); 2.675 (2.3); 2.671 (2.3); 2.666 (2.1); 2.662 (2.6); 2.655 (2.4); 2.651 (1.8); 2.642 (3.9); 2.629 (2.3); 2.622 (2.2); 2.609 (1.1); 2.541 (0.6); 2.524 (5.3); 2.519 (8.5); 2.511 (103.2); 2.506 (208.2); 2.502 (277.1); 2.497 (200.7); 2.493 (95.4); 2.337 (0.7); 2.333 (1.4); 2.328 (1.9); 2.324 (1.4); 2.319 (0.6); 1.351 (0.3); 1.336 (0.9); 1.298 (0.9); 1.259 (1.3); 1.249 (1.4); 1.243 (1.9); 1.230 (5.8); 1.224 (10.1); 1.217 (6.2); 1.209 (5.2); 1.202 (10.2); 1.195 (8.0); 1.188 (9.3); 1.182 (10.5); 1.176 (10.4); 1.170 (6.3); 1.156 (1.4); 1.147 (0.6); 0.008 (2.7); 0.000 (81.8); −0.009 (2.5)

I-1-320:
HPLC-MS: log P=2.20; mass (m/z): 336.1 (M+H)$^+$;
$^1$H-NMR (601.6 MHz, DMSO-D$_6$): δ=10.155 (2.5); 8.042 (1.8); 8.038 (1.8); 7.621 (0.6); 7.617 (0.5); 7.607 (1.1); 7.596 (0.6); 7.593 (0.7); 7.397 (1.8); 7.383 (3.1); 7.369 (1.5); 6.875 (2.6); 6.871 (2.6); 3.806 (16.0); 3.362 (756.0); 3.333 (0.5); 3.005 (0.5); 2.625 (0.4); 2.552 (27.0); 2.534 (0.6); 2.531 (0.7); 2.528 (0.6); 2.519 (18.6); 2.516 (40.9); 2.513 (57.6); 2.510 (42.5); 2.507 (20.3); 2.397 (0.4); 2.263 (8.5); 2.262 (8.3); 1.245 (1.2)

I-1-321:
HPLC-MS: log P=2.27; mass (m/z): 322.1 (M+H)$^+$;
$^1$H-NMR (601.6 MHz, DMSO-D$_6$): δ=11.051 (2.4); 8.099 (2.3); 8.095 (2.3); 7.645 (0.4); 7.635 (0.7); 7.631 (0.7); 7.623 (3.0); 7.616 (2.9); 7.610 (0.8); 7.606 (0.8); 7.596 (0.4); 7.408 (2.2); 7.394 (4.0); 7.380 (1.9); 6.922 (1.8); 6.918 (1.8); 3.977 (16.0); 3.391 (0.3); 3.353 (724.3); 2.625 (0.6); 2.552 (4.9); 2.534 (0.8); 2.531 (1.0); 2.528 (1.0); 2.519 (30.3); 2.516 (64.8); 2.513 (90.0); 2.510 (66.1); 2.507 (31.9); 2.397 (0.6); 1.245 (0.9); 0.010 (0.5)

I-1-322:
HPLC-MS: log P=2.80; mass (m/z): 386.1 (M+H)$^+$;
$^1$H-NMR (400.0 MHz, DMSO-D$_6$): δ=11.350 (11.5); 8.068 (8.6); 8.062 (8.5); 8.037 (0.5); 8.027 (0.5); 8.015 (0.5); 7.809 (3.6); 7.796 (3.8); 7.788 (5.1); 7.781 (5.9); 7.775 (9.8); 7.758 (5.1); 7.752 (5.3); 7.668 (2.8); 7.661 (2.6); 7.647 (5.3); 7.640 (5.1); 7.622 (4.6); 7.606 (2.4); 7.600 (6.2); 7.595 (2.5); 7.585 (2.8); 7.579 (4.0); 7.563 (1.9); 7.399 (9.8); 7.378 (16.0); 7.357 (7.5); 7.340 (0.8); 7.319 (1.0); 7.298 (0.6); 6.917 (15.2); 6.911 (15.5); 6.700 (0.9); 6.694 (1.0); 4.578 (0.4); 3.511 (4.0); 3.491 (0.4); 3.477 (0.5); 3.465 (0.5); 3.423 (0.7); 3.411 (0.8); 3.399 (0.6); 3.330 (1984.0); 3.294 (3.0); 3.265 (1.1); 3.207 (0.5); 2.995 (0.3); 2.680 (1.7); 2.675 (2.6); 2.671 (4.9); 2.666 (3.5); 2.662 (1.7); 2.541 (30.6); 2.524 (14.8); 2.519 (23.9); 2.511 (268.4); 2.506 (536.6); 2.502 (711.5); 2.497 (517.2); 2.493 (247.3); 2.338 (1.6); 2.333 (3.4); 2.329 (4.7); 2.324 (3.3); 2.319 (1.5); 2.289 (0.4); 2.074 (2.2); 1.336 (0.5); 1.298 (0.5); 1.258 (0.7); 1.249 (0.8); 1.235 (2.0); 1.147 (0.5); 0.008 (0.9); 0.000 (21.7); −0.009 (0.6)

I-1-323:
HPLC-MS: log P=3.47; mass (m/z): 472.1 (M+H)$^+$;
$^1$H-NMR (601.6 MHz, DMSO-D$_6$): δ=11.302 (2.6); 8.100 (2.0); 8.097 (2.0); 7.636 (0.8); 7.632 (0.8); 7.626 (5.8); 7.622 (1.5); 7.612 (0.7); 7.608 (0.8); 7.597 (0.3); 7.409 (2.0); 7.395 (3.6); 7.381 (1.7); 6.931 (2.4); 6.927 (2.4); 4.094 (3.4); 4.082 (3.5); 3.369 (0.4); 3.347 (442.3); 2.625 (0.4); 2.552 (48.7); 2.534 (0.7); 2.531 (0.9); 2.528 (0.8); 2.519 (23.5); 2.516 (51.1); 2.513 (70.8); 2.510 (50.9); 2.507 (24.3); 2.400 (0.3); 2.397 (0.5); 2.394 (0.3); 2.100 (0.4); 2.088 (0.8); 2.077 (1.1); 2.066 (0.9); 2.054 (0.5); 1.246 (0.3); 0.830 (16.0); 0.819 (16.0); 0.011 (0.5)

I-1-324:
HPLC-MS: log P=2.46; mass (m/z): 430.0 (M+H)$^+$;
$^1$H-NMR (601.6 MHz, DMSO-D$_6$): δ=11.277 (2.7); 8.106 (2.3); 7.647 (0.4); 7.637 (0.9); 7.633 (0.8); 7.622 (1.6); 7.608 (6.9); 7.598 (0.5); 7.408 (2.6); 7.394 (4.5); 7.380 (2.2); 6.949 (2.3); 6.945 (2.3); 3.950 (16.0); 3.355 (676.1); 3.354 (837.4); 2.628 (0.6); 2.625 (0.8); 2.622 (0.6); 2.552 (12.6); 2.534 (1.2); 2.531 (1.5); 2.528 (1.5); 2.519 (44.2); 2.516 (96.6); 2.513 (134.8); 2.510 (97.2); 2.507 (46.3); 2.400 (0.6); 2.397 (0.8); 2.394 (0.6); 1.245 (0.3); 0.010 (0.9)

I-1-325:
HPLC-MS: log P=3.11; mass (m/z): 458.1 (M+H)$^+$;
$^1$H-NMR (601.6 MHz, DMSO-D$_6$): δ=11.301 (4.3); 8.102 (3.3); 8.099 (3.3); 7.647 (0.5); 7.637 (1.2); 7.633 (1.2); 7.622 (10.2); 7.612 (1.3); 7.608 (1.4); 7.598 (0.6); 7.409 (3.4); 7.409 (3.4); 7.394 (6.0); 7.381 (2.9); 6.939 (3.8); 6.935 (3.9); 4.224 (2.9); 4.212 (5.6); 4.201 (3.0); 3.349 (680.2); 2.625 (0.6); 2.552 (18.8); 2.534 (0.8); 2.531 (1.1); 2.528 (1.1); 2.519 (28.9); 2.516 (63.6); 2.513 (89.7); 2.510 (66.1); 2.507 (31.9); 2.397 (0.6); 1.787 (0.5); 1.775 (2.3); 1.763 (4.6); 1.751 (4.6); 1.739 (2.5); 1.727 (0.6); 1.246 (0.4); 0.832 (7.5); 0.819 (16.0); 0.807 (7.3)

I-1-326:
HPLC-MS: log P=2.15; mass (m/z): 322.0 (M+H)$^+$;
$^1$H-NMR (400.0 MHz, DMSO-D$_6$): δ=11.688 (1.6); 8.109 (2.4); 8.106 (2.1); 8.102 (2.4); 7.649 (0.4); 7.633 (0.8); 7.627 (0.6); 7.618 (0.6); 7.612 (1.6); 7.606 (0.6); 7.595 (0.7); 7.590 (1.0); 7.575 (0.5); 7.416 (0.4); 7.407 (2.7); 7.385 (4.4); 7.365 (2.0); 6.938 (1.8); 6.932 (1.8); 5.756 (1.3); 3.337 (0.3); 3.323 (34.9); 2.827 (16.0); 2.524 (1.0); 2.520 (1.4); 2.511 (16.7); 2.507 (33.4); 2.502 (44.1); 2.497 (32.6); 2.493 (16.1); 0.008 (0.5); 0.000 (16.6); −0.009 (0.7)

I-1-327:
HPLC-MS: log P=2.24; mass (m/z): 305.0 (M+H)$^+$;
$^1$H-NMR (400.0 MHz, DMSO-D$_6$): δ=11.382 (2.5); 8.677 (5.4); 8.086 (2.3); 8.080 (2.4); 7.637 (0.7); 7.631 (0.7); 7.616 (1.4); 7.599 (0.7); 7.594 (0.9); 7.578 (0.4); 7.408 (2.4); 7.386 (4.0); 7.365 (1.8); 6.896 (2.7); 6.890 (2.7); 3.326 (33.4); 2.506 (38.2); 2.502 (48.8); 2.498 (36.7); 2.328 (0.3); 2.279 (16.0); 0.000 (9.5)

I-1-328:
HPLC-MS: log P=1.51; mass (m/z): 305.1 (M+H)$^+$;
$^1$H-NMR (400.0 MHz, DMSO-D$_6$): δ=11.159 (2.4); 8.715 (4.9); 8.083 (2.2); 8.078 (2.2); 7.654 (0.3); 7.638 (1.0); 7.633 (0.9); 7.617 (1.4); 7.611 (0.6); 7.600 (0.7); 7.595 (0.9); 7.579 (0.4); 7.406 (2.3); 7.385 (3.8); 7.365 (1.8); 7.356 (0.7); 7.295 (0.3); 7.274 (0.6); 6.876 (2.8); 6.870 (2.8); 5.756 (0.3); 5.741 (0.4); 5.735 (0.4); 4.966 (0.5); 3.922 (16.0); 3.322 (49.8); 2.675 (0.6); 2.671 (0.7); 2.666 (0.6);

2.541 (0.4); 2.510 (49.8); 2.506 (93.6); 2.502 (118.3); 2.497 (88.7); 2.333 (0.6); 2.328 (0.8); 2.324 (0.6); 2.027 (1.2); 0.000 (55.9)

I-1-329:
HPLC-MS: log P=3.11; mass (m/z): 402.1 (M+H)$^+$; $^1$H-NMR (400.0 MHz, DMSO-D$_6$): δ=11.412 (11.4); 8.076 (8.6); 8.073 (7.5); 8.070 (8.6); 7.872 (15.1); 7.866 (10.4); 7.852 (12.7); 7.788 (5.6); 7.786 (6.4); 7.783 (5.9); 7.781 (5.3); 7.767 (3.5); 7.765 (3.9); 7.762 (3.8); 7.760 (3.4); 7.639 (1.5); 7.624 (3.1); 7.617 (2.4); 7.608 (2.1); 7.602 (6.0); 7.596 (2.2); 7.586 (2.6); 7.581 (3.9); 7.565 (1.7); 7.408 (1.5); 7.404 (2.7); 7.399 (10.0); 7.378 (16.0); 7.357 (7.5); 7.352 (2.4); 6.925 (12.2); 6.918 (12.2); 3.516 (0.7); 3.346 (113.2); 2.713 (0.4); 2.558 (0.6); 2.543 (103.6); 2.530 (0.6); 2.527 (0.7); 2.522 (0.9); 2.513 (12.3); 2.509 (25.3); 2.504 (33.9); 2.499 (25.1); 2.495 (12.3); 2.369 (0.4); 0.000 (3.6)

I-1-330:
HPLC-MS: log P=2.14; mass (m/z): 336.0 (M+H)$^+$; $^1$H-NMR (400.0 MHz, DMSO-D$_6$): δ=11.565 (7.4); 9.260 (15.9); 9.147 (16.0); 8.316 (0.5); 8.124 (6.3); 8.119 (6.6); 7.648 (0.9); 7.632 (1.8); 7.627 (1.8); 7.611 (3.8); 7.595 (2.0); 7.590 (2.5); 7.574 (1.1); 7.408 (6.4); 7.387 (10.9); 7.366 (4.9); 6.946 (9.0); 6.940 (9.1); 3.328 (297.0); 2.671 (1.6); 2.506 (183.2); 2.502 (239.5); 2.498 (184.0); 2.329 (1.5); 0.000 (5.0)

I-1-331:
HPLC-MS: log P=2.80; mass (m/z): 386.1 (M+H)$^+$; $^1$H-NMR (400.0 MHz, DMSO-D$_6$): δ=11.405 (11.1); 8.078 (9.0); 8.072 (8.9); 7.932 (4.4); 7.920 (4.7); 7.910 (5.0); 7.898 (4.9); 7.691 (4.5); 7.685 (4.8); 7.669 (4.6); 7.663 (4.6); 7.639 (1.4); 7.623 (3.1); 7.617 (2.5); 7.608 (2.1); 7.602 (6.0); 7.596 (2.3); 7.586 (2.7); 7.581 (4.0); 7.565 (3.7); 7.546 (4.6); 7.540 (4.0); 7.524 (2.3); 7.519 (2.0); 7.408 (1.6); 7.399 (9.9); 7.378 (16.0); 7.357 (7.5); 6.928 (14.5); 6.922 (14.4); 3.516 (0.7); 3.340 (70.2); 2.543 (60.1); 2.529 (0.5); 2.526 (0.7); 2.521 (0.9); 2.512 (12.0); 2.508 (24.4); 2.503 (32.5); 2.499 (23.9); 2.494 (11.6); 2.075 (0.4); 0.000 (2.6)

I-1-332:
HPLC-MS: log P=2.45; mass (m/z): 322.0 (M+H)$^+$; $^1$H-NMR (400.0 MHz, DMSO-D$_6$): δ=11.196 (2.1); 8.097 (1.9); 8.091 (1.9); 7.636 (0.7); 7.631 (0.5); 7.620 (0.5); 7.615 (1.4); 7.609 (0.5); 7.598 (0.6); 7.593 (0.9); 7.577 (0.4); 7.418 (0.4); 7.409 (2.2); 7.388 (3.6); 7.367 (1.7); 7.361 (0.5); 6.953 (2.3); 6.947 (2.3); 3.324 (5.8); 2.903 (16.0); 2.512 (5.5); 2.507 (10.8); 2.503 (14.3); 2.498 (10.4); 2.494 (5.0); 0.008 (0.9); 0.000 (22.7); −0.009 (0.8)

I-1-333:
HPLC-MS: log P=2.30; mass (m/z): 320.1 (M+H)$^+$; $^1$H-NMR [DMSO-D$_6$] 1.75-1.81 (m, 2H), 1.98 (s, 3H), 2.30-2.33 (m, 2H), 3.94-3.96 (m, 2H), 6.82 (d, 1H), 7.34-7.38 (m, 2H), 7.54-7.62 (m, 1H), 7.96 (d, 1H), 10.04 (s, 1H).

I-1-334:
HPLC-MS: log P=2.70; mass (m/z): 378.0 (M+H)$^+$; $^1$H-NMR (400.0 MHz, DMSO-D$_6$): δ=11.510 (3.9); 11.214 (0.3); 8.063 (5.4); 8.057 (5.3); 7.845 (2.9); 7.826 (3.1); 7.823 (3.0); 7.603 (0.7); 7.586 (1.4); 7.582 (1.5); 7.575 (1.3); 7.570 (1.2); 7.565 (3.3); 7.561 (7.6); 7.559 (4.3); 7.555 (5.0); 7.545 (4.2); 7.542 (3.6); 7.526 (1.2); 7.522 (1.0); 7.446 (2.1); 7.440 (2.0); 7.430 (1.6); 7.426 (2.1); 7.424 (1.8); 7.420 (1.9); 7.410 (1.5); 7.404 (1.4); 7.246 (0.6); 7.243 (0.8); 7.236 (4.1); 7.217 (5.3); 7.196 (3.4); 7.189 (0.6); 6.895 (5.9); 6.889 (5.9); 5.756 (6.9); 3.326 (12.6); 2.524 (0.5); 2.519 (0.8); 2.511 (8.7); 2.506 (17.4); 2.502 (22.9); 2.497 (16.5); 2.493 (7.8); 1.989 (0.4); 1.397 (16.0); 1.234 (0.3); 1.071 (0.4); 0.008 (0.5); 0.000 (14.3); −0.009 (0.4)

I-1-335:
HPLC-MS: log P=3.02 (neutral); mass (m/z): 430.0 (M+H)$^+$; $^1$H-NMR (400.0 MHz, DMSO-D$_6$): δ=11.523 (10.4); 8.065 (13.6); 8.059 (13.6); 7.845 (7.0); 7.842 (7.2); 7.825 (7.9); 7.822 (7.9); 7.768 (0.9); 7.749 (2.6); 7.739 (1.4); 7.729 (5.7); 7.715 (9.7); 7.695 (16.0); 7.679 (4.5); 7.675 (3.5); 7.588 (2.6); 7.583 (4.0); 7.568 (10.6); 7.563 (11.1); 7.560 (7.2); 7.557 (6.4); 7.542 (7.2); 7.539 (7.3); 7.522 (2.8); 7.519 (2.8); 7.441 (4.9); 7.436 (5.0); 7.424 (4.4); 7.421 (5.3); 7.419 (4.7); 7.416 (5.1); 7.404 (3.4); 7.399 (3.3); 6.880 (14.7); 6.874 (14.6); 4.115 (1.0); 4.102 (3.2); 4.089 (3.2); 4.075 (1.1); 3.327 (20.0); 3.177 (15.6); 3.163 (15.2); 2.671 (0.4); 2.524 (1.2); 2.511 (22.0); 2.506 (44.2); 2.502 (58.1); 2.497 (42.0); 2.493 (20.2); 2.329 (0.4); 0.008 (1.8); 0.000 (48.4); −0.009 (1.6)

I-1-336:
HPLC-MS: log P=1.44; mass (m/z): 357.0 (M+H)$^+$; $^1$H-NMR (400.0 MHz, CD$_3$CN): δ=9.331 (0.8); 8.555 (1.7); 8.551 (1.8); 8.543 (1.8); 8.539 (1.8); 7.861 (1.6); 7.858 (1.6); 7.839 (4.2); 7.834 (3.2); 7.782 (2.3); 7.763 (2.8); 7.501 (3.1); 7.490 (5.5); 7.393 (1.5); 7.384 (1.1); 7.379 (1.1); 7.372 (1.6); 7.370 (1.4); 7.363 (1.0); 7.360 (1.1); 7.350 (1.0); 7.275 (1.5); 7.263 (1.5); 7.256 (1.5); 7.244 (1.4); 6.978 (2.4); 6.972 (2.4); 5.451 (2.0); 2.627 (16.0); 2.469 (0.3); 2.465 (0.3); 2.229 (85.5); 1.966 (0.7); 1.955 (10.9); 1.948 (20.5); 1.942 (28.8); 1.936 (19.9); 1.930 (10.3); 0.000 (4.9)

I-1-337: see Synthesis Example 37

I-1-338:
HPLC-MS: log P=3.23; mass (m/z): 390.0 (M+H)$^+$; $^1$H-NMR (601.6 MHz, CD$_3$CN): δ=9.194 (0.9); 7.826 (3.6); 7.822 (3.5); 7.684 (2.1); 7.682 (2.1); 7.670 (2.3); 7.668 (2.3); 7.553 (1.8); 7.550 (1.9); 7.540 (2.3); 7.537 (2.4); 7.466 (1.3); 7.464 (1.4); 7.453 (2.7); 7.451 (2.7); 7.441 (1.5); 7.439 (1.4); 7.420 (2.5); 7.419 (2.6); 7.396 (2.0); 7.394 (4.3); 7.383 (2.2); 7.381 (5.6); 7.371 (1.2); 7.368 (1.1); 7.260 (1.5); 7.259 (1.6); 7.257 (1.6); 7.256 (1.4); 7.246 (1.2); 7.245 (1.4); 7.244 (1.3); 7.242 (1.2); 6.949 (3.9); 6.944 (3.9); 5.448 (2.0); 2.472 (0.4); 2.386 (16.0); 2.159 (51.2); 1.972 (0.5); 1.965 (1.0); 1.957 (0.9); 1.953 (1.1); 1.949 (11.0); 1.945 (21.2); 1.941 (31.5); 1.937 (21.1); 1.933 (10.2); 1.436 (1.8); 0.000 (2.7)

I-1-339:
HPLC-MS: log P=3.20; mass (m/z): 346.0 (M+H)$^+$; $^1$H-NMR (601.6 MHz, CD$_3$CN): δ=9.228 (1.0); 7.824 (3.3); 7.820 (3.3); 7.594 (1.6); 7.591 (1.7); 7.581 (1.9); 7.579 (2.0); 7.509 (1.3); 7.496 (2.7); 7.481 (1.1); 7.478 (1.2); 7.468 (1.7); 7.466 (1.8); 7.455 (0.9); 7.453 (0.8); 7.419 (3.8); 7.409 (2.2); 7.392 (2.9); 7.379 (3.4); 7.256 (1.7); 7.243 (1.4); 6.952 (3.3); 6.947 (3.3); 5.448 (0.6); 2.471 (0.5); 2.385 (16.0); 2.160 (30.7); 1.965 (0.5); 1.957 (0.5); 1.952 (0.7); 1.949 (5.8); 1.945 (10.6); 1.941 (15.5); 1.937 (10.6); 1.933 (5.4); 1.436 (1.5); 0.000 (1.2)

I-1-340:
HPLC-MS: log P=3.15; mass (m/z): 410.1 (M+H)$^+$; $^1$H-NMR (400.0 MHz, DMSO-D$_6$): δ=11.192 (5.8); 10.394 (1.0); 10.385 (1.0); 8.316 (0.8); 7.828 (2.7); 7.809 (4.1); 7.797 (1.1); 7.778 (7.4); 7.772 (7.6); 7.753 (3.0); 7.735 (2.9); 7.699 (2.7); 7.685 (6.2); 7.667 (3.6); 7.592 (1.1); 7.574 (0.9); 7.495 (2.5); 7.474 (5.2); 7.453 (3.4); 7.228 (4.8); 7.219 (5.0); 7.207 (4.0); 7.199 (4.1); 7.024 (1.3); 7.015 (1.3); 6.979 (0.5); 6.973 (0.6); 6.961 (0.9); 6.956 (1.2); 6.945 (0.6); 6.930 (1.8); 6.924 (2.4); 6.904 (0.9); 6.827 (6.1); 6.821 (6.2); 4.158 (0.7); 4.140 (2.1); 4.123

(2.2); 4.112 (2.5); 4.106 (1.4); 4.094 (7.3); 4.077 (7.4); 4.059 (2.4); 3.321 (177.0); 2.890 (0.5); 2.731 (0.5); 2.675 (2.2); 2.670 (2.9); 2.666 (2.3); 2.540 (2.5); 2.505 (343.0); 2.501 (452.3); 2.497 (347.8); 2.328 (2.8); 2.324 (2.2); 1.753 (1.0); 1.384 (2.2); 1.367 (4.5); 1.349 (2.2); 1.221 (7.8); 1.204 (16.0); 1.187 (7.6); 0.146 (0.6); 0.008 (5.9); 0.000 (127.4); −0.150 (0.6)

I-1-341:
HPLC-MS: log P=2.17; mass (m/z): 376.1 (M+H)$^+$;
$^1$H-NMR (400.0 MHz, CD$_3$CN): δ=9.308 (0.6); 8.079 (1.5); 8.060 (1.6); 7.884 (2.4); 7.878 (2.4); 7.807 (0.5); 7.804 (0.5); 7.789 (1.6); 7.783 (0.7); 7.770 (1.4); 7.767 (1.2); 7.740 (0.8); 7.736 (1.3); 7.718 (3.7); 7.701 (1.6); 7.698 (1.6); 7.610 (1.1); 7.605 (0.8); 7.603 (0.7); 7.592 (1.3); 7.586 (1.4); 7.557 (1.0); 7.551 (1.1); 7.540 (1.0); 7.537 (1.0); 7.533 (1.6); 7.478 (0.4); 7.473 (0.6); 7.459 (1.5); 7.454 (1.4); 7.447 (1.5); 7.441 (2.3); 7.435 (1.1); 7.429 (1.3); 7.423 (1.1); 7.410 (0.4); 6.948 (2.5); 6.942 (2.4); 5.446 (1.3); 4.085 (0.4); 4.067 (1.1); 4.049 (1.2); 4.031 (0.4); 3.310 (16.0); 2.137 (1.9); 2.135 (1.7); 1.971 (5.1); 1.951 (4.6); 1.945 (8.8); 1.939 (12.5); 1.933 (8.6); 1.926 (4.4); 1.436 (2.8); 1.372 (0.9); 1.284 (0.3); 1.276 (1.1); 1.221 (1.4); 1.203 (2.7); 1.185 (1.3); 0.008 (0.6); 0.000 (16.0); −0.009 (0.5)

I-1-342:
HPLC-MS: log P=1.82; mass (m/z): 390.0 (M+H)$^+$;
$^1$H-NMR (400.0 MHz, CD$_3$CN): δ=8.643 (0.6); 7.999 (1.0); 7.999 (1.0); 7.996 (0.8); 7.981 (1.2); 7.977 (1.0); 7.711 (0.3); 7.708 (0.4); 7.692 (1.0); 7.689 (1.1); 7.675 (1.3); 7.672 (1.7); 7.667 (1.4); 7.653 (1.3); 7.649 (1.2); 7.634 (0.5); 7.630 (0.4); 7.599 (0.9); 7.594 (0.6); 7.586 (0.4); 7.583 (0.5); 7.579 (0.9); 7.574 (0.8); 7.491 (0.4); 7.484 (0.7); 7.477 (0.8); 7.476 (0.8); 7.468 (1.7); 7.463 (2.2); 7.459 (1.6); 7.452 (2.4); 7.446 (1.6); 7.442 (0.6); 7.432 (1.4); 7.428 (1.5); 7.415 (1.0); 7.413 (1.0); 7.410 (1.0); 6.489 (2.8); 5.446 (2.1); 3.212 (16.0); 2.285 (11.2); 2.132 (10.2); 1.963 (0.8); 1.957 (1.1); 1.951 (9.3); 1.945 (17.2); 1.939 (24.0); 1.933 (16.5); 1.927 (8.5); 1.372 (3.2); 1.340 (1.2); 1.285 (1.6); 1.277 (3.6); 1.271 (0.7)

I-1-343:
HPLC-MS: log P=2.87; mass (m/z): 396.0 (M+H)$^+$;
$^1$H-NMR (400.0 MHz, CD$_3$CN): δ=8.534 (2.7); 7.607 (4.4); 7.593 (8.8); 7.580 (4.6); 7.575 (8.8); 7.560 (5.5); 7.557 (5.4); 7.541 (4.1); 7.537 (3.8); 7.507 (2.2); 7.498 (2.6); 7.493 (3.1); 7.484 (5.8); 7.465 (7.2); 7.457 (16.0); 7.442 (4.9); 7.439 (3.9); 7.427 (5.0); 7.408 (6.8); 7.389 (2.9); 7.350 (4.9); 7.330 (4.0); 6.489 (10.0); 5.447 (0.7); 2.276 (45.3); 2.146 (34.7); 2.113 (0.5); 2.107 (0.4); 1.963 (1.9); 1.957 (2.6); 1.951 (18.2); 1.945 (34.7); 1.939 (49.0); 1.933 (35.8); 1.927 (19.6); 1.372 (5.9); 1.340 (0.4); 1.285 (0.8); 1.276 (6.2); 0.080 (1.8); 0.008 (2.6); 0.000 (60.0)

I-1-344:
HPLC-MS: log P=3.10; mass (m/z): 383.0 (M+H)$^+$;
$^1$H-NMR (400.0 MHz, CD$_3$CN): δ=9.373 (3.8); 8.426 (6.9); 8.414 (7.0); 8.282 (6.8); 8.263 (7.0); 7.893 (10.8); 7.888 (11.0); 7.610 (5.5); 7.607 (5.0); 7.590 (6.8); 7.574 (0.7); 7.556 (5.1); 7.539 (7.8); 7.480 (8.5); 7.466 (12.4); 7.462 (13.1); 7.448 (16.0); 7.435 (6.3); 7.433 (6.4); 7.417 (2.1); 7.253 (0.3); 7.236 (0.4); 6.974 (10.8); 6.969 (10.9); 3.843 (0.7); 2.462 (0.4); 2.147 (20.7); 2.143 (34.3); 2.111 (0.4); 2.107 (0.5); 2.101 (0.3); 1.952 (25.4); 1.949 (27.8); 1.946 (49.1); 1.943 (50.1); 1.940 (69.9); 1.937 (66.5); 1.934 (50.4); 1.931 (45.8); 1.928 (27.0); 1.925 (23.2); 1.768 (0.4); 1.436 (0.6); 1.372 (5.8); 1.349 (0.5); 1.340 (0.9); 1.282 (1.5); 1.276 (6.0); 0.146 (0.5); 0.000 (89.3); −0.002 (79.0); −0.150 (0.5)

I-1-345:
HPLC-MS: log P=3.01; mass (m/z): 380.1 (M+H)$^+$;
$^1$H-NMR (400.0 MHz, DMSO-D$_6$): δ=10.538 (3.9); 7.952 (4.8); 7.951 (4.8); 7.857 (1.7); 7.851 (0.6); 7.839 (2.7); 7.812 (0.8); 7.794 (2.0); 7.776 (1.8); 7.727 (1.9); 7.718 (3.0); 7.709 (2.3); 7.701 (1.9); 7.690 (1.0); 7.684 (2.3); 7.680 (1.9); 7.665 (2.7); 7.661 (2.5); 7.587 (1.6); 7.583 (1.9); 7.568 (2.6); 7.563 (3.0); 7.527 (1.1); 7.523 (1.3); 7.508 (2.6); 7.504 (2.3); 7.489 (1.9); 7.485 (3.4); 7.480 (2.1); 7.466 (2.2); 7.461 (2.1); 7.447 (0.8); 7.442 (0.7); 5.753 (0.6); 4.056 (0.4); 4.038 (1.2); 4.020 (1.2); 4.003 (0.4); 3.399 (0.4); 3.357 (194.9); 2.525 (0.6); 2.512 (11.8); 2.508 (23.3); 2.503 (30.2); 2.499 (21.1); 2.494 (9.6); 2.073 (1.5); 2.044 (16.0); 1.989 (5.7); 1.397 (1.8); 1.193 (1.5); 1.175 (2.9); 1.157 (1.4); 0.000 (0.3)

I-1-346:
HPLC-MS: log P=2.53; mass (m/z): 391.0 (M+H)$^+$;
$^1$H-NMR (400.0 MHz, CD$_3$CN): δ=8.968 (2.5); 8.115 (0.4); 8.089 (16.0); 7.780 (3.6); 7.764 (4.6); 7.758 (5.1); 7.745 (1.1); 7.727 (0.6); 7.706 (0.4); 7.692 (1.4); 7.677 (5.6); 7.672 (7.4); 7.663 (13.4); 7.659 (8.7); 7.656 (10.5); 7.639 (9.0); 7.637 (8.6); 7.591 (3.3); 7.585 (3.6); 7.573 (4.8); 7.568 (6.4); 7.549 (6.3); 7.548 (6.3); 7.536 (9.0); 7.523 (8.1); 7.520 (7.2); 7.506 (5.5); 7.503 (5.5); 7.486 (2.4); 7.483 (2.1); 7.445 (1.0); 7.433 (4.6); 7.427 (4.9); 7.412 (4.5); 5.448 (1.7); 3.871 (4.7); 3.833 (1.6); 3.784 (0.6); 3.772 (1.0); 3.772 (1.0); 3.759 (0.9); 3.657 (0.9); 3.644 (1.0); 3.633 (0.6); 2.148 (37.0); 2.108 (1.1); 2.102 (0.9); 1.965 (1.3); 1.953 (15.7); 1.947 (29.8); 1.940 (42.2); 1.934 (30.8); 1.928 (17.5); 1.372 (4.6); 1.340 (0.6); 1.285 (0.9); 1.276 (5.1); 0.008 (2.2); 0.000 (51.7)

I-1-347:
HPLC-MS: log P=2.58; mass (m/z): 380.0 (M+H)$^+$;
$^1$H-NMR (400.0 MHz, CD$_3$CN): δ=8.552 (2.2); 7.736 (3.4); 7.719 (4.6); 7.715 (4.5); 7.652 (1.2); 7.634 (3.8); 7.620 (7.4); 7.615 (7.2); 7.599 (3.7); 7.598 (3.7); 7.588 (2.7); 7.585 (4.5); 7.570 (3.1); 7.567 (5.5); 7.564 (4.0); 7.554 (0.4); 7.495 (1.7); 7.486 (2.3); 7.480 (2.6); 7.472 (5.1); 7.459 (3.7); 7.450 (16.0); 7.440 (7.7); 7.436 (7.6); 7.418 (3.7); 6.483 (12.4); 5.447 (3.2); 2.279 (50.1); 2.152 (135.0); 2.118 (0.5); 2.114 (0.4); 2.107 (0.5); 2.101 (0.3); 1.964 (3.3); 1.958 (3.7); 1.952 (27.2); 1.946 (50.7); 1.940 (70.3); 1.934 (48.5); 1.928 (25.0); 1.768 (0.4); 0.008 (0.6); 0.000 (15.6); −0.009 (0.6)

I-1-348:
HPLC-MS: log P=2.53; mass (m/z): 381.0 (M+H)$^+$;
$^1$H-NMR (400.0 MHz, DMSO-D$_6$): δ=10.720 (1.1); 8.862 (0.6); 8.852 (0.6); 8.850 (0.6); 8.214 (0.5); 8.196 (0.6); 8.194 (0.6); 7.962 (1.3); 7.961 (1.3); 7.864 (0.5); 7.852 (0.5); 7.844 (0.5); 7.832 (0.5); 7.686 (0.6); 7.682 (0.5); 7.668 (0.8); 7.663 (0.7); 7.588 (0.5); 7.583 (0.6); 7.568 (0.7); 7.564 (0.9); 7.524 (0.4); 7.510 (0.8); 7.505 (0.7); 7.490 (1.1); 7.485 (0.9); 7.471 (0.6); 7.466 (0.6); 5.755 (16.0); 3.323 (3.9); 2.519 (0.4); 2.511 (4.8); 2.506 (9.7); 2.502 (12.7); 2.497 (9.0); 2.493 (4.2); 2.057 (4.5); 1.989 (0.3); 0.000 (6.8)

I-1-349:
HPLC-MS: log P=2.13; mass (m/z): 381.0 (M+H)$^+$;
$^1$H-NMR (400.0 MHz, CD$_3$CN): δ=8.739 (4.5); 8.728 (4.6); 8.664 (2.1); 7.847 (4.0); 7.829 (4.7); 7.828 (4.8); 7.639 (4.1); 7.627 (4.2); 7.619 (3.7); 7.607 (3.4); 7.585 (4.8); 7.570 (3.7); 7.567 (6.1); 7.501 (1.9); 7.491 (2.8); 7.488 (2.9); 7.482 (1.3); 7.478 (5.1); 7.473 (1.6); 7.468 (2.3); 7.459 (6.8); 7.452 (15.9); 7.450 (16.0); 7.443 (5.2); 7.441 (4.8); 7.439 (5.0); 7.435 (7.2); 7.419 (0.7); 7.416 (0.5); 6.520 (13.7); 5.447 (7.5); 2.281 (53.3); 2.149 (45.2); 2.120 (0.6); 2.113 (0.4); 2.107 (0.4); 1.964 (1.9); 1.957 (2.4); 1.952

(19.1); 1.946 (35.7); 1.939 (50.0); 1.933 (34.9); 1.927 (18.3); 0.008 (2.2); 0.000 (58.1); −0.009 (2.7)

I-1-350:

HPLC-MS: log P=3.20; mass (m/z): 366.0 (M+H)$^+$; $^1$H-NMR (601.6 MHz, CD$_3$CN): δ=9.244 (3.5); 9.200 (0.6); 7.890 (13.3); 7.885 (13.4); 7.665 (7.2); 7.662 (7.7); 7.651 (8.1); 7.649 (8.5); 7.604 (6.3); 7.601 (5.4); 7.592 (7.8); 7.589 (7.7); 7.578 (0.4); 7.558 (0.4); 7.556 (0.4); 7.539 (6.0); 7.536 (6.8); 7.526 (13.9); 7.524 (16.0); 7.513 (9.4); 7.511 (9.2); 7.470 (2.6); 7.467 (3.2); 7.458 (7.6); 7.455 (7.5); 7.445 (12.1); 7.442 (10.8); 7.432 (7.0); 7.429 (6.6); 7.420 (2.8); 7.416 (10.8); 7.403 (13.8); 7.390 (6.7); 7.355 (0.5); 7.341 (0.5); 6.971 (13.8); 6.967 (13.6); 5.449 (0.7); 2.152 (176.2); 2.056 (0.5); 2.052 (0.8); 2.048 (0.5); 1.972 (0.4); 1.965 (5.0); 1.957 (4.0); 1.953 (5.3); 1.949 (49.8); 1.945 (92.0); 1.941 (132.5); 1.937 (91.5); 1.933 (46.6); 1.831 (0.5); 1.826 (0.8); 1.822 (0.5); 1.436 (5.6); 1.284 (0.7); 1.269 (1.4); 1.213 (0.6); 1.201 (1.0); 1.189 (0.5); 1.026 (0.5); 1.015 (1.0); 1.003 (0.5); 0.005 (0.7); 0.000 (22.6); −0.006 (0.7)

I-1-351:

HPLC-MS: log P=3.00; mass (m/z): 366.0 (M+H)$^+$; $^1$H-NMR (601.6 MHz, CD$_3$CN): δ=9.329 (1.5); 7.892 (7.3); 7.888 (7.4); 7.608 (3.6); 7.605 (2.6); 7.604 (2.6); 7.596 (4.8); 7.592 (4.4); 7.547 (3.3); 7.543 (4.2); 7.535 (2.9); 7.534 (3.2); 7.531 (4.9); 7.486 (6.8); 7.484 (8.0); 7.479 (0.3); 7.4721 (15.4); 7.4715 (16.0); 7.460 (4.7); 7.457 (4.6); 7.449 (5.4); 7.448 (5.4); 7.445 (5.8); 7.440 (8.4); 7.436 (4.4); 7.433 (4.0); 7.428 (5.4); 7.425 (4.6); 7.421 (1.3); 7.413 (3.0); 7.377 (0.5); 7.367 (0.3); 6.978 (8.0); 6.974 (8.0); 5.448 (2.4); 2.151 (90.6); 2.052 (0.4); 1.965 (2.9); 1.957 (2.2); 1.953 (2.6); 1.949 (28.0); 1.945 (51.8); 1.941 (74.6); 1.937 (51.9); 1.933 (26.5); 1.924 (0.5); 1.826 (0.4); 1.436 (0.7); 0.000 (11.3); −0.006 (0.4)

I-1-352:

HPLC-MS: log P=2.70; mass (m/z): 348.1 (M+H)$^+$; $^1$H-NMR (400.0 MHz, DMSO-D$_6$): δ=10.719 (3.4); 7.965 (4.6); 7.963 (4.5); 7.739 (0.4); 7.686 (2.0); 7.682 (1.7); 7.668 (2.7); 7.663 (2.5); 7.618 (0.5); 7.601 (1.1); 7.594 (1.9); 7.588 (2.2); 7.585 (0.9); 7.580 (2.1); 7.575 (2.7); 7.570 (3.1); 7.563 (1.1); 7.559 (1.2); 7.542 (0.6); 7.527 (0.9); 7.523 (1.1); 7.508 (2.6); 7.504 (2.3); 7.490 (4.1); 7.485 (3.7); 7.471 (2.2); 7.466 (2.1); 7.453 (0.8); 7.448 (0.7); 7.383 (0.3); 7.265 (0.6); 7.258 (3.2); 7.238 (4.3); 7.218 (2.7); 7.210 (0.5); 7.040 (0.4); 5.753 (0.5); 3.354 (307.1); 2.526 (0.6); 2.521 (1.1); 2.512 (17.0); 2.508 (34.7); 2.503 (45.6); 2.499 (32.2); 2.494 (15.0); 2.073 (1.3); 2.031 (16.0); 1.994 (1.4); 1.044994 (1.4); 1.028 (0.3); 0.000 (0.5)

I-1-353:

HPLC-MS: log P=2.97; mass (m/z): 326.1 (M+H)$^+$; $^1$H-NMR (601.6 MHz, CD$_3$CN): δ=9.063 (0.4); 7.895 (1.7); 7.895 (1.7); 7.894 (1.7); 7.891 (1.8); 7.890 (1.7); 7.603 (0.9); 7.600 (0.8); 7.590 (1.3); 7.587 (1.1); 7.534 (0.9); 7.531 (1.1); 7.522 (1.0); 7.521 (1.0); 7.519 (1.2); 7.466 (0.5); 7.463 (0.6); 7.453 (1.3); 7.451 (1.1); 7.441 (0.9); 7.438 (0.8); 7.434 (1.1); 7.431 (1.1); 7.421 (1.0); 7.418 (1.1); 7.409 (0.4); 7.406 (0.4); 7.235 (0.6); 7.222 (1.2); 7.209 (1.0); 7.102 (2.1); 7.089 (1.7); 7.006 (2.0); 7.002 (1.9); 2.318 (16.0); 2.248 (0.4); 2.191 (73.9); 1.973 (0.4); 1.967 (17.6); 1.958 (0.6); 1.954 (0.7); 1.950 (6.2); 1.946 (11.6); 1.942 (16.6); 1.938 (10.8); 1.934 (5.5); 0.000 (0.6)

I-1-354:

HPLC-MS: log P=2.86; mass (m/z): 390.0 (M+H)$^+$; $^1$H-NMR (400.0 MHz, DMSO-D$_6$): δ=10.442 (3.7); 8.310 (0.4); 7.948 (4.8); 7.727 (2.4); 7.726 (2.4); 7.708 (2.8); 7.706 (2.7); 7.682 (2.0); 7.678 (1.9); 7.663 (2.5); 7.659 (2.4); 7.586 (1.6); 7.582 (1.9); 7.567 (4.0); 7.562 (4.4); 7.548 (3.0); 7.544 (2.9); 7.525 (1.2); 7.521 (1.4); 7.515 (1.7); 7.512 (1.8); 7.507 (2.7); 7.503 (2.5); 7.496 (2.9); 7.494 (2.8); 7.488 (2.1); 7.483 (3.3); 7.477 (3.2); 7.463 (2.2); 7.458 (2.0); 7.444 (1.0); 7.439 (2.0); 7.434 (1.6); 7.419 (2.0); 7.415 (1.9); 7.400 (1.0); 7.396 (0.9); 5.751 (6.2); 3.422 (0.5); 3.365 (324.7); 3.325 (0.7); 2.526 (0.7); 2.521 (1.1); 2.513 (14.9); 2.508 (30.1); 2.504 (39.1); 2.499 (27.3); 2.494 (12.4); 2.083 (16.0); 2.072 (2.4); 2.063 (0.4); 1.989 (0.9); 1.397 (0.7); 1.175 (0.4); 0.000 (0.6)

I-1-355:

HPLC-MS: log P=1.94; mass (m/z): 391.0 (M+H)$^+$; $^1$H-NMR (400.0 MHz, CD$_3$CN): δ=8.888 (1.4); 7.673 (3.4); 7.671 (3.4); 7.653 (4.0); 7.651 (3.9); 7.613 (2.5); 7.608 (3.1); 7.595 (2.7); 7.593 (3.0); 7.590 (3.7); 7.528 (2.5); 7.523 (2.8); 7.509 (4.7); 7.505 (5.7); 7.493 (3.3); 7.487 (3.7); 7.475 (3.7); 7.470 (2.9); 7.468 (3.6); 7.456 (6.0); 7.452 (5.2); 7.438 (7.0); 7.434 (9.4); 7.429 (4.0); 7.419 (2.7); 7.416 (3.3); 7.409 (1.3); 7.385 (2.8); 7.380 (2.8); 7.365 (3.3); 7.360 (3.2); 7.346 (1.6); 7.342 (1.4); 6.085 (11.7); 5.446 (16.0); 4.257 (1.1); 4.067 (0.3); 2.155 (4.8); 2.112 (0.8); 2.106 (0.7); 2.100 (0.5); 2.094 (0.4); 1.971 (1.3); 1.963 (1.8); 1.957 (1.8); 1.951 (14.1); 1.945 (26.5); 1.939 (36.8); 1.933 (25.2); 1.926 (13.0); 1.913 (0.3); 1.436 (0.4); 1.372 (1.5); 1.340 (0.6); 1.285 (0.8); 1.276 (1.9); 1.269 (0.8); 1.221 (0.4); 1.203 (0.7); 1.185 (0.4); 0.008 (0.5); 0.000 (16.3); −0.009 (0.6)

I-1-356:

HPLC-MS: log P=2.45; mass (m/z): 390.0 (M+H)$^+$; $^1$H-NMR (400.0 MHz, CD$_3$CN): δ=8.467 (3.2); 7.588 (7.7); 7.580 (5.9); 7.568 (10.6); 7.561 (6.8); 7.556 (5.5); 7.493 (2.4); 7.486 (2.9); 7.484 (2.6); 7.477 (5.4); 7.471 (8.5); 7.464 (9.5); 7.459 (9.6); 7.454 (16.0); 7.449 (10.3); 7.441 (2.7); 7.438 (3.5); 7.433 (3.2); 7.418 (1.5); 7.414 (1.2); 7.396 (1.5); 7.377 (5.3); 7.362 (14.1); 7.355 (12.3); 7.343 (3.3); 7.335 (7.0); 7.329 (3.8); 7.316 (5.4); 7.313 (4.0); 7.309 (3.8); 7.299 (2.7); 7.293 (2.4); 6.480 (14.3); 5.445 (4.8); 4.066 (0.6); 4.048 (0.6); 2.436 (0.3); 2.279 (53.7); 2.176 (0.9); 2.117 (0.5); 1.969 (2.8); 1.962 (1.2); 1.955 (1.7); 1.950 (12.8); 1.944 (23.9); 1.938 (33.5); 1.932 (23.6); 1.925 (12.6); 1.436 (1.5); 1.371 (3.6); 1.284 (0.5); 1.276 (3.7); 1.220 (0.7); 1.202 (1.4); 1.184 (0.7); 0.007 (2.8); 0.000 (60.2); −0.008 (3.7); −0.150 (0.3)

I-1-357:

HPLC-MS: log P=2.23; mass (m/z): 392.9 (M+H)$^+$; $^1$H-NMR (400.0 MHz, DMSO-D$_6$): δ=10.632 (3.7); 8.501 (2.1); 8.496 (2.3); 8.489 (2.3); 8.484 (2.2); 8.315 (0.3); 8.006 (2.1); 8.001 (2.2); 7.987 (2.4); 7.982 (2.3); 7.956 (4.6); 7.685 (1.9); 7.681 (1.7); 7.666 (2.4); 7.662 (2.3); 7.589 (2.7); 7.581 (2.2); 7.577 (2.6); 7.570 (2.9); 7.562 (3.1); 7.558 (2.6); 7.526 (0.9); 7.522 (1.0); 7.508 (2.3); 7.503 (2.1); 7.488 (2.9); 7.482 (2.4); 7.468 (2.0); 7.463 (1.9); 7.450 (0.7); 7.445 (0.6); 3.321 (88.1); 2.675 (0.5); 2.670 (0.8); 2.666 (0.6); 2.540 (0.4); 2.523 (1.9); 2.510 (46.9); 2.506 (94.1); 2.501 (123.0); 2.497 (87.4); 2.492 (41.3); 2.332 (0.6); 2.328 (0.8); 2.323 (0.6); 2.094 (16.0); 2.074 (0.3); 2.041 (0.6); 0.000 (0.6)

I-1-358:

HPLC-MS: log P=2.22; mass (m/z): 376.9 (M+H)$^+$; $^1$H-NMR (400.0 MHz, DMSO-D$_6$): δ=11.383 (4.1); 11.344 (0.9); 8.480 (2.2); 8.475 (3.1); 8.468 (3.1); 8.463 (3.3); 8.446 (1.1); 8.439 (1.2); 8.435 (1.1); 8.154 (0.5); 8.140 (0.5); 8.135 (0.7); 8.129 (0.7); 8.108 (3.7); 8.102 (5.2); 8.085 (1.0); 8.079 (1.1); 8.069 (1.1); 7.995 (2.2); 7.990 (3.1); 7.976 (2.5); 7.971 (3.4); 7.955 (0.9); 7.936 (0.7); 7.697 (2.1); 7.691 (2.6); 7.679 (2.5); 7.674 (3.3); 7.639 (1.0); 7.612 (2.0); 7.606 (2.7); 7.593 (2.6); 7.588 (3.7); 7.565 (3.2); 7.560 (2.7); 7.553 (3.4); 7.547 (4.1); 7.534

(3.7); 7.530 (3.7); 7.517 (3.7); 7.512 (4.6); 7.505 (4.4); 7.498 (5.3); 7.493 (4.8); 7.486 (3.8); 7.481 (3.8); 7.467 (2.1); 7.462 (2.0); 7.351 (0.4); 7.332 (0.7); 7.181 (0.7); 7.176 (0.7); 6.921 (3.6); 6.915 (5.2); 6.882 (1.0); 5.756 (0.3); 4.056 (0.5); 4.051 (0.4); 4.038 (1.1); 4.034 (0.9); 4.020 (1.2); 4.015 (0.9); 4.002 (0.6); 3.998 (0.6); 3.322 (34.4); 3.318 (26.1); 3.281 (4.1); 3.056 (0.4); 3.000 (0.4); 2.981 (0.5); 2.941 (0.4); 2.908 (0.4); 2.899 (0.5); 2.865 (0.4); 2.859 (0.4); 2.671 (0.9); 2.666 (0.9); 2.626 (0.6); 2.501 (72.4); 2.497 (70.9); 2.466 (15.8); 2.462 (16.0); 2.328 (0.5); 2.324 (0.5); 1.989 (4.3); 1.983 (2.8); 1.949 (0.7); 1.397 (0.6); 1.336 (4.4); 1.297 (1.7); 1.258 (2.1); 1.249 (5.3); 1.245 (4.2); 1.210 (1.6); 1.193 (1.9); 1.188 (1.5); 1.175 (2.8); 1.170 (2.0); 1.157 (1.8); 1.153 (1.4); 1.135 (0.7); 1.117 (0.4); 0.993 (0.4); 0.008 (1.7); 0.000 (15.7); −0.005 (9.5); −0.040 (2.3)

I-1-359:
HPLC-MS: log P=1.85; mass (m/z): 390.9 (M+H)$^+$; $^1$H-NMR (400.0 MHz, CD$_3$CN): δ=8.679 (1.9); 8.386 (5.8); 8.381 (5.9); 8.374 (6.1); 8.369 (5.8); 7.714 (4.6); 7.709 (4.6); 7.695 (5.3); 7.690 (5.1); 7.657 (1.7); 7.652 (1.7); 7.638 (1.9); 7.633 (1.9); 7.589 (4.2); 7.585 (2.5); 7.578 (1.5); 7.570 (5.0); 7.565 (3.9); 7.506 (2.0); 7.499 (2.2); 7.490 (0.7); 7.483 (6.8); 7.479 (3.3); 7.473 (7.6); 7.467 (13.6); 7.460 (7.9); 7.449 (3.8); 7.445 (2.1); 7.438 (2.2); 7.426 (3.2); 7.419 (2.3); 7.405 (5.5); 7.393 (5.2); 7.386 (4.8); 7.374 (4.6); 7.262 (0.4); 7.256 (0.3); 7.241 (0.6); 7.235 (0.6); 7.171 (0.5); 7.165 (0.4); 6.514 (12.4); 4.085 (0.8); 4.067 (2.4); 4.050 (2.4); 4.032 (0.8); 3.697 (0.4); 3.681 (0.4); 3.664 (0.3); 3.627 (0.9); 3.351 (0.3); 3.334 (0.4); 3.318 (0.4); 3.189 (0.3); 3.171 (0.6); 3.153 (0.6); 3.134 (0.4); 3.117 (0.6); 3.099 (0.6); 3.082 (0.3); 2.589 (0.5); 2.470 (1.9); 2.460 (0.6); 2.455 (0.4); 2.379 (0.4); 2.283 (49.6); 2.261 (0.5); 2.257 (0.7); 2.254 (0.7); 2.242 (0.5); 2.232 (0.6); 2.219 (1.8); 2.167 (56.7); 2.122 (1.1); 2.114 (0.9); 2.107 (1.0); 2.107 (0.0); 2.101 (0.8); 2.095 (0.6); 2.082 (0.3); 1.972 (11.0); 1.964 (3.2); 1.958 (3.9); 1.952 (34.8); 1.946 (65.0); 1.940 (90.5); 1.934 (61.8); 1.928 (31.5); 1.915 (0.7); 1.775 (0.4); 1.768 (0.6); 1.762 (0.4); 1.386 (0.7); 1.372 (14.8); 1.340 (6.3); 1.321 (0.5); 1.303 (0.7); 1.285 (8.3); 1.276 (16.0); 1.270 (4.8); 1.229 (5.7); 1.221 (3.3); 1.216 (1.5); 1.211 (11.4); 1.203 (6.2); 1.193 (5.6); 1.186 (3.1); 1.052 (5.5); 1.034 (11.1); 1.017 (5.3); 0.918 (2.5); 0.898 (0.4); 0.881 (0.9); 0.874 (0.4); 0.864 (0.5); 0.856 (0.4); 0.000 (1.1)

I-1-360:
HPLC-MS: log P=2.80; mass (m/z): 346.1 (M+H)$^+$; $^1$H-NMR (400.0 MHz, DMSO-D$_6$): δ=10.448 (3.7); 7.951 (4.7); 7.683 (1.9); 7.679 (1.8); 7.664 (2.3); 7.660 (2.3); 7.596 (1.8); 7.592 (2.1); 7.587 (2.0); 7.582 (2.5); 7.573 (4.2); 7.568 (3.1); 7.563 (3.1); 7.555 (3.2); 7.553 (3.1); 7.525 (2.0); 7.521 (2.3); 7.506 (4.3); 7.502 (4.0); 7.487 (3.1); 7.482 (4.1); 7.477 (2.4); 7.473 (2.3); 7.469 (2.2); 7.463 (2.3); 7.458 (2.4); 7.454 (2.6); 7.451 (2.3); 7.445 (1.0744 0.9); 7.440 (0.9); 7.436 (1.0); 5.754 (4.8); 4.038 (0.4); 4.020 (0.4); 3.340 (261.8); 2.671 (0.4); 2.525 (0.9); 2.520 (1.5); 2.511 (22.2); 2.507 (45.1); 2.502 (58.9); 2.498 (41.7); 2.493 (19.4); 2.329 (0.4); 2.086 (0.4); 2.073 (1.6); 2.061 (16.0); 1.989 (1.9); 1.398 (0.8); 1.193 (0.5); 1.175 (1.0); 1.157 (0.5); 0.000 (1.1)

I-1-361:
HPLC-MS: log P=1.88; mass (m/z): 347.1 (M+H)$^+$; $^1$H-NMR (400.0 MHz, CD$_3$CN): δ=8.905 (1.5); 7.610 (2.2); 7.606 (2.5); 7.590 (2.7); 7.587 (3.2); 7.567 (2.4); 7.563 (2.4); 7.549 (3.0); 7.544 (3.0); 7.508 (1.2); 7.503 (1.5); 7.497 (1.9); 7.490 (3.0); 7.485 (3.7); 7.481 (4.3); 7.477 (4.6); 7.472 (4.3); 7.469 (3.7); 7.465 (4.9); 7.451 (5.6); 7.449 (5.4); 7.435 (2.5); 7.431 (3.8); 7.427 (5.6); 7.422 (3.3); 7.412 (3.0); 7.408 (3.8); 7.403 (1.5); 7.393 (3.1); 7.390 (2.9); 7.375 (1.2); 7.371 (1.1); 6.088 (8.5); 5.446 (6.0); 4.252 (4.4); 2.146 (21.2); 1.963 (0.9); 1.957 (1.1); 1.951 (8.5); 1.945 (15.8); 1.938 (21.9); 1.932 (14.9); 1.926 (7.6); 1.340 (0.7); 1.285 (0.9); 1.268 (0.8); 1.254 (0.7); 1.247 (0.4); 0.008 (0.7); 0.000 (18.9); −0.009 (0.7)

I-1-362:
HPLC-MS: log P=2.37; mass (m/z): 357.0 (M+H)$^+$; $^1$H-NMR (400.0 MHz, CD$_3$CN): δ=8.954 (0.5); 8.109 (0.5); 8.109 (0.8); 8.088 (1.5); 7.642 (2.6); 7.633 (0.8); 7.623 (4.1); 7.618 (3.6); 7.599 (0.3); 7.596 (0.4); 7.582 (1.8); 7.577 (2.2); 7.564 (3.8); 7.560 (4.9); 7.549 (4.2); 7.545 (5.3); 7.543 (5.7); 7.531 (0.6); 7.520 (3.8); 7.516 (3.8); 7.503 (2.5); 7.499 (2.9); 7.490 (0.7); 7.482 (1.3); 7.479 (1.3); 7.472 (0.4); 7.466 (0.5); 7.460 (2.6); 7.455 (3.2); 7.446 (6.7); 7.444 (7.3); 7.442 (9.2); 7.428 (1.5); 7.417 (1.4); 7.413 (1.7); 7.399 (4.2); 7.396 (5.5); 7.387 (4.1); 7.382 (3.2); 7.373 (2.5); 7.367 (2.9); 7.361 (1.1); 7.355 (1.0); 7.348 (0.9); 5.448 (16.0); 3.829 (3.3); 2.154 (15.2); 2.114 (0.6); 2.108 (0.5); 2.101 (0.5); 1.964 (1.9); 1.958 (2.3); 1.953 (15.9); 1.946 (29.6); 1.940 (40.9); 1.934 (28.5); 1.928 (14.8); 0.008 (0.4); 0.000 (10.2); −0.009 (0.4)

I-1-363:
HPLC-MS: log P=2.45; mass (m/z): 334.0 (M+H)$^+$; $^1$H-NMR (400.0 MHz, CD$_3$CN): δ=9.902 (1.9); 8.635 (6.3); 8.629 (9.8); 8.611 (9.8); 8.605 (6.3); 8.457 (0.8); 7.920 (7.4); 7.914 (7.4); 7.617 (3.5); 7.612 (2.9); 7.599 (4.3); 7.593 (4.6); 7.581 (3.5); 7.576 (3.8); 7.562 (3.8); 7.557 (5.1); 7.541 (0.5); 7.506 (0.5); 7.493 (0.5); 7.488 (1.5); 7.483 (2.0); 7.469 (4.6); 7.465 (4.4); 7.455 (5.0); 7.452 (5.6); 7.449 (5.9); 7.436 (4.2); 7.431 (3.6); 7.418 (1.9); 7.413 (1.1); 7.261 (0.4); 7.256 (0.4); 7.240 (0.7); 7.235 (0.7); 7.170 (0.5); 7.164 (0.5); 7.149 (0.4); 7.143 (0.3); 7.017 (7.7); 7.011 (7.6); 5.446 (2.4); 4.996 (0.4); 3.685 (0.4); 3.667 (0.4); 3.524 (0.5); 3.507 (0.4); 3.030 (0.8); 3.015 (0.8); 2.136 (12.0); 2.135 (11.9); 2.107 (0.4); 1.964 (1.6); 1.952 (21.1); 1.946 (39.7); 1.940 (55.6); 1.933 (38.6); 1.927 (20.1); 1.768 (0.3); 1.371 (16.0); 1.340 (3.4); 1.306 (0.4); 1.285 (4.5); 1.276 (16.0); 1.241 (0.4); 1.222 (0.6); 1.216 (0.7); 1.204 (0.3); 1.124 (1.4); 1.106 (2.6); 1.088 (1.3); 1.062 (0.5); 0.881 (0.4); 0.000 (7.0)

I-1-364:
HPLC-MS: log P=2.38; mass (m/z): 317.1 (M+H)$^+$; $^1$H-NMR (400.0 MHz, CD$_3$CN): δ=9.311 (2.2); 8.436 (2.5); 8.431 (3.4); 8.417 (2.9); 8.408 (15.1); 8.402 (4.4); 8.395 (11.0); 7.929 (13.1); 7.923 (13.2); 7.644 (0.3); 7.3); 7.640 (5.2); 7.638 (4.9); 7.626 (9.5); 7.62 (9.8); 7.601 (4.7); 7.596 (5.2); 7.582 (5.1); 7.577 (7.3); 7.563 (0.4); 7.517 (2.7); 7.512 (3.9); 7.498 (13.7); 7.493 (13.2); 7.484 (12.2); 7.480 (16.0); 7.478 (14.7); 7.475 (8.6); 7.465 (10.4); 7.460 (8.5); 7.447 (2.8); 7.442 (2.1); 7.011 (9.8); 7.004 (9.8); 5.477 (2.5); 2.227 (252.6); 2.224 (387.2); 2.222 (387.9); 2.143 (0.4); 2.137 (0.6); 2.131 (0.4); 1.994 (4.6); 1.988 (4.0); 1.982 (39.4); 1.976 (74.8); 1.970 (106.6); 1.964 (72.0); 1.958 (36.3); 1.804 (0.4); 1.798 (0.6); 1.792 (0.4); 1.297 (0.7); 1.144 (0.4)

I-1-365:
HPLC-MS: log P=2.99; mass (m/z): 438.0 (M+H)$^+$; $^1$H-NMR (400.0 MHz, DMSO-D$_6$): δ=10.397 (4.1); 7.948 (6.7); 7.930 (3.0); 7.682 (1.9); 7.679 (1.9); 7.663 (2.4); 7.659 (2.3); 7.589 (1.5); 7.584 (1.7); 7.569 (2.5); 7.565 (2.7); 7.525 (1.4); 7.522 (1.3); 7.507 (4.9); 7.500 (4.2); 7.492 (6.8); 7.482 (3.2); 7.477 (2.2); 7.462 (2.1); 7.458 (1.9); 7.444 (0.8); 7.439 (0.7); 7.247 (1.1); 7.239 (1.2); 7.232 (1.3); 7.226 (1.5); 7.219 (1.2); 7.212 (1.1); 7.204 (0.9); 5.751 (2.9); 4.038 (0.7); 4.020 (0.7); 3.438 (0.5);

3.432 (0.5); 3.413 (1.0); 3.363 (502.0); 3.307 (0.4); 3.298 (0.5); 2.673 (0.5); 2.673 ((0.4); 2.512 (22.2); 2.508 (43.0); 2.504 (55.2); 2.499 (39.5); 2.495 (18.8); 2.330 (0.4); 2.114 (16.0); 2.072 (1.9); 1.989 (3.2); 1.397 (0.7); 1.193 (0.9); 1.175 (1.7); 1.157 (0.8); 0.000 (0.4)

I-1-366:
HPLC-MS: log P=3.12; mass (m/z): 501.9 (M+H)$^+$; $^1$H-NMR (601.6 MHz, CD$_3$CN): δ=8.524 (1.6); 8.074 (1.2); 8.061 (3.7); 8.057 (3.5); 8.014 (2.2); 8.013 (2.2); 8.001 (2.4); 7.999 (2.4); 7.981 (2.7); 7.970 (2.9); 7.944 (0.7); 7.937 (0.5); 7.893 (0.7); 7.888 (0.7); 7.876 (0.5); 7.844 (0.6); 7.841 (0.6); 7.831 (0.7); 7.828 (0.6); 7.726 (1.8); 7.723 (1.8); 7.713 (2.0); 7.710 (2.1); 7.619 (3.5); 7.574 (4.5); 7.541 (1.6); 7.538 (1.6); 7.534 (1.7); 7.532 (1.7); 7.522 (3.1); 7.520 (3.3); 7.509 (4.2); 7.507 (4.1); 7.491 (8.6); 7.489 (8.8); 7.478 (9.0); 7.477 (8.5); 7.466 (3.6); 7.464 (3.3); 7.447 (1.0); 7.444 (0.9); 7.439 (0.9); 7.430 (0.7); 7.427 (0.8); 7.411 (0.5); 7.386 (0.4); 7.359 (0.3); 7.306 (0.5); 7.304 (0.5); 7.294 (0.6); 7.291 (0.6); 7.281 (0.5); 7.278 (0.5); 7.240 (3.3); 7.237 (3.5); 7.227 (4.6); 7.225 (4.3); 7.215 (3.1); 7.212 (2.8); 6.972 (0.5); 6.968 (0.5); 5.590 (0.8); 5.579 (0.8); 5.446 (1.6); 4.365 (2.4); 4.353 (7.3); 4.341 (7.6); 4.329 (2.5); 2.625 (0.4); 2.602 (0.4); 2.152 (53.0); 2.148 (64.3); 2.144 (67.0); 2.142 (64.7); 2.138 (72.9); 2.058 (0.6); 2.054 (2); 2.050 (1.8); 2.046 (1.2); 2.042 (0.6); 1.964 (9.2); 1.956 (8.1); 1.951 (9.4); 1.948 (118.8); 1.943 (217.3); 1.939 (304.0); 1.935 (198.5); 1.931 (96.9); 1.926 (3.0); 1.922 (1.4); 1.833 (0.6); 1.829 (1.2); 1.825 (1.8); 1.820 (1.2); 1.816 (0.6); 1.736 (4.2); 1.725 (4.0); 1.639 (0.4); 1.627 (0.4); 1.373 (7.8); 1.361 (16.0); 1.350 (7.8); 1.301 (0.6); 1.29 (0.3); 1.291 (0.6); 1.283 (0.5); 1.270 (1.0); 1.264 (0.5); 1.259 (0.3); 1.253 (0.4); 1.008 (0.4); 0.096 (0.00 (4); 0.005 (4.3); 0.000 (160.3); −0.006 (4.7); −0.100 (0.6)

I-1-367:
HPLC-MS: log P=3.18; mass (m/z): 549.8 (M+H)$^+$; $^1$H-NMR (400.0 MHz, CD$_3$CN): δ=8.568 (3.7); 8.122 (0.4); 8.099 (0.4); 8.046 (7.5); 8.019 (2.8); 8.017 (2.8); 7.997 (4.2); 7.986 (5.4); 7.967 (5.6); 7.918 (0.6); 7.908 (1.0); 7.890 (0.6); 7.879 (0.5); 7.869 (0.6); 7.858 (0.5); 7.838 (0.4); 7.805 (0.3); 7.801 (0.4); 7.780 (0.6); 7.774 (0.6); 7.732 (1.7); 7.728 (1.8); 7.721 (0.4); 7.712 (2.2); 7.708 (2.1); 7.696 (0.5); 7.685 (0.5); 7.622 (7.6); 7.617 (7.9); 7.610 (8.5); 7.584 (9.2); 7.538 (5.7); 7.529 (5.7); 7.515 (7.1); 7.508 (6.9); 7.491 (14.9); 7.480 (16.0); 7.431 (1.3); 7.423 (1.3); 7.411 (1.0); 7.404 (1.0); 7.389 (0.8); 7.385 (0.8); 7.380 (0.7); 7.371 (0.7); 7.366 (0.7); 7.346 (0.6); 7.342 (0.6); 7.325 (0.5); 7.320 (0.5); 7.310 (0.5); 7.249 (4.9); 7.244 (4.8); 7.230 (7.3); 7.226 (6.3); 7.217 (3.7); 7.211 (4.1); 7.206 (3.3); 7.149 (0.8); 7.146 (0.7); 7.135 (0.7); 7.131 (0.8); 7.110 (0.4); 6.552 (0.4); 6.548 (0.4); 6.537 (0.4); 6.533 (0.4); 5.449 (1.6); 4.826 (0.4); 4.373 (1.9); 4.356 (5.9); 4.338 (6.0); 4.320 (2.0); 2.673 (1.0); 2.669 (1.0); 2.630 (1.5); 2.601 (0.4); 2.567 (0.4); 2.473 (0.6); 2.468 (1.2); 2.464 (1.6); 2.459 (1.1); 2.454 (0.6); 2.178 (350.1); 2.172 (396.0); 2.121 (1.6); 2.115 (2.2); 2.108 (2.6); 2.102 (1.9); 2.096 (1.2); 2.016 (0.4); 1.965 (14.1); 1.959 (15.8); 1.953 (134.8); 1.947 (253.2); 1.941 (354.6); 1.935 (244.9); 1.929 (126.5); 1.854 (0.3); 1.848 (0.3); 1.782 (0.9); 1.776 (1.6); 1.770 (2.2); 1.763 (1.6); 1.757 (0.9); 1.739 (0.4); 1.676 (0.7); 1.658 (0.7); 1.640 (0.4); 1.622 (0.4); 1.379 (6.6); 1.361 (13.0); 1.343 (6.6); 1.331 (0.3); 1.325 (0.4); 1.300 (0.6); 1.282 (1.1); 1.268 (3.8); 1.258 (1.0); 1.247 (1.2); 1.244 (1.0); 1.229 (1.6); 1.226 (1.4); 1.219 (0.5); 1.211 (1.0); 1.209 (0.8); 1.200 (0.4); 1.195 (0.4); 1.101 (0.3); 1.085 (0.3); 1.025 (0.7); 1.014 (1.5); 1.007 (1.3); 0.997 (1.5); 0.989 (0.8); 0.898 (0.4); 0.891 (0.4); 0.881 (0.7); 0.858 (0.5); 0.840 (0.5); 0.774 (0.4); 0.770 (0.4); 0.757 (0.4); 0.751 (0.5); 0.740 (0.4); 0.731 (0.3); 0.723 (0.4); 0.146 (0.6); 0.008 (4.4); 0.000 (149.5); −0.009 (4.9); −0.149 (0.6)

I-1-368:
HPLC-MS: log P=2.51; mass (m/z): 448.9 (M+H)$^+$; $^1$H-NMR (400.0 MHz, CD$_3$CN): δ=8.866 (2.2); 8.112 (0.5); 8.090 (16.0); 7.904 (4.7); 7.902 (4.9); 7.884 (5.0); 7.882 (5.1); 7.640 (3.0); 7.636 (2.8); 7.635 (2.5); 7.620 (4.9); 7.619 (5.3); 7.617 (4.6); 7.616 (4.4); 7.609 (0.6); 7.590 (0.3); 7.583 (2.5); 7.576 (3.9); 7.571 (3.1); 7.563 (3.3); 7.560 (6.7); 7.558 (6.0); 7.556 (8.9); 7.551 (3.2); 7.537 (4.3); 7.532 (2.4); 7.523 (5.1); 7.518 (5.1); 7.513 (0.8); 7.504 (3.1); 7.503 (2.9); 7.500 (4.7); 7.485 (1.7); 7.481 (1.6); 7.455 (2.5); 7.452 (2.6); 7.446 (0.4); 7.436 (5.6); 7.433 (5.8); 7.427 (0.6); 7.417 (3.8); 7.415 (3.7); 7.298 (4.6); 7.294 (5.4); 7.279 (3.8); 7.275 (4.0); 7.209 (3.3); 7.204 (3.1); 7.195 (0.4); 7.189 (4.4); 7.185 (4.3); 7.170 (2.8); 7.166 (2.7); 5.447 (2.2); 4.066 (0.6); 4.048 (0.6); 3.843 (2.0); 2.146 (19.9); 1.971 (3.0); 1.965 (1.0); 1.958 (1.2); 1.953 (11.1); 1.946 (21.1); 1.940 (29.8); 1.934 (20.8); 1.928 (10.8); 1.436 (1.4); 1.372 (3.6); 1.340 (0.3); 1.284 (0.5); 1.276 (4.1); 1.221 (0.8); 1.203 (1.6); 1.185 (0.8); 0.936 (0.3); 0.008 (1.5); 0.000 (37.8); −0.009 (1.6)

I-1-369:
HPLC-MS: log P=2.27; mass (m/z): 424.9 (M+H)$^+$; $^1$H-NMR (400.0 MHz, CD$_3$CN): δ=9.215 (3.3); 8.425 (6.2); 8.420 (6.4); 8.413 (6.5); 8.408 (6.2); 7.901 (11.5); 7.895 (11.4); 7.768 (6.4); 7.763 (6.3); 7.749 (7.3); 7.744 (6.9); 7.615 (5.3); 7.611 (4.5); 7.597 (6.2); 7.592 (6.8); 7.578 (0.5); 7.560 (4.8); 7.555 (5.2); 7.536 (7.8); 7.524 (0.6); 7.481 (2.9); 7.468 (11.5); 7.462 (7.9); 7.456 (11.7); 7.449 (16.0); 7.443 (5.9); 7.437 (10.1); 7.431 (5.2); 7.417 (1.8); 7.412 (1.3); 6.970 (11.7); 6.964 (11.4); 5.447 (3.8); 2.461 (0.4); 2.136 (90.8); 2.132 (76.9); 2.113 (1.7); 2.107 (2.2); 2.101 (1.6); 2.095 (0.9); 1.963 (9.1); 1.952 (125.9); 1.945 (233.6); 1.939 (326.4); 1.933 (224.8); 1.927 (115.7); 1.780 (0.7); 1.774 (1.4); 1.768 (1.9); 1.762 (1.3); 1.756 (0.7); 1.270 (0.7); 0.146 (0.4); 0.008 (3.3); 0.000 (77.8); −0.150 (0.4)

I-1-370:
HPLC-MS: log P=2.71; mass (m/z): 302.0 (M+H)$^+$; $^1$H-NMR (400.0 MHz, CD$_3$CN): δ=8.824 (0.7); 7.859 (2.5); 7.859 (2.5); 7.853 (2.5); 7.603 (1.3); 7.599 (1.1); 7.597 (1.1); 7.584 (1.8); 7.579 (1.7); 7.560 (1.2); 7.555 (1.5); 7.542 (1.3); 7.541 (1.4); 7.536 (1.8); 7.474 (0.7); 7.470 (0.8); 7.455 (1.9); 7.451 (1.7); 7.437 (1.7); 7.434 (1.9); 7.432 (1.5); 7.429 (1.8); 7.415 (1.5); 7.410 (1.5); 7.396 (0.8); 7.390 (2.8); 7.384 (2.7); 6.941 (2.6); 6.935 (2.5); 6.821 (2.5); 6.816 (2.5); 5.446 (0.5); 2.587 (16.0); 2.169 (25.7); 1.964 (4.0); 1.958 (0.8); 1.952 (4.1); 1.946 (7.5); 1.939 (10.4); 1.933 (7.1); 1.927 (3.7); 1.436 (0.4)

I-1-371:
HPLC-MS: log P=2.88; mass (m/z): 386.9 (M+H)$^+$; $^1$H-NMR (400.0 MHz, CD$_3$CN): δ=9.478 (0.4); 7.880 (2.3); 7.874 (2.3); 7.609 (1.2); 7.604 (0.8); 7.600 (0.8); 7.591 (1.2); 7.585 (1.6); 7.541 (0.7); 7.535 (0.8); 7.518 (1.3); 7.480 (0.4); 7.475 (0.7); 7.461 (1.7); 7.456 (1.9); 7.453 (2.0); 7.445 (2.8); 7.435 (1.7); 7.429 (1.2); 7.416 (0.5); 7.411 (0.3); 6.894 (1.1); 2.734 (16.0); 2.699 (0.6); 2.145 (9.8); 1.971 (0.5); 1.964 (0.5); 1.952 (7.9); 1.946 (14.9); 1.940 (21.0); 1.933 (14.6); 1.927 (7.7); 1.372 (5.7); 1.340 (1.2); 1.285 (1.6); 1.276 (5.8); 0.000 (6.5)

I-1-372:
HPLC-MS: log P=2.75; mass (m/z): 336.0 (M+H)$^+$; $^1$H-NMR (400.0 MHz, DMSO-D$_6$): δ=10.370 (2.2); 8.039 (2.9); 8.033 (2.9); 7.681 (1.8); 7.677 (1.1); 7.675 (1.1); 7.662 (1.8); 7.657 (1.7); 7.593 (1.1); 7.588 (1.4); 7.574 (1.4); 7.569 (1.9); 7.521 (0.6); 7.516 (0.8); 7.502 (1.7);

7.498 (1.6); 7.485 (2.3); 7.479 (2.2); 7.466 (1.5); 7.461 (1.4); 7.448 (0.5); 7.443 (0.4); 6.773 (2.7); 6.766 (2.7); 5.756 (1.6); 4.287 (2.1); 4.276 (2.4); 4.265 (2.2); 3.323 (16.3); 3.044 (2.3); 3.032 (2.4); 3.021 (2.1); 2.524 (0.5); 2.511 (11.3); 2.506 (22.3); 2.502 (29.0); 2.497 (20.6); 2.493 (9.8); 2.017 (16.0); 1.235 (1.2); 0.000 (2.9)

I-1-373:

HPLC-MS: log P=3.85; mass (m/z): 354.1 (M+H)$^+$; $^1$H-NMR (601.6 MHz, CD$_3$CN): δ=7.892 (0.8); 7.888 (0.8); 7.602 (0.4); 7.600 (0.4); 7.589 (0.5); 7.587 (0.5); 7.566 (0.4); 7.565 (0.4); 7.553 (0.5); 7.552 (0.5); 7.535 (0.4); 7.532 (0.4); 7.523 (0.5); 7.520 (0.5); 7.453 (0.5); 7.450 (0.5); 7.440 (0.4); 7.433 (0.4); 7.429 (0.4); 7.420 (0.4); 7.417 (0.4); 7.401 (0.3); 7.399 (0.4); 7.338 (0.4); 7.336 (0.4); 7.326 (0.5); 7.323 (0.5); 7.274 (0.4); 7.272 (0.4); 7.262 (0.5); 7.260 (0.5); 6.972 (0.9); 6.967 (0.8); 2.162 (10.0); 1.966 (0.5); 1.950 (2.2); 1.945 (3.9); 1.941 (5.7); 1.937 (3.9); 1.933 (2.0); 1.436 (0.7); 1.429 (16.0); 1.344 (0.5); 0.000 (2.6)

I-1-374:

HPLC-MS: log P=3.15; mass (m/z): 354.0 (M+H)$^+$; $^1$H-NMR (400.0 MHz, DMSO-D$_6$): δ=11.326 (11.6); 8.315 (0.5); 8.108 (16.0); 8.102 (15.0); 7.916 (11.7); 7.903 (12.2); 7.703 (7.0); 7.698 (5.6); 7.685 (8.2); 7.679 (7.9); 7.664 (0.5); 7.628 (6.1); 7.622 (6.4); 7.611 (6.9); 7.608 (6.9); 7.604 (8.8); 7.591 (0.6); 7.571 (5.0); 7.542 (2.6); 7.537 (3.3); 7.523 (8.6); 7.519 (8.1); 7.510 (9.3); 7.505 (11.3); 7.500 (6.5); 7.492 (7.6); 7.487 (6.1); 7.473 (2.5); 7.468 (1.8); 7.432 (10.7); 7.410 (13.2); 7.397 (12.4); 7.294 (5.2); 6.871 (14.9); 6.865 (13.9); 5.756 (1.8); 3.322 (125.3); 2.675 (1.2); 2.671 (1.4); 2.541 (1.2); 2.506 (188.1); 2.502 (221.9); 2.497 (156.1); 2.333 (1.2); 2.328 (1.4); 2.179 (0.5); 1.235 (8.6); 0.871 (0.4); 0.854 (0.8); 0.836 (0.3); 0.000 (62.8); −0.008 (2.9)

I-1-375:

HPLC-MS: log P=3.15; mass (m/z): 372.0 (M+H)$^+$; $^1$H-NMR (400.0 MHz, DMSO-D$_6$): δ=11.490 (7.5); 8.315 (0.7); 8.104 (15.4); 8.098 (15.0); 8.083 (0.4); 7.921 (8.4); 7.908 (8.8); 7.711 (0.5); 7.700 (7.0); 7.695 (5.0); 7.692 (4.5); 7.682 (7.3); 7.676 (8.5); 7.663 (0.6); 7.619 (5.4); 7.613 (5.3); 7.603 (4.8); 7.600 (5.6); 7.595 (8.1); 7.584 (0.6); 7.537 (2.2); 7.532 (3.3); 7.519 (9.1); 7.514 (8.6); 7.509 (9.1); 7.502 (14.8); 7.495 (6.5); 7.490 (7.8); 7.485 (6.5); 7.471 (2.3); 7.466 (1.7); 7.447 (16.0); 7.434 (15.2); 6.889 (0.5); 6.883 (0.6); 6.861 (7.0); 6.856 (6.7); 5.756 (4.6); 3.322 (168.7); 2.675 (1.3); 2.671 (1.7); 2.666 (1.3); 2.541 (1.2); 2.524 (5.3); 2.510 (104.8); 2.506 (203.1); 2.502 (261.3); 2.497 (184.6); 2.493 (86.1); 2.337 (0.6); 2.333 (1.2); 2.328 (1.7); 2.324 (1.2); 2.178 (0.6); 2.160 (0.4); 1.258 (0.6); 1.235 (9.2); 0.854 (1.0); 0.836 (0.4); 0.146 (0.4); 0.008 (4.8); 0.000 (94.9); −0.009 (3.2); −0.150 (0.4)

I-1-376:

HPLC-MS: log P=2.57; mass (m/z): 381.1 (M+H)$^+$; $^1$H-NMR (400.0 MHz, CD$_3$CN): δ=9.520 (2.1); 8.674 (4.5); 8.662 (4.5); 8.243 (4.3); 8.222 (4.6); 7.686 (3.1); 7.674 (3.1); 7.666 (3.0); 7.654 (2.8); 7.640 (0.5); 7.632 (3.9); 7.629 (3.2); 7.614 (5.8); 7.611 (4.7); 7.544 (2.0); 7.536 (2.3); 7.529 (3.0); 7.521 (5.3); 7.511 (3.7); 7.502 (12.0); 7.499 (16.0); 7.495 (10.3); 7.487 (2.3); 7.483 (3.3); 7.479 (2.3); 7.468 (0.4); 7.464 (0.7); 7.460 (0.8); 7.441 (0.4); 7.436 (0.4); 6.558 (13.5); 6.395 (0.8); 5.447 (1.4); 2.449 (0.3); 2.291 (53.9); 2.254 (3.1); 2.147 (46.9); 2.120 (0.3); 2.113 (0.4); 2.107 (4.5); 1.964 (2.2); 1.958 (3.0); 1.952 (23.2); 1.946 (43.3); 1.940 (60.2); 1.934 (41.3); 1.927 (21.2); 1.768 (0.3); 1.269 (0.6); 0.000 (0.9)

I-1-377:

HPLC-MS: log P=3.29; mass (m/z): 338.0 (M+H)$^+$; $^1$H-NMR (400.0 MHz, CD$_3$CN): δ=9.252 (2.3); 7.896 (9.6); 7.890 (9.6); 7.728 (10.8); 7.714 (11.3); 7.615 (4.6); 7.610 (3.7); 7.609 (3.4); 7.596 (6.1); 7.591 (6.0); 7.575 (4.5); 7.569 (5.1); 7.557 (4.5); 7.555 (4.7); 7.551 (6.7); 7.535 (0.4); 7.488 (2.1); 7.483 (2.7); 7.469 (6.4); 7.465 (6.1); 7.453 (7.2); 7.451 (6.9); 7.447 (7.2); 7.434 (5.5); 7.429 (4.8); 7.416 (1.9); 7.411 (1.4); 7.134 (11.5); 7.121 (10.9); 6.930 (9.8); 6.924 (9.6); 6.298 (0.4); 5.447 (1.2); 2.244 (0.4); 2.233 (0.5); 2.227 (0.6); 2.169 (446.8); 2.120 (0.9); 2.114 (0.9); 2.107 (0.9); 2.101 (0.7); 2.095 (0.6); 2.087 (0.4); 2.084 (0.4); 2.076 (0.3); 1.972 (1.2); 1.964 (3.8); 1.958 (5.0); 1.952 (26.5); 1.946 (48.4); 1.940 (66.4); 1.934 (46.0); 1.928 (23.9); 1.775 (0.4); 1.768 (0.5); 1.762 (0.4); 1.690 (0.4); 1.437 (16.0); 1.269 (0.5); 0.911 (0.3); 0.000 (1.5)

I-1-378:

HPLC-MS: log P=2.96; mass (m/z): 413.8 (M+H)$^+$; $^1$H-NMR (400.0 MHz, DMSO-D$_6$): δ=10.867 (7.2); 8.095 (9.5); 8.089 (9.5); 7.924 (12.4); 7.920 (12.6); 7.696 (4.5); 7.692 (3.7); 7.690 (3.6); 7.677 (6.1); 7.672 (5.6); 7.624 (3.9); 7.619 (5.0); 7.606 (4.2); 7.604 (4.6); 7.600 (6.2); 7.538 (2.0); 7.534 (2.5); 7.519 (5.8); 7.515 (5.3); 7.501 (9.5); 7.495 (8.3); 7.482 (4.9); 7.477 (5.0); 7.463 (1.9); 7.458 (1.5); 6.910 (13.2); 6.906 (13.1); 6.865 (9.9); 6.859 (10.0); 5.757 (16.0); 4.039 (0.4); 4.021 (0.4); 3.330 (13.5); 2.526 (0.6); 2.521 (1.0); 2.513 (11.5); 2.508 (23.5); 2.504 (31.1); 2.499 (22.3); 2.495 (10.5); 1.990 (1.9); 1.396 (0.7); 1.193 (0.5); 1.175 (1.1); 1.158 (0.5); 0.000 (6.7)

I-1-379:

HPLC-MS: log P=3.34; mass (m/z): 429.9 (M+H)$^+$; $^1$H-NMR (600.1 MHz, CD$_3$CN): δ=9.213 (2.3); 8.519 (0.4); 8.517 (0.4); 8.512 (0.5); 8.509 (0.5); 8.035 (0.5); 8.033 (0.5); 8.02 (0.6); 8.019 (0.6); 7.894 (11.3); 7.890 (11.2); 7.626 (15.0); 7.621 (0.7); 7.617 (15.9); 7.613 (6.2); 7.611 (5.2); 7.610 (5.3); 7.600 (7.6); 7.597 (7.1); 7.572 (5.6); 7.569 (6.5); 7.559 (6.3); 7.556 (7.5); 7.546 (0.6); 7.538 (0.6); 7.532 (0.6); 7.525 (0.5); 7.483 (2.8); 7.480 (3.4); 7.470 (7.6); 7.468 (6.9); 7.458 (5.8); 7.455 (5.0); 7.451 (6.4); 7.448 (6.4); 7.438 (6.5); 7.435 (6.6); 7.428 (1.4); 7.426 (2.9); 7.423 (2.4); 7.272 (16.0); 7.264 (15.4); 7.103 (1.1); 7.095 (1.0); 6.929 (10.4); 6.925 (10.3); 5.446 (7.3); 2.127 (117.8); 2.058 (0.5); 2.054 (1.0); 2.050 (1.4); 2.046 (1.0); 2.042 (0.5); 1.963 (5.5); 1.955 (5.7); 1.951 (7.7); 1.947 (91.7); 1.943 (175.3); 1.939 (258.1); 1.935 (176.2); 1.931 (88.5); 1.922 (1.4); 1.914 (0.4); 1.832 (0.5); 1.828 (1.0); 1.824 (1.5); 1.820 (1.0); 1.816 (0.5); 1.377 (1.1); 1.372 (8.2); 1.340 (2.2); 1.299 (0.4); 1.289 (0.6); 1.285 (2.8); 1.277 (8.7); 1.264 (0.3); 1.217 (1.2); 0.097 (0.8); 0.005 (5.9); 0.000 (202.9); −0.006 (6.3); −0.100 (0.8)

I-1-380:

HPLC-MS: log P=2.09; mass (m/z): 381.0 (M+H)$^+$; $^1$H-NMR (400.0 MHz, CD$_3$CN): δ=8.846 (4.1); 8.833 (4.2); 8.775 (1.4); 8.678 (7.7); 7.661 (4.8); 7.648 (4.6); 7.598 (2.0); 7.595 (3.2); 7.592 (1.9); 7.581 (2.4); 7.577 (4.6); 7.574 (3.2); 7.565 (0.4); 7.505 (1.6); 7.496 (1.7); 7.490 (2.1); 7.481 (4.2); 7.471 (2.6); 7.463 (12.0); 7.461 (11.8); 7.457 (6.9); 7.450 (2.3); 7.446 (2.6); 7.442 (1.2); 7.427 (0.8); 7.423 (0.6); 7.420 (0.4); 7.253 (0.6); 7.240 (0.4); 7.235 (0.8); 7.197 (0.7); 7.178 (0.4); 7.171 (0.4); 7.165 (0.4); 7.150 (0.4); 6.523 (9.0); 5.447 (3.6); 4.085 (1.3); 4.067 (4.0); 4.049 (4.1); 4.032 (1.4); 2.966 (0.4); 2.887 (0.4); 2.328 (2.7); 2.285 (35.8); 2.274 (1.5); 2.218 (0.6); 2.154 (30.6); 2.131 (0.3); 2.123 (0.4); 2.107 (0.4); 1.971 (18.0); 1.964 (1.6); 1.957 (1.9); 1.952 (16.5); 1.946 (30.9); 1.939 (43.1); 1.933 (29.7); 1.927 (15.3); 1.913 (0.8); 1.553 (1.1); 1.437 (16.0); 1.372 (6.0); 1.341 (1.4); 1.296 (0.4);

1.25 (1.9); 1.285 (6 (6.9); 1.276 (6.9); 1.250 (0.6); 1.231 (0.3); 1.221 (4.9); 1.203 (9.6); 1.185 (4.7); 0.881 (0.3); 0.000 (1.9)

I-1-381:

HPLC-MS: log P=2.19; mass (m/z): 333.0 (M+H)$^+$; $^1$H-NMR (400.0 MHz, CD$_3$CN): δ=18.011 (0.6); 17.562 (0.7); 15.449 (0.6); 9.391 (2.7); 8.783 (16.0); 8.631 (8.9); 8.618 (9.1); 7.928 (10.1); 7.922 (10.4); 7.645 (5.0); 7.639 (3.9); 7.627 (5.8); 7.621 (6.3); 7.587 (4.3); 7.581 (4.8); 7.570 (14.0); 7.563 (7.9); 7.556 (9.9); 7.510 (2.4); 7.496 (6.3); 7.491 (6.1); 7.485 (6.8); 7.479 (10.4); 7.472 (4.6); 7.467 (5.8); 7.462 (4.3); 7.448 (1.4); 7.011 (10.3); 7.005 (9.8); 5.477 (2.0); 4.097 (0.6); 4.079 (0.7); 3.306 (0.7); 2.332 (0.7); 2.318 (0.9); 2.290 (1.3); 2.229 (869.1); 2.223 (1835.6); 2.162 (7.5); 2.150 (1.1); 2.144 (2.0); 2.137 (2.7); 2.131 (1.8); 2.125 (1.0); 2.104 (0.7); 2.087 (0.7); 2.074 (0.6); 2.067 (0.6); 2.042 (0.7); 2.035 (0.8); 1.994 (1128.9); 1.982 (176.2); 1.976 (314.2); 1.970 (437.3); 1.964 (294.7); 1.957 (147.0); 1.920 (0.7); 1.863 (0.6); 1.822 (6.6); 1.815 (0.7); 1.805 (1.8); 1.798 (2.4); 1.792 (1.9); 1.786 (1.1); 1.710 (0.6); 1.317 (0.6); 1.299 (2.2); 1.251 (0.8); 1.233 (1.5); 1.214 (0.6); 0.941 (1.0); 0.029 (1.8)

I-1-382:

HPLC-MS: log P=2.15; mass (m/z): 334.1 (M+H)$^+$; $^1$H-NMR (601.6 MHz, CD$_3$CN): δ=8.090 (1.0); 8.089 (1.8); 8.088 (1.1); 8.076 (1.1); 8.075 (2.0); 8.074 (1.2); 7.652 (3.7); 7.650 (3.9); 7.648 (2.1); 7.646 (2.0); 7.643 (2.0); 7.641 (1.9); 7.629 (0.3); 7.627 (0.3); 7.525 (1.0); 7.521 (1.0); 7.516 (0.9); 7.511 (1.3); 7.507 (0.9); 7.502 (0.8); 7.498 (0.8); 5.451 (0.9); 3.746 (9.2); 3.743 (9.2); 2.410 (16.0); 2.177 (4.9); 1.967 (10.4); 1.959 (0.3); 1.955 (0.4); 1.951 (4.6); 1.947 (8.5); 1.943 (12.4); 1.939 (8.6); 1.935 (4.4); 0.000 (1.1)

I-1-383:

HPLC-MS: log P=2.86; mass (m/z): 387.9 (M+H)$^+$; $^1$H-NMR (400.0 MHz, CD$_3$CN): δ=8.824 (1.4); 7.870 (6.0); 7.864 (5.9); 7.832 (0.7); 7.827 (0.7); 7.623 (0.3); 7.608 (3.1); 7.604 (2.3); 7.602 (2.2); 7.590 (4.1); 7.585 (3.9); 7.578 (0.5); 7.573 (0.5); 7.569 (0.4); 7.558 (2.7); 7.552 (3.4); 7.541 (2.6); 7.538 (3.0); 7.534 (4.4); 7.480 (1.2); 7.476 (1.8); 7.462 (4.4); 7.457 (4.0); 7.448 (4.2); 7.444 (4.4); 7.442 (4.5); 7.438 (3.0); 7.429 (3.7); 7.424 (3.2); 7.416 (0.4); 7.410 (1.1); 7.406 (0.8); 7.402 (0.4); 6.892 (4.4); 6.886 (4.4); 5.446 (1.3); 3.813 (15.9); 3.811 (16.0); 3.408 (0.3); 3.321 (1.5); 2.150 (235.5); 2.132 (1.3); 2.119 (0.5); 2.113 (0.4); 2.107 (0.5); 2.101 (0.4); 2.074 (0.5); 1.976 (1.1); 1.972 (1.5); 1.964 (158.3); 1.958 (4.2); 1.952 (31.5); 1.946 (60.2); 1.940 (87.3); 1.933 (59.2); 1.927 (29.8); 1.792 (0.8); 1.774 (0.4); 1.768 (0.5); 1.762 (0.4); 1.285 (0.4); 1.270 (1.0); 1.135 (0.4); 1.117 (0.8); 1.099 (0.4); 0.000 (2.6)

I-1-384:

HPLC-MS: log P=3.05; mass (m/z): 384.0 (M+H)$^+$; $^1$H-NMR (400.0 MHz, DMSO-D$_6$): δ=11.543 (7.4); 8.110 (9.5); 8.104 (9.4); 7.770 (0.6); 7.750 (1.9); 7.741 (1.1); 7.730 (4.2); 7.716 (6.9); 7.696 (16.0); 7.689 (4.1); 7.678 (7.5); 7.672 (7.6); 7.660 (0.5); 7.624 (4.0); 7.618 (4.0); 7.607 (3.3); 7.605 (3.8); 7.600 (5.9); 7.588 (0.4); 7.531 (1.3); 7.526 (2.0); 7.512 (5.4); 7.507 (5.2); 7.502 (5.5); 7.495 (9.1); 7.488 (4.0); 7.483 (4.9); 7.478 (4.1); 7.464 (1.5); 7.459 (1.0); 6.892 (10.3); 6.885 (10.2); 5.756 (9.7); 3.323 (19.7); 2.675 (0.5); 2.671 (0.6); 2.666 (0.4); 2.524 (1.8); 2.511 (37.2); 2.506 (74.9); 2.502 (98.1); 2.497 (69.8); 2.493 (33.0); 2.333 (0.5); 2.329 (0.6); 2.324 (0.4); 1.989 (1.3); 1.193 (0.4); 1.175 (0.7); 1.157 (0.4); 0.008 (2.3); 0.000 (63.6); −0.009 (2.2)

I-1-385:

HPLC-MS: log P=2.94; mass (m/z): 368.0 (M+H)$^+$; $^1$H-NMR (400.0 MHz, DMSO-D$_6$): δ=11.590 (1.4); 8.840 (1.7); 8.837 (1.5); 8.696 (1.8); 8.693 (1.4); 8.579 (1.5); 8.572 (1.3); 7.855 (0.8); 7.836 (1.0); 7.803 (0.3); 7.785 (0.8); 7.766 (0.7); 7.734 (0.7); 7.716 (1.8); 7.697 (0.8); 7.049 (1.5); 7.042 (1.4); 3.336 (13.5); 2.510 (4.7); 2.505 (5.6); 2.501 (3.8); 0.000 (0.6)

I-1-386:

HPLC-MS: log P=2.45; mass (m/z): 369.0 (M+H)$^+$; $^1$H-NMR (400.0 MHz, DMSO-D$_6$): δ=11.951 (0.4); 11.745 (12.4); 8.863 (6.7); 8.851 (7.0); 8.843 (15.3); 8.839 (16.0); 8.705 (15.3); 8.702 (14.8); 8.681 (0.5); 8.678 (0.6); 8.597 (13.6); 8.590 (13.5); 8.531 (0.5); 8.524 (0.5); 8.316 (0.9); 8.309 (0.4); 8.306 (0.4); 8.229 (6.2); 8.212 (6.6); 7.855 (5.7); 7.843 (5.6); 7.836 (5.3); 7.824 (5.1); 7.049 (14.2); 7.042 (14.1); 6.924 (0.5); 6.916 (0.4); 5.756 (2.5); 4.055 (0.4); 4.038 (1.2); 4.020 (1.2); 4.002 (0.4); 3.320 (66.4); 2.675 (2.1); 2.671 (2.9); 2.666 (2.1); 2.541 (1.5); 2.524 (7.0); 2.510 (163.2); 2.506 (331.2); 2.502 (437.3); 2.497 (315.2); 2.493 (151.7); 2.333 (2.0); 2.328 (2.8); 2.324 (2.1); 2.197 (0.4); 2.179 (0.8); 2.160 (0.4); 1.989 (5.1); 1.398 (2.1); 1.258 (0.6); 1.235 (11.4); 1.193 (1.4); 1.175 (2.7); 1.157 (1.4); 0.870 (0.4); 0.854 (1.1); 0.836 (0.5); 0.146 (1.4); 0.008 (9.9); 0.000 (306.1); −0.008 (11.2); −0.150 (1.4)

I-1-387:

HPLC-MS: log P=2.67; mass (m/z): 336.0 (M+H)$^+$; $^1$H-NMR (400.0 MHz, DMSO-D$_6$): δ=11.798 (10.1); 8.944 (0.3); 8.849 (15.7); 8.846 (16.0); 8.704 (15.6); 8.700 (14.8); 8.656 (0.4); 8.596 (12.3); 8.589 (12.0); 8.315 (2.1); 7.629 (1.4); 7.612 (3.0); 7.608 (2.6); 7.591 (5.4); 7.574 (2.8); 7.570 (3.2); 7.554 (1.4); 7.255 (9.6); 7.235 (13.5); 7.214 (7.8); 7.207 (1.5); 7.049 (14.1); 7.042 (13.7); 5.755 (0.7); 3.373 (0.6); 3.321 (583.0); 3.285 (0.5); 3.278 (0.4); 3.095 (1.9); 2.675 (3.5); 2.671 (4.7); 2.666 (3.4); 2.635 (0.4); 2.541 (2.9); 2.524 (11.6); 2.519 (18.7); 2.511 (269.9); 2.506 (550.6); 2.502 (724.4); 2.497 (511.8); 2.493 (238.6); 2.413 (0.4); 2.337 (1.7); 2.333 (3.3); 2.328 (4.5); 2.324 (3.2); 1.230 (0.3); 1.190 (2.9); 1.171 (4.9); 1.154 (2.9); 0.008 (0.5); 0.000 (12.3)

I-1-388:

HPLC-MS: log P=2.84; mass (m/z): 378.0 (M+H)$^+$; $^1$H-NMR (400.0 MHz, DMSO-D$_6$): δ=11.482 (5.8); 8.948 (1.7); 8.944 (1.8); 8.839 (7.2); 8.836 (7.4); 8.695 (7.6); 8.692 (7.5); 8.577 (7.5); 8.570 (6.3); 8.315 (0.4); 7.718 (3.8); 7.715 (3.9); 7.698 (4.6); 7.695 (4.5); 7.565 (2.4); 7.561 (2.8); 7.546 (4.2); 7.542 (4.4); 7.503 (2.3); 7.500 (2.5); 7.484 (4.9); 7.481 (4.8); 7.471 (1.7); 7.466 (3.7); 7.462 (2.7); 7.441 (3.3); 7.436 (3.3); 7.421 (3.7); 7.417 (3.7); 7.402 (1.8); 7.398 (1.7); 7.064 (6.6); 7.057 (6.6); 6.647 (1.2); 5.755 (16.0); 5.449 (1.9); 5.445 (1.9); 3.346 (0.7); 3.322 (72.3); 2.676 (0.6); 2.671 (0.8); 2.667 (0.6); 2.541 (0.4); 2.525 (2.0); 2.511 (45.6); 2.507 (92.8); 2.502 (122.0); 2.498 (86.3); 2.493 (40.3); 2.333 (0.6); 2.329 (0.8); 2.324 (0.6); 1.506 (1.2); 0.000 (0.8)

I-1-389:

HPLC-MS: log P=2.82; mass (m/z): 334.1 (M+H)$^+$; $^1$H-NMR (400.0 MHz, DMSO-D$_6$): δ=11.498 (12.8); 8.841 (14.8); 8.838 (15.0); 87695 (16.0); 8.692 (15.3); 8.579 (13.1); 8.572 (13.1); 8.316 (0.3); 7.598 (6.4); 7.594 (6.8); 7.580 (8.4); 7.576 (8.9); 7.568 (5.4); 7.565 (6.0); 7.548 (11.9); 7.545 (12.2); 7.529 (5.7); 7.525 (5.8); 7.511 (9.3); 7.507 (8.0); 7.491 (4.9); 7.487 (4.3); 7.463 (7.4); 7.459 (7.1); 7.444 (9.5); 7.441 (9.1); 7.426 (3.6); 7.423 (3.3); 7.068 (13.4); 7.061 (13.2); 5.756 (1.1); 3.323 (80.8); 2.676 (0.7); 2.672 (0.9); 2.668 (0.7); 2.542 (0.6); 2.525 (2.7); 2.511 (54.6); 2.507 (107.6); 2.503 (139.7); 2.498 (99.7); 2.494 (47.6); 2.334 (0.6); 2.329 (0.9); 2.325 (0.6); 0.000 (0.7)

I-1-390:

HPLC-MS: log P=2.96; mass (m/z): 425.9 (M+H)$^+$;
$^1$H-NMR (400.0 MHz, DMSO-D$_6$): δ=11.424 (9.2); 9.024 (0.4); 8.840 (10.6); 8.837 (10.2); 8.747 (0.5); 8.744 (0.4); 8.694 (11.0); 8.691 (10.3); 8.576 (8.6); 8.570 (8.5); 7.935 (7.3); 7.916 (8.0); 7.882 (0.4); 7.514 (0.9); 7.493 (8.4); 7.490 (8.6); 7.480 (16.0); 7.259 (0.4); 7.249 (3.2); 7.241 (2.9); 7.236 (3.0); 7.229 (3.9); 7.227 (3.6); 7.220 (2.7); 7.216 (3.0); 7.207 (2.6); 7.064 (8.8); 7.058 (8.7); 4.056 (0.4); 4.038 (1.1); 4.020 (1.1); 4.002 (0.4); 3.322 (45.6); 2.671 (0.6); 2.667 (0.4); 2.541 (0.4); 2.506 (75.6); 2.502 (96.2); 2.498 (68.9); 2.333 (0.5); 2.329 (0.6); 2.325 (0.4); 1.989 (4.7); 1.193 (1.3); 1.175 (2.5); 1.157 (1.2); 0.000 (0.4)

I-1-391:

HPLC-MS: log P=2.31; mass (m/z): 367.0 (M+H)$^+$;
$^1$H-NMR (400.0 MHz, CD$_3$CN): δ=9.277 (4.2); 8.436 (6.5); 8.432 (7.2); 8.425 (7.1); 8.420 (7.0); 7.997 (11.4); 7.991 (11.8); 7.953 (7.0); 7.948 (7.4); 7.933 (7.8); 7.929 (7.9); 7.824 (5.8); 7.805 (7.5); 7.764 (0.3); 7.750 (1.9); 7.738 (2.3); 7.730 (6.3); 7.715 (7.0); 7.692 (16.0); 7.674 (8.6); 7.656 (2.2); 7.640 (0.4); 7.635 (0.3); 7.615 (0.3); 7.510 (7.3); 7.498 (7.4); 7.490 (7.1); 7.479 (6.7); 7.426 (0.5); 7.420 (0.5); 7.241 (0.3); 7.236 (0.4); 7.003 (12.0); 6.996 (12.3); 5.448 (7.9); 2.150 (57.8); 2.114 (0.4); 2.108 (0.4); 1.972 (1.1); 1.965 (2.3); 1.953 (24.1); 1.947 (45.3); 1.941 (63.2); 1.935 (45.6); 1.928 (24.2); 1.769 (0.4); 1.372 (8.3); 1.340 (1.1); 1.313 (0.6); 1.297 (0.7); 1.284 (1.7); 1.276 (9.3); 1.203 (0.4); 0.146 (0.4); 0.000 (97.0); −0.150 (0.4)

I-1-392:

HPLC-MS: log P=2.13; mass (m/z): 333.0 (M+H)$^+$;
$^1$H-NMR (400.0 MHz, CD$_3$CN): δ=9.317 (4.2); 8.438 (7.6); 8.434 (8.3); 8.427 (8.2); 8.422 (8.2); 7.999 (13.1); 7.993 (13.3); 7.962 (7.5); 7.958 (7.7); 7.942 (8.3); 7.938 (8.3); 7.860 (0.4); 7.854 (0.4); 7.631 (0.8); 7.613 (7.0); 7.610 (7.3); 7.595 (8.4); 7.591 (8.8); 7.527 (4.6); 7.514 (10.9); 7.511 (12.7); 7.507 (14.1); 7.503 (13.4); 7.496 (12.7); 7.483 (16.0); 7.479 (9.3); 7.471 (1.9); 7.463 (4.5); 7.459 (3.8); 7.444 (7.0); 7.440 (6.5); 7.426 (9.5); 7.422 (8.9); 7.408 (3.8); 7.404 (3.5); 7.389 (0.4); 7.384 (0.4); 7.368 (0.4); 7.364 (0.4); 7.350 (0.4); 7.345 (0.4); 7.261 (0.3); 7.256 (0.4); 7.240 (0.5); 7.235 (0.6); 7.172 (0.5); 7.166 (0.5); 7.025 (13.4); 7.019 (13.4); 6.985 (0.5); 6.633 (0.4); 6.626 (0.4); 5.449 (3.7); 4.085 (0.4); 4.067 (1.2); 4.049 (1.2); 4.031 (0.4); 3.993 (0.4); 3.259 (0.4); 2.473 (0.5); 2.468 (0.9); 2.463 (1.3); 2.459 (0.9); 2.454 (0.5); 2.433 (0.4); 2.176 (295.1); 2.121 (0.7); 2.115 (0.9); 2.109 (1.1); 2.103 (0.8); 2.096 (0.5); 1.972 (6.2); 1.966 (5.9); 1.954 (61.0); 1.947 (113.7); 1.941 (158.7); 1.935 (112.0); 1.929 (59.9); 1.782 (0.4); 1.776 (0.7); 1.770 (1.0); 1.764 (0.7); 1.757 (0.4); 1.436 (2.7); 1.385 (0.7); 1.371 (14.6); 1.340 (1.9); 1.310 (2.8); 1.293 (3.1); 1.285 (3.1); 1.276 (14.4); 1.221 (1.5); 1.216 (1.0); 1.204 (2.8); 1.186 (1.4); 0.881 (0.6); 0.858 (0.5); 0.146 (1.3); 0.008 (12.5); 0.000 (261.9); −0.008 (14.8); −0.150 (1.3)

I-1-393 see Synthesis Example 29

I-1-394:

HPLC-MS: log P=2.53; mass (m/z): 415.0 (M+H)$^+$;
$^1$H-NMR (400.0 MHz, CD$_3$CN): δ=9.341 (2.2); 8.126 (8.5); 8.119 (8.8); 7.948 (7.0); 7.928 (6.9); 7.867 (4.9); 7.864 (5.3); 7.847 (5.5); 7.844 (5.9); 7.794 (2.2); 7.790 (2.2); 7.773 (5.5); 7.755 (4.4); 7.751 (4.2); 7.707 (7.5); 7.688 (4.4); 7.518 (4.2); 7.515 (4.3); 7.506 (2.3); 7.494 (16.0); 7.488 (9.8); 7.477 (9.9); 7.458 (1.7); 7.456 (1.7); 7.231 (3.4); 7.224 (3.0); 7.215 (3.1); 7.211 (4.1); 7.208 (3.9); 7.205 (3.3); 7.195 (2.8); 7.188 (2.8); 7.074 (8.6); 7.068 (8.7); 5.448 (5.4); 2.168 (30.1); 2.109 (0.3); 1.965 (1.9); 1.959 (2.5); 1.953 (17.9); 1.947 (33.3); 1.941 (46.3); 1.935 (32.5); 1.929 (17.1); 1.372 (4.0); 1.340 (0.5); 1.311 (0.8); 1.295 (0.8); 1.284 (0.8); 1.276 (4.5); 0.008 (0.5); 0.000 (13.4); −0.009 (0.5)

I-1-395:

HPLC-MS: log P=3.21; mass (m/z): 411.0 (M+H)$^+$;
$^1$H-NMR (400.0 MHz, DMSO-D$_6$): δ=11.571 (0.7); 11.504 (4.3); 8.849 (3.2); 8.838 (3.3); 8.254 (0.6); 8.247 (1.1); 8.217 (7.9); 8.211 (7.7); 8.195 (3.4); 7.841 (2.4); 7.829 (2.6); 7.822 (2.3); 7.810 (2.2); 7.745 (0.4); 7.727 (0.7); 7.709 (0.4); 7.602 (3.2); 7.598 (3.3); 7.582 (3.5); 7.578 (3.4); 7.531 (3.0); 7.527 (2.9); 7.511 (3.7); 7.507 (3.1); 7.405 (0.4); 7.384 (0.7); 7.381 (0.8); 7.360 (0.3); 7.305 (3.2); 7.285 (5.6); 7.265 (2.4); 6.966 (1.3); 6.959 (1.3); 6.929 (5.7); 6.923 (5.7); 5.758 (2.5); 3.826 (2.3); 3.808 (7.2); 3.791 (7.3); 3.773 (2.2); 3.321 (216.7); 2.675 (3.3); 2.670 (4.1); 2.666 (3.0); 2.604 (0.5); 2.588 (0.4); 2.577 (0.5); 2.506 (507.4); 2.501 (635.4); 2.497 (456.0); 2.441 (0.7); 2.381 (0.6); 2.332 (3.3); 2.328 (4.2); 2.324 (2.9); 1.227 (7.8); 1.210 (16.0); 1.192 (7.3); 0.146 (2.8); 0.050 (0.4); 0.008 (30.0); 0.000 (619.9); −0.009 (24.1); −0.030 (1.0); −0.065 (0.3); −0.150 (3.0)

I-1-396:

HPLC-MS: log P=2.91; mass (m/z): 404.1 (M+H)$^+$;
$^1$H-NMR (400.0 MHz, CD$_3$CN): δ=9.280 (1.0); 7.695 (3.2); 7.694 (3.1); 7.676 (3.8); 7.674 (3.7); 7.601 (6.7); 7.567 (6.9); 7.506 (0.9); 7.500 (1.7); 7.486 (4.8); 7.481 (8.1); 7.466 (4.6); 7.464 (4.3); 7.454 (0.5); 7.448 (1.8); 7.445 (1.7); 7.437 (3.4); 7.431 (2.6); 7.418 (2.9); 7.412 (2.5); 7.400 (1.4); 7.395 (1.3); 7.238 (1.7); 7.233 (2.4); 7.228 (1.7); 7.218 (2.8); 7.217 (2.9); 7.213 (3.0); 7.210 (2.7); 7.151 (1.0); 7.136 (1.4); 7.130 (3.6); 7.117 (4.3); 7.115 (4.6); 7.112 (5.0); 7.096 (3.2); 7.091 (3.1); 7.086 (3.1); 7.070 (1.0); 7.065 (0.7); 5.446 (0.6); 4.785 (5.2); 4.751 (5.1); 4.227 (2.2); 4.225 (2.1); 4.209 (6.1); 4.207 (6.1); 4.192 (6.1); 4.189 (6.1); 4.174 (2.0); 4.172 (2.1); 4.090 (0.4); 4.087 (0.4); 4.072 (0.4); 4.069 (0.4); 2.655 (0.4); 2.642 (0.4); 2.148 (21.1); 1.964 (1.4); 1.957 (1.7); 1.952 (12.8); 1.945 (23.9); 1.939 (33.3); 1.933 (23.0); 1.927 (11.9); 1.874 (1.3); 1.860 (1.3); 1.486 (0.4); 1.360 (8.1); 1.359 (8.1); 1.3424 (16.0); 1.3416 (15.9); 1.325 (8.0); 1.261 (0.6); 1.259 (0.4); 1.244 (1.1); 1.241 (0.8); 1.226 (0.5); 1.223 (0.4); 1.183 (0.9); 1.165 (1.7); 1.147 (0.8); 0.008 (1.0); 0.000 (26.1); −0.009 (0.9)

I-1-397:

HPLC-MS: log P=2.74; mass (m/z): 360.1 (M+H)$^+$;
$^1$H-NMR (400.0 MHz, CD$_3$CN): δ=9.487 (0.9); 7.613 (5.6); 7.578 (5.8); 7.546 (3.3); 7.543 (2.4); 7.527 (4.6); 7.517 (6.9); 7.515 (7.1); 7.509 (5.4); 7.503 (4.7); 7.500 (3.1); 7.483 (0.8); 7.479 (1.0); 7.456 (0.5); 7.444 (2.7); 7.436 (1.9); 7.430 (1.8); 7.425 (2.0); 7.422 (2.0); 7.418 (1.7); 7.410 (1.4); 7.403 (1.3); 7.215 (1.6); 7.211 (2.3); 7.206 (1.5); 7.195 (2.7); 7.193 (3.0); 7.191 (2.8); 7.187 (2.6); 7.147 (1.1); 7.132 (1.4); 7.126 (3.3); 7.111 (5.7); 7.104 (3.4); 7.092 (2.5); 7.084 (3.0); 7.079 (2.7); 7.063 (1.0); 7.058 (0.8); 5.448 (1.9); 4.741 (5.3); 4.707 (5.2); 4.224 (2.3); 4.208 (6.2); 4.207 (6.2); 4.191 (6.1); 4.189 (6.1); 4.173 (2.1); 4.172 (2.1); 2.196 (21.5); 2.189 (36.9); 2.186 (38.3); 1.964 (1.2); 1.958 (1.4); 1.952 (10.5); 1.946 (19.4); 1.940 (27.0); 1.934 (18.6); 1.928 (9.6); 1.874 (0.9); 1.860 (0.9); 1.362 (8.1); 1.345 (16.0); 1.327 (8.0); 1.262 (0.4); 1.245 (0.7); 1.240 (0.4); 1.227 (0.4); 1.182 (0.4); 1.164 (0.8); 1.147 (0.6); 0.008 (0.9); 0.000 (23.3); −0.009 (0.8)

I-1-398:

HPLC-MS: log P=3.03; mass (m/z): 420.0 (M+H)$^+$;
$^1$H-NMR (400.0 MHz, DMSO-D$_6$): δ=11.097 (2.3); 7.775 (2.7); 7.769 (2.7); 7.696 (1.5); 7.694 (1.5); 7.677 (1.8); 7.674 (1.8); 7.546 (1.0); 7.542 (1.2); 7.527 (1.8); 7.523

(1.8); 7.495 (1.4); 7.475 (2.9); 7.461 (2.0); 7.458 (2.0); 7.454 (2.0); 7.442 (1.1); 7.439 (1.1); 7.411 (1.1); 7.406 (1.1); 7.391 (1.3); 7.387 (1.3); 7.372 (0.6); 7.368 (0.6); 7.227 (2.2); 7.219 (2.4); 7.216 (1.9); 7.206 (1.8); 7.199 (2.0); 7.196 (1.6); 6.850 (3.0); 6.844 (2.9); 4.111 (1.1); 4.093 (3.5); 4.076 (3.6); 4.058 (1.2); 4.038 (0.7); 4.020 (0.7); 3.321 (53.8); 3.233 (0.5); 3.019 (0.5); 2.675 (0.6); 2.670 (0.9); 2.666 (0.7); 2.523 (2.5); 2.510 (51.4); 2.506 (102.4); 2.501 (134.1); 2.497 (96.8); 2.492 (46.5); 2.332 (0.7); 2.328 (0.9); 2.323 (0.6); 1.989 (2.9); 1.398 (16.0); 1.330 (0.4); 1.221 (3.7); 1.2213.7); 1.204 (7.9); 1.192 (1.3); 1.187 (3.7); 1.179 (0.8); 1.175 (1.7); 1.161 (0.3); 1.157 (0.8); 0.008 (2.7); 0.000 (73.6); −0.009 (2.4); −0.150 (0.3)

I-1-399:
HPLC-MS: log P=2.87; mass (m/z): 404.0 (M+H)$^+$; $^1$H-NMR (400.0 MHz, CD$_3$CN): δ=4.132 (0.4); 4.115 (0.4); 2.327 (16.0); 2.324 (15.8); 1.982 (0.6); 1.976 (1.2); 1.970 (1.6); 1.964 (1.1); 1.958 (0.6); 1.319 (0.4); 1.302 (0.9); 1.284 (0.4)

I-1-400:
HPLC-MS: mass (m/z): 300.1 (M+H)$^+$; $^1$H-NMR (400.0 MHz, DMSO-D$_6$): δ=10.564 (3.9); 8.316 (0.3); 8.127 (2.2); 8.120 (4.2); 8.114 (2.2); 7.808 (1.0); 7.803 (1.1); 7.789 (2.1); 7.784 (1.9); 7.770 (1.1); 7.764 (1.2); 7.493 (0.9); 7.489 (1.0); 7.473 (1.4); 7.469 (1.5); 7.464 (1.0); 7.458 (1.0); 7.444 (1.1); 7.439 (1.5); 7.418 (0.6); 7.413 (0.7); 7.407 (0.6); 7.400 (1.5); 7.395 (1.2); 7.388 (1.5); 7.382 (1.6); 7.376 (2.8); 7.371 (2.9); 7.363 (1.1); 7.357 (2.3); 7.352 (2.1); 7.338 (0.8); 7.334 (0.7); 6.930 (4.8); 6.924 (4.8); 6.801 (4.5); 3.903 (2.2); 3.328 (194.0); 2.675 (0.7); 2.671 (0.9); 2.667 (0.7); 2.523 (23.9); 2.511 (64.2); 2.507 (123.5); 2.502 (157.3); 2.498 (112.4); 2.436 (0.5); 2.333 (0.8); 2.329 (1.0); 2.324 (0.7); 2.315 (0.5); 2.241 (16.0)

I-1-401:
HPLC-MS: log P=3.33; mass (m/z): 352.1 (M+H)$^+$; $^1$H-NMR (400.0 MHz, DMSO-D$_6$): δ=20.008 (1.0); 12.063 (1.1); 11.621 (6.1); 8.973 (5.0); 8.963 (5.1); 8.615 (5.4); 8.594 (5.1); 8.552 (6.3); 8.545 (6.3); 8.315 (4.9); 7.852 (3.1); 7.835 (4.8); 7.802 (1.4); 7.784 (3.2); 7.765 (3.5); 7.734 (3.2); 7.716 (7.8); 7.697 (3.6); 7.680 (1.0); 7.057 (7.1); 7.050 (6.3); 3.525 (1.0); 3.505 (1.1); 3.490 (1.2); 3.472 (1.2); 3.447 (1.3); 3.430 (1.4); 3.406 (3.2); 3.398 (2.2); 3.393 (2.1); 3.329 (5383.3); 3.268 (3.1); 3.231 (1.4); 3.216 (1.2); 3.204 (1.5); 3.194 (1.1); 3.191 (1.1); 2.721 (1.1); 2.675 (11.6); 2.671 (16.0); 2.666 (11.9); 2.585 (2.7); 2.541 (94.2); 2.511 (970.1); 2.506 (1928.6); 2.502 (2517.8); 2.497 (1817.5); 2.493 (878.5); 2.444 (3.4); 2.383 (1.3); 2.370 (1.4); 2.333 (11.5); 2.329 (16.0); 2.324 (11.1); 2.290 (1.0); 1.297 (1.5); 1.259 (2.3); 1.235 (2.5); 0.827 (1.0); 0.000 (6.0); −3.400 (1.2)

I-1-402:
HPLC-MS: log P=2.76; mass (m/z): 353.1 (M+H)$^+$; $^1$H-NMR (400.0 MHz, DMSO-D$_6$): δ=16.885 (1.2); 11.782 (9.5); 8.977 (8.5); 8.967 (8.0); 8.865 (5.3); 8.854 (5.6); 8.626 (8.2); 8.606 (8.3); 8.572 (9.9); 8.566 (10.3); 8.315 (5.9); 8.239 (5.6); 8.220 (5.7); 7.858 (4.4); 7.847 (4.7); 7.839 (4.5); 7.826 (4.2); 7.062 (11.0); 7.055 (11.0); 3.573 (1.1); 3.537 (1.4); 3.481 (1.6); 3.473 (1.1); 3.440 (1.9); 3.423 (1.6); 3.373 (5.2); 3.327 (3958.0); 3.305 (11.2); 3.290 (4.8); 3.278 (1.7); 3.250 (1.4); 3.135 (1.1); 2.788 (1.1); 2.675 (11.9); 2.671 (16.0); 2.635 (1.6); 2.616 (1.6); 2.598 (1.7); 2.541 (91.1); 2.506 (224.8); 2.52 (2524.4); 2.498 (1779.8); 2.431 (1.6); 2.422 (1.7); 2.333 (11.7); 2.329 (15.5); 1.301 (1.5); 1.259 (2.3); 1.236 (4.4); 0.854 (1.1); 0.000 (12.1)

I-1-403:
HPLC-MS: log P=2.32; mass (m/z): 320.1 (M+H)$^+$; $^1$H-NMR (400.0 MHz, DMSO-D$_6$): δ=11.207 (1.6); 11.202 (1.2); 9.078 (1.6); 8.717 (1.7); 8.696 (1.9); 8.315 (4.8); 7.903 (1.6); 7.639 (1.2); 7.598 (1.2); 7.300 (1.3); 7.281 (2.0); 7.260 (1.3); 6.779 (1.7); 3.733 (1.2); 3.584 (1.1); 3.530 (1.1); 3.503 (1.1); 3.481 (1.3); 3.463 (1.5); 3.436 (1.6); 3.421 (1.6); 3.397 (2.2); 3.383 (4.0); 3.326 (3356.3); 3.301 (3.9); 3.295 (3.2); 3.262 (2.3); 3.164 (1.1); 3.092 (1.1); 2.728 (1.2); 2.675 (12.2); 2.671 (16.0); 2.614 (1.3); 2.591 (1.6); 2.575 (2.5); 2.541 (74.5); 2.506 (2031.7); 2.502 (2577.3); 2.497 (1866.6); 2.436 (2.4); 2.374 (1.1); 2.363 (1.2); 2.333 (12.0); 2.329 (16.0); 2.290 (1.1); 2.259 (1.3); 1.297 (1.8); 1.258 (2.6); 1.234 (2.6); 0.858 (1.1); 0.008 (1.1); 0.000 (7.7); −1.654 (1.1); −3.506 (1.0)

I-1-404:
HPLC-MS: log P=3.19; mass (m/z): 364.0 (M+H)$^+$; $^1$H-NMR (400.0 MHz, DMSO-D$_6$): δ=11.519 (13.3); 8.973 (11.1); 8.963 (11.1); 8.947 (0.9); 8.612 (12.1); 8.592 (12.1); 8.551 (14.5); 8.544 (14.2); 8.480 (1.2); 8.315 (5.5); 7.718 (9.4); 7.701 (11.2); 7.698 (11.2); 7.570 (5.7); 7.566 (6.7); 7.551 (9.5); 7.547 (10.1); 7.505 (5.7); 7.502 (6.2); 7.487 (11.9); 7.484 (11.9); 7.468 (6.4); 7.465 (6.5); 7.444 (8.3); 7.439 (8.1); 7.424 (9.0); 7.420 (8.9); 7.405 (4.4); 7.401 (3.8); 7.076 (15.2); 7.069 (14.8); 5.071 (0.9); 4.612 (0.9); 3.550 (1.2); 3.534 (0.9); 3.516 (1.2); 3.495 (1.4); 3.486 (1.3); 3.473 (1.2); 3.468 (1.7); 3.453 (1.3); 3.439 (1.8); 3.433 (1.3); 3.423 (1.5); 3.415 (1.9); 3.408 (3.2); 3.394 (4.3); 3.373 (7.0); 3.357 (17.8); 3.329 (5998.7); 3.289 (3.4); 3.281 (2.1); 3.268 (1.2); 3.247 (1.6); 3.238 (1.2); 3.234 (1.3); 3.210 (1.0); 3.203 (1.3); 3.150 (2.3); 2.994 (1.0); 2.770 (1.0); 2.767 (1.0); 2.696 (0.9); 2.676 (11.8); 2.671 (16.0); 2.666 (12.2); 2.606 (1.3); 2.541 (134.0); 2.524 (54.1); 2.520 (84.7); 2.511 (942.6); 2.506 (1902.0); 2.502 (2501.8); 2.497 (1787.9); 2.493 (846.4); 2.419 (1.4); 2.337 (5.0); 2.333 (11.2); 2.329 (15.2); 2.324 (10.9); 2.290 (1.2); 1.336 (0.9); 1.298 (1.9); 1.258 (2.5); 1.235 (5.2); 0.854 (1.0); 0.000 (8.6)

I-1-405:
HPLC-MS: log P=3.28; mass (m/z): 410.0 (M+H)$^+$; $^1$H-NMR (400.0 MHz, DMSO-D$_6$): δ=16.864 (1.0); 16.266 (1.1); 16.176 (1.0); 11.478 (1.1); 11.460 (8.0); 8.975 (6.7); 8.964 (6.5); 8.611 (7.2); 8.591 (7.4); 8.551 (8.1); 8.544 (8.4); 8.316 (5.1); 7.937 (7.0); 7.917 (7.7); 7.495 (10.8); 7.484 (15.5); 7.252 (3.7); 7.242 (3.2); 7.239 (3.5); 7.232 (4.0); 7.220 (3.8); 7.209 (3.2); 7.076 (8.8); 7.069 (8.4); 3.471 (1.1); 3.445 (1.2); 3.429 (1.1); 3.418 (1.3); 3.403 (1.4); 3.370 (2.4); 3.324 (2280.3); 3.295 (2.9); 3.281 (1.5); 3.273 (1.3); 3.190 (1.0); 2.756 (1.1); 2.752 (1.2); 2.675 (11.7); 2.671 (16.0); 2.666 (11.6); 2.628 (1.8); 2.606 (1.6); 2.541 (99.5); 2.524 (54.6); 2.511 (999.9); 2.506 (1969.9); 2.502 (2550.4); 2.497 (1811.4); 2.493 (859.8); 2.333 (11.4); 2.328 (15.2); 2.324 (11.1); 2.289 (1.5); 1.298 (1.7); 1.259 (2.7); 1.235 (5.7); 0.854 (1.1); 0.831 (1.2); 0.000 (11.0)

I-1-406:
HPLC-MS: log P=2.84; mass (m/z): 362.1 (M+H)$^+$; $^1$H-NMR (400.0 MHz, DMSO-D$_6$): δ=11.269 (2.4); 8.126 (2.9); 8.120 (2.9); 7.832 (1.3); 7.812 (1.6); 7.779 (0.5); 7.761 (1.3); 7.742 (1.2); 7.706 (1.0); 7.686 (1.4); 7.678 (1.8); 7.668 (0.6); 7.659 (1.2); 7.603 (1.5); 7.599 (1.6); 7.584 (1.7); 7.580 (1.7); 7.365 (0.6); 7.361 (0.6); 7.344 (1.3); 7.340 (1.1); 7.326 (1.1); 7.322 (1.1); 7.258 (1.8); 7.256 (2.0); 7.238 (1.3); 7.235 (1.2); 7.093 (1.0); 7.090 (1.0); 7.073 (1.6); 7.071 (1.5); 7.055 (0.8); 7.051 (0.8); 6.846 (3.2); 6.840 (3.1); 5.756 (1.7); 3.883 (16.0); 3.323 (8.7); 2.524 (0.4); 2.524 (0.4); 2.510 (8.3); 2.506 (16.5); 2.501 (21.6); 2.497 (15.3); 2.492 (7.2); 0.008 (1.0); 0.000 (24.9); −0.009 (0.9)

I-1-407:

HPLC-MS: log P=2.37; mass (m/z): 363.1 (M+H)$^+$; $^1$H-NMR (400.0 MHz, DMSO-D$_6$): δ=11.445 (2.1); 8.843 (1.1); 8.840 (1.2); 8.831 (1.2); 8.829 (1.2); 8.192 (1.1); 8.189 (1.1); 8.172 (1.2); 8.170 (1.2); 8.142 (2.8); 8.136 (2.8); 7.834 (1.1); 7.822 (1.1); 7.814 (1.0); 7.802 (1.0); 7.597 (1.5); 7.593 (1.6); 7.577 (1.7); 7.573 (1.6); 7.371 (0.6); 7.367 (0.7); 7.353 (0.9); 7.351 (1.2); 7.346 (1.1); 7.332 (1.2); 7.328 (1.1); 7.263 (1.7); 7.260 (1.8); 7.242 (1.3); 7.239 (1.2); 7.094 (1.0); 7.091 (1.0); 7.075 (1.4); 7.073 (1.4); 7.056 (0.9); 7.053 (0.8); 6.850 (3.1); 6.844 (3.1); 3.884 (16.0); 3.869 (0.8); 3.322 (12.7); 2.524 (0.5); 2.519 (0.8); 2.511 (10.9); 2.506 (22.2); 2.502 (29.3); 2.497 (20.7); 2.492 (9.6); 1.989 (1.2); 1.235 (0.4); 1.193 (0.3); 1.175 (0.7); 1.157 (0.3); 0.008 (1.3); 0.000 (39.1); −0.009 (1.2)

I-1-408:

HPLC-MS: log P=2.57; mass (m/z): 330.1 (M+H)$^+$; $^1$H-NMR (400.0 MHz, DMSO-D$_6$): δ=11.491 (2.1); 8.138 (2.8); 8.132 (2.8); 7.600 (1.7); 7.595 (1.6); 7.583 (0.9); 7.580 (2.2); 7.576 (1.8); 7.567 (0.5); 7.562 (1.3); 7.558 (0.5); 7.546 (0.6); 7.541 (0.8); 7.525 (0.3); 7.373 (0.7); 7.369 (0.7); 7.355 (1.0); 7.352 (1.2); 7.351 (1.1); 7.348 (1.1); 7.334 (1.2); 7.330 (1.1); 7.261 (1.7); 7.258 (1.9); 7.240 (1.5); 7.237 (1.5); 7.232 (2.3); 7.212 (2.9); 7.192 (1.8); 7.184 (0.4) 7.096 (1.0); 7.093 (1.0); 7.076 (1.5); 7.074 (1.4); 7.058 (0.9); 7.054 (0.8); 6.851 (3.2); 6.845 (3.1); 5.756 (0.8); 3.881 (16.0); 3.322 (7.9); 2.524 (0.4); 2.511 (8.4); 2.506 (16.8); 2.502 (22.0); 2.497 (15.6); 2.492 (7.4); 1.989 (0.3); 0.008 (1.0); 0.000 (27.4); −0.009 (1.0)

I-1-409:

HPLC-MS: log P=2.12; mass (m/z): 373.0 (M+H)$^+$; $^1$H-NMR (400.0 MHz, DMSO-D$_6$): δ=11.351 (2.2); 8.477 (1.6); 8.472 (1.7); 8.465 (1.7); 8.460 (1.6); 8.140 (2.8); 8.134 (2.9); 7.982 (1.6); 7.977 (1.6); 7.963 (1.8); 7.958 (1.7); 7.600 (1.5); 7.596 (1.5); 7.580 (1.6); 7.576 (1.6); 7.562 (1.7); 7.550 (1.7); 7.543 (1.6); 7.531 (1.7); 7.370 (0.7); 7.366 (0.6); 7.349 (1.3); 7.346 (1.1); 7.331 (1.1); 7.327 (1.0); 7.262 (1.9); 7.259 (2.0); 7.241 (1.3); 7.238 (1.2); 7.096 (1.0); 7.093 (1.0); 7.077 (1.6); 7.074 (1.5); 7.058 (0.9); 7.055 (0.8); 6.865 (3.0); 6.859 (3.0); 5.755 (1.6); 4.038 (0.5); 4.020 (0.5); 3.883 (16.0); 3.869 (0.5); 3.856 (0.3); 3.320 (38.0); 2.675 (0.4); 2.671 (0.5); 2.666 (0.4); 2.524 (1.2); 2.510 (31.2); 2.506 (62.5); 2.501 (81.5); 2.497 (58.0); 2.492 (27.4); 2.333 (0.4); 2.328 (0.5); 2.324 (0.4); 1.988 (2.1); 1.193 (0.6); 1.175 (1.1); 1.157 (0.5); 0.146 (0.4); 0.008 (3.4); 0.000 (89.0); −0.009 (3.1); −0.150 (0.4)

I-1-410:

HPLC-MS: log P=2.70; mass (m/z): 328.1 (M+H)$^+$; $^1$H-NMR (400.0 MHz, DMSO-D$_6$): δ=11.183 (2.3); 8.128 (2.9); 8.122 (2.9); 7.605 (1.5); 7.601 (1.6); 7.585 (1.7); 7.581 (1.7); 7.567 (1.2); 7.563 (1.3); 7.548 (2.3); 7.544 (2.8); 7.527 (2.1); 7.524 (2.2); 7.504 (1.0); 7.500 (1.0); 7.486 (1.7); 7.481 (1.4); 7.466 (1.0); 7.461 (0.8); 7.444 (1.4); 7.440 (1.4); 7.426 (1.7); 7.422 (1.6); 7.407 (0.7); 7.404 (0.6); 7.364 (0.7); 7.360 (0.7); 7.345 (1.0); 7.343 (1.3); 7.339 (1.2); 7.325 (1.2); 7.321 (1.1); 7.257 (1.8); 7.254 (2.0); 7.236 (1.3); 7.233 (1.2); 7.093 (1.0); 7.090 (1.0); 7.074 (1.5); 7.072 (1.5); 7.055 (0.9); 7.052 (0.8); 6.866 (3.2); 6.860 (3.1); 5.755 (5.7); 3.882 (16.0); 3.323 (9.2); 2.523 (0.3); 2.510 (7.9); 2.506 (16.0); 2.501 (21.0); 2.496 (14.9); 2.492 (7.0); 1.988 (1.0); 1.397 (1.2); 1.175 (0.5); 0.008 (1.0); 0.000 (26.5); −0.009 (0.9)

I-1-411:

HPLC-MS: log P=2.83; mass (m/z): 420.0 (M+H)$^+$; $^1$H-NMR (400.0 MHz, DMSO-D$_6$): δ=11.106 (2.5); 8.127 (3.0); 8.120 (2.9); 7.919 (1.8); 7.899 (2.1); 7.609 (1.5); 7.605 (1.6); 7.589 (1.7); 7.585 (1.6); 7.496 (0.4); 7.493 (0.4); 7.477 (1.5); 7.474 (1.5); 7.461 (2.9); 7.457 (3.4); 7.444 (0.7); 7.362 (0.7); 7.358 (0.6); 7.341 (1.3); 7.338 (1.1); 7.323 (1.2); 7.319 (1.1); 7.257 (1.9); 7.255 (2.1); 7.236 (1.4); 7.234 (1.3); 7.226 (1.0); 7.219 (0.9); 7.209 (1.0); 7.206 (1.1); 7.203 (1.0); 7.199 (0.9); 7.190 (0.8); 7.183 (0.8); 7.094 (1.0); 7.091 (1.0); 7.074 (1.6); 7.072 (1.5); 7.056 (0.8); 7.053 (0.8); 6.862 (3.2); 6.856 (3.1); 5.755 (5.2); 4.037 (0.6); 4.020 (0.6); 3.884 (16.0); 3.321 (11.9); 2.523 (0.4); 2.510 (9.9); 2.505 (20.0); 2.501 (26.3); 2.496 (18.6); 2.492 (8.7); 1.988 (2.7); 1.397 (1.1); 1.192 (0.7); 1.175 (1.5); 1.157 (0.7); 0.008 (1.2); 0.000 (31.6); −0.009 (1.0)

I-1-412:

HPLC-MS: mass (m/z): 314.0 (M+H)$^+$; $^1$H-NMR (400.0 MHz, DMSO-D$_6$): δ=10.718 (2.3); 8.379 (2.7); 8.373 (2.6); 8.229 (2.8); 8.223 (3.3); 8.160 (3.3); 8.153 (2.8); 6.971 (2.8); 6.964 (2.8); 6.835 (2.7); 4.039 (16.0); 3.903 (2.9); 3.903 (2.9); 3.329 (55.9); 2.672 (0.3); 2.526 (12.9); 2.511 (21.1); 2.507 (41.7); 2.503 (53.4); 2.498 (37.5); 2.494 (17.4); 2.329 (0.3); 2.237 (9.3)

I-1-413:

HPLC-MS: mass (m/z): 374.0 (M+H)$^+$; $^1$H-NMR (400.0 MHz, DMSO-D$_6$): δ=11.377 (2.4); 8.401 (2.7); 8.395 (2.7); 8.257 (3.1); 8.250 (3.6); 8.175 (3.5); 8.168 (3.0); 7.709 (1.6); 7.707 (1.6); 7.689 (1.9); 7.687 (1.8); 7.552 (1.0); 7.547 (1.1); 7.533 (1.8); 7.528 (1.9); 7.495 (0.9); 7.492 (0.9); 7.476 (1.9); 7.474 (1.7); 7.458 (1.0); 7.455 (0.9); 7.429 (1.2); 7.424 (1.1); 7.409 (1.4); 7.405 (1.3); 7.391 (0.6); 7.386 (0.6); 6.987 (2.9); 6.981 (2.8); 4.038 (16.0); 3.909 (4.1); 3.335 (152.9); 2.682 (0.4); 2.677 (0.6); 2.673 (0.4); 2.530 (1.5); 2.517 (37.6); 2.513 (75.6); 2.508 (98.3); 2.504 (70.0); 2.499 (33.4); 2.339 (0.4); 2.335 (0.6); 2.330 (0.4)

I-1-414:

HPLC-MS: mass (m/z): 296.1 (M+H)$^+$; $^1$H-NMR (400.0 MHz, DMSO-D$_6$): δ=10.423 (2.8); 7.937 (3.5); 7.931 (3.5); 7.406 (0.8); 7.399 (1.1); 7.388 (1.9); 7.384 (2.3); 7.374 (1.7); 7.366 (3.4); 7.354 (3.2); 7.349 (3.3); 7.340 (3.4); 7.331 (1.5); 7.327 (0.9); 6.839 (3.6); 6.833 (3.5); 6.781 (3.2); 3.909 (2.2); 3.333 (66.9); 2.682 (0.3); 2.677 (0.4); 2.526 (17.6); 2.513 (52.6); 2.508 (66.7); 2.504 (47.6); 2.334 (0.4); 2.273 (16.0); 2.240 (11.9)

I-1-415:

HPLC-MS: log P=2.63; mass (m/z): 377.1 (M+H)$^+$; $^1$H-NMR (400.0 MHz, DMSO-D$_6$): δ=11.332 (10.6); 8.257 (10.7); 8.250 (11.0); 8.025 (6.7); 8.005 (7.4); 7.862 (1.7); 7.859 (1.8); 7.842 (5.9); 7.839 (5.7); 7.821 (16.0); 7.815 (11.9); 7.802 (8.5); 7.766 (2.1); 7.748 (5.9); 7.730 (5.3); 7.700 (4.8); 7.681 (6.0); 7.667 (8.5); 7.650 (8.6); 7.629 (5.9); 7.613 (3.1); 7.608 (3.0); 6.946 (11.1); 6.939 (11.2); 5.758 (12.3); 4.056 (0.7); 4.038 (2.2); 4.020 (2.2); 4.002 (0.7); 3.326 (49.0); 2.890 (0.4); 2.671 (0.6); 2.506 (76.5); 2.502 (98.0); 2.498 (75.7); 2.328 (0.6); 1.989 (9.3); 1.236 (0.6); 1.192 (2.5); 1.174 (4.9); 1.157 (2.5); 0.000 (9.8)

I-1-416:

HPLC-MS: log P=2.16; mass (m/z): 378.1 (M+H)$^+$; $^1$H-NMR (400.0 MHz, DMSO-D$_6$): δ=11.478 (11.1); 8.833 (6.0); 8.823 (5.9); 8.821 (5.9); 8.287 (12.7); 8.281 (12.7); 8.193 (5.7); 8.175 (6.1); 8.173 (6.1); 8.029 (6.6); 8.027 (7.0); 8.009 (7.4); 8.007 (7.6); 7.866 (1.8); 7.863 (1.7); 7.846 (6.4); 7.843 (6.2); 7.827 (16.0); 7.822 (15.4); 7.808 (8.1); 7.801 (6.0); 7.789 (4.8); 7.655 (4.5); 7.650 (4.1); 7.638 (4.5); 7.635 (5.5); 7.630 (4.1); 7.619 (3.7); 7.613 (3.3); 6.950 (13.6); 6.944 (13.6); 5.758 (11.6); 3.323 (112.0); 2.675 (1.8); 2.671 (2.5); 2.666 (1.8); 2.524 (8.8); 2.510

(143.1); 2.506 (280.1); 2.501 (363.7); 2.497 (264.2); 2.493 (129.3); 2.333 (1.8); 2.328 (2.4); 2.324 (1.8); 0.146 (0.7); 0.008 (6.5); 0.000 (168.4); −0.009 (6.8); −0.150 (0.7)

I-1-417:

HPLC-MS: log P=2.34; mass (m/z): 345.1 (M+H)$^+$; $^1$H-NMR (400.0 MHz, DMSO-D$_6$): δ=11.551 (10.4); 8.288 (12.5); 8.282 (12.2); 8.032 (6.4); 8.029 (6.8); 8.011 (7.2); 8.009 (7.4); 7.866 (1.7); 7.863 (1.7); 7.846 (6.1); 7.843 (5.7); 7.826 (16.0); 7.821 (11.3); 7.805 (3.3); 7.801 (1.7); 7.658 (4.3); 7.653 (4.0); 7.640 (4.4); 7.637 (5.5); 7.633 (4.1); 7.621 (3.5); 7.615 (3.2); 7.599 (1.4); 7.582 (3.0); 7.578 (2.8); 7.561 (5.5); 7.544 (2.9); 7.540 (3.3); 7.523 (1.5); 7.233 (1.8); 7.227 (9.3); 7.207 (13.8); 7.186 (8.1); 7.179 (1.9); 6.954 (13.1); 6.948 (13.0); 5.758 (13.8); 4.038 (0.8); 4.020 (0.9); 3.326 (54.5); 2.676 (0.6); 2.671 (0.7); 2.666 (0.6); 2.524 (2.6); 2.511 (42.7); 2.506 (82.2); 2.502 (105.8); 2.497 (76.7); 2.493 (37.2); 2.333 (0.5); 2.329 (0.7); 2.324 (0.5); 1.989 (3.7); 1.235 (0.5); 1.192 (1.0); 1.175 (2.0); 1.175 (2.0); 1.157 (1.0); 0.008 (0.5); 0.000 (12.7); −0.008 (0.4)

I-1-418:

HPLC-MS: log P=2.50; mass (m/z): 389.0 (M+H)$^+$; $^1$H-NMR (400.0 MHz, DMSO-D$_6$): δ=11.243 (12.7); 11.214 (0.3); 8.253 (13.1); 8.246 (12.9); 8.025 (8.0); 8.023 (7.8); 8.005 (9.0); 7.860 (2.4); 7.857 (2.2); 7.840 (7.5); 7.823 (8.7); 7.820 (8.8); 7.814 (11.5); 7.810 (11.9); 7.794 (4.2); 7.790 (2.9); 7.687 (8.3); 7.668 (9.8); 7.649 (5.2); 7.645 (4.8); 7.628 (7.2); 7.611 (3.9); 7.607 (3.5); 7.523 (4.9); 7.519 (5.4); 7.504 (9.3); 7.500 (9.2); 7.472 (4.8); 7.470 (4.7); 7.454 (9.2); 7.435 (4.9); 7.433 (4.3); 7.410 (5.8); 7.406 (5.5); 7.391 (7.0); 7.387 (6.5); 7.372 (3.1); 7.368 (2.7); 6.963 (13.2); 6.957 (13.0); 5.757 (16.0); 4.055 (0.4); 4.038 (1.3); 4.020 (1.3); 4.002 (0.4); 3.324 (99.1); 2.675 (0.9); 2.670 (1.2); 2.666 (0.9); 2.506 (140.0); 2.501 (173.0); 2.497 (127.7); 2.328 (0.2); 2.324 (0.9); 1.989 (5.4); 1.236 (0.6); 1.192 (1.5); 1.174 (2.9); 1.157 (1.5); 0.000 (17.8)

I-1-419:

HPLC-MS: log P=2.61; mass (m/z): 435.0 (M+H)$^+$; $^1$H-NMR (400.0 MHz, DMSO-D$_6$): δ=11.213 (0.4); 11.184 (11.8); 8.251 (11.9); 8.244 (12.1); 8.219 (0.3); 8.213 (0.3); 8.025 (7.1); 8.023 (7.7); 8.003 (8.5); 7.906 (8.9); 7.886 (10.2); 7.861 (2.1); 7.858 (2.1); 7.840 (6.6); 7.838 (6.1); 7.823 (8.0); 7.817 (11.1); 7.812 (11.4); 7.796 (3.6); 7.792 (2.4); 7.648 (4.5); 7.643 (4.4); 7.627 (6.5); 7.610 (3.6); 7.606 (3.5); 7.481 (1.9); 7.462 (7.3); 7.448 (14.9); 7.444 (16.0); 7.431 (3.0); 7.425 (1.1); 7.415 (0.5); 7.220 (4.0); 7.213 (3.8); 7.203 (4.3); 7.200 (5.1); 7.197 (4.9); 7.194 (4.2); 7.184 (3.6); 7.177 (3.3); 7.163 (0.4); 6.962 (12.3); 6.956 (12.4); 5.757 (14.7); 4.055 (0.7); 4.038 (2.2); 4.020 (2.2); 4.002 (0.7); 3.324 (82.5); 2.675 (0.9); 2.670 (1.3); 2.666 (1.0); 2.506 (140.5); 2.501 (183.1); 2.497 (136.5); 2.332 (0.9); 2.328 (1.2); 2.324 (0.9); 1.989 (9.3); 1.235 (0.6); 1.192 (2.5); 1.174 (5.0); 1.157 (2.5); 0.008 (0.8); 0.000 (19.6); −0.008 (0.9)

I-1-420:

HPLC-MS: log P=2.33; mass (m/z): 299.1 (M+H)$^+$; $^1$H-NMR (601.6 MHz, CD$_3$CN): δ=9.281 (4.1); 8.525 (15.9); 8.520 (16.0); 8.415 (7.8); 8.407 (7.9); 7.902 (4.2); 7.899 (4.4); 7.888 (8.3); 7.876 (5.6); 7.874 (5.6); 7.784 (12.7); 7.771 (9.9); 7.614 (7.9); 7.612 (8.5); 7.602 (9.2); 7.599 (9.7); 7.523 (6.5); 7.510 (13.6); 7.496 (5.6); 7.493 (5.9); 7.483 (8.6); 7.481 (8.9); 7.470 (4.4); 7.468 (4.2); 7.439 (6.7); 7.437 (7.1); 7.427 (9.9); 7.425 (10.5); 7.414 (4.0); 7.413 (4.2); 7.262 (7.0); 7.254 (7.4); 7.250 (7.2); 7.241 (6.7); 7.005 (15.8); 7.001 (15.8); 5.449 (0.5); 2.187 (0.5); 2.163 (312.3); 2.057 (0.5); 2.052 (0.8); 2.048 (0.5); 1.966 (4.5); 1.958 (4.2); 1.954 (5.5); 1.950 (50.8); 1.946 (93.5); 1.942 (136.3); 1.938 (93.3); 1.934 (47.4); 1.831 (0.5); 1.827 (0.8); 1.823 (0.5); 1.436 (1.6); 1.267 (0.9); 1.211 (0.5); 1.199 (1.0); 1.188 (0.5); 0.000 (10.1); −0.006 (0.3)

I-1-421:

HPLC-MS: log P=3.43; mass (m/z): 492.8 (M+H)$^+$; $^1$H-NMR (400.0 MHz, CD$_3$CN): δ=9.515 (6.0); 8.730 (14.8); 8.728 (15.0); 8.318 (13.9); 8.314 (14.3); 8.303 (15.9); 8.296 (16.0); 7.901 (12.5); 7.882 (12.5); 7.881 (12.9); 7.481 (4.3); 7.476 (5.6); 7.462 (13.7); 7.457 (13.9); 7.449 (11.7); 7.446 (11.8); 7.431 (13.0); 7.428 (13.6); 7.412 (5.1); 7.409 (5.1); 7.241 (0.4); 7.235 (0.4); 7.194 (7.7); 7.189 (7.3); 7.176 (8.0); 7.174 (9.8); 7.171 (9.8); 7.169 (9.0); 7.156 (6.1); 7.151 (6.6); 7.091 (15.1); 7.085 (15.2); 5.448 (10.7); 2.154 (69.1); 2.121 (0.5); 2.115 (0.6); 2.109 (0.8); 2.102 (0.5); 1.972 (1.4); 1.965 (4.8); 1.959 (5.8); 1.954 (45.5); 1.947 (85.2); 1.941 (119.5); 1.935 (83.7); 1.929 (43.7); 1.776 (0.5); 1.770 (0.7); 1.763 (0.5); 1.436 (1.1); 1.372 (9.7); 1.340 (0.9); 1.284 (1.4); 1.276 (11.0); 1.221 (0.4); 1.216 (0.7); 1.204 (0.6); 1.186 (0.4); 0.008 (1.2); 0.000 (37.1); −0.009 (1.5)

I-1-422:

HPLC-MS: log P=2.72; mass (m/z): 401.2 (M+H)$^+$; $^1$H-NMR (400.0 MHz, DMSO-D$_6$): δ=11.341 (9.6); 8.818 (5.1); 8.815 (5.4); 8.806 (5.3); 8.803 (5.2); 8.457 (5.4); 8.453 (5.4); 8.437 (5.7); 8.433 (5.5); 8.343 (10.7); 8.337 (10.7); 7.835 (5.1); 7.816 (7.0); 7.783 (1.9); 7.766 (5.5); 7.747 (5.0); 7.714 (8.4); 7.696 (16.0); 7.680 (7.7); 6.964 (11.6); 6.958 (11.6); 3.326 (425.1); 2.995 (0.5); 2.711 (1.0); 2.680 (0.7); 2.675 (1.4); 2.671 (1.9); 2.666 (1.4); 2.589 (0.4); 2.541 (276.2); 2.529 (2.9); 2.524 (5.9); 2.511 (110.0); 2.506 (219.0); 2.502 (286.3); 2.497 (211.3); 2.493 (104.9); 2.368 (1.0); 2.338 (0.6); 2.333 (1.3); 2.329 (1.8); 2.324 (1.3); 2.075 (6.0); 1.259 (0.3); 1.235 (0.8); 0.008 (1.7); 0.000 (48.3); −0.009 (1.9)

I-1-423:

HPLC-MS: log P=2.46; mass (m/z): 369.1 (M+H)$^+$; $^1$H-NMR (400.0 MHz, DMSO-D$_6$): δ=11.567 (11.4); 8.822 (6.4); 8.819 (6.6); 8.810 (6.7); 8.807 (6.4); 8.464 (6.9); 8.460 (6.7); 8.444 (7.3); 8.440 (6.8); 8.369 (14.1); 8.362 (14.1); 7.722 (5.0); 7.710 (5.0); 7.703 (4.9); 7.690 (4.6); 7.614 (1.5); 7.597 (3.4); 7.593 (3.1); 7.576 (6.3); 7.559 (3.3); 7.555 (3.7); 7.538 (1.6); 7.250 (2.1); 7.243 (11.0); 7.223 (16.0); 7.203 (9.1); 7.196 (1.8); 6.979 (15.5); 6.972 (15.3); 3.464 (0.4); 3.337 (1001.1); 2.996 (0.5); 2.712 (2.3); 2.676 (1.5); 2.672 (2.0); 2.667 (1.5); 2.585 (0.7); 2.577 (0.8); 2.542 (523.9); 2.525 (6.3); 2.512 (116.3); 2.507 (227.0); 2.503 (293.2); 2.498 (212.4); 2.494 (103.0); 2.368 (2.2); 2.339 (0.7); 2.334 (1.4); 2.329 (1.8); 2.325 (1.3); 2.075 (2.0); 1.259 (0.3); 1.235 (0.7); 0.000 (5.2)

I-1-424:

HPLC-MS: log P=2.61; mass (m/z): 411.1 (M+H)$^+$; $^1$H-NMR (400.0 MHz, DMSO-D$_6$): δ=11.266 (13.4); 8.816 (7.5); 8.813 (7.7); 8.804 (7.8); 8.801 (7.5); 8.455 (7.9); 8.452 (7.7); 8.435 (8.4); 8.432 (7.9); 8.344 (14.9); 8.337 (14.8); 7.711 (6.6); 7.701 (13.6); 7.691 (6.7); 7.681 (14.3); 7.553 (5.9); 7.549 (6.6); 7.534 (10.1); 7.530 (10.2); 7.489 (5.0); 7.489 (5.0); 7.486 (5.1); 7.471 (10.2); 7.468 (9.6); 7.452 (5.5); 7.449 (5.0); 7.425 (6.4); 7.420 (6.4); 7.406 (7.8); 7.401 (7.5); 7.387 (3.5); 7.382 (3.1); 6.986 (16.0); 6.980 (15.7); 3.400 (0.4); 3.367 (1.0); 3.327 (1143.5); 2.675 (3.1); 2.671 (4.3); 2.666 (3.1); 2.662 (1.4); 2.541 (14.5); 2.524 (12.6); 2.511 (258.5); 2.506 (511.5); 2.502 (663.7); 2.497 (475.1); 2.493 (225.0); 2.422 (0.4); 2.419 (0.4); 2.338 (1.4); 2.333 (3.2); 2.328 (4.3); 2.324 (3.1); 2.288 (0.4); 2.075 (5.8); 1.298 (0.5); 1.258 (0.6); 1.235 (0.6); 1.147 (0.5); 0.008 (2.6); 0.000 (78.5); −0.008 (2.3)

I-1-425:
HPLC-MS: log P=2.57; mass (m/z): 367.1 (M+H)$^+$;
$^1$H-NMR (400.0 MHz, DMSO-D$_6$): δ=11.281 (13.6); 8.816 (8.2); 8.814 (8.4); 8.805 (8.5); 8.456 (8.5); 8.452 (8.3); 8.436 (9.0); 8.433 (8.4); 8.344 (15.1); 8.338 (14.9); 7.713 (6.6); 7.700 (6.6); 7.693 (6.5); 7.681 (6.0); 7.583 (7.2); 7.580 (7.6); 7.565 (9.6); 7.561 (10.0); 7.553 (6.1); 7.550 (6.4); 7.533 (12.9); 7.530 (12.8); 7.513 (5.5); 7.509 (5.6); 7.495 (9.4); 7.490 (8.1); 7.475 (5.0); 7.470 (4.1); 7.449 (7.5); 7.445 (7.1); 7.430 (9.5); 7.427 (8.8); 7.412 (3.6); 7.409 (3.1); 6.989 (16.0); 6.983 (15.7); 3.428 (0.4); 3.414 (0.5); 3.399 (0.7); 3.329 (1012.7); 2.711 (0.5); 2.675 (2.4); 2.671 (3.3); 2.667 (2.4); 2.662 (1.2); 2.541 (109.9); 2.524 (11.1); 2.511 (199.6); 2.506 (387.5); 2.502 (498.8); 2.497 (358.8); 2.493 (172.4); 2.368 (0.4); 2.333 (2.4); 2.329 (3.2); 2.324 (2.3); 2.075 (3.0); 1.298 (0.4); 1.258 (0.5); 1.236 (0.6); 1.148 (0.3); 0.008 (1.3); 0.000 (36.0); −0.009 (1.2)

I-1-426:
HPLC-MS: log P=2.69; mass (m/z): 402.1 (M+H)$^+$;
$^1$H-NMR (400.0 MHz, DMSO-D$_6$): δ=11.334 (8.8); 8.925 (5.2); 8.924 (5.2); 8.914 (5.3); 8.824 (4.9); 8.821 (5.1); 8.813 (5.1); 8.809 (4.9); 8.466 (5.3); 8.462 (5.3); 8.446 (5.7); 8.442 (5.4); 8.378 (11.8); 8.372 (16.0); 8.352 (5.5); 7.808 (3.6); 7.807 (3.6); 7.795 (3.6); 7.788 (3.4); 7.776 (3.3); 7.721 (3.9); 7.709 (3.9); 7.702 (3.7); 7.690 (3.6); 6.976 (12.6); 6.969 (12.4); 3.412 (0.3); 3.398 (0.5); 3.383 (0.7); 3.330 (854.2); 2.680 (0.8); 2.676 (1.7); 2.671 (2.4); 2.667 (1.7); 2.662 (0.8); 2.541 (27.7); 2.524 (7.2); 2.520 (11.5); 2.511 (138.4); 2.507 (274.7); 2.502 (357.8); 2.497 (254.2); 2.493 (118.8); 2.338 (0.8); 2.333 (1.7); 2.329 (2.3); 2.324 (1.6); 2.320 (0.7); 2.075 (2.5); 1.299 (0.3); 1.259 (0.5); 1.235 (0.6); 0.008 (0.9); 0.000 (25.8); −0.009 (0.8)

I-1-427:
HPLC-MS: log P=2.72; mass (m/z): 459.0 (M+H)$^+$;
$^1$H-NMR (400.0 MHz, DMSO-D$_6$): δ=11.207 (8.8); 8.816 (4.9); 8.813 (5.0); 8.804 (5.0); 8.801 (4.8); 8.455 (5.1); 8.451 (5.1); 8.435 (5.5); 8.432 (5.2); 8.343 (9.4); 8.336 (9.4); 7.921 (7.2); 7.901 (8.1); 7.710 (4.0); 7.698 (4.0); 7.690 (3.9); 7.678 (3.7); 7.501 (0.8); 7.477 (9.4); 7.468 (16.0); 7.244 (0.5); 7.234 (3.1); 7.225 (3.0); 7.221 (3.2); 7.214 (3.6); 7.212 (3.4); 7.205 (2.9); 7.202 (3.3); 7.192 (2.5); 7.182 (0.4); 6.985 (10.0); 6.978 (9.9); 3.493 (0.3); 3.482 (0.4); 3.456 (0.6); 3.447 (0.6); 3.428 (0.8); 3.413 (1.0); 3.331 (2037.1); 3.283 (1.1); 3.246 (0.3); 2.712 (0.5); 2.680 (1.8); 2.676 (2.6); 2.671 (5.0); 2.666 (3.6); 2.662 (1.7); 2.617 (0.3); 2.604 (0.4); 2.541 (109.5); 2.524 (16.4); 2.519 (26.0); 2.511 (293.4); 2.506 (579.0); 2.502 (751.7); 2.497 (537.4); 2.493 (254.0); 2.432 (0.3); 2.368 (0.4); 2.333 (3.5); 2.329 (4.8); 2.324 (3.4); 2.289 (0.6); 2.074 (4.2); 1.298 (0.6); 1.258 (0.8); 1.235 (1.8); 1.148 (0.5); 0.008 (2.0); 0.000 (59.5); −0.009 (1.8)

I-1-428:
HPLC-MS: log P=3.05; mass (m/z): 401.1 (M+H)$^+$;
$^1$H-NMR (400.0 MHz, DMSO-D$_6$): δ=11.408 (6.6); 8.620 (8.0); 8.615 (8.7); 8.511 (8.1); 8.506 (7.3); 8.268 (7.7); 8.261 (7.6); 7.835 (3.6); 7.816 (4.6); 7.783 (1.3); 7.766 (3.8); 7.747 (3.3); 7.713 (3.0); 7.694 (8.9); 7.675 (4.2); 6.956 (8.4); 6.950 (8.3); 5.756 (16.0); 3.324 (13.3); 2.525 (0.8); 2.512 (14.6); 2.507 (29.0); 2.503 (37.9); 2.498 (26.7); 2.493 (12.4); 1.989 (0.6); 1.397 (10.0); 1.175 (0.4); 0.008 (2.3); 0.000 (55.8); −0.009 (1.8)

I-1-429:
HPLC-MS: log P=2.77; mass (m/z): 369.0 (M+H)$^+$;
$^1$H-NMR (400.0 MHz, DMSO-D$_6$): δ=11.633 (4.8); 8.623 (6.6); 8.618 (7.2); 8.516 (7.2); 8.510 (6.5); 8.286 (5.7); 8.279 (5.7); 7.611 (0.6); 7.594 (1.4); 7.590 (1.2); 7.577 (1.0); 7.573 (2.5); 7.569 (1.0); 7.556 (1.3); 7.552 (1.5); 7.535 (0.6); 7.246 (0.8); 7.240 (4.3); 7.220 (6.0); 7.199 (3.6); 7.192 (0.7); 6.966 (6.5); 6.959 (6.4); 5.756 (16.0); 3.328 (21.7); 2.526 (0.4); 2.513 (7.8); 2.508 (15.6); 2.504 (20.4); 2.499 (14.4); 2.495 (6.8); 0.008 (1.1); 0.000 (26.5); −0.009 (0.9)

I-1-430:
HPLC-MS: log P=2.95; mass (m/z): 410.8 (M+H)$^+$;
$^1$H-NMR (400.0 MHz, DMSO-D$_6$): δ=11.308 (4.6); 8.618 (5.5); 8.613 (5.9); 8.508 (6.0); 8.503 (5.4); 8.264 (5.1); 8.258 (5.0); 7.703 (2.8); 7.700 (2.8); 7.683 (3.3); 7.680 (3.2); 7.550 (2.0); 7.545 (2.2); 7.531 (3.4); 7.527 (3.4); 7.488 (1.6); 7.485 (1.7); 7.470 (3.3); 7.467 (3.1); 7.451 (1.8); 7.448 (1.6); 7.423 (2.2); 7.418 (2.2); 7.403 (2.5); 7.399 (2.5); 7.385 (1.2); 7.380 (1.1); 6.975 (5.5); 6.968 (5.4); 5.755 (16.0); 3.324 (9.0); 2.525 (0.4); 2.520 (0.6); 2.511 (7.6); 2.507 (15.2); 2.502 (19.8); 2.498 (13.9); 2.493 (6.4); 0.008 (1.0); 0.000 (28.2); −0.009 (0.9)

I-1-431:
HPLC-MS: log P=2.29; mass (m/z): 413.9 (M+H)$^+$;
$^1$H-NMR (400.0 MHz, DMSO-D$_6$): δ=11.486 (11.0); 8.623 (14.3); 8.617 (15.6); 8.515 (16.0); 8.510 (14.4); 8.483 (7.4); 8.478 (8.0); 8.471 (8.0); 8.466 (7.8); 8.311 (1.2); 8.283 (12.6); 8.277 (12.6); 8.000 (7.4); 7.995 (7.7); 7.981 (8.6); 7.976 (8.0); 7.566 (8.1); 7.554 (7.9); 7.547 (7.7); 7.535 (7.5); 7.286 (0.7); 7.262 (0.7); 7.239 (0.3); 6.976 (13.8); 6.969 (13.8); 3.594 (0.3); 3.589 (0.3); 3.578 (0.4); 3.533 (0.4); 3.533 (0.6); 3.518 (0.4); 3.509 (0.5); 3.496 (0.4); 3.486 (0.5); 3.474 (0.8); 3.456 (0.8); 3.439 (1.1); 3.420 (1.9); 3.409 (3.2); 3.350 (2513.1); 3.284 (1.5); 3.268 (1.5); 3.253 (0.9); 3.248 (0.9); 3.238 (1.0); 3.219 (0.6); 3.207 (0.7); 3.199 (0.5); 3.186 (0.4); 3.179 (0.4); 3.153 (0.3); 3.143 (0.4); 2.677 (2.0); 2.672 (2.8); 2.668 (1.9); 2.663 (0.9); 2.543 (3.1); 2.536 (0.9); 2.526 (6.3); 2.521 (10.8); 2.512 (160.9); 2.508 (328.4); 2.503 (431.2); 2.499 (304.0); 2.494 (141.3); 2.339 (1.0); 2.335 (2.0); 2.330 (2.7); 2.325 (1.9); 2.321 (0.9); 2.073 (15.0); 2.047 (0.4); 1.654 (0.9); 0.000 (8.0)

I-1-432:
HPLC-MS: log P=2.91; mass (m/z): 366.9 (M+H)$^+$;
$^1$H-NMR (400.0 MHz, DMSO-D$_6$): δ=11.326 (4.6); 8.618 (5.2); 8.613 (5.6); 8.508 (5.7); 8.503 (5.1); 8.266 (5.0); 8.259 (4.9); 7.582 (2.2); 7.578 (2.3); 7.563 (3.0); 7.559 (3.1); 7.551 (1.8); 7.548 (2.0); 7.531 (3.8); 7.528 (3.9); 7.511 (1.8); 7.506 (1.8); 7.492 (3.1); 7.488 (2.7); 7.473 (1.7); 7.468 (1.7); 7.448 (2.4); 7.444 (2.3); 7.429 (3.0); 7.426 (2.8); 7.411 (1.2); 7.408 (1.1); 6.979 (5.3); 6.972 (5.2); 5.756 (16.0); 3.326 (8.0); 2.512 (6.9); 2.507 (13.8); 2.503 (18.0); 2.498 (12.9); 2.494 (6.1); 1.396 (0.4); 0.008 (1.0); 0.000 (24.2); −0.009 (0.9)

I-1-433:
HPLC-MS: log P=3.06; mass (m/z): 458.9 (M+H)$^+$;
$^1$H-NMR (400.0 MHz, DMSO-D$_6$): δ=11.247 (3.0); 8.618 (3.3); 8.612 (3.5); 8.508 (3.6); 8.502 (3.2); 8.264 (3.2); 8.257 (3.1); 7.922 (2.2); 7.902 (2.5); 7.479 (2.4); 7.475 (2.8); 7.466 (4.9); 7.456 (0.5); 7.232 (1.0); 7.223 (1.0); 7.218 (1.0); 7.212 (1.1); 7.209 (1.1); 7.203 (0.9); 7.199 (1.0); 7.189 (0.8); 6.973 (3.3); 6.967 (3.2); 5.754 (16.0); 3.324 (11.4); 2.511 (6.1); 2.506 (11.9); 2.502 (15.2); 2.497 (10.7); 2.493 (4.9); 1.397 (1.4); 0.008 (1.0); 0.000 (20.8); −0.009 (0.7)

I-1-434:
HPLC-MS: log P=2.61; mass (m/z): 387.1 (M+H)$^+$;
$^1$H-NMR (400.0 MHz, DMSO-D$_6$): δ=20.006 (0.8); 11.548 (11.0); 8.484 (10.9); 8.478 (11.9); 8.361 (9.9); 8.354 (10.2); 8.285 (3.2); 8.279 (3.0); 8.264 (3.5); 8.258 (6.2); 8.252 (3.5); 8.237 (3.5); 8.231 (3.2); 7.851 (1.7); 7.831 (3.9); 7.817 (4.0); 7.797 (2.6); 7.636 (3.6); 7.608 (4.1); 7.586 (3.1); 7.489 (7.2); 7.470 (6.6); 6.958 (13.5); 6.951 (13.6);

4.593 (0.7); 4.578 (1.4); 4.565 (0.9); 3.511 (16.0); 3.491 (1.8); 3.477 (2.2); 3.465 (1.1); 3.423 (3.0); 3.411 (3.4); 3.399 (2.7); 3.331 (4647.8); 2.711 (1.1); 2.675 (9.2); 2.671 (12.2); 2.667 (8.9); 2.541 (137.4); 2.524 (38.2); 2.511 (696.8); 2.506 (1362.8); 2.502 (1781.8); 2.497 (1302.9); 2.493 (634.2); 2.367 (0.8); 2.333 (8.5); 2.329 (11.6); 2.324 (8.2); 2.289 (0.7); 2.074 (5.0); 1.336 (2.7); 1.298 (1.3); 1.259 (1.9); 1.249 (3.5); 1.235 (6.8); 1.148 (1.2); 0.907 (0.6); 0.888 (1.2); 0.869 (0.7); 0.854 (0.7); 0.000 (33.3)

I-1-435:
HPLC-MS: log P=1.83; mass (m/z): 431.0 (M+H)$^+$; $^1$H-NMR (400.0 MHz, DMSO-D$_6$): δ=10.817 (2.9); 8.475 (2.7); 8.469 (2.9); 8.429 (5.8); 8.315 (2.3); 8.310 (2.2); 8.308 (2.2); 8.278 (0.9); 8.272 (0.8); 8.257 (0.9); 8.251 (1.6); 8.245 (0.8); 8.230 (0.9); 8.224 (0.8); 6.968 (3.8); 6.961 (3.8); 3.895 (16.0); 3.513 (0.5); 3.336 (50.5); 2.544 (5.8); 2.527 (0.3); 2.522 (0.5); 2.514 (6.8); 2.509 (13.9); 2.504 (18.6); 2.500 (13.6); 2.495 (6.5); 0.000 (1.0)

I-1-436:
HPLC-MS: log P=2.61; mass (m/z): 387.1 (M+H)$^+$; $^1$H-NMR (400.0 MHz, DMSO-D$_6$): δ=11.486 (13.3); 8.482 (11.5); 8.476 (12.0); 8.357 (11.1); 8.351 (10.9); 8.283 (3.2); 8.277 (3.1); 8.262 (3.6); 8.255 (6.0); 8.249 (3.4); 8.234 (3.3); 8.228 (3.0); 7.810 (4.0); 7.797 (4.6); 7.789 (5.8); 7.779 (6.6); 7.775 (9.9); 7.757 (5.3); 7.751 (5.4); 7.671 (3.3); 7.665 (3.0); 7.650 (5.7); 7.644 (5.0); 7.629 (2.6); 7.622 (2.2); 6.978 (16.0); 6.971 (15.7); 3.516 (1.3); 3.339 (118.8); 3.000 (0.8); 2.715 (0.6); 2.575 (0.4); 2.570 (0.5); 2.545 (152.8); 2.528 (1.3); 2.523 (1.9); 2.515 (17.8); 2.510 (35.2); 2.506 (46.8); 2.501 (34.4); 2.496 (16.7); 2.371 (0.6); 2.078 (0.4); 1.233 (0.3); 0.000 (2.9)

I-1-437:
HPLC-MS: log P=2.93; mass (m/z): 403.1 (M+H)$^+$; $^1$H-NMR (400.0 MHz, DMSO-D$_6$): δ=11.536 (12.7); 8.484 (12.3); 8.478 (12.9); 8.362 (11.1); 8.355 (11.1); 8.285 (3.6); 8.279 (3.3); 8.264 (3.8); 8.258 (6.7); 8.252 (3.5); 8.237 (3.6); 8.231 (3.3); 7.872 (8.8); 7.864 (10.0); 7.860 (11.0); 7.851 (13.5); 7.790 (6.7); 7.787 (6.2); 7.768 (3.9); 7.765 (3.8); 6.971 (16.0); 6.964 (15.9); 3.514 (1.5); 3.365 (0.9); 3.338 (229.4); 2.998 (0.4); 2.714 (0.4); 2.678 (0.4); 2.673 (0.5); 2.669 (0.4); 2.563 (0.4); 2.544 (105.3); 2.532 (0.7); 2.527 (1.6); 2.522 (2.3); 2.513 (29.3); 2.509 (58.9); 2.504 (78.3); 2.500 (57.2); 2.495 (27.6); 2.370 (0.4); 2.336 (0.4); 2.331 (0.5); 2.326 (0.4); 1.233 (0.4); 0.000 (3.8)

I-1-438: see Synthesis Example 48

I-1-439:
HPLC-MS: log P=2.85; mass (m/z): 383.1 (M+H)$^+$; $^1$H-NMR (400.0 MHz, DMSO-D$_6$): δ=11.442 (7.7); 8.316 (6.4); 8.310 (5.9); 8.179 (3.5); 8.157 (3.9); 8.153 (3.9); 8.131 (3.5); 7.832 (4.0); 7.812 (4.9); 7.779 (1.4); 7.762 (4.0); 7.743 (3.7); 7.709 (3.2); 7.689 (9.0); 7.669 (4.4); 6.964 (9.3); 6.958 (9.2); 3.322 (182.2); 2.680 (0.5); 2.675 (1.0); 2.671 (1.5); 2.666 (1.0); 2.662 (0.5); 2.524 (4.0); 2.519 (6.2); 2.511 (76.9); 2.506 (156.5); 2.502 (210.7); 2.497 (154.4); 2.492 (73.5); 2.464 (16.0); 2.458 (15.4); 2.456 (15.4); 2.337 (0.5); 2.333 (1.1); 2.328 (1.4); 2.324 (1.0); 2.319 (0.5); 1.989 (0.6); 1.398 (1.0); 1.235 (0.4); 1.175 (0.3); 0.008 (0.5); 0.000 (17.4); −0.009 (0.5)

I-1-440:
HPLC-MS: log P=2.38; mass (m/z): 384.1 (M+H)$^+$; $^1$H-NMR (400.0 MHz, DMSO-D$_6$): δ=11.623 (7.4); 8.844 (3.9); 8.834 (3.8); 8.832 (3.8); 8.343 (6.0); 8.337 (5.9); 8.209 (3.5); 8.206 (3.7); 8.187 (7.3); 8.165 (3.8); 8.160 (3.8); 8.139 (3.4); 7.835 (3.6); 7.824 (3.5); 7.816 (3.8); 7.804 (3.2); 6.969 (9.5); 6.963 (9.4); 5.758 (2.2); 3.322 (233.2); 2.680 (1.0); 2.675 (2.2); 2.670 (3.0); 2.666 (2.2); 2.661 (1.0); 2.524 (8.5); 2.519 (13.4); 2.510 (166.2); 2.506 (336.3); 2.501 (444.8); 2.497 (318.7); 2.492 (149.9); 2.467 (14.8); 2.465 (16.0); 2.459 (15.4); 2.457 (15.1); 2.337 (1.0); 2.333 (2.2); 2.328 (3.0); 2.324 (2.2); 2.319 (1.0); 1.146 (0.3); 0.146 (0.9); 0.008 (7.8); 0.000 (238.1); −0.009 (7.2); −0.150 (0.9)

I-1-441:
HPLC-MS: log P=2.56; mass (m/z): 351.0 (M+H)$^+$; $^1$H-NMR (400.0 MHz, DMSO-D$_6$): δ=11.671 (7.3); 8.340 (6.1); 8.333 (6.0); 8.316 (0.6); 8.185 (3.4); 8.163 (3.9); 8.159 (3.8); 8.137 (3.4); 7.607 (0.9); 7.590 (2.1); 7.586 (1.8); 7.573 (1.5); 7.569 (3.8); 7.552 (1.9); 7.548 (2.3); 7.531 (1.0); 7.242 (1.3); 7.235 (6.7); 7.215 (9.4); 7.194 (5.5); 7.187 (1.1); 6.971 (8.9); 6.964 (8.8); 5.756 (0.9); 3.322 (178.1); 2.675 (1.3); 2.671 (1.8); 2.666 (1.3); 2.524 (6.0); 2.511 (96.3); 2.506 (188.7); 2.502 (249.0); 2.497 (183.7); 2.493 (89.7); 2.465 (16.0); 2.460 (15.4); 2.458 (15.1); 2.337 (0.6); 2.333 (1.2); 2.328 (1.7); 2.324 (1.2); 2.319 (0.6); 1.336 (0.7); 1.298 (0.5); 1.259 (0.7); 1.250 (0.8); 1.235 (0.5); 0.000 (3.9)

I-1-442:
HPLC-MS: log P=2.71; mass (m/z): 395.0 (M+H)$^+$; $^1$H-NMR (400.0 MHz, DMSO-D$_6$): δ=11.339 (7.6); 8.315 (6.0); 8.308 (5.8); 8.178 (3.2); 8.156 (3.7); 8.152 (3.8); 8.130 (3.2); 7.699 (4.5); 7.697 (4.5); 7.679 (5.3); 7.677 (5.2); 7.545 (2.9); 7.540 (3.3); 7.526 (5.2); 7.521 (5.3); 7.484 (2.5); 7.482 (2.7); 7.466 (5.1); 7.463 (5.0); 7.447 (2.8); 7.444 (2.6); 7.420 (3.2); 7.415 (3.3); 7.400 (4.0); 7.396 (3.9); 7.382 (1.8); 7.377 (1.6); 6.984 (7.9); 6.977 (7.8); 5.756 (1.9); 3.322 (145.3); 2.675 (1.0); 2.671 (1.4); 2.666 (1.1); 2.524 (4.2); 2.510 (81.1); 2.506 (158.6); 2.502 (209.1); 2.497 (155.2); 2.493 (77.1); 2.464 (16.0); 2.458 (15.8); 2.333 (1.1); 2.328 (1.4); 2.324 (1.1); 1.336 (0.4); 1.298 (0.3); 1.259 (0.5); 1.250 (0.4); 1.235 (0.4); 0.000 (2.9)

I-1-443:
HPLC-MS: log P=2.16; mass (m/z): 341.1 (M+H)$^+$; $^1$H-NMR (400.0 MHz, DMSO-D$_6$): δ=11.676 (12.3); 8.520 (0.6); 8.514 (0.8); 8.499 (13.2); 8.493 (13.8); 8.483 (0.8); 8.463 (4.6); 8.378 (10.6); 8.376 (10.8); 8.371 (10.8); 8.370 (10.4); 8.316 (10.5); 8.309 (5.4); 8.303 (4.5); 8.288 (5.0); 8.282 (8.8); 8.276 (4.6); 8.261 (4.8); 8.255 (4.4); 8.170 (5.0); 7.939 (11.2); 7.936 (11.0); 7.458 (10.6); 7.456 (10.7); 7.016 (0.8); 7.009 (0.8); 6.990 (16.0); 6.983 (15.8); 6.812 (0.7); 5.757 (0.9); 4.038 (0.7); 4.020 (0.7); 3.324 (113.5); 2.681 (0.4); 2.676 (0.8); 2.672 (1.2); 2.667 (0.8); 2.663 (0.4); 2.525 (3.4); 2.520 (5.4); 2.512 (64.3); 2.507 (128.7); 2.503 (170.4); 2.498 (123.2); 2.494 (58.3); 2.431 (1.9); 2.338 (0.4); 2.334 (0.8); 2.329 (1.2); 2.325 (0.8); 2.320 (0.4); 1.989 (3.2); 1.397 (0.6); 1.336 (1.3); 1.299 (0.5); 1.259 (0.7); 1.250 (1.7); 1.234 (0.5); 1.193 (0.9); 1.175 (1.7); 1.157 (0.9); 0.008 (1.8); 0.000 (53.2); −0.009 (1.7)

I-1-444:
HPLC-MS: log P=2.65; mass (m/z): 373.0 (M+H)$^+$; $^1$H-NMR (400.0 MHz, DMSO-D$_6$): δ=11.594 (2.5); 8.495 (3.7); 8.489 (3.9); 8.382 (3.1); 8.377 (3.1); 8.316 (1.1); 8.307 (1.3); 8.301 (1.2); 8.286 (1.4); 8.280 (2.5); 8.274 (1.3); 8.259 (1.3); 8.253 (1.2); 8.019 (1.3); 7.874 (3.2); 7.730 (1.6); 6.951 (2.4); 6.944 (2.4); 3.322 (526.6); 2.680 (1.1); 2.675 (2.3); 2.670 (3.2); 2.666 (2.3); 2.661 (1.0); 2.541 (11.1); 2.524 (8.2); 2.519 (12.8); 2.511 (177.2); 2.506 (361.6); 2.501 (478.3); 2.497 (338.8); 2.492 (156.9); 2.337 (1.1); 2.333 (2.3); 2.328 (3.1); 2.324 (2.2); 2.319 (1.0); 2.280 (16.0); 1.259 (0.4); 1.235 (1.0); 0.008 (1.6); 0.000 (51.8); −0.009 (1.5)

I-1-445:
HPLC-MS: log P=1.60; mass (m/z): 333.2 (M+H)$^+$; $^1$H-NMR (400.0 MHz, CD$_3$CN): δ=8.526 (0.7); 8.269 (2.1); 8.263 (2.1); 8.170 (1.7); 8.164 (1.7); 7.699 (0.7); 7.693

(0.7); 7.679 (0.8); 7.673 (1.3); 7.667 (0.7); 7.652 (0.7); 7.646 (0.7); 7.636 (0.3); 6.991 (2.4); 6.985 (2.3); 5.448 (1.1); 3.685 (15.2); 3.671 (0.3); 3.233 (0.9); 3.030 (0.9); 2.469 (0.4); 2.464 (0.5); 2.459 (0.4); 2.428 (15.9); 2.357 (16.0); 2.174 (55.4); 2.120 (0.3); 2.114 (0.5); 2.108 (0.6); 2.102 (0.4); 1.965 (5.5); 1.959 (8.4); 1.953 (33.9); 1.947 (58.3); 1.940 (75.4); 1.934 (51.7); 1.928 (26.6); 1.842 (0.3); 1.775 (0.3); 1.769 (0.4); 0.008 (1.5); 0.000 (34.5); −0.009 (1.3)

I-1-446:
HPLC-MS: log P=1.54; mass (m/z): 319.1 (M+H)$^+$;
$^1$H-NMR (400.0 MHz, DMSO-D$_6$): δ=10.654 (2.6); 8.470 (2.5); 8.464 (2.6); 8.445 (4.6); 8.292 (2.0); 8.285 (2.0); 8.275 (0.8); 8.269 (0.8); 8.254 (0.9); 8.248 (1.5); 8.241 (0.8); 8.227 (0.8); 8.220 (0.7); 6.969 (3.2); 6.963 (3.2); 5.757 (0.5); 3.792 (15.2); 3.323 (75.2); 2.675 (0.5); 2.671 (0.7); 2.666 (0.5); 2.524 (1.8); 2.519 (2.8); 2.511 (38.3); 2.506 (77.4); 2.502 (102.8); 2.497 (74.5); 2.493 (35.6); 2.363 (16.0); 2.333 (0.5); 2.328 (0.7); 2.324 (0.5); 2.075 (0.4); 0.008 (1.4); 0.000 (44.6); −0.009 (1.4)

I-1-447:
HPLC-MS: log P=2.03; mass (m/z): 364.1 (M+H)$^+$;
$^1$H-NMR (400.0 MHz, DMSO-D$_6$): δ=11.987 (2.1); 8.493 (2.3); 8.487 (2.4); 8.410 (2.1); 8.404 (2.1); 8.315 (0.7); 8.298 (0.7); 8.292 (0.6); 8.277 (0.8); 8.271 (1.3); 8.265 (0.7); 8.250 (0.7); 8.244 (0.7); 7.021 (2.9); 7.014 (2.9); 3.845 (16.0); 3.371 (0.4); 3.325 (432.6); 2.995 (1.0); 2.680 (0.6); 2.675 (1.3); 2.671 (1.7); 2.666 (1.3); 2.662 (0.6); 2.541 (59.5); 2.524 (5.1); 2.511 (97.8); 2.506 (197.2); 2.502 (259.9); 2.497 (187.0); 2.493 (89.1); 2.449 (14.3); 2.338 (0.6); 2.333 (1.2); 2.328 (1.7); 2.324 (1.2); 2.319 (0.6); 1.235 (1.1); 0.008 (0.6); 0.000 (15.6); −0.009 (0.5)

I-1-448:
HPLC-MS: log P=1.83; mass (m/z): 364.1 (M+H)$^+$;
$^1$H-NMR (400.0 MHz, DMSO-D$_6$): δ=11.480 (2.8); 8.481 (2.8); 8.475 (3.0); 8.360 (2.5); 8.353 (2.5); 8.316 (0.4); 8.284 (0.9); 8.278 (0.8); 8.263 (1.0); 8.257 (1.6); 8.250 (0.9); 8.235 (0.9); 8.229 (0.8); 6.973 (3.3); 6.967 (3.2); 3.870 (16.0); 3.323 (93.8); 2.675 (0.7); 2.671 (0.9); 2.666 (0.7); 2.610 (15.4); 2.541 (0.5); 2.524 (2.6); 2.511 (55.6); 2.506 (109.1); 2.502 (140.4); 2.497 (100.3); 2.493 (48.4); 2.333 (0.7); 2.329 (0.9); 2.324 (0.7); 0.146 (0.4); 0.008 (3.9); 0.000 (94.2); −0.008 (3.9); −0.150 (0.4)

I-1-449:
HPLC-MS: log P=1.67; mass (m/z): 306.1 (M+H)$^+$;
$^1$H-NMR (601.6 MHz, DMF): δ=10.909 (0.4); 8.499 (1.9); 8.495 (1.9); 8.453 (1.9); 8.4493 (1.8); 8.4488 (1.8); 8.261 (0.7); 8.257 (0.6); 8.248 (0.7); 8.243 (1.3); 8.239 (0.6); 8.230 (0.7); 8.225 (0.6); 8.131 (4.4); 8.025 (4.3); 7.074 (2.1); 7.069 (2.0); 5.817 (0.4); 4.286 (16.0); 3.471 (4.4); 2.952 (4.4); 2.922 (2.2); 2.919 (4.3); 2.916 (6.3); 2.912 (4.3); 2.909 (2.0); 2.784 (4.2); 2.751 (2.5); 2.748 (4.8); 2.745 (6.8); 2.741 (4.8); 2.738 (2.4); 2.616 (0.7); 0.005 (0.4); 0.000 (1.9)

I-1-450:
HPLC-MS: log P=3.65; mass (m/z): 491.1 (M+H)$^+$;
$^1$H-NMR (400.0 MHz, DMSO-D$_6$): δ=12.141 (3.6); 8.498 (3.6); 8.492 (3.8); 8.420 (3.2); 8.413 (3.2); 8.315 (1.1); 8.307 (1.2); 8.300 (1.2); 8.286 (1.3); 8.279 (2.3); 8.273 (1.1); 8.258 (1.2); 8.252 (1.1); 6.990 (4.6); 6.983 (4.5); 4.002 (16.0); 3.920 (0.4); 3.414 (0.4); 3.392 (0.5); 3.387 (0.5); 3.374 (0.8); 3.359 (1.4); 3.326 (1280.7); 3.296 (1.1); 3.273 (1.1); 3.271 (0.4); 2.680 (1.2); 2.675 (2.4); 2.671 (3.4); 2.666 (2.4); 2.662 (1.1); 2.541 (83.9); 2.524 (8.4); 2.511 (65.2); 2.506 (384.4); 2.502 (509.9); 2.497 (363.2); 2.493 (169.8); 2.367 (0.3); 2.338 (1.1); 2.333 (2.4); 2.328 (3.3); 2.324 (2.3); 2.319 (1.1); 2.289 (0.6); 1.258 (0.4); 1.235 (1.1); 0.008 (0.6); 0.000 (18.6); −0.009 (0.6)

I-1-451:
HPLC-MS: log P=2.79; mass (m/z): 441.0 (M+H)$^+$;
$^1$H-NMR (400.0 MHz, DMSO-D$_6$): δ=11.728 (4.9); 8.484 (4.7); 8.478 (5.0); 8.364 (4.3); 8.357 (4.3); 8.292 (1.5); 8.286 (1.3); 8.271 (1.6); 8.265 (2.7); 8.258 (1.4); 8.243 (1.5); 8.237 (1.3); 6.930 (6.0); 6.923 (5.9); 5.758 (3.3); 4.127 (16.0); 3.323 (109.4); 2.680 (0.4); 2.675 (0.9); 2.671 (1.2); 2.666 (0.9); 2.662 (0.4); 2.524 (3.5); 2.511 (66.0); 2.506 (130.7); 2.502 (170.6); 2.497 (122.5); 2.493 (58.0); 2.333 (0.8); 2.329 (1.2); 2.324 (0.8); 2.320 (0.4); 0.008 (0.9); 0.000 (25.5); −0.009 (0.8)

I-1-452:
HPLC-MS: log P=2.27; mass (m/z): 349.1 (M+H)$^+$;
$^1$H-NMR (400.0 MHz, DMSO-D$_6$): δ=11.199 (3.1); 8.487 (2.8); 8.480 (3.0); 8.335 (2.6); 8.329 (2.5); 8.317 (0.9); 8.297 (0.9); 8.291 (0.8); 8.270 (1.5); 8.249 (1.1); 8.238 (3.1); 8.234 (3.1); 7.890 (3.6); 7.885 (3.5); 6.955 (3.2); 6.948 (3.2); 3.977 (16.0); 3.403 (0.4); 3.325 (350.6); 2.670 (3.1); 2.506 (393.9); 2.502 (484.1); 2.498 (358.1); 2.445 (0.5); 2.421 (0.4); 2.412 (0.4); 2.332 (2.3); 2.328 (2.9); 1.988 (0.4); 1.259 (0.5); 1.235 (0.8); 0.146 (0.5); 0.000 (90.0); −0.150 (0.4)

I-1-453:
HPLC-MS: log P=1.69; mass (m/z): 350.1 (M+H)$^+$;
$^1$H-NMR (400.0 MHz, DMSO-D$_6$): δ=11.534 (2.8); 8.891 (5.4); 8.482 (2.8); 8.476 (2.9); 8.371 (2.5); 8.364 (2.5); 8.316 (0.9); 8.286 (0.8); 8.280 (0.7); 8.264 (0.9); 8.258 (1.6); 8.252 (0.8); 8.237 (0.8); 8.231 (0.8); 6.985 (3.2); 6.978 (3.1); 5.756 (1.2); 3.947 (16.0); 3.324 (384.8); 2.675 (1.9); 2.671 (2.5); 2.666 (1.8); 2.541 (1.6); 2.510 (151.1); 2.506 (293.3); 2.502 (379.5); 2.497 (271.7); 2.493 (130.3); 2.333 (1.8); 2.328 (2.4); 2.324 (1.8); 0.146 (1.3); 0.008 (11.8); 0.000 (287.0); −0.008 (10.7); −0.150 (1.3)

I-1-454:
HPLC-MS: log P=1.58; mass (m/z): 350.0 (M+H)$^+$;
$^1$H-NMR (400.0 MHz, DMSO-D$_6$): δ=11.335 (3.1); 8.480 (2.8); 8.474 (3.1); 8.365 (2.7); 8.359 (2.7); 8.316 (0.4); 8.284 (0.9); 8.277 (0.8); 8.262 (1.0); 8.256 (1.7); 8.250 (0.9); 8.235 (0.9); 8.229 (0.8); 8.085 (5.0); 6.984 (3.3); 6.977 (3.3); 3.930 (16.0); 3.324 (123.4); 2.675 (0.7); 2.671 (0.9); 2.666 (0.7); 2.541 (0.5); 2.524 (2.2); 2.506 (108.4); 2.502 (142.0); 2.498 (103.9); 2.333 (0.7); 2.329 (0.9); 2.324 (0.7); 0.146 (0.4); 0.008 (3.1); 0.000 (89.8); −0.008 (3.8); −0.150 (0.4)

I-1-455:
HPLC-MS: log P=3.37; mass (m/z): 381.1 (M+H)$^+$;
$^1$H-NMR (400.0 MHz, DMSO-D$_6$): δ=11.542 (4.1); 8.491 (5.3); 8.485 (5.6); 8.368 (4.2); 8.361 (4.2); 8.315 (1.2); 8.300 (1.6); 8.293 (1.5); 8.279 (1.8); 8.272 (3.0); 8.266 (1.6); 8.251 (1.6); 8.245 (1.4); 7.689 (8.6); 6.987 (3.7); 6.981 (3.7); 4.537 (0.8); 4.522 (1.3); 4.500 (1.3); 4.485 (0.9); 3.458 (0.3); 3.440 (0.4); 3.419 (0.7); 3.395 (0.9); 3.328 (1742.5); 3.284 (1.2); 3.255 (0.4); 2.995 (0.8); 2.675 (3.3); 2.671 (4.4); 2.667 (3.2); 2.541 (14.1); 2.524 (12.6); 2.511 (266.7); 2.506 (516.9); 2.502 (665.9); 2.498 (479.9); 2.493 (233.4); 2.333 (3.2); 2.329 (4.3); 2.324 (3.1); 2.290 (0.5); 1.875 (0.8); 1.856 (1.1); 1.840 (1.5); 1.821 (1.6); 1.800 (1.3); 1.781 (0.4); 1.765 (0.3); 1.746 (1.2); 1.732 (1.5); 1.728 (1.4); 1.714 (1.8); 1.698 (1.0); 1.680 (0.7); 1.421 (12.4); 1.405 (12.3); 1.298 (0.5); 1.259 (0.7); 1.235 (2.1); 0.726 (7.4); 0.708 (16.0); 0.689 (6.9); 0.008 (0.8); 0.000 (20.1); −0.008 (0.7)

I-1-456:
HPLC-MS: log P=3.28; mass (m/z): 473.0 (M+H)$^+$;
$^1$H-NMR (400.0 MHz, DMSO-D$_6$): δ=11.474 (5.2); 8.492

(5.7); 8.486 (6.0); 8.364 (4.3); 8.358 (4.3); 8.315 (1.7); 8.297 (1.8); 8.291 (1.6); 8.276 (1.9); 8.269 (3.3); 8.263 (1.8); 8.248 (1.8); 8.242 (1.6); 7.630 (11.0); 6.989 (4.7); 6.983 (4.7); 4.461 (1.0); 4.445 (1.4); 4.424 (1.4); 4.409 (1.0); 4.394 (0.4); 3.479 (0.4); 3.466 (0.3); 3.443 (0.6); 3.431 (0.5); 3.417 (0.7); 3.408 (0.8); 3.388 (1.3); 3.328 (2368.1); 3.293 (1.9); 3.280 (1.2); 3.253 (0.5); 2.676 (3.9); 2.671 (5.3); 2.666 (3.9); 2.662 (1.9); 2.541 (29.9); 2.524 (13.6); 2.511 (303.8); 2.506 (613.8); 2.502 (810.3); 2.497 (583.1); 2.493 (277.8); 2.419 (0.3); 2.333 (3.8); 2.329 (5.2); 2.324 (3.8); 2.290 (0.7); 1.868 (0.8); 1.849 (1.1); 1.833 (1.5); 1.812 (1.6); 1.793 (1.3); 1.775 (0.4); 1.733 (1.2); 1.719 (1.5); 1.715 (1.5); 1.701 (1.9); 1.682 (1.1); 1.667 (0.8); 1.406 (12.4); 1.390 (12.3); 1.355 (0.4); 1.298 (0.7); 1.259 (1.0); 1.235 (3.1); 0.854 (0.4); 0.721 (7.4); 0.702 (16.0); 0.684 (7.0); 0.008 (0.6); 0.000 (20.3); −0.009 (0.6)

I-1-457:
HPLC-MS: log P=2.13; mass (m/z): 383.1 (M+H)$^+$; $^1$H-NMR (400.0 MHz, DMSO-D$_6$): δ=20.013 (0.3); 11.562 (12.8); 8.707 (9.4); 8.703 (10.5); 8.695 (10.5); 8.691 (10.4); 8.489 (14.9); 8.483 (16.0); 8.364 (11.6); 8.358 (11.9); 8.292 (5.0); 8.286 (4.6); 8.271 (5.3); 8.265 (9.4); 8.258 (5.0); 8.244 (5.1); 8.237 (4.7); 8.096 (7.5); 8.091 (7.9); 8.076 (8.5); 8.072 (8.3); 7.544 (8.5); 7.532 (8.6); 7.525 (8.4); 7.513 (8.1); 7.011 (14.4); 7.004 (14.6); 4.137 (4.1); 4.109 (12.8); 4.080 (13.4); 4.052 (4.6); 3.473 (0.5); 3.442 (0.7); 3.337 (3631.0); 3.211 (1.0); 3.147 (0.6); 2.995 (0.6); 2.681 (2.5); 2.676 (5.2); 2.671 (7.2); 2.667 (5.2); 2.662 (2.5); 2.542 (42.8); 2.525 (22.7); 2.520 (34.8); 2.511 (399.6); 2.507 (806.5); 2.502 (1065.4); 2.498 (765.9); 2.493 (362.6); 2.338 (2.4); 2.334 (5.0); 2.329 (6.9); 2.324 (4.9); 2.320 (2.3); 2.291 (0.4); 1.258 (0.3); 1.235 (0.7); 1.147 (0.7); 0.008 (2.2); 0.000 ((64.0); −0.009 (1.7)

I-1-458:
HPLC-MS: log P=2.53; mass (m/z): 367.1 (M+H)$^+$; $^1$H-NMR (400.0 MHz, DMSO-D$_6$): δ=11.161 (13.3); 8.480 (14.0); 8.474 (14.8); 8.344 (11.6); 8.337 (11.6); 8.316 (0.8); 8.280 (4.5); 8.274 (4.2); 8.259 (4.8); 8.253 (8.4); 8.247 (4.5); 8.232 (4.5); 8.226 (4.1); 7.636 (7.0); 7.632 (8.1); 7.617 (8.2); 7.613 (9.0); 7.585 (4.2); 7.581 (3.9); 7.565 (7.4); 7.562 (6.9); 7.546 (5.9); 7.541 (5.1); 7.386 (7.7); 7.364 (6.4); 7.362 (6.7); 7.345 (10.8); 7.343 (11.1); 7.326 (4.9); 7.324 (4.9); 7.277 (9.6); 7.257 (8.4); 7.202 (16.0); 7.017 (8.1); 6.997 (14.8); 6.990 (14.6); 5.756 (1.7); 3.323 (236.9); 2.680 (0.9); 2.675 (1.8); 2.671 (2.5); 2.666 (1.8); 2.662 (0.9); 2.524 (6.9); 2.519 (1.7); 2.511 (137.6); 2.506 (279.5); 2.502 (370.1); 2.497 (267.1); 2.493 (127.5); 2.338 (0.8); 2.333 (1.8); 2.328 (2.4); 2.324 (1.7); 2.319 (0.8); 1.989 (1.1); 1.298 (1.3); 1.259 (1.9); 1.235 (1.1); 1.193 (0.3); 1.175 (0.6); 0.146 (0.4); 0.008 (3.2); 0.000 (99.9); −0.009 (3.1); −0.150 (0.4)

I-1-459:
HPLC-MS: log P=2.50; mass (m/z): 351.1 (M+H)$^+$; $^1$H-NMR (400.0 MHz, DMSO-D$_6$): δ=11.485 (11.9); 8.495 (15.5); 8.489 (16.0); 8.361 (11.9); 8.355 (11.7); 8.296 (4.6); 8.290 (4.2); 8.275 (5.0); 8.269 (8.5); 8.263 (4.5); 8.248 (4.6); 8.242 (4.1); 7.794 (5.5); 7.776 (7.5); 7.762 (6.3); 7.744 (9.7); 7.709 (3.3); 7.706 (3.7); 7.691 (8.9); 7.687 (7.7); 7.673 (12.4); 7.669 (10.6); 7.654 (6.4); 7.635 (2.0); 7.493 (5.4); 7.354 (11.7); 7.215 (5.8); 7.008 (11.8); 7.002 (11.5); 3.508 (0.5); 3.496 (0.3); 3.474 (0.5); 3.457 (0.5); 3.439 (0.8); 3.410 (1.3); 3.345 (1104.0); 3.304 (1.9); 3.288 (1.0); 3.270 (0.4); 3.223 (0.3); 3.001 (1.9); 2.718 (1.4); 2.682 (1.8); 2.677 (2.3); 2.673 (1.7); 2.610 (0.3); 2.607 (0.4); 2.548 (321.5); 2.517 (146.6); 2.513 (274.7); 2.508 (346.5); 2.504 (247.4); 2.500 (118.6); 2.467 (0.7); 2.374 (1.3); 2.340 (1.6); 2.335 (2.2); 2.330 (1.5); 2.298 (0.3); 1.250 (0.4); 1.240 (0.9); 0.006 (0.3)

I-1-460:
HPLC-MS: log P=1.77; mass (m/z): 352.0 (M+H)$^+$; $^1$H-NMR (400.0 MHz, DMSO-D$_6$): δ=11.621 (14.7); 8.811 (8.5); 8.808 (8.9); 8.799 (9.1); 8.796 (8.6); 8.490 (14.6); 8.484 (15.3); 8.373 (13.0); 8.367 (12.9); 8.316 (1.7); 8.293 (4.4); 8.287 (4.1); 8.272 (4.8); 8.266 (8.4); 8.260 (4.4); 8.245 (4.5); 8.239 (4.1); 8.193 (7.7); 8.174 (8.2); 7.703 (6.1); 7.691 (6.3); 7.683 (6.0); 7.671 (5.6); 7.333 (6.4); 7.198 (14.3); 7.063 (7.0); 7.011 (16.0); 7.005 (15.8); 4.056 (0.4); 4.038 (1.0); 4.020 (1.1); 4.002 (0.3); 3.321 (311.5); 3.175 (0.5); 3.161 (0.5); 2.675 (4.2); 2.671 (5.7); 2.666 (4.1); 2.662 (2.0); 2.541 (3.4); 2.524 (14.6); 2.510 (316.6); 2.506 (634.8); 2.502 (831.9); 2.497 (594.2); 2.493 (281.7); 2.337 (1.9); 2.333 (4.0); 2.328 (5.5); 2.324 (4.0); 1.989 (4.4); 1.235 (0.6); 1.193 (1.2); 1.175 (2.3); 1.157 (1.2); 0.146 (3.1); 0.008 (23.1); 0.000 (669.5); −0.009 (22.8); −0.150 (3.1)

I-1-461:
HPLC-MS: log P=2.14; mass (m/z): 348.0 (M+H)$^+$; $^1$H-NMR (400.0 MHz, DMSO-D$_6$): δ=11.368 (2.1); 8.583 (1.5); 8.579 (1.7); 8.571 (1.7); 8.567 (1.7); 8.486 (2.5); 8.480 (2.7); 8.354 (2.2); 8.348 (2.2); 8.290 (0.7); 8.284 (0.7); 8.269 (0.8); 8.263 (1.4); 8.256 (0.8); 8.242 (0.7); 8.235 (0.7); 7.980 (1.3); 7.976 (1.4); 7.961 (1.5); 7.957 (1.5); 7.236 (1.5); 7.224 (1.6); 7.217 (1.6); 7.205 (1.5); 6.996 (1.5); 6.991 (1.5); 3.328 (72.2); 3.175 (0.9); 3.162 (0.9); 2.671 (0.4); 2.506 (46.3); 2.502 (61.4); 2.498 (46.5); 2.464 (16.0); 2.329 (0.4); 0.000 (1.4)

I-1-462:
HPLC-MS: log P=1.69; mass (m/z): 379.1 (M+H)$^+$; $^1$H-NMR (400.0 MHz, CD$_3$CN): δ=8.264 (0.7); 8.258 (0.7); 8.214 (0.6); 8.208 (0.6); 8.061 (0.3); 8.058 (0.5); 8.041 (0.4); 8.038 (0.5); 7.767 (0.5); 7.749 (0.5); 7.745 (0.4); 7.726 (0.3); 7.722 (0.5); 7.703 (1.2); 7.687 (0.6); 7.684 (0.6); 7.681 (0.6); 7.661 (0.5); 7.011 (0.7); 7.004 (0.7); 3.297 (5.6); 2.502 (16.0); 2.156 (1.4); 1.964 (0.7); 1.958 (1.0); 1.952 (4.2); 1.946 (7.4); 1.940 (9.6); 1.934 (6.6); 1.927 (3.4); 0.000 (4.6)

I-1-463:
HPLC-MS: log P=2.77; mass (m/z): 385.1 (M+H)$^+$; $^1$H-NMR (400.0 MHz, DMSO-D$_6$): δ=11.367 (13.5); 8.483 (14.3); 8.477 (15.1); 8.348 (12.1); 8.342 (12.1); 8.317 (0.8); 8.285 (4.4); 8.279 (4.1); 8.264 (4.8); 8.258 (8.2); 8.252 (4.4); 8.237 (4.5); 8.231 (4.0); 7.982 (0.3); 7.716 (7.2); 7.712 (8.2); 7.697 (8.8); 7.693 (9.5); 7.660 (3.9); 7.656 (3.8); 7.640 (8.0); 7.636 (7.5); 7.620 (6.7); 7.616 (5.9); 7.520 (7.3); 7.501 (11.6); 7.485 (11.6); 7.465 (6.1); 7.447 (0.4); 6.986 (15.1); 6.980 (14.9); 5.757 (16.0); 4.038 (0.5); 4.020 (0.5); 3.323 (175.0); 2.680 (1.0); 2.675 (2.1); 2.671 (2.8); 2.667 (2.1); 2.662 (1.0); 2.524 (8.4); 2.511 (154.2); 2.506 (305.6); 2.502 (399.3); 2.497 (287.5); 2.493 (137.6); 2.338 (0.9); 2.333 (1.9); 2.329 (2.6); 2.324 (1.9); 2.320 (0.9); 1.989 (2.0); 1.352 (0.3); 1.336 (2.5); 1.298 (0.8); 1.259 (1.2); 1.250 (3.1); 1.235 (1.0); 1.193 (0.6); 1.175 (1.1); 1.157 (0.6); 1.148 (0.3); 1.141 (0.3); 1.124 (0.6); 1.001 (0.6); 0.146 (1.0); 0.008 (8.1); 0.000 (221.7); −0.009 (7.2); −0.150 (0.9)

I-1-464:
HPLC-MS: log P=2.53; mass (m/z): 386.1 (M+H)$^+$; $^1$H-NMR (400.0 MHz, DMSO-D$_6$): δ=11.554 (10.5); 8.494 (11.0); 8.487 (16.0); 8.482 (7.5); 8.474 (6.9); 8.470 (6.7); 8.380 (9.3); 8.374 (9.1); 8.297 (3.3); 8.291 (3.0); 8.276 (3.5); 8.270 (6.0); 8.263 (3.2); 8.248 (3.4); 8.242 (3.3); 8.234 (6.8); 8.229 (6.7); 8.215 (7.3); 8.210 (6.7); 7.560 (6.9); 7.547 (6.8); 7.541 (6.7); 7.528 (6.4); 7.007 (12.3);

7.001 (12.0); 3.381 (0.5); 3.365 (1.3); 3.338 (403.0); 3.3063 (0.6); 3.299 (0.4); 2.687 (0.4); 2.682 (0.8); 2.678 (1.1); 2.673 (0.8); 2.669 (0.4); 2.548 (28.7); 2.531 (3.5); 2.526 (5.7); 2.518 (63.8); 2.513 (126.2); 2.509 (164.6); 2.504 (117.3); 2.499 (55.3); 2.344 (0.4); 2.340 (0.8); 2.335 (1.1); 2.331 (0.7); 2.326 (0.4); 1.240 (0.5)

I-1-465:
HPLC-MS: log P=2.44; mass (m/z): 387.0 (M+H)$^+$; $^1$H-NMR (400.0 MHz, CD$_3$CN): δ=8.840 (3.8); 8.829 (4.9); 8.791 (0.6); 8.282 (9.8); 8.276 (11.9); 8.270 (10.6); 8.258 (7.4); 8.212 (1.0); 8.206 (1.0); 8.181 (0.3); 8.061 (0.8); 8.054 (0.7); 7.846 (5.7); 7.828 (8.0); 7.807 (1.8); 7.786 (1.3); 7.776 (2.1); 7.757 (6.9); 7.740 (16.0); 7.718 (10.1); 7.697 (12.4); 7.677 (6.4); 7.671 (5.2); 7.648 (2.1); 7.622 (1.4); 7.603 (1.3); 7.584 (0.6); 7.570 (1.3); 7.550 (0.9); 7.520 (0.7); 7.502 (0.7); 7.493 (0.4); 7.482 (0.4); 7.476 (0.3); 7.462 (0.3); 7.455 (0.5); 7.019 (1.1); 7.012 (1.0); 6.248 (0.4); 6.235 (0.3); 6.219 (0.5); 6.206 (0.3); 6.161 (0.4); 6.152 (0.4); 5.869 (0.3); 5.459 (0.3); 5.448 (0.3); 4.193 (0.3); 2.619 (0.4); 2.569 (0.5); 2.466 (0.9); 2.352 (1.3); 2.315 (2.0); 2.309 (1.8); 2.270 (1.7); 2.241 (1.7); 2.179 (1.5); 2.132 (1.3); 2.119 (1.7); 2.113 (2.3); 2.107 (2.7); 2.101 (2.1); 2.095 (1.4); 2.086 (0.9); 1.964 (52.9); 1.958 (32.2); 1.952 (140.9); 1.946 (247.6); 1.940 (322.7); 1.933 (221.8); 1.927 (114.2); 1.915 (3.4); 1.900 (1.8); 1.843 (0.8); 1.792 (0.7); 1.786 (0.6); 1.780 (1.2); 1.774 (1.8); 1.768 (2.3); 1.762 (1.6); 1.756 (1.0); 1.730 (0.4); 1.718 (0.4); 1.705 (0.4); 1.340 (0.5); 1.295 (0.4); 1.270 (1.3); 1.130 (0.6); 1.064 (0.4); 0.888 (0.4); 0.881 (0.4); 0.871 (0.4); 0.866 (0.4); 0.856 (0.4); 0.146 (0.8); 0.008 (6.8); 0.000 (188.6); −0.009 (6.5); −0.150 (0.9)

I-1-466:
HPLC-MS: log P=3.18; mass (m/z): 385.1 (M+H)$^+$; $^1$H-NMR (400.0 MHz, CD$_3$CN): δ=10.724 (1.0); 8.330 (0.4); 8.330 (0.4); 8.325 (0.4); 8.301 (4.7); 8.295 (4.8); 8.270 (3.7); 8.263 (3.7); 8.209 (0.4); 8.204 (0.4); 7.754 (2.6); 7.734 (3.3); 7.726 (1.8); 7.719 (1.7); 7.705 (1.9); 7.699 (3.6); 7.693 (2.9); 7.678 (3.7); 7.675 (3.5); 7.658 (2.2); 7.610 (6.0); 7.604 (6.9); 7.586 (2.6); 7.567 (1.1); 7.551 (3.3); 7.532 (2.4); 7.484 (0.4); 7.445 (0.3); 5.450 (0.5); 5.444 (0.4); 3.831 (0.5); 2.470 (0.4); 2.465 (0.5); 2.460 (0.4); 2.266 (0.6); 2.248 (1.0); 2.171 (287.5); 2.120 (2.6); 2.114 (2.6); 2.107 (2.7); 2.101 (2.0); 2.095 (1.4); 2.044 (0.5); 2.029 (0.5); 2.008 (0.4); 1.972 (2.2); 1.964 (12.7); 1.958 (17.6); 1.952 (99.2); 1.946 (180.5); 1.940 (244.9); 1.934 (168.5); 1.928 (86.7); 1.781 (0.7); 1.775 (1.1); 1.769 (1.5); 1.762 (1.1); 1.756 (0.6); 1.477 (6.4); 1.437 (1.6); 1.386 (1.3); 1.376 (0.8); 1.371 (1.2); 1.363 (0.5); 1.340 (3.3); 1.326 (0.5); 1.285 (5.1); 1.269 (16.0); 1.222 (0.4); 1.216 (0.7); 1.210 (0.4); 1.204 (0.5); 0.898 (0.5); 0.882 (1.3); 0.864 (0.7); 0.837 (0.3); 0.146 (1.2); 0.008 (12.1); 0.000 (291.0); −0.009 (12.1); −0.025 (0.5); −0.150 (1.2)

I-1-467:
HPLC-MS: log P=2.96; mass (m/z): 383.1 (M+H)$^+$; $^1$H-NMR (400.0 MHz, DMSO-D$_6$): δ=8.496 (3.5); 8.412 (4.6); 8.407 (4.7); 8.395 (3.7); 8.317 (0.3); 8.295 (1.0); 8.273 (1.9); 8.252 (1.2); 8.219 (1.4); 8.213 (1.4); 8.192 (2.4); 8.171 (1.4); 8.165 (1.3); 8.143 (4.5); 8.137 (4.3); 7.914 (2.2); 7.894 (2.7); 7.853 (1.1); 7.835 (2.4); 7.817 (1.8); 7.755 (2.0); 7.736 (4.7); 7.716 (6.0); 7.698 (2.4); 7.567 (4.5); 7.558 (5.3); 7.549 (4.2); 7.388 (2.5); 7.382 (2.5); 7.368 (2.2); 7.135 (3.6); 7.130 (3.5); 5.968 (4.5); 5.963 (4.4); 5.758 (1.8); 3.444 (21.8); 3.324 (332.6); 3.196 (16.0); 2.680 (0.9); 2.676 (1.9); 2.671 (2.7); 2.666 (1.9); 2.662 (0.9); 2.524 (8.1); 2.520 (12.6); 2.511 (15.8); 2.507 (302.6); 2.502 (396.3); 2.497 (279.2); 2.493 (129.4); 2.338 (0.9); 2.333 (1.9); 2.329 (2.6); 2.324 (1.9); 2.320 (0.9); 1.351 (0.4); 1.258 (0.5); 1.235 (1.0); 0.146 (0.9); 0.008 (7.2); 0.000 (215.4); −0.009 (6.4); −0.150 (0.9)

I-1-468:
HPLC-MS: log P=3.23; mass (m/z): 397.1 (M+H)$^+$; $^1$H-NMR (400.0 MHz, DMSO-D$_6$): δ=8.501 (1.2); 8.415 (4.9); 8.410 (5.1); 8.383 (1.3); 8.317 (0.5); 8.291 (0.4); 8.270 (0.7); 8.244 (0.5); 8.219 (1.5); 8.213 (1.5); 8.192 (2.8); 8.171 (2.1); 8.166 (2.1); 8.151 (5.2); 8.145 (5.4); 8.078 (1.5); 8.073 (1.7); 7.895 (1.2); 7.870 (1.9); 7.864 (2.0); 7.832 (1.1); 7.819 (1.2); 7.794 (0.5); 7.767 (1.3); 7.741 (2.9); 7.717 (4.5); 7.702 (3.4); 7.696 (3.2); 7.554 (2.4); 7.535 (6.5); 7.527 (6.4); 7.518 (5.1); 7.343 (3.4); 7.335 (3.5); 7.322 (2.6); 7.047 (1.3); 6.933 (0.6); 6.060 (5.2); 6.054 (5.4); 5.757 (0.7); 5.722 (1.6); 5.717 (1.7); 4.206 (0.6); 4.189 (0.6); 4.128 (0.8); 4.111 (2.0); 4.094 (2.1); 4.077 (0.7); 3.937 (3.2); 3.833 (0.7); 3.480 (0.5); 3.322 (131.8); 2.675 (2.4); 2.671 (3.2); 2.667 (2.5); 2.506 (379.2); 2.502 (482.3); 2.497 (374.3); 2.333 (2.4); 2.328 (3.2); 2.324 (2.5); 1.352 (0.7); 1.336 (1.2); 1.319 (0.7); 1.260 (2.2); 1.243 (4.7); 1.227 (9.5); 1.210 (16.0); 1.192 (7.9); 1.122 (3.3); 1.107 (2.6); 0.146 (1.3); 0.000 (278.2); −0.150 (1.4)

I-1-469:
HPLC-MS: log P=3.38; mass (m/z): 409.1 (M+H)$^+$; $^1$H-NMR (400.0 MHz, CD$_3$CN): δ=8.277 (1.0); 8.270 (0.8); 8.244 (0.8); 8.201 (3.6); 8.196 (3.5); 8.041 (0.5); 8.025 (0.5); 8.012 (0.4); 7.965 (2.0); 7.959 (2.2); 7.948 (3.9); 7.942 (3.8); 7.830 (1.1); 7.824 (1.3); 7.821 (1.2); 7.815 (1.3); 7.809 (1.2); 7.761 (0.7); 7.752 (0.4); 7.740 (1.1); 7.733 (1.3); 7.728 (1.5); 7.719 (2.2); 7.704 (3.6); 7.698 (4.3); 7.691 (4.5); 7.685 (4.3); 7.669 (5.0); 7.652 (1.7); 7.646 (1.9); 7.640 (1.6); 7.620 (2.3); 7.600 (1.6); 7.594 (1.3); 7.582 (1.0); 7.563 (1.0); 7.484 (5.2); 7.475 (5.4); 7.465 (5.3); 7.447 (1.4); 7.424 (0.5); 7.385 (1.3); 7.379 (1.2); 7.371 (0.9); 7.359 (1.5); 7.353 (1.8); 7.342 (3.2); 7.328 (2.8); 7.077 (0.8); 7.020 (0.4); 7.013 (0.5); 6.980 (0.4); 6.564 (0.9); 6.078 (0.3); 6.052 (0.5); 6.035 (0.7); 6.015 (4.5); 6.009 (4.9); 5.985 (2.0); 5.969 (2.2); 5.956 (1.9); 5.943 (1.9); 5.928 (1.1); 5.913 (0.7); 5.900 (0.5); 5.885 (0.4); 5.846 (2.2); 5.840 (2.1); 5.815 (0.6); 5.808 (0.5); 5.797 (0.4); 5.791 (0.4); 5.438 (0.4); 5.434 (0.7); 5.431 (0.6); 5.427 (0.3); 5.395 (0.4); 5.391 (0.6); 5.387 (0.6); 5.328 (1.3); 5.312 (2.9); 5.296 (1.9); 5.285 (3.0); 5.282 (2.8); 5.270 (2.5); 5.256 (2.3); 5.189 (2.7); 5.163 (2.7); 5.110 (0.3); 5.080 (0.7); 5.060 (0.7); 4.971 (0.5); 4.928 (0.6); 4.925 (0.6); 4.825 (0.8); 4.821 (1.1); 4.818 (0.7); 4.810 (0.7); 4.807 (1.1); 4.803 (0.7); 4.667 (0.7); 4.639 (0.4); 4.576 (7.4); 4.478 (0.5); 4.470 (0.5); 4.65 (0.5); 4.118 (0.4); 4.086 (2.4); 4.068 (6.5); 4.050 (6.4); 4.032 (2.2); 3.549 (1.3); 3.095 (0.4); 3.077 (0.4); 3.032 (0.3); 2.135 (12.8); 2.119 (0.5); 2.113 (0.5); 2.107 (0.6); 2.101 (0.5); 1.971 (27.7); 1.964 (6.0); 1.958 (8.6); 1.952 (36.2); 1.946 (63.4); 1.939 (82.4); 1.933 (56.7); 1.927 (29.4); 1.864 (0.3); 1.808 (0.3); 1.780 (0.4); 1.774 (0.6); 1.768 (0.7); 1.762 (0.5); 1.756 (0.4); 1.614 (0.3); 1.558 (0.3); 1.542 (0.4); 1.525 (0.4); 1.372 (1.2); 1.360 (0.5); 1.353 (0.6); 1.342 (0.6); 1.269 (10.2); 1.221 (8.4); 1.214 (1.4); 1.203 (16.0); 1.198 (9.7); 1.191 (3.1); 1.186 (8.7); 1.178 (2.3); 1.173 (4.3); 1.155 (2.3); 1.139 (0.6); 1.110 (0.6); 1.092 (1.0); 1.076 (0.9); 1.043 (0.4); 1.038 (0.4); 1.033 (0.4); 1.025 (2.1); 1.015 (0.4); 1.007 (3.9); 0.998 (0.5); 0.989 (2.0); 0.980 (0.4); 0.969 (0.3); 0.950 (0.4); 0.933 (0.4); 0.925 (0.4); 0.897 (1.2); 0.888 (2.1); 0.881 (2.6); 0.876 (2.0); 0.863 (1.9); 0.858 (2.2); 0.840 (1.4); 0.080 (0.4); 0.000 (4.7)

I-1-470:
HPLC-MS: log P=3.05; mass (m/z): 407.0 (M+H)$^+$; $^1$H-NMR (400.0 MHz, DMSO-D$_6$): δ=8.511 (1.5); 8.419 (13.8); 8.416 (13.8); 8.316 (1.7); 8.302 (0.8); 8.275 (1.1);

8.219 (4.4); 8.193 (8.3); 8.177 (15.0); 8.173 (16.0); 7.909 (1.3); 7.855 (1.3); 7.817 (0.8); 7.731 (8.6); 7.722 (7.8); 7.663 (0.4); 7.562 (13.5); 7.551 (14.5); 7.541 (12.5); 7.351 (6.8); 7.343 (7.4); 7.061 (1.5); 6.144 (13.0); 6.139 (12.7); 4.734 (15.4); 4.647 (0.5); 4.565 (0.8); 4.342 (0.7); 3.323 (299.4); 3.238 (13.2); 2.676 (3.4); 2.671 (4.6); 2.667 (3.3); 2.524 (13.3); 2.511 (282.2); 2.507 (556.0); 2.502 (720.8); 2.497 (515.7); 2.493 (245.9); 2.333 (3.5); 2.329 (4.7); 2.324 (3.4); 0.008 (1.8); 0.000 (48.9); −0.009 (1.6)

I-1-471:
HPLC-MS: log P=3.62; mass (m/z): 423.1 (M+H)$^+$; $^1$H-NMR (400.0 MHz, DMSO-D$_6$): δ=8.502 (1.6); 8.415 (15.1); 8.409 (15.3); 8.316 (1.7); 8.267 (1.1); 8.240 (1.0); 8.219 (4.6); 8.213 (4.4); 8.192 (8.1); 8.171 (4.6); 8.166 (4.3); 8.145 (15.2); 8.138 (14.8); 7.882 (1.2); 7.828 (1.2); 7.812 (1.1); 7.730 (8.5); 7.718 (9.0); 7.708 (8.0); 7.540 (14.5); 7.529 (16.0); 7.518 (14.1); 7.327 (7.5); 7.318 (7.8); 7.307 (6.4); 7.021 (1.6); 6.047 (15.5); 6.041 (15.2); 5.756 (3.7); 3.819 (6.9); 3.710 (0.5); 3.670 (0.7); 3.651 (0.8); 3.635 (0.8); 3.604 (0.4); 3.474 (0.8); 3.322 (187.3); 2.676 (2.5); 2.671 (3.5); 2.667 (2.5); 2.662 (1.2); 2.541 (1.9); 2.525 (10.1); 2.511 (209.5); 2.507 (422.5); 2.502 (555.8); 2.498 (398.2); 2.493 (190.6); 2.437 (0.5); 2.431 (0.5); 2.408 (0.4); 2.338 (1.3); 2.333 (2.6); 2.329 (3.5); 2.324 (2.6); 2.239 (0.6); 1.235 (1.2); 1.149 (3.6); 1.131 (5.3); 1.120 (4.0); 1.113 (4.0); 1.101 (2.3); 1.081 (0.9); 1.041 (0.9); 0.463 (14.4); 0.444 (13.7); 0.396 (0.8); 0.334 (2.2); 0.323 (2.2); 0.284 (15.7); 0.274 (14.9); 0.146 (0.4); 0.025 (2.3); 0.008 (3.3); 0.000 (65.5); −0.009 (2.7)

I-1-472:
HPLC-MS: log P=2.80; mass (m/z): 408.1 (M+H)$^+$; $^1$H-NMR (400.0 MHz, DMSO-D$_6$): δ=8.441 (8.2); 8.316 (0.9); 8.250 (3.0); 8.226 (5.1); 8.204 (9.4); 7.953 (0.4); 7.779 (5.0); 7.616 (9.0); 7.470 (4.5); 6.043 (7.2); 5.757 (16.0); 5.040 (12.9); 4.743 (0.5); 3.324 (120.7); 2.676 (1.1); 2.672 (1.5); 2.667 (1.1); 2.663 (0.5); 2.542 (1.0); 2.525 (4.4); 2.512 (89.2); 2.507 (180.6); 2.503 (238.3); 2.498 (170.2); 2.494 (80.9); 2.338 (0.5); 2.334 (1.1); 2.329 (1.5); 2.325 (1.1); 2.321 (0.6); 2.075 (0.6); 0.000 (0.9)

I-1-473:
HPLC-MS: log P=2.62; mass (m/z): 403.1 (M+H)$^+$; $^1$H-NMR (400.0 MHz, CD$_3$CN): δ=8.690 (4.5); 8.365 (11.3); 8.296 (11.3); 8.292 (11.2); 7.846 (6.2); 7.827 (8.0); 7.748 (15.9); 7.715 (10.1); 7.695 (7.9); 7.427 (0.6); 7.420 (0.7); 7.241 (0.6); 7.236 (0.5); 7.171 (0.5); 7.165 (0.4); 5.446 (2.0); 2.138 (44.8); 2.119 (0.5); 2.113 (0.8); 2.107 (1.0); 2.107 (1.0); 2.01 (0.7); 2.094 (0.4); 1.964 (6.0); 1.958 (7.3); 1.952 (60.8); 1.946 (113.6); 1.939 (157.6); 1.933 (106.8); 1.927 (53.7); 1.920 (1.3); 1.914 (0.5); 1.780 (0.3); 1.774 (0.7); 1.768 (0.9); 1.762 (0.6); 1.387 (0.6); 1.383 (0.5); 1.372 (13.7); 1.340 (3.1); 1.285 (4.3); 1.276 (16.0); 1.270 (3.2); 1.216 (0.5); 0.881 (0.5); 0.146 (1.2); 0.008 (11.2); 0.000 (295.9); −0.009 (8.7); −0.150 (1.2)

I-1-474:
HPLC-MS: log P=2.61; mass (m/z): 449.0 (M+H)$^+$; $^1$H-NMR (400.0 MHz, CD$_3$CN): δ=8.633 (4.3); 8.380 (10.0); 8.298 (9.7); 7.846 (5.6); 7.827 (7.2); 7.756 (12.4); 7.717 (8.7); 7.697 (7.1); 7.426 (0.7); 7.420 (0.7); 7.241 (0.6); 7.235 (0.5); 7.171 (0.5); 7.165 (0.4); 5.446 (3.4); 2.566 (1.0); 2.134 (51.7); 2.119 (0.6); 2.113 (0.8); 2.107 (1.1); 2.101 (0.8); 2.094 (0.4); 1.964 (7.7); 1.957 (10.4); 1.952 (65.5); 1.946 (119.4); 1.939 (162.3); 1.933 (109.9); 1.927 (55.5); 1.914 (0.7); 1.780 (0.4); 1.774 (0.7); 1.768 (0.9); 1.762 (0.6); 1.372 (14.1); 1.340 (2.7); 1.285 (3.9); 1.276 (16.0); 1.271 (3.4); 1.216 (0.6); 0.881 (0.5); 0.146 (1.0); 0.023 (0.4); 0.021 (0.5); 0.020 (0.6); 0.018 (0.7); 0.008 (9.2); 0.000 (234.8); −0.007 (4.0); −0.009 (7.0); −0.013 (0.6); −0.014 (0.6); −0.015 (0.5); −0.0156 (0.4); −0.0163 (0.4); −0.017 (0.4); −0.150 (1.0)

I-1-475:
HPLC-MS: log P=2.63; mass (m/z): 414.0 (M+H)$^+$; $^1$H-NMR (400.0 MHz, CD$_3$CN): δ=9.306 (3.0); 8.987 (16.0); 8.985 (15.8); 8.381 (0.3); 8.367 (9.2); 8.361 (9.3); 7.863 (5.2); 7.843 (6.9); 7.804 (3.5); 7.798 (4.2); 7.788 (11.1); 7.778 (13.7); 7.758 (4.1); 7.752 (3.7); 7.742 (3.0); 7.741 (3.1); 7.734 (2.0); 7.728 (3.1); 7.721 (2.9); 7.713 (1.4); 7.708 (2.1); 7.701 (1.0); 5.447 (1.8); 2.149 (135.3); 2.120 (0.5); 2.114 (0.6); 2.107 (0.7); 2.101 (0.5); 1.964 (5.1); 1.958 (6.5); 1.952 (41.1); 1.946 (75.1); 1.940 (101.9); 1.934 (69.4); 1.928 (35.3); 1.915 (0.4); 1.775 (0.4); 1.769 (0.6); 1.762 (0.4); 1.285 (0.3); 1.269 (0.4); 0.146 (0.5); 0.018 (0.5); 0.0162 (0.6); 0.0155 (0.6); 0.013 (0.8); 0.008 (5.2); 0.000 (141.2); −0.007 (2.8); −0.009 (4.6); −0.013 (0.5); −0.150 (0.5)

I-1-476:
HPLC-MS: log P=2.72; mass (m/z): 369.0 (M+H)$^+$; $^1$H-NMR (400.0 MHz, DMSO-D$_6$): δ=11.504 (1.5); 11.462 (10.9); 8.583 (0.3); 8.521 (5.2); 8.515 (5.0); 8.490 (6.7); 8.484 (15.8); 8.478 (12.6); 8.430 (0.8); 8.362 (10.2); 8.355 (10.1); 8.329 (2.2); 8.322 (2.6); 8.316 (4.2); 8.308 (3.3); 9.301 (3.5); 8.295 (2.2); 8.286 (4.7); 8.280 (5.4); 8.265 (4.8); 8.253 (4.3); 8.238 (5.3); 8.232 (3.6); 8.202 (0.9); 8.145 (0.5); 8.064 (0.5); 8.014 (0.4); 8.007 (0.5); 7.977 (0.4); 7.961 (0.4); 7.927 (0.4); 7.807 (0.5); 7.773 (1.1); 7.769 (1.5); 7.760 (7.0); 7.756 (7.5); 7.749 (1.8); 7.740 (8.1); 7.736 (7.9); 7.680 (0.5); 7.630 (0.3); 7.561 (6.7); 7.557 (6.5); 7.542 (10.5); 7.538 (8.9); 7.497 (0.6); 7.489 (1.3); 7.478 (8.8); 7.470 (2.0); 7.458 (1.8); 7.439 (5.4); 7.356 (0.4); 7.097 (0.9); 7.090 (1.0); 7.027 (1.5); 7.015 (5.7); 7.008 (5.7); 6.997 (12.7); 6.990 (12.7); 6.960 (0.4); 6.929 (0.5); 6.904 (0.9); 6.898 (0.7); 6.868 (0.4); 6.810 (5.3); 6.737 (0.8); 6.179 (0.5); 5.757 (3.0); 5.589 (0.7); 4.143 (0.3); 3.774 (0.3); 3.621 (0.4); 3.593 (0.4); 3.539 (0.5); 3.529 (0.7); 3.511 (0.5); 3.411 (0.8); 3.322 (817.4); 3.264 (2.0); 3.237 (0.7); 3.189 (1.3); 3.114 (0.7); 3.105 (0.7); 3.078 (1.1); 3.035 (1.0); 2.994 (1.1); 2.989 (0.9); 2.978 (0.8); 2.966 (1.0); 2.941 (1.0); 2.916 (2.0); 2.900 (2.2); 2.882 (1.1); 2.860 (1.4); 2.843 (0.9); 2.825 (0.9); 2.749 (0.8); 2.726 (1.5); 2.709 (1.2); 2.675 (10.5); 2.671 (14.0); 2.666 (10.5); 2.541 (94.9); 2.524 (52.2); 2.510 (827.8); 2.506 (1578.9); 2.502 (2019.5); 2.497 (1471.5); 2.493 (729.1); 2.430 (16.0); 2.368 (0.4); 2.333 (9.7); 2.328 (12.8); 2.324 (9.3); 2.288 (1.4); 1.234 (1.1); 1.147 (1.3); 1.131 (0.3); 0.909 (0.4); 0.854 (0.3); 0.146 (2.0); 0.008 (20.4); 0.000 (500.3); −0.008 (20.3); −0.149 (2.0)

I-1-477:
HPLC-MS: log P=4.47; mass (m/z): 542.9 (M+H)$^+$; $^1$H-NMR (400.0 MHz, DMSO-D$_6$): δ=8.521 (0.5); 8.515 (0.5); 8.490 (0.7); 8.483 (0.8); 8.473 (7.7); 8.467 (8.0); 8.322 (8.2); 8.315 (8.3); 8.301 (0.4); 8.295 (0.4); 8.283 (2.3); 8.277 (2.1); 8.262 (2.5); 8.256 (3.8); 8.251 (2.3); 8.236 (2.2); 8.230 (2.0); 7.759 (0.5); 7.756 (0.5); 7.739 (1.0); 7.729 (6.5); 7.726 (14.6); 7.723 (14.5); 7.720 (6.8); 7.710 (6.9); 7.707 (15.3); 7.703 (16.0); 7.635 (0.4); 7.449 (0.5); 7.431 (9.8); 7.411 (14.1); 7.392 (7.7); 7.015 (0.5); 7.008 (0.4); 6.810 (0.6); 6.800 (9.3); 6.793 (9.2); 5.757 (5.1); 3.322 (171.4); 2.675 (1.9); 2.671 (2.5); 2.666 (1.9); 2.662 (0.9); 2.541 (10.5); 2.524 (8.7); 2.510 (148.0); 2.506 (286.4); 2.502 (371.5); 2.497 (271.6); 2.493 (133.8); 2.430 (1.6); 2.333 (1.8); 2.328 (2.5); 2.324 (1.8); 0.146 (0.4); 0.008 (3.3); 0.000 (85.3); −0.008 (3.4); −0.150 (0.4)

I-1-478:
HPLC-MS: log P=1.88; mass (m/z): 336.0 (M+H)$^+$; $^1$H-NMR (400.0 MHz, DMSO-D$_6$): δ=11.038 (2.5); 8.483

(2.7); 8.476 (2.8); 8.327 (2.2); 8.322 (2.2); 8.291 (0.9); 8.285 (0.8); 8.270 (0.9); 8.264 (1.6); 8.258 (0.8); 8.243 (0.9); 8.237 (0.8); 6.927 (3.3); 6.921 (3.2); 5.757 (2.1); 3.323 (70.8); 2.675 (0.7); 2.671 (1.0); 2.666 (0.8); 2.649 (16.0); 2.555 (18.1); 2.524 (2.9); 2.511 (49.5); 2.506 (97.6); 2.502 (127.4); 2.497 (92.7); 2.493 (45.0); 2.333 (0.6); 2.328 (0.8); 2.324 (0.6); 0.008 (1.1); 0.000 (28.5); −0.009 (1.0)

I-1-479:
HPLC-MS: log P=2.51; mass (m/z): 369.1 (M+H)$^+$;
$^1$H-NMR (400.0 MHz, DMSO-D$_6$): δ=11.604 (6.0); 8.484 (6.4); 8.478 (6.7); 8.367 (5.7); 8.360 (5.6); 8.285 (2.1); 8.278 (1.9); 8.264 (2.2); 8.257 (3.8); 8.251 (2.0); 8.236 (2.1); 8.230 (1.9); 7.563 (6.5); 7.558 (8.0); 7.540 (16.0); 7.498 (8.0); 7.481 (5.1); 7.475 (3.9); 7.466 (0.4); 7.458 (2.8); 7.001 (8.2); 6.994 (8.1); 3.405 (0.4); 3.377 (1.2); 3.343 (385.4); 3.300 (0.6); 3.289 (0.4); 2.677 (0.5); 2.672 (0.6); 2.668 (0.4); 2.542 (2.7); 2.526 (2.0); 2.512 (36.4); 2.508 (71.9); 2.503 (94.1); 2.499 (67.9); 2.494 (32.4); 2.334 (0.4); 2.330 (0.6); 2.325 (0.4); 0.000 (2.2)

I-1-480:
HPLC-MS: log P=2.51; mass (m/z): 329.1 (M+H)$^+$;
$^1$H-NMR (400.0 MHz, CD$_3$CN): δ=9.331 (3.0); 8.249 (5.7); 8.245 (5.7); 8.212 (7.3); 8.205 (7.2); 7.669 (3.7); 7.663 (3.7); 7.656 (0.4); 7.649 (3.9); 7.643 (6.7); 7.636 (3.8); 7.622 (3.7); 7.616 (3.6); 7.180 (4.1); 7.160 (7.2); 7.141 (7.1); 7.085 (7.8); 7.078 (7.7); 7.053 (0.4); 7.035 (16.0); 7.016 (11.7); 5.447 (3.3); 2.432 (0.7); 2.275 (112.3); 2.237 (1.8); 2.156 (117.0); 2.125 (0.4); 2.120 (0.5); 2.114 (1.1); 2.107 (0.6); 2.101 (0.4); 1.964 (4.4); 1.958 (5.5); 1.952 (35.9); 1.946 (65.2); 1.940 (88.4); 1.934 (61.0); 1.928 (31.0); 1.915 (0.3); 1.774 (0.4); 1.768 (0.5); 1.762 (0.3); 1.340 (0.4); 1.285 (0.7); 1.269 (1.7); 1.254 (0.5); 0.146 (0.4); 0.008 (3.7); 0.000 (104.2); −0.009 (2.9); −0.150 (0.4)

I-1-481:
HPLC-MS: log P=2.22; mass (m/z): 343.1 (M+H)$^+$;
$^1$H-NMR (400.0 MHz, DMSO-D$_6$): δ=8.293 (3.7); 8.287 (3.8); 8.072 (1.2); 8.066 (1.1); 8.051 (1.3); 8.045 (2.2); 8.039 (1.2); 8.024 (1.4); 8.015 (4.8); 8.008 (4.4); 7.820 (2.1); 7.807 (0.4); 7.800 (3.2); 7.739 (1.1); 7.736 (1.1); 7.720 (2.6); 7.702 (2.0); 7.699 (1.8); 7.674 (4.6); 7.615 (2.9); 7.611 (3.4); 7.598 (3.2); 7.591 (2.5); 7.580 (1.3); 5.758 (2.0); 5.421 (4.4); 5.414 (4.4); 3.324 (51.5); 2.675 (0.4); 2.671 (0.6); 2.667 (0.4); 2.524 (2.2); 2.511 (31.9); 2.507 (61.3); 2.502 (78.9); 2.497 (56.4); 2.493 (26.6); 2.333 (0.4); 2.329 (0.5); 2.324 (0.3); 1.989 (0.5); 1.906 (16.0); 1.299 (1.8); 1.259 (2.5); 1.235 (0.9); 0.008 (1.3); 0.000 (30.3); −0.009 (0.9)

I-1-482:
HPLC-MS: log P=1.77; mass (m/z): 382.0 (M+H)$^+$;
$^1$H-NMR (400.0 MHz, DMSO-D$_6$): δ=11.525 (11.7); 8.485 (13.0); 8.479 (16.0); 8.470 (8.4); 8.465 (8.0); 8.370 (10.6); 8.364 (10.5); 8.333 (0.4); 8.326 (0.4); 8.316 (3.3); 8.288 (3.8); 8.282 (3.6); 8.267 (4.1); 8.261 (6.9); 8.254 (3.6); 8.239 (3.8); 8.233 (3.3); 8.126 (0.3); 8.099 (0.3); 8.056 (0.4); 8.048 (0.4); 8.000 (7.7); 7.995 (7.9); 7.981 (8.7); 7.977 (8.1); 7.565 (8.4); 7.553 (8.0); 7.546 (7.8); 7.534 (7.6); 7.000 (13.9); 6.994 (13.7); 5.825 (0.5); 5.819 (0.4); 5.756 (5.9); 5.213 (0.5); 3.395 (0.3); 3.381 (0.4); 3.321 (476.1); 2.752 (0.4); 2.740 (0.5); 2.679 (3.5); 2.675 (6.9); 2.671 (9.5); 2.666 (7.1); 2.644 (0.6); 2.524 (30.1); 2.510 (548.2); 2.506 (1095.4); 2.502 (1433.5); 2.497 (1029.5); 2.492 (494.2); 2.337 (3.1); 2.333 (6.6); 2.328 (9.0); 2.324 (6.5); 0.147 (0.4); 0.008 (3.2); 0.000 (94.4); −0.009 (3.3); −0.149 (0.4)

I-1-483:
HPLC-MS: log P=2.51; mass (m/z): 364.1 (M+H)$^+$;
$^1$H-NMR (400.0 MHz, DMSO-D$_6$): δ=11.327 (2.2); 8.481 (2.2); 8.475 (2.3); 8.347 (1.9); 8.341 (1.9); 8.283 (0.7); 8.277 (0.7); 8.262 (0.8); 8.256 (1.4); 8.249 (0.7); 8.235 (0.8); 8.228 (0.7); 7.435 (2.8); 7.065 (1.8); 7.057 (1.5); 7.043 (1.6); 7.035 (1.4); 6.996 (2.7); 6.989 (2.7); 3.805 (16.0); 3.329 (65.6); 2.542 (0.4); 2.525 (0.6); 2.520 (1.0); 2.511 (12.0); 2.507 (24.3); 2.502 (32.1); 2.498 (23.0); 2.493 (10.7); 0.000 (5.8)

I-1-484:
HPLC-MS: log P=2.38; mass (m/z): 353.1 (M+H)$^+$;
$^1$H-NMR (400.0 MHz, DMSO-D$_6$): δ=11.649 (5.5); 8.486 (5.6); 8.480 (5.8); 8.371 (5.1); 8.364 (5.0); 8.288 (1.8); 8.282 (1.7); 8.267 (1.9); 8.261 (3.4); 8.255 (1.7); 8.240 (1.8); 8.234 (1.6); 7.558 (1.3); 7.542 (1.6); 7.537 (3.1); 7.521 (3.2); 7.516 (2.3); 7.501 (2.2); 7.428 (5.2); 7.408 (3.5); 7.373 (2.4); 7.371 (2.3); 7.350 (4.0); 7.329 (1.9); 7.327 (1.8); 6.993 (7.0); 6.987 (6.9); 5.757 (16.0); 3.322 (50.0); 3.028 (0.5); 2.813 (0.5); 2.675 (0.8); 2.671 (1.0); 2.666 (0.8); 2.524 (3.3); 2.511 (61.4); 2.506 (118.6); 2.502 (153.3); 2.497 (110.0); 2.493 (52.7); 2.333 (0.8); 2.328 (1.0); 2.324 (0.7); 2.319 (0.4); 1.336 (0.9); 1.298 (0.4); 1.259 (0.6); 1.249 (1.1); 1.235 (0.4); 0.146 (0.4); 0.008 (3.7); 0.000 (82.2); −0.009 (2.8); −0.150 (0.4)

I-1-485:
HPLC-MS: log P=1.89; mass (m/z): 337.0 (M+H)$^+$;
$^1$H-NMR (400.0 MHz, DMSO-D$_6$): δ=11.635 (9.8); 8.786 (0.4); 8.772 (13.7); 8.766 (15.8); 8.702 (16.0); 8.695 (13.3); 8.497 (10.5); 8.491 (10.8); 8.409 (9.8); 8.403 (9.6); 8.300 (3.1); 8.294 (2.8); 8.279 (3.4); 8.273 (5.7); 8.266 (3.0); 8.252 (3.1); 8.245 (2.8); 7.016 (12.8); 7.009 (12.5); 3.339 (200.7); 2.682 (0.5); 2.678 (0.7); 2.673 (0.5); 2.548 (34.4); 2.531 (2.2); 2.517 (41.0); 2.513 (79.5); 2.508 (102.4); 2.504 (73.7); 2.500 (35.5); 2.340 (0.5); 2.335 (0.7); 2.331 (0.5)

I-1-486:
HPLC-MS: log P=2.68; mass (m/z): 341.1 (M+H)$^+$;
$^1$H-NMR (400.0 MHz, DMSO-D$_6$): δ=11.154 (6.6); 8.478 (6.9); 8.472 (7.1); 8.326 (6.0); 8.320 (6.0); 8.278 (2.1); 8.272 (2.0); 8.256 (2.5); 8.251 (3.9); 8.245 (2.4); 8.229 (2.2); 8.224 (2.0); 7.406 (4.1); 7.387 (5.1); 7.375 (2.8); 7.356 (4.8); 7.337 (3.0); 7.235 (3.5); 7.217 (5.4); 7.198 (2.3); 7.022 (6.3); 7.016 (6.3); 6.988 (5.4); 6.969 (4.9); 4.038 (0.5); 4.020 (0.5); 3.322 (67.7); 2.671 (1.1); 2.502 (177.6); 2.328 (1.1); 2.253 (0.7); 2.240 (1.6); 2.232 (2.0); 2.220 (2.2); 2.207 (2.1); 2.199 (1.7); 2.186 (0.8); 1.989 (1.9); 1.397 (16.0); 1.193 (0.5); 1.175 (1.0); 1.157 (0.5); 0.944 (2.1); 0.933 (5.9); 0.929 (6.5); 0.918 (4.4); 0.912 (6.2); 0.908 (6.3); 0.898 (2.6); 0.700 (2.7); 0.686 (8.2); 0.674 (7.6); 0.662 (2.4); 0.146 (0.3); 0.000 (66.2); −0.150 (0.3)

I-1-487:
HPLC-MS: log P=2.69; mass (m/z): 347.1 (M+H)$^+$;
$^1$H-NMR (400.0 MHz, DMSO-D$_6$): δ=11.432 (4.2); 8.481 (4.3); 8.475 (4.5); 8.347 (3.6); 8.340 (3.6); 8.315 (0.8); 8.281 (1.5); 8.275 (1.4); 8.261 (1.6); 8.254 (2.8); 8.248 (1.4); 8.233 (1.5); 8.227 (1.3); 7.438 (1.1); 7.423 (1.3); 7.418 (2.0); 7.403 (2.0); 7.398 (1.5); 7.383 (1.4); 7.168 (3.3); 7.148 (2.9); 7.142 (1.8); 7.119 (2.7); 7.098 (1.4); 7.006 (5.6); 7.000 (5.6); 3.394 (0.4); 3.327 (714.8); 3.326 (732.3); 3.286 (0.5); 2.680 (1.5); 2.675 (4.1); 2.671 (4.1); 2.666 (2.9); 2.661 (1.8); 2.656 (5.0); 2.637 (5.1); 2.618 (1.8); 2.541 (34.6); 2.524 (10.1); 2.519 (15.4); 2.511 (203.4); 2.506 (415.9); 2.502 (549.7); 2.497 (392.9); 2.492 (185.1); 2.454 (0.5); 2.419 (0.4); 2.338 (1.1); 2.333 (2.5); 2.328 (3.5); 2.324 (2.5); 2.319 (1.2); 2.074 (15.6); 1.298 (0.6); 1.259 (0.9); 1.244 (0.5); 1.235 (1.3); 1.196 (7.0); 1.177 (16.0); 1.158 (6.9); 0.008 (2.4); 0.000 (81.5); −0.009 (2.5

I-1-488:

HPLC-MS: log P=2.69; mass (m/z): 329.1 (M+H)$^+$;
$^1$H-NMR (400.0 MHz, DMSO-D$_6$): δ=11.140 (3.2); 8.485 (4.5); 8.479 (4.6); 8.332 (3.1); 8.326 (3.1); 8.283 (1.4); 8.277 (1.3); 8.262 (1.5); 8.256 (2.5); 8.250 (1.3); 8.235 (1.4); 8.229 (1.3); 7.455 (2.1); 7.435 (3.0); 7.414 (3.0); 7.411 (2.5); 7.395 (2.3); 7.392 (1.9); 7.334 (3.6); 7.317 (2.3); 7.295 (2.0); 7.292 (1.7); 7.276 (2.9); 7.274 (2.6); 7.258 (1.2); 7.255 (1.1); 7.012 (3.0); 7.006 (3.0); 3.434 (0.4); 3.429 (0.4); 3.416 (0.5); 3.408 (0.5); 3.349 (446.7); 3.298 (0.7); 2.786 (1.5); 2.767 (4.5); 2.749 (4.7); 2.730 (1.6); 2.718 (1.2); 2.682 (0.6); 2.678 (0.8); 2.673 (0.6); 2.583 (0.4); 2.572 (0.8); 2.548 (246.6); 2.531 (2.8); 2.518 (49.0); 2.513 (94.0); 2.509 (120.2); 2.504 (86.9); 2.500 (42.3); 2.374 (1.1); 2.340 (0.6); 2.335 (0.8); 2.331 (0.6); 1.241 (0.4); 1.195 (7.3); 1.176 (16.0); 1.157 (7.1)

I-1-489:

HPLC-MS: log P=2.42; mass (m/z): 331.1 (M+H)$^+$;
$^1$H-NMR (400.0 MHz, DMSO-D$_6$): δ=11.212 (4.2); 8.765 (5.0); 8.759 (5.2); 8.591 (4.9); 8.585 (4.5); 8.491 (4.3); 8.485 (4.5); 8.381 (4.1); 8.375 (4.0); 8.316 (0.4); 8.296 (1.3); 8.290 (1.2); 8.275 (1.4); 8.269 (2.4); 8.263 (1.3); 8.248 (1.3); 8.242 (1.1); 7.025 (5.0); 7.018 (4.9); 3.325 (444.3); 3.286 (0.3); 3.104 (1.9); 3.085 (5.9); 3.067 (6.1); 3.048 (2.0); 2.675 (1.9); 2.671 (2.5); 2.666 (1.9); 2.541 (2.1); 2.524 (7.6); 2.510 (154.0); 2.506 (297.2); 2.502 (383.3); 2.497 (279.7); 2.493 (137.9); 2.333 (1.8); 2.328 (2.4); 2.324 (1.8); 2.074 (7.7); 1.298 (0.6); 1.284 (7.6); 1.265 (16.0); 1.247 (7.6); 1.235 (1.2); 0.008 (2.5); 0.000 (62.0); −0.008 (2.2)

I-1-490:

HPLC-MS: log P=1.29; mass (m/z): 330.1 (M+H)$^+$;
$^1$H-NMR (400.0 MHz, DMSO-D$_6$): δ=11.352 (2.0); 8.589 (1.4); 8.584 (1.5); 8.577 (1.5); 8.572 (1.5); 8.484 (2.3); 8.478 (2.5); 8.351 (1.9); 8.345 (1.9); 8.316 (0.7); 8.285 (0.7); 8.279 (0.7); 8.264 (0.9); 8.258 (1.5); 8.252 (1.2); 8.237 (0.9); 8.231 (0.7); 7.859 (1.1); 7.855 (1.2); 7.840 (1.3); 7.836 (1.3); 7.324 (1.3); 7.312 (1.3); 7.305 (1.3); 7.292 (1.2); 7.017 (2.0); 7.011 (2.0); 3.327 (785.0); 2.909 (1.0); 2.890 (2.9); 2.871 (3.0); 2.852 (1.0); 2.675 (3.0); 2.671 (4.2); 2.666 (3.1); 2.662 (1.5); 2.541 (11.4); 2.524 (12.2); 2.519 (19.0); 2.511 (236.8); 2.506 (479.5); 2.502 (634.6); 2.497 (460.5); 2.492 (222.5); 2.419 (0.4); 2.337 (1.4); 2.333 (2.9); 2.328 (4.1); 2.324 (3.0); 2.289 (0.5); 2.074 (16.0); 1.298 (0.5); 1.258 (0.7); 1.241 (4.3); 1.222 (8.7); 1.203 (3.9); 1.148 (0.4); 0.146 (0.3); 0.008 (3.1); 0.000 (87.1); −0.009 (2.4); −0.150 (0.4)

I-1-491:

HPLC-MS: log P=2.57; mass (m/z): 387.1 (M+H)$^+$;
$^1$H-NMR (400.0 MHz, DMSO-D$_6$): δ=11.702 (10.0); 8.486 (9.8); 8.480 (10.4); 8.376 (9.7); 8.369 (9.8); 8.285 (2.7); 8.279 (2.5); 8.264 (2.9); 8.258 (5.1); 8.251 (2.7); 8.237 (2.7); 8.230 (2.5); 7.778 (0.8); 7.757 (2.6); 7.748 (1.5); 7.738 (5.3); 7.722 (8.2); 7.701 (16.0); 7.684 (4.6); 7.679 (3.9); 6.981 (12.1); 6.974 (12.0); 3.518 (1.0); 3.343 (97.1); 3.002 (0.4); 2.716 (0.5); 2.571 (0.3); 2.563 (0.7); 2.546 (116.6); 2.530 (0.6); 2.525 (0.9); 2.516 (12.3); 2.512 (25.3); 2.507 (34.0); 2.502 (25.0); 2.498 (12.2); 2.372 (0.5); 0.000 (1.4)

I-1-492:

HPLC-MS: log P=2.56; mass (m/z): 443.9 (M+H)$^+$;
$^1$H-NMR (400.0 MHz, DMSO-D$_6$): δ=11.544 (6.4); 8.486 (6.4); 8.480 (6.7); 8.368 (5.7); 8.362 (5.6); 8.288 (2.0); 8.282 (1.8); 8.267 (2.1); 8.261 (3.7); 8.255 (1.9); 8.240 (2.0); 8.234 (1.8); 7.739 (4.8); 7.737 (4.8); 7.720 (5.2); 7.718 (5.0); 7.379 (1.9); 7.377 (1.9); 7.356 (4.5); 7.335 (3.0); 7.333 (2.7); 7.285 (2.5); 7.270 (3.0); 7.265 (3.2); 7.250 (3.3); 7.244 (1.7); 7.229 (1.5); 6.994 (7.9); 6.987 (7.8); 3.323 (53.2); 2.675 (0.7); 2.671 (1.0); 2.666 (0.7); 2.524 (3.7); 2.511 (59.4); 2.506 (113.0); 2.502 (143.6); 2.497 (101.7); 2.493 (47.6); 2.337 (0.3); 2.333 (0.7); 2.328 (0.9); 2.324 (0.6); 1.989 (0.9); 1.398 (16.0); 1.175 (0.5); 0.008 (3.0); 0.000 (72.0); −0.009 (2.3)

I-1-493:

HPLC-MS: log P=2.31; mass (m/z): 319.1 (M+H)$^+$;
$^1$H-NMR (400.0 MHz, DMSO-D$_6$): δ=11.232 (10.4); 8.483 (15.3); 8.477 (16.0); 8.354 (11.8); 8.347 (11.6); 8.286 (4.6); 8.280 (4.3); 8.265 (5.0); 8.259 (8.7); 8.253 (4.5); 8.238 (4.6); 8.232 (4.2); 7.701 (3.5); 7.697 (4.0); 7.683 (6.7); 7.678 (7.5); 7.664 (4.0); 7.659 (4.2); 7.603 (2.2); 7.598 (2.2); 7.589 (2.6); 7.585 (5.0); 7.582 (3.9); 7.580 (3.8); 7.578 (3.4); 7.570 (4.2); 7.566 (3.9); 7.564 (5.2); 7.559 (2.9); 7.550 (2.9); 7.546 (2.5); 7.348 (5.9); 7.328 (13.2); 7.324 (7.6); 7.311 (12.6); 7.309 (11.8); 7.303 (5.1); 7.301 (4.9); 7.293 (6.3); 7.290 (5.2); 7.000 (10.8); 6.994 (10.6); 3.441 (0.5); 3.429 (0.5); 3.344 (925.4); 3.268 (0.4); 2.996 (1.7); 2.713 (1.0); 2.682 (0.6); 2.677 (1.1); 2.672 (1.5); 2.668 (1.1); 2.663 (0.5); 2.576 (0.4); 2.543 (275.3); 2.526 (4.7); 2.521 (7.4); 2.512 (85.2); 2.508 (171.2); 2.503 (226.8); 2.499 (163.8); 2.494 (77.8); 2.369 (1.0); 2.339 (0.5); 2.335 (1.1); 2.330 (1.5); 2.326 (1.1); 2.321 (0.5); 0.000 (2.7)

I-1-494:

HPLC-MS: log P=2.53; mass (m/z): 433.0 (M+H)$^+$;
$^1$H-NMR (400.0 MHz, DMSO-D$_6$): δ=11.058 (15.7); 8.492 (14.4); 8.486 (15.8); 8.343 (13.4); 8.336 (13.9); 8.295 (4.1); 8.289 (4.1); 8.274 (4.6); 8.268 (7.9); 8.263 (4.7); 8.247 (4.2); 8.241 (4.0); 7.807 (15.1); 7.793 (16.0); 7.410 (14.0); 7.396 (13.2); 6.994 (9.7); 6.989 (10.0); 6.966 (0.5); 3.481 (0.4); 3.437 (0.5); 3.426 (0.5); 3.421 (0.6); 3.336 (696.2); 3.284 (1.3); 3.259 (0.9); 3.218 (0.3); 3.002 (1.1); 2.718 (3.7); 2.677 (2.7); 2.654 (0.7); 2.634 (0.7); 2.596 (2.0); 2.548 (688.0); 2.509 (383.3); 2.433 (1.2); 2.374 (3.7); 2.335 (2.5); 2.297 (0.4); 1.241 (1.2); 1.155 (0.4)

I-1-495:

HPLC-MS: log P=1.79; mass (m/z): 428.0 (M+H)$^+$;
$^1$H-NMR (400.0 MHz, DMSO-D$_6$): δ=13.527 (0.3); 11.480 (13.3); 10.125 (0.3); 8.493 (13.0); 8.487 (13.7); 8.429 (8.8); 8.424 (9.5); 8.417 (9.7); 8.412 (9.2); 8.397 (0.5); 8.376 (11.6); 8.370 (11.6); 8.294 (4.1); 8.288 (3.7); 8.273 (4.3); 8.267 (7.6); 8.261 (3.9); 8.246 (4.1); 8.240 (3.7); 7.839 (8.5); 7.834 (8.7); 7.820 (10.1); 7.815 (9.3); 7.534 (0.5); 7.527 (9.9); 7.515 (9.3); 7.508 (8.8); 7.496 (8.7); 7.209 (0.9); 7.081 (1.0); 7.006 (16.0); 6.999 (15.9); 6.954 (0.7); 3.891 (0.3); 3.876 (0.4); 3.802 (0.4); 3.743 (0.4); 3.739 (0.3); 3.691 (0.4); 3.681 (0.4); 3.665 (0.5); 3.647 (0.5); 3.631 (0.4); 3.608 (0.4); 3.577 (0.4); 3.568 (0.5); 3.554 (0.6); 3.537 (0.7); 3.505 (0.8); 3.498 (0.8); 3.484 (0.6); 3.466 (1.4); 3.458 (1.2); 3.443 (1.4); 3.430 (1.3); 3.414 (1.8); 3.395 (3.2); 3.341 (3202.7); 3.309 (7.4); 3.295 (3.7); 3.276 (1.5); 3.258 (0.9); 3.232 (0.8); 3.220 (0.8); 3.200 (0.5); 3.192 (0.6); 3.138 (0.3); 3.102 (0.3); 3.098 (0.4); 3.024 (0.4); 3.002 (0.5); 2.718 (1.3); 2.687 (2.4); 2.682 (5.1); 2.678 (7.1); 2.673 (5.2); 2.669 (2.6); 2.639 (0.5); 2.605 (0.7); 2.599 (0.7); 2.590 (0.8); 2.569 (1.8); 2.548 (310.4); 2.531 (22.0); 2.526 (34.8); 2.518 (413.6); 2.513 (826.0); 2.509 (1080.9); 2.504 (770.7); 2.500 (365.0); 2.442 (0.8); 2.421 (0.5); 2.411 (0.4); 2.391 (0.4); 2.374 (1.2); 2.357 (0.4); 2.344 (2.3); 2.340 (5.0); 2.335 (6.8); 2.331 (4.9); 2.326 (2.1); 2.297 (0.8); 2.253 ((0.4); 1.440 (0.5); (0.4); 1.265 (0.5); 1.251 (1.2); 1.243 (2.5); 1.162 (0.4); 1.154 (0.7); −1.685 (0.3); −3.450 (0.4)

I-1-496:

HPLC-MS: log P=2.55; mass (m/z): 331.1 (M+H)$^+$;
$^1$H-NMR (400.0 MHz, DMSO-D$_6$): δ=10.622 (2.6); 8.482

(2.9); 8.476 (3.0); 8.329 (2.2); 8.322 (2.2); 8.316 (0.5); 8.286 (1.0); 8.280 (0.9); 8.265 (1.1); 8.259 (1.9); 8.253 (1.0); 8.238 (1.0); 8.232 (0.9); 7.773 (1.5); 7.769 (1.6); 7.754 (1.6); 7.750 (1.6); 7.557 (1.6); 7.553 (0.9); 7.539 (1.2); 7.536 (1.4); 7.532 (1.2); 7.518 (1.1); 7.514 (1.0); 7.216 (2.2); 7.196 (1.9); 7.105 (1.3); 7.103 (1.3); 7.087 (2.3); 7.085 (2.2); 7.068 (1.2); 7.066 (1.1); 7.011 (2.9); 7.004 (2.8); 3.941 (16.0); 3.767 (0.4); 3.324 (38.4); 2.671 (0.4); 2.525 (1.2); 2.520 (1.8); 2.511 (19.4); 2.507 (38.7); 2.502 (51.0); 2.497 (36.7); 2.493 (17.5); 2.329 (0.3); 1.336 (0.4); 1.250 (0.6); 0.008 (1.0); 0.000 (28.8); −0.009 (0.9)

I-1-497:
HPLC-MS: log P=2.35; mass (m/z): 390.0 (M+H)$^+$; $^1$H-NMR (400.0 MHz, DMSO-D$_6$): δ=11.855 (1.7); 8.488 (2.9); 8.482 (3.1); 8.367 (2.5); 8.361 (2.4); 8.317 (0.4); 8.297 (0.9); 8.291 (0.9); 8.276 (1.0); 8.270 (1.7); 8.264 (0.9); 8.249 (0.9); 8.243 (0.8); 6.934 (1.6); 6.928 (1.6); 5.757 (0.4); 3.322 (176.6); 2.759 (16.0); 2.675 (2.2); 2.671 (2.9); 2.666 (2.1); 2.541 (6.7); 2.523 (11.8); 2.510 (170.2); 2.506 (326.4); 2.501 (421.8); 2.497 (306.9); 2.493 (151.0); 2.333 (2.0); 2.328 (2.8); 2.324 (2.0); 0.146 (0.4); 0.008 (4.1); 0.000 (97.2); −0.008 (3.7); −0.150 (0.5)

I-1-498:
HPLC-MS: log P=2.17; mass (m/z): 339.0 (M+H)$^+$; $^1$H-NMR (400.0 MHz, DMSO-D$_6$): δ=10.506 (2.1); 8.466 (2.1); 8.465 (2.2); 8.459 (2.3); 8.288 (1.9); 8.281 (1.9); 8.273 (0.9); 8.267 (0.8); 8.252 (0.9); 8.246 (1.5); 8.239 (0.8); 8.225 (0.8); 8.218 (0.8); 6.851 (2.6); 6.844 (2.6); 5.756 (0.4); 4.289 (1.9); 4.281 (1.5); 4.278 (2.0); 4.275 (1.5); 4.266 (2.0); 3.324 (33.6); 3.045 (2.0); 3.037 (1.5); 3.033 (2.1); 3.030 (1.5); 3.022 (1.9); 2.525 (0.5); 2.520 (0.8); 2.512 (10.8); 2.507 (21.7); 2.502 (28.8); 2.498 (20.8); 2.493 (9.7); 2.013 (16.0); 0.000 (8.1)

I-1-499:
HPLC-MS: log P=2.36; mass (m/z): 315.2 (M+H)$^+$; $^1$H-NMR (400.0 MHz, DMSO-D$_6$): δ=11.101 (2.5); 8.479 (3.6); 8.473 (3.8); 8.327 (2.6); 8.321 (2.6); 8.279 (1.2); 8.273 (1.1); 8.258 (1.3); 8.252 (2.2); 8.246 (1.2); 8.231 (1.2); 8.225 (1.1); 7.484 (1.8); 7.465 (2.0); 7.395 (0.8); 7.392 (0.8); 7.376 (2.1); 7.373 (2.1); 7.358 (1.8); 7.354 (1.6); 7.293 (3.0); 7.284 (1.9); 7.274 (2.1); 7.265 (2.4); 7.246 (0.9); 7.010 (2.1); 7.004 (2.1); 5.757 (6.0); 3.322 (23.1); 2.675 (0.4); 2.671 (0.5); 2.666 (0.3); 2.524 (1.6); 2.510 (30.4); 2.506 (57.8); 2.502 (73.8); 2.497 (53.5); 2.493 (26.1); 2.396 (16.0); 2.333 (0.4); 2.328 (0.5); 2.324 (0.4); 1.336 (0.5); 1.250 (0.6); 0.008 (1.5); 0.000 (36.4); −0.008 (1.4)

I-1-500:
HPLC-MS: log P=2.06; mass (m/z): 373.1 (M+H)$^+$; $^1$H-NMR (400.0 MHz, DMSO-D$_6$): δ=10.918 (4.5); 8.488 (5.1); 8.482 (5.3); 8.348 (4.3); 8.342 (4.3); 8.298 (1.5); 8.292 (1.4); 8.277 (1.6); 8.271 (2.8); 8.264 (1.5); 8.250 (1.5); 8.244 (1.4); 7.271 (2.3); 7.137 (5.3); 7.002 (2.5); 6.922 (4.9); 6.916 (4.8); 4.180 (0.7); 3.822 (16.0); 3.540 (0.9); 3.335 (197.1); 2.718 (0.5); 2.682 (0.8); 2.678 (1.1); 2.673 (0.7); 2.548 (117.1); 2.531 (3.7); 2.518 (65.5); 2.513 (129.3); 2.509 (168.3); 2.504 (120.5); 2.500 (57.3); 2.374 (0.5); 2.340 (0.8); 2.336 (1.1); 2.331 (0.8); 1.242 (0.5)

I-1-501:
HPLC-MS: log P=2.20; mass (m/z): 371.1 (M+H)$^+$; $^1$H-NMR (400.0 MHz, DMSO-D$_6$): δ=11.704 (11.9); 9.091 (10.1); 9.085 (11.9); 9.031 (12.3); 9.025 (10.1); 8.902 (0.4); 8.893 (0.3); 8.497 (12.5); 8.490 (13.1); 8.410 (11.6); 8.403 (11.4); 8.296 (3.7); 8.290 (3.4); 8.275 (4.0); 8.269 (7.0); 8.263 (3.7); 8.248 (3.8); 8.242 (3.4); 6.994 (16.0); 6.987 (15.8); 3.418 (0.4); 3.408 (0.5); 3.355 (473.6); 3.299 (0.5); 2.683 (0.5); 2.679 (0.6); 2.674 (0.4); 2.549 (47.3); 2.532 (2.0); 2.527 (3.2); 2.519 (37.9); 2.514 (75.7); 2.509 (98.6); 2.505 (70.5); 2.500 (33.2); 2.341 (0.5); 2.336 (0.6); 2.332 (0.5)

I-1-502:
HPLC-MS: log P=2.38; mass (m/z): 370.0 (M+H)$^+$; $^1$H-NMR (400.0 MHz, DMSO-D$_6$): δ=11.474 (10.8); 8.924 (6.2); 8.912 (6.3); 8.494 (11.1); 8.488 (11.4); 8.383 (10.8); 8.376 (16.0); 8.356 (6.6); 8.294 (3.2); 8.288 (2.9); 8.273 (3.5); 8.267 (5.9); 8.261 (3.1); 8.246 (3.1); 8.240 (2.9); 7.810 (4.3); 7.798 (4.3); 7.790 (4.1); 7.778 (3.9); 6.989 (13.9); 6.982 (13.6); 3.390 (0.5); 3.346 (297.6); 3.316 (0.9); 2.719 (1.2); 2.684 (0.4); 2.679 (0.6); 2.6745); 2.593 (0.5); 2.593 (0.3); 2.572 (1.0); 2.549 (274.0); 2.532 (2.2); 2.527 (3.1); 2.519 (36.3); 2.514 (71.1); 2.510 (92.1); 2.505 (66.2); 2.501 (31.8); 2.376 (1.3); 2.341 (0.5); 2.337 (0.6); 2.332 (0.4); 1.240 (0.4)

I-1-503:
HPLC-MS: log P=2.61; mass (m/z): 341.0 (M+H)$^+$; $^1$H-NMR (400.0 MHz, DMSO-D$_6$): δ=10.972 (10.5); 8.495 (11.6); 8.488 (12.1); 8.357 (9.8); 8.350 (9.7); 8.303 (3.4); 8.297 (3.2); 8.282 (3.7); 8.276 (6.4); 8.270 (3.4); 8.255 (3.5); 8.249 (3.1); 7.929 (14.9); 7.916 (15.4); 7.217 (16.0); 7.204 (15.5); 6.944 (12.8); 6.937 (12.6); 3.337 (356.3); 3.310 (0.8); 2.682 (0.8); 2.678 (1.0); 2.673 (0.7); 2.548 (34.3); 2.517 (66.5); 2.513 (126.1); 2.509 (160.9); 2.504 (116.0); 2.500 (56.6); 2.340 (0.8); 2.335 (1.1); 2.331 (0.8); 1.240 (0.4)

I-1-504:
HPLC-MS: log P=2.16; mass (m/z): 336.0 (M+H)$^+$; $^1$H-NMR (400.0 MHz, DMSO-D$_6$): δ=11.380 (12.2); 8.628 (0.3); 8.614 (9.7); 8.611 (10.0); 8.602 (10.1); 8.599 (9.9); 8.507 (0.4); 8.493 (13.2); 8.487 (13.8); 8.382 (12.0); 8.376 (12.0); 8.295 (3.8); 8.289 (3.6); 8.274 (4.1); 8.268 (7.2); 8.261 (3.9); 8.246 (3.8); 8.240 (3.5); 8.105 (9.1); 8.101 (9.3); 8.084 (10.0); 8.081 (9.6); 7.612 (10.1); 7.600 (9.7); 7.591 (9.2); 7.579 (9.2); 7.027 (0.4); 7.013 (16.0); 7.006 (16.0); 3.375 (0.6); 3.370 (0.6); 3.353 (5.0); 3.339 (234.0); 3.310 (0.5); 2.682 (0.5); 2.678 (0.7); 2.673 (0.5); 2.548 (9.3); 2.531 (2.7); 2.526 (4.2); 2.518 (40.2); 2.513 (79.8); 2.509 (105.1); 2.504 (76.9); 2.500 (37.7); 2.340 (0.5); 2.335 (0.7); 2.331 (0.5); 1.238 (0.3)

I-1-505:
HPLC-MS: log P=1.50; mass (m/z): 331.1 (M+H)$^+$; $^1$H-NMR (400.0 MHz, DMSO-D$_6$): δ=11.667 (2.1); 9.259 (2.6); 9.246 (2.7); 8.491 (2.1); 8.485 (2.3); 8.385 (1.9); 8.378 (1.9); 8.316 (0.5); 8.295 (0.7); 8.289 (0.6); 8.274 (0.7); 8.268 (1.3); 8.261 (0.7); 8.247 (0.7); 8.241 (0.7); 7.761 (2.7); 7.748 (2.7); 7.015 (2.7); 7.008 (2.7); 3.326 (667.3); 3.081 (1.0); 3.062 (3.0); 3.043 (3.1); 3.024 (1.0); 2.995 (0.5); 2.680 (1.2); 2.675 (2.5); 2.671 (3.5); 2.666 (2.5); 2.661 (1.2); 2.541 (12.6); 2.524 (9.9); 2.519 (15.2); 2.511 (195.0); 2.506 (395.4); 2.502 (520.7); 2.497 (370.7); 2.492 (174.1); 2.419 (0.3); 2.337 (1.2); 2.333 (2.5); 2.328 (3.4); 2.324 (2.4); 2.319 (1.1); 2.074 (16.0); 1.308 (3.9); 1.298 (0.7); 1.289 (8.6); 1.271 (3.8); 1.258 (0.7); 1.244 (0.5); 1.235 (1.1); 1.148 (0.3); 0.146 (0.4); 0.008 (3.0); 0.000 (91.5); −0.009 (2.5); −0.150 (0.3)

I-1-506:
HPLC-MS: log P=2.65; mass (m/z): 387.1 (M+H)$^+$; $^1$H-NMR (400.0 MHz, DMSO-D$_6$): δ=11.525 (12.5); 8.485 (12.6); 8.479 (13.1); 8.361 (11.1); 8.355 (11.0); 8.286 (4.1); 8.280 (3.8); 8.265 (4.4); 8.259 (7.7); 8.252 (4.0); 8.238 (4.1); 8.231 (3.7); 7.931 (4.6); 7.918 (4.8); 7.909 (5.2); 7.896 (5.0); 7.681 (4.5); 7.674 (4.9); 7.659 (4.7); 7.652 (4.7); 7.570 (2.5); 7.565 (2.2); 7.549 (4.7); 7.543 (3.9); 7.528 (2.3); 7.522 (1.9); 6.971 (16.0); 6.965 (15.9); 3.512 (2.4); 3.492 (0.4); 3.478 (0.4); 3.424 (0.6); 3.411 (0.7); 3.397

(0.7); 3.388 (0.8); 3.334 (794.3); 2.995 (0.4); 2.681 (0.6); 2.676 (1.3); 2.672 (1.7); 2.667 (1.3); 2.662 (0.6); 2.542 (38.7); 2.525 (4.8); 2.520 (7.3); 2.512 (95.5); 2.507 (193.4); 2.502 (257.2); 2.498 (186.6); 2.493 (88.4); 2.338 (0.6); 2.334 (1.2); 2.329 (1.7); 2.325 (1.2); 2.320 (0.5); 2.074 (0.7); 1.249 (0.4); 1.235 (0.9); 0.000 (4.9)

I-1-507:

HPLC-MS: log P=2.69; mass (m/z): 433.0 (M+H)$^+$; $^1$H-NMR (400.0 MHz, DMSO-D$_6$): δ=11.088 (9.2); 8.496 (9.8); 8.490 (10.2); 8.355 (7.7); 8.348 (7.7); 8.301 (3.0); 8.295 (2.8); 8.280 (3.2); 8.274 (5.6); 8.268 (2.9); 8.253 (3.0); 8.247 (2.7); 7.808 (14.7); 7.796 (15.3); 7.285 (16.0); 7.272 (15.2); 6.951 (11.2); 6.944 (11.1); 3.365 (0.4); 3.335 (236.3); 3.315 (0.6); 2.682 (0.7); 2.678 (0.9); 2.673 (0.6); 2.548 (79.9); 2.531 (2.8); 2.526 (4.5); 2.518 (52.9); 2.513 (106.2); 2.509 (139.2); 2.504 (99.2); 2.499 (46.7); 2.374 (0.3); 2.344 (0.3); 2.340 (0.7); 2.335 (0.9); 2.331 (0.6); 1.240 (0.4)

I-1-508:

HPLC-MS: log P=3.02; mass (m/z): 406.1 (M+H)$^+$; $^1$H-NMR (400.0 MHz, DMSO-D$_6$): δ=11.995 (2.5); 8.492 (2.5); 8.486 (2.8); 8.414 (2.4); 8.407 (2.5); 8.297 (0.8); 8.291 (0.7); 8.276 (0.8); 8.270 (1.5); 8.264 (0.8); 8.249 (0.8); 8.243 (0.7); 7.021 (3.1); 7.014 (3.1); 3.857 (16.0); 3.326 (251.2); 2.995 (0.5); 2.754 (4.0); 2.737 (4.3); 2.675 (0.6); 2.671 (0.9); 2.666 (0.7); 2.541 (47.1); 2.524 (2.2); 2.506 (97.0); 2.502 (127.5); 2.497 (94.3); 2.493 (47.3); 2.333 (0.6); 2.328 (0.8); 2.324 (0.6); 2.052 (0.4); 2.035 (0.8); 2.018 (1.0); 2.001 (0.8); 1.984 (0.4); 1.235 (0.5); 0.946 (14.4); 0.930 (14.0); 0.000 (4.9)

I-1-509:

HPLC-MS: log P=2.72; mass (m/z): 392.1 (M+H)$^+$; $^1$H-NMR (400.0 MHz, DMSO-D$_6$): δ=11.970 (2.8); 8.492 (2.5); 8.486 (2.7); 8.409 (2.3); 8.402 (2.4); 8.315 (0.3); 8.297 (0.7); 8.291 (0.7); 8.276 (0.8); 8.269 (1.4); 8.263 (0.7); 8.248 (0.8); 8.242 (0.7); 7.016 (3.0); 7.010 (3.0); 3.855 (16.0); 3.520 (0.4); 3.503 (1.1); 3.486 (1.5); 3.469 (1.2); 3.452 (0.5); 3.325 (243.8); 2.995 (0.4); 2.675 (0.8); 2.671 (1.0); 2.666 (0.8); 2.541 (46.0); 2.524 (2.6); 2.510 (59.1); 2.506 (119.6); 2.502 (158.6); 2.497 (116.6); 2.493 (57.8); 2.333 (0.7); 2.329 (1.0); 2.324 (0.8); 1.280 (15.5); 1.263 (15.3); 1.236 (0.6); 0.008 (0.5); 0.000 (15.5); −0.008 (0.6)

I-1-510:

HPLC-MS: log P=2.38; mass (m/z): 321.0 (M+H)$^+$; $^1$H-NMR (400.0 MHz, DMSO-D$_6$): δ=10.801 (2.4); 8.488 (2.6); 8.482 (2.7); 8.327 (2.0); 8.321 (2.0); 8.293 (0.9); 8.287 (0.8); 8.272 (0.9); 8.266 (1.6); 8.260 (0.8); 8.245 (0.9); 8.239 (0.8); 7.682 (2.8); 7.669 (2.9); 7.025 (2.8); 7.013 (2.7); 6.940 (3.2); 6.933 (3.2); 3.408 (0.4); 3.350 (409.2); 3.303 (0.5); 3.298 (0.5); 2.718 (0.3); 2.682 (0.4); 2.678 (0.6); 2.673 (0.4); 2.548 (92.8); 2.531 (1.9); 2.526 (3.1); 2.518 (35.8); 2.513 (70.6); 2.508 (91.3); 2.504 (65.3); 2.499 (30.9); 2.473 (16.0); 2.374 (0.3); 2.340 (0.4); 2.335 (0.6); 2.331 (0.4)

I-1-511:

HPLC-MS: log P=2.61; mass (m/z): 374.1 (M+H)$^+$; $^1$H-NMR (400.0 MHz, DMSO-D$_6$): δ=11.788 (0.9); 8.491 (1.9); 8.485 (2.0); 8.387 (1.7); 8.380 (1.7); 8.316 (0.8); 8.300 (0.6); 8.294 (0.6); 8.279 (0.7); 8.273 (1.1); 8.267 (0.6); 8.251 (0.6); 8.246 (0.5); 6.961 (2.3); 6.955 (2.3); 3.323 (629.4); 2.679 (1.7); 2.675 (3.5); 2.670 (4.8); 2.666 (3.5); 2.661 (1.7); 2.541 (3.7); 2.524 (14.5); 2.519 (22.5); 2.510 (272.2); 2.506 (546.9); 2.501 (719.1); 2.497 (518.4); 2.492 (247.3); 2.418 (12.0); 2.337 (1.5); 2.333 (3.3); 2.328 (4.6); 2.324 (3.3); 2.319 (1.5); 2.074 (16.0); 1.298 (0.7); 1.258 (0.9); 1.244 (0.4); 1.236 (0.7); 1.147 (0.5); 0.146 (0.8); 0.008 (6.3); 0.000 (196.3); −0.009 (6.1); −0.150 (0.8)

I-1-512:

HPLC-MS: log P=3.11; mass (m/z): 406.1 (M+H)$^+$; $^1$H-NMR (400.0 MHz, DMSO-D$_6$): δ=11.975 (1.1); 8.491 (1.0); 8.485 (1.1); 8.405 (1.0); 8.398 (1.0); 8.315 (0.4); 8.275 (0.4); 8.269 (0.6); 8.248 (0.3); 7.003 (1.3); 6.997 (1.2); 3.830 (6.8); 3.353 (0.8); 3.325 (347.8); 3.294 (0.3); 2.995 (0.5); 2.675 (0.9); 2.671 (1.2); 2.666 (0.8); 2.662 (0.4); 2.541 (32.0); 2.524 (3.1); 2.511 (71.5); 2.506 (139.7); 2.502 (179.3); 2.497 (127.2); 2.493 (59.8); 2.337 (0.4); 2.333 (0.9); 2.328 (1.1); 2.324 (0.8); 1.396 (16.0); 1.235 (0.8); 0.008 (0.6); 0.000 (16.6); −0.009 (0.6)

I-1-513:

HPLC-MS: log P=3.89; mass (m/z): 395.1 (M+H)$^+$; $^1$H-NMR (400.0 MHz, DMSO-D$_6$): δ=11.415 (0.7); 8.488 (0.9); 8.482 (1.0); 8.363 (0.7); 8.356 (0.7); 8.274 (0.3); 8.267 (0.6); 6.975 (0.5); 6.969 (0.5); 3.844 (5.8); 3.327 (91.5); 2.541 (0.5); 2.524 (0.6); 2.520 (0.9); 2.511 (14.7); 2.506 (30.2); 2.502 (40.0); 2.497 (28.6); 2.493 (13.5); 1.355 (16.0); 0.000 (3.5)

I-1-514:

HPLC-MS: log P=2.13; mass (m/z): 369.1 (M+H)$^+$; $^1$H-NMR (400.0 MHz, DMSO-D$_6$): δ=11.655 (2.2); 8.491 (4.2); 8.485 (4.5); 8.369 (3.2); 8.363 (3.3); 8.315 (1.1); 8.297 (1.4); 8.291 (1.2); 8.276 (1.4); 8.270 (2.5); 8.264 (1.3); 8.249 (1.4); 8.243 (1.2); 7.145 (1.3); 7.008 (3.0); 6.978 (2.0); 6.973 (2.0); 6.871 (1.5); 3.993 (0.4); 3.847 (16.0); 3.388 (0.4); 3.374 (0.6); 3.326 (1334.4); 3.282 (1.0); 3.275 (0.7); 3.246 (0.4); 2.995 (1.1); 2.675 (2.6); 2.671 (3.6); 2.666 (2.6); 2.541 (37.1); 2.524 (8.4); 2.519 (13.0); 2.511 (200.2); 2.506 (410.1); 2.502 (544.2); 2.497 (389.5); 2.493 (184.5); 2.423 (0.5); 2.337 (1.2); 2.333 (2.6); 2.328 (3.5); 2.324 (2.5); 2.319 (1.2); 2.289 (0.7); 2.262 (14.1); 1.298 (0.4); 1.259 (0.6); 1.235 (2.0); 0.008 (0.6); 0.000 (16.9); −0.009 (0.5)

I-1-515:

HPLC-MS: log P=2.00; mass (m/z): 370.1 (M+H)$^+$; $^1$H-NMR (400.0 MHz, DMSO-D$_6$): δ=11.699 (11.2); 8.987 (16.0); 8.974 (9.5); 8.972 (9.4); 8.961 (9.0); 8.494 (10.4); 8.488 (12.7); 8.386 (9.4); 8.379 (11.4); 8.294 (3.6); 8.287 (3.8); 8.273 (4.1); 8.266 (7.3); 8.260 (4.8); 8.245 (4.0); 8.239 (3.9); 7.892 (8.9); 7.879 (9.9); 7.000 (13.0); 6.993 (15.1); 3.555 (0.3); 3.550 (0.3); 3.533 (0.4); 3.454 (0.9); 3.446 (1.0); 3.429 (1.3); 3.425 (1.3); 3.360 (1310.0); 3.352 (358.2); 3.299 (2.3); 3.281 (1.3); 3.272 (0.9); 3.262 (0.8); 3.256 (0.7); 3.237 (0.6); 3.228 (0.7); 3.217 (0.6); 3.207 (0.6); 3.198 (0.5); 3.002 (1.3); 2.719 (2.3); 2.688 (0.5); 2.683 (0.9); 2.679 (1.4); 2.674 (1.2); 2.607 (0.3); 2.601 (0.4); 2.587 (0.9); 2.583 (0.9); 2.579 (0.9); 2.576 (1.1); 2.573 (1.1); 2.549 (641.4); 2.542 (88.5); 2.539 (84.7); 2.528 (8.3); 2.519 (70.7); 2.514 (154.9); 2.510 (223.4); 2.505 (190.9); 2.501 (128.5); 2.462 (0.8); 2.426 (0.4); 2.418 (0.4); 2.395 (0.3); 2.386 (0.3); 2.375 (2.4); 2.370 (0.7); 2.368 (0.7); 2.345 (0.6); 2.341 (1.1); 2.336 (1.5); 2.332 (1.3); 2.327 (0.9); 1.240 (0.6)

I-1-516:

HPLC-MS: log P=2.98; mass (m/z): 423.0 (M+H)$^+$; $^1$H-NMR (601.6 MHz, DMSO-D$_6$): δ=11.830 (14.2); 10.109 (0.4); 8.486 (13.4); 8.482 (13.7); 8.418 (0.4); 8.405 (0.4); 8.391 (12.3); 8.387 (12.0); 8.314 (1.5); 8.281 (3.9); 8.277 (3.8); 8.268 (4.3); 8.263 (7.5); 8.259 (3.8); 8.249 (4.0); 8.245 (3.5); 8.232 (0.5); 8.077 (2.7); 8.066 (3.1); 8.051 (2.5); 6.961 (16.0); 6.956 (15.9); 6.200 (0.4); 6.143 (0.5); 6.138 (0.4); 5.755 (0.8); 3.320 (392.5); 2.617 (1.9); 2.613 (2.6); 2.610 (2.1); 2.541 (0.5); 2.523 (4.1); 2.520 (4.8); 2.517 (4.4); 2.508 (135.6); 2.505 (302.4); 2.502 (429.8);

2.499 (317.3); 2.496 (152.4); 2.448 (0.4); 2.389 (2.1); 2.386 (2.7); 2.383 (2.0); 1.523 (0.4); 1.339 (0.4); 1.234 (0.4); 0.096 (0.5); 0.005 (2.4); 0.000 (97.9); −0.006 (4.1); −0.100 (0.5); −1.806 (0.4)

I-1-517:
HPLC-MS: log P=2.53; mass (m/z): 397.0 (M+H)$^+$; $^1$H-NMR (400.0 MHz, DMSO-D$_6$): δ=11.351 (1.9); 8.490 (2.7); 8.484 (2.8); 8.365 (2.1); 8.359 (2.1); 8.315 (1.0); 8.297 (0.9); 8.291 (0.8); 8.276 (1.0); 8.270 (1.6); 8.263 (0.9); 8.249 (0.9); 8.242 (0.8); 6.979 (1.4); 6.974 (1.3); 3.871 (16.0); 3.354 (0.7); 3.323 (551.5); 2.679 (1.0); 2.675 (2.1); 2.671 (2.9); 2.666 (2.1); 2.662 (0.9); 2.541 (5.7); 2.524 (6.9); 2.519 (10.6); 2.510 (162.2); 2.506 (330.6); 2.501 (436.1); 2.497 (310.9); 2.492 (146.9); 2.337 (1.0); 2.333 (2.0); 2.328 (2.9); 2.324 (2.1); 2.319 (1.0); 2.288 (0.4); 2.161 (14.8); 1.259 (0.4); 1.234 (0.7); 0.008 (1.1); 0.000 (36.9); −0.009 (1.1)

I-1-518:
HPLC-MS: log P=2.61; mass (m/z): 397.0 (M+H)$^+$; $^1$H-NMR (400.0 MHz, DMSO-D$_6$): δ=11.474 (2.1); 8.491 (4.4); 8.485 (4.6); 8.369 (3.4); 8.363 (3.4); 8.315 (1.3); 8.299 (1.4); 8.293 (1.3); 8.278 (1.5); 8.271 (2.6); 8.265 (1.3); 8.251 (1.4); 8.244 (1.2); 7.661 (8.1); 6.987 (2.6); 6.981 (2.6); 4.290 (1.7); 4.272 (5.3); 4.254 (5.4); 4.235 (1.8); 3.322 (718.9); 3.279 (0.6); 2.679 (1.4); 2.675 (3.0); 2.670 (4.2); 2.666 (3.1); 2.661 (1.6); 2.541 (15.3); 2.524 (18.3); 2.510 (235.9); 2.506 (480.5); 2.501 (643.1); 2.497 (474.8); 2.492 (235.1); 2.337 (1.4); 2.333 (3.0); 2.328 (4.2); 2.323 (3.1); 2.319 (1.5); 2.288 (0.6); 1.359 (7.2); 1.341 (16.0); 1.323 (7.0); 1.298 (0.4); 1.258 (0.5); 1.233 (1.0); 0.008 (1.8); 0.000 (52.7); −0.009 (2.1)

I-1-519:
HPLC-MS: log P=2.93; mass (m/z): 413.0 (M+H)$^+$; $^1$H-NMR (400.0 MHz, DMSO-D$_6$): δ=11.387 (2.0); 8.490 (2.9); 8.484 (3.1); 8.360 (2.3); 8.354 (2.3); 8.315 (0.5); 8.297 (0.9); 8.291 (0.9); 8.276 (1.0); 8.270 (1.8); 8.264 (0.9); 8.249 (1.0); 8.243 (0.9); 6.978 (1.6); 6.973 (1.6); 4.223 (1.0); 4.205 (3.3); 4.187 (3.3); 4.169 (1.1); 3.359 (0.5); 3.325 (474.0); 3.295 (0.7); 2.675 (1.1); 2.671 (1.6); 2.666 (1.2); 2.541 (5.2); 2.524 (3.6); 2.511 (88.2); 2.506 (182.2); 2.502 (243.4); 2.497 (178.3); 2.493 (87.5); 2.333 (1.2); 2.329 (1.6); 2.324 (1.2); 2.173 (16.0); 1.338 (4.4); 1.320 (9.8); 1.302 (4.4); 1.235 (0.5); 0.008 (0.4); 0.000 (11.8); −0.008 (0.4)

I-1-520:
HPLC-MS: log P=2.15; mass (m/z): 385.0 (M+H)$^+$; $^1$H-NMR (400.0 MHz, DMSO-D$_6$): δ=10.367 (2.6); 8.479 (2.4); 8.473 (2.5); 8.334 (2.2); 8.327 (2.3); 8.316 (0.6); 8.289 (0.8); 8.283 (0.7); 8.268 (0.8); 8.262 (1.5); 8.255 (0.8); 8.241 (0.8); 8.234 (0.7); 8.119 (5.3); 6.930 (2.5); 6.924 (2.4); 3.937 (16.0); 3.323 (139.8); 2.671 (1.4); 2.666 (1.0); 2.541 (0.8); 2.506 (166.2); 2.502 (211.3); 2.497 (153.0); 2.328 (1.3); 2.324 (1.0); 0.146 (0.6); 0.008 (5.5); 0.000 (141.0); −0.009 (5.4); −0.150 (0.6)

I-1-521:
HPLC-MS: log P=2.23; mass (m/z): 385.0 (M+H)$^+$; $^1$H-NMR (400.0 MHz, DMSO-D$_6$): δ=11.435 (1.6); 8.491 (2.5); 8.485 (2.7); 8.373 (2.0); 8.367 (2.1); 8.314 (0.8); 8.297 (0.7); 8.291 (0.7); 8.276 (0.8); 8.270 (1.5); 8.264 (0.8); 8.249 (0.8); 8.243 (0.7); 7.648 (4.6); 6.982 (1.5); 3.937 (16.0); 3.330 (1166.4); 2.675 (2.0); 2.671 (2.7); 2.667 (2.0); 2.541 (6.1); 2.524 (7.5); 2.511 (151.5); 2.506 (301.2); 2.502 (394.8); 2.497 (286.7); 2.493 (139.0); 2.333 (1.9); 2.329 (2.6); 2.324 (1.9); 2.290 (0.3); 1.258 (0.4); 1.233 (0.7); 0.000 (8.1)

I-1-522:
HPLC-MS: log P=3.19; mass (m/z): 451.0 (M+H)$^+$; $^1$H-NMR (400.0 MHz, DMSO-D$_6$): δ=11.777 (3.2); 8.497 (3.4); 8.491 (3.6); 8.401 (3.0); 8.395 (3.0); 8.315 (1.5); 8.304 (1.1); 8.298 (1.0); 8.283 (1.1); 8.277 (1.9); 8.271 (1.0); 8.256 (1.1); 8.250 (0.9); 6.998 (3.4); 6.991 (3.3); 4.022 (16.0); 3.406 (0.4); 3.374 (0.7); 3.324 (1094.0); 3.281 (0.6); 2.680 (1.4); 2.675 (3.0); 2.671 (4.1); 2.666 (3.0); 2.662 (1.4); 2.541 (10.2); 2.524 (10.2); 2.519 (16.1); 2.511 (233.2); 2.506 (473.3); 2.502 (624.0); 2.497 (448.3); 2.493 (212.8); 2.338 (1.4); 2.333 (2.9); 2.328 (4.0); 2.324 (2.9); 2.320 (1.4); 2.289 (0.6); 1.298 (0.4); 1.259 (0.6); 1.235 (1.4); 0.008 (1.1); 0.000 (36.8); −0.008 (1.2)

I-1-523:
HPLC-MS: log P=3.18; mass (m/z): 399.0 (M+H)$^+$; $^1$H-NMR (400.0 MHz, DMSO-D$_6$): δ=10.849 (3.1); 8.478 (3.3); 8.472 (3.5); 8.326 (2.8); 8.320 (2.8); 8.284 (1.0); 8.278 (0.9); 8.263 (1.1); 8.256 (1.9); 8.250 (1.0); 8.235 (1.0); 8.229 (0.9); 6.950 (2.3); 6.943 (2.3); 5.757 (1.6); 3.327 (126.0); 2.675 (0.6); 2.671 (0.9); 2.667 (0.7); 2.510 (54.2); 2.506 (108.6); 2.502 (143.0); 2.498 (104.2); 2.493 (52.0); 2.400 (16.0); 2.333 (0.7); 2.329 (0.9); 2.324 (0.7); 2.251 (15.4); 2.233 (0.6); 1.351 (0.3); 1.259 (0.4); 1.234 (0.7); 0.008 (1.3); 0.000 (31.0); −0.008 (1.3)

I-1-524:
HPLC-MS: log P=2.30; mass (m/z): 384.9 (M+H)$^+$; $^1$H-NMR (400.0 MHz, DMSO-D$_6$): δ=11.223 (11.1); 8.483 (12.1); 8.477 (12.8); 8.339 (10.6); 8.332 (10.6); 8.316 (0.7); 8.288 (3.6); 8.282 (3.3); 8.267 (3.9); 8.261 (6.8); 8.255 (3.8); 8.240 (16.0); 8.232 (14.5); 7.776 (14.7); 7.768 (14.1); 6.978 (7.5); 6.972 (7.5); 5.757 (4.0); 3.328 (283.1); 3.304 (0.8); 2.676 (1.4); 2.671 (1.8); 2.542 (0.9); 2.507 (223.5); 2.502 (289.7); 2.498 (210.9); 2.440 (0.3); 2.333 (1.3); 2.329 (1.8); 1.235 (6.3); 0.853 (0.6); 0.147 (0.3); 0.008 (2.6); 0.000 (66.7); −0.008 (2.8)

I-1-525:
HPLC-MS: log P=2.84; mass (m/z): 389.0 (M+H)$^+$; $^1$H-NMR (400.0 MHz, DMSO-D$_6$): δ=11.735 (2.7); 8.495 (3.8); 8.489 (3.8); 8.384 (3.0); 8.378 (2.9); 8.315 (0.6); 8.304 (1.1); 8.298 (1.0); 8.283 (1.2); 8.277 (2.0); 8.271 (1.1); 8.256 (1.1); 8.250 (1.0); 7.984 (1.2); 7.840 (2.8); 7.696 (1.4); 6.970 (2.9); 6.964 (2.8); 3.388 (0.5); 3.328 (805.5); 2.675 (1.4); 2.671 (1.9); 2.666 (1.4); 2.541 (8.2); 2.510 (116.4); 2.506 (221.4); 2.502 (286.3); 2.497 (208.7); 2.493 (101.9); 2.333 (1.4); 2.329 (1.8); 2.324 (1.4); 2.290 (0.4); 2.269 (16.0); 1.234 (0.6); 0.000 (8.1)

I-1-526:
HPLC-MS: log P=2.42; mass (m/z): 353.0 (M+H)$^+$; $^1$H-NMR (400.0 MHz, DMSO-D$_6$): δ=10.387 (3.9); 8.481 (3.9); 8.475 (4.1); 8.338 (3.4); 8.331 (3.4); 8.316 (0.6); 8.291 (1.3); 8.285 (1.2); 8.270 (1.4); 8.264 (2.5); 8.258 (1.3); 8.243 (1.3); 8.237 (1.2); 8.183 (10.3); 6.941 (3.9); 6.934 (3.8); 4.230 (1.9); 4.211 (6.1); 4.193 (6.2); 4.175 (2.0); 3.323 (310.6); 2.680 (0.6); 2.675 (1.2); 2.671 (1.7); 2.666 (1.2); 2.662 (0.6); 2.541 (4.0); 2.524 (3.9); 2.519 (6.1); 2.511 (94.7); 2.506 (194.4); 2.502 (257.6); 2.497 (184.0); 2.493 (86.8); 2.337 (0.6); 2.333 (1.2); 2.328 (1.7); 2.324 (1.2); 2.319 (0.5); 1.453 (7.3); 1.435 (16.0); 1.417 (7.2); 1.234 (0.5); 0.008 (0.6); 0.000 (21.0); −0.009 (0.7)

I-1-527:
HPLC-MS: log P=2.93; mass (m/z): 367.0 (M+H)$^+$; $^1$H-NMR (400.0 MHz, DMSO-D$_6$): δ=11.354 (2.2); 8.490 (2.8); 8.484 (3.0); 8.361 (2.3); 8.355 (2.2); 8.297 (0.9); 8.290 (0.8); 8.276 (1.0); 8.270 (1.7); 8.263 (0.9); 8.249 (0.9); 8.242 (0.8); 6.975 (1.4); 6.971 (1.4); 4.236 (1.0); 4.218 (3.3); 4.200 (3.4); 4.182 (1.1); 3.376 (0.4); 3.331 (300.37); 2.676 (0.4); 2.671 (0.6); 2.667 (0.5); 2.542 (2.8); 2.525 (1.5); 2.511 (35.2); 2.507 (70.9); 2.502 (93.4); 2.498

(67.7); 2.493 (32.8); 2.334 (0.5); 2.329 (0.6); 2.325 (0.5); 2.177 (16.0); 1.339 (4.3); 1.321 (9.7); 1.303 (4.3); 0.000 (1.8)

I-1-528:
HPLC-MS: log P=3.11; mass (m/z): 412.0 (M+H)$^+$; $^1$H-NMR (400.0 MHz, DMSO-D$_6$): δ=12.011 (3.1); 8.501 (2.9); 8.495 (3.0); 8.416 (2.6); 8.409 (2.6); 8.315 (0.4); 8.311 (0.9); 8.305 (0.8); 8.290 (0.9); 8.284 (1.6); 8.278 (0.9); 8.263 (0.9); 8.257 (0.8); 7.007 (3.4); 7.001 (3.4); 4.901 (0.4); 4.885 (1.1); 4.868 (1.6); 4.852 (1.2); 4.835 (0.4); 3.324 (142.5); 2.995 (2.2); 2.676 (0.5); 2.671 (0.7); 2.667 (0.5); 2.541 (90.6); 2.524 (1.6); 2.520 (2.4); 2.511 (38.9); 2.507 (80.6); 2.502 (107.3); 2.497 (77.0); 2.493 (36.5); 2.368 (0.3); 2.333 (0.5); 2.329 (0.7); 2.324 (0.5); 1.478 (16.0); 1.462 (16.0); 1.235 (0.4); 0.000 (8.1)

I-1-529:
HPLC-MS: log P=2.23; mass (m/z): 339.0 (M+H)$^+$; $^1$H-NMR (400.0 MHz, DMSO-D$_6$): δ=11.413 (1.4); 8.492 (2.5); 8.486 (2.5); 8.374 (1.9); 8.368 (1.9); 8.300 (0.8); 8.294 (0.7); 8.279 (0.8); 8.273 (1.4); 8.267 (0.8); 8.252 (0.8); 8.246 (0.7); 7.658 (4.7); 6.985 (1.2); 6.980 (1.1); 3.939 (16.0); 3.322 (85.9); 2.675 (0.5); 2.671 (0.6); 2.666 (0.5); 2.541 (2.1); 2.524 (1.8); 2.511 (38.7); 2.506 (76.8); 2.502 (100.6); 2.497 (71.7); 2.492 (33.8); 2.333 (0.5); 2.328 (0.6); 2.324 (0.5); 0.008 (0.3); 0.000 (8.8)

I-1-530:
HPLC-MS: log P=2.50; mass (m/z): 384.0 (M+H)$^+$; $^1$H-NMR (400.0 MHz, DMSO-D$_6$): δ=11.918 (0.7); 11.103 (2.4); 8.500 (0.7); 8.490 (2.4); 8.484 (2.5); 8.414 (0.6); 8.408 (0.6); 8.361 (2.0); 8.354 (2.0); 8.315 (0.8); 8.300 (0.8); 8.294 (0.8); 8.284 (0.5); 8.279 (1.0); 8.273 (1.5); 8.267 (0.8); 8.252 (0.8); 8.246 (0.7); 7.001 (0.7); 6.995 (0.7); 6.948 (1.8); 6.941 (1.8); 5.756 (0.8); 4.242 (16.0); 4.075 (4.0); 3.322 (231.2); 2.675 (1.4); 2.670 (2.0); 2.666 (1.5); 2.541 (3.6); 2.524 (8.8); 2.510 (108.9); 2.506 (219.9); 2.501 (292.2); 2.497 (214.6); 2.493 (105.6); 2.333 (1.4); 2.328 (1.9); 2.324 (1.4); 1.233 (0.5); 0.146 (0.7); 0.008 (6.7); 0.000 (170.1); −0.009 (6.2); −0.150 (0.7)

I-1-531:
HPLC-MS: log P=3.42; mass (m/z): 381.1 (M+H)$^+$; $^1$H-NMR (400.0 MHz, DMSO-D$_6$): δ=11.334 (1.3); 8.489 (2.6); 8.483 (2.7); 8.365 (2.1); 8.359 (2.1); 8.315 (0.6); 8.297 (0.8); 8.291 (0.7); 8.276 (0.9); 8.270 (1.5); 8.263 (0.8); 8.249 (0.8); 8.242 (0.7); 6.974 (1.3); 3.882 (16.0); 3.323 (324.1); 2.675 (1.4); 2.670 (2.0); 2.666 (1.5); 2.541 (4.7); 2.524 (7.6); 2.519 (7.7); 2.510 (108.7); 2.506 (224.1); 2.501 (296.3); 2.497 (215.9); 2.493 (105.2); 2.337 (0.6); 2.333 (1.4); 2.328 (1.9); 2.324 (1.4); 1.656 (1.3); 1.637 (2.4); 1.619 (2.4); 1.600 (1.3); 1.234 (0.6); 0.947 (3.8); 0.929 (7.8); 0.911 (3.529 (7.8); 0.008 (0.8); 0.000 (26.4); −0.009 (0.9)

I-1-532:
HPLC-MS: log P=3.09; mass (m/z): 381.1 (M+H)$^+$; $^1$H-NMR (400.0 MHz, DMSO-D$_6$): δ=10.274 (2.5); 8.479 (2.4); 8.473 (2.5); 8.332 (2.1); 8.326 (2.1); 8.316 (0.6); 8.289 (0.8); 8.283 (0.7); 8.268 (0.8); 8.262 (1.4); 8.255 (0.8); 8.241 (0.8); 8.234 (0.7); 6.929 (2.5); 6.923 (2.5); 3.897 (16.0); 3.324 (194.2); 2.715 (1.7); 2.696 (2.9); 2.677 (2.5); 2.671 (1.6); 2.666 (1.1); 2.541 (0.8); 2.524 (3.6); 2.511 (79.5); 2.506 (158.1); 2.502 (205.3); 2.497 (146.8); 2.493 (70.2); 2.333 (1.0); 2.328 (1.3); 2.324 (1.0); 1.617 (1.1); 1.598 (2.0); 1.580 (2.0); 1.561 (1.1); 0.946 (3.6); 0.928 (7.4); 0.910 (3.2); 0.146 (0.6); 0.008 (5.3); 0.000 (136.9); −0.008 (4.9); −0.150 (0.6)

I-1-533:
HPLC-MS: log P=2.85; mass (m/z): 367.0 (M+H)$^+$; $^1$H-NMR (400.0 MHz, DMSO-D$_6$): δ=10.389 (5.3); 8.481 (5.3); 8.475 (5.5); 8.341 (4.7); 8.335 (4.7); 8.318 (0.4); 8.292 (1.6); 8.286 (1.4); 8.271 (1.7); 8.265 (2.9); 8.259 (1.5); 8.244 (1.5); 8.238 (1.4); 8.180 (12.1); 6.942 (4.7); 6.936 (4.7); 5.758 (0.4); 4.146 (4.1); 4.128 (8.1); 4.111 (4.1); 3.328 (43.9); 2.672 (0.4); 2.508 (47.6); 2.503 (61.7); 2.499 (44.8); 2.330 (0.4); 1.905 (0.5); 1.887 (2.5); 1.869 (5.0); 1.851 (5.1); 1.833 (2.6); 1.815 (0.6); 0.886 (0.3); 0.874 (7.8); 0.856 (16.0); 0.837 (7.2); 0.008 (0.6); 0.000 (13.7)

I-1-534:
HPLC-MS: log P=2.98; mass (m/z): 367.0 (M+H)$^+$; $^1$H-NMR (400.0 MHz, DMSO-D$_6$): δ=11.326 (1.9); 8.490 (2.5); 8.484 (2.6); 8.365 (1.9); 8.358 (1.8); 8.316 (0.5); 8.298 (0.9); 8.292 (0.8); 8.277 (0.9); 8.271 (1.6); 8.264 (0.8); 8.250 (0.9); 8.243 (0.8); 6.975 (1.1); 6.970 (1.1); 3.883 (16.0); 3.322 (194.5); 2.680 (0.4); 2.675 (0.9); 2.671 (1.2); 2.666 (0.9); 2.661 (0.4); 2.597 (1.1); 2.578 (3.6); 2.559 (3.7); 2.541 (5.8); 2.524 (2.8); 2.519 (4.6); 2.511 (69.3); 2.506 (141.5); 2.502 (186.1); 2.497 (131.7); 2.492 (61.0); 2.338 (0.4); 2.333 (0.9); 2.328 (1.2); 2.324 (0.9); 2.319 (0.4); 1.235 (0.5); 1.209 (4.4); 1.190 (9.6); 1.172 (4.2); 0.008 (0.5); 0.000 (17.2); −0.009 (0.5)

I-1-535:
HPLC-MS: log P=3.19; mass (m/z): 448.1 (M+H)$^+$; $^1$H-NMR (400.0 MHz, DMSO-D$_6$): δ=12.285 (3.4); 8.505 (3.6); 8.499 (3.9); 8.435 (3.4); 8.428 (3.4); 8.315 (1.6); 8.309 (1.0); 8.294 (1.2); 8.288 (2.0); 8.282 (1.1); 8.267 (1.1); 8.261 (1.1); 7.011 (3.1); 7.005 (3.1); 4.137 (16.0); 3.329 (1158.1); 2.995 (1.5); 2.676 (1.7); 2.671 (2.3); 2.667 (1.6); 2.541 (57.7); 2.524 (6.6); 2.511 (130.2); 2.507 (257.5); 2.502 (336.2); 2.497 (239.4); 2.493 (112.6); 2.333 (1.6); 2.329 (2.2); 2.324 (1.6); 2.290 (0.3); 1.298 (0.3); 1.259 (0.4); 1.235 (1.4); 0.000 (6.8)

I-1-536:
HPLC-MS: log P=2.76; mass (m/z): 398.1 (M+H)$^+$; $^1$H-NMR (400.0 MHz, DMSO-D$_6$): δ=12.250 (1.6); 8.505 (3.6); 8.499 (3.9); 8.432 (3.3); 8.425 (3.4); 8.315 (1.9); 8.310 (1.1); 8.295 (1.1); 8.288 (2.0); 8.282 (1.1); 8.267 (1.1); 8.261 (1.0); 7.010 (2.8); 7.003 (2.9); 4.124 (16.0); 3.381 (0.9); 3.329 (1809.3); 3.271 (0.9); 3.257 (0.7); 3.216 (0.4); 2.676 (2.7); 2.671 (3.7); 2.667 (2.8); 2.541 (10.1); 2.524 (9.7); 2.511 (207.6); 2.507 (421.9); 2.502 (559.4); 2.497 (405.9); 2.493 (196.3); 2.333 (2.7); 2.329 (3.7); 2.324 (2.7); 2.290 (0.5); 1.298 (0.5); 1.259 (0.7); 1.235 (1.3); 0.000 (14.8); −0.008 (0.4)

I-1-537:
HPLC-MS: log P=2.45; mass (m/z): 349.0 (M+H)$^+$; $^1$H-NMR (400.0 MHz, DMSO-D$_6$): δ=11.856 (7.5); 8.494 (15.3); 8.488 (16.0); 8.384 (13.3); 8.383 (13.2); 8.378 (13.4); 8.316 (1.1); 8.303 (5.2); 8.297 (4.7); 8.282 (5.5); 8.276 (9.6); 8.270 (5.0); 8.255 (5.2); 8.249 (4.7); 6.995 (8.0); 6.989 (7.8); 5.757 (3.7); 3.357 (0.6); 3.322 (480.7); 2.680 (3.2); 2.675 (4.6); 2.671 (6.6); 2.666 (6.7); 2.661 (4.2); 2.646 (5.5); 2.634 (3.4); 2.626 (3.2); 2.613 (1.7); 2.593 (0.5); 2.58276 (0.5); 2.576 (0.6); 2.541 (2.5); 2.524 (16.2); 2.519 (25.2); 2.511 (297.1); 2.506 (593.5); 2.502 (785.5); 2.497 (567.9); 2.492 (269.0); 2.338 (1.8); 2.333 (3.8); 2.328 (5.2); 2.324 (3.7); 2.319 (1.7); 1.351 (0.6); 1.335 (1.8); 1.298 (1.3); 1.259 (2.0); 1.249 (2.9); 1.244 (2.9); 1.231 (8.5); 1.224 (14.4); 1.218 (8.7); 1.210 (7.4); 1.203 (14.7); 1.196 (12.0); 1.189 (13.2); 1.183 (15.0); 1.177 (15.0); 1.171 (8.9); 1.157 (1.9); 1.147 (1.1); 0.146 (0.9); 0.008 (7.5); 0.000 (225.1); −0.009 (7.0); −0.150 (0.9)

I-1-538:
HPLC-MS: log P=2.03; mass (m/z): 323.0 (M+H)$^+$; $^1$H-NMR (400.0 MHz, DMSO-D$_6$): δ=11.162 (2.5); 8.489 (3.1); 8.483 (3.3); 8.367 (2.7); 8.361 (2.7); 8.315 (0.4); 8.299 (1.0); 8.293 (0.9); 8.278 (1.1); 8.272 (1.9); 8.266

(1.0); 8.251 (1.0); 8.245 (0.9); 7.620 (3.3); 7.609 (3.3); 6.965 (2.7); 6.958 (2.7); 3.968 (16.0); 3.327 (374.8); 3.303 (0.7); 2.676 (0.8); 2.671 (1.1); 2.667 (0.8); 2.541 (2.3); 2.524 (3.0); 2.511 (61.7); 2.507 (122.4); 2.502 (159.4); 2.498 (113.9); 2.493 (54.1); 2.333 (0.7); 2.329 (1.0); 2.324 (0.7); 2.320 (0.3); 0.008 (0.4); 0.000 (12.8); −0.009 (0.4)

I-1-539:
HPLC-MS: log P=3.28; mass (m/z): 473.0 (M+H)$^+$; $^1$H-NMR (400.0 MHz, DMSO-D$_6$): δ=11.439 (2.3); 8.491 (2.7); 8.485 (3.1); 8.363 (2.1); 8.357 (2.3); 8.314 (0.8); 8.296 (0.8); 8.290 (0.8); 8.275 (0.9); 8.268 (1.6); 8.263 (0.9); 8.248 (0.9); 8.241 (0.8); 7.615 (6.2); 6.975 (1.9); 6.969 (1.9); 4.085 (3.4); 4.066 (3.5); 3.420 (0.4); 3.330 (1398.6); 3.226 (0.4); 2.676 (2.3); 2.671 (3.1); 2.667 (2.3); 2.541 (11.4); 2.524 (7.5); 2.511 (168.6); 2.507 (341.8); 2.502 (452.0); 2.498 (328.4); 2.494 (161.0); 2.333 (2.1); 2.329 (2.9); 2.325 (2.1); 2.290 (0.4); 2.090 (0.4); 2.072 (0.8); 2.055 (1.0); 2.038 (0.8); 2.021 (0.4); 1.298 (0.3); 1.258 (0.4); 1.235 (1.4); 0.815 (16.0); 0.799 (15.5); 0.000 (8.5)

I-1-540:
HPLC-MS: log P=2.20; mass (m/z): 431.0 (M+H)$^+$; $^1$H-NMR (400.0 MHz, DMSO-D$_6$): δ=11.393 (1.2); 8.493 (2.8); 8.486 (3.0); 8.372 (2.1); 8.365 (2.2); 8.315 (1.3); 8.297 (0.9); 8.291 (0.9); 8.276 (0.9); 8.270 (1.6); 8.264 (0.9); 8.249 (0.9); 8.243 (0.8); 7.599 (5.3); 6.990 (1.5); 6.984 (1.5); 3.939 (16.0); 3.323 (791.9); 2.675 (3.1); 2.671 (4.2); 2.666 (3.2); 2.541 (8.9); 2.524 (11.2); 2.511 (241.7); 2.506 (488.2); 2.502 (644.7); 2.497 (467.3); 2.493 (229.9); 2.333 (3.1); 2.328 (4.1); 2.324 (3.0); 2.288 (0.6); 1.298 (0.4); 1.259 (0.5); 1.233 (1.2); 0.008 (1.6); 0.000 (46.7); −0.009 (1.6)

I-1-541:
HPLC-MS: log P=2.93; mass (m/z): 459.0 (M+H)$^+$; $^1$H-NMR (400.0 MHz, DMSO-D$_6$): δ=11.431 (3.6); 8.492 (4.6); 8.486 (4.9); 8.365 (3.5); 8.359 (3.5); 8.315 (0.4); 8.297 (1.4); 8.291 (1.3); 8.276 (1.5); 8.270 (2.6); 8.264 (1.4); 8.249 (1.4); 8.243 (1.3); 7.611 (9.7); 6.982 (2.8); 6.976 (2.8); 4.218 (2.9); 4.200 (5.7); 4.183 (3.0); 3.359 (0.4); 3.324 (329.0); 2.995 (0.3); 2.675 (1.0); 2.671 (1.4); 2.666 (1.1); 2.662 (0.5); 2.541 (11.2); 2.524 (3.3); 2.511 (79.7); 2.506 (163.6); 2.502 (218.0); 2.497 (159.9); 2.493 (78.7); 2.337 (0.5); 2.333 (1.0); 2.328 (1.4); 2.324 (1.0); 1.785 (0.5); 1.767 (2.2); 1.748 (4.3); 1.731 (4.4); 1.713 (2.3); 1.694 (0.5); 1.235 (0.8); 0.820 (7.5); 0.802 (16.0); 0.783 (7.0); 0.000 (10.5); −0.008 (0.4)

I-1-542:
HPLC-MS: log P=2.22; mass (m/z): 307.0 (M+H)$^+$; $^1$H-NMR (400.0 MHz, DMSO-D$_6$): δ=11.909 (7.2); 8.500 (14.3); 8.494 (14.6); 8.388 (12.3); 8.387 (12.9); 8.381 (12.4); 8.380 (12.2); 8.310 (4.6); 8.303 (4.2); 8.289 (5.1); 8.282 (8.6); 8.276 (4.5); 8.261 (4.7); 8.255 (4.2); 6.963 (16.0); 6.956 (15.7); 5.757 (3.1); 5.336 (0.4); 5.325 (0.6); 5.313 (0.3); 3.427 (0.3); 3.396 (0.5); 3.390 (0.6); 3.330 (776.8); 2.710 (0.6); 2.680 (0.9); 2.676 (1.8); 2.671 (2.4); 2.667 (1.7); 2.662 (0.8); 2.547 (94.3); 2.524 (8.4); 2.511 (137.0); 2.507 (265.0); 2.502 (344.8); 2.497 (250.9); 2.493 (121.2); 2.407 (0.5); 2.381 (0.5); 2.338 (0.8); 2.333 (1.6); 2.329 (2.2); 2.324 (1.6); 2.320 (0.7); 2.027 (0.6); 2.009 (1.1); 1.989 (1.1); 1.973 (0.5); 1.454 (0.4); 1.336 (2.3); 1.298 (1.0); 1.258 (2.2); 1.249 (4.7); 1.235 (5.0); 1.187 (0.3); 1.153 (0.3); 1.148 (0.4); 0.870 (0.5); 0.854 (1.6); 0.836 (0.6); 0.008 (1.1); 0.000 (27.2); −0.009 (1.0)

I-1-543:
HPLC-MS: log P=2.00; mass (m/z): 306.1 (M+H)$^+$; $^1$H-NMR (400.0 MHz, DMSO-D$_6$): δ=11.494 (2.0); 8.684 (4.8); 8.496 (2.5); 8.490 (2.7); 8.357 (2.3); 8.351 (2.4); 8.305 (0.7); 8.299 (0.7); 8.284 (0.8); 8.278 (1.4); 8.272 (0.8); 8.257 (0.8); 8.251 (0.7); 6.941 (2.6); 6.935 (2.6); 3.331 (62.7); 3.329 (60.7); 2.672 (0.3); 2.507 (42.4); 2.503 (54.1); 2.498 (39.8); 2.329 (0.3); 2.281 (16.0); 0.000 (6.9); −0.008 (0.4)

I-1-544:
HPLC-MS: log P=1.29; mass (m/z): 306.1 (M+H)$^+$; $^1$H-NMR (400.0 MHz, CD$_3$CN): δ=9.678 (0.5); 8.326 (3.3); 8.286 (2.0); 8.280 (2.0); 8.229 (1.8); 8.222 (1.8); 7.725 (0.7); 7.719 (0.7); 7.705 (0.8); 7.699 (1.4); 7.692 (0.7); 7.678 (0.7); 7.672 (0.7); 6.996 (2.4); 6.989 (2.3); 3.973 (16.0); 2.135 (21.1); 2.107 (0.4); 1.964 (4.1); 1.958 (6.2); 1.952 (26.9); 1.946 (46.9); 1.940 (60.9); 1.934 (41.5); 1.927 (21.2); 1.768 (0.4); 0.008 (1.1); 0.000 (31.0); −0.009 (1.0)

I-1-545:
HPLC-MS: log P=1.92; mass (m/z): 337.0 (M+H)$^+$; $^1$H-NMR (400.0 MHz, DMSO-D$_6$): δ=11.690 (6.9); 9.260 (15.6); 9.147 (16.0); 8.494 (6.7); 8.488 (7.1); 8.403 (6.4); 8.397 (6.5); 8.316 (0.9); 8.299 (2.1); 8.292 (1.9); 8.278 (2.2); 8.271 (3.9); 8.265 (2.1); 8.250 (2.1); 8.244 (2.0); 6.995 (7.9); 6.988 (7.9); 5.756 (1.4); 3.324 (317.6); 2.675 (1.7); 2.671 (2.4); 2.666 (1.8); 2.565 (0.8); 2.541 (1.2); 2.524 (5.4); 2.506 (284.6); 2.502 (372.5); 2.497 (273.9); 2.333 (1.8); 2.329 (2.4); 2.324 (1.8); 1.258 (0.4); 1.234 (0.6); 0.146 (0.6); 0.008 (5.0); 0.000 (142.6); −0.008 (5.5); −0.150 (0.6)

I-1-546:
HPLC-MS: log P=2.15; mass (m/z): 323.1 (M+H)$^+$; $^1$H-NMR (400.0 MHz, DMSO-D$_6$): δ=11.269 (1.9); 8.496 (2.2); 8.490 (2.3); 8.377 (1.9); 8.370 (1.9); 8.304 (0.7); 8.298 (0.7); 8.283 (0.8); 8.277 (1.4); 8.271 (0.7); 8.256 (0.8); 8.250 (0.7); 6.996 (1.8); 6.990 (1.8); 3.403 (0.8); 3.322 (72.1); 3.033 (0.8); 2.910 (1.1); 2.903 (16.0); 2.891 (1.0); 2.732 (0.7); 2.675 (0.4); 2.671 (0.5); 2.666 (0.4); 2.524 (1.6); 2.511 (31.0); 2.506 (60.5); 2.502 (78.5); 2.497 (56.7); 2.493 (27.5); 2.333 (0.4); 2.329 (0.5); 2.324 (0.4); 0.146 (0.4); 0.008 (5.3); 0.000 (103.4); −0.009 (4.1); −0.150 (0.5)

I-1-547:
HPLC-MS: log P=1.37; mass (m/z): 306.1 (M+H)$^+$; $^1$H-NMR (400.0 MHz, DMSO-D$_6$): δ=12.237 (1.0); 8.385 (1.0); 8.379 (1.0); 8.198 (1.5); 8.179 (1.5); 8.167 (0.7); 8.160 (1.2); 8.153 (1.0); 8.146 (0.4); 8.140 (0.3); 6.961 (1.5); 6.942 (1.4); 6.851 (1.1); 6.844 (1.1); 3.313 (1.4); 3.157 (13.5); 3.096 (0.3); 2.725 (1.6); 2.485 (6.8); 2.481 (8.5); 2.477 (6.4); 1.995 (5.6); 0.961 (0.5); −0.024 (0.9)

I-1-548:
HPLC-MS: log P=2.10; mass (m/z): 321.1 (M+H)$^+$; $^1$H-NMR [DMSO-D$_6$] 1.76-1.82 (m, 2H), 1.98 (s, 3H), 2.31-2.34 (m, 2H), 3.94-3.97 (m, 2H), 6.88 (d, 1H), 8.21-8.26 (m, 2H), 8.46 (d, 1H), 10.15 (s, 1H).

I-1-549:
HPLC-MS: log P=2.42; mass (m/z): 411.1 (M+H)$^+$; $^1$H-NMR (400.0 MHz, DMSO-D$_6$): δ=11.425 (0.5); 11.359 (11.9); 8.586 (0.6); 8.580 (0.8); 8.567 (8.5); 8.563 (9.0); 8.555 (9.0); 8.551 (8.7); 8.364 (8.6); 8.360 (8.4); 8.344 (9.2); 8.340 (8.5); 8.218 (14.5); 8.212 (14.1); 7.836 (6.8); 7.817 (8.2); 7.783 (2.4); 7.766 (6.9); 7.747 (6.3); 7.711 (5.6); 7.692 (16.0); 7.673 (7.7); 7.477 (8.9); 7.465 (8.7); 7.457 (8.4); 7.445 (8.3); 6.949 (0.6); 6.943 (0.7); 6.921 (15.7); 6.915 (15.3); 3.327 (570.7); 3.285 (0.4); 2.995 (0.4); 2.711 (0.4); 2.679 (0.9); 2.675 (1.7); 2.671 (2.3); 2.666 (1.7); 2.662 (0.8); 2.541 (107.5); 2.524 (7.5); 2.510 (143.4); 2.506 (276.2); 2.502 (354.1); 2.497 (253.6); 2.493 (121.1); 2.367 (0.5); 2.333 (1.7); 2.328 (2.3); 2.324 (1.6); 2.319 (0.8); 2.074 (2.4); 1.258 (0.4); 1.235 (0.8); 0.008 (1.8); 0.000 (44.9); −0.009 (1.5)

I-1-550:

HPLC-MS: log P=2.34; mass (m/z): 414.1 (M+H)$^+$; $^1$H-NMR (400.0 MHz, DMSO-D$_6$): δ=11.366 (11.2); 8.920 (6.4); 8.918 (6.4); 8.908 (6.4); 8.572 (8.9); 8.568 (9.4); 8.560 (9.3); 8.556 (9.2); 8.369 (15.1); 8.365 (10.2); 8.349 (16.0); 8.345 (10.5); 8.244 (14.2); 8.238 (14.1); 7.804 (4.4); 7.802 (4.5); 7.790 (4.5); 7.783 (4.2); 7.782 (4.1); 7.771 (4.0); 7.770 (3.9); 7.482 (9.8); 7.471 (9.3); 7.462 (9.1); 7.451 (9.1); 6.929 (15.9); 6.922 (15.7); 3.453 (0.3); 3.427 (0.4); 3.420 (0.5); 3.396 (0.8); 3.335 (1022.8); 3.297 (0.8); 2.680 (0.7); 2.676 (1.5); 2.671 (2.0); 2.667 (1.5); 2.662 (0.7); 2.542 (85.1); 2.525 (6.4); 2.520 (9.9); 2.511 (117.1); 2.507 (234.5); 2.502 (307.5); 2.498 (219.7); 2.493 (103.6); 2.338 (0.7); 2.334 (1.4); 2.329 (2.0); 2.325 (1.4); 2.320 (0.6); 2.074 (1.3); 1.298 (0.3); 1.258 (0.5); 1.235 (0.8); 0.008 (0.3); 0.000 (10.8); −0.009 (0.3)

I-1-551:

HPLC-MS: log P=2.13; mass (m/z): 379.0 (M+H)$^+$; $^1$H-NMR (400.0 MHz, DMSO-D$_6$): δ=11.650 (0.4); 11.583 (10.1); 8.603 (0.5); 8.597 (0.5); 8.570 (9.0); 8.566 (9.5); 8.559 (9.5); 8.555 (9.3); 8.368 (9.3); 8.364 (9.2); 8.348 (10.1); 8.344 (9.2); 8.237 (14.4); 8.230 (14.2); 7.776 (0.4); 7.609 (1.5); 7.592 (3.4); 7.587 (2.9); 7.575 (2.3); 7.571 (6.1); 7.566 (2.3); 7.554 (3.0); 7.549 (3.6); 7.533 (1.6); 7.484 (10.1); 7.473 (9.6); 7.464 (9.4); 7.453 (9.5); 7.250 (1.7); 7.247 (2.0); 7.240 (11.0); 7.220 (14.6); 7.200 (8.9); 7.192 (1.6); 6.957 (0.5); 6.950 (0.6); 6.931 (16.0); 6.924 (15.8); 3.399 (0.6); 3.379 (1.1); 3.334 (980.8); 3.279 (0.3); 2.712 (0.5); 2.680 (0.7); 2.676 (1.4); 2.671 (1.9); 2.667 (1.4); 2.662 (0.6); 2.541 (152.4); 2.525 (6.2); 2.520 (9.8); 2.511 (109.8); 2.507 (218.6); 2.502 (285.8); 2.498 (203.4); 2.493 (95.2); 2.367 (0.5); 2.338 (0.6); 2.333 (1.4); 2.329 (1.8); 2.324 (1.3); 2.320 (0.6); 2.074 (1.8); 1.258 (0.4); 1.235 (0.6); 0.008 (0.4); 0.000 (11.8); −0.009 (0.4)

I-1-552:

HPLC-MS: log P=2.31; mass (m/z): 423.0 (M+H)$^+$; $^1$H-NMR (400.0 MHz, DMSO-D$_6$): δ=11.326 (0.5); 11.260 (12.8); 8.586 (0.6); 8.579 (0.8); 8.566 (8.7); 8.562 (9.5); 8.555 (9.2); 8.551 (9.3); 8.362 (8.7); 8.359 (8.9); 8.342 (9.3); 8.339 (9.0); 8.215 (14.7); 8.208 (14.7); 7.773 (0.4); 7.752 (0.4); 7.704 (8.3); 7.701 (8.6); 7.684 (9.7); 7.682 (9.7); 7.548 (5.6); 7.544 (6.7); 7.530 (9.8); 7.525 (10.1); 7.489 (4.9); 7.486 (5.3); 7.476 (10.4); 7.471 (10.5); 7.468 (11.0); 7.465 (11.2); 7.456 (9.5); 7.452 (6.2); 7.449 (5.7); 7.445 (9.2); 7.433 (0.7); 7.422 (6.1); 7.418 (6.2); 7.403 (7.3); 7.398 (7.2); 7.384 (3.4); 7.379 (3.1); 6.969 (0.6); 6.962 (0.6); 6.940 (16.0); 6.934 (15.9); 3.330 (609.4); 2.995 (0.9); 2.711 (1.4); 2.675 (1.3); 2.671 (1.8); 2.666 (1.3); 2.662 (0.7); 2.586 (0.3); 2.541 (354.6); 2.524 (6.4); 2.511 (101.4); 2.506 (202.1); 2.502 (265.6); 2.497 (194.3); 2.493 (95.7); 2.367 (1.4); 2.337 (0.6); 2.333 (1.3); 2.328 (1.7); 2.324 (1.3); 2.320 (0.6); 2.074 (8.2); 1.258 (0.4); 1.235 (0.9); 0.008 (0.8); 0.000 (23.2); −0.009 (0.8)

I-1-553:

HPLC-MS: log P=2.23; mass (m/z): 379.0 (M+H)$^+$; $^1$H-NMR (400.0 MHz, DMSO-D$_6$): δ=11.344 (0.5); 11.278 (13.1); 8.588 (0.6); 8.581 (0.7); 8.567 (8.9); 8.563 (9.5); 8.555 (9.3); 8.551 (9.3); 8.363 (9.0); 8.359 (9.0); 8.343 (9.7); 8.339 (9.1); 8.216 (15.3); 8.210 (15.1); 7.775 (0.4); 7.754 (0.4); 7.579 (6.9); 7.575 (7.5); 7.561 (9.47556 10.3); 7.556 (10.3); 7.550 (6.5); 7.533 (11.5); 7.530 (11.9); 7.510 (4.9); 7.506 (5.3); 7.492 (8.8); 7.488 (7.7); 7.477 (10.2); 7.472 (5.9); 7.466 (10.9); 7.457 (9.6); 7.445 (15.3); 7.430 (8.7); 7.427 (8.4); 7.412 (3.2); 7.409 (3.0); 6.972 (0.5); 6.965 (0.6); 6.943 (16.0); 6.937 (15.7); 3.438 (0.3); 3.421 (0.4); 3.413 (0.5); 3.333 (1101.5); 3.280 (0.4); 2.995 (0.9); 2.711 (2.1); 2.675 (1.8); 2.671 (2.4); 2.666 (1.7); 2.662 (0.9); 2.541 (484.3); 2.524 (8.6); 2.511 (141.2); 2.506 (277.7); 2.502 (362.3); 2.497 (261.9); 2.493 (126.5); 2.367 (2.1); 2.337 (0.8); 2.333 (1.7); 2.329 (2.3); 2.324 (1.7); 2.320 (0.8); 2.074 (2.5); 1.258 (0.4); 1.235 (0.9); 0.008 (0.5); 0.000 (14.9); −0.008 (0.5)

I-1-554:

HPLC-MS: log P=2.42; mass (m/z): 471.0 (M+H)$^+$; $^1$H-NMR (400.0 MHz, DMSO-D$_6$): δ=11.199 (7.6); 8.585 (0.3); 8.579 (0.4); 8.567 (5.4); 8.563 (5.8); 8.555 (5.7); 8.551 (5.6); 8.363 (5.4); 8.359 (5.4); 8.343 (5.8); 8.339 (5.4); 8.215 (9.0); 8.208 (8.9); 7.923 (6.0); 7.903 (7.0); 7.501 (0.9); 7.499 (0.9); 7.481 (5.6); 7.479 (6.3); 7.475 (12.3); 7.465 (16.0); 7.455 (6.9); 7.444 (5.5); 7.243 (0.4); 7.231 (2.9); 7.223 (2.8); 7.217 (2.8); 7.212 (3.2); 7.209 (3.0); 7.203 (2.5); 7.197 (2.7); 7.189 (2.3); 6.938 (9.8); 6.932 (9.6); 3.328 (489.1); 2.680 (0.6); 2.675 (1.2); 2.671 (1.6); 2.666 (1.2); 2.662 (0.6); 2.541 (65.9); 2.524 (5.0); 2.519 (7.7); 2.511 (94.1); 2.506 (189.5); 2.501 (249.3); 2.497 (178.3); 2.492 (84.3); 2.337 (0.6); 2.333 (1.2); 2.328 (1.6); 2.324 (1.2); 2.319 (0.5); 2.074 (2.3); 1.258 (0.3); 1.235 (0.6); 0.008 (1.1); 0.000 (36.1); −0.009 (1.1)

I-1-555:

HPLC-MS: log P=3.37; mass (m/z): 384.1 (M+H)$^+$; $^1$H-NMR (400.0 MHz, DMSO-D$_6$): δ=11.405 (6.5); 11.339 (0.5); 8.234 (3.6); 8.227 (6.7); 8.221 (3.6); 8.203 (0.6); 8.197 (0.6); 7.842 (3.9); 7.822 (4.9); 7.789 (1.4); 7.771 (3.9); 7.752 (5.2); 7.730 (4.1); 7.718 (3.7); 7.714 (3.7); 7.709 (3.1); 7.697 (8.6); 7.678 (4.4); 7.616 (1.8); 7.612 (1.9); 7.596 (4.0); 7.579 (2.3); 7.575 (2.1); 7.521 (0.4); 7.518 (0.4); 7.502 (0.5); 7.498 (0.4); 7.401 (2.5); 7.398 (2.5); 7.381 (4.2); 7.378 (4.3); 7.361 (1.9); 7.357 (1.9); 7.282 (0.6); 6.963 (7.5); 6.957 (7.5); 6.927 (0.6); 6.921 (0.6); 5.757 (16.0); 3.813 (0.7); 3.795 (0.7); 3.657 (0.8); 3.325 (48.1); 2.676 (0.4); 2.671 (0.6); 2.667 (0.5); 2.507 (68.9); 2.502 (87.7); 2.498 (64.8); 2.333 (0.4); 2.329 (0.6); 2.324 (0.4); 1.336 (0.6); 1.259 (0.4); 1.250 (0.7); 1.234 (1.0); 1.216 (1.5); 1.199 (0.7); 0.008 (1.7); 0.000 (31.2); −0.008 (1.5)

I-1-556:

HPLC-MS: log P=3.12; mass (m/z): 352.1 (M+H)$^+$; $^1$H-NMR (400.0 MHz, DMSO-D$_6$): δ=11.624 (11.3); 11.560 (1.0); 8.315 (0.4); 8.252 (6.4); 8.245 (11.9); 8.239 (6.8); 8.210 (1.2); 8.203 (1.1); 7.752 (3.3); 7.749 (3.4); 7.731 (6.9); 7.714 (4.0); 7.710 (3.8); 7.625 (3.2); 7.621 (3.5); 7.615 (2.5); 7.605 (7.6); 7.601 (6.8); 7.594 (5.0); 7.588 (5.6); 7.584 (5.7); 7.577 (7.2); 7.560 (3.7); 7.556 (3.9); 7.540 (1.7); 7.532 (1.0); 7.511 (1.0); 7.405 (4.5); 7.402 (4.4); 7.385 (7.8); 7.382 (7.5); 7.364 (3.7); 7.361 (3.5); 7.307 (0.7); 7.296 (0.3); 7.286 (1.0); 7.265 (0.7); 7.245 (9.9); 7.224 (16.0); 7.204 (8.9); 6.968 (12.9); 6.961 (13.0); 6.933 (1.2); 6.927 (1.1); 5.756 (1.5); 3.819 (0.4); 3.802 (1.2); 3.784 (1.3); 3.766 (0.4); 3.646 (1.3); 3.323 (181.9); 2.671 (1.8); 2.667 (1.4); 2.506 (221.1); 2.502 (274.8); 2.498 (211.3); 2.329 (1.8); 2.324 (1.4); 1.336 (1.1); 1.298 (0.6); 1.259 (0.8); 1.250 (1.2); 1.235 (0.5); 1.223 (1.4); 1.205 (2.8); 1.188 (1.5); 0.146 (0.4); 0.000 (78.6); −0.150 (0.4)

I-1-557:

HPLC-MS: log P=3.31; mass (m/z): 394.0 (M+H)$^+$; $^1$H-NMR (400.0 MHz, DMSO-D$_6$): δ=11.303 (15.1); 11.241 (1.2); 8.316 (0.3); 8.232 (8.0); 8.226 (14.6); 8.219 (7.9); 8.202 (1.6); 8.196 (1.4); 7.751 (4.3); 7.747 (4.6); 7.730 (9.0); 7.709 (15.2); 7.689 (12.2); 7.662 (0.5); 7.644 (0.5); 7.628 (0.4); 7.615 (4.2); 7.611 (4.4); 7.594 (9.1); 7.578 (5.7); 7.574 (4.9); 7.551 (6.6); 7.547 (7.2); 7.532 (12.0); 7.528 (11.9); 7.491 (6.3); 7.475 (11.5); 7.473 (11.6); 7.456 (6.1); 7.454 (6.0); 7.428 (7.2); 7.424 (7.5); 7.409 (9.5); 7.404 (12.0); 7.390 (4.7); 7.382 (10.7); 7.379 (10.2); 7.361 (4.5);

7.358 (4.6); 7.304 (0.8); 7.292 (0.4); 7.283 (1.2); 7.263 (0.6); 6.980 (16.0); 6.974 (15.8); 6.946 (1.5); 6.940 (1.3); 5.757 (1.3); 3.826 (0.5); 3.809 (1.5); 3.791 (1.6); 3.774 (0.5); 3.654 (1.6); 3.324 (136.1); 2.671 (1.8); 2.506 (212.6); 2.502 (265.7); 2.498 (197.4); 2.333 (1.2); 2.329 (1.6); 1.352 (0.7); 1.298 (0.5); 1.259 (0.8); 1.234 (3.1); 1.217 (3.6); 1.199 (1.6); 1.188 (0.3); 0.146 (0.5); 0.000 (81.9); −0.150 (0.4)

I-1-558:
HPLC-MS: log P=2.64; mass (m/z): 395.0 (M+H)$^+$; $^1$H-NMR (400.0 MHz, DMSO-D$_6$): δ=11.483 (14.0); 11.419 (1.4); 10.742 (0.4); 10.678 (0.5); 8.489 (8.8); 8.484 (9.8); 8.477 (9.5); 8.472 (9.4); 8.316 (0.5); 8.251 (7.6); 8.244 (14.3); 8.238 (7.4); 8.215 (1.6); 8.209 (1.6); 8.147 (0.3); 8.140 (0.6); 8.109 (0.6); 8.102 (0.7); 8.002 (9.0); 7.998 (9.1); 7.984 (10.1); 7.979 (9.4); 7.751 (3.9); 7.747 (4.2); 7.729 (7.8); 7.712 (4.6); 7.708 (4.7); 7.623 (3.9); 7.619 (4.1); 7.602 (9.1); 7.599 (6.1); 7.586 (5.4); 7.582 (5.6); 7.572 (10.0); 7.560 (9.6); 7.553 (9.3); 7.541 (8.7); 7.529 (1.1); 7.525 (1.0); 7.508 (1.2); 7.505 (1.1); 7.480 (0.5); 7.476 (0.5); 7.406 (5.3); 7.403 (5.3); 7.386 (9.1); 7.382 (8.9); 7.365 (4.4); 7.362 (4.2); 7.344 (0.4); 7.337 (0.4); 7.316 (0.4); 7.307 (1.0); 7.287 (1.6); 7.271 (1.0); 7.267 (0.8); 7.250 (0.5); 7.186 (0.4); 6.983 (16.0); 6.977 (15.8); 6.956 (0.5); 6.949 (1.7); 6.942 (1.5); 6.836 (0.5); 6.829 (0.5); 6.797 (0.7); 6.791 (0.6); 5.757 (13.4); 3.824 (0.6); 3.806 (1.7); 3.789 (1.8); 3.777 (0.5); 3.771 (0.7); 3.759 (1.0); 3.742 (1.0); 3.651 (1.9); 3.628 (0.5); 3.323 (238.3); 3.288 (0.4); 2.676 (1.8); 2.671 (2.4); 2.667 (1.8); 2.511 (154.4); 2.506 (289.1); 2.502 (367.7); 2.497 (266.1); 2.455 (1.1); 2.439 (0.7); 2.417 (0.8); 2.333 (1.9); 2.329 (2.4); 2.324 (1.7); 2.044 (3.1); 2.038 (3.4); 1.989 (0.4); 1.351 (0.5); 1.336 (4.0); 1.298 (1.6); 1.259 (2.3); 1.250 (5.0); 1.235 (3.2); 1.230 (3.0); 1.212 (4.2); 1.194 (2.8); 1.176 (2.5); 1.158 (1.2); 0.854 (0.4); 0.146 (0.7); 0.008 (6.8); 0.000 (140.6); −0.009 (5.2); −0.150 (0.6)

I-1-559:
HPLC-MS: log P=3.30; mass (m/z): 350.0 (M+H)$^+$; $^1$H-NMR (400.0 MHz, DMSO-D$_6$): δ=11.319 (14.4); 11.258 (0.5); 8.316 (0.9); 8.234 (7.7); 8.227 (14.6); 8.221 (7.7); 8.201 (0.7); 7.751 (3.9); 7.747 (4.3); 7.730 (8.1); 7.713 (4.5); 7.709 (4.6); 7.616 (4.1); 7.612 (4.2); 7.595 (9.0); 7.592 (6.1); 7.578 (12.9); 7.564 (10.2); 7.559 (14.1); 7.538 (12.7); 7.535 (13.6); 7.516 (5.6); 7.512 (6.0); 7.498 (9.8); 7.494 (8.6); 7.478 (5.2); 7.474 (4.4); 7.453 (7.6); 7.450 (7.8); 7.435 (9.6); 7.431 (9.7); 7.416 (3.8); 7.413 (3.8); 7.403 (5.5); 7.399 (5.6); 7.382 (9.1); 7.379 (9.4); 7.362 (4.1); 7.358 (4.2); 7.304 (0.4); 7.292 (0.4); 7.284 (0.5); 6.982 (16.0); 6.976 (15.8); 6.955 (0.4); 6.949 (0.8); 6.942 (0.5); 5.757 (2.5); 4.038 (0.4); 4.020 (0.4); 3.805 (0.6); 3.788 (0.6); 3.651 (1.8); 3.321 (196.8); 2.890 (1.0); 2.731 (0.8); 2.675 (3.0); 2.671 (4.1); 2.666 (3.0); 2.662 (1.5); 2.524 (12.9); 2.510 (237.3); 2.506 (468.1); 2.502 (612.8); 2.497 (446.5); 2.493 (218.2); 2.333 (2.9); 2.328 (4.0); 2.324 (2.9); 1.989 (1.4); 1.398 (0.8); 1.351 (1.2); 1.298 (0.8); 1.259 (1.2); 1.231 (2.3); 1.213 (1.6); 1.196 (0.8); 1.175 (0.8); 1.157 (0.5); 0.146 (1.5); 0.008 (12.2); 0.000 (323.3); −0.008 (10.9); −0.150 (1.5)

I-1-560:
HPLC-MS: log P=3.41; mass (m/z): 435.0 (M+H)$^+$; $^1$H-NMR (400.0 MHz, CD$_3$CN): δ=9.493 (3.5); 8.735 (8.9); 8.732 (9.0); 8.320 (8.7); 8.316 (8.8); 8.296 (11.0); 8.289 (11.2); 7.803 (5.4); 7.784 (6.7); 7.726 (1.4); 7.716 (1.4); 7.707 (5.2); 7.693 (7.5); 7.690 (7.1); 7.679 (16.0); 7.662 (6.3); 7.659 (6.0); 7.657 (6.0); 7.642 (1.7); 7.639 (1.7); 7.065 (11.6); 7.058 (11.6); 5.448 (2.1); 2.154 (32.6); 2.108 (0.4); 1.972 (0.4); 1.965 (2.5); 1.959 (3.2); 1.953 (23.3); 1.947 (43.6); 1.941 (60.9); 1.935 (42.8); 1.929 (22.5); 1.770 (0.4); 1.372 (4.3); 1.340 (0.4); 1.285 (0.6); 1.276 (4.8); 0.008 (0.6); 0.000 (17.9); −0.009 (0.8)

I-1-561:
HPLC-MS: log P=3.30; mass (m/z): 401.0 (M+H)$^+$; $^1$H-NMR (400.0 MHz, CD$_3$CN): δ=9.455 (4.7); 8.734 (11.2); 8.732 (11.3); 8.321 (10.4); 8.317 (10.4); 8.299 (11.4); 8.292 (11.5); 7.592 (6.4); 7.576 (7.4); 7.573 (7.6); 7.499 (1.8); 7.495 (3.1); 7.475 (16.0); 7.461 (9.3); 7.456 (8.4); 7.441 (3.3); 7.436 (3.0); 7.426 (0.5); 7.414 (7.0); 7.408 (6.0); 7.395 (7.2); 7.390 (6.7); 7.378 (3.6); 7.373 (3.3); 7.089 (11.0); 7.083 (11.0); 5.448 (1.8); 2.144 (27.6); 2.115 (0.4); 2.108 (0.6); 2.102 (0.4); 1.965 (3.7); 1.959 (4.4); 1.953 (34.0); 1.947 (63.6); 1.941 (88.7); 1.935 (61.8); 1.929 (32.2); 1.776 (0.4); 1.769 (0.5); 1.763 (0.3); 1.372 (4.6); 1.340 (0.4); 1.285 (0.6); 1.276 (5.0); 0.008 (0.9); 0.000 (27.8); −0.009 (1.1)

I-1-562:
HPLC-MS: log P=1.98; mass (m/z): 368.1 (M+H)$^+$; $^1$H-NMR (400.0 MHz, DMSO-D$_6$): δ=11.547 (12.6); 8.845 (7.5); 8.835 (7.5); 8.536 (8.5); 8.532 (8.8); 8.524 (8.9); 8.521 (8.7); 8.316 (0.8); 8.287 (15.4); 8.281 (15.3); 8.221 (9.6); 8.217 (13.5); 8.201 (10.6); 8.197 (15.0); 7.838 (6.3); 7.826 (6.3); 7.818 (5.9); 7.806 (5.5); 7.556 (8.8); 7.544 (8.5); 7.536 (8.2); 7.524 (8.0); 6.943 (16.0); 6.937 (15.6); 3.322 (94.2); 2.675 (1.7); 2.671 (2.2); 2.667 (1.6256 (258.7); 2.506 (258.7); 2.502 (327.5); 2.497 (237.6); 2.333 (1.6); 2.329 (2.1); 2.324 (1.5); 2.075 (0.5); 0.146 (0.8); 0.008 (7.7); 0.000 (166.2); −0.008 (6.4); −0.149 (0.8)

I-1-563:
HPLC-MS: mass (m/z): 317.0 (M+H)$^+$; $^1$H-NMR (400.0 MHz, DMSO-D$_6$): δ=10.546 (3.9); 8.526 (2.7); 8.522 (2.8); 8.515 (2.9); 8.511 (2.8); 8.214 (7.0); 8.208 (5.0); 8.195 (3.0); 8.191 (2.8); 7.542 (2.8); 7.530 (2.7); 7.522 (2.6); 7.510 (2.5); 6.919 (4.8); 6.913 (4.8); 6.807 (4.5); 3.902 (1.6); 3.347 (1.2); 3.328 (152.1); 2.676 (0.5); 2.671 (0.7); 2.667 (0.5); 2.524 (22.8); 2.511 (45.2); 2.507 (91.4); 2.502 (119.1); 2.498 (85.3); 2.493 (41.2); 2.333 (0.5); 2.329 (0.7); 2.324 (0.5); 2.238 (16.0)

I-1-564:
HPLC-MS: log P=2.12; mass (m/z): 335.1 (M+H)$^+$; $^1$H-NMR (400.0 MHz, DMSO-D$_6$): δ=13.913 (0.7); 11.602 (10.9); 8.537 (7.9); 8.533 (7.8); 8.525 (8.3); 8.521 (7.8); 8.316 (0.7); 8.283 (13.0); 8.277 (13.0); 8.222 (8.0); 8.218 (7.7); 8.202 (8.6); 8.198 (7.8); 7.608 (1.5); 7.592 (3.5); 7.587 (3.3); 7.571 (6.2); 7.558 (9.3); 7.547 (9.0); 7.538 (8.0); 7.533 (2.4); 7.526 (7.6); 7.239 (10.1); 7.219 (16.0); 7.199 (9.8); 7.178 (0.9); 6.945 (13.7); 6.938 (13.6); 5.756 (0.7); 3.322 (32.0); 2.675 (1.7); 2.671 (2.2); 2.666 (1.5); 2.506 (269.1); 2.502 (337.6); 2.497 (244.0); 2.437 (0.5); 2.333 (1.8); 2.329 (2.2); 1.337 (0.4); 1.299 (0.4); 1.259 (0.5); 1.250 (0.6); 1.234 (0.4); 1.146 (0.3); 0.000 (2.0)

I-1-565:
HPLC-MS: log P=1.68; mass (m/z): 377.9 (M+H)$^+$; $^1$H-NMR (400.0 MHz, DMSO-D$_6$): δ=11.458 (11.7); 8.535 (8.6); 8.532 (9.0); 8.524 (9.0); 8.520 (8.8); 8.481 (8.0); 8.476 (8.6); 8.469 (8.5); 8.464 (8.3); 8.315 (2.2); 8.282 (15.0); 8.275 (14.8); 8.220 (8.9); 8.216 (8.8); 8.200 (9.6); 8.196 (9.0); 8.002 (8.2); 7.997 (8.4); 7.983 (9.3); 7.978 (8.7); 7.565 (9.0); 7.555 (13.2); 7.546 (9.9); 7.543 (10.4); 7.535 (16.0); 7.523 (8.7); 6.959 (15.8); 6.953 (15.6); 3.321 (223.6); 2.675 (3.2); 2.671 (4.4); 2.666 (3.2); 2.662 (1.5); 2.524 (12.4); 2.511 (257.8); 2.506 (517.6); 2.502 (678.7); 2.497 (489.0); 2.493 (234.8); 2.337 (1.6); 2.333 (3.3); 2.328 (4.5); 2.324 (3.2); 0.146 (0.7); 0.008 (5.8); 0.000 (175.4); −0.008 (6.3); −0.150 (0.8)

I-1-566:

HPLC-MS: log P=2.46; mass (m/z): 431.0 (M+H)$^+$;
$^1$H-NMR (400.0 MHz, DMSO-D$_6$): δ=10.988 (9.2); 8.536 (8.0); 8.532 (8.7); 8.524 (8.6); 8.520 (8.7); 8.316 (1.3); 8.251 (13.5); 8.244 (13.7); 8.222 (8.1); 8.218 (8.3); 8.202 (8.9); 8.198 (8.6); 7.799 (15.0); 7.785 (16.0); 7.554 (9.0); 7.542 (8.8); 7.534 (8.5); 7.522 (8.4); 7.396 (10.0); 7.382 (9.5); 6.939 (6.0); 6.934 (6.0); 4.038 (0.8); 4.020 (0.8); 3.321 (134.1); 2.680 (1.5); 2.675 (3.2); 2.671 (4.4); 2.666 (3.3); 2.662 (1.6); 2.524 (16.2); 2.511 (257.4); 2.506 (514.2); 2.502 (678.5); 2.497 (492.5); 2.493 (241.0); 2.337 (1.6); 2.333 (3.2); 2.328 (4.4); 2.324 (3.2); 1.989 (3.7); 1.236 (0.6); 1.193 (1.0); 1.175 (2.0); 1.157 (1.1); 0.000 (7.8)

I-1-567:

HPLC-MS: log P=3.15; mass (m/z): 386.0 (M+H)$^+$;
$^1$H-NMR (400.0 MHz, DMSO-D$_6$): δ=11.570 (11.4); 8.542 (10.5); 8.535 (10.7); 7.837 (5.6); 7.819 (7.8); 7.788 (2.0); 7.771 (5.7); 7.752 (5.3); 7.719 (4.9); 7.701 (13.8); 7.683 (6.6); 7.366 (16.0); 7.029 (11.0); 7.022 (11.1); 4.102 (0.4); 4.089 (0.4); 3.326 (149.7); 3.176 (1.4); 3.163 (1.4); 2.699 (0.4); 2.692 (0.4); 2.675 (0.7); 2.671 (0.9); 2.667 (0.7); 2.541 (57.3); 2.532 (55.5); 2.507 (97.5); 2.502 (130.4); 2.498 (101.0); 2.379 (0.3); 2.369 (0.3); 2.333 (0.6); 2.329 (0.9); 2.325 (0.7); 1.233 (0.7); 1.178 (0.5); 0.146 (0.5); 0.008 (4.4); 0.000 (103.4); −0.150 (0.5)

I-1-568 see Synthesis Example 36
I-1-569 see Synthesis Example 31
I-1-570 see Synthesis Example 40
I-1-571 see Synthesis Example 33
I-1-572:

HPLC-MS: log P=2.92; mass (m/z): 372.1 (M+H)$^+$;
$^1$H-NMR (400.0 MHz, DMSO-D$_6$): δ=11.595 (3.4); 8.578 (3.2); 8.572 (3.2); 8.322 (3.3); 8.302 (3.4); 7.839 (1.6); 7.820 (2.4); 7.790 (0.6); 7.772 (1.7); 7.753 (1.7); 7.720 (1.5); 7.705 (3.7); 7.686 (1.8); 7.406 (3.3); 7.386 (3.1); 7.047 (3.3); 7.040 (3.3); 3.326 (4.9); 2.595 (16.0); 2.507 (13.0); 2.503 (16.3); 2.499 (11.9); 0.007 (0.6); 0.000 (11.1); −0.001 (10.5); −0.008 (0.5)

I-1-573 see Synthesis Example 39
I-1-574 see Synthesis Example 43
I-1-575 see Synthesis Example 25
I-1-576:

HPLC-MS: log P=2.96; mass (m/z): 476.9 (M+H)$^+$;
$^1$H-NMR (400.0 MHz, CD$_3$CN): δ=9.540 (1.7); 8.293 (4.0); 8.293 (4.0); 8.287 (3.9); 7.929 (4.7); 7.917 (5.4); 7.777 (2.3); 7.769 (4.2); 7.759 (7.3); 7.747 (2.9); 7.691 (0.6); 7.674 (1.8); 7.658 (3.8); 7.654 (3.9); 7.648 (3.9); 7.636 (4.7); 7.623 (1.9); 7.050 (4.8); 7.043 (4.6); 5.447 (16.0); 2.156 (18.3); 1.972 (1.1); 1.964 (1.0); 1.958 (2.3); 1.953 (9.0); 1.946 (15.6); 1.940 (19.8); 1.934 (13.8); 1.928 (7.1); 1.203 (0.5); 1.172 (0.4); 1.006 (0.4); 0.000 (23.8)

I-1-577:

HPLC-MS: log P=2.33; mass (m/z): 368.0 (M+H)$^+$;
$^1$H-NMR (400.0 MHz, DMSO-D$_6$): δ=11.571 (13.2); 8.482 (8.3); 8.478 (9.1); 8.470 (9.0); 8.465 (8.9); 8.446 (13.0); 8.439 (12.8); 8.428 (0.5); 8.420 (0.3); 8.384 (5.7); 8.381 (9.4); 8.372 (6.1); 8.370 (9.5); 8.233 (8.7); 8.228 (8.7); 8.214 (9.6); 8.210 (8.8); 8.030 (4.6); 8.027 (4.5); 8.010 (5.2); 8.006 (5.1); 8.001 (4.9); 7.998 (4.8); 7.981 (4.9); 7.978 (4.8); 7.555 (9.0); 7.543 (9.0); 7.536 (8.9); 7.524 (10.1); 7.518 (6.2); 7.515 (5.6); 7.506 (8.5); 7.497 (4.9); 7.494 (4.9); 7.486 (4.1); 7.012 (16.0); 7.006 (15.7); 4.118 (0.4); 4.104 (1.1); 4.091 (1.2); 4.078 (0.4); 3.330 (51.8); 3.179 (5.5); 3.166 (5.4); 2.679 (0.4); 2.674 (0.5); 2.670 (0.4); 2.545 (0.4); 2.528 (1.4); 2.514 (30.4); 2.510 (61.4); 2.505 (80.3); 2.501 (56.9); 2.496 (26.4); 2.337 (0.4); 2.332 (0.5); 2.327 (0.4); 1.232 (0.4); 1.160 (0.4); 1.142 (0.8); 1.125 (0.4); 1.025 (0.4); 1.007 (0.8); 0.989 (0.4); 0.146 (0.5); 0.015 (0.4); 0.008 (4.2); 0.000 (114.1); −0.009 (3.7); −0.150 (0.5)

I-1-578:

HPLC-MS: log P=1.57; mass (m/z): 363.9 (M+H)$^+$;
$^1$H-NMR (400.0 MHz, DMSO-D$_6$): δ=11.543 (12.3); 8.482 (9.1); 8.477 (9.8); 8.470 (9.8); 8.465 (9.5); 8.441 (12.7); 8.434 (12.6); 8.380 (5.5); 8.377 (9.2); 8.374 (5.6); 8.368 (5.9); 8.365 (9.3); 8.316 (1.5); 8.027 (4.6); 8.023 (4.6); 8.006 (6.3); 8.003 (13.9); 7.998 (14.0); 7.995 (5.9); 7.984 (10.6); 7.979 (11.7); 7.974 (5.3); 7.565 (10.0); 7.553 (9.7); 7.546 (9.4); 7.534 (9.3); 7.522 (5.0); 7.514 (5.6); 7.511 (5.3); 7.502 (8.5); 7.493 (4.7); 7.490 (4.7); 7.482 (4.1); 7.007 (16.0); 7.000 (15.9); 5.756 (6.5); 3.365 (0.4); 3.322 (277.4); 3.102 (0.4); 3.083 (0.4); 2.675 (3.4); 2.671 (4.6); 2.666 (3.3); 2.662 (1.6); 2.524 (14.5); 2.511 (265.0); 2.506 (529.4); 2.502 (695.0); 2.497 (498.0); 2.493 (238.6); 2.337 (1.6); 2.333 (3.3); 2.328 (4.5); 2.324 (3.2); 2.319 (1.5); 1.790 (1.0); 1.236 (0.5); 0.146 (0.8); 0.008 (7.6); 0.000 (221.1); −0.009 (7.8); −0.150 (0.9)

I-1-579:

HPLC-MS: log P=1.53; mass (m/z): 318.1 (M+H)$^+$;
$^1$H-NMR (400.0 MHz, CD$_3$CN): δ=9.529 (4.4); 8.463 (9.7); 8.459 (9.8); 8.451 (10.4); 8.447 (9.6); 8.313 (15.0); 8.307 (15.8); 8.298 (12.4); 8.286 (11.8); 7.969 (9.9); 7.965 (9.5); 7.950 (10.8); 7.946 (10.0); 7.750 (5.7); 7.748 (5.1); 7.729 (6.8); 7.727 (6.6); 7.722 (6.4); 7.701 (6.3); 7.698 (5.6); 7.429 (10.0); 7.417 (10.4); 7.410 (10.0); 7.398 (9.3); 7.389 (5.9); 7.380 (7.5); 7.378 (6.6); 7.369 (9.9); 7.360 (6.6); 7.357 (5.9); 7.349 (4.7); 7.049 (16.0); 7.042 (15.8); 5.448 (2.6); 2.149 (37.6); 2.114 (0.4); 2.108 (0.4); 1.965 (2.4); 1.953 (23.6); 1.947 (43.1); 1.941 (59.2); 1.934 (41.4); 1.928 (21.5); 1.769 (0.3); 0.000 (4.0)

I-1-580:

HPLC-MS: log P=2.36; mass (m/z): 369.1 (M+H)$^+$;
$^1$H-NMR (400.0 MHz, DMSO-D$_6$): δ=14.226 (0.5); 11.712 (9.7); 8.441 (9.1); 8.434 (9.2); 8.377 (6.5); 8.366 (6.6); 8.026 (3.2); 8.023 (3.2); 8.005 (3.6); 8.002 (3.7); 7.997 (3.5); 7.994 (3.4); 7.976 (3.5); 7.973 (3.4); 7.772 (0.8); 7.753 (2.6); 7.744 (1.9); 7.734 (5.4); 7.719 (8.8); 7.697 (16.0); 7.680 (4.8); 7.675 (4.5); 7.523 (3.1); 7.514 (3.9); 7.512 (3.8); 7.502 (5.5); 7.493 (3.4); 7.491 (3.4); 7.482 (2.7); 6.979 (10.5); 6.972 (10.5); 5.757 (1.1); 3.324 (6.8); 2.672 (0.8); 2.507 (108.0); 2.503 (137.3); 2.498 (103.0); 2.329 (0.9); 0.000 (0.8)

I-1-581:

HPLC-MS: log P=2.30; mass (m/z): 431.9 (M+H)$^+$;
$^1$H-NMR (400.0 MHz, DMSO-D$_6$): δ=11.070 (6.4); 8.405 (5.8); 8.399 (5.9); 8.377 (4.8); 8.368 (3.2); 8.365 (4.9); 8.025 (2.5); 8.021 (2.5); 8.004 (2.8); 8.001 (2.7); 7.996 (2.6); 7.992 (2.5); 7.975 (2.7); 7.972 (2.6); 7.801 (9.5); 7.794 (0.7); 7.787 (10.1); 7.517 (2.5); 7.509 (3.0); 7.506 (2.8); 7.497 (4.4); 7.488 (2.5); 7.485 (2.5); 7.477 (2.1); 7.416 (7.3); 7.402 (6.9); 7.001 (3.8); 6.995 (3.8); 5.757 (0.6); 4.117 (1.2); 4.104 (3.4); 4.091 (3.5); 4.078 (1.2); 3.331 (12.5); 3.179 (16.0); 3.166 (15.4); 2.527 (0.8); 2.514 (11.5); 2.509 (22.3); 2.505 (29.0); 2.500 (21.1); 2.496 (10.3); 0.000 (1.6)

I-1-582:

HPLC-MS: log P=2.16; mass (m/z): 398.9 (M+H)$^+$;
$^1$H-NMR (400.0 MHz, DMSO-D$_6$): δ=10.989 (9.3); 8.406 (8.9); 8.400 (8.9); 8.382 (4.2); 8.379 (7.0); 8.376 (4.3); 8.370 (4.4); 8.367 (7.1); 8.365 (4.1); 8.031 (3.4); 8.028 (3.4); 8.011 (3.8); 8.007 (3.8); 8.003 (3.6); 7.999 (3.5); 7.982 (3.7); 7.979 (3.6); 7.938 (14.8); 7.934 (14.8); 7.523 (3.8); 7.514 (4.3); 7.511 (4.0); 7.502 (6.5); 7.493 (3.5); 7.490 (3.6); 7.482 (3.1); 6.953 (11.7); 6.946 (11.6); 6.921 (16.0); 6.917

(15.5); 5.761 (3.4); 3.339 (7.6); 2.531 (0.5); 2.518 (9.6); 2.513 (19.2); 2.509 (25.2); 2.504 (18.1); 2.500 (8.6); 0.000 (5.2)

I-1-583 see Synthesis Example 42
I-1-584 see Synthesis Example 30
I-1-585 see Synthesis Example 37
I-1-586 see Synthesis Example 38

I-1-587:
HPLC-MS: log P=2.91; mass (m/z): 444.8 (M+H)$^+$; $^1$H-NMR (400.0 MHz, DMSO-D$_6$): δ=11.489 (2.0); 8.471 (1.9); 8.467 (2.0); 8.411 (1.8); 8.404 (1.7); 8.372 (1.2); 8.367 (1.1); 8.345 (1.2); 8.340 (1.1); 7.836 (1.0); 7.817 (1.4); 7.785 (0.4); 7.767 (1.1); 7.748 (1.0); 7.715 (0.9); 7.697 (2.5); 7.679 (1.2); 7.009 (2.1); 7.003 (2.1); 5.757 (16.0); 3.330 (1.8); 2.509 (5.8); 2.505 (7.3); 2.500 (5.3); 1.397 (0.9); 0.000 (3.0)

I-1-588:
HPLC-MS: log P=2.60; mass (m/z): 448.8 (M+H)$^+$; $^1$H-NMR (400.0 MHz, DMSO-D$_6$): δ=11.712 (6.0); 8.477 (6.3); 8.472 (7.1); 8.432 (5.7); 8.425 (5.7); 8.383 (4.4); 8.378 (3.9); 8.356 (4.3); 8.350 (4.0); 7.612 (0.8); 7.596 (1.7); 7.591 (1.5); 7.579 (1.2); 7.574 (3.2); 7.570 (1.2); 7.558 (1.6); 7.553 (1.9); 7.537 (0.8); 7.247 (1.0); 7.240 (5.6); 7.220 (7.8); 7.199 (4.7); 7.192 (1.0); 7.010 (7.4); 7.003 (7.4); 5.757 (16.0); 4.101 (0.4); 4.088 (0.5); 3.324 (30.2); 3.176 (1.9); 3.163 (2.0); 2.676 (0.4); 2.672 (0.5); 2.667 (0.4); 2.525 (1.7); 2.520 (2.6); 2.512 (29.9); 2.507 (59.8); 2.503 (78.4); 2.498 (56.2); 2.494 (26.7); 2.334 (0.4); 2.329 (0.5); 2.325 (0.4); 1.145 (0.3); 0.000 (2.4)

I-1-589:
HPLC-MS: log P=2.78; mass (m/z): 351.0 (M+H)$^+$; $^1$H-NMR (400.0 MHz, DMSO-D$_6$): δ=11.387 (6.8); 8.470 (6.6); 8.465 (6.6); 8.408 (6.1); 8.402 (5.8); 8.371 (4.0); 8.366 (3.4); 8.344 (3.9); 8.339 (3.4); 7.703 (4.6); 7.683 (5.2); 7.553 (3.0); 7.548 (3.1); 7.534 (5.0); 7.530 (4.7); 7.489 (2.6); 7.470 (5.1); 7.452 (2.8); 7.425 (3.2); 7.420 (2.9); 7.405 (3.9); 7.401 (3.5); 7.386 (1.7); 7.382 (1.4); 7.027 (7.0); 7.020 (6.6); 5.758 (16.0); 3.328 (4.0); 2.508 (21.8); 2.504 (26.0); 2.500 (18.4); 0.000 (6.3)

I-1-590:
HPLC-MS: log P=2.74; mass (m/z): 442.9 (M+H)$^+$; $^1$H-NMR (400.0 MHz, DMSO-D$_6$): δ=11.404 (5.5); 8.470 (5.5); 8.465 (5.9); 8.410 (4.9); 8.403 (4.8); 8.372 (3.5); 8.367 (3.1); 8.345 (3.5); 8.340 (3.2); 7.585 (2.7); 7.581 (2.9); 7.566 (3.6); 7.562 (3.7); 7.552 (2.1); 7.549 (2.4); 7.532 (4.8); 7.529 (4.9); 7.513 (2.2); 7.508 (2.3); 7.495 (3.7); 7.490 (3.1); 7.475 (2.1); 7.470 (1.7); 7.448 (2.9); 7.445 (2.8); 7.430 (3.7); 7.427 (3.5); 7.412 (1.4); 7.408 (1.3); 7.030 (5.9); 7.023 (5.8); 5.758 (16.0); 3.329 (4.6); 2.526 (0.5); 2.513 (8.9); 2.509 (17.3); 2.504 (22.2); 2.500 (15.8); 2.495 (7.5); 1.231 (0.4); 0.000 (6.2)

I-1-591:
HPLC-MS: log P=2.98; mass (m/z): 353.1 (M+H)$^+$; $^1$H-NMR (400.0 MHz, DMSO-D$_6$): δ=11.746 (4.7); 8.475 (4.8); 8.470 (5.4); 8.433 (4.3); 8.426 (4.3); 8.377 (3.2); 8.372 (2.9); 8.350 (3.2); 8.344 (3.0); 7.778 (0.4); 7.758 (1.1); 7.748 (0.7); 7.738 (2.3); 7.723 (3.2); 7.700 (7.0); 7.683 (2.0); 7.678 (1.9); 7.005 (5.5); 6.998 (5.5); 5.759 (16.0); 3.333 (3.1); 2.529 (0.3); 2.516 (5.9); 2.511 (11.7); 2.507 (15.3); 2.502 (11.1); 2.498 (5.4); 1.992 (0.5); 1.396 (2.0); 0.000 (0.5)

I-1-592:
HPLC-MS: log P=2.99; mass (m/z): 394.9 (M+H)$^+$; $^1$H-NMR (400.0 MHz, DMSO-D$_6$): δ=11.093 (6.2); 8.475 (6.3); 8.470 (6.8); 8.393 (5.3); 8.386 (5.5); 8.379 (4.2); 8.374 (3.6); 8.352 (3.9); 8.347 (3.6); 7.802 (7.6); 7.788 (8.0); 7.410 (6.5); 7.396 (6.1); 7.016 (3.7); 7.010 (3.6); 5.758 (16.0); 3.326 (9.6); 2.512 (16.3); 2.508 (31.2); 2.503 (40.2); 2.499 (29.1); 0.008 (0.6); 0.000 (14.7); −0.008 (0.5)

I-1-593:
HPLC-MS: log P=2.89; mass (m/z): 385.0 (M+H)$^+$; $^1$H-NMR (400.0 MHz, DMSO-D$_6$): δ=11.323 (5.9); 8.471 (5.6); 8.466 (6.1); 8.407 (5.0); 8.400 (4.9); 8.372 (3.7); 8.367 (3.3); 8.345 (3.6); 8.340 (3.4); 7.921 (4.5); 7.901 (5.0); 7.500 (0.5); 7.479 (5.3); 7.476 (5.8); 7.467 (10.0); 7.457 (1.0); 7.233 (2.0); 7.224 (1.9); 7.219 (2.0); 7.213 (2.3); 7.211 (2.1); 7.204 (1.8); 7.200 (2.0); 7.191 (1.6); 7.024 (6.0); 7.017 (5.9); 5.757 (16.0); 3.326 (7.4); 2.525 (0.7); 2.512 (12.6); 2.507 (24.5); 2.503 (31.7); 2.498 (22.8); 2.494 (11.0); 0.008 (0.6); 0.000 (14.7); −0.009 (0.4)

I-1-594:
HPLC-MS: log P=2.34; mass (m/z): 359.0 (M+H)$^+$; $^1$H-NMR (400.0 MHz, DMSO-D$_6$): δ=19.999 (0.4); 11.791 (6.4); 9.293 (16.0); 9.239 (15.8); 9.048 (0.5); 8.780 (0.6); 8.756 (6.8); 8.749 (6.8); 8.315 (2.4); 7.850 (3.3); 7.831 (5.5); 7.801 (1.3); 7.783 (3.6); 7.764 (3.7); 7.734 (3.9); 7.722 (5.6); 7.705 (3.3); 7.159 (6.4); 7.151 (6.2); 5.756 (6.5); 3.319 (151.2); 2.675 (5.7); 2.670 (7.7); 2.666 (5.7); 2.540 (4.9); 2.510 (464.4); 2.506 (895.7); 2.501 (1158.0); 2.497 (833.7); 2.492 (404.2); 2.332 (5.3); 2.328 (7.3); 2.323 (5.3); 0.146 (1.9); 0.008 (20.7); 0.000 (408.1); −0.008 (16.0); −0.150 (1.8)

I-1-595:
HPLC-MS: log P=2.03; mass (m/z): 327.1 (M+H)$^+$; $^1$H-NMR (400.0 MHz, DMSO-D$_6$): δ=11.980 (0.5); 9.306 (1.0); 9.248 (1.0); 8.775 (0.5); 8.768 (0.5); 7.262 (0.4); 7.243 (0.6); 7.222 (0.4); 7.165 (0.6); 7.158 (0.6); 5.755 (16.0); 3.321 (15.5); 2.524 (0.5); 2.511 (12.0); 2.506 (23.8); 2.502 (30.9); 2.497 (22.0); 2.493 (10.4); 0.008 (0.5); 0.000 (13.8); −0.009 (0.5)

I-1-596:
HPLC-MS: log P=2.88; mass (m/z): 351.1 (M+H)$^+$; $^1$H-NMR (400.0 MHz, DMSO-D$_6$): δ=11.423 (2.8); 8.528 (3.4); 8.521 (3.3); 8.493 (2.8); 8.486 (2.7); 7.967 (0.9); 7.960 (0.8); 7.947 (1.3); 7.945 (1.4); 7.939 (1.2); 7.937 (1.3); 7.924 (1.1); 7.917 (1.0); 7.847 (1.5); 7.828 (2.0); 7.807 (1.8); 7.797 (2.2); 7.784 (1.7); 7.778 (1.9); 7.775 (2.0); 7.759 (1.5); 7.725 (1.3); 7.707 (3.7); 7.688 (1.8); 6.954 (3.7); 6.948 (3.5); 4.119 (1.3); 4.106 (3.5); 4.093 (3.5); 4.079 (1.2); 3.334 (16.7); 3.179 (16.0); 3.166 (15.0); 2.514 (7.1); 2.509 (12.3); 2.505 (15.2); 2.500 (10.6); 2.496 (5.1); 0.008 (0.9); 0.000 (10.4); −0.009 (0.4)

I-1-597:
HPLC-MS: log P=2.32; mass (m/z): 352.0 (M+H)$^+$; $^1$H-NMR (400.0 MHz, DMSO-D$_6$): δ=11.587 (11.2); 8.859 (6.7); 8.847 (6.7); 8.546 (15.5); 8.540 (15.6); 8.500 (11.6); 8.493 (11.9); 8.225 (6.4); 8.206 (6.9); 7.972 (3.4); 7.965 (3.3); 7.950 (5.5); 7.943 (5.4); 7.929 (4.5); 7.922 (4.3); 7.851 (6.0); 7.839 (6.0); 7.832 (5.7); 7.820 (5.4); 7.805 (7.1); 7.796 (7.4); 7.783 (5.6); 7.773 (5.4); 6.959 (16.0); 6.953 (16.0); 5.758 (1.7); 4.102 (0.7); 4.089 (0.7); 3.327 (36.1); 3.178 (2.8); 3.165 (2.7); 2.678 (0.4); 2.673 (0.5); 2.669 (0.4); 2.543 (0.3); 2.526 (1.4); 2.513 (31.1); 2.509 (63.5); 2.504 (83.9); 2.500 (60.4); 2.495 (29.1); 2.335 (0.4); 2.331 (0.5); 2.326 (0.4); 0.008 (1.2); 0.000 (36.5); −0.008 (1.3)

I-1-598:
HPLC-MS: log P=2.61; mass (m/z): 319.1 (M+H)$^+$; $^1$H-NMR (400.0 MHz, DMSO-D$_6$): δ=11.642 (11.7); 8.543 (14.4); 8.537 (14.4); 8.499 (11.7); 8.492 (11.9); 7.974 (3.4); 7.967 (3.3); 7.952 (5.7); 7.945 (5.5); 7.931 (4.6); 7.924 (4.3); 7.811 (7.0); 7.801 (7.3); 7.788 (5.5); 7.779 (5.3); 7.622 (1.5); 7.605 (3.4); 7.601 (3.2); 7.584 (6.3); 7.567 (3.4); 7.563 (3.8); 7.547 (1.7); 7.257 (2.3); 7.251 (10.9); 7.231

(16.0); 7.210 (9.2); 7.203 (2.1); 6.958 (15.5); 6.951 (15.4); 3.324 (79.5); 2.676 (0.7); 2.672 (0.9); 2.668 (0.7); 2.542 (0.5); 2.525 (2.3); 2.512 (57.2); 2.507 (111.1); 2.503 (143.0); 2.498 (104.4); 2.494 (52.2); 2.334 (0.7); 2.330 (0.9); 2.325 (0.7); 0.008 (3.5); 0.000 (71.0); −0.008 (3.5)

I-1-599:

HPLC-MS: log P=2.78; mass (m/z): 409.0 (M+H)$^+$; $^1$H-NMR (400.0 MHz, DMSO-D$_6$): δ=11.265 (4.0); 8.526 (4.3); 8.520 (4.2); 8.490 (3.7); 8.482 (3.7); 7.967 (1.1); 7.960 (1.1); 7.945 (2.0); 7.934 (3.5); 7.924 (1.7); 7.914 (3.8); 7.810 (2.1); 7.801 (2.2); 7.788 (1.7); 7.778 (1.6); 7.512 (0.3); 7.491 (3.9); 7.488 (4.2); 7.479 (6.9); 7.470 (0.8); 7.244 (1.4); 7.235 (1.4); 7.231 (1.5); 7.224 (1.6); 7.222 (1.5); 7.215 (1.3); 7.212 (1.5); 7.202 (1.2); 6.974 (4.6); 6.967 (4.4); 5.757 (16.0); 3.330 (7.3); 2.513 (5.9); 2.509 (11.4); 2.504 (14.7); 2.500 (10.3); 2.495 (4.9); 0.000 (3.6)

I-1-600:

HPLC-MS: log P=2.13; mass (m/z): 352.1 (M+H)$^+$; $^1$H-NMR (400.0 MHz, DMSO-D$_6$): δ=11.559 (3.9); 8.9382 (16.0); 8.9378 (16.0); 8.581 (4.9); 8.575 (4.9); 7.848 (2.2); 7.828 (2.7); 7.796 (0.7); 7.779 (2.1); 7.760 (1.9); 7.725 (1.7); 7.704 (4.7); 7.685 (2.3); 6.999 (5.3); 6.992 (5.3); 5.758 (2.3); 3.327 (25.0); 2.526 (0.6); 2.521 (0.9); 2.512 (11.2); 2.508 (22.5); 2.503 (29.7); 2.499 (21.3); 2.494 (10.0); 0.008 (0.4); 0.000 (13.6); −0.009 (0.4)

I-1-601:

HPLC-MS: log P=1.73; mass (m/z): 353.0 (M+H)$^+$; $^1$H-NMR (400.0 MHz, DMSO-D$_6$): δ=11.734 (3.8); 8.944 (16.0); 8.861 (1.9); 8.859 (2.1); 8.849 (2.0); 8.847 (2.0); 8.598 (4.8); 8.591 (4.8); 8.223 (1.8); 8.221 (1.9); 8.203 (2.1); 8.201 (2.1); 7.854 (1.9); 7.842 (1.9); 7.835 (1.8); 7.823 (1.7); 6.997 (5.5); 6.990 (5.4); 5.757 (0.6); 3.323 (61.1); 2.676 (0.4); 2.671 (0.6); 2.667 (0.4); 2.525 (1.8); 2.520 (2.8); 2.511 (30.7); 2.507 (61.6); 2.502 (81.3); 2.498 (58.4); 2.493 (27.4); 2.334 (0.4); 2.329 (0.5); 2.324 (0.4); 0.000 (7.4)

I-1-602:

HPLC-MS: log P=1.83; mass (m/z): 320.0 (M+H)$^+$; $^1$H-NMR (400.0 MHz, DMSO-D$_6$): δ=11.776 (3.6); 8.944 (16.0); 8.598 (5.1); 8.591 (5.1); 7.623 (0.5); 7.606 (1.2); 7.601 (1.0); 7.589 (0.8); 7.585 (2.1); 7.581 (0.8); 7.568 (1.1); 7.564 (1.3); 7.564 (0.6); 7.547 (0.6); 7.258 (0.7); 7.251 (3.8); 7.231 (5.4); 7.211 (3.1); 7.204 (0.6); 7.000 (5.6); 6.994 (5.5); 3.324 (29.4); 2.672 (0.4); 2.525 (1.3); 2.512 (20.6); 2.507 (40.1); 2.503 (52.3); 2.498 (38.0); 2.494 (18.3); 2.330 (0.3); 0.008 (0.8); 0.000 (20.5); −0.009 (0.7)

I-1-603:

HPLC-MS: log P=1.94; mass (m/z): 362.0 (M+H)$^+$; $^1$H-NMR (400.0 MHz, DMSO-D$_6$): δ=11.446 (3.9); 8.937 (16.0); 8.580 (4.1); 8.573 (4.0); 7.713 (2.6); 7.712 (2.7); 7.694 (3.1); 7.692 (3.1); 7.560 (1.7); 7.556 (1.8); 7.541 (2.9); 7.537 (2.9); 7.499 (1.5); 7.496 (1.6); 7.480 (3.1); 7.478 (3.0); 7.462 (1.6); 7.459 (1.5); 7.434 (2.0); 7.429 (2.0); 7.414 (2.4); 7.410 (2.3); 7.396 (1.1); 7.391 (1.0); 7.017 (4.3); 7.010 (4.2); 4.038 (0.5); 4.020 (0.5); 3.322 (59.5); 2.675 (0.5); 2.671 (0.7); 2.666 (0.5); 2.510 (43.3); 2.506 (82.4); 2.502 (106.7); 2.497 (78.5); 2.493 (39.2); 2.333 (0.6); 2.328 (0.7); 2.324 (0.5); 1.989 (2.3); 1.193 (0.6); 1.175 (1.2); 1.157 (0.6); 0.008 (0.4); 0.000 (8.2); −0.008 (0.3)

I-1-604:

HPLC-MS: log P=1.91; mass (m/z): 318.0 (M+H)$^+$; $^1$H-NMR (400.0 MHz, DMSO-D$_6$): δ=11.469 (3.9); 8.937 (16.0); 8.582 (4.2); 8.576 (4.1); 7.593 (2.1); 7.590 (2.2); 7.575 (2.8); 7.571 (2.8); 7.562 (1.8); 7.559 (1.9); 7.542 (3.9); 7.540 (3.8); 7.522 (1.8); 7.518 (1.8); 7.504 (3.0); 7.500 (2.6); 7.484 (1.6); 7.480 (1.3); 7.458 (2.4); 7.455 (2.3); 7.440 (3.0); 7.437 (2.8); 7.422 (1.2); 7.418 (1.0); 7.022 (4.2); 7.016 (4.1); 5.757 (10.3); 3.324 (20.9); 2.507 (33.6); 2.503 (42.6); 2.498 (31.4); 0.000 (2.0)

I-1-605:

HPLC-MS: log P=2.05; mass (m/z): 410.0 (M+H)$^+$; $^1$H-NMR (400.0 MHz, DMSO-D$_6$): δ=11.386 (3.8); 9.032 (1.4); 8.936 (16.0); 8.907 (2.2); 8.580 (3.9); 8.573 (3.9); 7.933 (3.2); 7.913 (3.7); 7.510 (0.4); 7.508 (0.4); 7.491 (3.0); 7.489 (3.4); 7.485 (3.8); 7.477 (6.9); 7.467 (0.7); 7.381 (0.7); 7.377 (0.7); 7.242 (1.6); 7.233 (1.4); 7.228 (1.4); 7.222 (1.7); 7.219 (1.6); 7.213 (1.3); 7.209 (1.4); 7.200 (1.3); 7.020 (4.1); 7.013 (4.0); 6.615 (0.6); 5.756 (9.4); 5.421 (0.9); 5.416 (0.8); 3.325 (31.9); 2.525 (0.9); 2.512 (13.9); 2.507 (27.1); 2.503 (35.4); 2.498 (25.7); 2.494 (12.4); 1.989 (0.9); 1.175 (0.5); 0.000 (2.2)

I-1-606 see Synthesis Example 44

I-1-607 see Synthesis Example 34

I-1-608 see Synthesis Example 35

I-1-609:

HPLC-MS: mass (m/z): 284.1 (M+H)$^+$; $^1$H-NMR (400.0 MHz, DMSO-D$_6$): δ=10.845 (3.9); 10.029 (0.4); 9.579 (0.4); 9.5798.887 (1.0); 8.875 (1.0); 8.867 (1.0); 8.863 (1.0); 8.855 (1.5); 8.843 (9.9); 8.831 (9.7); 8.679 (0.4); 8.672 (0.5); 8.656 (0.4); 8.649 (0.5); 8.639 (0.3); 8.632 (0.4); 8.624 (0.3); 8.594 (4.2); 8.587 (4.3); 8.322 (0.5); 7.919 (0.5); 7.485 (0.4); 7.473 (0.6); 7.460 (0.7); 7.439 (2.7); 7.427 (4.6); 7.415 (2.4); 7.019 (4.5); 7.012 (4.5); 6.923 (0.4); 6.916 (0.4); 6.849 (4.7); 3.909 (12.1); 3.395 (0.9); 3.389 (0.8); 3.337 (100.1); 3.174 (4.7); 2.712 (0.8); 2.677 (1.3); 2.535 (22.2); 2.513 (184.6); 2.508 (236.8); 2.504 (179.1); 2.443 (1.5); 2.422 (0.8); 2.396 (0.6); 2.389 (0.6); 2.371 (0.5); 2.339 (1.3); 2.335 (1.6); 2.304 (0.4); 2.290 (0.5); 2.248 (16.0); 1.915 (1.2); 1.836 (1.1); 1.819 (0.3); 1.799 (0.4); 1.575 (0.3); 1.241 (0.3); 0.005 (0.4)

I-1-610:

HPLC-MS: log P=3.00; mass (m/z): 382.1 (M+H)$^+$; $^1$H-NMR (601.6 MHz, DMSO-D$_6$): δ=11.222 (11.4); 8.056 (8.8); 8.053 (8.9); 7.654 (6.7); 7.641 (7.4); 7.628 (1.4); 7.617 (2.9); 7.613 (2.7); 7.603 (5.3); 7.593 (2.9); 7.589 (3.4); 7.578 (1.5); 7.545 (2.2); 7.543 (2.4); 7.531 (6.7); 7.521 (6.4); 7.519 (6.3); 7.496 (9.5); 7.485 (8.2); 7.475 (7.2); 7.462 (2.9); 7.460 (2.7); 7.396 (9.1); 7.382 (16.0); 7.368 (7.6); 6.940 (12.3); 6.935 (12.4); 4.029 (2.4); 4.010 (7.6); 3.991 (8.1); 3.971 (2.8); 3.331 (356.1); 2.996 (0.5); 2.654 (0.8); 2.617 (1.4); 2.613 (1.9); 2.611 (1.4); 2.541 (225.8); 2.523 (3.2); 2.520 (4.1); 2.517 (4.2); 2.508 (99.9); 2.505 (213.4); 2.502 (294.6); 2.499 (217.0); 2.496 (103.9); 2.425 (0.9); 2.389 (1.4); 2.386 (1.9); 2.383 (1.4); 2.076 (0.4); 1.235 (0.8); 0.005 (2.2); 0.000 (69.8); −0.006 (2.3)

I-1-611:

HPLC-MS: log P=2.53; mass (m/z): 374.1 (M+H)$^+$; $^1$H-NMR (400.0 MHz, DMSO-D$_6$): δ=10.987 (7.9); 8.038 (9.0); 8.032 (8.8); 7.637 (1.3); 7.622 (2.9); 7.616 (2.5); 7.606 (2.1); 7.600 (5.7); 7.594 (2.3); 7.584 (2.7); 7.579 (3.6); 7.563 (1.6); 7.394 (9.6); 7.373 (16.0); 7.352 (7.4); 6.809 (8.1); 6.803 (8.0); 6.779 (3.3); 6.648 (7.6); 6.517 (3.7); 4.386 (9.1); 4.375 (10.7); 4.364 (9.3); 3.339 (103.8); 3.304 (0.3); 3.193 (9.1); 3.182 (10.6); 3.171 (8.6); 2.543 (57.8); 2.526 (0.8); 2.512 (16.0); 2.508 (31.7); 2.503 (41.0); 2.499 (29.5); 2.495 (14.3); 0.000 (2.9)

I-1-612:

HPLC-MS: log P=3.53; mass (m/z): 411.1 (M+H)$^+$; $^1$H-NMR (400.0 MHz, DMSO-D$_6$): δ=12.182 (6.1); 11.414 (7.9); 8.081 (12.1); 8.061 (6.4); 7.997 (5.0); 7.978 (5.3); 7.661 (3.1); 7.641 (5.9); 7.622 (4.2); 7.613 (4.1); 7.591 (2.7); 7.575 (1.1); 7.406 (7.8); 7.385 (16.0); 7.364 (7.9);

6.920 (7.4); 6.915 (7.6); 3.325 (43.8); 2.671 (0.8); 2.502 (115.1); 2.502 (115.1); 2.328 (0.7); 2.074 (0.5); 1.234 (0.3); −0.001 (26.4)

I-1-613:
HPLC-MS: log P=2.72; mass (m/z): 396.0 (M+H)$^+$; $^1$H-NMR (601.6 MHz, DMSO-D$_6$): δ=19.968 (0.6); 11.302 (1.1); 8.073 (1.1); 7.743 (0.7); 7.734 (0.7); 7.728 (0.7); 7.720 (0.7); 7.603 (0.6); 7.526 (0.7); 7.521 (0.8); 7.512 (0.7); 7.507 (0.8); 7.395 (1.1); 7.381 (1.9); 7.367 (1.0); 7.300 (0.8); 6.937 (2.0); 6.933 (2.1); 3.329 (1933.2); 2.616 (11.4); 2.613 (16.0); 2.610 (11.6); 2.541 (53.2); 2.523 (25.7); 2.520 (33.1); 2.516 (34.2); 2.508 (809.0); 2.505 (1748.8); 2.502 (2415.0); 2.499 (1771.5); 2.496 (834.3); 2.389 (11.2); 2.386 (15.6); 2.383 (11.3); 2.286 (0.6); 2.076 (0.8); 1.298 (1.0); 1.258 (1.5); 1.235 (4.3); 0.854 (0.7); 0.097 (2.1); 0.005 (17.1); 0.000 (554.1); −0.006 (18.0); −0.100 (2.3)

I-1-614:
HPLC-MS: log P=2.86; mass (m/z): 402.0 (M+H)$^+$; $^1$H-NMR (400.0 MHz, DMSO-D$_6$): δ=11.484 (11.8); 8.079 (9.4); 8.074 (9.4); 7.909 (7.6); 7.889 (9.2); 7.827 (7.4); 7.808 (9.9); 7.712 (5.4); 7.692 (8.2); 7.672 (3.4); 7.636 (1.3); 7.620 (2.7); 7.615 (2.6); 7.599 (5.5); 7.583 (2.8); 7.578 (3.5); 7.562 (1.6); 7.400 (9.2); 7.379 (16.0); 7.358 (7.2); 6.924 (13.3); 6.918 (13.3); 5.758 (3.4); 3.329 (71.3); 2.671 (0.9); 2.506 (114.6); 2.502 (145.6); 2.498 (107.8); 2.329 (0.9); 1.235 (0.4); 1.141 (0.5); 1.030 (0.5); 0.008 (2.4); 0.000 (56.9)

I-1-615:
HPLC-MS: log P=2.42; mass (m/z): 322.1 (M+H)$^+$; $^1$H-NMR (400.0 MHz, DMSO-D$_6$): δ=9.625 (2.3); 7.996 (1.8); 7.990 (1.8); 7.605 (0.6); 7.599 (0.5); 7.589 (0.4); 7.584 (1.2); 7.578 (0.5); 7.568 (0.6); 7.563 (0.8); 7.547 (0.3); 7.382 (2.0); 7.361 (3.4); 7.340 (1.5); 6.825 (2.9); 6.819 (2.8); 4.171 (1.7); 4.162 (2.4); 4.157 (2.1); 4.152 (2.5); 4.066 (2.5); 4.060 (2.1); 4.055 (2.4); 4.046 (1.7); 3.337 (54.7); 2.542 (4.0); 2.511 (8.1); 2.507 (15.8); 2.503 (20.3); 2.498 (14.6); 2.197 (16.0); 0.000 (1.3)

I-1-616:
HPLC-MS: log P=1.80; mass (m/z): 370.0 (M+H)$^+$; $^1$H-NMR (400.0 MHz, DMSO-D$_6$): δ=10.832 (3.1); 8.317 (0.4); 8.049 (3.1); 7.634 (0.4); 7.618 (0.9); 7.612 (0.9); 7.597 (1.8); 7.580 (1.0); 7.575 (1.2); 7.560 (0.5); 7.396 (3.0); 7.375 (5.1); 7.354 (2.4); 6.846 (3.0); 6.841 (3.1); 5.757 (2.8); 4.736 (2.6); 4.723 (2.9); 4.709 (2.8); 3.597 (2.8); 3.584 (2.9); 3.570 (2.7); 3.328 (96.3); 2.671 (1.6); 2.506 (198.1); 2.502 (252.4); 2.329 (1.6); 2.028 (16.0); 1.259 (0.4); 1.235 (0.5); 0.146 (0.4); 0.000 (89.8); −0.150 (0.4)

I-1-617:
HPLC-MS: log P=2.72; mass (m/z): 374.9 (M+H)$^+$; $^1$H-NMR (400.0 MHz, DMSO-D$_6$): δ=11.520 (7.9); 8.452 (8.3); 8.445 (8.4); 7.932 (1.7); 7.916 (2.2); 7.911 (4.1); 7.895 (4.2); 7.890 (2.9); 7.874 (2.3); 7.842 (4.5); 7.822 (5.6); 7.790 (1.6); 7.773 (4.4); 7.754 (4.1); 7.720 (3.7); 7.699 (16.0); 7.679 (10.0); 7.545 (3.4); 7.523 (6.0); 7.501 (3.1); 7.038 (8.5); 7.031 (8.5); 5.757 (8.9); 3.326 (82.1); 2.671 (0.6); 2.667 (0.5); 2.507 (75.0); 2.502 (97.7); 2.498 (73.2); 2.329 (0.6); 1.989 (0.6); 1.175 (0.3); 0.146 (0.6); 0.008 (6.6); 0.000 (128.8); −0.008 (6.7); −0.150 (0.6)

I-1-618:
HPLC-MS: log P=2.26; mass (m/z): 375.9 (M+H)$^+$; $^1$H-NMR (400.0 MHz, DMSO-D$_6$): δ=11.665 (15.1); 8.854 (8.8); 8.842 (8.8); 8.472 (15.5); 8.466 (15.4); 8.317 (1.0); 8.220 (8.2); 8.201 (9.0); 7.936 (3.3); 7.920 (4.2); 7.915 (7.5); 7.899 (7.7); 7.894 (5.0); 7.878 (4.3); 7.845 (7.2); 7.833 (7.3); 7.826 (6.8); 7.814 (6.3); 7.708 (12.6); 7.687 (10.3); 7.553 (6.3); 7.531 (11.0); 7.509 (5.5); 7.043 (16.0); 7.037 (15.9); 5.758 (3.0); 3.328 (363.0); 3.037 (0.7); 2.671 (3.4); 2.667 (2.6); 2.541 (2.2); 2.506 (412.2); 2.502 (525.5); 2.498 (388.1); 2.333 (2.6); 2.329 (3.3); 1.299 (0.7); 1.259 (1.2); 1.235 (1.3); 0.146 (0.9); 0.008 (8.3); 0.000 (200.8); −0.149 (1.0)

I-1-619:
HPLC-MS: log P=2.45; mass (m/z): 343.0 (M+H)$^+$; $^1$H-NMR (400.0 MHz, DMSO-D$_6$): δ=11.735 (11.8); 8.469 (14.5); 8.462 (14.6); 7.936 (3.0); 7.920 (3.5); 7.915 (7.0); 7.899 (7.0); 7.894 (4.6); 7.878 (4.0); 7.709 (10.8); 7.688 (8.9); 7.619 (1.5); 7.602 (3.3); 7.598 (3.2); 7.581 (6.3); 7.564 (3.4); 7.560 (4.1); 7.553 (5.5); 7.543 (2.1); 7.531 (9.4); 7.509 (4.6); 7.253 (2.1); 7.246 (10.9); 7.226 (16.0); 7.206 (9.1); 7.199 (1.9); 7.046 (15.1); 7.039 (15.2); 5.757 (3.3); 4.038 (0.4); 4.020 (0.5); 3.326 (90.4); 2.676 (0.6); 2.672 (0.8); 2.667 (0.6); 2.542 (0.4); 2.525 (2.3); 2.511 (47.8); 2.507 (96.5); 2.503 (127.0); 2.498 (91.9); 2.494 (44.8); 2.334 (0.6); 2.329 (0.8); 2.325 (0.6); 1.989 (2.0); 1.235 (0.5); 1.193 (0.5); 1.175 (1.0); 1.158 (0.5); 0.146 (0.7); 0.008 (6.4); 0.000 (164.4); −0.009 (6.4); −0.150 (0.8)

I-1-620:
HPLC-MS: log P=2.61; mass (m/z): 384.9 (M+H)$^+$; $^1$H-NMR (400.0 MHz, DMSO-D$_6$): δ=11.431 (15.3); 8.450 (15.9); 8.443 (16.0); 8.316 (0.4); 7.931 (3.4); 7.915 (4.3); 7.910 (8.0); 7.894 (8.1); 7.889 (5.4); 7.873 (4.5); 7.707 (10.9); 7.697 (13.7); 7.688 (12.9); 7.676 (10.9); 7.551 (6.4); 7.546 (10.5); 7.533 (11.5); 7.528 (12.4); 7.522 (13.2); 7.500 (6.9); 7.495 (6.4); 7.476 (11.3); 7.457 (5.8); 7.431 (6.8); 7.427 (6.7); 7.412 (8.5); 7.407 (8.3); 7.393 (3.7); 7.388 (3.3); 7.055 (16.0); 7.049 (15.9); 5.756 (1.8); 4.038 (0.4); 4.020 (0.4); 3.325 (165.0); 2.675 (0.9); 2.671 (1.2); 2.667 (0.9); 2.506 (142.6); 2.502 (185.6); 2.498 (135.4); 2.333 (0.9); 2.329 (1.2); 2.325 (0.9); 1.989 (1.7); 1.397 (0.4); 1.259 (0.5); 1.234 (0.6); 1.193 (0.5); 1.175 (0.9); 1.157 (0.5); 0.146 (1.2); 0.008 (10.3); 0.000 (240.6); −0.008 (10.1); −0.150 (1.2)

I-1-621:
HPLC-MS: log P=2.57; mass (m/z): 340.9 (M+H)$^+$; $^1$H-NMR (400.0 MHz, DMSO-D$_6$): δ=11.444 (15.0); 8.450 (16.0); 8.444 (16.0); 8.316 (0.4); 7.932 (3.5); 7.915 (4.5); 7.911 (8.2); 7.894 (8.3); 7.890 (5.6); 7.873 (4.6); 7.697 (12.5); 7.676 (10.4); 7.582 (5.7); 7.578 (8.2); 7.563 (10.5); 7.559 (14.8); 7.545 (8.5); 7.538 (14.5); 7.535 (14.8); 7.523 (13.5); 7.514 (7.1); 7.500 (15.9); 7.497 (9.8); 7.480 (5.4); 7.476 (4.5); 7.454 (7.9); 7.451 (7.8); 7.436 (9.9); 7.433 (9.7); 7.418 (3.7); 7.415 (3.5); 7.057 (15.9); 7.051 (15.9); 5.756 (5.7); 3.325 (140.0); 2.675 (1.0); 2.671 (1.3); 2.667 (1.0); 2.506 (151.5); 2.502 (197.2); 2.498 (143.7); 2.333 (0.9); 2.329 (1.2); 2.324 (0.9); 1.989 (0.8); 1.259 (0.4); 1.234 (0.8); 1.175 (0.4); 0.146 (1.1); 0.007 (10.3); 0.000 (219.7); −0.008 (9.9); −0.150 (1.1)

I-1-622:
HPLC-MS: log P=1.95; mass (m/z): 342.0 (M+H)$^+$; $^1$H-NMR (400.0 MHz, DMSO-D$_6$): δ=11.597 (13.9); 11.528 (0.5); 8.527 (8.6); 8.523 (9.3); 8.515 (9.2); 8.511 (9.1); 8.469 (15.7); 8.463 (15.8); 8.354 (0.6); 8.347 (0.5); 8.316 (1.4); 8.077 (8.7); 8.072 (8.9); 8.058 (9.6); 8.053 (9.2); 7.936 (3.4); 7.920 (4.0); 7.915 (7.6); 7.899 (7.8); 7.894 (5.0); 7.878 (4.4); 7.832 (0.4); 7.819 (0.4); 7.783 (0.3); 7.705 (11.9); 7.684 (9.9); 7.555 (10.9); 7.543 (9.8); 7.537 (9.9); 7.530 (11.9); 7.525 (10.4); 7.508 (5.5); 7.061 (16.0); 7.054 (15.9); 7.013 (0.5); 7.007 (0.6); 5.757 (1.2); 3.324 (396.8); 3.038 (0.7); 2.675 (3.0); 2.671 (4.1); 2.666 (2.9); 2.524 (11.9); 2.511 (244.1); 2.506 (484.8); 2.502 (632.6); 2.497 (450.9); 2.493 (215.8); 2.333 (3.0); 2.329 (4.1); 2.324 (3.0);

2.074 (0.9); 1.299 (0.5); 1.259 (0.8); 1.235 (0.8); 0.146 (2.3); 0.008 (19.6); 0.000 (508.7); −0.008 (18.2); −0.150 (2.5)

I-1-623:
HPLC-MS: log P=2.68; mass (m/z): 393.0 (M+H)$^+$;
$^1$H-NMR (400.0 MHz, DMSO-D$_6$): δ=11.751 (10.1); 8.469 (11.2); 8.463 (11.1); 8.316 (0.7); 7.932 (2.5); 7.916 (3.0); 7.911 (5.4); 7.895 (5.6); 7.890 (3.6); 7.874 (3.1); 7.781 (0.9); 7.761 (2.6); 7.752 (1.7); 7.742 (5.1); 7.727 (7.4); 7.711 (10.4); 7.704 (16.0); 7.690 (9.1); 7.682 (4.3); 7.548 (4.1); 7.526 (7.3); 7.503 (3.6); 7.044 (0.5); 7.031 (12.0); 7.024 (11.8); 3.324 (199.3); 3.295 (0.5); 2.680 (0.7); 2.676 (1.3); 2.671 (1.8); 2.667 (1.4); 2.558 (0.6); 2.511 (113.7); 2.506 (221.7); 2.502 (287.0); 2.498 (207.1); 2.333 (1.4); 2.329 (1.8); 2.325 (1.4); 1.259 (0.5); 1.235 (0.5); 0.146 (1.2); 0.008 (11.1); 0.000 (251.8); −0.009 (10.5); −0.027 (0.5); −0.030 (0.5); −0.150 (1.2)

I-1-624:
HPLC-MS: log P=2.79; mass (m/z): 438.8 (M+H)$^+$;
$^1$H-NMR (400.0 MHz, DMSO-D$_6$): δ=20.005 (0.4); 11.109 (10.4); 8.659 (0.6); 8.652 (0.6); 8.521 (0.4); 8.493 (0.4); 8.434 (12.9); 8.428 (12.8); 8.316 (6.13); 8.308 (1.2); 8.301 (1.1); 8.277 (0.4); 8.157 (0.4); 8.140 (1.5); 7.997 (0.4); 7.939 (2.8); 7.923 (3.4); 7.918 (6.4); 7.902 (6.7); 7.897 (4.2); 7.881 (3.6); 7.821 (0.9); 7.809 (15.2); 7.795 (16.0); 7.784 (1.1); 7.771 (0.8); 7.696 (9.5); 7.675 (8.2); 7.650 (1.0); 7.555 (4.5); 7.532 (8.1); 7.511 (4.2); 7.389 (13.3); 7.375 (12.3); 7.347 (0.4); 7.285 (0.7); 7.271 (0.6); 7.236 (0.4); 7.215 (0.5); 7.192 (0.4); 7.170 (0.4); 7.062 (0.7); 7.055 (0.9); 7.038 (7.0); 7.032 (6.8); 6.965 (0.4); 6.359 (0.7); 6.347 (1.1); 6.340 (1.1); 5.757 (6.0); 3.411 (0.6); 3.384 (0.7); 3.324 (1622.0); 3.092 (2.7); 3.058 (1.0); 3.035 (3.2); 2.946 (3.2); 2.679 (5.0); 2.675 (10.3); 2.671 (14.3); 2.666 (10.1); 2.662 (4.7); 2.541 (6.4); 2.524 (38.4); 2.519 (61.1); 2.511 (807.8); 2.506 (1644.2); 2.502 (2160.1); 2.497 (1531.6); 2.493 (717.1); 2.427 (1.0); 2.338 (4.8); 2.333 (10.1); 2.328 (14.0); 2.324 (10.1); 2.212 (0.4); 2.074 (1.3); 1.259 (0.6); 1.235 (1.6); 0.146 (8.1); 0.008 (67.0); 0.000 (1989.3); −0.009 (68.7); −0.081 (0.7); −0.150 (8.5)

I-1-625
HPLC-MS: log P=2.63; mass (m/z): 433.0 (M+H)$^+$;
$^1$H-NMR [DMSO-D$_6$] 7.05-7.06 (m, 1H), 7.20-7.25 (m, 1H), 7.46-7.52 (m, 3H), 7.68-7.70 (m, 1H), 7.87-7.93 (m, 2H), 8.45 (d, 1H), 11.38 (s, 1H).

I-1-626:
HPLC-MS: log P=2.67; mass (m/z): 375.1 (M+H)$^+$;
$^1$H-NMR (400.0 MHz, DMSO-D$_6$): δ=11.444 (15.0); 8.337 (15.5); 8.330 (15.7); 8.316 (0.7); 8.071 (7.0); 8.064 (7.3); 8.051 (7.2); 8.043 (7.2); 7.850 (4.8); 7.838 (12.2); 7.827 (11.2); 7.818 (11.6); 7.815 (12.6); 7.795 (6.0); 7.788 (7.8); 7.775 (7.4); 7.768 (13.6); 7.751 (8.2); 7.716 (6.3); 7.693 (12.8); 7.673 (7.3); 6.990 (15.9); 6.984 (16.0); 5.756 (3.5); 3.772 (0.5); 3.325 (125.6); 2.675 (0.9); 2.671 (1.2); 2.667 (0.9); 2.506 (139.1); 2.502 (183.6); 2.498 (135.7); 2.333 (0.8); 2.329 (1.1); 2.324 (0.9); 1.989 (0.3); 1.259 (0.4); 1.235 (1.1); 0.146 (1.1); 0.008 (9.6); 0.000 (235.1); −0.008 (10.4); −0.150 (1.1)

I-1-627:
HPLC-MS: log P=2.21; mass (m/z): 375.9 (M+H)$^+$;
$^1$H-NMR (400.0 MHz, DMSO-D$_6$): δ=20.011 (0.4); 11.597 (15.1); 8.849 (8.5); 8.838 (8.6); 8.407 (0.8); 8.400 (0.8); 8.356 (15.1); 8.350 (15.7); 8.316 (2.5); 8.283 (0.5); 8.264 (0.4); 8.210 (8.1); 8.191 (9.0); 8.110 (1.0); 8.076 (6.6); 8.069 (7.1); 8.055 (6.9); 8.048 (7.0); 7.998 (0.6); 7.976 (0.7); 7.940 (0.5); 7.858 (4.7); 7.841 (8.6); 7.835 (11.1); 7.829 (8.8); 7.822 (15.5); 7.809 (6.7); 7.800 (6.1); 7.793 (5.4); 7.780 (6.5); 7.773 (6.2); 7.757 (3.2); 7.750 (3.0); 7.639 (0.4); 7.617 (0.5); 7.604 (0.5); 7.559 (0.8); 7.553 (0.8); 7.342 (0.4); 7.333 (0.5); 7.310 (0.4); 6.995 (15.7); 6.988 (16.0); 6.313 (0.7); 6.307 (0.7); 6.283 (0.6); 5.756 (4.3); 5.618 (0.7); 5.612 (0.7); 4.945 (1.2); 3.325 (881.4); 3.025 (1.5); 2.997 (1.6); 2.934 (1.6); 2.671 (7.1); 2.506 (829.8); 2.5022 (1 (086.7); 2.498 (822.1); 2.328 (7.1); 1.235 (0.7); 0.146 (6.1); 0.008 (51.9); 0.000 (1266.1); −0.150 (6.2)

I-1-628:
HPLC-MS: log P=2.39; mass (m/z): 343.0 (M+H)$^+$;
$^1$H-NMR (400.0 MHz, DMSO-D$_6$): δ=11.662 (12.5); 8.353 (14.6); 8.347 (14.6); 8.316 (0.4); 8.076 (6.4); 8.068 (6.6); 8.055 (6.6); 8.048 (6.5); 7.859 (4.3); 7.847 (4.8); 7.837 (8.9); 7.824 (8.5); 7.800 (5.3); 7.793 (4.9); 7.780 (5.8); 7.773 (5.3); 7.758 (2.7); 7.751 (2.5); 7.613 (1.5); 7.597 (3.3); 7.592 (3.1); 7.575 (6.2); 7.559 (3.3); 7.554 (3.7); 7.538 (1.6); 7.249 (2.0); 7.242 (10.9); 7.222 (16.0); 7.202 (9.2); 7.195 (2.0); 6.997 (15.4); 6.991 (15.4); 5.757 (4.3); 4.056 (0.6); 4.038 (1.8); 4.020 (1.9); 4.002 (0.6); 3.325 (107.8); 3.024 (0.6); 2.857 (0.5); 2.676 (0.7); 2.671 (1.0); 2.667 (0.7); 2.524 (2.8); 2.511 (56.8); 2.507 (114.6); 2.502 (151.2); 2.498 (109.0); 2.493 (52.7); 2.333 (0.7); 2.329 (1.0); 2.325 (0.7); 1.989 (8.0); 1.397 (0.6); 1.193 (2.1); 1.175 (4.2); 1.157 (2.1); 0.146 (0.9); 0.008 (7.9); 0.000 (205.6); −0.009 (7.8); −0.150 (0.9)

I-1-629:
HPLC-MS: log P=2.55; mass (m/z): 384.9 (M+H)$^+$;
$^1$H-NMR (400.0 MHz, DMSO-D$_6$): δ=11.351 (10.5); 8.335 (11.3); 8.328 (11.3); 8.316 (0.5); 8.070 (5.2); 8.063 (5.3); 8.049 (5.3); 8.042 (5.3); 7.846 (3.0); 7.833 (3.6); 7.823 (7.2); 7.811 (6.9); 7.795 (4.5); 7.788 (4.1); 7.775 (4.9); 7.768 (4.5); 7.752 (2.1); 7.745 (2.0); 7.706 (6.7); 7.704 (6.7); 7.686 (7.8); 7.684 (7.6); 7.547 (4.1); 7.542 (4.7); 7.528 (7.7); 7.523 (7.8); 7.492 (3.8); 7.489 (4.0); 7.473 (7.6); 7.471 (7.2); 7.455 (3.9); 7.452 (3.6); 7.427 (4.8); 7.422 (4.8); 7.407 (5.8); 7.403 (5.6); 7.389 (2.7); 7.384 (2.4); 7.008 (11.9); 7.001 (11.8); 5.756 (16.0); 4.056 (1.2); 4.038 (3.6); 4.020 (3.7); 4.002 (1.2); 3.324 (64.7); 2.675 (0.5); 2.671 (0.7); 2.666 (0.5); 2.541 (0.4); 2.524 (2.2); 2.511 (42.8); 2.506 (85.1); 2.502 (110.9); 2.497 (79.1); 2.493 (37.7); 2.333 (0.5); 2.329 (0.7); 2.324 (0.5); 1.989 (15.8); 1.397 (5.7); 1.193 (4.3); 1.175 (8.6); 1.157 (4.2); 1.045 (0.5); 1.030 (0.5); 0.146 (0.7); 0.008 (6.9); 0.000 (166.9); −0.009 (6.2); −0.150 (0.7)

I-1-630:
HPLC-MS: log P=2.52; mass (m/z): 341.0 (M+H)$^+$;
$^1$H-NMR (400.0 MHz, DMSO-D$_6$): δ=11.366 (10.9); 8.335 (11.6); 8.329 (11.7); 8.316 (0.6); 8.071 (5.5); 8.064 (5.7); 8.050 (5.7); 8.043 (5.7); 7.846 (3.1); 7.833 (3.7); 7.823 (7.4); 7.811 (7.1); 7.795 (4.7); 7.788 (4.4); 7.775 (5.1); 7.768 (4.7); 7.753 (2.2); 7.746 (2.1); 7.577 (5.1); 7.573 (5.7); 7.558 (7.8); 7.554 (11.2); 7.535 (9.3); 7.532 (9.7); 7.514 (4.1); 7.510 (4.4); 7.496 (7.1); 7.492 (6.1); 7.476 (4.0); 7.472 (3.2); 7.451 (5.6); 7.448 (5.6); 7.433 (7.0); 7.429 (6.9); 7.415 (2.6); 7.411 (2.5); 7.010 (12.2); 7.004 (12.2); 5.756 (16.0); 4.056 (0.6); 4.038 (1.7); 4.020 (1.8); 4.002 (0.6); 3.325 (92.6); 2.675 (0.6); 2.671 (0.9); 2.666 (0.6); 2.541 (0.4); 2.524 (2.5); 2.511 (48.8); 2.506 (99.4); 2.502 (131.4); 2.497 (94.2); 2.493 (44.9); 2.333 (0.6); 2.329 (0.8); 2.324 (0.6); 1.989 (7.6); 1.397 (1.3); 1.234 (0.4); 1.193 (2.1); 1.175 (4.1); 1.157 (2.0); 0.146 (0.8); 0.008 (7.2); 0.000 (187.3); −0.009 (6.7); −0.150 (0.8)

I-1-631:
HPLC-MS: log P=1.91; mass (m/z): 342.1 (M+H)$^+$;
$^1$H-NMR (400.0 MHz, DMSO-D$_6$): δ=11.528 (13.9); 8.524 (8.2); 8.519 (8.9); 8.512 (8.9); 8.507 (8.7); 8.354 (15.3); 8.347 (15.3); 8.316 (2.7); 8.076 (7.3); 8.070 (13.8); 8.066 (10.5); 8.055 (8.6); 8.052 (11.9); 8.048 (14.7); 7.872 (0.4);

7.854 (4.2); 7.842 (4.8); 7.831 (9.5); 7.819 (9.0); 7.801 (5.8); 7.793 (5.3); 7.781 (6.3); 7.773 (5.8); 7.758 (2.8); 7.751 (2.7); 7.552 (8.9); 7.540 (8.7); 7.534 (8.6); 7.522 (8.3); 7.013 (16.0); 7.007 (16.0); 5.844 (0.4); 5.838 (0.5); 5.233 (0.6); 3.324 (675.9); 2.997 (0.7); 2.675 (4.7); 2.671 (6.5); 2.666 (4.7); 2.541 (3.0); 2.524 (17.9); 2.510 (372.2); 2.506 (747.8); 2.502 (976.6); 2.497 (698.4); 2.493 (333.4); 2.333 (4.6); 2.328 (6.4); 2.324 (4.6); 2.074 (1.9); 0.146 (3.7); 0.008 (30.3); 0.000 (825.1); −0.009 (29.7); −0.150 (3.6)

I-1-632:
HPLC-MS: log P=2.64; mass (m/z): 393.0 (M+H)$^+$; $^1$H-NMR (400.0 MHz, DMSO-D$_6$): δ=11.679 (10.7); 8.355 (11.9); 8.348 (11.7); 8.072 (5.3); 8.064 (5.4); 8.051 (5.4); 8.043 (5.2); 7.865 (3.7); 7.853 (4.2); 7.842 (7.0); 7.830 (6.7); 7.797 (4.1); 7.790 (3.8); 7.777 (5.5); 7.770 (4.6); 7.755 (4.3); 7.747 (3.7); 7.738 (5.3); 7.722 (7.8); 7.701 (16.0); 7.684 (4.6); 7.678 (3.9); 6.984 (12.3); 6.978 (12.2); 5.757 (1.7); 3.325 (82.1); 2.676 (0.6); 2.671 (0.8); 2.667 (0.6); 2.541 (0.5); 2.511 (52.9); 2.507 (101.6); 2.502 (130.2); 2.498 (93.0); 2.333 (0.7); 2.329 (0.9); 2.325 (0.6); 1.989 (1.2); 1.260 (0.4); 1.193 (0.3); 1.175 (0.6); 1.157 (0.3); 0.146 (0.6); 0.008 (6.1); 0.000 (124.0); −0.008 (4.6); −0.150 (0.6)

I-1-633:
HPLC-MS: log P=2.73; mass (m/z): 438.8 (M+H)$^+$; $^1$H-NMR (400.0 MHz, DMSO-D$_6$): δ=11.046 (10.4); 8.427 (10.3); 8.324 (11.9); 8.317 (12.3); 8.187 (0.5); 8.180 (0.5); 8.112 (0.6); 8.082 (5.2); 8.075 (5.3); 8.062 (5.3); 8.055 (5.3); 7.847 (3.0); 7.835 (3.7); 7.825 (7.7); 7.812 (7.9); 7.805 (13.9); 7.801 (6.1); 7.792 (16.0); 7.781 (5.5); 7.773 (5.1); 7.758 (2.4); 7.751 (2.0); 7.733 (0.4); 7.696 (0.4); 7.676 (0.4); 7.511 (0.3); 7.386 (11.2); 7.372 (10.6); 7.266 (0.3); 7.253 (0.4); 7.246 (0.5); 7.233 (0.4); 6.993 (6.8); 6.987 (6.6); 6.595 (0.4); 6.290 (0.4); 6.283 (0.4); 5.757 (12.1); 3.324 (197.3); 3.039 (1.1); 3.026 (1.0); 3.014 (0.6); 2.999 (1.2); 2.934 (1.0); 2.675 (1.8); 2.671 (2.3); 2.666 (1.7); 2.541 (1.2); 2.506 (279.3); 2.502 (358.7); 2.497 (256.6); 2.333 (1.7); 2.329 (2.3); 2.324 (1.7); 1.235 (0.4); 0.146 (1.4); 0.008 (11.5); 0.000 (303.0); −0.009 (12.0); −0.150 (1.3)

I-1-634:
HPLC-MS: log P=2.57; mass (m/z): 433.0 (M+H)$^+$; $^1$H-NMR (400.0 MHz, DMSO-D$_6$): δ=11.294 (10.1); 8.336 (10.0); 8.329 (10.0); 8.316 (0.8); 8.071 (4.8); 8.064 (3.9); 8.050 (4.9); 8.043 (4.9); 7.924 (7.4); 7.904 (8.3); 7.848 (2.8); 7.835 (3.3); 7.825 (6.4); 7.813 (6.0); 7.796 (4.0); 7.789 (3.6); 7.776 (4.4); 7.769 (4.1); 7.753 (1.9); 7.746 (1.7); 7.501 (1.4); 7.482 (6.4); 7.472 (9.3); 7.466 (16.0); 7.454 (2.2); 7.250 (0.3); 7.236 (3.3); 7.229 (3.2); 7.220 (3.5); 7.216 (4.0); 7.209 (3.1); 7.201 (2.9); 7.193 (2.6); 7.007 (10.3); 7.000 (10.3); 5.756 (3.6); 4.055 (0.7); 4.038 (2.1); 4.020 (2.1); 4.002 (0.7); 3.323 (134.2); 2.671 (1.5); 2.506 (176.0); 2.502 (229.1); 2.497 (168.3); 2.328 (1.4); 2.324 (1.1); 1.989 (9.0); 1.398 (0.4); 1.259 (0.4); 1.235 (0.6); 1.193 (2.5); 1.175 (4.8); 1.157 (2.4); 0.146 (0.9); 0.008 (8.2); 0.000 (189.4); −0.008 (8.2); −0.150 (0.9)

I-1-635:
HPLC-MS: log P=2.80; mass (m/z): 383.1 (M+H)$^+$; $^1$H-NMR (601.6 MHz, DMSO-D$_6$): δ=11.396 (0.9); 11.342 (11.1); 8.486 (15.4); 8.482 (16.0); 8.337 (11.4); 8.333 (11.4); 8.298 (1.6); 8.283 (4.7); 8.279 (4.4); 8.269 (5.0); 8.265 (8.8); 8.261 (4.7); 8.251 (4.8); 8.247 (4.4); 8.237 (2.7); 8.227 (0.8); 8.214 (0.4); 7.661 (8.9); 7.648 (9.6); 7.56 (0.5); 7.560 (0.5); 7.549 (3.8); 7.547 (5.8); 7.535 (9.6); 7.524 (8.3); 7.522 (8.0); 7.505 (2.3); 7.495 (13.5); 7.491 (9.8); 7.483 (7.2); 7.478 (10.2); 7.466 (3.7); 7.464 (3.4); 7.027 (1.6); 7.023 (1.6); 6.991 (13.4); 6.986 (13.5); 4.024 (3.3); 4.005 (10.2); 3.986 (10.7); 3.967 (3.8); 3.330 (740.6); 2.654 (0.3); 2.617 (4.2); 2.614 (5.8); 2.610 (4.3); 2.608 (2.0); 2.541 (107.4); 2.523 (9.6); 2.520 (12.2); 2.517 (12.2); 2.508 (293.4); 2.505 (638.6); 2.502 (886.8); 2.499 (648.0); 2.496 (303.5); 2.425 (0.5); 2.389 (4.2); 2.386 (5.7); 2.383 (4.2); 2.076 (0.4); 1.298 (0.5); 1.258 (0.7); 1.235 (2.0); 0.854 (0.4); 0.096 (0.9); 0.005 (6.4); 0.000 (218.1); −0.006 (7.0); −0.100 (0.8)

I-1-636:
HPLC-MS: log P=2.31; mass (m/z): 375.0 (M+H)$^+$; $^1$H-NMR (400.0 MHz, DMSO-D$_6$): δ=11.101 (11.1); 8.477 (15.8); 8.471 (16.0); 8.320 (14.0); 8.314 (13.5); 8.288 (4.9); 8.282 (4.4); 8.267 (5.4); 8.261 (9.0); 8.255 (4.8); 8.240 (4.8); 8.240 (4.9); 8.234 (4.4); 6.855 (10.9); 6.849 (10.5); 6.767 (4.7); 6.636 (11.5); 6.505 (5.5); 4.389 (12.5); 4.379 (14.5); 4.367 (12.6); 3.333 (181.6); 3.196 (12.5); 3.185 (14.3); 3.174 (11.6); 2.998 (0.4); 2.677 (0.4); 2.673 (0.6); 2.668 (0.4); 2.543 (53.4); 2.513 (37.1); 2.508 (71.2); 2.504 (90.8); 2.499 (64.8); 2.495 (31.1); 2.335 (0.4); 2.331 (0.6); 2.326 (0.4); 1.234 (0.5); 0.000 (7.8)

I-1-637:
HPLC-MS: log P=2.50; mass (m/z): 397.0 (M+H)$^+$; $^1$H-NMR (601.6 MHz, DMSO-D$_6$): δ=11.433 (6.9); 8.485 (12.8); 8.481 (13.4); 8.359 (11.9); 8.354 (11.8); 8.312 (0.7); 8.282 (3.6); 8.278 (3.5); 8.268 (3.9); 8.264 (6.9); 8.260 (3.8); 8.250 (3.8); 8.246 (3.7); 8.219 (0.4); 7.742 (6.2); 7.734 (6.5); 7.727 (6.6); 7.719 (6.3); 7.523 (6.3); 7.518 (6.6); 7.508 (6.7); 7.503 (6.3); 7.317 (3.7); 7.312 (3.5); 7.303 (6.5); 7.298 (5.8); 7.289 (3.5); 7.284 (3.0); 7.020 (1.0); 7.015 (1.0); 6.989 (15.9); 6.985 (16.0); 3.330 (826.5); 2.996 (0.4); 2.654 (0.9); 2.617 (3.9); 2.614 (5.4); 2.611 (4.0); 2.541 (226.1); 2.523 (8.7); 2.520 (11.0); 2.517 (11.5); 2.507 (274.7); 2.505 (587.5); 2.502 (81.6); 2.499 (609.9); 2.425 (1.0); 2.389 (3.8); 2.386 (5.3); 2.383 (3.9); 1.298 (0.4); 1.258 (0.6); 1.235 (2.2); 0.854 (0.3); 0.097 (0.7); 0.005 (5.5); 0.000 (168.9); −0.006 (6.3); −0.100 (0.7)

I-1-638:
HPLC-MS: log P=2.70; mass (m/z): 403.0 (M+H)$^+$; $^1$H-NMR (400.0 MHz, DMSO-D$_6$): δ=11.627 (14.4); 11.483 (0.9); 8.484 (13.8); 8.478 (14.6); 8.367 (12.7); 8.361 (12.8); 8.317 (0.7); 8.287 (4.1); 8.280 (3.9); 8.266 (4.4); 8.259 (7.7); 8.253 (4.1); 8.238 (4.2); 8.232 (3.8); 8.079 (0.8); 7.907 (9.1); 7.887 (11.0); 7.826 (8.7); 7.806 (12.0); 7.713 (6.5); 7.693 (9.8); 7.673 (4.0); 7.599 (0.5); 7.400 (0.7); 7.379 (1.3); 7.358 (0.6); 6.980 (16.0); 6.973 (15.9); 6.923 (1.1); 6.917 (1.1); 5.758 (1.3); 3.328 (207.6); 3.101 (0.5); 3.086 (0.4); 2.676 (1.5); 2.671 (2.1); 2.667 (1.5); 2.507 (244.3); 2.502 (317.7); 2.498 (231.5); 2.333 (1.5); 2.329 (2.0); 2.325 (1.5); 1.259 (0.4); 1.235 (0.7); 1.191 (0.8); 1.173 (1.4); 1.158 (0.9); 1.141 (0.6); 1.030 (0.5); 0.146 (0.6); 0.008 (5.7); 0.000 (133.5); −0.008 (5.4); −0.150 (0.6)

I-1-639:
HPLC-MS: log P=2.16; mass (m/z): 323.1 (M+H)$^+$; $^1$H-NMR (400.0 MHz, DMSO-D$_6$): δ=9.672 (2.2); 8.462 (2.4); 8.456 (2.4); 8.293 (2.2); 8.287 (2.1); 8.270 (0.7); 8.264 (0.6); 8.249 (0.8); 8.243 (1.3); 8.236 (0.7); 8.221 (0.7); 8.215 (0.6); 6.883 (2.8); 6.877 (2.7); 4.183 (1.7); 4.174 (2.4); 4.169 (2.1); 4.163 (2.5); 4.084 (2.6); 4.079 (2.1); 4.074 (2.4); 4.065 (1.6); 3.345 (19.7); 2.545 (7.8); 2.514 (3.6); 2.510 (6.9); 2.506 (8.8); 2.501 (6.2); 2.497 (2.9); 2.199 (16.0); 0.000 (0.5)

I-1-640 see Synthesis Example 23
I-1-641 see Synthesis Example 32
I-1-642:
HPLC-MS: log P=3.40; mass (m/z): 445.0 (M+H)$^+$; $^1$H-NMR (400.0 MHz, DMSO-D$_6$): δ=11.458 (4.1); 8.430

(3.2); 8.424 (3.4); 8.417 (5.1); 8.405 (5.1); 8.080 (1.3); 7.852 (0.3); 7.837 (2.1); 7.830 (0.7); 7.819 (3.0); 7.791 (2.3); 7.786 (1.8); 7.778 (2.8); 7.769 (4.3); 7.759 (2.6); 7.756 (2.3); 7.750 (2.3); 7.714 (1.8); 7.697 (4.8); 7.679 (2.3); 7.639 (2.1); 7.627 (4.0); 7.614 (2.1); 7.450 (0.5); 7.442 (3.7); 7.437 (1.2); 7.425 (1.4); 7.420 (6.9); 7.415 (1.4); 7.403 (1.1); 7.403 (1.1); 7.398 (3.3); 7.390 (0.3); 7.144 (0.4); 6.998 (4.5); 6.991 (4.5); 4.056 (1.2); 4.038 (3.7); 4.020 (3.8); 4.003 (1.3); 3.326 (23.2); 2.671 (0.3); 2.511 (20.3); 2.507 (40.2); 2.503 (52.7); 2.498 (38.1); 2.494 (18.4); 2.329 (0.3); 1.989 (16.0); 1.193 (4.3); 1.175 (8.5); 1.157 (4.2); 0.008 (0.9); 0.000 (22.5); −0.009 (0.8)

I-1-643 see Synthesis Example 24

I-1-644:
HPLC-MS: log P=0.99; mass (m/z): 304.1 (M+H)$^+$; $^1$H-NMR (400.0 MHz, DMSO-D$_6$): δ=10.958 (1.2); 8.035 (0.9); 8.032 (0.9); 8.029 (0.9); 7.937 (1.9); 7.935 (1.8); 7.829 (1.7); 7.598 (0.6); 7.576 (0.4); 7.397 (1.1); 7.376 (1.8); 7.355 (0.8); 6.905 (1.6); 6.899 (1.6); 4.123 (1.2); 4.109 (3.7); 4.096 (3.8); 4.083 (1.3); 3.877 (7.2); 3.341 (27.3); 3.177 (16.0); 3.164 (15.3); 2.513 (3.4); 2.508 (6.8); 2.504 (8.8); 2.499 (6.4); 2.495 (3.1); 0.008 (0.6); 0.000 (13.6); −0.008 (0.6)

I-1-645:
HPLC-MS: log P=2.41; mass (m/z): 303.1 (M+H)$^+$; $^1$H-NMR (400.0 MHz, DMSO-D$_6$): δ=10.571 (2.6); 8.001 (2.0); 7.996 (2.0); 7.611 (0.6); 7.605 (0.6); 7.595 (0.5); 7.589 (1.3); 7.584 (0.5); 7.573 (0.6); 7.568 (0.8); 7.552 (0.4); 7.390 (2.2); 7.369 (3.7); 7.348 (1.7); 7.188 (1.6); 7.184 (1.8); 7.178 (1.8); 7.174 (1.7); 7.009 (1.6); 7.004 (2.4); 6.999 (1.6); 6.899 (3.2); 6.893 (3.2); 6.064 (1.8); 6.058 (1.9); 6.055 (1.9); 6.048 (1.7); 5.757 (1.7); 3.896 (16.0); 3.330 (11.0); 2.511 (5.0); 2.507 (9.8); 2.503 (12.8); 2.498 (9.2); 2.494 (4.6)

I-1-646:
HPLC-MS: log P=0.70; mass (m/z): 305.0 (M+H)$^+$; $^1$H-NMR (400.0 MHz, DMSO-D$_6$): δ=11.065 (3.1); 8.480 (2.8); 8.474 (2.9); 8.320 (2.5); 8.314 (2.5); 8.288 (0.8); 8.282 (0.8); 8.267 (0.9); 8.261 (1.6); 8.255 (0.9); 8.240 (0.8); 8.234 (0.8); 7.985 (4.6); 7.839 (4.1); 6.967 (3.2); 6.960 (3.2); 3.878 (16.0); 3.330 (8.2); 2.508 (14.0); 2.504 (18.1); 2.500 (13.7)

I-1-647:
HPLC-MS: log P=2.16; mass (m/z): 304.1 (M+H)$^+$; $^1$H-NMR (400.0 MHz, DMSO-D$_6$): δ=10.673 (2.9); 8.472 (2.6); 8.466 (2.7); 8.291 (2.3); 8.285 (2.3); 8.276 (0.9); 8.270 (0.8); 8.255 (0.9); 8.249 (1.5); 8.243 (0.8); 8.228 (0.8); 8.222 (0.8); 7.241 (1.7); 7.237 (1.8); 7.231 (1.8); 7.227 (1.8); 7.021 (1.7); 7.017 (2.5); 7.012 (1.7); 6.962 (3.1); 6.956 (3.1); 6.075 (1.7); 6.069 (1.9); 6.065 (1.9); 6.059 (1.7); 3.898 (16.0); 3.332 (19.5); 2.508 (11.1); 2.504 (14.2); 2.500 (10.4)

I-4-1
HPLC-MS: log P=2.75; mass (m/z): 336.1 (M+H)$^+$; $^1$H-NMR [CD$_3$CN] 3.45 (t, 2H), 3.79 (t, 2H), 6.93-7.01 (m, 2H), 7.10-7.18 (m, 1H), 7.39-7.51 (m, 3H), 7.54-7.57 (m, 1H), 9.01 (br. s, 1H).

I-4-2
see Synthesis Example 6

I-4-3
HPLC-MS: log P=2.59; mass (m/z): 338.1 (M+H)$^+$; $^1$H-NMR [DMSO-D$_6$] 3.41 (t, 2H), 3.76 (t, 2H), 7.06-7.12 (m, 2H), 7.17-7.23 (m, 3H), 7.53-7.61 (m, 1H), 11.46 (br. s, 1H).

I-4-4:
HPLC-MS: log P=2.31; mass (m/z): 428.0 (M+H)$^+$; $^1$H-NMR (400.0 MHz, CD$_3$CN): δ=8.772 (2.9); 7.888 (4.7); 7.886 (4.5); 7.868 (4.9); 7.866 (4.6); 7.455 (2.4); 7.453 (2.2); 7.437 (5.6); 7.434 (5.3); 7.418 (3.8); 7.415 (3.5); 7.382 (0.4); 7.338 (4.8); 7.333 (5.2); 7.319 (3.6); 7.314 (3.5); 7.214 (1.0); 7.199 (2.3); 7.195 (3.8); 7.191 (4.1); 7.184 (1.4); 7.177 (6.7); 7.172 (5.3); 7.164 (1.9); 7.161 (2.0); 7.157 (5.3); 7.153 (2.7); 7.142 (1.6); 7.133 (0.4); 7.036 (0.7); 7.030 (1.1); 7.020 (6.5); 7.014 (0.9); 7.010 (1.0); 6.999 (8.3); 6.997 (8.4); 6.987 (1.2); 6.976 (4.5); 6.965 (0.9); 6.961 (0.6); 6.954 (0.4); 6.932 (0.6); 6.910 (0.3); 3.815 (2.6); 3.812 (4.3); 3.809 (2.5); 3.799 (5.4); 3.796 (8.9); 3.792 (5.0); 3.783 (3.0); 3.780 (4.6); 3.776 (2.6); 2.816 (8.0); 2.800 (16.0); 2.784 (7.5); 2.626 (0.5); 2.132 (38.3); 2.119 (0.6); 2.113 (0.7); 2.107 (0.9); 2.100 (0.6); 1.971 (1.2); 1.964 (4.9); 1.957 (6.0); 1.952 (53.4); 1.945 (100.4); 1.939 (140.1); 1.933 (95.4); 1.927 (48.4); 1.920 (1.6); 1.914 (0.8); 1.780 (0.3); 1.774 (0.6); 1.768 (0.9); 1.762 (0.6); 1.437 (5.1); 1.372 (0.8); 1.285 (0.4); 1.277 (1.0); 1.270 (0.4); 1.203 (0.6); 0.146 (1.0); 0.008 (9.1); 0.000 (253.6); −0.009 (7.8); −0.150 (1.1)

I-4-5:
HPLC-MS: log P=2.21; mass (m/z): 316.1 (M+H)$^+$; $^1$H-NMR (400.0 MHz, CD$_3$CN): δ=8.768 (3.7); 7.470 (0.3); 7.426 (0.4); 7.420 (0.4); 7.371 (2.1); 7.368 (2.3); 7.349 (10.6); 7.331 (10.4); 7.307 (0.6); 7.287 (0.8); 7.270 (1.0); 7.267 (2.6); 7.246 (7.6); 7.228 (7.7); 7.207 (2.5); 7.183 (1.3); 7.168 (2.3); 7.163 (2.1); 7.161 (1.8); 7.153 (1.6); 7.147 (4.2); 7.141 (2.3); 7.133 (2.0); 7.130 (2.1); 7.126 (3.2); 7.111 (1.8); 7.095 (0.5); 7.087 (0.5); 7.074 (0.5); 7.068 (0.4); 7.062 (0.4); 7.058 (0.4); 7.054 (0.5); 7.039 (0.4); 7.029 (0.9); 7.023 (1.3); 7.012 (6.9); 7.003 (1.3); 6.990 (9.4); 6.989 (9.4); 6.978 (1.6); 6.968 (5.2); 6.956 (1.2); 6.952 (1.1); 6.940 (1.1); 6.927 (0.5); 6.918 (0.7); 6.905 (0.4); 6.882 (0.4); 3.832 (0.5); 3.813 (4.9); 3.797 (9.8); 3.781 (5.3); 3.692 (0.5); 3.669 (0.9); 3.645 (0.6); 3.130 (0.6); 3.106 (1.1); 3.082 (0.7); 2.881 (0.4); 2.765 (8.2); 2.749 (16.0); 2.733 (7.8); 2.452 (0.7); 2.430 (0.7); 2.407 (1.2); 2.391 (1.5); 2.353 (0.4); 2.343 (0.4); 2.308 (1.5); 2.275 (38.7); 2.248 (0.8); 2.225 (4.0); 2.136 (25.8); 2.119 (0.4); 2.112 (0.6); 2.106 (0.6); 2.100 (0.4); 1.963 (2.8); 1.957 (3.5); 1.951 (27.3); 1.945 (50.8); 1.939 (70.1); 1.933 (47.4); 1.926 (24.0); 1.912 (1.0); 1.767 (0.4); 1.599 (0.6); 1.372 (5.8); 1.362 (0.5); 1.340 (2.7); 1.294 (0.7); 1.285 (3.4); 1.276 (7.0); 1.271 (1.8); 1.263 (0.8); 1.260 (0.7); 1.243 (0.4); 1.215 (1.3); 1.197 (2.4); 1.179 (1.2); 1.001 (1.2); 0.983 (2.3); 0.966 (1.1); 0.146 (0.6); 0.008 (5.4); 0.000 (132.4); −0.009 (4.1); −0.150 (0.6)

I-4-6:
HPLC-MS: log P=4.45; mass (m/z): 434.1 (M+H)$^+$; $^1$H-NMR (400.0 MHz, CD$_3$CN): δ=7.618 (1.8); 7.598 (1.9); 7.381 (0.7); 7.378 (0.7); 7.362 (1.9); 7.359 (1.8); 7.343 (1.4); 7.340 (1.2); 7.261 (1.3); 7.242 (2.2); 7.235 (2.3); 7.223 (1.0); 7.216 (1.7); 7.153 (0.4); 7.148 (0.4); 7.132 (0.9); 7.126 (0.3); 7.118 (0.4); 7.111 (0.6); 6.949 (1.5); 6.928 (2.2); 6.906 (1.1); 3.841 (1.2); 3.816 (2.6); 3.791 (1.4); 3.159 (1.4); 3.134 (2.7); 3.109 (1.2); 2.352 (16.0); 2.141 (6.7); 1.963 (0.5); 1.957 (0.7); 1.951 (4.8); 1.945 (8.9); 1.939 (12.2); 1.933 (8.3); 1.927 (4.2); 1.341 (0.3); 1.285 (0.4); 0.008 (0.9); 0.000 (19.9); −0.009 (0.6)

I-4-7:
HPLC-MS: log P=2.34; mass (m/z): 370.1 (M+H)$^+$; $^1$H-NMR (400.0 MHz, CD$_3$CN): δ=8.897 (2.7); 7.763 (3.1); 7.745 (4.3); 7.698 (1.3); 7.682 (3.7); 7.680 (3.6); 7.664 (4.0); 7.659 (3.5); 7.655 (3.1); 7.653 (3.5); 7.636 (3.3); 7.634 (3.2); 7.617 (1.4); 7.604 (0.7); 7.594 (0.5); 7.541 (3.9); 7.540 (3.9); 7.524 (3.0); 7.523 (3.2); 7.240 (0.3); 7.218 (1.1); 7.203 (2.1); 7.198 (1.5); 7.196 (1.5); 7.188 (1.2); 7.182 (4.0); 7.176 (1.6); 7.168 (1.5); 7.166 (1.7);

7.161 (2.9); 7.146 (1.5); 7.035 (0.7); 7.030 (1.2); 7.020 (6.6); 7.014 (1.1); 7.009 (1.1); 6.997 (8.9); 6.986 (1.4); 6.975 (4.8); 6.965 (0.9); 6.960 (0.7); 6.945 (0.5); 6.922 (0.7); 6.901 (0.4); 3.797 (2.7); 3.794 (4.5); 3.791 (2.8); 3.781 (5.5); 3.778 (9.1); 3.775 (5.3); 3.765 (3.0); 3.762 (4.7); 3.759 (2.7); 3.445 (0.7); 3.427 (0.4); 3.279 (0.5); 3.266 (0.5); 2.754 (8.2); 2.738 (16.0); 2.721 (7.6); 2.146 (9.8); 1.963 (0.8); 1.957 (1.1); 1.951 (8.9); 1.945 (16.6); 1.939 (23.0); 1.932 (15.7); 1.926 (8.0); 1.373 (2.1); 1.341 (0.9); 1.285 (1.2); 1.276 (2.8); 1.270 (1.5); 1.171 (0.5); 1.006 (0.5); 0.008 (1.9); 0.000 (47.8); −0.009 (1.5)

I-4-8:

HPLC-MS: log P=2.37; mass (m/z): 378.0 (M+H)$^+$;
$^1$H-NMR (400.0 MHz, CD$_3$CN): δ=8.819 (2.3); 7.650 (4.1); 7.631 (4.4); 7.629 (4.4); 7.498 (3.4); 7.495 (3.7); 7.478 (4.5); 7.474 (4.7); 7.458 (0.7); 7.450 (1.6); 7.445 (4.2); 7.439 (9.8); 7.432 (7.3); 7.422 (8.8); 7.421 (8.8); 7.404 (1.5); 7.401 (1.4); 7.397 (0.6); 7.384 (3.2); 7.377 (2.6); 7.368 (2.1); 7.364 (3.1); 7.361 (2.2); 7.358 (2.5); 7.348 (3.5); 7.343 (3.3); 7.328 (3.8); 7.325 (3.8); 7.308 (2.4); 7.304 (2.2); 7.290 (0.4); 7.286 (0.4); 7.259 (0.3); 7.253 (0.5); 7.245 (0.6); 7.236 (0.6); 7.231 (0.4); 7.149 (2.8); 7.146 (2.9); 7.130 (3.7); 7.127 (3.8); 7.111 (1.9); 7.107 (1.9); 5.447 (2.0); 3.813 (5.6); 3.797 (11.7); 3.780 (6.0); 3.390 (0.4); 3.373 (0.9); 3.355 (0.4); 2.876 (7.8); 2.860 (16.0); 2.843 (7.4); 2.713 (0.5); 2.172 (41.2); 2.169 (40.4); 1.964 (1.2); 1.958 (1.5); 1.952 (12.1); 1.946 (22.9); 1.940 (32.1); 1.934 (22.5); 1.928 (12.0); 1.372 (2.2); 1.340 (0.8); 1.285 (1.0); 1.276 (2.5); 1.271 (1.0); 0.008 (0.7); 0.000 (19.6)

I-2-1 see Synthesis Example 20

I-2-2

HPLC-MS: log P=2.89; mass (m/z): 333.0 (M+H)$^+$;
$^1$H-NMR [CD$_3$CN] 7.43-7.47 (m, 1H), 7.48-7.55 (m, 4H), 7.60-7.66 (m, 3H), 8.38 (s, 1H), 9.50 (br. s, 1H).

I-2-3

HPLC-MS: log P=3.03; mass (m/z): 424.9 (M+H)$^+$;
$^1$H-NMR [CD$_3$CN] 7.22-7.26 (m, 1H), 7.48-7.55 (m, 4H), 7.61-7.66 (m, 2H), 7.97-7.99 (m, 1H), 8.38 (s, 1H), 9.43 (br. s, 1H).

I-2-4

HPLC-MS: log P=2.54; mass (m/z): 368.0 (M+H)$^+$;
$^1$H-NMR [CD$_3$CN] 7.48-7.56 (m, 2H), 7.62-7.66 (m, 2H), 7.73-7.76 (m, 1H), 8.11-8.13 (m, 1H), 8.36 (s, 1H), 8.83-8.84 (m, 1H), 9.68 (br. s, 1H).

I-2-5

HPLC-MS: log P=2.20; mass (m/z): 334.0 (M+H)$^+$;
$^1$H-NMR [CD$_3$CN] 7.46-7.56 (m, 3H), 7.56-7.66 (m, 2H), 8.01-8.03 (m, 1H), 8.38 (s, 1H), 8.51-8.53 (m, 1H), 9.64 (br. s, 1H).

I-2-6

HPLC-MS: log P=3.03; mass (m/z): 410.9 (M+H)$^+$;
$^1$H-NMR [CD$_3$CN] 7.45-7.47 (m, 1H), 7.53-7.56 (m, 1H), 7.58-7.60 (m, 1H), 7.69-7.77 (m, 3H), 7.81-7.85 (m, 2H), 8.35 (s, 1H), 9.50 (br. s, 1H).

I-2-7

HPLC-MS: log P=2.93; mass (m/z): 376.9 (M+H)$^+$;
$^1$H-NMR [CD$_3$CN] 7.42-7.64 (m, 7H), 7.81-7.83 (m, 1H), 8.37 (s, 1H), 9.59 (br. s, 1H).

I-2-8

HPLC-MS: log P=2.58; mass (m/z): 411.9 (M+H)$^+$;
$^1$H-NMR [CD$_3$CN] 7.43-7.49 (m, 1H), 7.53-7.61 (m, 2H), 7.73-7.76 (m, 1H), 7.81-7.83 (m, 1H), 8.11-8.13 (m, 1H), 8.35 (s, 1H), 8.83-8.84 (m, 1H), 9.67 (br. s, 1H).

I-2-9

HPLC-MS: log P=2.29; mass (m/z): 377.9 (M+H)$^+$;
$^1$H-NMR [CD$_3$CN] 7.44-7.50 (m, 2H), 7.53-7.61 (m, 2H), 7.81-7.83 (m, 1H), 8.01-8.03 (m, 1H), 8.37 (s, 1H), 8.51-8.53 (m, 1H), 9.62 (br. s, 1H).

I-2-10

HPLC-MS: log P=2.38; mass (m/z): 368.1 (M+H)$^+$;
$^1$H-NMR [DMSO-D$_6$] 7.70-7.81 (m, 4H), 7.87-7.88 (m, 1H), 8.32-8.34 (m, 1H), 8.42 (s, 1H), 8.61-8.63 (m, 1H), 11.85 (br. s, 1H).

I-2-11

HPLC-MS: log P=2.60; mass (m/z): 402.0 (M+H)$^+$;
$^1$H-NMR [CD$_3$CN] 7.58-7.61 (m, 1H), 7.72-7.76 (m, 3H), 7.84-7.86 (m, 1H), 8.12-8.14 (m, 1H), 8.55-8.56 (m, 1H), 8.94 (br. s, 1H).

I-2-12

HPLC-MS: log P=2.22; mass (m/z): 334.0 (M+H)$^+$;
$^1$H-NMR [DMSO-D$_6$] 7.45-7.49 (m, 1H), 7.51-7.60 (m, 2H), 7.64-7.66 (m, 1H), 7.70-7.73 (m, 1H), 8.32-8.34 (m, 1H), 8.44 (s, 1H), 8.61-8.63 (m, 1H), 11.77 (s, 1H).

I-2-13

HPLC-MS: log P=2.26; mass (m/z): 377.9 (M+H)$^+$;
$^1$H-NMR [DMSO-D$_6$] 7.43-7.47 (m, 1H), 7.49-7.53 (m, 1H), 7.60-7.63 (m, 1H), 7.71-7.75 (m, 2H), 8.32-8.34 (m, 1H), 8.44 (s, 1H), 8.61-8.63 (m, 1H), 11.75 (s, 1H).

I-2-14

HPLC-MS: log P=2.36; mass (m/z): 425.9 (M+H)$^+$;
$^1$H-NMR [DMSO-D$_6$] 7.23-7.28 (m, 1H), 7.49-7.56 (m, 2H), 7.70-7.72 (m, 1H), 7.94-7.96 (m, 1H), 8.32-8.34 (m, 1H), 8.43 (s, 1H), 8.61-8.63 (m, 1H), 11.69 (s, 1H).

I-2-15

HPLC-MS: log P=2.09; mass (m/z): 336.1 (M+H)$^+$;
$^1$H-NMR [DMSO-D$_6$] 7.25-7.30 (m, 2H), 7.59-7.67 (m, 1H), 7.71-7.74 (m, 1H), 8.32-8.35 (m, 1H), 8.44 (s, 1H), 8.62-8.63 (m, 1H), 12.07 (s, 1H).

I-2-16

HPLC-MS: log P=2.19; mass (m/z): 389.9 (M+H)$^+$;
$^1$H-NMR [DMSO-D$_6$] 3.88 (s, 3H), 7.70-7.73 (m, 1H), 8.31-8.34 (m, 1H), 8.38 (s, 1H), 8.61-8.63 (m, 1H), 11.60 (s, 1H).

I-2-17

HPLC-MS: log P=2.46; mass (m/z): 412.0 (M+H)$^+$;
$^1$H-NMR [DMSO-D$_6$] 7.61-7.65 (m, 1H), 7.72-7.83 (m, 3H), 7.87-7.88 (m, 1H), 8.39 (s, 1H), 8.45-8.47 (m, 1H), 8.64-8.66 (m, 1H), 11.84 (s, 1H).

I-2-18

HPLC-MS: log P=2.43; mass (m/z): 469.8 (M+H)$^+$;
$^1$H-NMR [DMSO-D$_6$] 7.23-7.28 (m, 1H), 7.49-7.56 (m, 2H), 7.61-7.64 (m, 1H), 7.94-7.96 (m, 1H), 8.40 (s, 1H), 8.44-8.47 (m, 1H), 8.64-8.65 (m, 1H), 11.68 (s, 1H).

I-2-19:

HPLC-MS: log P=3.21; mass (m/z): 401.0 (M+H)$^+$;
$^1$H-NMR (400.0 MHz, DMSO-D$_6$): δ=11.142 (10.9); 7.903 (4.9); 7.884 (7.4); 7.855 (2.3); 7.837 (5.7); 7.818 (6.2); 7.811 (6.5); 7.807 (6.4); 7.792 (11.9); 7.787 (10.1); 7.773 (16.0); 7.764 (8.2); 7.673 (2.6); 7.670 (2.9); 7.655 (6.0); 7.651 (5.8); 7.635 (4.5); 7.631 (4.3); 7.621 (5.3); 7.618 (5.3); 7.602 (6.0); 7.599 (6.0); 7.583 (2.5); 3.324 (66.4); 2.675 (0.9); 2.671 (1.2); 2.666 (0.9); 2.662 (0.4); 2.524 (4.5); 2.511 (67.9); 2.506 (132.1); 2.502 (171.5); 2.497 (123.4); 2.493 (59.6); 2.333 (0.8); 2.329 (1.1); 2.324 (0.8); 1.989 (0.4); 1.397 (1.3); 1.336 (1.5); 1.299 (2.5); 1.259 (3.5); 1.249 (1.5); 1.235 (1.4); 0.008 (0.4); 0.000 (9.1)

I-2-20:

HPLC-MS: log P=4.87; mass (m/z): 573.0 (M+H)$^+$;
$^1$H-NMR (400.0 MHz, DMSO-D$_6$): δ=7.924 (9.9); 7.903 (11.4); 7.880 (11.4); 7.840 (5.8); 7.824 (11.5); 7.805 (6.5); 7.783 (7.7); 7.764 (9.3); 7.745 (3.5); 7.698 (3.5); 7.694 (9.3); 7.677 (8.7); 7.675 (7.2); 7.664 (4.7); 7.660 (5.9); 7.656 (5.0); 7.652 (4.2); 7.642 (9.4); 7.637 (9.4); 7.633

(3.7); 7.618 (3.8); 7.613 (2.4); 7.580 (5.2); 7.576 (4.9); 7.561 (5.8); 7.557 (5.5); 7.542 (2.3); 7.538 (2.1); 3.831 (0.3); 3.812 (0.3); 3.789 (0.4); 3.770 (0.5); 3.750 (0.3); 3.329 (18.1); 3.179 (0.5); 3.166 (0.5); 2.678 (0.4); 2.674 (0.5); 2.669 (0.3); 2.527 (2.2); 2.514 (31.1); 2.509 (59.6); 2.505 (76.3); 2.500 (54.7); 2.496 (26.5); 2.336 (0.4); 2.332 (0.5); 2.327 (0.4); 1.339 (4.1); 1.301 (2.0); 1.259 (2.9); 1.250 (5.0); 1.235 (2.1); 0.000 (4.5)

I-2-21:

HPLC-MS: log P=2.93; mass (m/z): 381.0 (M+H)$^+$; $^1$H-NMR (400.0 MHz, CD$_3$CN): δ=8.847 (1.0); 7.854 (1.4); 7.834 (1.9); 7.760 (2.3); 7.752 (4.9); 7.732 (0.4); 7.721 (0.9); 7.712 (1.0); 7.701 (1.0); 7.692 (0.8); 7.680 (0.4); 7.649 (1.1); 7.643 (1.0); 7.635 (0.9); 7.630 (1.2); 7.625 (1.9); 7.622 (1.5); 7.615 (1.1); 7.610 (1.0); 7.607 (1.1); 7.605 (1.1); 7.597 (1.7); 7.528 (0.6); 7.516 (1.9); 7.510 (2.8); 7.502 (2.9); 7.492 (2.1); 7.475 (0.4); 5.446 (2.0); 2.367 (16.0); 2.141 (22.9); 1.963 (0.7); 1.952 (7.5); 1.945 (13.8); 1.939 (19.2); 1.933 (13.2); 1.927 (6.7); 0.000 (1.4)

I-2-22:

HPLC-MS: log P=4.54; mass (m/z): 553.2 (M+H)$^+$; $^1$H-NMR (400.0 MHz, CD$_3$CN): δ=7.815 (2.2); 7.797 (3.1); 7.699 (1.4); 7.695 (2.7); 7.691 (2.6); 7.684 (9.7); 7.682 (8.0); 7.675 (3.1); 7.665 (1.5); 7.656 (1.4); 7.646 (1.2); 7.633 (0.5); 7.552 (0.7); 7.548 (1.5); 7.532 (1.8); 7.528 (2.0); 7.515 (0.9); 7.511 (1.0); 7.497 (1.6); 7.493 (1.5); 7.477 (0.8); 7.473 (0.8); 7.463 (1.1); 7.458 (1.0); 7.444 (1.5); 7.439 (1.4); 7.425 (0.9); 7.421 (0.8); 7.347 (1.7); 7.343 (1.5); 7.328 (1.3); 7.323 (1.1); 2.386 (16.0); 2.146 (9.3); 1.964 (0.6); 1.957 (1.0); 1.952 (8.9); 1.946 (16.7); 1.939 (23.3); 1.933 (16.0); 1.927 (8.2); 1.436 (6.0); 1.372 (3.1); 1.341 (0.6); 1.285 (0.8); 1.276 (3.5); 0.000 (1.6)

I-2-23:

HPLC-MS: log P=3.64; mass (m/z): 550.9 (M+H)$^+$; $^1$H-NMR (400.0 MHz, CD$_3$CN): δ=8.489 (11.3); 8.484 (11.6); 8.477 (11.6); 8.472 (11.4); 8.050 (11.4); 8.045 (11.2); 8.031 (12.2); 8.026 (11.6); 7.778 (4.5); 7.775 (4.8); 7.759 (5.7); 7.755 (5.9); 7.572 (1.6); 7.568 (1.9); 7.553 (5.2); 7.549 (4.8); 7.534 (6.1); 7.530 (5.4); 7.522 (3.8); 7.516 (6.0); 7.502 (4.3); 7.497 (7.6); 7.490 (7.9); 7.485 (5.2); 7.478 (2.6); 7.472 (16.0); 7.466 (4.2); 7.460 (12.3); 7.453 (11.8); 7.441 (11.3); 7.426 (0.4); 7.420 (0.4); 7.241 (0.4); 7.235 (0.4); 5.448 (4.6); 2.464 (0.4); 2.269 (0.4); 2.224 (0.4); 2.224 (0.4); 2.161 (62.5); 2.114 (0.5); 2.108 (0.6); 2.102 (0.4); 2.042 (0.4); 1.965 (5.5); 1.959 (9.0); 1.953 (39.4); 1.947 (68.6); 1.940 (89.5); 1.934 (60.7); 1.928 (30.8); 1.915 (0.3); 1.775 (0.4); 1.769 (0.5); 1.763 (0.4); 1.386 (0.7); 1.372 (9.0); 1.340 (2.1); 1.285 (3.0); 1.276 (10.2); 1.270 (1.9); 1.216 (0.4); 0.881 (0.4); 0.146 (0.6); 0.008 (6.2); 0.000 (143.9); −0.009 (4.3); −0.150 (0.6)

I-2-24:

HPLC-MS: log P=2.92; mass (m/z): 439.0 (M+H)$^+$; $^1$H-NMR (400.0 MHz, CD$_3$CN): δ=8.793 (1.0); 7.989 (2.0); 7.989 (2.0); 7.970 (2.1); 7.650 (1.2); 7.637 (1.3); 7.626 (2.9); 7.614 (1.7); 7.603 (1.8); 7.574 (1.3); 7.555 (2.4); 7.532 (1.9); 7.513 (4.6); 7.501 (3.7); 7.493 (3.1); 7.475 (0.6); 7.256 (1.1); 7.239 (1.9); 7.219 (0.9); 2.424 (16.0); 2.143 (18.3); 1.971 (0.4); 1.964 (1.3); 1.957 (1.9); 1.952 (12.6); 1.946 (23.4); 1.939 (32.3); 1.933 (22.4); 1.927 (11.7); 1.372 (3.1); 1.340 (0.7); 1.284 (1.0); 1.276 (3.3); 1.220 (0.4); 0.000 (0.9)

I-2-25:

HPLC-MS: log P=4.68; mass (m/z): 668.9 (M+H)$^+$; $^1$H-NMR (400.0 MHz, CD$_3$CN): δ=7.922 (2.8); 7.921 (2.9); 7.902 (3.0); 7.901 (3.0); 7.608 (2.2); 7.604 (2.4); 7.589 (3.0); 7.585 (3.7); 7.581 (1.4); 7.565 (1.5); 7.561 (1.7); 7.526 (0.6); 7.521 (0.7); 7.507 (1.3); 7.503 (1.3); 7.488 (0.9); 7.483 (0.9); 7.478 (1.0); 7.474 (1.0); 7.464 (1.8); 7.462 (1.9); 7.459 (1.7); 7.455 (1.5); 7.445 (3.1); 7.443 (3.2); 7.436 (0.8); 7.426 (1.6); 7.424 (1.6); 7.388 (1.6); 7.383 (1.4); 7.368 (1.1); 7.364 (1.0); 7.192 (1.6); 7.188 (1.6); 7.172 (2.5); 7.169 (2.6); 7.153 (1.3); 7.149 (1.4); 5.447 (6.0); 2.443 (16.0); 2.286 (0.6); 2.146 (27.6); 1.964 (0.5); 1.958 (0.8); 1.952 (7.2); 1.946 (13.6); 1.940 (19.1); 1.933 (13.1); 1.927 (6.7); 1.372 (2.4); 1.340 (0.4); 1.284 (0.6); 1.276 (2.7); 1.263 (0.6); 1.216 (0.5); 0.000 (1.3)

I-2-26:

HPLC-MS: log P=3.22; mass (m/z): 444.9 (M+H)$^+$; $^1$H-NMR (400.0 MHz, CD$_3$CN): δ=8.914 (3.7786 (6.0); 7.860 (6.0); 7.844 (9.7); 7.830 (7.3); 7.758 (15.3); 7.735 (5.1); 7.715 (4.7); 7.651 (4.2); 7.632 (6.7); 7.592 (4.0); 7.573 (7.0); 7.554 (3.9); 7.517 (4.8); 7.497 (6.6); 7.480 (2.9); 7.447 (0.4); 7.426 (0.8); 7.420 (0.8); 7.262 (0.4); 7.257 (0.4); 7.241 (0.6); 7.236 (0.5); 7.171 (0.5); 7.165 (0.5); 7.150 (0.3); 5.447 (1.4); 2.144 (88.5); 2.119 (0.6); 2.113 (0.9); 2.107 (1.0); 2.101 (0.7); 2.095 (0.4); 1.964 (7.6); 1.958 (11.2); 1.952 (60.9); 1.946 (110.3); 1.940 (148.5); 1.933 (101.8); 1.927 (52.0); 1.914 (0.8); 1.780 (0.3); 1.774 (0.6); 1.768 (0.9); 1.762 (0.6); 1.756 (0.4); 1.402 (0.4); 1.396 (0.4); 1.386 (0.6); 1.372 (14.2); 1.340 (2.3); 1.284 (3.2); 1.276 (16.0); 1.216 (0.5); 0.881 (0.3); 0.146 (0.8); 0.008 (7.3); 0.000 (194.2); −0.009 (6.2); −0.150 (0.8)

I-2-27:

HPLC-MS: log P=4.87; mass (m/z): 617.0 (M+H)$^+$; $^1$H-NMR (400.0 MHz, CD$_3$CN): δ=7.837 (6.5); 7.819 (8.5); 7.816 (8.0); 7.779 (0.4); 7.769 (2.5); 7.765 (3.8); 7.745 (16.0); 7.741 (10.2); 7.726 (14.8); 7.722 (12.9); 7.704 (8.4); 7.686 (5.6); 7.682 (5.1); 7.668 (1.9); 7.664 (1.7); 7.552 (1.5); 7.549 (1.8); 7.534 (4.8); 7.530 (5.0); 7.515 (5.3); 7.511 (4.8); 7.504 (3.8); 7.499 (5.1); 7.485 (4.1); 7.480 (5.3); 7.473 (0.4); 7.466 (1.9); 7.461 (1.7); 7.443 (6.0); 7.438 (5.4); 7.424 (3.6); 7.419 (3.7); 2.467 (0.3); 2.463 (0.5); 2.458 (0.3); 2.269 (0.5); 2.148 (89.1); 2.119 (0.6); 2.113 (0.8); 2.107 (1.0); 2.101 (0.7); 2.095 (0.4); 1.964 (8.3); 1.958 (13.5); 1.952 (65.0); 1.946 (116.5); 1.940 (154.0); 1.933 (105.1); 1.927 (53.8); 1.914 (0.8); 1.780 (0.4); 1.774 (0.7); 1.768 (0.9); 1.762 (0.6); 1.756 (0.3); 1.437 (2.0); 1.376 (1.5); 1.372 (6.0); 1.340 (1.2); 1.285 (1.6); 1.276 (6.7); 1.217 (0.4); 0.146 (1.0); 0.008 (8.3); 0.000 (245.9); −0.009 (8.2); −0.150 (1.0)

I-2-28:

HPLC-MS: log P=2.77; mass (m/z): 445.9 (M+H)$^+$; $^1$H-NMR (400.0 MHz, CD$_3$CN): δ=8.999 (3.6); 8.855 (6.0); 8.844 (6.1); 8.816 (0.7); 8.156 (5.6); 8.137 (6.1); 8.100 (0.6); 7.852 (5.8); 7.832 (6.5); 7.771 (4.5); 7.759 (5.2); 7.752 (4.8); 7.740 (4.5); 7.723 (0.9); 7.711 (0.7); 7.693 (0.4); 7.680 (0.5); 7.651 (4.3); 7.632 (7.4); 7.596 (3.9); 7.577 (6.8); 7.558 (3.7); 7.521 (4.5); 7.502 (6.3); 7.484 (2.9); 7.464 (0.8); 7.458 (0.8); 7.447 (0.7); 7.426 (1.0); 7.420 (0.9); 7.261 (0.4); 7.256 (0.4); 7.241 (0.7); 7.235 (0.7); 7.171 (0.5); 7.165 (0.5); 7.150 (0.4); 7.144 (0.3); 5.447 (0.4); 2.141 (55.3); 2.113 (2.5); 2.107 (2.2); 2.101 (1.5); 2.095 (0.9); 1.964 (9.6); 1.958 (15.8); 1.952 (80.9); 1.946 (144.9); 1.940 (193.5); 1.934 (133.4); 1.927 (69.0); 1.780 (0.5); 1.774 (0.9); 1.768 (1.2); 1.762 (0.8); 1.756 (0.5); 1.386 (0.8); 1.372 (15.0); 1.340 (4.2); 1.285 (5.5); 1.276 (16.0); 1.217 (0.6); 0.881 (0.6); 0.858 (0.4); 0.146 (1.0); 0.008 (9.4); 0.000 (227.6); −0.009 (9.5); −0.150 (1.1)

I-2-29:

HPLC-MS: log P=3.09; mass (m/z): 412.9 (M+H)$^+$; $^1$H-NMR (400.0 MHz, CD$_3$CN): δ=8.843 (1.6); 7.844 (3.2); 7.825 (3.6); 7.644 (4.1); 7.588 (2.8); 7.569 (5.0); 7.549 (4.4); 7.537 (5.5); 7.515 (6.5); 7.495 (6.1); 7.472 (4.0); 7.453 (3.1); 7.426 (1.5); 7.420 (1.2); 7.261 (0.4); 7.256

(0.4); 7.240 (0.6); 7.235 (0.6); 7.171 (0.5); 7.165 (0.5); 7.150 (0.3); 7.143 (0.3); 5.446 (0.7); 2.139 (37.2); 2.119 (0.4); 2.113 (0.5); 2.107 (0.7); 2.101 (0.4); 1.964 (4.9); 1.958 (7.3); 1.952 (39.9); 1.946 (71.4); 1.939 (95.7); 1.933 (65.2); 1.927 (33.2); 1.914 (0.4); 1.774 (0.4); 1.768 (0.6); 1.762 (0.4); 1.432 (1.3); 1.386 (0.7); 1.372 (15.0); 1.340 (2.8); 1.284 (3.7); 1.276 (16.0); 1.216 (0.8); 0.881 (0.4); 0.857 (0.4); 0.146 (0.6); 0.008 (4.8); 0.000 (127.1); −0.009 (3.7); −0.149 (0.6)

I-2-30:
HPLC-MS: log P=4.87; mass (m/z): 550.9 (M+H)$^+$; $^1$H-NMR (400.0 MHz, CD$_3$CN): δ=7.774 (2.2); 7.771 (2.3); 7.755 (2.8); 7.751 (2.8); 7.685 (3.0); 7.682 (4.9); 7.679 (3.7); 7.666 (3.5); 7.664 (5.0); 7.663 (4.8); 7.661 (4.2); 7.560 (0.8); 7.556 (1.0); 7.541 (2.6); 7.537 (2.8); 7.522 (2.8); 7.518 (2.6); 7.512 (0.7); 7.508 (2.2); 7.503 (2.8); 7.495 (0.5); 7.488 (2.3); 7.484 (3.2); 7.474 (0.9); 7.463 (11.2); 7.460 (5.3); 7.454 (16.0); 7.451 (8.7); 7.446 (1.2); 7.440 (2.0); 7.435 (2.2); 7.431 (1.0); 7.425 (1.2); 7.414 (4.3); 7.403 (5.0); 7.395 (3.7); 7.393 (2.8); 7.386 (2.7); 7.383 (2.8); 7.374 (1.9); 5.446 (0.8); 2.547 (1.0); 2.295 (0.3); 2.137 (11.6); 1.964 (2.5); 1.958 (4.0); 1.952 (18.6); 1.946 (32.8); 1.940 (43.2); 1.933 (29.8); 1.927 (15.3); 1.372 (2.4); 1.340 (0.4); 1.284 (0.6); 1.276 (2.6); 1.217 (0.3); 0.015 (0.3); 0.008 (2.5); 0.000 (69.8); −0.009 (2.3)

I-2-31:
HPLC-MS: log P=2.46; mass (m/z): 411.9 (M+H)$^+$; $^1$H-NMR (400.0 MHz, CD$_3$CN): δ=9.068 (2.5); 8.524 (4.9); 8.045 (3.9); 8.028 (4.2); 7.848 (4.7); 7.828 (5.3); 7.650 (3.1); 7.632 (4.7); 7.591 (3.9); 7.573 (6.6); 7.554 (3.8); 7.517 (5.4); 7.498 (9.7); 7.482 (6.7); 7.426 (1.0); 7.420 (1.0); 7.411 (0.4); 7.399 (0.3); 7.393 (0.3); 7.261 (0.4); 7.256 (0.4); 7.240 (0.6); 7.235 (0.6); 7.171 (0.5); 7.165 (0.5); 7.150 (0.3); 2.465 (0.4); 2.460 (0.5); 2.455 (0.4); 2.158 (128.3); 2.120 (0.7); 2.114 (0.9); 2.107 (1.1); 2.101 (0.8); 2.095 (0.4); 1.964 (8.6); 1.958 (14.3); 1.952 (67.7); 1.946 (119.5); 1.940 (156.8); 1.934 (106.8); 1.928 (54.6); 1.915 (1.0); 1.781 (0.4); 1.775 (0.7); 1.769 (1.0); 1.762 (0.7); 1.756 (0.4); 1.386 (1.1); 1.372 (14.4); 1.340 (3.8); 1.308 (0.4); 1.297 (0.7); 1.284 (5.1); 1.276 (16.0); 1.270 (3.4); 1.217 (0.7); 1.200 (0.6); 1.017 (0.5); 0.963 (0.4); 0.881 (0.6); 0.856 (0.5); 0.708 (0.4); 0.146 (1.1); 0.008 (9.6); 0.000 (260.2); −0.009 (8.5); −0.150 (1.2)

I-2-32:
HPLC-MS: log P=3.24; mass (m/z): 502.9 (M+H)$^+$; $^1$H-NMR (400.0 MHz, CD$_3$CN): δ=8.786 (1.3); 7.997 (1.8); 7.978 (1.9); 7.846 (2.2); 7.827 (2.4); 7.634 (1.8); 7.589 (2.2); 7.572 (4.2); 7.554 (3.4); 7.540 (2.1); 7.516 (3.8); 7.496 (3.6); 7.477 (1.4); 7.448 (0.4); 7.426 (0.8); 7.420 (0.8); 7.262 (1.4); 7.256 (1.6); 7.248 (1.9); 7.241 (1.7); 7.235 (1.6); 7.171 (0.5); 7.165 (0.6); 7.150 (0.4); 7.143 (0.4); 5.446 (0.5); 4.055 (0.5); 2.134 (27.2); 2.119 (0.4); 2.113 (0.5); 2.107 (0.5); 2.101 (0.4); 1.971 (1.1); 1.964 (4.1); 1.958 (6.4); 1.952 (33.2); 1.946 (59.2); 1.939 (78.9); 1.933 (54.2); 1.927 (27.9); 1.774 (0.3); 1.768 (0.5); 1.437 (1.0); 1.432 (0.4); 1.386 (0.6); 1.372 (15.5); 1.340 (2.9); 1.285 (4.0); 1.276 (16.0); 1.216 (1.6); 1.203 (0.5); 0.881 (0.4); 0.146 (0.5); 0.008 (4.5); 0.000 (110.1); −0.009 (4.0); −0.150 (0.5)

I-2-33:
HPLC-MS: log P=3.06; mass (m/z): 471.0 (M+H)$^+$; $^1$H-NMR (400.0 MHz, CD$_3$CN): δ=9.482 (2.7); 8.371 (16.0); 7.986 (6.8); 7.967 (6.9); 7.833 (5.6); 7.830 (5.7); 7.813 (6.3); 7.810 (6.3); 7.611 (3.1); 7.607 (3.7); 7.591 (7.6); 7.587 (7.8); 7.571 (4.4); 7.568 (4.4); 7.553 (8.0); 7.550 (8.3); 7.534 (11.2); 7.529 (15.7); 7.511 (6.6); 7.509 (6.6); 7.492 (2.3); 7.490 (2.3); 7.483 (4.4); 7.479 (4.1); 7.463 (5.2); 7.460 (4.8); 7.445 (2.6); 7.440 (2.4); 7.264 (3.4); 7.258 (3.4); 7.246 (4.0); 7.244 (4.4); 7.241 (4.4); 7.238 (3.9); 7.226 (2.8); 7.221 (2.7); 2.462 (0.4); 2.148 (212.3); 2.146 (201.8); 2.119 (0.9); 2.113 (1.2); 2.107 (1.3); 2.101 (0.9); 2.095 (0.5); 1.964 (12.7); 1.958 (20.2); 1.952 (86.6); 1.946 (151.0); 1.940 (197.2); 1.933 (135.1); 1.927 (69.2); 1.780 (0.5); 1.774 (0.8); 1.768 (1.1); 1.762 (0.8); 1.756 (0.4); 0.146 (1.2); 0.008 (12.3); 0.000 (262.3); −0.009 (9.9); −0.150 (1.2)

I-2-34:
HPLC-MS: log P=5.06; mass (m/z): 732.7 (M+H)$^+$; $^1$H-NMR (400.0 MHz, CD$_3$CN): δ=7.934 (7.3); 7.932 (7.5); 7.914 (7.8); 7.912 (7.8); 7.782 (3.0); 7.778 (3.2); 7.763 (3.6); 7.759 (3.9); 7.664 (6.0); 7.660 (6.3); 7.645 (7.5); 7.641 (7.4); 7.569 (1.0); 7.565 (1.2); 7.550 (3.3); 7.546 (3.2); 7.531 (3.7); 7.527 (3.3); 7.515 (2.2); 7.510 (3.7); 7.496 (2.8); 7.490 (7.0); 7.487 (5.3); 7.483 (5.5); 7.478 (3.6); 7.470 (8.9); 7.468 (8.7); 7.460 (2.5); 7.451 (4.2); 7.449 (4.4); 7.420 (0.4); 7.212 (4.3); 7.208 (4.4); 7.192 (6.8); 7.188 (6.8); 7.173 (3.6); 7.169 (3.6); 5.446 (1.7); 4.068 (0.5); 4.050 (0.5); 2.306 (0.4); 2.140 (20.6); 2.113 (0.4); 2.107 (0.5); 2.101 (0.3); 1.971 (2.4); 1.964 (3.9); 1.958 (6.4); 1.952 (31.1); 1.946 (55.0); 1.940 (72.4); 1.933 (49.2); 1.927 (25.2); 1.914 (0.4); 1.768 (0.4); 1.436 (16.0); 1.386 (0.3); 1.371 (4.8); 1.340 (0.9); 1.284 (1.2); 1.276 (5.1); 1.221 (0.6); 1.204 (1.1); 1.186 (0.6); 0.146 (0.6); 0.008 (4.8); 0.000 (132.6); −0.009 (4.1); −0.150 (0.6)

I-2-35 see Synthesis Example 21

I-2-36:
HPLC-MS: log P=2.71; mass (m/z): 381.0 (M+H)$^+$; $^1$H-NMR (400.0 MHz, DMSO-D$_6$): δ=11.736 (7.7); 8.464 (16.0); 7.773 (0.9); 7.757 (2.0); 7.751 (2.2); 7.742 (6.1); 7.735 (4.2); 7.725 (6.0); 7.722 (6.6); 7.714 (2.6); 7.698 (1.1); 7.627 (3.7); 7.622 (4.1); 7.608 (5.1); 7.603 (5.4); 7.526 (2.3); 7.523 (2.6); 7.507 (5.3); 7.505 (5.6); 7.488 (6.5); 7.485 (8.6); 7.464 (12.2); 7.446 (5.5); 7.442 (8.8); 7.427 (2.0); 7.423 (1.8); 5.757 (4.0); 3.327 (14.2); 2.957 (0.4); 2.511 (18.0); 2.507 (35.2); 2.503 (45.8); 2.498 (33.8); 2.087 (1.6); 1.990 (0.3); 0.008 (1.3); 0.000 (30.5); −0.008 (1.2)

I-2-37:
HPLC-MS: log P=2.09; mass (m/z): 380.0 (M+H)$^+$; $^1$H-NMR (400.0 MHz, DMSO-D$_6$): δ=11.907 (8.8); 8.526 (4.9); 8.522 (5.6); 8.515 (5.4); 8.510 (5.4); 8.476 (16.0); 8.089 (4.9); 8.084 (5.2); 8.070 (5.5); 8.065 (5.4); 7.777 (0.9); 7.761 (2.0); 7.756 (2.0); 7.739 (3.8); 7.723 (2.1); 7.718 (2.5); 7.702 (1.1); 7.609 (4.9); 7.597 (5.0); 7.590 (5.0); 7.578 (4.5); 7.490 (6.1); 7.469 (10.8); 7.447 (5.0); 7.355 (0.4); 7.333 (0.6); 5.758 (1.2); 5.461 (0.4); 3.328 (16.4); 2.672 (0.3); 2.508 (43.2); 2.504 (54.1); 2.499 (42.0); 2.330 (0.3); 2.087 (0.8); 0.000 (0.8)

I-2-38:
HPLC-MS: log P=2.66; mass (m/z): 335.0 (M+H)$^+$; $^1$H-NMR (400.0 MHz, DMSO-D$_6$): δ=11.753 (7.9); 8.470 (16.0); 7.774 (0.9); 7.758 (2.1); 7.752 (1.8); 7.736 (3.9); 7.731 (1.6); 7.720 (2.0); 7.715 (2.4); 7.699 (1.1); 7.659 (4.3); 7.656 (4.3); 7.641 (5.3); 7.637 (5.1); 7.595 (3.1); 7.593 (3.3); 7.575 (7.2); 7.573 (6.9); 7.555 (3.2); 7.551 (3.2); 7.537 (5.1); 7.533 (4.5); 7.517 (2.7); 7.513 (2.3); 7.486 (9.9); 7.465 (15.1); 7.449 (3.2); 7.444 (5.7); 5.758 (2.2); 3.330 (10.7); 2.508 (30.3); 2.504 (37.8); 2.499 (27.3); 2.087 (0.8); 0.000 (26.6); −0.008 (1.1)

I-2-39:
HPLC-MS: log P=2.88; mass (m/z): 387.0 (M+H)$^+$; $^1$H-NMR (400.0 MHz, DMSO-D$_6$): δ=12.099 (5.7); 8.465 (16.0); 7.828 (0.5); 7.809 (1.7); 7.800 (1.1); 7.789 (3.6); 7.776 (6.4); 7.754 (10.5); 7.739 (5.2); 7.731 (3.6); 7.723

(1.8); 7.718 (2.2); 7.702 (1.1); 7.603 (0.4); 7.492 (5.1); 7.470 (8.8); 7.449 (4.0); 7.446 (2.8); 7.376 (0.5); 7.355 (0.9); 7.333 (1.6); 5.758 (1.8); 5.462 (0.8); 3.327 (8.0); 2.960 (2.0); 2.673 (0.3); 2.526 (1.2); 2.513 (20.5); 2.509 (40.7); 2.504 (53.3); 2.500 (38.8); 2.495 (18.9); 2.331 (0.3); 0.000 (1.2)

I-2-40:
HPLC-MS: log P=2.90; mass (m/z): 432.9 (M+H)$^+$;
$^1$H-NMR (400.0 MHz, DMSO-D$_6$): δ=11.440 (9.1); 8.458 (13.3); 8.393 (0.6); 7.844 (12.1); 7.830 (12.8); 7.772 (1.1); 7.756 (2.5); 7.750 (2.2); 7.740 (1.8); 7.734 (4.8); 7.728 (2.5); 7.718 (2.3); 7.713 (3.0); 7.697 (1.4); 7.488 (7.2); 7.467 (12.5); 7.444 (16.0); 7.430 (10.8); 7.134 (0.7); 7.120 (0.6); 5.757 (1.5); 3.326 (19.4); 2.677 (0.3); 2.672 (0.5); 2.668 (0.4); 2.526 (1.6); 2.512 (30.0); 2.508 (60.1); 2.503 (79.2); 2.499 (58.5); 2.495 (29.4); 2.335 (0.4); 2.330 (0.5); 2.326 (0.4); 0.000 (1.7)

I-2-41:
HPLC-MS: log P=2.81; mass (m/z): 427.0 (M+H)$^+$;
$^1$H-NMR (400.0 MHz, DMSO-D$_6$): δ=11.679 (7.8); 8.465 (16.0); 7.961 (5.4); 7.942 (5.6); 7.773 (0.9); 7.757 (1.9); 7.751 (1.7); 7.741 (1.3); 7.735 (3.6); 7.730 (1.4); 7.719 (1.8); 7.714 (2.2); 7.698 (1.0); 7.559 (1.9); 7.554 (2.6); 7.540 (6.5); 7.535 (6.3); 7.528 (4.4); 7.527 (4.4); 7.509 (5.1); 7.489 (4.7); 7.485 (5.7); 7.464 (9.6); 7.443 (4.5); 7.275 (2.6); 7.269 (2.7); 7.255 (3.6); 7.250 (3.6); 7.237 (2.3); 7.232 (2.2); 5.757 (4.2); 3.333 (39.2); 2.512 (11.3); 2.508 (22.1); 2.503 (28.8); 2.499 (20.7); 2.495 (9.9); 2.087 (1.1); 0.008 (0.9); 0.000 (21.4); −0.009 (0.7)

I-2-42:
HPLC-MS: log P=3.02; mass (m/z): 402.1 (M+H)$^+$;
$^1$H-NMR (400.0 MHz, DMSO-D$_6$): δ=12.014 (3.8); 8.987 (2.7); 8.985 (2.6); 8.983 (2.6); 8.981 (2.6); 8.529 (8.6); 8.498 (0.6); 8.480 (1.6); 8.474 (1.6); 8.457 (1.7); 8.452 (1.7); 8.169 (2.7); 8.148 (2.4); 7.894 (2.0); 7.874 (2.5); 7.841 (0.8); 7.822 (1.7); 7.806 (2.2); 7.786 (3.2); 7.772 (2.1); 7.755 (1.7); 7.737 (0.7); 5.759 (16.0); 3.328 (8.6); 2.528 (0.6); 2.523 (0.9); 2.515 (10.1); 2.510 (19.8); 2.505 (26.0); 2.501 (18.8); 2.496 (8.9); 1.397 (0.9); 1.338 (2.5); 1.301 (0.5); 1.260 (0.8); 1.251 (3.1); 1.123 (0.5); 0.984 (0.5); 0.008 (0.9); 0.000 (23.4); −0.009 (0.7)

I-2-43:
HPLC-MS: log P=3.04; mass (m/z): 460.0 (M+H)$^+$;
$^1$H-NMR (400.0 MHz, DMSO-D$_6$): δ=11.850 (8.8); 8.986 (6.2); 8.984 (6.2); 8.983 (6.2); 8.980 (6.1); 8.539 (16.0); 8.479 (3.7); 8.473 (3.7); 8.456 (4.3); 8.451 (4.1); 8.168 (6.2); 8.146 (5.4); 7.972 (6.8); 7.953 (6.9); 7.564 (1.4); 7.558 (2.6); 7.545 (8.7); 7.540 (13.0); 7.523 (6.2); 7.521 (6.2); 7.504 (2.0); 7.502 (2.0); 7.288 (3.8); 7.282 (3.6); 7.271 (3.6); 7.268 (4.2); 7.265 (4.0); 7.262 (3.9); 7.251 (3.0); 7.245 (3.1); 5.757 (1.3); 3.325 (84.7); 2.676 (0.6); 2.672 (0.8); 2.667 (0.5); 2.525 (2.5); 2.520 (3.9); 2.512 (42.4); 2.507 (83.7); 2.503 (110.3); 2.498 (79.8); 2.494 (37.8); 2.334 (0.6); 2.330 (0.7); 2.325 (0.5); 1.233 (0.4); 0.008 (1.0); 0.000 (27.0); −0.009 (0.8)

I-2-44:
HPLC-MS: log P=2.18; mass (m/z): 352.1 (M+H)$^+$;
$^1$H-NMR (400.0 MHz, DMSO-D$_6$): δ=11.905 (6.1); 8.481 (2.6); 8.478 (4.0); 8.476 (2.7); 8.469 (3.0); 8.467 (4.7); 8.462 (16.0); 8.150 (2.2); 8.146 (2.2); 8.129 (2.5); 8.125 (2.6); 8.123 (2.5); 8.119 (2.2); 8.102 (2.4); 8.098 (2.3); 7.883 (3.1); 7.864 (4.0); 7.829 (0.9); 7.811 (2.7); 7.794 (3.7); 7.776 (5.3); 7.761 (3.8); 7.742 (2.7); 7.725 (1.1); 7.711 (2.6); 7.702 (2.9); 7.700 (2.6); 7.691 (4.3); 7.681 (2.3); 7.679 (2.3); 7.670 (2.0); 5.758 (1.5); 4.039 (0.8); 4.021 (0.9); 3.326 (24.9); 2.754 (0.4); 2.742 (0.4); 2.673 (0.3); 2.526 (1.1); 2.521 (1.7); 2.513 (20.7); 2.508 (41.2); 2.503 (53.8); 2.499 (38.0); 2.494 (17.5); 2.330 (0.4); 1.990 (3.9); 1.337 (1.5); 1.300 (0.3); 1.259 (0.5); 1.250 (1.9); 1.234 (0.6); 1.193 (1.1); 1.175 (2.2); 1.158 (1.1); 0.008 (1.2); 0.000 (33.9); −0.009 (1.0)

I-2-45:
HPLC-MS: log P=1.76; mass (m/z): 352.9 (M+H)$^+$;
$^1$H-NMR (400.0 MHz, DMSO-D$_6$): δ=12.069 (5.8); 8.893 (3.2); 8.881 (3.2); 8.482 (3.9); 8.474 (16.0); 8.302 (3.1); 8.283 (3.3); 8.154 (1.9); 8.151 (1.9); 8.133 (2.1); 8.130 (2.4); 8.128 (2.3); 8.124 (1.9); 8.107 (2.1); 8.103 (2.0); 7.890 (2.8); 7.878 (2.8); 7.870 (2.7); 7.858 (2.5); 7.717 (1.9); 7.708 (2.5); 7.706 (2.3); 7.696 (3.5); 7.687 (2.1); 7.685 (2.0); 7.676 (1.6); 3.328 (28.6); 3.177 (0.6); 3.164 (0.6); 2.526 (0.9); 2.513 (18.0); 2.508 (35.9); 2.504 (47.0); 2.499 (33.7); 2.495 (16.1); 0.008 (1.2); 0.000 (33.5); −0.009 (1.1)

I-2-46:
HPLC-MS: log P=2.04; mass (m/z): 363.9 (M+H)$^+$;
$^1$H-NMR (400.0 MHz, DMSO-D$_6$): δ=11.804 (6.0); 8.476 (16.0); 8.466 (4.4); 8.147 (2.1); 8.143 (2.0); 8.126 (2.4); 8.122 (2.8); 8.120 (2.6); 8.116 (2.2); 8.099 (2.4); 8.096 (2.2); 7.747 (3.9); 7.745 (3.8); 7.728 (4.7); 7.725 (4.3); 7.710 (2.2); 7.701 (2.8); 7.698 (2.5); 7.689 (3.9); 7.680 (2.4); 7.677 (2.2); 7.668 (1.9); 7.624 (2.9); 7.620 (3.2); 7.606 (4.1); 7.601 (4.3); 7.592 (0.4); 7.530 (2.0); 7.528 (2.0); 7.512 (4.5); 7.512 (4.5); 7.509 (4.2); 7.493 (2.7); 7.490 (2.4); 7.470 (2.9); 7.465 (3.0); 7.451 (3.5); 7.446 (3.4); 7.432 (1.6); 7.427 (1.4); 7.373 (0.6); 5.757 (13.5); 5.571 (0.3); 4.057 (0.9); 4.039 (2.9); 4.021 (2.9); 4.004 (1.0); 3.336 (102.3); 2.527 (0.7); 2.513 (15.4); 2.509 (30.7); 2.504 (39.9); 2.500 (28.4); 2.496 (13.7); 1.990 (12.5); 1.194 (3.3); 1.176 (6.6); 1.158 (3.2); 0.008 (1.6); 0.000 (40.4); −0.009 (1.5)

I-2-47:
HPLC-MS: log P=1.49; mass (m/z): 365.0 (M+H)$^+$;
$^1$H-NMR (400.0 MHz, DMSO-D$_6$): δ=11.976 (5.7); 8.528 (3.6); 8.523 (3.8); 8.516 (3.9); 8.511 (3.7); 8.494 (0.3); 8.482 (16.0); 8.469 (3.8); 8.152 (1.9); 8.148 (1.8); 8.131 (2.2); 8.127 (2.5); 8.125 (2.3); 8.121 (2.0); 8.104 (2.1); 8.100 (2.0); 8.081 (3.6); 8.076 (3.7); 8.062 (4.1); 8.057 (3.8); 7.715 (1.9); 7.706 (2.5); 7.703 (2.2); 7.694 (3.5); 7.685 (2.1); 7.683 (2.0); 7.674 (1.6); 7.611 (3.9); 7.599 (3.8); 7.592 (3.7); 7.580 (3.6); 5.756 (6.7); 3.324 (56.1); 2.676 (0.4); 2.672 (0.5); 2.668 (0.3); 2.542 (0.3); 2.525 (1.4); 2.512 (28.8); 2.507 (56.4); 2.503 (72.6); 2.498 (51.9); 2.494 (24.9); 2.334 (0.3); 2.330 (0.4); 2.325 (0.3); 0.146 (0.4); 0.008 (3.4); 0.000 (83.3); −0.009 (3.1); −0.150 (0.4)

I-2-48:
HPLC-MS: log P=1.99; mass (m/z): 318.0 (M+H)$^+$;
$^1$H-NMR (400.0 MHz, DMSO-D$_6$): δ=11.819 (5.6); 8.478 (16.0); 8.466 (4.2); 8.147 (2.1); 8.144 (2.1); 8.126 (2.4); 8.123 (2.6); 8.120 (2.5); 8.117 (2.2); 8.099 (2.3); 8.096 (2.3); 7.709 (2.4); 7.700 (2.7); 7.698 (2.6); 7.689 (4.2); 7.680 (2.3); 7.677 (2.3); 7.668 (2.0); 7.656 (3.1); 7.652 (3.2); 7.637 (3.9); 7.633 (4.0); 7.597 (2.1); 7.593 (2.5); 7.577 (5.2); 7.574 (5.4); 7.558 (2.5); 7.554 (2.6); 7.540 (3.9); 7.535 (3.5); 7.520 (2.1); 7.515 (1.8); 7.489 (3.1); 7.486 (3.1); 7.471 (4.1); 7.467 (4.0); 7.452 (1.6); 7.449 (1.5); 5.757 (2.8); 4.039 (0.5); 4.021 (0.5); 3.328 (41.2); 2.672 (0.3); 2.526 (1.0); 2.512 (19.3); 2.508 (38.8); 2.503 (51.0); 2.499 (36.4); 2.494 (17.3); 1.990 (2.1); 1.193 (0.7); 1.175 (1.3); 1.158 (0.6); 0.008 (1.9); 0.000 (49.7); −0.009 (1.8)

I-2-49:
HPLC-MS: log P=2.26; mass (m/z): 370.0 (M+H)$^+$;
$^1$H-NMR (400.0 MHz, DMSO-D$_6$): δ=12.170 (5.7); 8.483 (4.0); 8.474 (16.0); 8.461 (0.7); 8.155 (1.9); 8.152 (2.1); 8.135 (2.2); 8.131 (2.5); 8.129 (2.4); 8.125 (2.1); 8.108

(2.2); 8.104 (2.1); 8.059 (0.3); 7.832 (0.5); 7.811 (1.5); 7.802 (0.9); 7.792 (3.1); 7.778 (5.1); 7.755 (7.9); 7.738 (2.3); 7.732 (2.7); 7.719 (2.1); 7.710 (2.5); 7.707 (2.4); 7.698 (3.7); 7.689 (2.1); 7.677 (1.8); 7.614 (0.4); 7.602 (0.4); 7.594 (0.3); 7.582 (0.4); 7.376 (1.0); 5.760 (1.6); 5.575 (0.6); 4.058 (0.6); 4.041 (1.7); 4.023 (1.7); 4.005 (0.6); 3.332 (12.9); 2.529 (0.5); 2.515 (11.8); 2.511 (23.1); 2.506 (30.0); 2.502 (21.6); 1.992 (7.3); 1.195 (1.9); 1.177 (3.9); 1.159 (1.9); 0.008 (1.2); 0.000 (29.7); −0.009 (1.0)

I-2-50:
HPLC-MS: log P=2.20; mass (m/z): 415.9 (M+H)$^+$; $^1$H-NMR (400.0 MHz, DMSO-D$_6$): δ=11.536 (8.6); 8.477 (16.0); 8.464 (5.3); 8.147 (2.6); 8.144 (2.6); 8.126 (3.0); 8.123 (3.2); 8.120 (3.1); 8.117 (2.7); 8.099 (2.9); 8.096 (2.8); 7.850 (9.6); 7.836 (10.3); 7.703 (2.7); 7.694 (3.2); 7.691 (3.1); 7.682 (4.8); 7.673 (2.7); 7.671 (2.7); 7.662 (2.2); 7.476 (9.7); 7.463 (9.0); 5.757 (0.4); 3.329 (61.9); 2.674 (0.3); 2.513 (19.2); 2.509 (38.1); 2.505 (49.9); 2.500 (36.1); 2.496 (17.6); 1.990 (0.5); 0.008 (1.8); 0.000 (45.1); −0.008 (1.7)

I-2-51:
HPLC-MS: log P=2.14; mass (m/z): 410.0 (M+H)$^+$; $^1$H-NMR (400.0 MHz, DMSO-D$_6$): δ=11.745 (6.8); 8.474 (16.0); 8.469 (4.1); 8.466 (4.9); 8.449 (0.3); 8.147 (2.3); 8.143 (2.2); 8.126 (2.6); 8.122 (2.9); 8.120 (2.8); 8.117 (2.4); 8.099 (2.5); 8.096 (2.4); 7.963 (5.1); 7.944 (5.3); 7.709 (2.4); 7.700 (3.1); 7.698 (2.8); 7.689 (4.2); 7.679 (2.5); 7.677 (2.4); 7.668 (2.0); 7.556 (1.1); 7.551 (2.0); 7.537 (6.4); 7.531 (9.8); 7.514 (4.6); 7.512 (4.5); 7.495 (1.5); 7.493 (1.4); 7.372 (0.4); 7.277 (2.4); 7.272 (2.4); 7.260 (2.7); 7.258 (3.0); 7.254 (3.0); 7.240 (2.0); 7.235 (2.0); 5.756 (14.7); 4.039 (0.7); 4.021 (0.7); 3.333 (94.6); 2.513 (17.3); 2.508 (33.6); 2.504 (43.3); 2.499 (31.0); 2.495 (15.1); 1.990 (3.0); 1.193 (0.8); 1.176 (1.5); 1.158 (0.7); 0.008 (1.7); 0.000 (40.5); −0.008 (1.6)

I-2-52:
HPLC-MS: log P=3.74; mass (m/z): 540.1 (M+H)$^+$; $^1$H-NMR (400.0 MHz, DMSO-D$_6$): δ=8.600 (3.9); 8.596 (4.1); 8.588 (4.1); 8.585 (4.1); 8.424 (16.0); 8.256 (4.0); 8.252 (4.0); 8.235 (4.4); 8.231 (4.2); 8.023 (4.7); 8.004 (5.4); 7.867 (5.2); 7.847 (6.4); 7.792 (2.6); 7.790 (2.7); 7.774 (5.8); 7.771 (5.5); 7.755 (3.9); 7.736 (4.6); 7.724 (8.0); 7.716 (4.5); 7.704 (8.9); 7.686 (1.9); 3.326 (20.7); 2.672 (0.4); 2.525 (1.3); 2.521 (1.9); 2.512 (23.3); 2.508 (47.0); 2.503 (62.0); 2.498 (44.2); 2.494 (21.0); 2.330 (0.4); 1.337 (1.3); 1.300 (0.3); 1.259 (0.6); 1.250 (1.6); 1.235 (0.5); 1.091 (0.4); 0.000 (7.9)

I-2-53:
HPLC-MS: log P=2.33; mass (m/z): 382.0 (M+H)$^+$; $^1$H-NMR (400.0 MHz, CD$_3$CN): δ=8.899 (0.8); 8.530 (1.7); 8.521 (1.8); 8.101 (1.5); 8.098 (1.5); 8.080 (1.6); 8.078 (1.6); 7.855 (1.5); 7.836 (1.9); 7.769 (3.2); 7.758 (4.3); 7.736 (0.4); 7.723 (0.9); 7.712 (1.1); 7.703 (1.0); 7.692 (0.8); 7.683 (0.4); 7.554 (1.4); 7.543 (1.4); 7.534 (1.4); 7.522 (1.3); 4.068 (0.6); 4.050 (0.6); 2.385 (16.0); 2.142 (10.7); 1.971 (2.8); 1.964 (0.8); 1.952 (10.4); 1.946 (19.4); 1.939 (27.2); 1.933 (18.7); 1.927 (9.5); 1.372 (4.0); 1.340 (0.8); 1.285 (1.2); 1.277 (4.5); 1.221 (0.7); 1.203 (1.4); 1.186 (0.7); 0.000 (3.4)

I-2-54:
HPLC-MS: log P=3.93; mass (m/z): 554.1 (M+H)$^+$; $^1$H-NMR (400.0 MHz, CD$_3$CN): δ=8.491 (1.5); 8.487 (1.5); 8.479 (1.6); 8.475 (1.5); 8.009 (1.5); 8.006 (1.5); 7.989 (1.7); 7.985 (1.6); 7.808 (2.4); 7.790 (3.2); 7.697 (4.6); 7.687 (8.8); 7.672 (2.2); 7.660 (1.8); 7.653 (1.4); 7.641 (1.3); 7.630 (0.5); 7.554 (1.7); 7.542 (1.6); 7.534 (1.5); 7.522 (1.5); 2.409 (16.0); 2.138 (12.5); 2.137 (12.4); 1.964 (0.9); 1.952 (11.7); 1.946 (21.9); 1.939 (30.7); 1.933 (21.1); 1.927 (10.8); 1.372 (4.0); 1.341 (0.8); 1.285 (1.0); 1.276 (4.3); 0.000 (3.7)

I-2-55:
HPLC-MS: log P=1.95; mass (m/z): 369.0 (M+H)$^+$; $^1$H-NMR (400.0 MHz, DMSO-D$_6$): δ=11.994 (1.1); 8.890 (2.9); 8.881 (2.8); 8.879 (2.9); 8.630 (4.1); 8.626 (4.3); 8.618 (4.3); 8.615 (4.3); 8.434 (16.0); 8.346 (4.2); 8.342 (4.2); 8.326 (4.7); 8.322 (4.4); 8.317 (0.4); 8.307 (2.6); 8.305 (2.8); 8.288 (3.0); 8.285 (3.0); 7.887 (2.7); 7.875 (2.7); 7.867 (2.5); 7.855 (2.5); 7.735 (4.8); 7.724 (4.5); 7.715 (4.4); 7.703 (4.3); 3.327 (33.8); 3.176 (0.6); 3.164 (0.6); 2.672 (0.4); 2.525 (1.1); 2.521 (1.7); 2.512 (21.3); 2.508 (43.0); 2.503 (56.8); 2.498 (40.9); 2.494 (19.4); 2.330 (0.4)

I-2-56:
HPLC-MS: log P=1.66; mass (m/z): 369.1 (M+H)$^+$; $^1$H-NMR (400.0 MHz, DMSO-D$_6$): δ=11.930 (5.8); 8.630 (4.9); 8.626 (5.2); 8.618 (5.2); 8.615 (5.2); 8.566 (4.2); 8.561 (4.5); 8.554 (4.5); 8.549 (4.4); 8.527 (0.5); 8.522 (0.5); 8.515 (0.5); 8.510 (0.5); 8.448 (16.0); 8.444 (2.8); 8.345 (5.0); 8.341 (5.0); 8.325 (5.5); 8.321 (5.2); 8.158 (4.3); 8.153 (4.4); 8.139 (4.8); 8.134 (4.5); 8.086 (0.5); 8.081 (0.5); 8.067 (0.5); 8.062 (0.5); 7.735 (5.6); 7.724 (5.3); 7.715 (5.2); 7.703 (5.1); 7.610 (0.5); 7.594 (4.7); 7.582 (4.6); 7.575 (4.5); 7.563 (4.4); 5.757 (0.6); 3.324 (21.5); 2.676 (0.4); 2.671 (0.5); 2.667 (0.4); 2.525 (1.6); 2.512 (29.7); 2.507 (58.9); 2.502 (77.0); 2.498 (55.1); 2.493 (26.1); 2.334 (0.4); 2.329 (0.5); 2.325 (0.3); 0.008 (2.1); 0.000 (57.1); −0.009 (1.8)

I-2-57:
HPLC-MS: log P=2.48; mass (m/z): 335.0 (M+H)$^+$; $^1$H-NMR (400.0 MHz, DMSO-D$_6$): δ=12.107 (6.3); 8.630 (4.7); 8.627 (4.9); 8.619 (4.9); 8.615 (4.9); 8.434 (16.0); 8.347 (4.8); 8.343 (4.8); 8.326 (5.3); 8.323 (5.0); 7.829 (0.5); 7.809 (1.5); 7.800 (0.9); 7.790 (3.4); 7.776 (5.4); 7.754 (9.0); 7.737 (7.7); 7.731 (3.0); 7.725 (5.3); 7.716 (5.0); 7.705 (4.9); 4.117 (0.4); 4.103 (1.1); 4.090 (1.1); 4.077 (0.4); 3.329 (21.5); 3.178 (5.2); 3.165 (5.0); 2.526 (0.8); 2.521 (1.2); 2.513 (14.6); 2.509 (29.3); 2.504 (38.6); 2.499 (27.7); 2.495 (13.2); 1.338 (0.8); 1.250 (1.0); 0.008 (1.0); 0.000 (27.6); −0.009 (0.9)

I-2-58:
HPLC-MS: log P=2.44; mass (m/z): 386.0 (M+H)$^+$; $^1$H-NMR (400.0 MHz, DMSO-D$_6$): δ=11.470 (3.1); 8.626 (2.6); 8.622 (2.8); 8.614 (2.7); 8.610 (2.7); 8.430 (4.9); 8.341 (2.7); 8.337 (2.7); 8.320 (2.9); 8.317 (2.8); 7.846 (5.0); 7.833 (5.3); 7.725 (3.0); 7.714 (2.9); 7.705 (2.7); 7.694 (2.8); 7.454 (4.4); 7.440 (4.2); 3.323 (22.8); 2.671 (0.4); 2.524 (1.2); 2.520 (1.8); 2.511 (21.9); 2.507 (44.0); 2.502 (57.8); 2.497 (41.3); 2.493 (19.6); 2.329 (0.4); 2.075 (16.0); 0.008 (1.3); 0.000 (36.9); −0.009 (1.2)

I-2-59:
HPLC-MS: log P=2.28; mass (m/z): 439.9 (M+H)$^+$; $^1$H-NMR (400.0 MHz, CD$_3$CN): δ=8.788 (1.4); 8.529 (2.2); 8.519 (2.2); 8.097 (1.8); 8.077 (2.0); 7.990 (2.0); 7.970 (2.1); 7.583 (1.3); 7.564 (2.4); 7.552 (2.0); 7.540 (2.2); 7.532 (3.0); 7.516 (2.5); 7.496 (1.0); 7.426 (0.5); 7.420 (0.5); 7.257 (1.2); 7.240 (2.1); 7.220 (0.9); 7.171 (0.4); 7.165 (0.3); 5.446 (0.7); 4.068 (0.9); 4.050 (0.9); 2.438 (16.0); 2.136 (22.3); 1.971 (3.9); 1.964 (0.8); 1.952 (10.2); 1.946 (19.1); 1.939 (26.8); 1.933 (18.5); 1.927 (9.6); 1.372 (8.9); 1.340 (1.9); 1.285 (2.5); 1.276 (9.5); 1.221 (1.1); 1.216 (0.3); 1.203 (2.0); 1.185 (1.0); 0.000 (2.4)

I-2-60:

HPLC-MS: log P=2.57; mass (m/z): 459.9 (M+H)$^+$; $^1$H-NMR (400.0 MHz, CD$_3$CN): δ=8.818 (1.7); 8.562 (4.4); 8.560 (4.4); 8.551 (4.5); 8.135 (3.4); 8.115 (3.6); 8.040 (0.5); 8.019 (0.7); 7.998 (3.0); 7.978 (3.0); 7.612 (4.6); 7.600 (4.9); 7.591 (5.0); 7.580 (5.6); 7.563 (2.9); 7.540 (2.5); 7.522 (3.0); 7.503 (1.3); 7.481 (0.4); 7.470 (0.6); 7.458 (0.5); 7.449 (0.6); 7.426 (0.6); 7.420 (0.6); 7.269 (1.8); 7.262 (1.6); 7.250 (2.9); 7.241 (1.8); 7.235 (1.9); 7.171 (0.5); 7.165 (0.4); 6.986 (0.5); 5.446 (0.8); 4.597 (0.4); 3.598 (0.3); 2.133 (31.8); 2.119 (0.5); 2.113 (0.5); 2.107 (0.7); 2.101 (0.5); 1.971 (1.3); 1.964 (4.1); 1.952 (40.8); 1.946 (73.8); 1.940 (99.7); 1.933 (67.6); 1.927 (34.1); 1.914 (0.7); 1.774 (0.5); 1.768 (0.6); 1.762 (0.4); 1.386 (1.1); 1.372 (14.7); 1.340 (5.7); 1.310 (1.1); 1.294 (1.9); 1.285 (8.3); 1.276 (16.0); 1.271 (7.7); 1.221 (0.6); 1.216 (1.4); 1.204 (0.6); 1.186 (0.4); 0.898 (0.7); 0.881 (1.7); 0.874 (1.1); 0.864 (1.1); 0.857 (1.3); 0.838 (0.8); 0.000 (6.2)

I-2-61:

HPLC-MS: log P=4.03; mass (m/z): 669.9 (M+H)$^+$; $^1$H-NMR (400.0 MHz, CD$_3$CN): δ=8.511 (1.4); 8.507 (1.4); 8.499 (1.5); 8.495 (1.4); 8.043 (1.5); 8.039 (1.4); 8.022 (1.6); 8.019 (1.5); 7.910 (3.2); 7.890 (3.4); 7.614 (2.4); 7.610 (2.4); 7.595 (3.1); 7.591 (3.0); 7.565 (1.5); 7.553 (1.4); 7.545 (1.4); 7.533 (1.3); 7.462 (1.9); 7.460 (1.8); 7.443 (3.5); 7.424 (1.8); 7.422 (1.7); 7.185 (1.7); 7.181 (1.6); 7.165 (2.9); 7.162 (2.7); 7.146 (1.5); 7.142 (1.3); 5.446 (1.5); 2.467 (16.0); 2.133 (18.1); 1.972 (0.5); 1.964 (0.7); 1.952 (9.5); 1.946 (17.8); 1.939 (24.7); 1.933 (17.0); 1.927 (8.7); 1.372 (2.9); 1.341 (0.6); 1.285 (0.8); 1.276 (3.1); 0.000 (2.4)

I-2-62:

HPLC-MS: log P=2.77; mass (m/z): 370.0 (M+H)$^+$; $^1$H-NMR (400.0 MHz, DMSO-D$_6$): δ=11.988 (6.4); 8.511 (16.0); 8.459 (1.5); 8.452 (1.9); 8.440 (2.3); 8.433 (2.9); 8.422 (1.3); 8.415 (2.1); 8.401 (4.6); 8.396 (4.8); 8.389 (3.2); 7.879 (3.5); 7.860 (4.2); 7.826 (1.0); 7.805 (3.3); 7.790 (3.6); 7.763 (8.3); 7.743 (4.6); 7.724 (1.1); 5.756 (0.9); 3.323 (34.1); 2.676 (0.5); 2.672 (0.6); 2.667 (0.5); 2.525 (2.0); 2.512 (36.4); 2.507 (72.3); 2.503 (94.3); 2.498 (67.4); 2.493 (32.1); 2.334 (0.4); 2.329 (0.6); 2.325 (0.4); 1.352 (0.6); 1.336 (2.4); 1.299 (0.8); 1.259 (1.3); 1.250 (2.6); 1.234 (0.8); 1.188 (0.3); 0.008 (2.3); 0.000 (62.3); −0.009 (2.0)

I-2-63: see Synthesis Example 45

I-2-64:

HPLC-MS: log P=2.54; mass (m/z): 402.9 (M+H)$^+$; $^1$H-NMR (400.0 MHz, DMSO-D$_6$): δ=12.039 (7.3); 8.888 (3.7); 8.878 (3.6); 8.720 (7.2); 8.715 (8.3); 8.655 (8.1); 8.649 (6.8); 8.459 (16.0); 8.316 (0.9); 8.299 (3.5); 8.281 (3.8); 7.884 (3.1); 7.872 (3.1); 7.865 (2.9); 7.853 (2.8); 3.320 (137.4); 2.675 (2.0); 2.671 (2.7); 2.666 (2.0); 2.524 (7.9); 2.510 (156.8); 2.506 (305.6); 2.501 (398.3); 2.497 (293.2); 2.493 (143.3); 2.333 (2.0); 2.328 (2.7); 2.324 (2.0); 2.102 (0.3); 1.336 (1.9); 1.298 (0.3); 1.259 (0.5); 1.250 (2.3); 1.135 (0.4); 0.989 (0.4); 0.000 (2.0)

I-2-65:

HPLC-MS: log P=3.04; mass (m/z): 459.9 (M+H)$^+$; $^1$H-NMR (400.0 MHz, DMSO-D$_6$): δ=11.722 (8.3); 8.716 (8.8); 8.711 (10.3); 8.649 (8.8); 8.643 (7.5); 8.470 (0.5); 8.459 (16.0); 8.444 (0.7); 7.961 (5.5); 7.942 (5.7); 7.880 (0.3); 7.553 (1.3); 7.547 (2.2); 7.534 (7.3); 7.529 (11.1); 7.511 (5.0); 7.509 (5.1); 7.493 (1.7); 7.490 (1.7); 7.451 (0.3); 7.444 (0.3); 7.337 (0.4); 7.332 (0.4); 7.276 (3.0); 7.270 (3.0); 7.258 (3.2); 7.256 (3.5); 7.253 (3.3); 7.250 (3.3); 7.239 (2.6); 7.233 (2.5); 7.187 (0.7); 7.182 (0.8); 7.176 (0.4); 5.756 (7.2); 3.322 (49.2); 2.676 (0.5); 2.671 (0.8); 2.666 (0.5); 2.524 (2.3); 2.520 (3.6); 2.511 (41.0); 2.506 (82.0); 2.502 (108.7); 2.497 (78.3); 2.493 (36.7); 2.333 (0.5); 2.329 (0.7); 2.324 (0.5); 1.336 (7.0); 1.299 (1.5); 1.259 (2.4); 1.249 (9.4); 1.234 (0.8); 1.195 (0.6); 1.187 (0.3); 1.177 (1.3); 1.159 (0.6); 1.013 (0.5); 0.995 (1.2); 0.977 (0.5); 0.146 (0.3); 0.008 (3.2); 0.000 (90.9); −0.009 (2.7); −0.150 (0.4)

I-2-66:

HPLC-MS: log P=2.43; mass (m/z): 370.0 (M+H)$^+$; $^1$H-NMR (400.0 MHz, DMSO-D$_6$): δ=11.900 (6.8); 11.873 (0.6); 8.770 (0.9); 8.638 (0.6); 8.632 (0.7); 8.582 (6.3); 8.576 (6.6); 8.511 (0.5); 8.462 (16.0); 8.436 (0.38404 (2.2); 8.404 (2.2); 8.397 (2.1); 8.389 (0.4); 8.383 (2.3); 8.377 (3.5); 8.372 (2.1); 8.357 (2.2); 8.351 (2.0); 7.882 (3.5); 7.862 (4.4); 7.827 (1.1); 7.808 (3.1); 7.792 (3.9); 7.772 (5.7); 7.761 (3.6); 7.757 (4.0); 7.742 (3.3); 7.724 (1.2); 5.756 (7.4); 3.324 (31.3); 2.676 (0.5); 2.672 (0.6); 2.667 (0.4); 2.525 (2.1); 2.520 (3.2); 2.512 (34.8); 2.507 (69.2); 2.503 (90.5); 2.498 (64.6); 2.494 (30.5); 2.334 (0.4); 2.330 (0.6); 2.325 (0.4); 1.989 (1.2); 1.352 (0.7); 1.337 (3.0); 1.299 (1.1); 1.259 (1.6); 1.250 (3.5); 1.234 (1.0); 1.193 (0.4); 1.175 (0.7); 1.158 (0.4); 0.008 (2.2); 0.000 (63.5); −0.009 (2.1)

I-2-67:

HPLC-MS: log P=2.00; mass (m/z): 371.0 (M+H)$^+$; $^1$H-NMR (400.0 MHz, DMSO-D$_6$): δ=12.060 (7.9); 8.890 (4.1); 8.879 (4.1); 8.586 (6.9); 8.580 (7.3); 8.472 (16.0); 8.409 (2.2); 8.403 (2.1); 8.388 (2.4); 8.382 (3.8); 8.377 (2.2); 8.362 (2.2); 8.356 (2.0); 8.316 (0.6); 8.296 (3.9); 8.278 (4.3); 7.887 (3.5); 7.875 (3.5); 7.867 (3.3); 7.855 (3.2); 5.756 (3.5); 3.321 (104.9); 2.675 (1.5); 2.671 (2.0); 2.666 (1.5); 2.541 (1.0); 2.524 (5.1); 2.510 (117.0); 2.506 (231.7); 2.502 (303.0); 2.497 (221.1); 2.493 (108.8); 2.333 (1.5); 2.329 (2.0); 2.324 (1.5); 0.146 (1.1); 0.008 (9.9); 0.000 (246.6); −0.008 (9.3); −0.150 (1.2)

I-2-68:

HPLC-MS: log P=2.27; mass (m/z): 382.0 (M+H)$^+$; $^1$H-NMR (400.0 MHz, DMSO-D$_6$): δ=11.802 (7.3); 8.582 (6.5); 8.576 (6.7); 8.477 (13.5); 8.401 (2.2); 8.395 (2.0); 8.380 (2.4); 8.375 (3.6); 8.369 (2.1); 8.354 (2.1); 8.348 (1.9); 7.747 (4.4); 7.727 (5.1); 7.725 (4.6); 7.622 (3.2); 7.618 (3.4); 7.603 (4.6); 7.599 (4.5); 7.530 (2.3); 7.527 (2.2); 7.511 (5.1); 7.509 (4.5); 7.493 (3.0); 7.490 (2.6); 7.470 (3.2); 7.465 (3.2); 7.450 (4.0); 7.446 (3.7); 7.431 (1.8); 7.427 (1.5); 5.757 (16.0); 3.328 (19.5); 2.509 (22.6); 2.504 (28.4); 2.500 (20.2); 1.990 (0.7); 1.396 (0.4); 1.178 (0.4); 1.176 (0.5); 1.161 (0.7); 0.993 (0.6); 0.008 (0.5); 0.000 (10.7); −0.009 (0.4)

I-2-69:

HPLC-MS: log P=1.71; mass (m/z): 382.9 (M+H)$^+$; $^1$H-NMR (400.0 MHz, DMSO-D$_6$): δ=11.973 (7.3); 8.586 (6.8); 8.580 (7.4); 8.529 (4.4); 8.524 (5.0); 8.517 (4.8); 8.512 (4.8); 8.484 (16.0); 8.406 (2.2); 8.400 (2.1); 8.385 (2.5); 8.380 (3.8); 8.374 (2.4); 8.359 (2.2); 8.353 (2.0); 8.079 (4.4); 8.074 (4.8); 8.060 (5.0); 8.056 (4.9); 7.611 (4.8); 7.599 (4.7); 7.592 (4.6); 7.580 (4.3); 4.114 (0.3); 4.101 (1.0); 4.088 (1.0); 4.074 (0.4); 3.326 (7.4); 3.177 (3.9); 3.163 (3.8); 2.673 (0.4); 2.508 (46.7); 2.503 (61.5); 2.499 (46.2); 2.330 (0.4); 0.008 (1.7); 0.000 (37.9)

I-2-70:

HPLC-MS: log P=2.22; mass (m/z): 336.0 (M+H)$^+$; $^1$H-NMR (400.0 MHz, DMSO-D$_6$): δ=11.818 (7.9); 8.582 (7.7); 8.576 (8.0); 8.481 (16.0); 8.402 (2.6); 8.395 (2.4); 8.381 (2.8); 8.375 (4.2); 8.370 (2.5); 8.355 (2.6); 8.349 (2.3); 7.655 (3.9); 7.651 (4.1); 7.636 (5.1); 7.632 (5.0); 7.597 (2.7); 7.594 (3.1); 7.577 (6.8); 7.574 (6.8); 7.558 (3.3); 7.554 (3.3); 7.540 (5.1); 7.536 (4.4); 7.521 (2.8);

7.516 (2.3); 7.490 (4.1); 7.486 (3.8); 7.471 (5.3); 7.468 (5.0); 7.453 (2.2); 7.449 (2.0); 5.757 (8.1); 3.328 (19.6); 2.948 (0.6); 2.527 (0.6); 2.513 (13.9); 2.509 (27.4); 2.504 (35.2); 2.500 (24.7); 2.495 (11.5); 1.991 (1.0); 1.397 (0.7); 1.176 (0.6); 1.173 (0.4); 1.155 (0.8); 1.138 (0.4); 1.006 (0.3); 0.988 (0.7); 0.970 (0.3); 0.008 (0.6); 0.000 (14.6); −0.009 (0.5)

I-2-71:

HPLC-MS: log P=2.51; mass (m/z): 388.0 (M+H)$^+$; $^1$H-NMR (400.0 MHz, DMSO-D$_6$): δ=12.166 (6.6); 8.587 (6.2); 8.580 (6.6); 8.475 (16.0); 8.408 (2.2); 8.402 (2.0); 8.387 (2.3); 8.382 (3.5); 8.376 (2.1); 8.362 (2.2); 8.355 (2.0); 7.832 (0.5); 7.811 (1.5); 7.802 (0.9); 7.792 (3.1); 7.777 (5.0); 7.754 (8.2); 7.737 (2.3); 7.731 (2.7); 5.758 (4.8); 3.330 (26.6); 2.528 (0.5); 2.515 (11.2); 2.510 (22.7); 2.506 (29.8); 2.501 (21.1); 2.497 (9.8); 1.991 (0.7); 1.397 (0.8); 1.177 (0.4); 0.000 (1.8)

I-2-72:

HPLC-MS: log P=2.44; mass (m/z): 433.9 (M+H)$^+$; $^1$H-NMR (400.0 MHz, DMSO-D$_6$): δ=11.525 (10.8); 8.580 (10.3); 8.574 (11.0); 8.476 (16.0); 8.402 (3.5); 8.396 (3.2); 8.381 (3.6); 8.377 (4.6); 8.371 (3.6); 8.356 (3.4); 8.349 (3.0); 7.848 (13.6); 7.834 (14.4); 7.769 (0.4); 7.756 (0.5); 7.735 (0.7); 7.721 (0.8); 7.468 (13.5); 7.454 (12.7); 7.127 (0.7); 7.113 (0.8); 6.941 (0.5); 6.928 (0.5); 5.757 (5.9); 4.039 (0.7); 4.021 (0.7); 3.325 (73.9); 2.677 (0.4); 2.673 (0.6); 2.668 (0.4); 2.543 (0.5); 2.526 (1.7); 2.513 (34.4); 2.508 (68.7); 2.504 (89.4); 2.499 (63.3); 2.495 (29.6); 2.335 (0.4); 2.330 (0.5); 2.326 (0.4); 1.990 (2.9); 1.397 (1.2); 1.193 (0.8); 1.176 (1.9); 1.158 (1.4); 1.006 (0.6); 0.000 (4.6)

I-2-73:

HPLC-MS: log P=2.39; mass (m/z): 427.9 (M+H)$^+$; $^1$H-NMR (400.0 MHz, DMSO-D$_6$): δ=11.738 (5.5); 8.581 (5.5); 8.575 (5.9); 8.471 (11.4); 8.402 (1.7); 8.396 (1.6); 8.381 (1.9); 8.376 (3.0); 8.370 (1.8); 8.355 (1.8); 8.349 (1.6); 8.315 (0.6); 7.960 (4.4); 7.941 (4.4); 7.551 (0.8); 7.545 (1.5); 7.532 (5.8); 7.526 (8.6); 7.511 (3.9); 7.510 (3.9); 7.492 (1.2); 7.276 (2.1); 7.270 (2.0); 7.259 (2.2); 7.256 (2.5); 7.253 (2.5); 7.250 (2.3); 7.239 (1.8); 7.233 (1.7); 3.321 (141.3); 2.942 (0.7); 2.675 (1.1); 2.671 (1.5); 2.666 (1.1); 2.541 (0.9); 2.524 (3.8); 2.510 (86.2); 2.506 (171.5); 2.502 (223.6); 2.497 (160.3); 2.493 (77.4); 2.333 (1.1); 2.328 (1.5); 2.324 (1.1); 1.989 (1.4); 1.398 (16.0); 1.193 (0.4); 1.175 (0.8); 1.157 (0.4); 0.146 (0.4); 0.008 (2.9); 0.000 (80.1); −0.008 (3.0); −0.150 (0.4)

I-2-74:

HPLC-MS: log P=3.28; mass (m/z): 436.0 (M+H)$^+$; $^1$H-NMR (400.0 MHz, DMSO-D$_6$): δ=11.968 (6.7); 9.050 (4.1); 9.048 (4.7); 9.045 (4.7); 9.043 (4.1); 9.034 (0.4); 8.881 (4.6); 8.880 (4.8); 8.876 (4.5); 8.526 (16.0); 7.889 (3.0); 7.869 (3.9); 7.834 (0.7); 7.816 (2.5); 7.800 (3.9); 7.797 (3.8); 7.787 (5.2); 7.771 (3.2); 7.769 (3.0); 7.751 (2.3); 7.749 (2.4); 7.747 (2.2); 7.734 (1.0); 7.729 (0.9); 7.716 (0.3); 5.758 (8.3); 3.329 (22.1); 2.528 (0.6); 2.523 (1.0); 2.514 (11.4); 2.510 (22.8); 2.505 (30.4); 2.500 (21.9); 2.496 (10.2); 1.339 (1.3); 1.301 (0.7); 1.260 (1.0); 1.250 (1.4); 1.233 (0.9); 1.123 (0.4); 0.984 (0.5); 0.008 (0.8); 0.000 (24.4); −0.009 (0.7)

I-2-75:

HPLC-MS: log P=3.28; mass (m/z): 493.9 (M+H)$^+$; $^1$H-NMR (400.0 MHz, DMSO-D$_6$): δ=11.805 (8.4); 9.047 (6.3); 9.044 (6.3); 8.879 (6.5); 8.875 (6.1); 8.534 (16.0); 7.967 (5.6); 7.948 (5.8); 7.563 (1.6); 7.558 (2.4); 7.544 (7.0); 7.538 (7.2); 7.536 (6.2); 7.533 (5.2); 7.518 (5.1); 7.516 (5.2); 7.499 (1.8); 7.497 (1.8); 7.282 (2.9); 7.277 (3.0); 7.264 (3.3); 7.262 (3.6); 7.259 (3.5); 7.257 (3.5); 7.245 (2.5); 7.239 (2.4); 5.757 (6.5); 3.328 (1.052); 3.310 (0.6); 2.677 (0.3); 2.672 (0.4); 2.525 (1.6); 2.512 (25.0); 2.508 (48.3); 2.503 (62.9); 2.498 (45.7); 2.494 (21.9); 2.330 (0.4); 1.235 (0.6); 0.008 (0.5); 0.000 (11.6); −0.009 (0.4)

I-2-76:

HPLC-MS: log P=2.40; mass (m/z): 370.0 (M+H)$^+$; $^1$H-NMR (400.0 MHz, DMSO-D$_6$): δ=11.998 (7.3); 8.892 (4.0); 8.880 (3.9); 8.470 (16.0); 8.316 (3.7); 8.299 (4.0); 8.297 (4.0); 7.887 (3.3); 7.875 (3.4); 7.868 (3.2); 7.856 (3.0); 7.778 (0.8); 7.762 (1.8); 7.756 (1.6); 7.746 (1.2); 7.741 (3.4); 7.735 (1.3); 7.725 (1.7); 7.719 (2.2); 7.703 (1.0); 7.604 (0.4); 7.492 (5.3); 7.471 (9.2); 7.450 (4.3); 7.377 (0.5); 7.356 (0.9); 7.335 (1.7); 5.759 (0.3); 5.465 (0.8); 3.334 (18.9); 3.179 (1.1); 3.166 (1.1); 2.528 (0.5); 2.514 (12.6); 2.510 (25.4); 2.505 (33.5); 2.501 (24.3); 2.497 (11.9); 0.008 (0.7); 0.000 (17.6); −0.008 (0.6)

I-2-77:

HPLC-MS: log P=2.59; mass (m/z): 337.0 (M+H)$^+$; $^1$H-NMR (400.0 MHz, DMSO-D$_6$): δ=12.063 (11.5); 8.481 (14.2); 8.479 (15.2); 8.476 (16.0); 7.781 (0.9); 7.778 (1.0); 7.762 (3.3); 7.745 (4.6); 7.741 (4.9); 7.724 (3.8); 7.719 (2.6); 7.708 (1.3); 7.704 (1.2); 7.668 (1.0); 7.665 (1.1); 7.649 (3.7); 7.631 (5.0); 7.628 (5.1); 7.611 (4.0); 7.593 (1.2); 7.590 (1.1); 7.495 (7.9); 7.473 (13.4); 7.471 (13.1); 7.449 (6.8); 7.296 (7.3); 7.293 (7.4); 7.276 (13.1); 7.273 (13.1); 7.255 (6.3); 7.252 (6.6); 5.764 (1.8); 5.762 (2.0); 5.759 (2.1); 3.336 (28.5); 3.334 (30.6); 2.674 (0.4); 2.510 (66.0); 2.505 (64.1); 2.336 (0.4); 2.332 (0.4); 0.005 (49.3); 0.003 (48.7); 0.000 (50.2)

I-2-78:

HPLC-MS: log P=2.22; mass (m/z): 355.1 (M+H)$^+$; $^1$H-NMR (400.0 MHz, DMSO-D$_6$): δ=11.486 (3.8); 8.592 (3.9); 8.419 (8.0); 7.765 (0.4); 7.749 (0.9); 7.743 (0.8); 7.733 (0.6); 7.728 (1.7); 7.722 (0.6); 7.712 (0.8); 7.706 (1.0); 7.690 (0.5); 7.495 (1.9); 7.487 (2.7); 7.465 (4.6); 7.444 (2.1); 7.360 (3.5); 7.225 (1.6); 5.758 (0.5); 3.968 (16.0); 3.332 (44.8); 3.006 (0.8); 2.513 (12.8); 2.508 (24.4); 2.504 (30.9); 2.500 (21.7); 2.495 (10.1); 0.007 (0.7); 0.000 (12.2); −0.009 (0.4)

I-2-79:

HPLC-MS: log P=2.60; mass (m/z): 370.9 (M+H)$^+$; $^1$H-NMR (400.0 MHz, DMSO-D$_6$): δ=12.149 (4.7); 9.134 (5.2); 9.128 (6.1); 9.079 (6.3); 9.073 (5.1); 8.511 (0.3); 8.497 (16.0); 7.785 (0.8); 7.769 (1.6); 7.763 (1.4); 7.753 (1.1); 7.748 (3.2); 7.742 (1.2); 7.731 (1.5); 7.726 (2.0); 7.710 (0.8); 7.499 (4.8); 7.478 (8.3); 7.457 (3.8); 7.454 (2.6); 5.760 (1.4); 3.339 (13.6); 2.975 (0.5); 2.531 (0.4); 2.517 (8.1); 2.513 (16.4); 2.508 (21.6); 2.504 (15.5); 2.499 (7.3); 0.008 (0.4); 0.000 (12.4); −0.009 (0.4)

I-2-80:

HPLC-MS: log P=2.78; mass (m/z): 370.0 (M+H)$^+$; $^1$H-NMR (400.0 MHz, DMSO-D$_6$): δ=11.930 (7.0); 8.958 (4.3); 8.947 (4.3); 8.469 (16.0); 8.421 (4.1); 8.402 (4.4); 7.856 (2.9); 7.843 (2.9); 7.836 (2.8); 7.823 (2.6); 7.779 (0.9); 7.763 (1.8); 7.757 (1.7); 7.747 (1.3); 7.741 (3.6); 7.736 (1.4); 7.726 (1.8); 7.720 (2.2); 7.7704 (1.0); 7.493 (5.6); 7.472 (9.8); 7.451 (4.5); 7.332 (0.3); 5.758 (7.4); 3.330 (45.4); 2.673 (0.4); 2.513 (23.6); 2.508 (46.7); 2.504 (60.9); 2.500 (43.9); 2.331 (0.4); 1.233 (0.3); 0.008 (2.3); 0.000 (57.5); −0.009 (2.1)

I-2-81:

HPLC-MS: log P=2.36; mass (m/z): 370.0 (M+H)$^+$; $^1$H-NMR (400.0 MHz, DMSO-D$_6$): δ=12.093 (0.6); 9.120 (3.0); 9.046 (1.8); 9.033 (1.9); 8.464 (5.2); 8.104 (1.3); 8.100 (1.0); 8.091 (1.0); 8.087 (1.3); 7.883 (1.7); 7.870 (1.7); 7.763 (0.6); 7.757 (0.5); 7.747 (0.4); 7.741 (1.1); 7.736 (0.4); 7.725 (0.5); 7.720 (0.7); 7.492 (1.7); 7.471 (2.9); 7.450 (1.4); 7.331 (0.3); 6.592 (1.4); 6.588 (1.0);

6.579 (1.0); 6.575 (1.4); 3.329 (11.6); 2.946 (16.0); 2.525 (0.7); 2.508 (22.8); 2.503 (29.5); 2.499 (21.4); 1.990 (1.0); 1.235 (0.4); 1.175 (0.5); 0.008 (1.0); 0.000 (25.6); −0.008 (1.1)

I-2-82:

HPLC-MS: log P=2.95; mass (m/z): 375.0 (M+H)$^+$; $^1$H-NMR (400.0 MHz, DMSO-D$_6$): δ=11.997 (6.7); 8.436 (16.0); 7.993 (5.7); 7.980 (6.1); 7.779 (1.0); 7.763 (2.1); 7.757 (1.8); 7.747 (1.4); 7.741 (4.1); 7.735 (1.5); 7.725 (1.9); 7.720 (2.5); 7.704 (1.2); 7.500 (12.0); 7.496 (4.4); 7.493 (6.9); 7.487 (10.9); 7.472 (10.8); 7.450 (5.0); 7.447 (3.2); 5.758 (6.3); 3.329 (36.3); 2.673 (0.4); 2.527 (1.1); 2.513 (22.2); 2.509 (44.8); 2.504 (58.7); 2.500 (42.0); 2.495 (20.1); 2.331 (0.4); 0.008 (2.5); 0.000 (66.7); −0.009 (2.5)

I-2-83:

HPLC-MS: log P=2.36; mass (m/z): 370.0 (M+H)$^+$; $^1$H-NMR (400.0 MHz, DMSO-D$_6$): δ=12.077 (3.7); 9.083 (8.7); 9.012 (4.2); 9.000 (4.3); 8.477 (14.7); 8.103 (1.2); 8.099 (0.9); 8.091 (0.9); 8.087 (1.2); 7.933 (4.9); 7.920 (4.7); 7.779 (0.7); 7.763 (1.5); 7.757 (1.3); 7.747 (1.1); 7.742 (2.9); 7.736 (1.1); 7.726 (1.4); 7.720 (1.8); 7.704 (0.8); 7.494 (4.4); 7.473 (7.7); 7.452 (3.6); 6.590 (1.3); 6.586 (0.9); 6.578 (0.9); 6.574 (1.3); 5.758 (0.5); 3.329 (32.2); 2.946 (16.0); 2.673 (0.4); 2.513 (20.1); 2.508 (40.0); 2.504 (52.1); 2.499 (37.0); 2.495 (17.4); 2.330 (0.3); 1.990 (0.6); 0.008 (2.1); 0.000 (53.2); −0.009 (1.9)

I-2-84:

HPLC-MS: log P=2.28; mass (m/z): 371.0 (M+H)$^+$; $^1$H-NMR (400.0 MHz, DMSO-D$_6$): δ=11.997 (6.7); 8.964 (4.3); 8.952 (4.4); 8.591 (7.1); 8.585 (7.4); 8.495 (0.3); 8.483 (16.0); 8.471 (0.4); 8.423 (4.2); 8.411 (2.6); 8.404 (6.0); 8.390 (2.5); 8.385 (3.8); 8.379 (2.4); 8.364 (2.2); 8.358 (2.1); 7.859 (2.9); 7.847 (2.9); 7.839 (2.8); 7.827 (2.6); 5.760 (3.2); 3.338 (40.7); 2.954 (1.4); 2.511 (22.6); 2.507 (29.2); 2.503 (21.5); 1.992 (0.7); 1.177 (0.4); 0.007 (1.1); 0.000 (27.4); −0.008 (1.4)

I-2-85:

HPLC-MS: log P=2.50; mass (m/z): 376.0 (M+H)$^+$; $^1$H-NMR (400.0 MHz, DMSO-D$_6$): δ=12.078 (7.2); 8.587 (7.8); 8.581 (8.2); 8.459 (0.4); 8.448 (16.0); 8.411 (2.5); 8.405 (2.3); 8.390 (2.7); 8.385 (4.2); 8.379 (2.4); 8.364 (2.4); 8.358 (2.2); 7.998 (5.8); 7.985 (6.1); 7.503 (9.7); 7.490 (9.2); 5.758 (1.4); 3.332 (55.4); 2.510 (35.3); 2.505 (45.2); 2.501 (32.4); 0.008 (1.9); 0.000 (44.2); −0.008 (1.8)

I-5-1

I-5-2 see Synthesis Example 22

I-5-3:

HPLC-MS: log P=3.09; mass (m/z): 429.0 (M+H)$^+$; $^1$H-NMR (400.0 MHz, DMSO-D$_6$): δ=11.274 (11.8); 8.586 (12.2); 8.580 (12.5); 8.356 (3.1); 8.352 (3.1); 8.331 (5.7); 8.316 (2.4); 8.310 (3.2); 8.305 (2.9); 8.032 (11.5); 8.011 (12.2); 7.929 (14.5); 7.908 (16.0); 7.770 (6.9); 7.751 (7.9); 7.688 (5.8); 7.670 (7.1); 7.577 (7.1); 7.558 (12.6); 7.538 (12.2); 7.516 (4.6); 7.476 (5.0); 7.457 (6.6); 7.439 (2.9); 7.358 (9.7); 7.339 (13.8); 7.321 (7.6); 7.320 (7.8); 5.757 (14.0); 3.324 (114.0); 2.687 (2.8); 2.680 (0.9); 2.674 (3.7); 2.666 (1.4); 2.662 (0.7); 2.541 (1.3); 2.524 (6.1); 2.511 (106.1); 2.511 (106.3); 2.506 (212.0); 2.502 (277.8); 2.497 (198.5); 2.493 (94.1); 2.338 (0.6); 2.333 (1.3); 2.328 (1.7); 2.324 (1.3); 2.086 (5.7); 1.755 (0.4); 1.233 (1.1); 0.146 (1.0); 0.008 (9.1); 0.000 (232.6); −0.009 (8.0); −0.150 (1.0)

I-5-4:

HPLC-MS: log P=2.67; mass (m/z): 427.0 (M+H)$^+$; $^1$H-NMR (400.0 MHz, DMSO-D$_6$): δ=11.256 (3.7); 8.643 (2.5); 8.634 (2.5); 8.205 (2.0); 8.188 (2.1); 8.055 (2.6); 8.035 (2.8); 7.953 (0.9); 7.768 (2.3); 7.749 (2.6); 7.730 (2.0); 7.718 (2.1); 7.710 (2.1); 7.698 (1.8); 7.673 (2.0); 7.655 (2.4); 7.549 (1.3); 7.531 (2.6); 7.522 (2.2); 7.502 (3.1); 7.483 (2.5); 7.474 (1.8); 7.454 (2.1); 7.436 (1.0); 7.414 (0.5); 7.392 (0.5); 7.365 (0.5); 7.337 (0.8); 7.332 (0.9); 7.318 (3.5); 7.318 (3.5); 7.310 (3.6); 7.293 (4.2); 7.290 (4.3); 7.272 (2.6); 7.182 (1.0); 7.176 (0.6); 5.757 (16.0); 3.325 (98.5); 2.890 (6.8); 2.731 (5.5); 2.675 (0.6); 2.671 (0.8); 2.666 (0.6); 2.524 (2.6); 2.510 (42.6); 2.506 (82.0); 2.502 (106.3); 2.497 (77.2); 2.493 (37.2); 2.333 (0.5); 2.328 (0.7); 2.324 (0.5); 1.397 (0.3); 1.352 (1.1); 1.336 (11.6); 1.317 (0.4); 1.298 (6.1); 1.258 (8.6); 1.249 (13.2); 1.234 (1.7); 1.225 (1.0); 1.187 (0.5); 0.008 (0.6); 0.000 (14.6); −0.009 (0.5)

I-5-5:

HPLC-MS: log P=3.98; mass (m/z): 497.0 (M+H)$^+$; $^1$H-NMR (400.0 MHz, DMSO-D$_6$): δ=11.349 (7.9); 9.015 (8.3); 8.792 (6.5); 8.315 (1.6); 8.055 (11.9); 8.035 (12.8); 7.905 (14.0); 7.883 (16.0); 7.771 (4.5); 7.752 (5.1); 7.689 (4.0); 7.672 (4.8); 7.594 (6.8); 7.591 (7.0); 7.576 (9.1); 7.573 (11.4); 7.555 (9.5); 7.552 (9.3); 7.535 (5.0); 7.517 (3.3); 7.479 (3.8); 7.461 (4.8); 7.442 (2.5); 7.384 (9.2); 7.383 (9.5); 7.365 (13.7); 7.347 (7.7); 7.345 (7.6); 3.379 (0.6); 3.327 (402.0); 3.325 (467.8); 2.680 (1.7); 2.675 (3.6); 2.671 (4.9); 2.666 (3.6); 2.662 (1.7); 2.593 (0.4); 2.568 (0.4); 2.568 (0.6); 2.524 (13.0); 2.519 (20.4); 2.511 (266.0); 2.506 (535.6); 2.502 (713.4); 2.497 (518.8); 2.493 (246.5); 2.435 (0.3); 2.338 (1.6); 2.333 (3.5); 2.328 (4.8); 2.324 (3.4); 2.319 (1.6); 2.074 (4.3); 1.187 (0.6); 1.148 (0.5); 0.008 (2.3); 0.000 (75.6); −0.009 (2.3)

I-5-6:

HPLC-MS: log P=3.05; mass (m/z): 428.9 (M+H)$^+$; $^1$H-NMR (400.0 MHz, DMSO-D$_6$): δ=11.307 (10.7); 8.437 (8.1); 8.402 (3.7); 8.053 (7.8); 8.033 (8.3); 7.952 (1.8); 7.933 (0.4); 7.772 (5.1); 7.753 (5.8); 7.672 (4.3); 7.654 (5.4); 7.576 (16.0); 7.561 (10.0); 7.538 (7.1); 7.518 (3.6); 7.479 (3.9); 7.460 (5.2); 7.441 (2.4); 7.352 (4.3); 7.349 (3.9); 7.333 (6.8); 7.317 (3.4); 7.314 (3.5); 5.757 (1.2); 3.862 (1.1); 3.325 (54.6); 3.023 (0.3); 3.017 (0.5); 3.007 (0.5); 2.890 (9.9); 2.730 (9.3); 2.701 (0.6); 2.689 (0.6); 2.670 (0.9); 2.501 (138.1); 2.328 (0.9); 2.086 (0.9); 1.954 (0.3); 1.939 (0.8); 1.754 (1.2); 1.745 (0.3); 1.737 (0.3); 1.729 (0.7); 1.722 (0.3); 1.233 (0.6); 0.146 (0.4); 0.000 (66.9); −0.150 (0.4)

I-5-7:

HPLC-MS: log P=3.39; mass (m/z): 437.0 (M+H)$^+$; $^1$H-NMR (400.0 MHz, DMSO-D$_6$): δ=11.491 (11.8); 8.584 (0.5); 8.579 (0.5); 8.453 (10.2); 8.424 (5.6); 8.406 (3.1); 8.400 (2.4); 8.317 (0.5); 8.014 (0.3); 8.003 (0.3); 7.991 (0.3); 7.980 (0.3); 7.908 (7.3); 7.888 (9.5); 7.848 (16.0); 7.839 (13.1); 7.815 (2.0); 7.778 (3.9); 7.765 (4.9); 7.757 (4.9); 7.745 (3.4); 7.738 (2.1); 7.690 (9.3); 7.684 (9.9); 7.668 (10.6); 7.661 (11.0); 7.511 (4.6); 7.505 (4.1); 7.489 (8.0); 7.482 (6.7); 7.466 (3.7); 7.460 (3.3); 5.758 (5.9); 3.324 (134.6); 2.675 (1.8); 2.671 (2.4); 2.666 (1.7); 2.541 (1.2); 2.524 (8.2); 2.511 (141.8); 2.506 (275.5); 2.502 (353.2); 2.497 (253.0); 2.493 (121.7); 2.333 (1.7); 2.329 (2.3); 2.324 (1.6); 1.234 (0.8); 0.000 (0.8)

I-5-8: see Synthesis Example 47

I-5-9:

HPLC-MS: log P=3.11; mass (m/z): 417.0 (M+H)$^+$; $^1$H-NMR (400.0 MHz, DMSO-D$_6$): δ=11.497 (9.5); 8.897 (5.0); 8.885 (4.9); 8.345 (4.7); 8.327 (5.0); 7.993 (6.0); 7.973 (6.5); 7.902 (4.2); 7.890 (4.2); 7.882 (4.0); 7.870 (3.8); 7.800 (4.4); 7.794 (4.5); 7.783 (3.4); 7.780 (4.1); 7.776 (5.6); 7.763 (0.4); 7.678 (3.4); 7.673 (2.9); 7.670 (2.9); 7.661 (5.1); 7.654 (6.9); 7.644 (1.6); 7.639 (2.4); 7.626 (6.0); 7.620 (5.1); 7.614 (6.5); 7.608 (9.7); 7.601

(4.3); 7.595 (4.6); 7.591 (3.8); 7.577 (1.3); 7.572 (0.9); 7.502 (3.0); 7.483 (5.2); 7.465 (4.0); 7.463 (3.9); 7.297 (5.0); 7.279 (6.5); 7.260 (3.9); 7.259 (3.9); 7.222 (7.5); 7.200 (6.4); 5.757 (16.0); 3.327 (152.8); 2.676 (0.6); 2.671 (0.9); 2.667 (0.6); 2.541 (0.5); 24 (2.4); 2.511 (48.1); 2.507 (96.2); 2.502 (126.0); 2.497 (89.9); 2.493 (42.5); 2.333 (0.6); 2.329 (0.8); 2.324 (0.6); 1.397 (0.4); 0.008 (1.6); 0.000 (41.2); −0.009 (1.3)

I-5-10:
HPLC-MS: log P=3.26; mass (m/z): 461.0 (M+H)$^+$; $^1$H-NMR (400.0 MHz, DMSO-D$_6$): δ=11.200 (16.0); 8.433 (5.3); 8.419 (5.8); 8.408 (5.8); 8.394 (5.3); 8.316 (1.7); 8.070 (4.1); 8.054 (5.2); 8.033 (4.0); 7.906 (7.6); 7.886 (11.6); 7.859 (7.4); 7.841 (6.2); 7.781 (13.6); 7.764 (13.0); 7.615 (4.0); 7.602 (4.7); 7.594 (8.2); 7.582 (8.3); 7.574 (6.0); 7.562 (5.5); 7.454 (6.9); 7.446 (7.2); 7.433 (5.9); 7.425 (5.4); 7.164 (11.1); 7.144 (11.4); 7.138 (12.0); 7.119 (10.2); 5.756 (5.7); 3.322 (510.5); 2.675 (3.8); 2.671 (5.3); 2.666 (3.8); 2.541 (3.0); 2.524 (14.5); 2.510 (303.2); 2.506 (597.5); 2.501 (773.7); 2.497 (549.5); 2.492 (257.3); 2.333 (3.7); 2.328 (5.1); 2.324 (3.6); 2.074 (1.8); 1.236 (0.3); 0.146 (1.0); 0.008 (8.2); 0.000 (229.1); −0.009 (7.4); −0.150 (1.0)

I-5-11:
HPLC-MS: log P=2.99; mass (m/z): 429.1 (M+H)$^+$; $^1$H-NMR (400.0 MHz, DMSO-D$_6$): δ=11.378 (16.0); 8.435 (4.8); 8.421 (5.1); 8.410 (5.1); 8.396 (4.8); 8.315 (2.1); 8.102 (4.8); 8.087 (5.3); 8.079 (5.3); 8.063 (4.7); 7.669 (1.4); 7.653 (3.3); 7.649 (3.4); 7.632 (5.9); 7.617 (5.5); 7.611 (4.8); 7.606 (4.2); 7.597 (6.8); 7.585 (5.9); 7.577 (4.3); 7.565 (3.7); 7.454 (6.3); 7.445 (6.7); 7.433 (5.2); 7.424 (5.0); 7.301 (9.7); 7.281 (15.9); 7.261 (8.3); 7.204 (0.4); 7.164 (8.6); 7.144 (8.7); 7.138 (9.3); 7.119 (8.0); 5.756 (1.3); 4.039 (0.3); 4.020 (0.3); 3.550 (0.8); 3.536 (0.7); 3.509 (4.2); 3.495 (0.7); 3.482 (0.7); 3.408 (0.5); 3.392 (0.5); 3.382 (0.6); 3.369 (0.8); 3.322 (542.0); 2.675 (4.0); 2.671 (5.5); 2.66 (4.0); 2.662 (2.0); 2.631 (0.4); 2.541 (3.7); 2.524 (14.2); 2.519 (21.5); 2.511 (292.8); 2.506 (593.0); 2.502 (781.0); 2.497 (556.3); 2.493 (260.6); 2.337 (1.6); 2.333 (3.6); 2.328 (5.0); 2.324 (3.5); 1.989 (1.4); 1.298 (0.6); 1.259 (1.1); 1.234 (3.6); 1.193 (0.5); 1.175 (0.9); 1.157 (0.5); 1.050 (2.0); 1.034 (2.0); 1.020 (0.3); 0.854 (0.6); 0.836 (0.4); 0.807 (0.4); 0.146 (1.8); 0.008 (13.3); 0.000 (407.8); −0.008 (12.8); −0.150 (1.7)

I-3-1: see Synthesis Example 46

I-3-2:
HPLC-MS: log P=2.68; mass (m/z): 335.1 (M+H)$^+$; $^1$H-NMR (400.0 MHz, DMSO-D$_6$): δ=10.802 (10.4); 7.610 (1.4); 7.593 (3.2); 7.589 (3.0); 7.572 (5.8); 7.555 (3.3); 7.551 (3.5); 7.534 (1.8); 7.531 (1.6); 7.515 (2.7); 7.509 (2.3); 7.499 (2.1); 7.494 (5.5); 7.488 (2.5); 7.476 (2.6); 7.472 (3.9); 7.457 (1.8); 7.402 (9.0); 7.364 (10.0); 7.342 (16.0); 7.321 (6.8); 7.260 (2.3); 7.254 (10.0); 7.234 (14.6); 7.216 (8.3); 7.206 (1.8); 6.955 (7.7); 6.313 (8.7); 6.309 (9.2); 6.305 (9.0); 6.301 (7.9); 4.121 (0.5); 4.108 (1.3); 4.095 (1.4); 4.082 (0.5); 3.335 (183.4); 3.176 (6.2); 3.163 (5.9); 2.677 (0.5); 2.672 (0.7); 2.668 (0.5); 2.511 (42.8); 2.507 (77.4); 2.503 (97.5); 2.499 (71.9); 2.334 (0.5); 2.330 (0.6); 2.325 (0.5); 1.337 (0.4); 1.226 (0.5); 0.008 (0.3); 0.000 (5.7)

I-3-3:
HPLC-MS: log P=2.96; mass (m/z): 424.9 (M+H)$^+$; $^1$H-NMR (400.0 MHz, DMSO-D$_6$): δ=10.802 (10.5); 7.610 (1.4); 7.593 (3.2); 7.589 (3.0); 7.572 (5.8); 7.556 (3.2); 7.551 (3.6); 7.534 (1.8); 7.531 (1.6); 7.515 (2.7); 7.510 (2.3); 7.499 (2.0); 7.493 (5.5); 7.488 (2.5); 7.476 (2.6); 7.472 (3.9); 7.457 (1.8); 7.405 (9.0); 7.364 (10.0); 7.342 (16.0); 7.321 (7.4); 7.298 (0.6); 7.261 (2.1); 7.254 (10.0); 7.235 (14.6); 7.214 (8.4); 7.207 (1.9); 6.956 (7.7); 6.315 (8.5); 6.311 (9.3); 6.307 (9.1); 6.303 (8.2); 4.119 (0.5); 4.106 (1.5); 4.093 (1.5); 4.080 (0.5); 3.330 (20.7); 3.177 (6.7); 3.164 (6.4); 2.676 (0.3); 2.672 (0.4); 2.668 (0.3); 2.507 (45.6); 2.503 (58.5); 2.499 (43.6); 2.330 (0.4); 1.339 (1.1); 1.233 (0.4); 1.226 (1.5); 0.000 (4.7)

I-3-4:
HPLC-MS: log P=2.97; mass (m/z): 363.0 (M+H)$^+$; $^1$H-NMR (400.0 MHz, DMSO-D$_6$): δ=10.484 (2.3); 7.508 (0.5); 7.501 (0.5); 7.492 (0.4); 7.486 (1.1); 7.481 (0.6); 7.472 (0.5); 7.469 (0.6); 7.465 (0.9); 7.447 (2.9); 7.425 (3.0); 7.396 (1.8); 7.359 (2.1); 7.348 (0.5); 7.338 (3.2); 7.317 (1.3); 7.119 (2.3); 7.111 (3.2); 7.069 (1.8); 7.062 (1.5); 7.047 (1.6); 7.039 (1.5); 6.927 (1.6); 6.329 (1.7); 6.325 (1.9); 6.322 (2.1); 6.318 (2.0); 3.804 (16.0); 3.323 (34.4); 2.670 (0.5); 2.666 (0.4); 2.524 (1.2); 2.519 (1.8); 2.510 (22.0); 2.506 (47.2); 2.501 (66.3); 2.497 (54.3); 2.492 (32.5); 2.328 (0.4); 2.324 (0.4); 2.075 (0.5); 0.000 (0.7)

I-3-5:
HPLC-MS: log P=2.52; mass (m/z): 368.0 (M+H)$^+$; $^1$H-NMR (400.0 MHz, DMSO-D$_6$): δ=10.705 (11.0); 8.849 (6.4); 8.839 (6.2); 8.837 (6.3); 8.192 (6.0); 8.174 (6.5); 8.172 (6.6); 7.852 (5.7); 7.840 (5.6); 7.832 (5.3); 7.820 (5.0); 7.529 (1.2); 7.514 (2.6); 7.509 (2.0); 7.507 (2.1); 7.498 (1.8); 7.492 (5.4); 7.487 (2.3); 7.478 (2.1); 7.475 (2.4); 7.471 (4.0); 7.456 (1.8); 7.385 (8.4); 7.373 (1.9); 7.368 (2.6); 7.362 (10.1); 7.341 (16.0); 7.320 (6.4); 6.955 (7.1); 6.320 (8.2); 6.316 (9.0); 6.312 (8.9); 6.308 (8.3); 5.758 (0.6); 3.325 (92.7); 2.676 (0.7); 2.671 (1.0) 3.323 (34.4); 2.670 (0.5); 2.666 (0.4); 2.524 (1.2); 2.519 (1.8); 2.510 (22.0); 2.506 (47.2); 2.501 (663); 2.497 (54.3); 2.492 (32.5); 2.328 (0.4); 2.324 (0.4); 2.075 (0.5); 0.000 (0.7)

I-3-6:
HPLC-MS: log P=2.96; mass (m/z): 430.9 (M+H)$^+$; $^1$H-NMR (400.0 MHz, DMSO-D$_6$): δ=10.453 (9.0); 7.992 (0.5); 7.987 (0.5); 7.931 (15.0); 7.927 (14.9); 7.513 (1.1); 7.498 (2.3); 7.494 (1.6); 7.491 (1.7); 7.482 (1.5); 7.477 (4.5); 7.471 (1.9); 7.463 (1.6); 7.459 (1.9); 7.455 (3.4); 7.440 (1.8); 7.430 (4.8); 7.425 (6.3); 7.365 (1.3); 7.360 (2.0)); 7.355 (8.4); 7.343 (1.4); 7.333 (12.9); 7.323 (1.3); 7.313 (5.2); 7.306 (1.5); 7.204 (0.4); 6.949 (0.7); 6.945 (0.7); 6.926 (1.9); 6.922 (3.8); 6.919 (4.9); 6.915 (5.4); 6.909 (3.7); 6.906 (2.0); 6.893 (16.0); 6.889 (15.8); 6.491 (6.8); 6.489 (7.1); 6.483 (7.0); 6.479 (6.6); 5.757 (13.2); 3.821 (0.5); 3.327 (14.6); 2.672 (0.4); 2.526 (1.5); 2.512 (24.8); 2.508 (49.5); 2.503 (65.0); 2.499 (46.5); 2.494 (21.8); 2.330 (0.4); 2.325 (0.3); 1.233 (0.4); 0.008 (1.5); 0.000 (40.7); −0.009 (1.3)

I-3-7:
HPLC-MS: log P=3.07; mass (m/z): 414.9 (M+H)$^+$; $^1$H-NMR (400.0 MHz, DMSO-D$_6$): δ=10.224 (11.0); 8.316 (0.6); 7.822 (14.7); 7.808 (15.4); 7.518 (1.3); 7.502 (2.7); 7.497 (2.1); 7.495 (2.2); 7.486 (1.9); 7.481 (5.5); 7.475 (2.4); 7.467 (2.2); 7.464 (2.5); 7.460 (4.0); 7.444 (2.0); 7.419 (8.5); 7.367 (1.6); 7.356 (10.2); 7.335 (16.0); 7.314 (6.3); 7.308 (2.0); 7.284 (15.4); 7.271 (14.7); 6.926 (7.2); 6.380 (8.4); 6.377 (9.0); 6.373 (8.9); 6.369 (8.1); 5.756 (3.0); 3.321 (26.0); 2.675 (1.3); 2.671 (1.7); 2.666 (1.3); 2.524 (6.2); 2.510 (97.7); 2.506 (190.1); 2.502 (247.7); 2.497 (180.7); 2.493 (88.6); 2.333 (1.1); 2.328 (1.6); 2.324 (1.1); 1.989 (0.6); 1.398 (0.3); 1.384 (2.4); 1.234 (0.6); 1.175 (0.4); 0.000 (2.1)

1) Description of Method for Determination of the Log P Values (Formic Acid Method)

The log P values given in the table were determined in accordance with EEC Directive 79/831 Annex V.A8 by HPLC (High Performance Liquid Chromatography) using a reversed-phase column (C 18). Temperature: 55° C.

Eluents for determination in the acidic range (pH 3.4):

Eluent A: acetonitrile+1 ml of formic acid/liter. Eluent B: water+0.9 ml of formic acid/liter.

Gradient: from 10% eluent A/90% eluent B to 95% eluent A/5% eluent B in 4.25 min Calibration was carried out using unbranched alkan-2-ones (having from 3 to 16 carbon atoms) with known log P values (the log P values were determined by the retention times using linear interpolation between two successive alkanones). The lambda max values were determined in the maxima of the chromatographic signals using the UV spectra from 200 nm to 400 nm.

2) Measurement of the NMR Spectra of Selected Examples

The NMR spectra were determined using a Bruker Avance 400 fitted with a flow probe head (volume 60 µl). Solvents used were $CD_3CN$ or $DMSO-D_6$, and tetramethylsilane (0.00 ppm) was used as reference. In individual cases, the NMR spectra were determined using a Bruker Avance II 600. Solvents used were $CD_3CN$ or $DMSO-D_6$, and tetramethylsilane (0.00 ppm) was used as reference.

The NMR data for selected examples are listed either in conventional form (d values, number of hydrogen atoms, multiplet splitting) or as NMR peak lists.

The splitting of the signals was described as follows: s (singlet), d (doublet), t (triplet), q (quartet), quin (quintet), m (multiplet).

NMR Peak List Method

When the $^1$H NMR data for selected examples are noted in the form of $^1$H NMR peak lists, first the d value in ppm and then the signal intensity in round brackets are listed for each signal peak. The d value—signal intensity number pairs for different signal peaks are listed with separation from one another by semicolons.

The peak list for one example therefore takes the form of:

$\delta_1$ (intensity$_1$); $\delta_2$ (intensity$_2$); . . . ; $\delta_i$(intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and their relative intensities may be shown in comparison to the most intense signal in the spectrum.

For calibration of the chemical shift of the $^1$H NMR spectra we use tetramethylsilane and/or the chemical shift of the solvent, particularly in the case of spectra measured in DMSO. Therefore, the tetramethylsilane peak may but need not occur in the NMR peak lists.

The lists of the $^1$H NMR peaks are similar to the conventional $^1$H NMR printouts and thus usually contain all peaks listed in conventional NMR interpretations.

In addition, like conventional $^1$H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of $^1$H NMR peaks show the usual solvent peaks, for example peaks of DMSO in DMSO-$d_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional $^1$H NMR interpretation.

Further details of $^1$H NMR peak lists can be found in Research Disclosure Database Number 564025.

Use Examples

The examples which follow demonstrate the insecticidal, acaricidal and nematicidal action of the compounds according to the invention. Said compounds according to the invention relate to the compounds listed in Tables 1 to 5 with the corresponding reference numerals, for example I-1-1:

Example 1

*Boophilus microplus* Test (DIP)

Test animals: adult engorged *Boophilus microplus* females of the SP-resistant Parkhurst strain Solvent: dimethyl sulphoxide 10 mg of active compound are dissolved in 0.5 ml of dimethyl sulphoxide. For the purpose of preparing a suitable formulation, the active compound solution is diluted with water to the concentration desired in each case.

This active compound preparation is pipetted into tubes. 8-10 ticks are transferred into a further tube with holes. The tube is immersed into the active compound formulation, and all ticks are completely wetted. After the liquid has run out, the ticks are transferred onto filter discs in plastic dishes and stored in a climate-controlled room.

The activity is assessed after 7 days by laying of fertile eggs. Eggs whose fertility is not visible from the outside are stored in a climate-controlled cabinet until the larvae hatch. An efficacy of 100% means that none of the ticks has laid any fertile eggs.

In this test, for example, the following compounds of the Preparation Examples showed an efficacy of 80% at an application rate of 100 ppm: I-1-32, I-1-82

In this test, for example, the following compounds of the Preparation Examples showed an efficacy of 90% at an application rate of 100 ppm: I-1-39, I-1-53, I-1-91

In this test, for example, the following compounds of the Preparation Examples showed an efficacy of 100% at an application rate of 100 ppm: I-1-5, I-1-33, I-1-48, I-1-83, I-1-96, I-1-99, I-2-1

*Boophilus microplus* Test (BOOPMI Injection)

Solvent: dimethyl sulphoxide

To produce a suitable preparation of active compound, 10 mg of active compound are mixed with 0.5 ml of solvent, and the concentrate is diluted with solvent to the desired concentration.

The active compound solution is injected into the abdomen (*Boophilus microplus*), and the animals are transferred into dishes and stored in a climate-controlled room.

The activity is assessed after 7 days by laying of fertile eggs. Eggs whose fertility is not visible from the outside are stored in a climate-controlled cabinet until the larvae hatch after about 42 days. An efficacy of 100% means that none of the ticks has laid any fertile eggs; 0% means that all eggs are fertile.

In this test, for example, the following compounds of the Preparation Examples showed an efficacy of 80% at an application rate of 20 µg/animal: I-1-55

In this test, for example, the following compounds of the Preparation Examples showed an efficacy of 100% at an application rate of 20 µg/animal:

| |
|---|
| I-1-4 |
| I-1-5 |
| I-1-6 |
| I-1-9 |
| I-1-11 |
| I-1-13 |
| I-1-14 |
| I-1-20 |
| I-1-21 |
| I-1-22 |
| I-1-23 |
| I-1-24 |
| I-1-25 |
| I-1-32 |
| I-1-33 |
| I-1-37 |
| I-1-39 |
| I-1-43 |
| I-1-48 |
| I-1-50 |
| I-1-51 |
| I-1-52 |
| I-1-53 |
| I-1-54 |
| I-1-63 |
| I-1-65 |
| I-1-67 |
| I-1-68 |
| I-1-69 |
| I-1-73 |
| I-1-75 |
| I-1-81 |
| I-1-82 |
| I-1-83 |
| I-1-84 |
| I-1-85 |
| I-1-90 |
| I-1-91 |
| I-1-93 |
| I-1-96 |
| I-1-99 |
| I-1-101 |
| I-1-102 |
| I-1-103 |
| I-1-107 |
| I-1-109 |
| I-1-110 |
| I-1-113 |
| I-1-122 |
| I-1-128 |
| I-1-131 |
| I-1-135 |
| I-1-136 |
| I-1-145 |
| I-1-186 |
| I-1-238 |
| I-1-240 |
| I-1-253 |
| I-1-254 |
| I-1-562 |
| I-2-1 |
| I-2-10 |
| I-2-2 |
| I-3-1 |
| I-3-2 |

*Ctenocephalides felis*—Oral Test (CTECFE)

Solvent: 1 part by weight of dimethyl sulphoxide

To produce a suitable preparation of active compound, 10 mg of active compound are mixed with 0.5 ml of dimethyl sulphoxide. A portion of the concentrate is diluted with citrated cattle blood, and the desired concentration is prepared.

About 20 unfed adult fleas (*Ctenocephalides felis*) are placed into a chamber which is closed at the top and bottom with gauze. A metal cylinder whose bottom end is closed with a parafilm is placed onto the chamber. The cylinder contains the blood/active compound preparation, which can be imbibed by the fleas through the Parafilm membrane.

After 2 days, the kill in % is determined 100% means that all fleas have been killed; 0% means that none of the fleas have been killed.

In this test, for example, the following compounds of the Preparation Examples showed an efficacy of 80% at an application rate of 100 ppm: I-1-91, I-1-99

In this test, for example, the following compounds of the Preparation Examples showed an efficacy of 85% at an application rate of 100 ppm: I-1-128

In this test, for example, the following compounds of the Preparation Examples showed an efficacy of 90% at an application rate of 100 ppm: I-1-131, I-2-1, I-2-10

*Lucilia cuprina* Test (LUCICU)

Solvent: dimethyl sulphoxide

To produce a suitable preparation of active compound, 10 mg of active compound are mixed with 0.5 ml of dimethyl sulphoxide, and the concentrate is diluted with water to the desired concentration.

Vessels containing horse meat treated with the active compound preparation of the desired concentration are populated with about 20 *Lucilia cuprina* larvae.

After 2 days, the kill in % is determined 100% means that all of the larvae have been killed; 0% means that none of the larvae have been killed.

In this test, for example, the following compounds of the Preparation Examples showed an efficacy of 80% at an application rate of 100 ppm: I-1-63, I-1-186, I-2-2, I-3-1

In this test, for example, the following compounds of the Preparation Examples showed an efficacy of 90% at an application rate of 100 ppm: I-1-20, I-1-37, I-1-51, I-1-69, I-1-145

In this test, for example, the following compounds of the Preparation Examples showed an efficacy of 95% at an application rate of 100 ppm: I-1-82

In this test, for example, the following compounds of the Preparation Examples showed an efficacy of 100% at an application rate of 100 ppm:

| |
|---|
| I-1-5 |
| I-1-6 |
| I-1-11 |
| I-1-14 |
| I-1-32 |
| I-1-33 |
| I-1-39 |
| I-1-43 |
| I-1-50 |
| I-1-52 |
| I-1-53 |
| I-1-54 |
| I-1-65 |
| I-1-67 |
| I-1-73 |
| I-1-75 |
| I-1-81 |
| I-1-83 |
| I-1-85 |
| I-1-91 |

-continued

I-1-93
I-1-96
I-1-99
I-1-101
I-1-107
I-1-109
I-1-110
I-1-113
I-1-128
I-1-131
I-1-135
I-1-254
I-1-562
I-2-1

*Musca domestica* Test (MUSCDO)

Solvent: dimethyl sulphoxide

To produce a suitable preparation of active compound, 10 mg of active compound are mixed with 0.5 ml of dimethyl sulphoxide, and the concentrate is diluted with water to the desired concentration.

Vessels containing a sponge treated with the active compound formulation of the desired concentration are populated with adult *Musca domestica*.

After 2 days, the kill in % is determined. 100% means that all of the flies have been killed; 0% means that none of the flies have been killed.

In this test, for example, the following compounds of the Preparation Examples showed an efficacy of 85% at an application rate of 20 ppm: I-1-91

In this test, for example, the following compounds of the Preparation Examples showed an efficacy of 90% at an application rate of 20 ppm: I-1-99

In this test, for example, the following compounds of the Preparation Examples showed an efficacy of 90% at an application rate of 100 ppm: I-1-562

*Cooperia curticei* Test (COOPCU)

Solvent: dimethyl sulphoxide

To produce a suitable preparation of active compound, 10 mg of active compound are mixed with 0.5 ml of dimethyl sulphoxide, and the concentrate is diluted with Ringer solution to the desired concentration.

Vessels containing the active compound preparation of the desired concentration are populated with about 40 nematode larvae (*Cooperia curticei*).

After 5 days, the kill in % is determined 100% means that all of the larvae have been killed; 0% means that none of the larvae have been killed.

In this test, for example, the following compounds of the Preparation Examples showed an efficacy of 80% at an application rate of 4 ppm: I-2-7, I-1-284

In this test, for example, the following compounds of the Preparation Examples showed an efficacy of 80% at an application rate of 20 ppm:

I-1-44
I-1-156
I-1-219
I-1-288
I-1-421
I-1-495
I-1-591
I-2-18
I-2-58
I-2-66
I-3-3

In this test, for example, the following compounds of the Preparation Examples showed an efficacy of 80% at an application rate of 100 ppm: I-1-22, I-1-69, I-1-121, I-1-211

In this test, for example, the following compounds of the Preparation Examples showed an efficacy of 90% at an application rate of 4 ppm: I-1-221, I-1-555

In this test, for example, the following compounds of the Preparation Examples showed an efficacy of 90% at an application rate of 20 ppm:

I-1-63
I-1-284
I-1-465
I-1-470
I-1-484
I-1-487
I-1-488
I-1-499
I-1-501
I-1-581
I-1-587
I-1-593
I-2-2
I-2-37
I-2-49

In this test, for example, the following compounds of the Preparation Examples showed an efficacy of 90% at an application rate of 100 ppm:

| | | | | | | | |
|---|---|---|---|---|---|---|---|
| I-1-11 | I-1-20 | I-1-39 | I-1-54 | I-1-91 | I-1-135 | I-1-562 |
| I-1-13 | I-1-32 | I-1-51 | I-1-79 | I-1-107 | I-1-136 | I-2-6 |
| I-1-14 | I-1-36 | I-1-52 | I-1-81 | I-1-132 | I-1-138 | I-4-3 |

In this test, for example, the following compounds of the Preparation Examples showed an efficacy of 100% at an application rate of 4 ppm: I-2-1

In this test, for example, the following compounds of the Preparation Examples showed an efficacy of 100% at an application rate of 20 ppm:

| | | | | | | | |
|---|---|---|---|---|---|---|---|
| I-1-6 | I-1-142 | I-1-277 | I-1-468 | I-1-502 | I-2-17 | I-2-40 | I-2-62 |
| I-1-9 | I-1-253 | I-1-335 | I-1-472 | I-1-507 | I-2-35 | I-2-41 | I-3-1 |
| I-1-10 | I-1-254 | I-1-459 | I-1-492 | I-1-575 | I-2-36 | I-2-44 | I-3-6 |
| I-1-64 | I-1-259 | I-1-467 | I-1-494 | I-1-580 | I-2-38 | I-2-57 | I-3-7 |

In this test, for example, the following compounds of the Preparation Examples showed an efficacy of 100% at an application rate of 100 ppm:

| | | | | | | | | |
|---|---|---|---|---|---|---|---|---|
| I-1-5 | I-1-62 | I-1-73 | I-1-85 | I-1-103 | I-1-119 | I-1-133 | I-1-146 | I-2-5 |
| I-1-33 | I-1-65 | I-1-75 | I-1-92 | I-1-104 | I-1-128 | I-1-140 | I-1-151 | I-2-10 |
| I-1-46 | I-1-66 | I-1-82 | I-1-93 | I-1-105 | I-1-129 | I-1-143 | I-1-162 | |
| I-1-50 | I-1-67 | I-1-83 | I-1-96 | I-1-109 | I-1-130 | I-1-144 | I-1-491 | |
| I-1-53 | I-1-71 | I-1-84 | I-1-99 | I-1-113 | I-1-131 | I-1-145 | I-1-506 | |

*Haemonchus contortus* Test (HAEMCO)

Solvent: dimethyl sulphoxide

To produce a suitable preparation of active compound, 10 mg of active compound are mixed with 0.5 ml of dimethyl sulphoxide, and the concentrate is diluted with Ringer solution to the desired concentration.

Vessels containing the active compound preparation of the desired concentration are populated with about 40 larvae of the red stomach worm (*Haemonchus contortus*).

After 5 days, the kill in % is determined 100% means that all of the larvae have been killed; 0% means that none of the larvae have been killed.

In this test, for example, the following compounds of the Preparation Examples showed an efficacy of 80% at an application rate of 4 ppm: I-2-1, I-2-51

In this test, for example, the following compounds of the Preparation Examples showed an efficacy of 80% at an application rate of 20 ppm:

| | | | | | | | |
|---|---|---|---|---|---|---|---|
| I-1-9 | I-1-63 | I-1-335 | I-1-467 | I-1-502 | I-1-554 | I-1-591 | I-2-55 |
| I-1-36 | I-1-259 | I-1-427 | I-1-484 | I-1-549 | I-1-589 | I-2-12 | I-2-66 |

In this test, for example, the following compounds of the Preparation Examples showed an efficacy of 80% at an application rate of 100 ppm:

| | | | | | | | |
|---|---|---|---|---|---|---|---|
| I-1-10 | I-1-20 | I-1-46 | I-1-81 | I-1-96 | I-1-129 | I-1-151 | I-1-562 |
| I-1-11 | I-1-33 | I-1-71 | I-1-85 | I-1-99 | I-1-136 | I-1-162 | |

In this test, for example, the following compounds of the Preparation Examples showed an efficacy of 90% at an application rate of 4 ppm: I-1-221, I-2-49

In this test, for example, the following compounds of the Preparation Examples showed an efficacy of 90% at an application rate of 20 ppm:

| | | | | | | | | |
|---|---|---|---|---|---|---|---|---|
| I-1-64 | I-1-186 | I-1-277 | I-1-366 | I-1-472 | I-1-582 | I-1-593 | I-2-48 | I-2-62 | I-3-7 |
| I-1-66 | I-1-252 | I-1-288 | I-1-378 | I-1-492 | I-1-587 | I-2-13 | I-2-58 | I-3-6 | |

In this test, for example, the following compounds of the Preparation Examples showed an efficacy of 90% at an application rate of 100 ppm:

| | | | | | | |
|---|---|---|---|---|---|---|
| I-1-13 | I-1-36 | I-1-73 | I-1-83 | I-1-103 | I-1-133 | I-1-491 |
| I-1-35 | I-1-54 | I-1-82 | I-1-84 | I-1-132 | I-1-251 | I-2-5 |

In this test, for example, the following compounds of the Preparation Examples showed an efficacy of 100% at an application rate of 20 ppm:

| | | | | | |
|---|---|---|---|---|---|
| I-1-68 | I-1-494 | I-1-581 | I-2-18 | I-2-38 | I-2-49 | I-3-1 |
| I-1-142 | I-1-575 | I-2-14 | I-2-35 | I-2-41 | I-2-50 | I-3-3 |
| I-1-219 | I-1-580 | I-2-17 | I-2-36 | I-2-44 | I-2-51 | I-3-5 |

In this test, for example, the following compounds of the Preparation Examples showed an efficacy of 100% at an application rate of 100 ppm:

| | | | | | | | | |
|---|---|---|---|---|---|---|---|---|
| I-1-66 | I-1-104 | I-1-105 | I-1-130 | I-1-140 | I-1-143 | I-1-144 | I-1-145 | I-1-146 | I-2-10 |

*Meloidogyne incognita* Test (MELGIN)

Solvent: 125.0 parts by weight of acetone

To prepare a suitable active compound preparation, 1 part by weight of active compound is mixed with the stated amount of solvent and the concentrate is diluted with water to the desired concentration.

Vessels are filled with sand, active compound solution, an egg/larvae suspension of the root-knot nematode (*Meloidogyne incognita*) and lettuce seeds. The lettuce seeds germinate and the plants develop. On the roots, galls are formed.

After 14 days, the nematicidal effect in % is determined by the formation of galls. 100% means that no galls have been found; 0% means that the number of galls on the treated plants corresponds to the untreated control.

In this test, for example, the following compounds of the Preparation Examples showed, at an application rate of 20 ppm, an effect of 80%: I-1-137

In this test, for example, the following compounds of the Preparation Examples showed, at an application rate of 20 ppm, an effect of 90%:

| I-1-6 | I-1-130 | I-1-255 | I-1-354 | I-1-419 | I-1-492 | I-1-535 | I-1-641 | I-2-56 | I-4-4 |
|---|---|---|---|---|---|---|---|---|---|
| I-1-20 | I-1-131 | I-1-256 | I-1-395 | I-1-438 | I-1-499 | I-1-540 | I-2-2 | I-2-68 | |
| I-1-59 | I-1-147 | I-1-274 | I-1-398 | I-1-455 | I-1-502 | I-1-555 | I-2-12 | I-2-70 | |
| I-1-77 | I-1-190 | I-1-284 | I-1-409 | I-1-466 | I-1-512 | I-1-588 | I-2-18 | I-2-76 | |
| I-1-100 | I-1-192 | I-1-308 | I-1-410 | I-1-471 | I-1-518 | I-1-596 | I-2-23 | I-2-80 | |
| I-1-120 | I-1-205 | I-1-335 | I-1-415 | I-1-482 | I-1-528 | I-1-598 | I-2-37 | I-2-84 | |
| I-1-125 | I-1-254 | I-1-345 | I-1-418 | I-1-484 | I-1-531 | I-1-599 | I-2-52 | I-3-1 | |

In this test, for example, the following compounds of the Preparation Examples showed, at an application rate of 20 ppm, an effect of 100%:

| I-1-3 | I-1-74 | I-1-86 | I-1-117 | I-1-142 | I-1-459 | I-1-574 | I-2-11 | I-2-46 | I-2-79 |
|---|---|---|---|---|---|---|---|---|---|
| I-1-14 | I-1-75 | I-1-90 | I-1-121 | I-1-143 | I-1-465 | I-1-575 | I-2-13 | I-2-48 | I-2-82 |
| I-1-50 | I-1-76 | I-1-91 | I-1-122 | I-1-144 | I-1-468 | I-1-591 | I-2-17 | I-2-49 | I-2-83 |
| I-1-57 | I-1-81 | I-1-92 | I-1-128 | I-1-145 | I-1-470 | I-1-622 | I-2-35 | I-2-51 | |
| I-1-65 | I-1-82 | I-1-93 | I-1-129 | I-1-146 | I-1-472 | I-1-626 | I-2-36 | I-2-62 | |
| I-1-67 | I-1-83 | I-1-95 | I-1-135 | I-1-152 | I-1-488 | I-1-629 | I-2-38 | I-2-66 | |
| I-1-70 | I-1-84 | I-1-96 | I-1-140 | I-1-191 | I-1-491 | I-1-631 | I-2-41 | I-2-67 | |
| I-1-73 | I-1-85 | I-1-99 | I-1-141 | I-1-208 | I-1-519 | I-2-10 | I-2-44 | I-2-71 | |

*Myzus persicae* Spray Test (MYZUPE)

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined 100% here means that all of the aphids have been killed; 0% means that no aphids have been killed.

In this test, for example, the following compounds of the Preparation Examples showed an efficacy of 80% at an application rate of 500 g/ha: I-1-25

In this test, for example, the following compounds of the Preparation Examples showed an efficacy of 90% at an application rate of 500 g/ha: I-1-63, I-1-80, I-1-133, I-1-145, I-1-280, I-2-39, I-2-58

In this test, for example, the following compounds of the Preparation Examples showed an efficacy of 90% at an application rate of 20 g/ha: I-1-86

*Phaedon cochleariae* Spray Test (PHAECO)

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all of the beetle larvae have been killed; 0% means that none of the beetle larvae have been killed.

In this test, for example, the following compounds of the Preparation Examples show an efficacy of 83% at an application rate of 500 g/ha:

| I-1-10 | I-1-19 | I-1-77 | I-1-108 | I-1-275 | I-1-415 | I-1-433 |
|---|---|---|---|---|---|---|
| I-1-16 | I-1-34 | I-1-102 | I-1-124 | I-1-317 | I-1-426 | I-1-551 |

In this test, for example, the following compounds of the Preparation Examples show an efficacy of 100% at an application rate of 500 g/ha:

| I-1-1 | I-1-28 | I-1-50 | I-1-74 | I-1-103 | I-1-132 | I-1-259 | I-1-555 | I-2-8 | I-3-1 |
|---|---|---|---|---|---|---|---|---|---|
| I-1-3 | I-1-29 | I-1-51 | I-1-75 | I-1-107 | I-1-133 | I-1-260 | I-1-556 | I-2-9 | I-3-2 |
| I-1-4 | I-1-31 | I-1-52 | I-1-76 | I-1-109 | I-1-134 | I-1-261 | I-1-559 | I-2-10 | I-3-5 |
| I-1-5 | I-1-32 | I-1-53 | I-1-78 | I-1-110 | I-1-135 | I-1-262 | I-1-562 | I-2-12 | I-4-1 |

-continued

| I-1-6 | I-1-33 | I-1-54 | I-1-81 | I-1-111 | I-1-136 | I-1-263 | I-1-564 | I-2-13 | I-4-2 |
|---|---|---|---|---|---|---|---|---|---|
| I-1-7 | I-1-35 | I-1-55 | I-1-82 | I-1-113 | I-1-137 | I-1-264 | I-1-565 | I-2-15 | I-4-3 |
| I-1-9 | I-1-36 | I-1-57 | I-1-83 | I-1-114 | I-1-138 | I-1-335 | I-1-566 | I-2-17 | |
| I-1-11 | I-1-37 | I-1-58 | I-1-84 | I-1-117 | I-1-168 | I-1-352 | I-1-578 | I-2-35 | |
| I-1-12 | I-1-38 | I-1-60 | I-1-85 | I-1-118 | I-1-190 | I-1-372 | I-1-580 | I-2-36 | |
| I-1-13 | I-1-39 | I-1-61 | I-1-86 | I-1-119 | I-1-231 | I-1-384 | I-1-596 | I-2-37 | |
| I-1-14 | I-1-40 | I-1-63 | I-1-90 | I-1-120 | I-1-238 | I-1-395 | I-1-599 | I-2-38 | |
| I-1-15 | I-1-41 | I-1-65 | I-1-91 | I-1-121 | I-1-240 | I-1-403 | I-1-642 | I-2-39 | |
| I-1-17 | I-1-42 | I-1-66 | I-1-92 | I-1-122 | I-1-243 | I-1-406 | I-2-1 | I-2-41 | |
| I-1-20 | I-1-43 | I-1-67 | I-1-93 | I-1-123 | I-1-248 | I-1-408 | I-2-2 | I-2-44 | |
| I-1-21 | I-1-44 | I-1-68 | I-1-94 | I-1-125 | I-1-253 | I-1-410 | I-2-3 | I-2-45 | |
| I-1-22 | I-1-45 | I-1-69 | I-1-95 | I-1-127 | I-1-254 | I-1-411 | I-2-4 | I-2-46 | |
| I-1-23 | I-1-46 | I-1-70 | I-1-96 | I-1-128 | I-1-255 | I-1-417 | I-2-5 | I-2-49 | |
| I-1-24 | I-1-48 | I-1-72 | I-1-99 | I-1-129 | I-1-256 | I-1-428 | I-2-6 | I-2-55 | |
| I-1-25 | I-1-49 | I-1-73 | I-1-101 | I-1-131 | I-1-258 | I-1-550 | I-2-7 | I-2-57 | |

*Spodoptera frugiperda* Spray Test (SPODFR)
Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Leaf discs of maize (*Zea mays*) are sprayed with an active compound formulation of the desired concentration and, after drying, populated with caterpillars of the armyworm (*Spodoptera frugiperda*).

After 7 days, the efficacy in % is determined. 100% means that all of the caterpillars have been killed; 0% means that none of the caterpillars have been killed.

In this test, for example, the following compounds of the Preparation Examples showed an efficacy of 83% at an application rate of 100 g/ha: I-1-118

In this test, for example, the following compounds of the Preparation Examples showed an efficacy of 83% at an application rate of 500 g/ha: I-1-17, I-1-29, I-1-34

In this test, for example, the following compounds of the Preparation Examples showed an efficacy of 100% at an application rate of 500 g/ha: I-1-35, I-1-75, I-1-136, I-1-259, I-1-403, I-2-41

Discs of bean leaves (*Phaseolus vulgaris*) which are infested by all stages of the greenhouse red spider mite (*Tetranychus urticae*) are sprayed with an active compound preparation of the desired concentration.

After 6 days, the efficacy in % is determined. 100% means that all of the spider mites have been killed; 0% means that none of the spider mites have been killed.

In this test, for example, the following compounds of the Preparation Examples showed, at an application rate of 500 g/ha, an efficacy of 80%: I-1-10, I-1-18, I-1-39, I-1-248

In this test, for example, the following compounds of the Preparation Examples showed, at an application rate of 500 g/ha, an efficacy of 85%: I-1-598

In this test, for example, the following compounds of the Preparation Examples showed, at an application rate of 500 g/ha, an efficacy of 90%:

| I-1-7 | I-1-51 | I-1-73 | I-1-103 | I-1-116 | I-1-188 | I-1-238 | I-1-281 | I-1-360 | I-1-472 |
|---|---|---|---|---|---|---|---|---|---|
| I-1-11 | I-1-52 | I-1-79 | I-1-107 | I-1-145 | I-1-203 | I-1-259 | I-1-338 | I-1-370 | I-1-558 |
| I-1-26 | I-1-53 | I-1-80 | I-1-109 | I-1-157 | I-1-212 | I-1-264 | I-1-354 | I-1-433 | |
| I-1-32 | I-1-69 | I-1-99 | I-1-113 | I-1-186 | I-1-213 | I-1-275 | I-1-355 | I-1-463 | |

In this test, for example, the following compounds of the Preparation Examples showed, at an application rate of 100/ha, an efficacy of 90%: I-1-43

In this test, for example, the following compounds of the Preparation Examples showed, at an application rate of 500 g/ha, an efficacy of 95%: I-1-210, I-1-258, I-1-262, I-1-263, I-1-428, I-1-596

In this test, for example, the following compounds of the Preparation Examples showed, at an application rate of 500 g/ha, an efficacy of 100%:

| I-1-5 | I-1-20 | I-1-35 | I-1-48 | I-1-66 | I-1-83 | I-1-185 | I-1-253 | I-1-372 | I-2-62 |
|---|---|---|---|---|---|---|---|---|---|
| I-1-6 | I-1-33 | I-1-37 | I-1-64 | I-1-67 | I-1-101 | I-1-214 | I-1-254 | I-1-403 | |

*Tetranychus urticae* Spray Test, OP-Resistant (TETRUR)
Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

The invention claimed is:
1. A pesticidal compound of formula (I)

in which
A represents a radical A-1

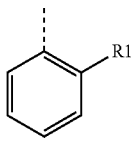

in which the broken line represents the bond to Q and in which A furthermore carries m substituents R2 at the 6-position of the radical A-1, Q represents a radical Q-1

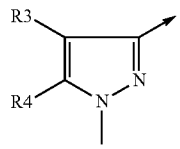

in which the nitrogen is attached to ring A and the arrow in each case represents the bond to D and D represents the radical of the formula

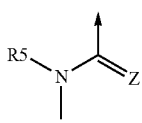

in which the nitrogen is attached to Q and the arrow represents the bond to B,

B represents a radical B-1

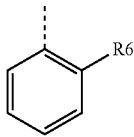

in which the broken line represents the bond to D and in which B furthermore carries n substituents R7, Z represents oxygen or sulphur, R1 represents a radical from the group consisting of halogen, cyano, nitro, amino, hydroxy, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, $C_4$-$C_{12}$-bicycloalkyl, aryl, aryloxy, arylamino, and arylthio, each of which is optionally substituted by one or more identical or different substituents, where the substituents independently of one another are selected from the group consisting of halogen, cyano, nitro, hydroxy, amino, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, aryl, aryloxy, and arylthio, R2 represents a radical from the group consisting of halogen, cyano, nitro, amino, hydroxy, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, di-($C_1$-$C_6$-alkyl)-amino, $C_1$-$C_6$-alkenylamino, $C_3$-$C_6$-alkynylamino, $C_3$-$C_6$-cycloalkylamino, $C_3$-$C_6$-alkylcarbonylamino, $C_1$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, $C_4$-$C_{12}$-bicycloalkyl, aryl, aryloxy, arylamino, and arylthio, each of which is optionally substituted by one or more identical or different substituents, where the substituents independently of one another are selected from the group consisting of halogen, cyano, nitro, hydroxy, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, aryl, aryloxy, and arylthio, R3 represents a radical from the group consisting of hydrogen, halogen, cyano, nitro, amino, hydroxy, $C_1$-$C_6$-alkyl, $C_1$-$C_6$-alkoxy, $C_1$-$C_6$-haloalkyl and $C_1$-$C_6$-haloalkoxy, R4 represents a radical from the group consisting of hydrogen, halogen, amino, $C_1$-$C_6$-alkyl, $C_1$-$C_6$-alkoxy, $C_1$-$C_6$-haloalkyl and $C_1$-$C_6$-haloalkoxy, R5 represents a radical from the group consisting of hydrogen, $C_1$-$C_6$-alkyl, $C_3$-$C_6$-cycloalkyl, $C_1$-$C_6$-haloalkyl, $C_2$-$C_6$-alkenyl, $C_3$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl or represents C(=O)—B, R6 represents a radical from the group consisting of halogen, cyano, nitro, amino, hydroxy, carboxyl, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$- alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-haloalkylcarbonylamino, $C_1$-$C_6$-alkylthiocarbonylamino, $C_4$-$C_{12}$-bicycloalkyl, aryl, and aryloxy, each of which is optionally substituted by one or more identical or different substituents, where the substituents independently of one another are selected from the group consisting of halogen, cyano, nitro, hydroxy, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, R7 represents a radical from the group consisting of halogen, nitro, cyano, amino, hydroxy, represents $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_3$-$C_6$-alkenoxy, $C_3$-$C_6$-alkynoxy, $C_3$-$C_6$-cycloalkoxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylcarbonylamino, $C_2$-$C_6$-alkenylcarbonylamino, $C_2$-$C_6$-alkynylcarbonylamino, $C_3$-$C_6$-cycloalkylcarbonylamino, $C_1$-$C_6$-alkoxycarbonylamino, $C_1$-$C_6$-alkylsulphonylamino, $C_1$-$C_6$-alkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, aryloxy, $C_4$-$C_{12}$-bicycloalkyl, each of which is optionally substituted by one or more identical or different substituents, where the substituents independently of one another are selected from the group consisting of halogen, cyano, nitro, hydroxy, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, m represents a number from the group consisting of 0 and 1, and n represents a number from the group consisting of 0, 1, 2 and 3, where for n>1 the radicals R7 may be identical or different capable of being used for controlling an animal pest.

2. A compound of formula (I) according to claim 1 in which

Z represents oxygen or sulphur,

R1 represents a radical from the group consisting of halogen, cyano, nitro, amino, hydroxy, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, and aryloxy, R2 represents a radical from the group consisting of halogen, cyano, nitro, amino, hydroxy, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, di-($C_1$-$C_6$-alkyl)-amino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, and aryloxy, R3 represents a radical from the group consisting of hydrogen, halogen, cyano, nitro, amino, $C_1$-$C_6$-alkyl and $C_1$-$C_6$-haloalkyl, R4 represents a radical from the group consisting of hydrogen, halogen, amino, $C_1$-$C_6$-alkyl, $C_1$-$C_6$-alkoxy, $C_1$-$C_6$-haloalkyl and $C_1$-$C_6$-haloalkoxy, R5 represents a radical from the group consisting of hydrogen, $C_1$-$C_6$-alkyl, $C_1$-$C_6$-haloalkyl, cyano-$C_1$-$C_6$-alkyl, $C_2$-$C_6$-alkenyl, $C_3$-$C_6$-alkynyl, $C_3$-$C_6$-cycloalkyl, $C_3$-$C_6$-cycloalkyl-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl, $C_1$-$C_6$-haloalkylsulphonyl and C($=$O)—B, R6 represents a radical from the group consisting of halogen, cyano, nitro, amino, hydroxy, carboxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_4$-haloalkylcarbonylamino, $C_1$-$C_6$-alkylthiocarbonylamino, aryl, and aryloxy, R7 represents a radical from the group consisting of halogen, cyano, nitro, amino, hydroxy, $C_1$-$C_6$-alkyl, $C_1$-$C_6$-haloalkyl, cyano-$C_1$-$C_6$-alkyl, $C_2$-$C_6$-alkenyl, $C_3$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$- alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$-alkyl)-aminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, aryl, and aryloxy, m represents a number from the group consisting of 0 and 1, and n represents a number from the group consisting of 0, 1, 2 and 3, where for n>1 the radicals R7 may be identical or different.

3. A compound of formula (I) according to claim 1 in which

Z represents oxygen or sulphur,

R1 represents a radical from the group consisting of halogen, cyano, nitro, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, and aryloxy, R2 represents a radical from the group consisting of halogen, cyano, nitro, amino, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkylcarbonyl, di-($C_1$-$C_6$-alkyl)-amino, $C_1$-$C_6$-alkoxyimino-$C_1$-$C_6$-alkyl, aryl, and aryloxy, R3 represents a radical from the group consisting of hydrogen, halogen, cyano, nitro, amino, $C_1$-$C_6$-alkyl and $C_1$-$C_6$-haloalkyl, R4 represents a radical from the group consisting of hydrogen, halogen, amino, $C_1$-$C_6$-alkyl, $C_1$-$C_6$-alkoxy, $C_1$-$C_6$-haloalkyl and $C_1$-$C_6$-haloalkoxy, R5 represents a radical from the group consisting of hydrogen, $C_1$-$C_6$-alkyl, $C_1$-$C_6$-haloalkyl, cyano-$C_1$-$C_6$-alkyl, $C_2$-$C_6$-alkenyl, $C_3$-$C_6$-alkynyl, $C_3$-$C_6$-cycloalkyl, $C_3$-$C_6$-cycloalkyl-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl, $C_1$-$C_6$-haloalkylsulphonyl and C(=O)—B, R6 represents a radical from the group consisting of halogen, cyano, nitro, hydroxy, carboxyl, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylsulphinyl, $C_1$-$C_6$-alkylthio, $C_1$-$C_6$-haloalkylthio, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkylcarbonylamino, $C_1$-$C_6$-haloalkylcarbonylamino, aryl, and aryloxy, R7 represents a radical from the group consisting of halogen, cyano, nitro, hydroxy, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-alkoxyimino-$C_1$-$C_6$-alkyl, aryl, and aryloxy, m represents a number from the group consisting of 0 and 1, and n represents a number from the group consisting of 0, 1, 2 and 3, where for n>1 the radicals R7 may be identical or different.

4. A compound of formula (I) according to claim 1 in which

Z represents oxygen or sulphur,

R1 represents a radical from the group consisting of halogen, cyano, nitro, $C_1$-$C_4$-alkyl, $C_1$-$C_4$-haloalkyl, $C_1$-$C_4$-alkoxy and $C_1$-$C_4$-alkylsulphonyl, R2 represents a radical from the group consisting of halogen, $C_1$-$C_4$-alkyl and $C_1$-$C_4$-alkoxy, R3 represents a radical from the group consisting of hydrogen and halogen, R4 represents a radical from the group consisting of hydrogen and $C_1$-$C_4$-alkyl, R5 represents a radical from the group consisting of hydrogen, $C_1$-$C_4$-alkyl, $C_3$-$C_4$-alkenyl, $C_3$-$C_4$-alkynyl, $C_3$-$C_6$-cycloalkyl-$C_1$-$C_4$-alkyl, $C_1$-$C_4$-alkylcarbonyl, cyano-$C_1$-$C_4$-alkyl and C(=O)—B, R6 represents a radical from the group consisting of halogen, nitro, hydroxy, $C_1$-$C_4$-alkyl, $C_1$-$C_4$-alkoxy, $C_1$-$C_4$-alkylthio, $C_1$-$C_4$-alkylsulphonyl, $C_1$-$C_4$-haloalkyl, $C_1$-$C_4$-haloalkoxy, and $C_1$-$C_4$-haloalkylthio, R7 represents a radical from the group consisting of halogen, $C_1$-$C_4$-alkyl and $C_1$-$C_4$-haloalkyl, m represents a number from the group consisting of 0 and 1, and n represents a number from the group consisting of 0 and 1.

5. A compound of formula (I) according to claim 1 in which

Z represents oxygen or sulphur,

R1 represents a radical from the group consisting of halogen, cyano, nitro, $C_1$-$C_4$-alkyl, $C_1$-$C_4$-haloalkyl, $C_1$-$C_4$-alkoxy and $C_1$-$C_4$-alkylsulphonyl, R2 represents a radical from the group consisting of halogen, cyano, nitro, amino, $C_1$-$C_4$-alkyl, $C_1$-$C_4$-haloalkyl, $C_3$-$C_6$-cycloalkyl, $C_1$-$C_4$-alkoxy, di-($C_1$-$C_6$-alkyl)-amino, $C_1$-$C_4$-alkylcarbonyl, aryl, R3 represents a radical from the group consisting of hydrogen, halogen, cyano, nitro, $C_1$-$C_4$-alkyl, R4 represents a radical from the group consisting of hydrogen, amino, $C_1$-$C_4$-alkyl, R5 represents a radical from the group consisting of hydrogen, $C_1$-$C_4$-alkyl, $C_3$-$C_4$-alkenyl, $C_3$-$C_4$-alkynyl, $C_3$-$C_6$-cycloalkyl-$C_1$-$C_4$-alkyl, $C_1$-$C_4$-alkylcarbonyl, cyano-$C_1$-$C_4$-alkyl and C(=O)—B, R6 represents a radical from the group consisting of halogen, cyano, nitro, hydroxy, carboxyl, $C_1$-$C_4$-alkyl, $C_1$-$C_4$-alkoxy, $C_1$-$C_4$-alkylthio, $C_1$-$C_4$-alkylsulphonyl, $C_1$-$C_4$-haloalkyl, $C_3$-$C_6$-cycloalkyl, $C_1$-$C_4$-haloalkoxy, $C_1$-$C_4$-haloalkylthio, $C_1$-$C_4$-alkylcarbonyl, $C_1$-$C_4$-alkylcarbonylamino, $C_1$-$C_4$- and haloalkylcarbonylamino, R7 represents a radical from the group consisting of halogen, cyano, nitro, hydroxy, $C_1$-$C_4$-alkyl, $C_1$-$C_4$-haloalkyl and $C_1$-$C_4$-alkoxy, m represents a number from the group consisting of 0 and 1, and n represents a number from the group consisting of 0, 1, 2 and 3, where for n>1 the radicals R7 may be identical or different.

6. A Composition comprising at least one compound of formula (I) as described in claim 1 and one or more auxiliaries.

7. A Composition comprising at least one compound of formula (I) as described in claim 5 and one or more auxiliaries.

8. Method for controlling one or more pests, comprising allowing a compound of formula (I) according to claim 1 to act on one or more pests and/or a habitat thereof.

9. A method as claimed in claim 8, wherein the pests are insects, arachnids, helminths, mollusks, or nematodes.

10. A compound according to claim 1, which is compound I-1-73, wherein A is 2,6-difluorophenyl, B is 2-methylphenyl, R3, R4, and R5 are H, and Z is oxygen.

11. A compound according to claim 1, which is the compound I-1-75, wherein A is 2,6-difluorophenyl, B is 2-(trifluoromethyl)phenyl, R3, R4, and R5 are H, and Z is oxygen.

12. A compound according to claim 1, which is the compound I-1-76, wherein A is 2,6-difluorophenyl, B is 2-(trifluoromethyl)phenyl, R3 is F, R4 and R5 are H, and Z is oxygen.

13. A compound according to claim 1, which is the compound I-1-81, wherein A is 2,6-difluorophenyl, B is 2-chlorophenyl, R3, R4 and R5 are H, and Z is oxygen.

14. A compound according to claim 1, which is the compound I-1-83, wherein A is 2,6-difluorophenyl, B is 2-iodophenyl, R3, R4 and R5 are H, and Z is oxygen.

15. A compound according to claim 1, which is the compound I-1-276, wherein A is 2,6-difluorophenyl, B is 2-fluoro-6-(trifluoromethyl) phenyl, R3, R4 and R5 are H, and Z is oxygen.

16. A compound according to claim 1, which is the compound I-1-335, wherein A is 2-bromophenyl, B is 2-fluoro-6-(trifluoromethyl)phenyl, R3, R4 and R5 are H, and Z is oxygen.

17. A compound according to claim 1, which is the compound I-1-322, wherein A is 2-6-difluorophenyl, B is 4-fluoro-2-(trifluoromethyl)phenyl, R3, R4 and R5 are H, and Z is oxygen.

18. A compound according to claim 1, which is the compound I-1-82, wherein A is 2-6-difluorophenyl, B is 2-bromophenyl, R3, R4 and R5 are H, and Z is oxygen.

19. A compound according to claim 1, which is the compound I-1-394, wherein A is 2-cyanophenyl, B is 2-iodophenyl, R3, R4 and R5 are H, and Z is oxygen.

20. A compound according to claim 1, which is the compound I-1-53, wherein A is 2-bromophenyl, B is 2-iodophenyl, R3, R4 and R5 are H, and Z is oxygen.

21. A compound according to claim 1, which is the compound I-1-50, wherein A is 2-bromophenyl, B is 2-(trifluoromethyl)phenyl, R3, R4 and R5 are H, and Z is oxygen.

22. A compound according to claim 1, which is the compound I-1-14, wherein A is 2-chlorophenyl, B is 2-(trifluoromethyl)phenyl, R3, R4 and R5 are H, and Z is oxygen.

23. A compound according to claim 1, which is the compound I-1-84, wherein A is 2,6-difluorophenyl, B is 2,6-difluorophenyl, R3, R4 and R5 are H, and Z is oxygen.

24. A compound according to claim 1, which is the compound I-1-74, wherein A is 2,6-difluorophenyl, B is 2-difluoromethylphenyl, R3, R4 and R5 are H, and Z is oxygen.

25. A compound according to claim 1, which is the compound I-1-6, wherein A is 2-(trifluoro)methylphenyl, B is 2-(trifluoromethyl)phenyl, R3, R4 and R5 are H, and Z is oxygen.

26. A compound according to claim 1, which is the compound I-1-117, wherein A is 2-ethoxy-6-fluorophenyl, B is 2-chlorophenyl, R3, R4 and R5 are H, and Z is oxygen.

27. A compound according to claim 1, wherein R4 represents a radical selected from the group consisting of hydrogen, halogen, amino, $C_1$-$C_6$-alkoxy, $C_1$-$C_6$-haloalkyl and $C_1$-$C_6$-haloalkoxy.

* * * * *